(12) United States Patent
Zink et al.

(10) Patent No.: US 11,005,048 B2
(45) Date of Patent: May 11, 2021

(54) ORGANIC MOLECULES, IN PARTICULAR FOR USE IN OPTOELECTRONIC DEVICES

(71) Applicant: CYNORA GMBH, Bruchsal (DE)

(72) Inventors: Daniel Zink, Bruchsal (DE); Michael Danz, Eggenstein-Leopoldshafen (DE); Larissa Bergmann, Karlsruhe (DE)

(73) Assignee: CYNORA GMBH, Bruchsal (DE)

( * ) Notice: Subject to any disclaimer, the term of this patent is extended or adjusted under 35 U.S.C. 154(b) by 260 days.

(21) Appl. No.: 16/034,290

(22) Filed: Jul. 12, 2018

(65) Prior Publication Data
US 2019/0019960 A1 Jan. 17, 2019

(30) Foreign Application Priority Data

Jul. 14, 2017 (EP) .................................. 17181353
Sep. 25, 2017 (EP) .................................. 17193016
Feb. 20, 2018 (EP) .................................. 18157734

(51) Int. Cl.
*H01L 51/00* (2006.01)
*C09K 11/06* (2006.01)
*C07D 491/048* (2006.01)
*C07D 487/04* (2006.01)
*C07D 495/04* (2006.01)
*C07D 403/14* (2006.01)
*C07D 405/14* (2006.01)
*H01L 51/50* (2006.01)
(Continued)

(52) U.S. Cl.
CPC ........ *H01L 51/0067* (2013.01); *C07D 403/14* (2013.01); *C07D 405/14* (2013.01); *C07D 487/04* (2013.01); *C07D 491/048* (2013.01); *C07D 495/04* (2013.01); *C09K 11/06* (2013.01); *H01L 51/0071* (2013.01); *H01L 51/0072* (2013.01); *C09K 2211/1018* (2013.01); *H01L 51/0558* (2013.01); *H01L 51/0575* (2013.01); *H01L 51/42* (2013.01); *H01L 51/5012* (2013.01); *H01L 51/5016* (2013.01); *H01L 51/5072* (2013.01); *H01L 51/5088* (2013.01); *H01L 51/5096* (2013.01); *H01L 2251/5384* (2013.01); *H01L 2251/552* (2013.01)

(58) Field of Classification Search
CPC .. C07D 403/14; C07D 405/14; C07D 487/04; C07D 491/048; C07D 495/04; C09K 11/06; C09K 2211/1018; H01L 2251/5384; H01L 2251/552; H01L 51/0067; H01L 51/0071; H01L 51/0072; H01L 51/0558; H01L 51/0575; H01L 51/42; H01L 1/5012; H01L 51/5016; H01L 51/5072; H01L 51/5088; H01L 51/5096
See application file for complete search history.

(56) References Cited

U.S. PATENT DOCUMENTS

2004/0086745 A1 5/2004 Iwakuma et al.
2012/0068170 A1* 3/2012 Pflumm ............... C07D 413/04
257/40
(Continued)

FOREIGN PATENT DOCUMENTS

CN 105294658 A 2/2016
KR 2011041727 A * 4/2011
WO 2016/181846 A1 11/2016

OTHER PUBLICATIONS

Google Patents machine translation for KR 2011041727 A (publication date Apr. 2011). (Year: 2011).*

*Primary Examiner* — Dawn L Garrett
(74) *Attorney, Agent, or Firm* — Maschoff Brennan

(57) ABSTRACT

The invention relates to an organic molecule, in particular for the application in organic optoelectronic devices. According to the invention, the organic molecule has
a first chemical moiety with a structure of Formula I,

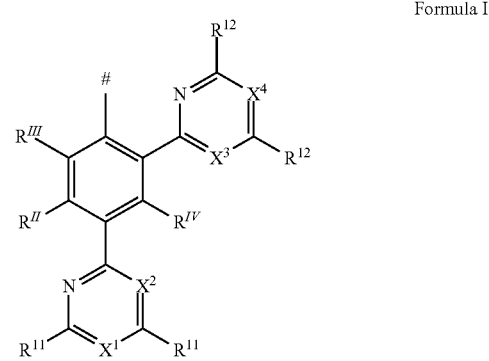

Formula I and
one second chemical moiety with a structure of Formula II,

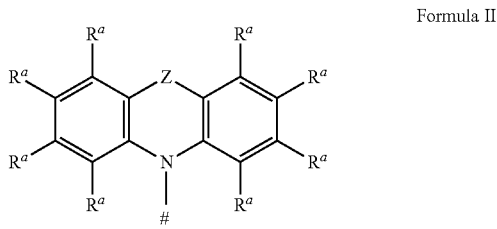

Formula II # represents the binding site of a single bond linking the first chemical moiety to the second chemical moiety;

(Continued)

wherein at least one variable of $X^1$, $X^2$ is N, and at least one variable of $X^3$, $X^4$ is N.

13 Claims, 15 Drawing Sheets

(51) Int. Cl.
*H01L 51/05* (2006.01)
*H01L 51/42* (2006.01)

(56) References Cited

U.S. PATENT DOCUMENTS

| | | | | |
|---|---|---|---|---|
| 2012/0080670 | A1* | 4/2012 | Park | H05B 33/14 |
| | | | | 257/40 |
| 2015/0318487 | A1* | 11/2015 | Ito | H01L 51/5076 |
| | | | | 257/40 |
| 2015/0318510 | A1* | 11/2015 | Ito | H01L 51/0067 |
| | | | | 257/40 |
| 2015/0349273 | A1 | 12/2015 | Hung et al. | |
| 2016/0329502 | A1* | 11/2016 | Dyatkin | H05B 33/20 |

* cited by examiner

ORGANIC MOLECULES, IN PARTICULAR FOR USE IN OPTOELECTRONIC DEVICES

The invention relates to organic molecules and their use in organic light-emitting diodes (OLEDs) and in other optoelectronic devices.

SUMMARY

The object of the present invention is to provide molecules which are suitable for use in optoelectronic devices.

This object is achieved by the invention which provides a new class of organic molecules.

FIGURES

Figure 1:
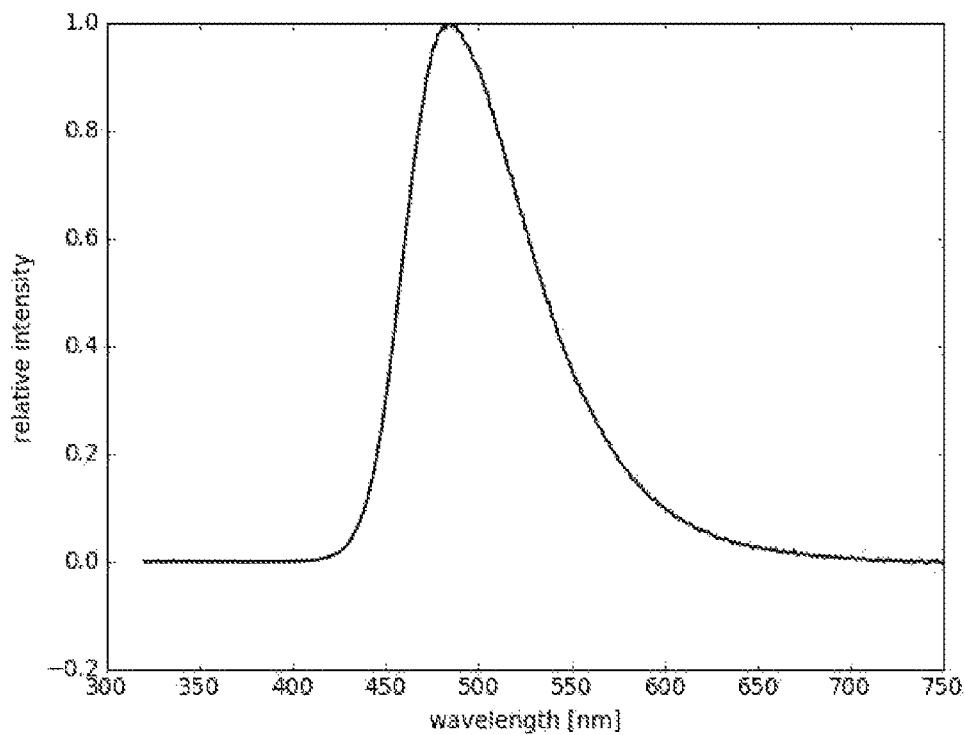

FIG. 1 Emission spectrum of example 1 (10% by weight) in PMMA.

Figure 2:
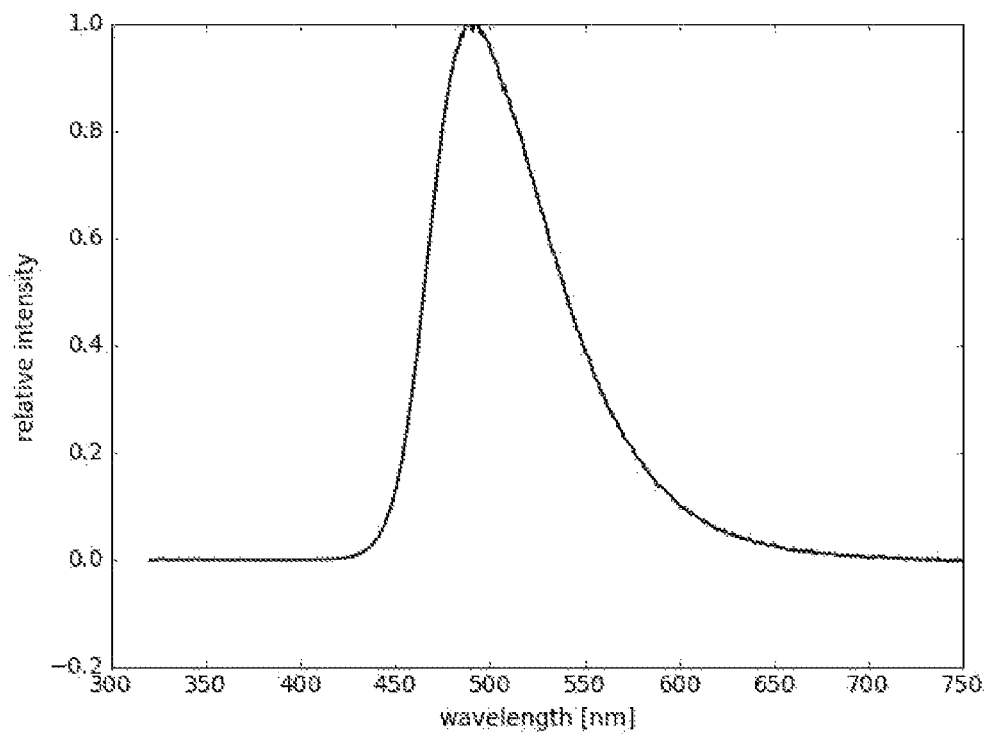

FIG. 2 Emission spectrum of example 2 (10% by weight) in PMMA.

Figure 3:
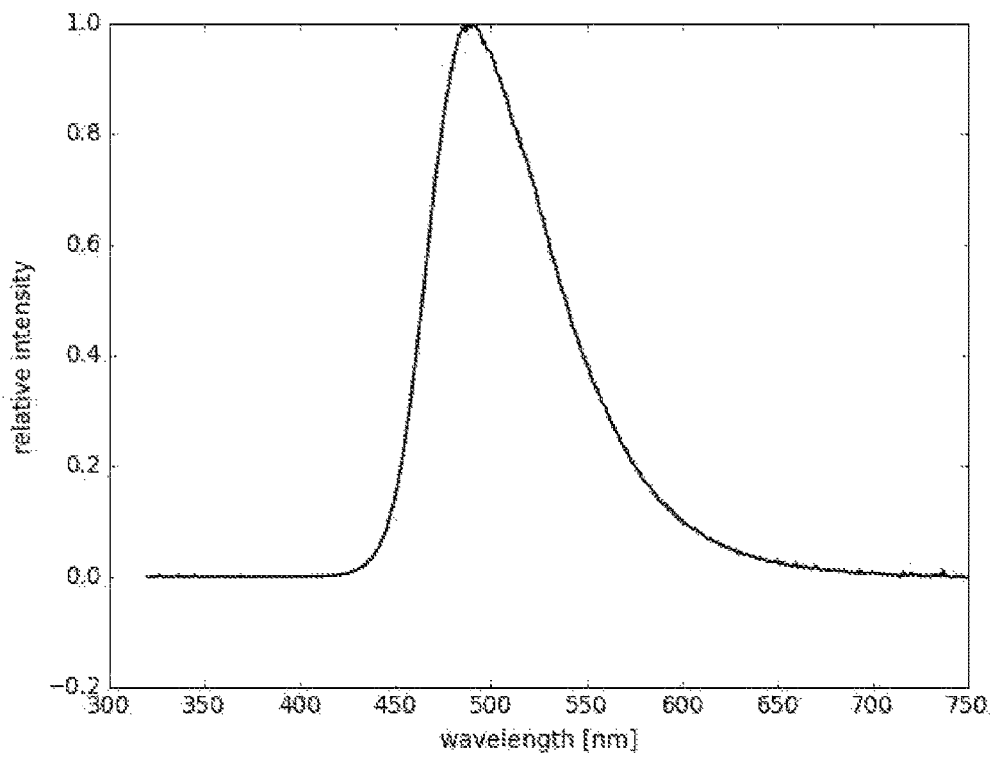

FIG. 3 Emission spectrum of example 3 (10% by weight) in PMMA.

Figure 4:
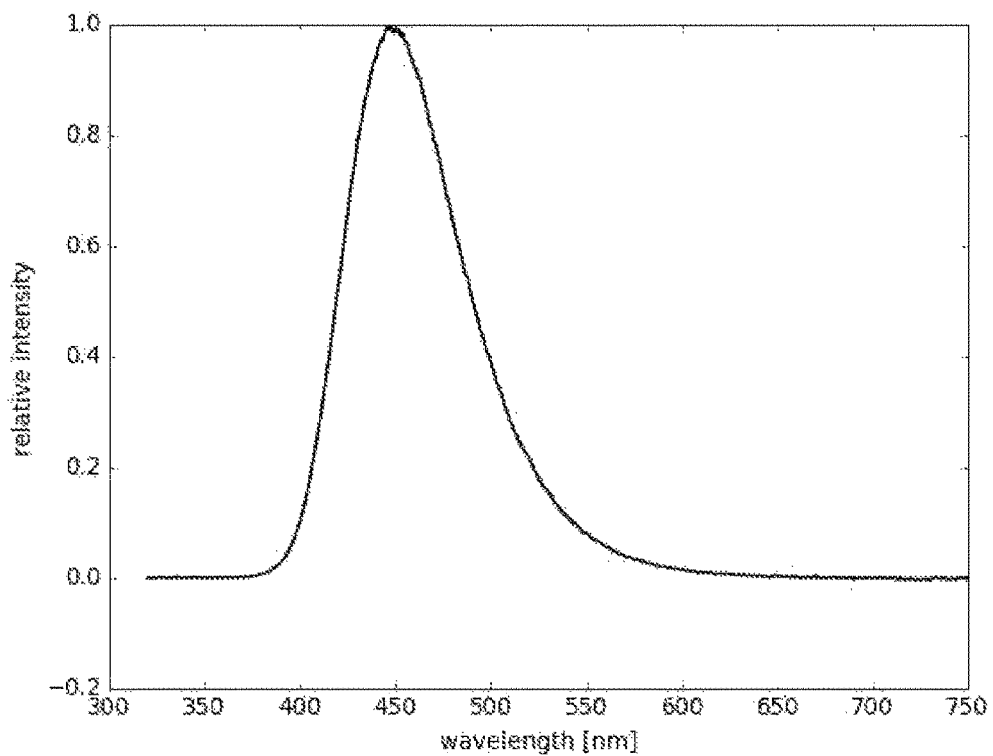

FIG. 4 Emission spectrum of example 4 (10% by weight) in PMMA.

Figure 5:
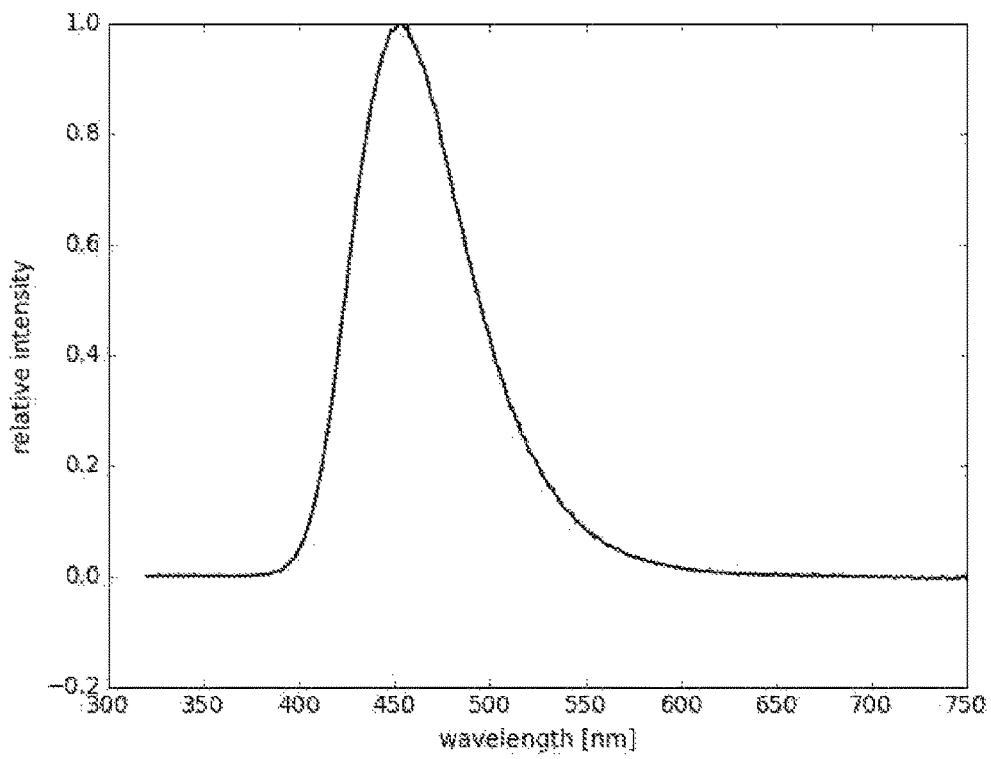

FIG. 5 Emission spectrum of example 5 (10% by weight) in PMMA.

Figure 6:
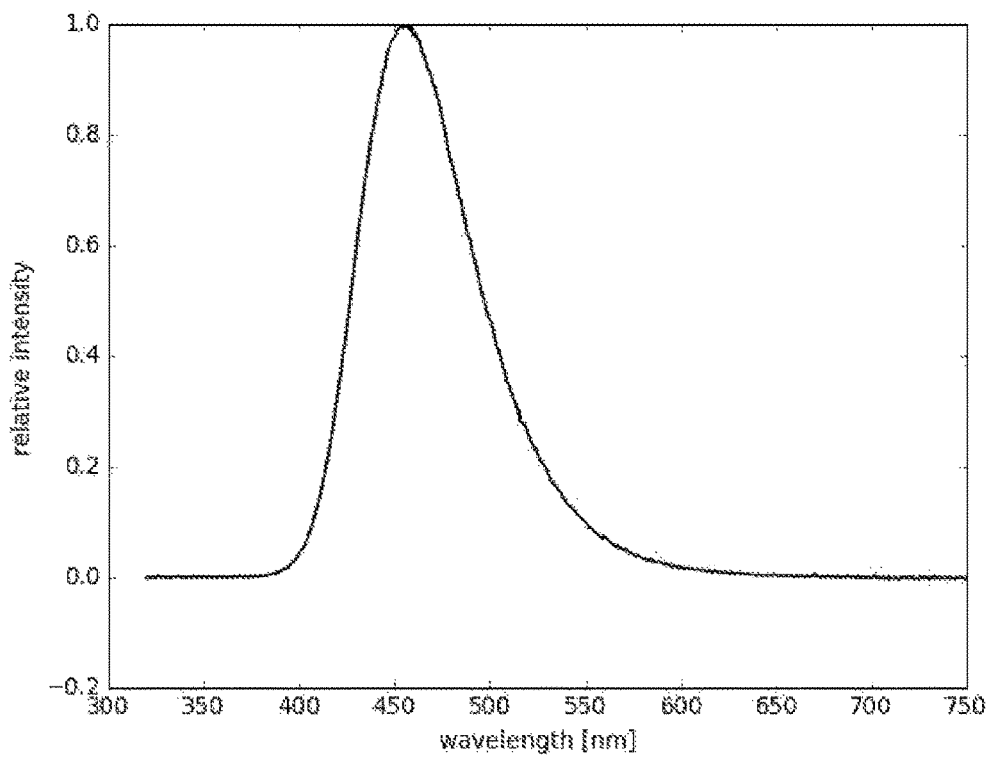

FIG. 6 Emission spectrum of example 6 (10% by weight) in PMMA.

Figure 7:
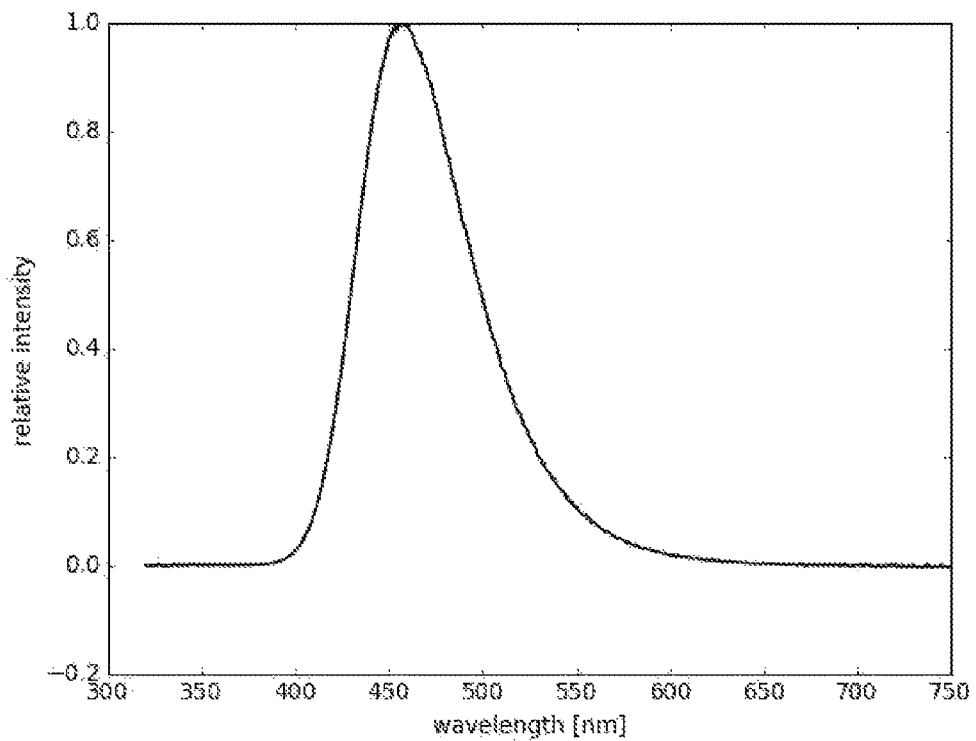

FIG. 7 Emission spectrum of example 7 (10% by weight) in PMMA.

Figure 8:
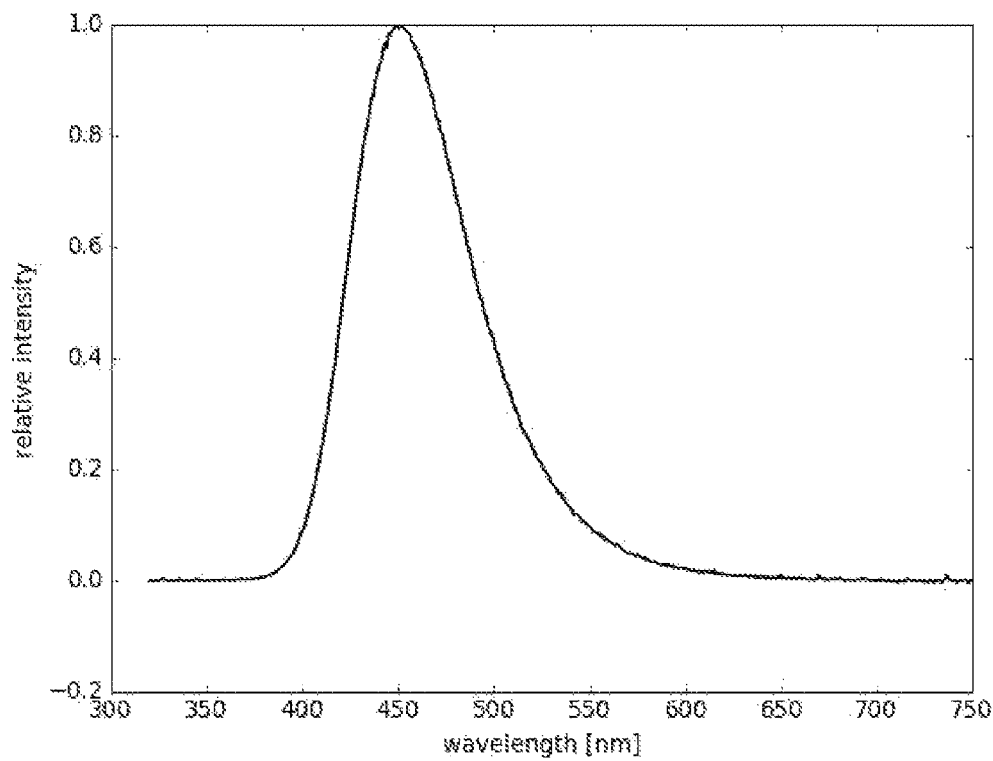

FIG. 8 Emission spectrum of example 8 (10% by weight) in PMMA.

Figure 9:
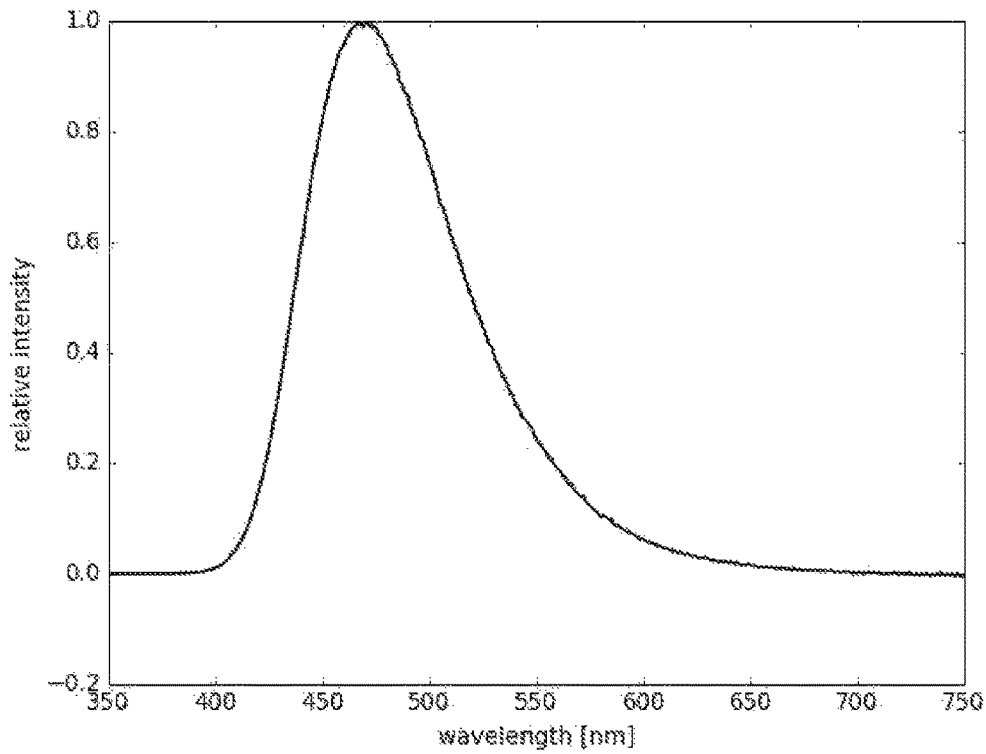

FIG. 9 Emission spectrum of example 9 (10% by weight) in PMMA.

Figure 10:
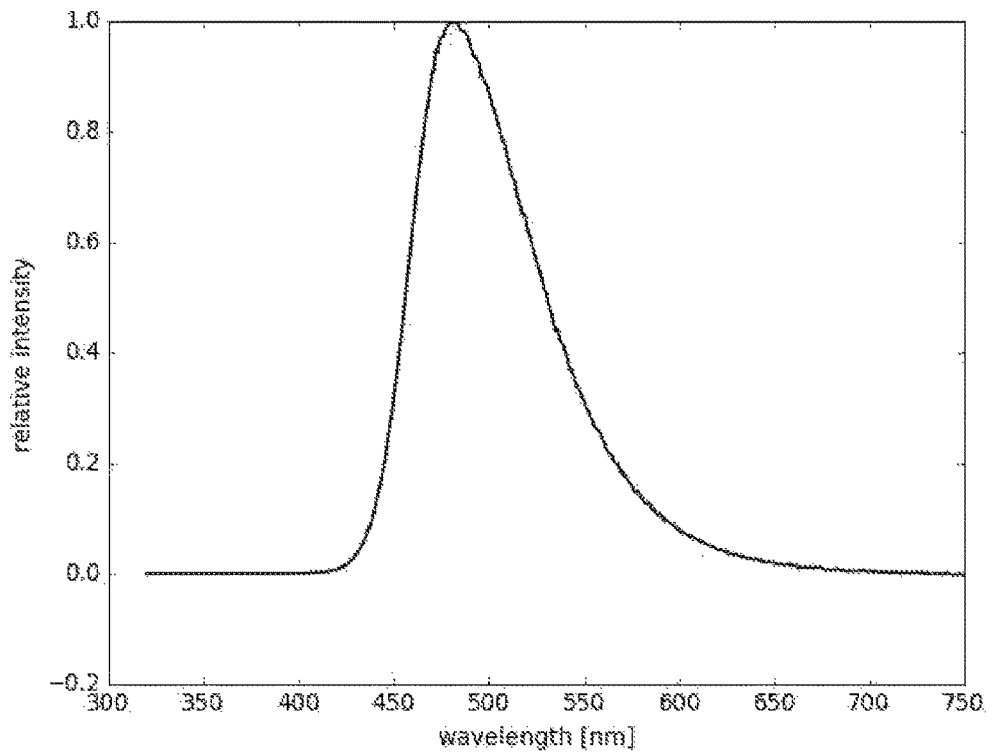

FIG. 10 Emission spectrum of example 10 (10% by weight) in PMMA.

Figure 11:
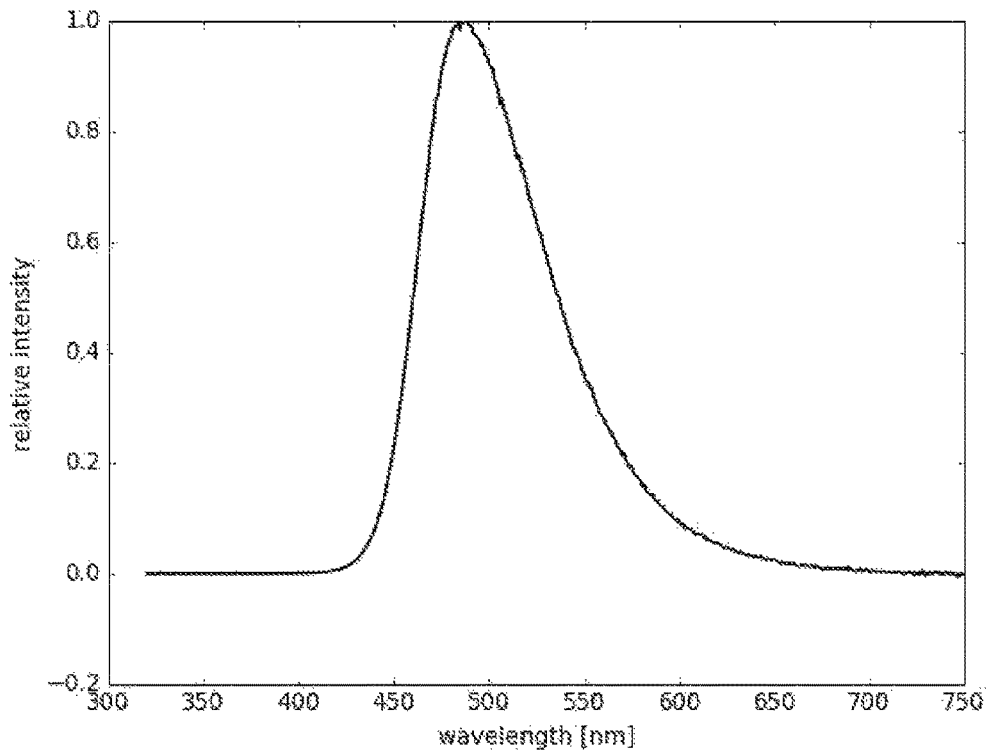

FIG. 11 Emission spectrum of example 11 (10% by weight) in PMMA.

Figure 12:
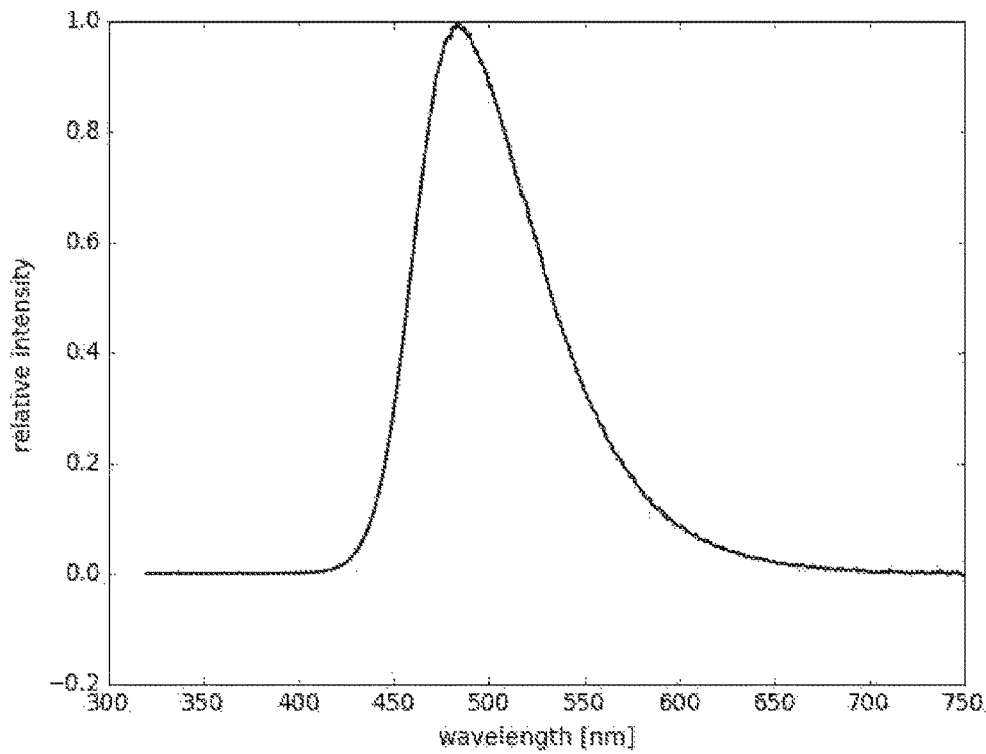

FIG. 12 Emission spectrum of example 12 (10% by weight) in PMMA.

Figure 13:
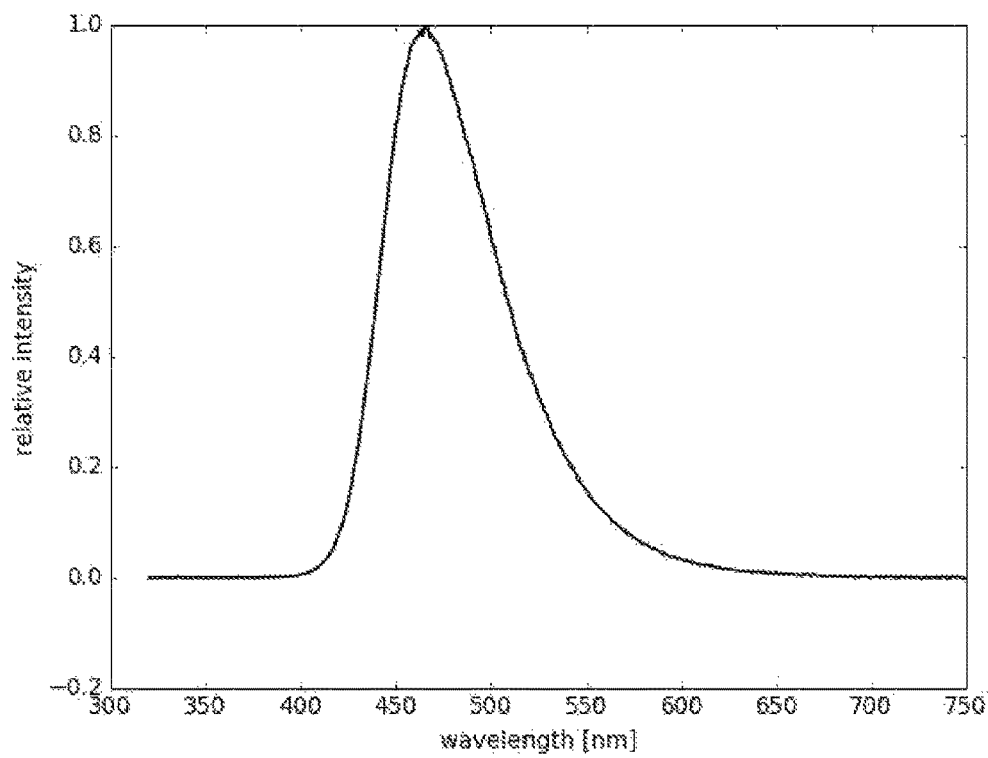

FIG. 13 Emission spectrum of example 13 (10% by weight) in PMMA.

Figure 14:
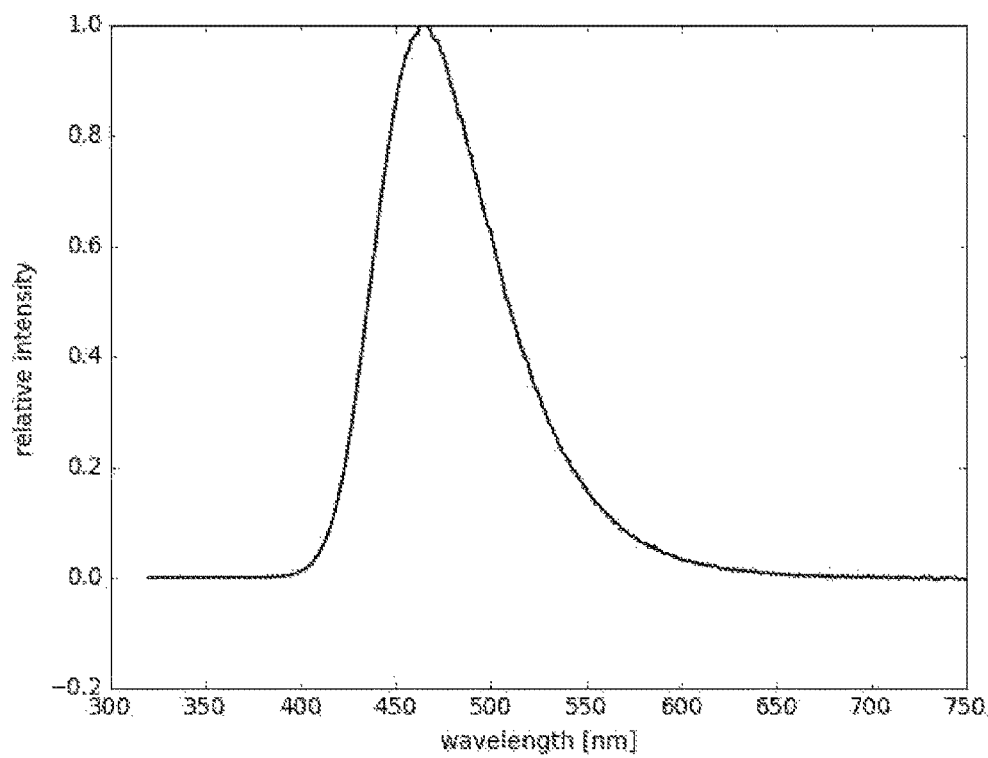

FIG. 14 Emission spectrum of example 14 (10% by weight) in PMMA.

Figure 15:
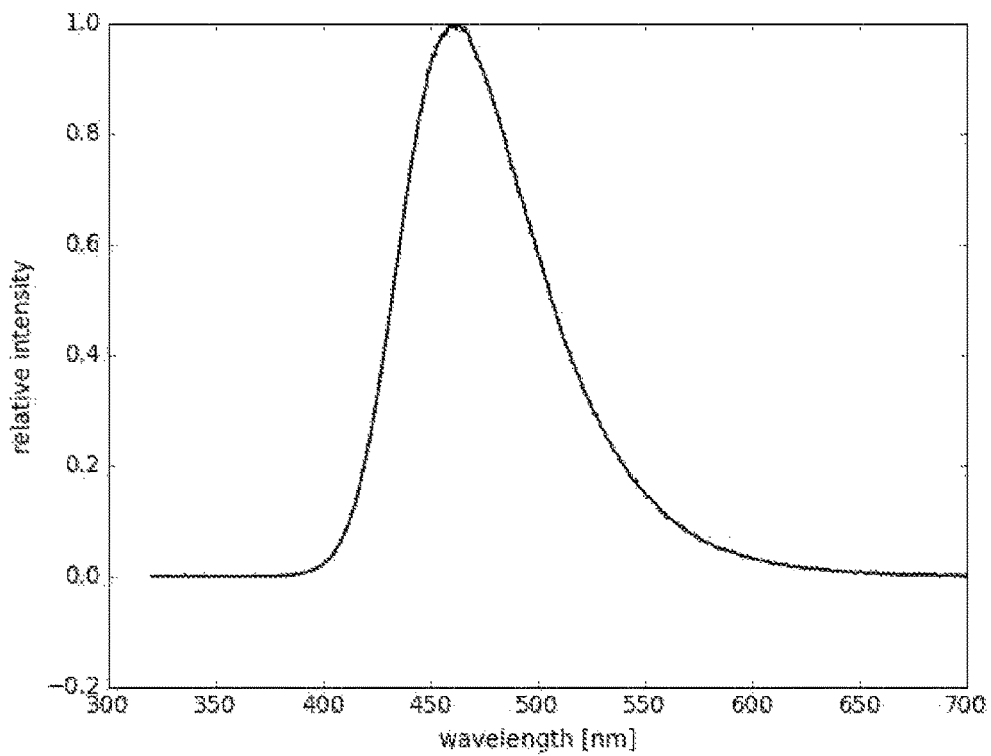

FIG. 15 Emission spectrum of example 15 (10% by weight) in PMMA.

Figure 16:
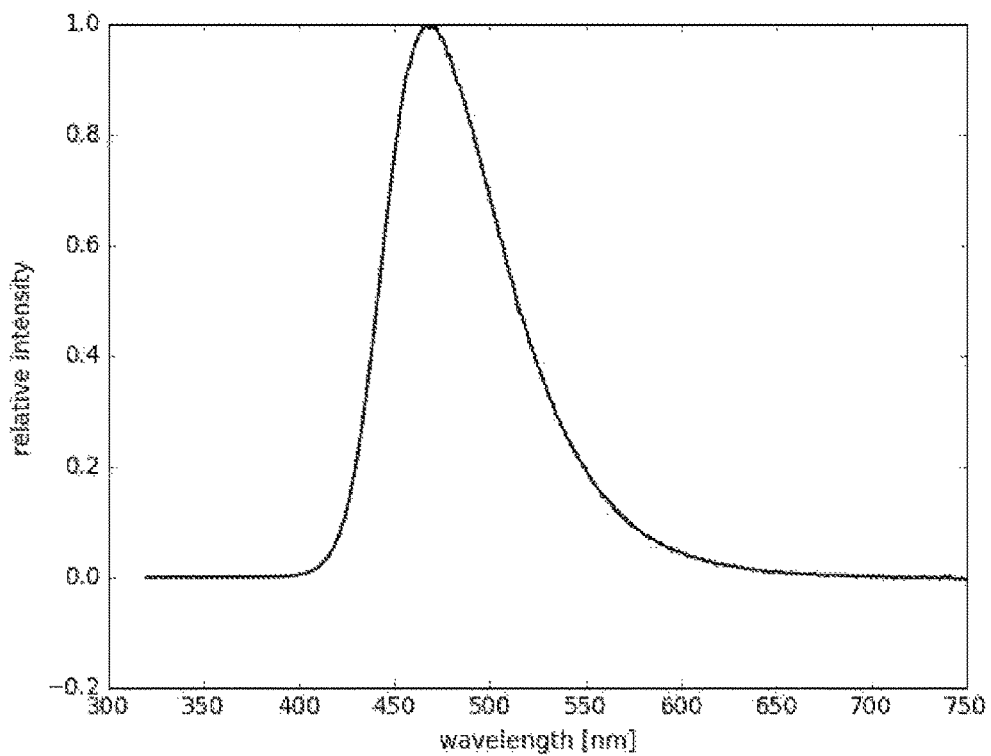

FIG. 16 Emission spectrum of example 16 (10% by weight) in PMMA.

Figure 17:
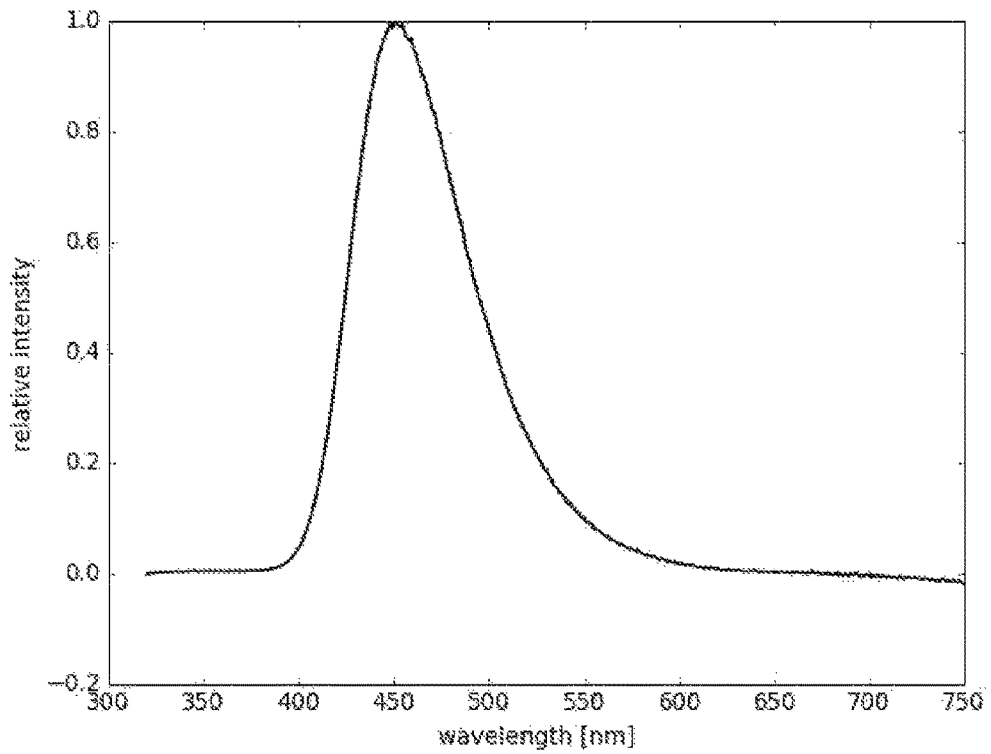

FIG. 17 Emission spectrum of example 17 (10% by weight) in PMMA.

Figure 18:
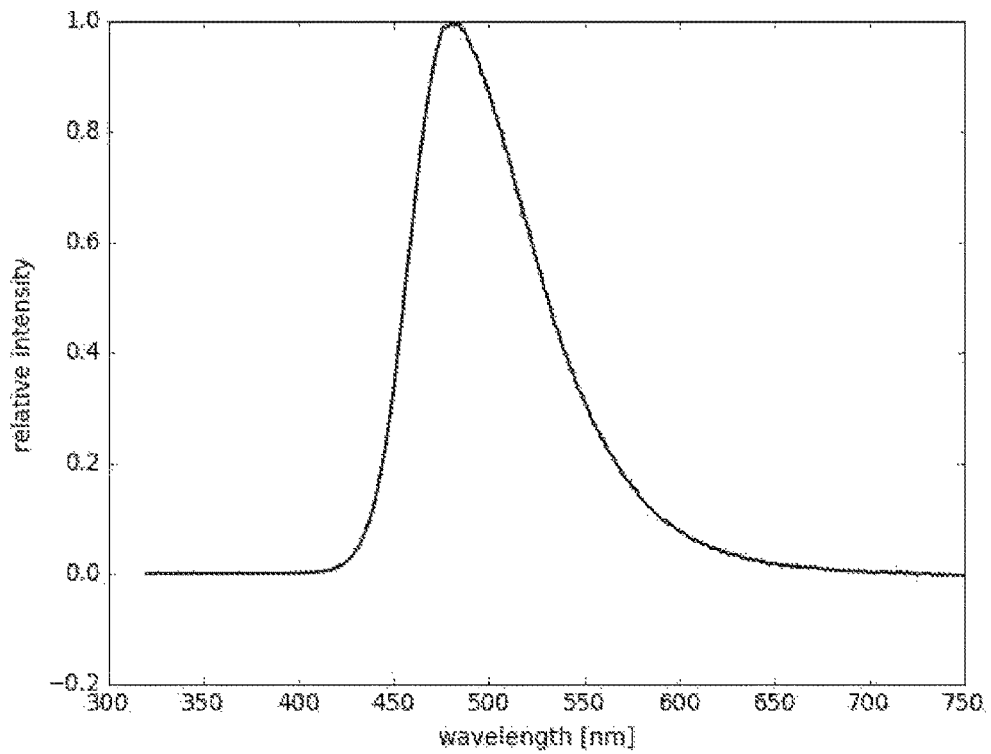

FIG. 18 Emission spectrum of example 18 (10% by weight) in PMMA.

Figure 19:
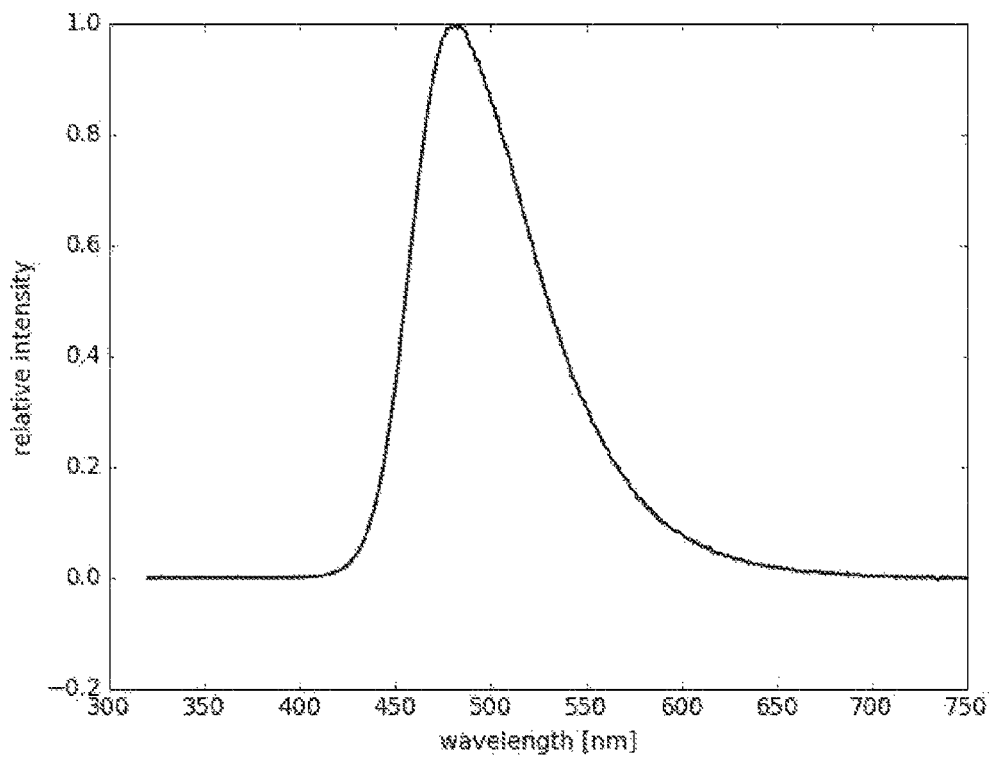

FIG. 19 Emission spectrum of example 19 (10% by weight) in PMMA.

Figure 20:
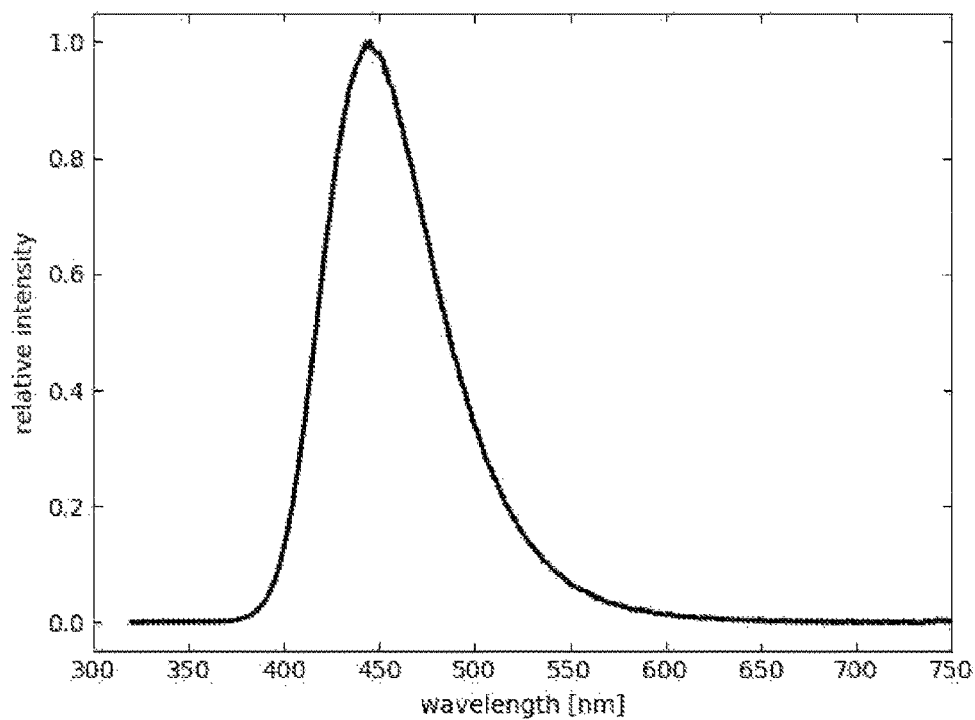

FIG. 20 Emission spectrum of example 20 (10% by weight) in PMMA.

Figure 21:
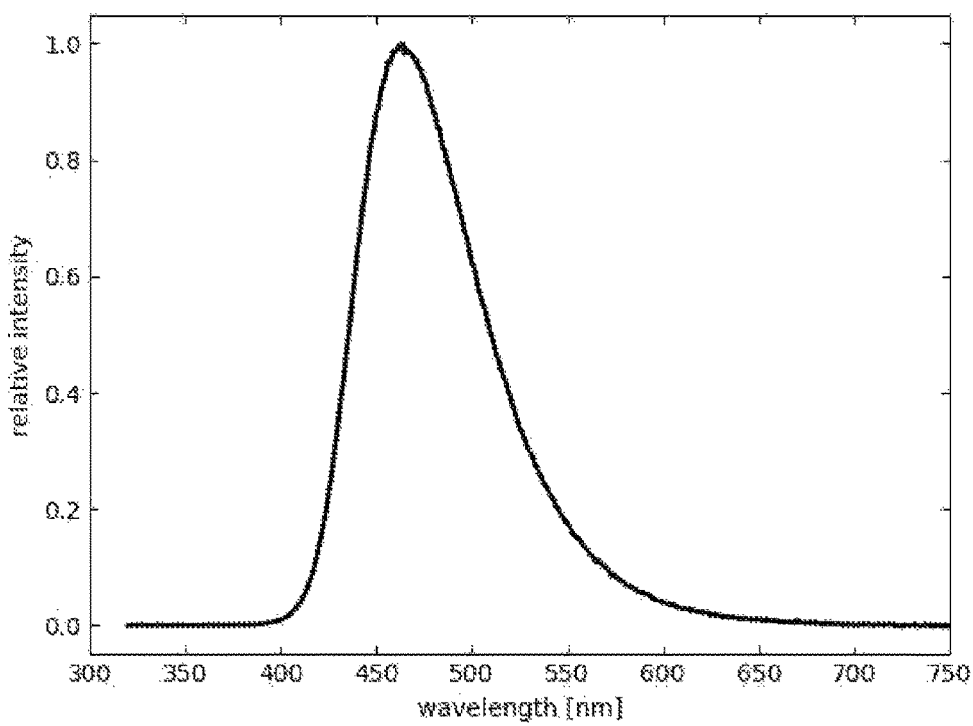

FIG. 21 Emission spectrum of example 21 (10% by weight) in PMMA.

Figure 22:
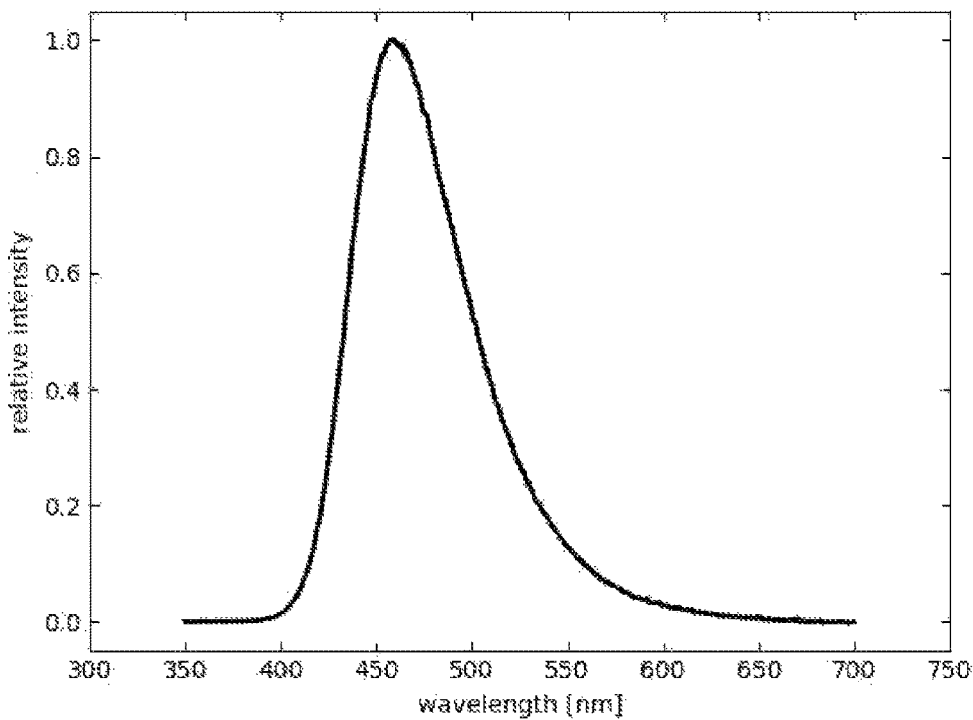

FIG. 22 Emission spectrum of example 22 (10% by weight) in PMMA.

Figure 23:
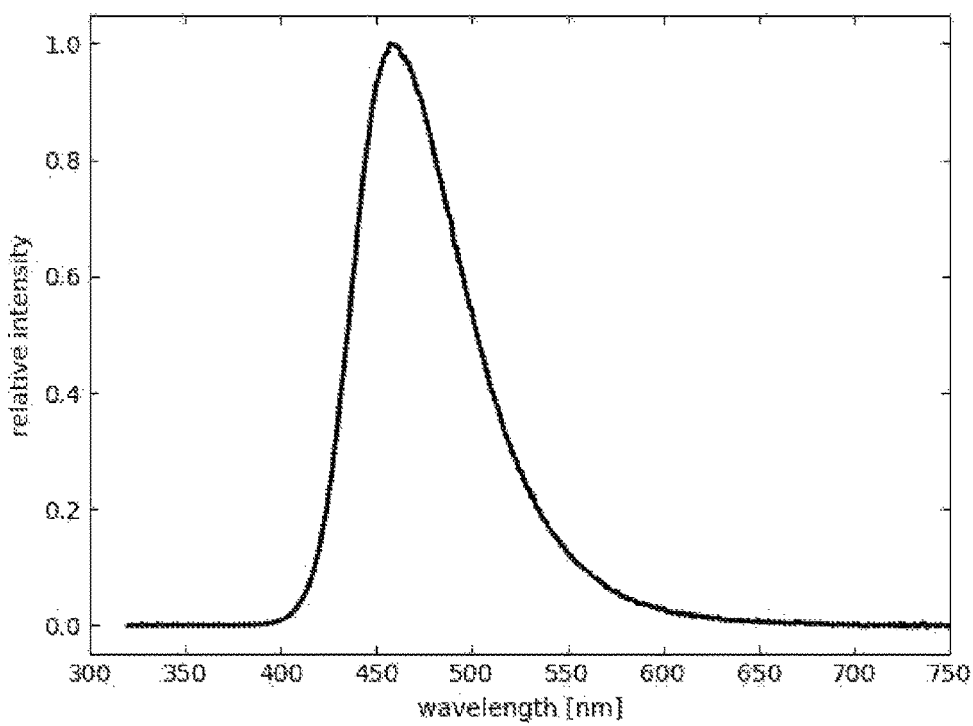

FIG. 23 Emission spectrum of example 23 (10% by weight) in PMMA.

Figure 24:
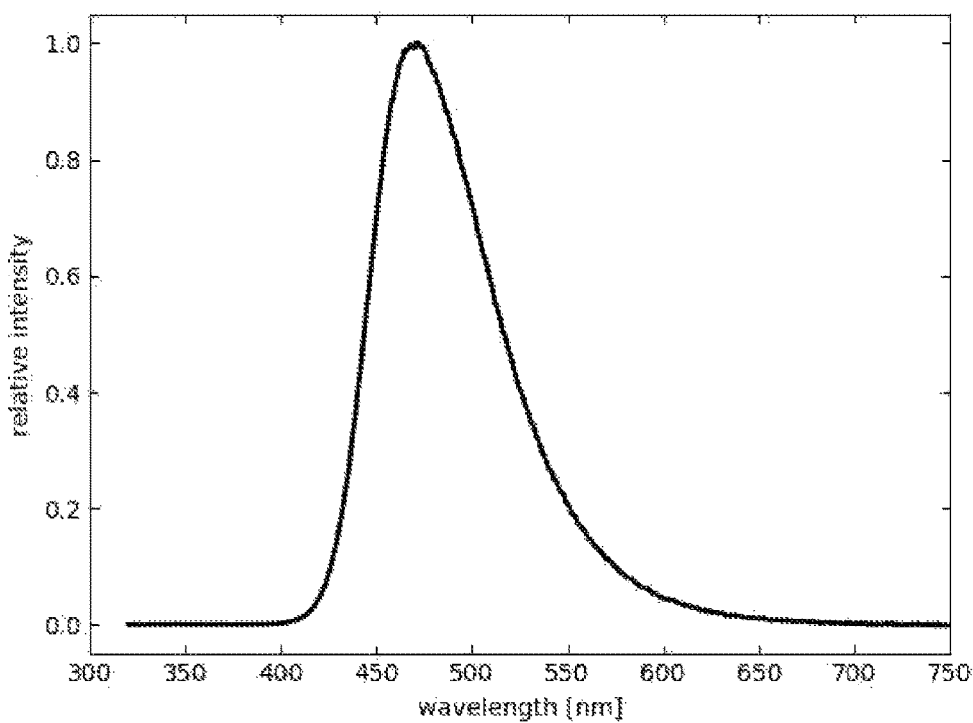

FIG. 24 Emission spectrum of example 24 (10% by weight) in PMMA.

Figure 25:
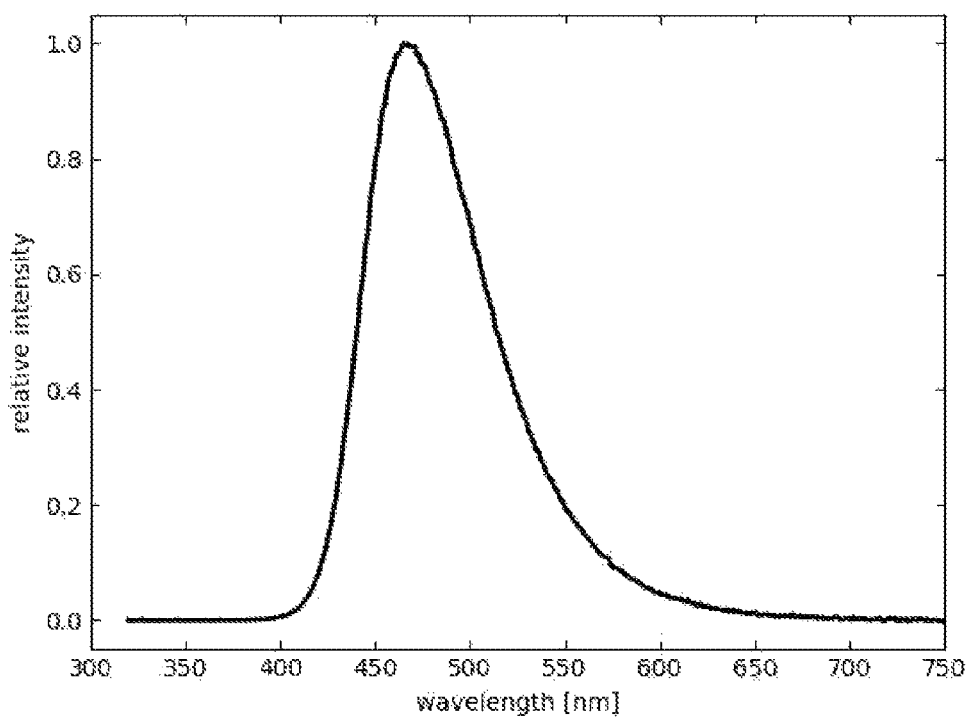

FIG. 25 Emission spectrum of example 25 (10% by weight) in PMMA.

Figure 26:
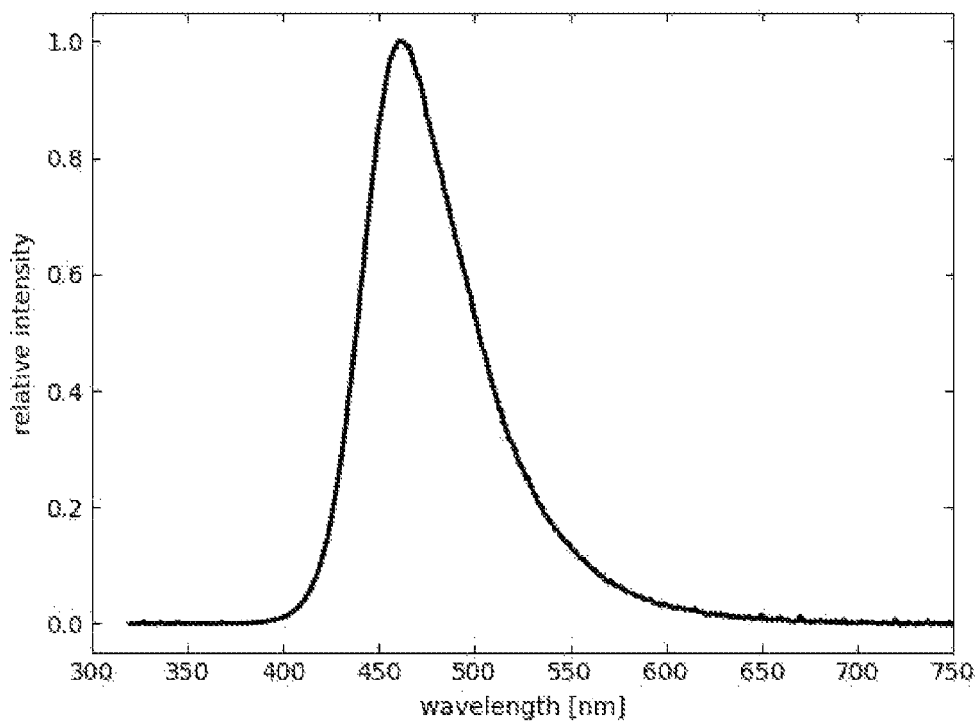

FIG. 26 Emission spectrum of example 26 (10% by weight) in PMMA.

Figure 27:
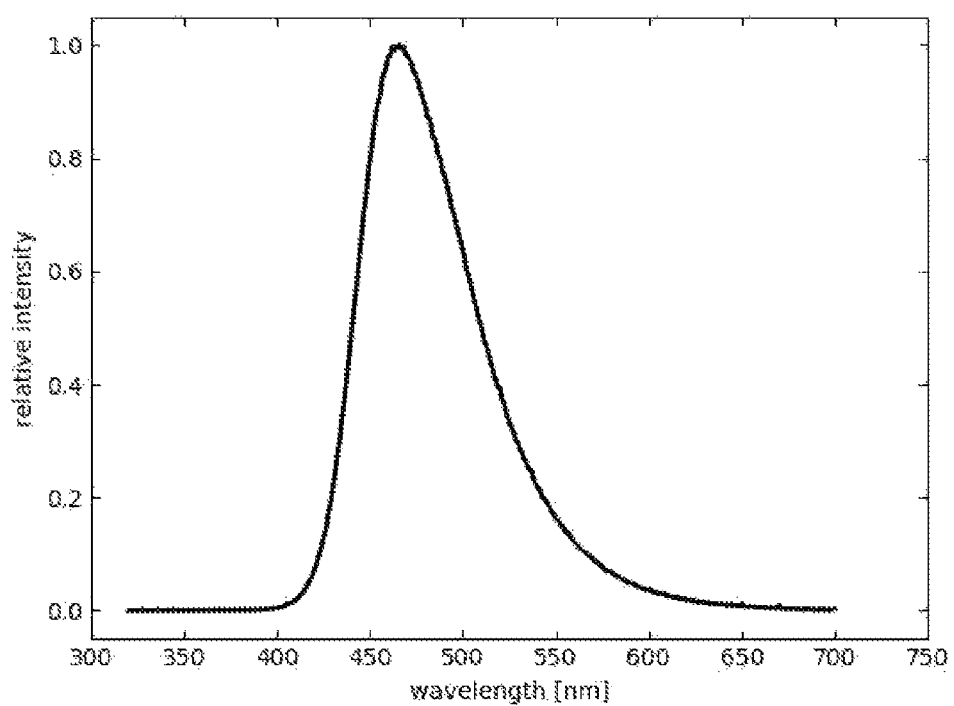

FIG. 27 Emission spectrum of example 27 (10% by weight) in PMMA.

Figure 28:
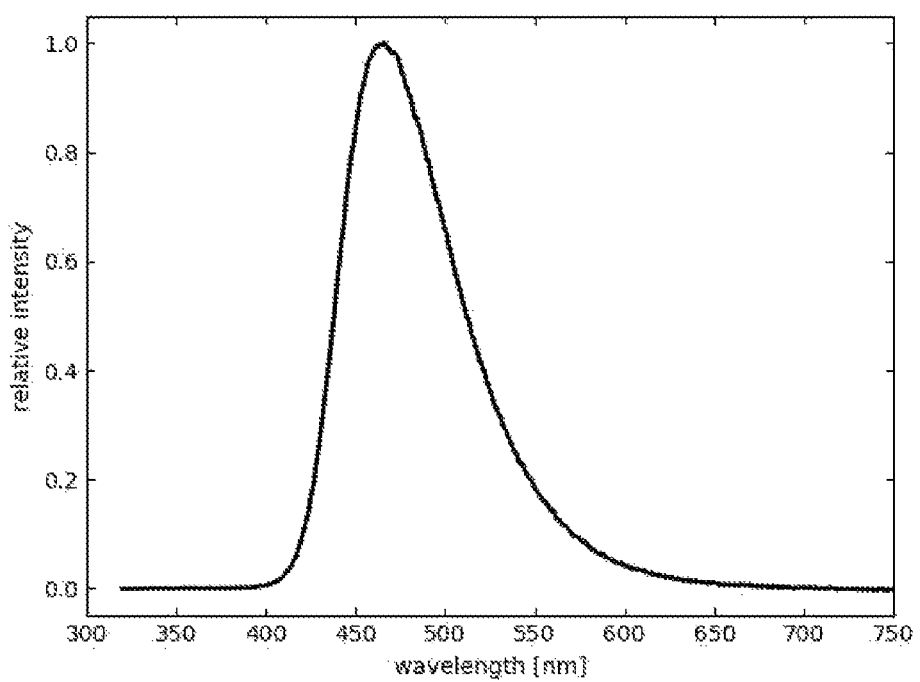

FIG. 28 Emission spectrum of example 28 (10% by weight) in PMMA.

Figure 29:
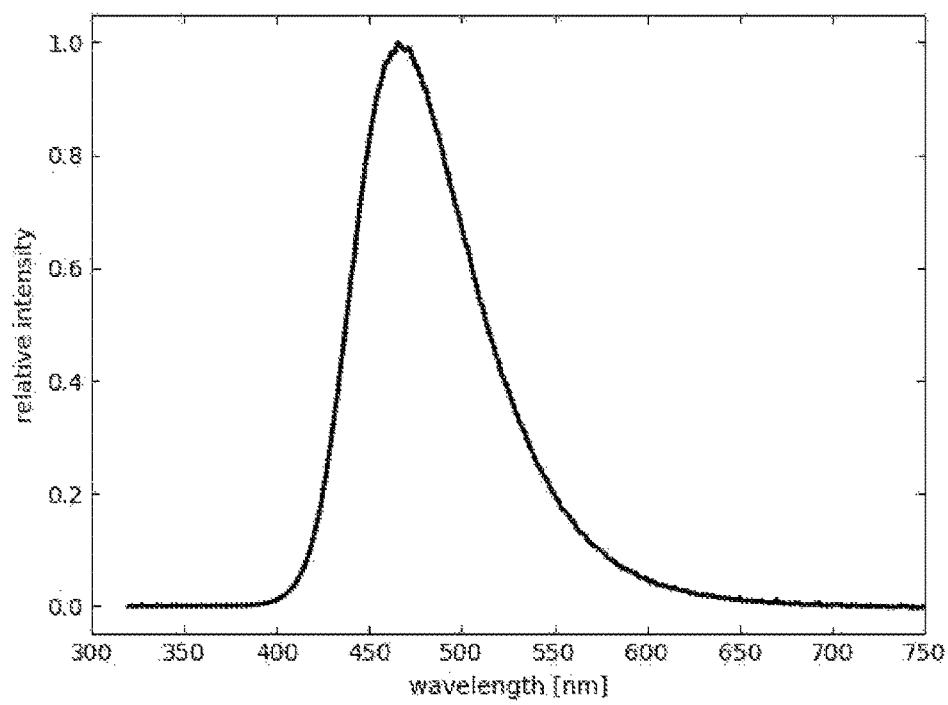

FIG. 29 Emission spectrum of example 29 (10% by weight) in PMMA.

Figure 30:
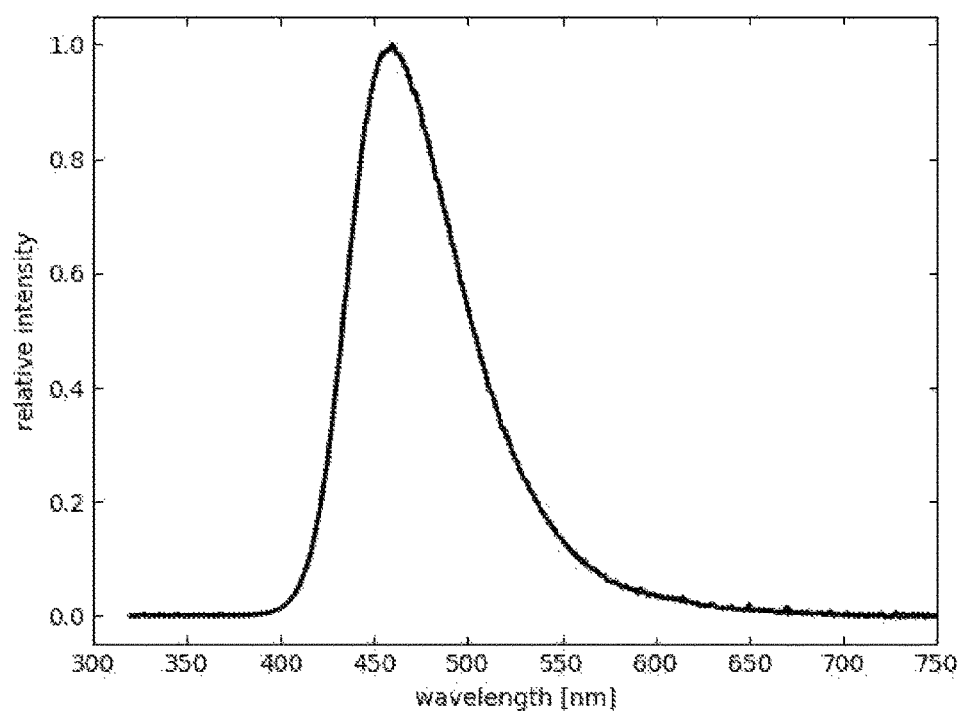

FIG. 30 Emission spectrum of example 30 (10% by weight) in PMMA.

DESCRIPTION

According to the invention, the organic molecules are purely organic molecules, i.e. they do not contain any metal ions in contrast to metal complexes known for use in optoelectronic devices.

According to the present invention, the organic molecules exhibit emission maxima in the blue, sky-blue or green spectral range. The organic molecules exhibit in particular emission maxima between 420 nm and 520 nm, in particular between 440 nm and 495 nm, preferably between 450 nm and 470 nm. The photoluminescence quantum yields of the organic molecules according to the invention are, in particular, 20% or more. The molecules according to the invention exhibit in particular thermally activated delayed fluorescence (TADF). The use of the molecules according to the invention in an optoelectronic device, for example an organic light-emitting diode (OLED), leads to higher efficiencies of the device. Corresponding OLEDs have a higher stability than OLEDs with known emitter materials and comparable color.

The organic light-emitting molecules according to the invention comprise or consist of a first chemical moiety comprising or consisting of a structure of formula I,

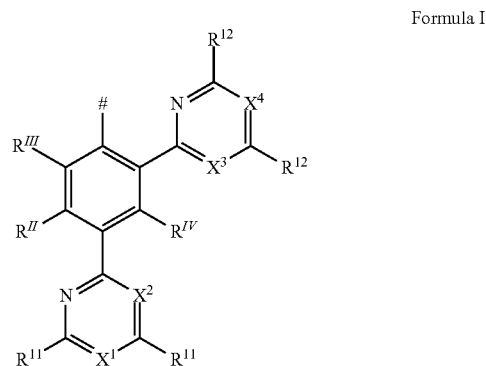

Formula I and
one second chemical moiety comprising or consisting of a structure of formula II,

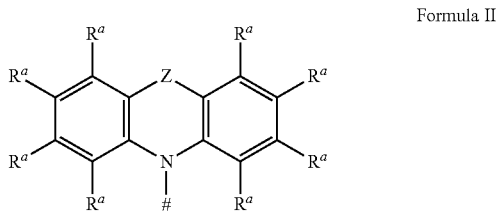

Formula II wherein the first chemical moiety is linked to the second chemical moiety via a single bond.

\# represents the binding site of a single bond linking the first chemical moiety to the second chemical moiety.

$X^1$ and $X^2$ is at each occurrence independently from another selected from the group consisting of $CR^{21}$ and N.

$X^3$ and $X^4$ is at each occurrence independently from another selected from the group consisting of $CR^{22}$ and N.

Z is at each occurrence independently from another selected from the group consisting of: a direct bond, $CR^3R^4$, $C=CR^3R^4$, $C=O$, $C=NR^3$, $NR^3$, O, $SiR^3R^4$, S, S(O) and $S(O)_2$.

$R^{11}$ is at each occurrence independently from another selected from the group consisting of:
hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$.

$R^{12}$ is at each occurrence independently from another selected from the group consisting of:
hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$.

$R^{21}$ is at each occurrence independently from another selected from the group consisting of:
hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$.

$R^{22}$ is at each occurrence independently from another selected from the group consisting of:
hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$.

$R^{II}$, $R^{III}$ and $R^{IV}$ is independently from another selected from the group consisting of:
hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.

$R^a$ is at each occurrence independently from another selected from the group consisting of:
hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkynyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_6$-$C_{60}$-aryl,
which is optionally substituted with one or more substituents $R^5$; and $C_3$-$C_{57}$-heteroaryl,
which is optionally substituted with one or more substituents $R^5$.

$R^5$ is at each occurrence independently from another selected from the group consisting of:
hydrogen, deuterium, $N(R^6)_2$, $OR^6$, $Si(R^6)_3$, $B(OR^6)_2$, $OSO_2R^6$, $CF_3$, $CN$, $F$, $Br$, $I$, $C_1$-$C_{40}$-alkyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_1$-$C_{40}$-alkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_1$-$C_{40}$-thioalkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_2$-$C_{40}$-alkenyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_2$-$C_{40}$-alkynyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_6$-$C_{60}$-aryl,
which is optionally substituted with one or more substituents $R^6$; and $C_3$-$C_{57}$-heteroaryl,
which is optionally substituted with one or more substituents $R^6$.

$R^6$ is at each occurrence independently from another selected from the group consisting of
hydrogen, deuterium, OPh, $CF_3$, $CN$, $F$, $C_1$-$C_5$-alkyl,
wherein optionally one or more hydrogen atoms are independently from each other substituted by deuterium, $CN$, $CF_3$, or $F$;

$C_1$-$C_5$-alkoxy,
wherein optionally one or more hydrogen atoms are independently from each other substituted by deuterium, $CN$, $CF_3$, or $F$;

$C_1$-$C_5$-thioalkoxy,
wherein optionally one or more hydrogen atoms are independently from each other substituted by deuterium, $CN$, $CF_3$, or $F$;

$C_2$-$C_5$-alkenyl,
wherein optionally one or more hydrogen atoms are independently from each other substituted by deuterium, $CN$, $CF_3$, or $F$;

$C_2$-$C_5$-alkynyl,
wherein optionally one or more hydrogen atoms are independently from each other substituted by deuterium, $CN$, $CF_3$, or $F$;

$C_6$-$C_{18}$-aryl,
which is optionally substituted with one or more $C_1$-$C_5$-alkyl substituents;

$C_3$-$C_{17}$-heteroaryl,
which is optionally substituted with one or more $C_1$-$C_5$-alkyl substituents;

$N(C_6$-$C_{18}$-aryl$)_2$;
$N(C_3$-$C_{17}$-heteroaryl$)_2$; and
$N(C_3$-$C_{17}$-heteroaryl)($C_6$-$C_{18}$-aryl).

The substituents $R^a$, $R^3$, $R^4$ or $R^5$, independently from each other, optionally form a mono- or polycyclic, aliphatic, aromatic and/or benzo-fused ring system with one or more substituents $R^a$, $R^3$, $R^4$ or $R^5$.

According to the invention, at least one variable selected from the group consisting of $X^1$, $X^2$ is N, and at least one variable selected from the group consisting of $X^3$, $X^4$ is N.

In one embodiment, $R^{11}$, $R^{12}$, $R^{21}$, $R^{22}$, $R^{II}$, $R^{III}$, and $R^{IV}$ is independently from each other at each occurrence selected from the group consisting of H, methyl and phenyl.

In one embodiment, $R^{11}$ and $R^{12}$ is Ph, which is optionally substituted with one or more substituents independently from each other selected from the group consisting of Me, $^i$Pr, $^t$Bu, CN, $CF_3$, and Ph.

In one embodiment of the organic molecule, $X^1$, $X^2$, $X^3$, and $X^4$ is N.

In one embodiment, $X^1$, $X^2$, and $X^3$ is N and $X^4$ is $CR^{22}$.
In one embodiment, $X^1$, $X^2$, and $X^4$ is N and $X^3$ is $CR^{22}$.
In one embodiment, $X^2$, $X^3$, and $X^4$ is N and $X^1$ is $CR^{21}$.
In one embodiment, $X^1$, $X^3$, and $X^4$ is N and $X^2$ is $CR^{21}$.
In one embodiment, $X^1$ and $X^3$ is N, $X^2$ is $CR^{21}$, and $X^4$ is $CR^{22}$.
In one embodiment, $X^1$ and $X^4$ is N, $X^2$ is $CR^{21}$, and $X^3$ is $CR^{22}$.
In one embodiment, $X^2$ and $X^3$ is N, $X^1$ is $CR^{21}$, and $X^4$ is $CR^{22}$.
In one embodiment, $X^2$ and $X^4$ is N, $X^1$ is $CR^{21}$, and $X^3$ is $CR^{22}$.

In one embodiment, $R^{II}$ is hydrogen.
In one embodiment, $R^{III}$ is hydrogen.
In one embodiment, $R^{IV}$ is hydrogen.

In a further embodiment of the invention, the second chemical moiety comprises or consists of a structure of formula IIa:

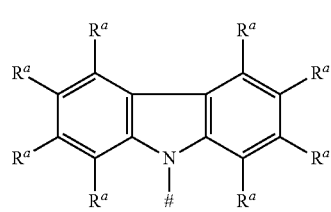

Formula IIa wherein # and $R^a$ are defined as above.

In a further embodiment of the invention, $R^a$ is at each occurrence independently from another selected from the group consisting of:
hydrogen,
Me,
$^i$Pr,
$^t$Bu,
CN,
$CF_3$,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, $^i$Pr, $^t$Bu, CN, $CF_3$, and Ph,
pyrimidinyl, which is optionally substituted with one or more substituents independently from each other selected from the group consisting of Me, $^i$Pr, $^t$Bu, CN, $CF_3$, and Ph,
carbazolyl, which is optionally substituted with one or more substituents independently from each other selected from the group consisting of Me, $^i$Pr, $^t$Bu, CN, $CF_3$, and Ph,
triazinyl, which is optionally substituted with one or more substituents independently from each other selected from the group consisting of Me, $^i$Pr, $^t$Bu, CN, $CF_3$, and Ph, and $N(Ph)_2$.

In a further embodiment of the invention, $R^a$ is at each occurrence independently from another selected from the group consisting of:
hydrogen,
Me,
$^i$Pr,
$^t$Bu,
CN,
$CF_3$,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, $^i$Pr, $^t$Bu, CN, $CF_3$, and Ph,
pyrimidinyl, which is optionally substituted with one or more substituents independently from each other selected from the group consisting of Me, $^i$Pr, $^t$Bu, CN, $CF_3$, and Ph, and
triazinyl, which is optionally substituted with one or more substituents independently from each other selected from the group consisting of Me, $^i$Pr, $^t$Bu, CN, $CF_3$, and Ph.

In a further embodiment of the invention, the second chemical moiety comprises or consists of a structure of formula IIb, a structure of formula IIb-2, a structure of formula IIb-3 or a structure of formula IIb-4:

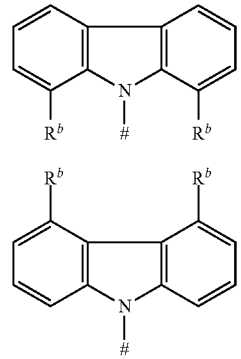

Formula IIb

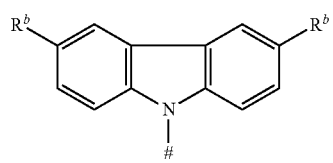

Formula IIb-2

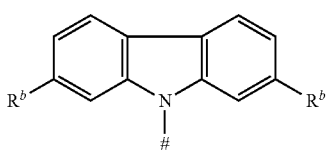

Formula IIb-3

Formula IIb-4 wherein
$R^b$ is at each occurrence independently from another selected from the group consisting of deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_6$-$C_{60}$-aryl,
which is optionally substituted with one or more substituents $R^5$; and
$C_3$-$C_{57}$-heteroaryl,
which is optionally substituted with one or more substituents $R^5$.

Apart from that, the aforementioned definitions apply.

In an additional embodiment of the invention, the second chemical moiety comprises or consists of a structure of Formula IIc, a structure of Formula IIc-2, a structure of Formula IIc-3 or a structure of Formula IIc-4:

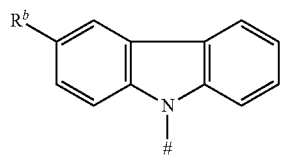

Formula IIc

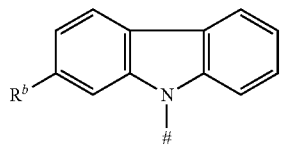

Formula IIc-2

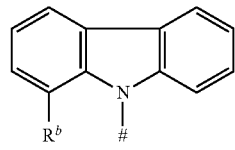

Formula IIc-3

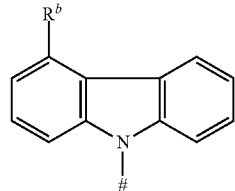

Formula IIc-4 wherein the aforementioned definitions apply.

In a further embodiment of the invention, $R^b$ is at each occurrence independently from another selected from the group consisting of:

Me, $^i$Pr, $^t$Bu, CN, CF$_3$,

Ph, which is optionally substituted with one or more substituents independently from each other selected from the group consisting of Me, $^i$Pr, $^t$Bu, CN, CF$_3$, and Ph, pyridinyl, which is optionally substituted with one or more substituents independently from each other selected from the group consisting of Me, $^i$Pr, $^t$Bu, CN, CF$_3$, and Ph, carbazolyl, which is optionally substituted with one or more substituents independently from each other selected from the group consisting of Me, $^i$Pr, $^t$Bu, CN, CF$_3$, and Ph, triazinyl, which is optionally substituted with one or more substituents independently from each other selected from the group consisting of Me, $^i$Pr, $^t$Bu, CN, CF$_3$, and Ph, and N(Ph)$_2$.

In a further embodiment of the invention, $R^b$ is at each occurrence independently from another selected from the group consisting of:

Me,
$^i$Pr,
$^t$Bu,
CN,
CF$_3$,
Ph, which is optionally substituted with one or more substituents independently from each other selected from the group consisting of Me, $^i$Pr, $^t$Bu, CN, CF$_3$, and Ph, pyridinyl, which is optionally substituted with one or more substituents independently from each other selected from the group consisting of Me, $^i$Pr, $^t$Bu, CN, CF$_3$, and Ph, pyrimidinyl, which is optionally substituted with one or more substituents independently from each other selected from the group consisting of Me, $^i$Pr, $^t$Bu, CN, CF$_3$, and Ph, and triazinyl, which is optionally substituted with one or more substituents independently from each other selected from the group consisting of Me, $^i$Pr, $^t$Bu, CN, CF$_3$, and Ph.

Below, examples for a second chemical moiety are shown:

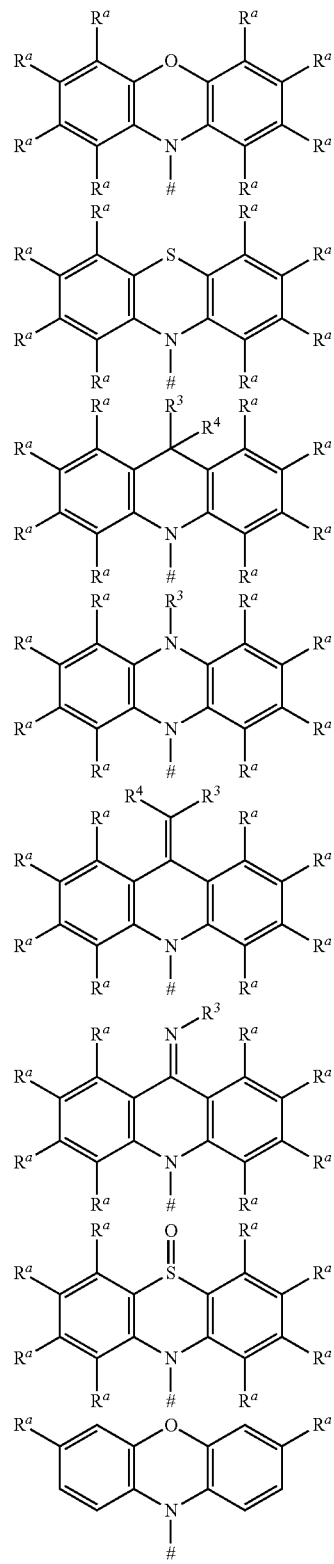

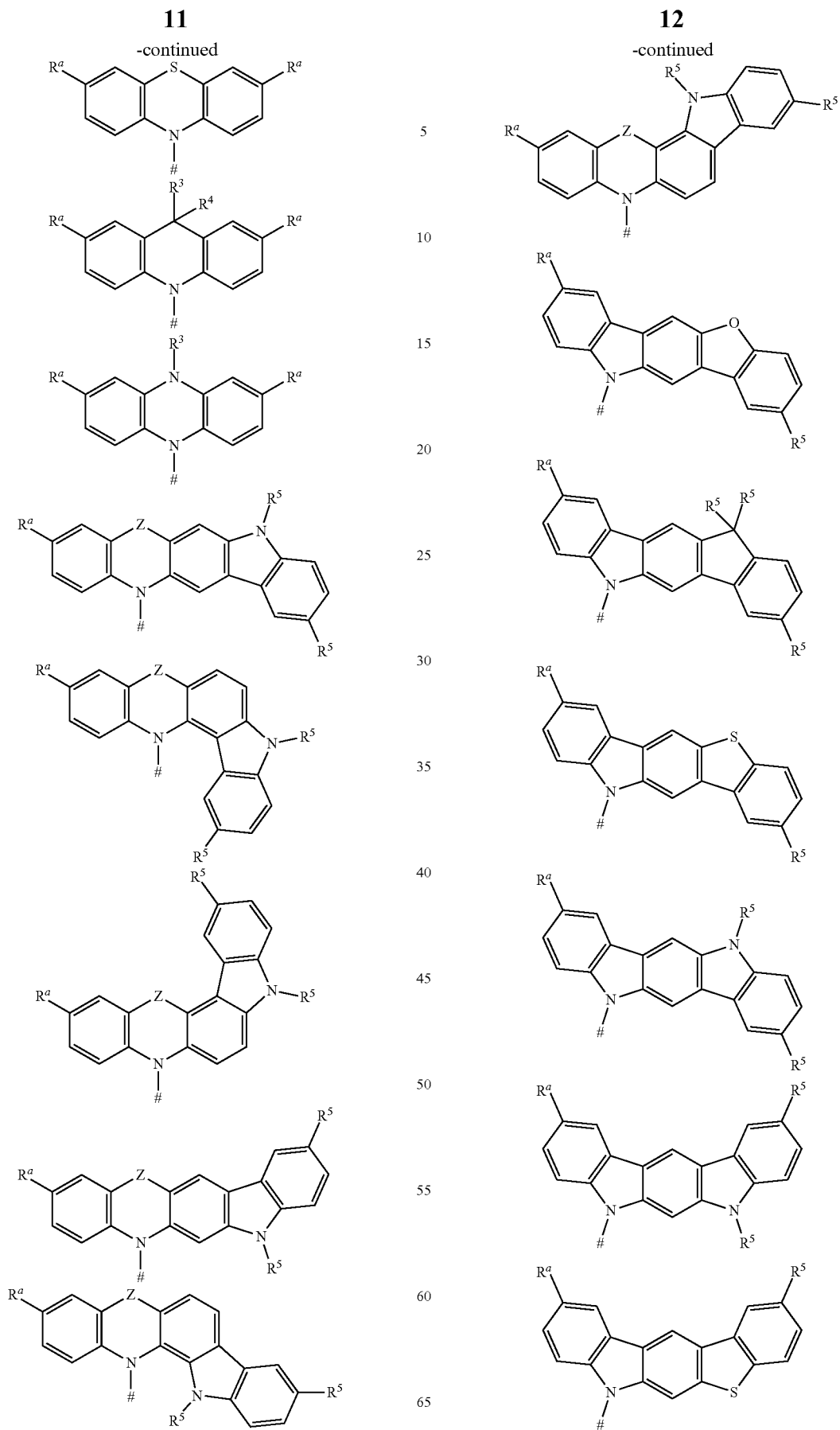

-continued
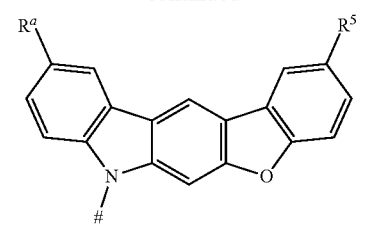
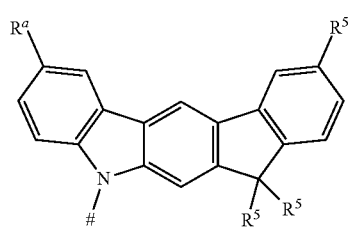
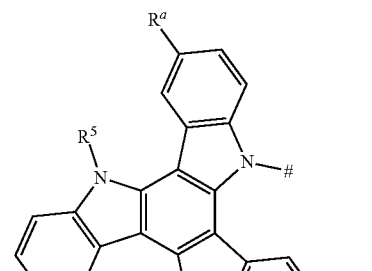
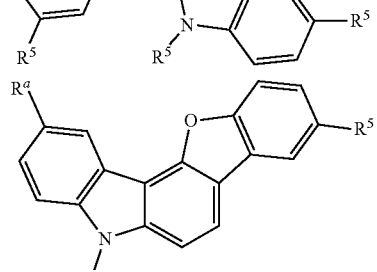
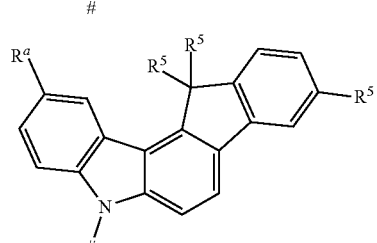
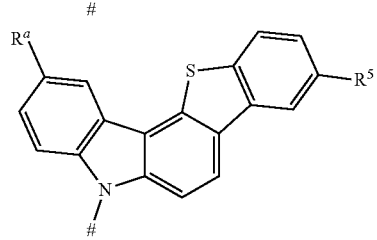
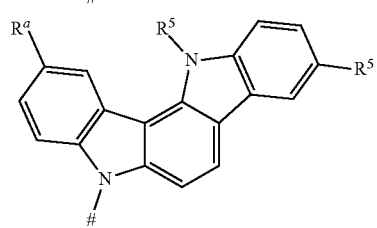
-continued
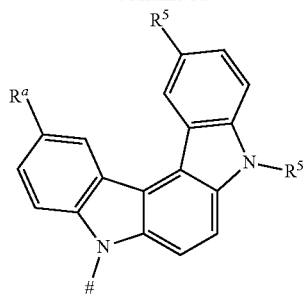
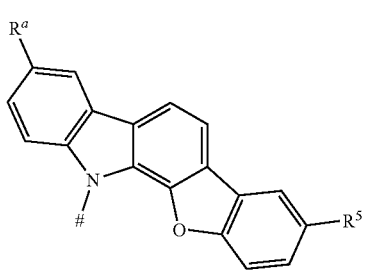
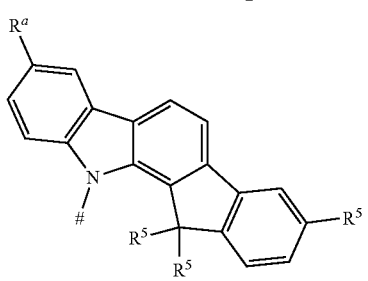
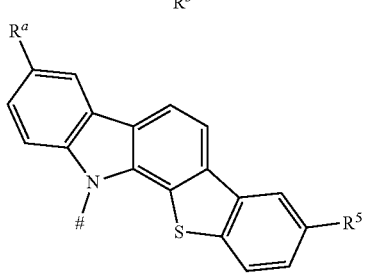
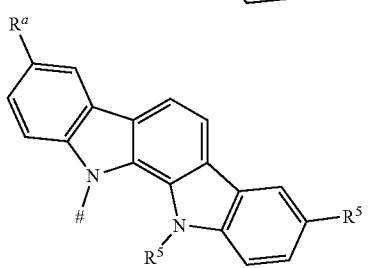
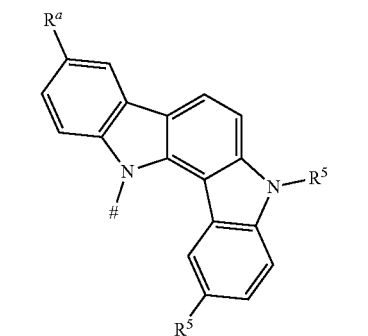

-continued

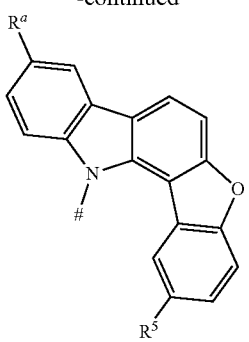

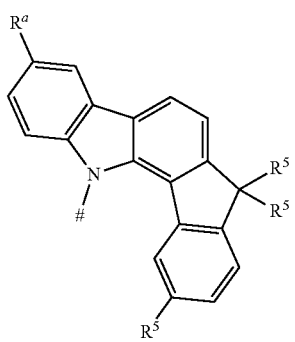

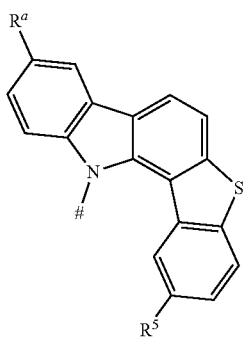

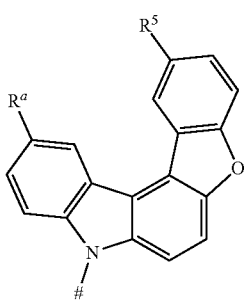

-continued

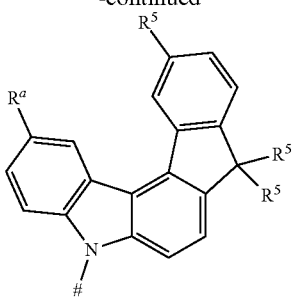

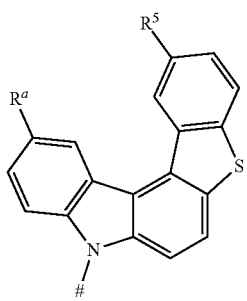

wherein for #, Z, $R^a$, $R^3$, $R^4$ and $R^5$ the aforementioned definitions apply.

In one embodiment, $R^a$ and $R^5$ is at each occurrence independently from another selected from the group consisting of hydrogen (H), methyl (Me), i-propyl (CH(CH$_3$)$_2$) ($^i$Pr), t-butyl ($^t$Bu), phenyl (Ph), CN, CF$_3$, and diphenylamine (NPh$_2$).

In one embodiment of the invention, the organic molecules comprise or consist of formula III:

Formula III

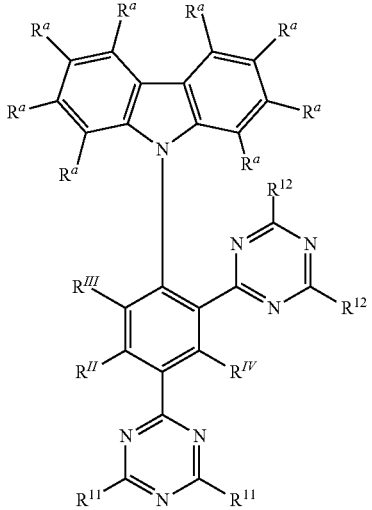

wherein the aforementioned definitions apply.

In a further embodiment of the invention, the organic molecules comprise or consist of a structure of Formula IIIa:

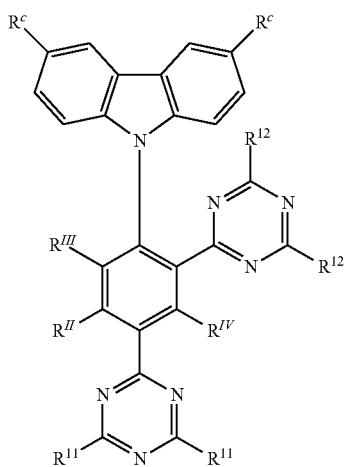

Formula IIIa wherein
$R^c$ is at each occurrence independently from another selected from the group consisting of:
Me,
$^i$Pr,
$^t$Bu,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, $^i$Pr, $^t$Bu, CN, $CF_3$, and Ph,
pyrimidinyl, which is optionally substituted with one or more substituents independently from each other selected from the group consisting of Me, $^i$Pr, $^t$Bu, CN, $CF_3$, and Ph,
carbazolyl, which is optionally substituted with one or more substituents independently from each other selected from the group consisting of Me, $^i$Pr, $^t$Bu, CN, $CF_3$, and Ph,
triazinyl, which is optionally substituted with one or more substituents independently from each other selected from the group consisting of Me, $^i$Pr, $^t$Bu, CN, $CF_3$, and Ph,
and
$N(Ph)_2$,
and wherein $R^{11}$, $R^{12}$, $R^{II}$, $R^{III}$ and $R^{IV}$ are defined as above.

In a further embodiment of the invention, the organic molecule comprise or consist of a structure of Formula IIIb:

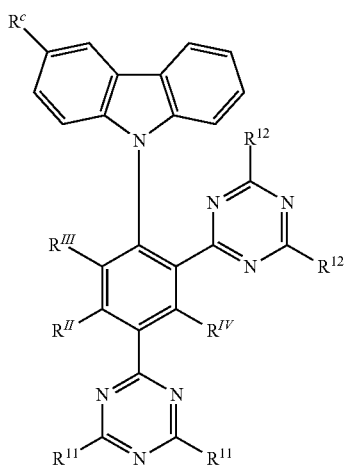

Formula IIIb wherein the aforementioned definitions apply.

In a further embodiment of the invention, the organic molecules comprise or consist of a structure of Formula IIIc:

Formula IIIc wherein the aforementioned definitions apply.

In a further embodiment of the invention, the organic molecules comprise or consist of a structure of Formula IIId:

Formula IIId wherein the aforementioned definitions apply.

In one embodiment of the invention, the organic molecules comprise or consist of Formula IV:

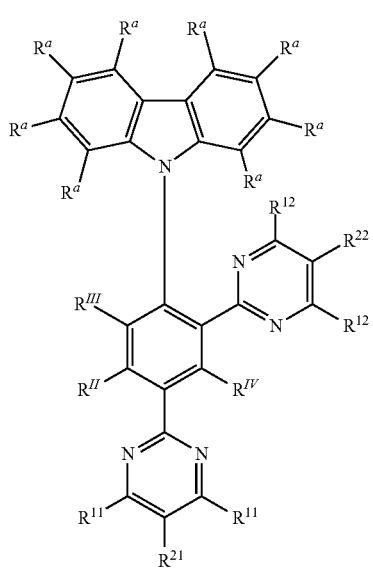

Formula IV wherein $R^{21}$ and $R^{22}$ are defined as described above and the aforementioned definitions apply.

In a further embodiment of the invention, the organic molecules comprise or consist of a structure of Formula IVa:

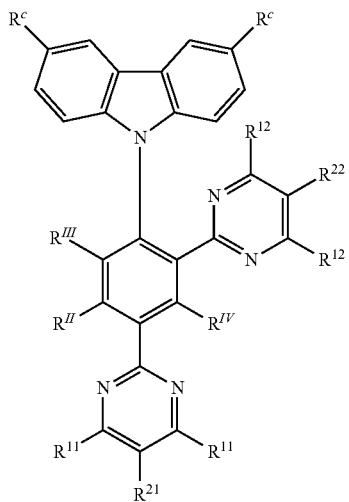

Formula IVa wherein the aforementioned definitions apply.

In a further embodiment of the invention, the organic molecules comprise or consist of a structure of Formula IVb:

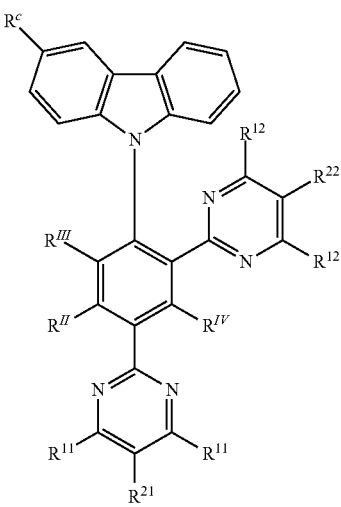

Formula IVb wherein the aforementioned definitions apply.

In a further embodiment of the invention, the organic molecules comprise or consist of a structure of Formula IVc:

Formula IVc wherein the aforementioned definitions apply.

In a further embodiment of the invention, the organic molecules comprise or consist of a structure of Formula IVd:

Formula IVd

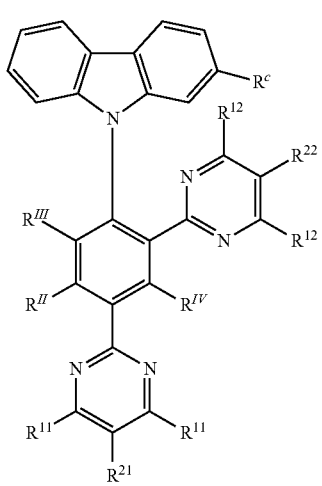

wherein the aforementioned definitions apply.

In one embodiment of the invention, the organic molecules comprise or consist of Formula V:

Formula V

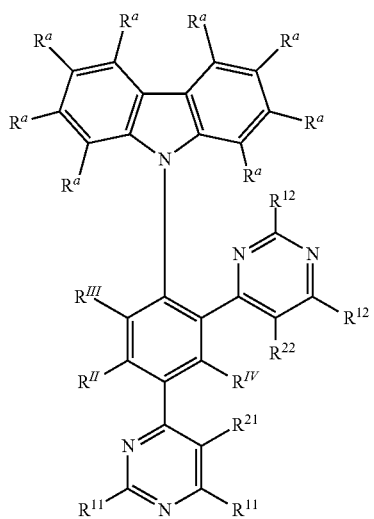

wherein the aforementioned definitions apply.

In a further embodiment of the invention, the organic molecule comprises or consists of a structure of Formula Va:

Formula Va

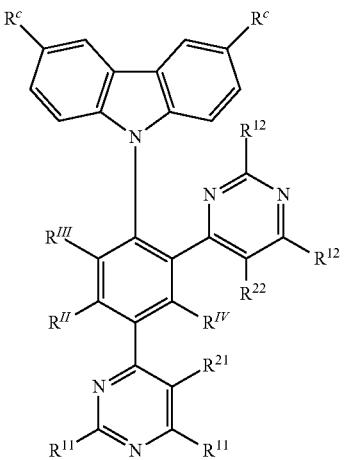

wherein the aforementioned definitions apply.

In a further embodiment of the invention, the organic molecule comprises or consists of a structure of Formula Vb:

Formula Vb

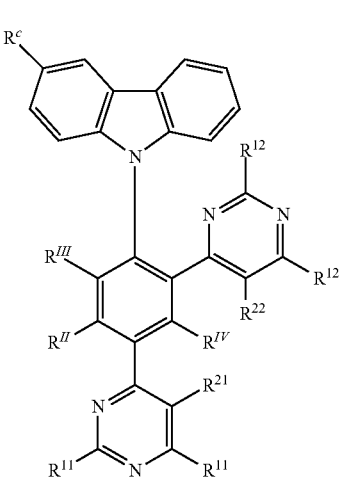

wherein the aforementioned definitions apply.

In a further embodiment of the invention, the organic molecules comprise or consist of a structure of Formula Vc:

Formula Vc

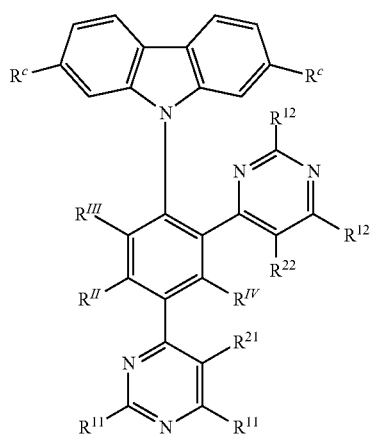

wherein the aforementioned definitions apply.

In a further embodiment of the invention, the organic molecules comprise or consist of a structure of Formula Vd:

Formula Vd

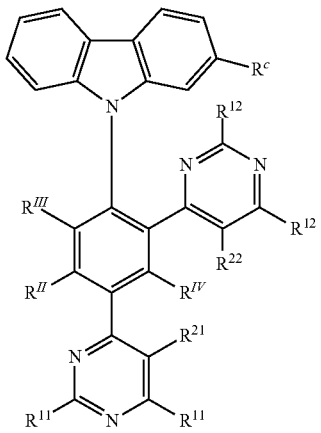

wherein the aforementioned definitions apply.

In one embodiment of the invention, the organic molecules comprise or consist of Formula VI:

Formula VI wherein the aforementioned definitions apply.

In a further embodiment of the invention, the organic molecules comprise or consist of a structure of Formula VIa:

Formula VIa wherein the aforementioned definitions apply.

In a further embodiment of the invention, the organic molecules comprise or consist of a structure of Formula VIb:

Formula VIb

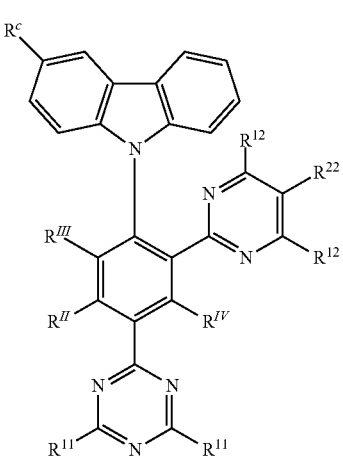

wherein the aforementioned definitions apply.

In a further embodiment of the invention, the organic molecules comprise or consist of a structure of Formula VIc:

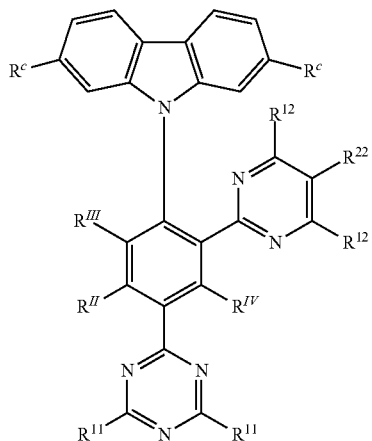

Formula VIc wherein the aforementioned definitions apply.

In a further embodiment of the invention, the organic molecules comprise or consist of a structure of Formula VId:

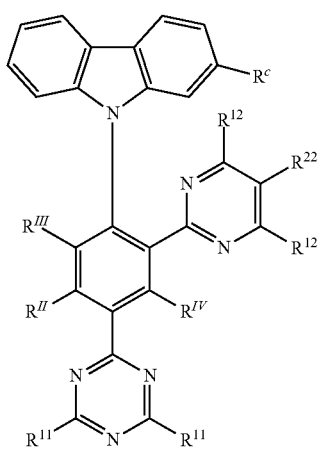

Formula VId wherein the aforementioned definitions apply.

In another embodiment of the invention, the organic molecules comprise or consist of Formula VII:

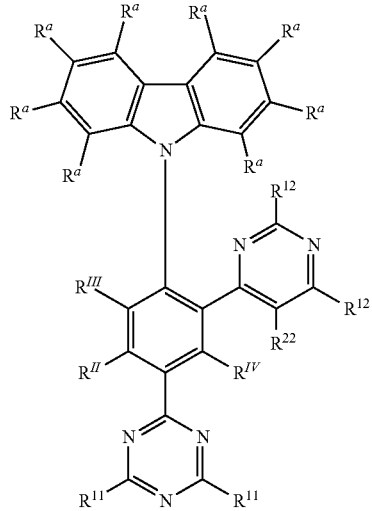

Formula VII wherein the aforementioned definitions apply.

In a further embodiment of the invention, the organic molecules comprise or consist of a structure of Formula VIIa:

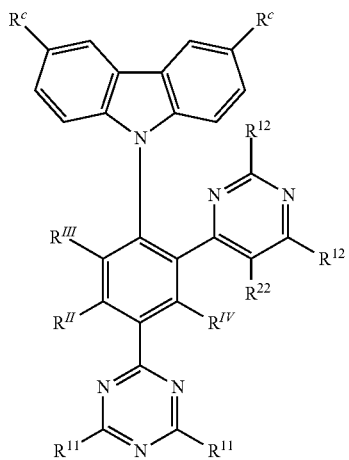

Formula VIIa wherein the aforementioned definitions apply.

In a further embodiment of the invention, the organic molecules comprise or consist of a structure of Formula VIIb:

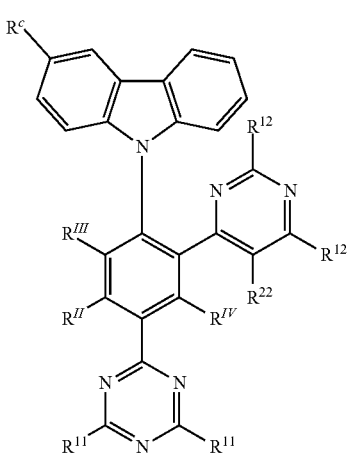

Formula VIIb wherein the aforementioned definitions apply.

In a further embodiment of the invention, the organic molecules comprise or consist of a structure of Formula VIIc:

Formula VIIc

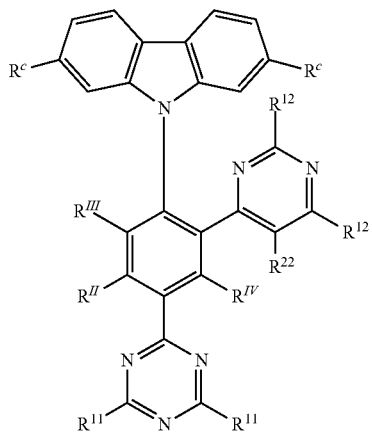

wherein the aforementioned definitions apply.

In a further embodiment of the invention, the organic molecules comprise or consist of a structure of Formula VIId:

Formula VIId wherein the aforementioned definitions apply.

In one embodiment of the invention, the organic molecules comprise or consist of Formula VIII:

Formula VIII wherein the aforementioned definitions apply.

In a further embodiment of the invention, the organic molecules comprise or consist of a structure of Formula VIIIa:

Formula VIIIa wherein the aforementioned definitions apply.

In a further embodiment of the invention, the organic molecules comprise or consist of a structure of Formula VIIIb:

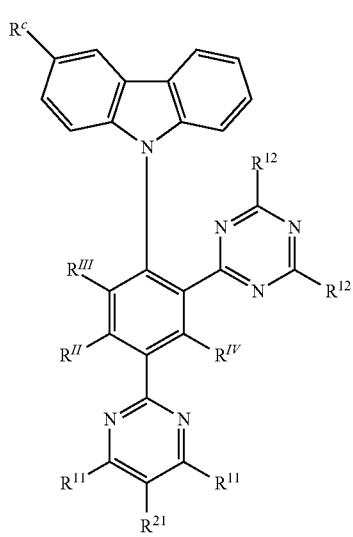

Formula VIIIb wherein the aforementioned definitions apply.

In a further embodiment of the invention, the organic molecules comprise or consist of a structure of Formula VIIIc:

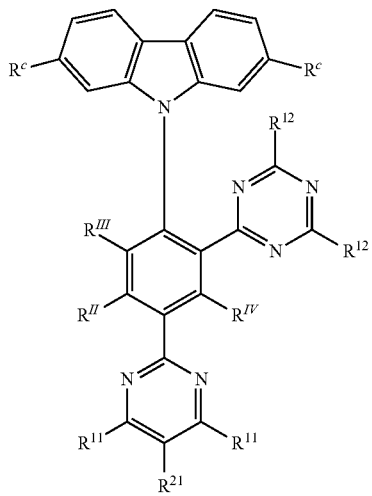

Formula VIIIc wherein the aforementioned definitions apply.

In a further embodiment of the invention, the organic molecules comprise or consist of a structure of Formula VIIId:

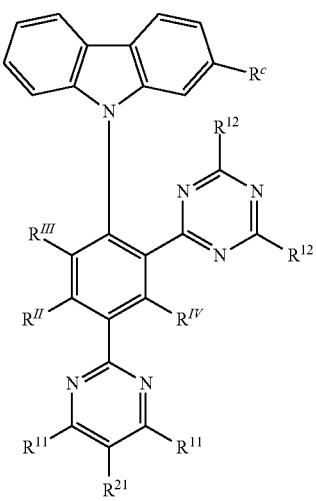

Formula VIIId wherein the aforementioned definitions apply.

In one embodiment of the invention, the organic molecules comprise or consist of Formula IX:

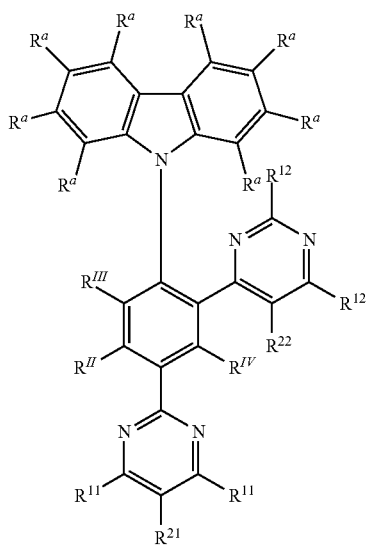

Formula IX wherein the aforementioned definitions apply.

In a further embodiment of the invention, the organic molecules comprise or consist of a structure of Formula IXa:

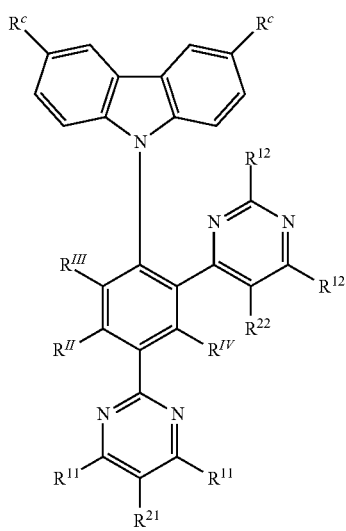

Formula IXa wherein the aforementioned definitions apply.

In a further embodiment of the invention, the organic molecules comprise or consist of a structure of Formula IXb:

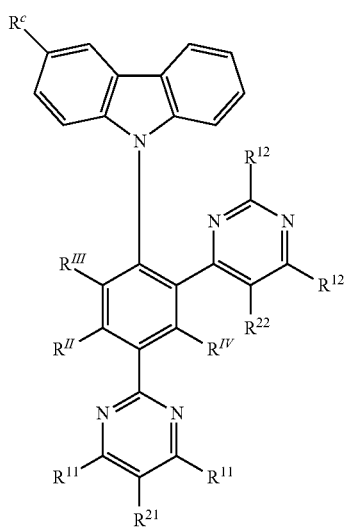

Formula IXb wherein the aforementioned definitions apply.

In a further embodiment of the invention, the organic molecules comprise or consist of a structure of Formula IXc:

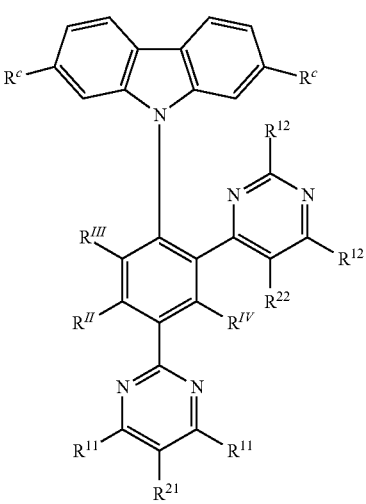

Formula IXc wherein the aforementioned definitions apply.

In a further embodiment of the invention, the organic molecules comprise or consist of a structure of Formula IXd:

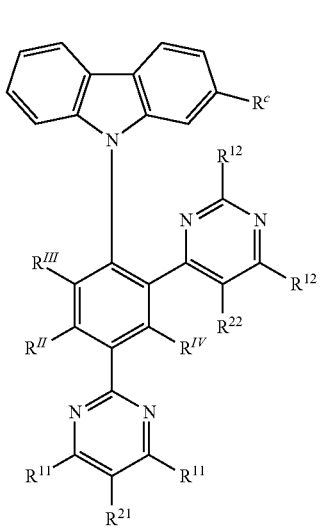

Formula IXd wherein the aforementioned definitions apply.

In one embodiment of the invention, the organic molecules comprise or consist of Formula X:

Formula X

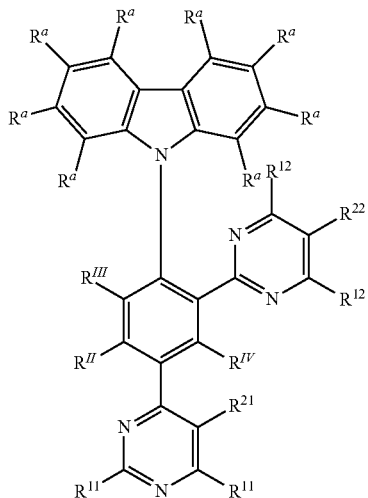

wherein the aforementioned definitions apply.

In a further embodiment of the invention, the organic molecules comprise or consist of a structure of Formula Xa:

Formula Xa

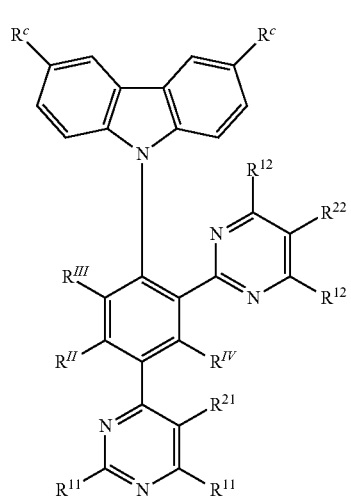

wherein the aforementioned definitions apply.

In a further embodiment of the invention, the organic molecules comprise or consist of a structure of Formula Xb:

Formula Xb

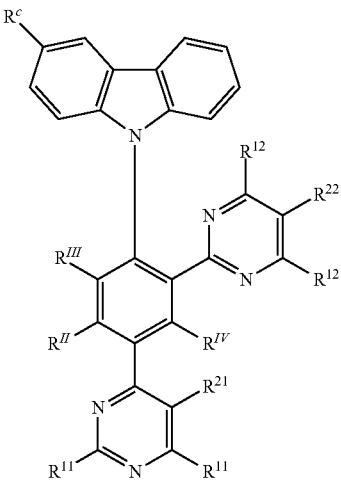

wherein the aforementioned definitions apply.

In a further embodiment of the invention, the organic molecules comprise or consist of a structure of Formula Xc:

Formula Xc

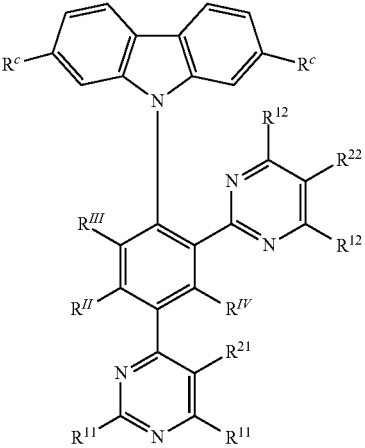

wherein the aforementioned definitions apply.

In a further embodiment of the invention, the organic molecules comprise or consist of a structure of Formula Xd:

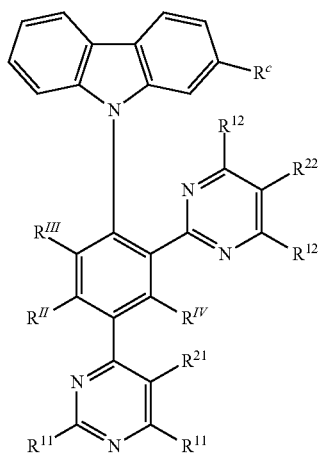

Formula Xd wherein the aforementioned definitions apply.

In one embodiment of the invention, the organic molecules comprise or consist of Formula XI:

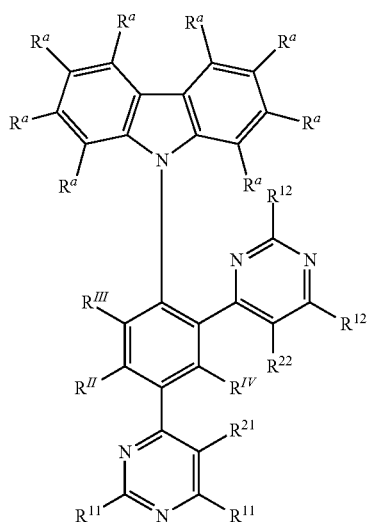

Formula XI wherein the aforementioned definitions apply.

In a further embodiment of the invention, the organic molecules comprise or consist of a structure of Formula XIa:

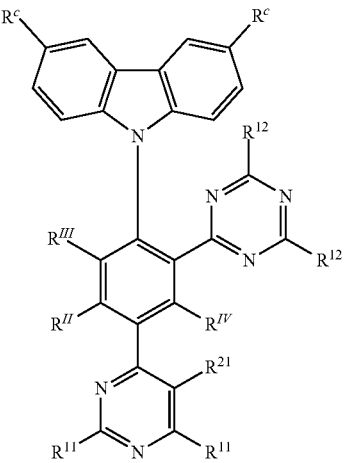

Formula XIa wherein the aforementioned definitions apply.

In a further embodiment of the invention, the organic molecules comprise or consist of a structure of Formula XIb:

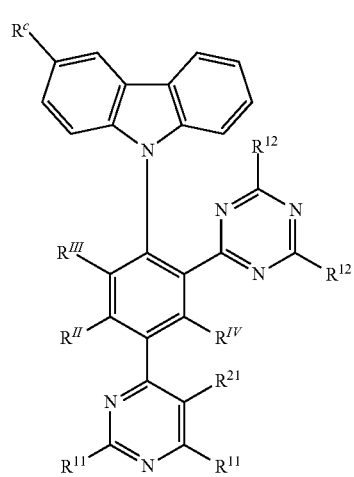

Formula XIb wherein the aforementioned definitions apply.

In a further embodiment of the invention, the organic molecules comprise or consist of a structure of Formula XIc:

Formula XIc

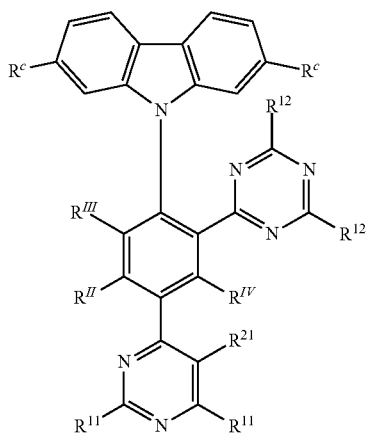

wherein the aforementioned definitions apply.

In a further embodiment of the invention, the organic molecules comprise or consist of a structure of Formula XId:

Formula XId

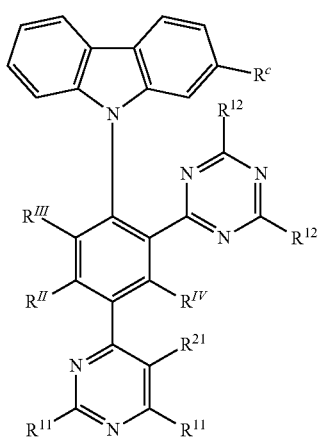

wherein the aforementioned definitions apply.

As used above and herein, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used above and herein, the term alkyl group may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used above and herein, the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used above and herein, the term alkynyl comprises linear, branched, and cyclic alkynyl substituents. The term alkynyl group exemplarily comprises ethynyl, propynyl, butynyl, pentynyl, hexynyl, heptynyl or octynyl.

As used above and herein, the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used above and herein, the term thioalkoxy comprises linear, branched, and cyclic thioalkoxy substituents, in which the O of the exemplarily alkoxy groups is replaced by S.

As used above and herein, the terms "halogen" and "halo" may be understood in the broadest sense as being fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 µs, of not more than 100 µs, in particular of not more than 50 µs, preferably of not more than 10 µs or not more than 7 µs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, in particular less than 3000 cm$^{-1}$, preferably less than 1500 cm$^{-1}$, more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, in particular less than 0.48 eV, preferably less than 0.45 eV, more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have an emission peak in the visible or nearest ultraviolet range, i.e., in the range of a wavelength of from 380 to 800 nm, with a full width at half maximum of less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly (methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing the organic molecules (with an optional subsequent reaction) of the invention, wherein a palladium catalyzed cross-coupling reaction is used:

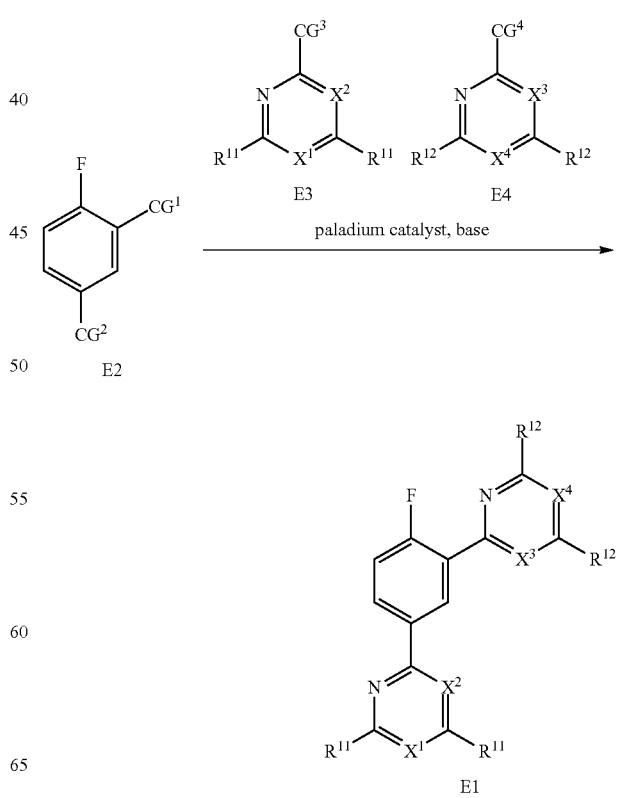

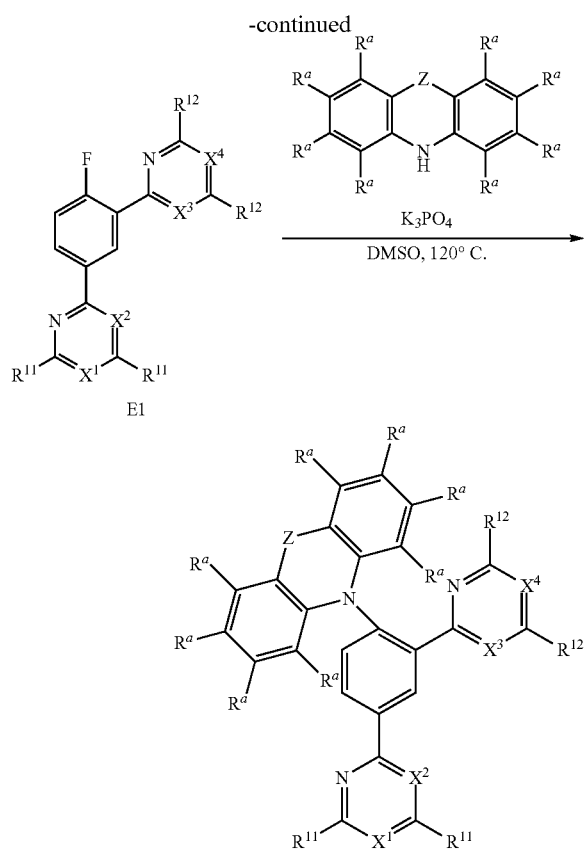

According to the invention, a 1-fluorobenzene, which is substituted with a coupling group CG¹ in 2-position and which is substituted with a coupling group CG² in 4-position, is used as a reactant, which is reacted with two heterocycles, one substituted with a coupling group CG³ (reactant E3) and one with a coupling group CG⁴ (reactant E4). The coupling groups CG¹ and CG⁴ are chosen as a reaction pair to introduce the heterocycle of E4 at the position of CG¹. Accordingly, coupling groups CG² and CG³ are chosen reaction pair for introducing the heterocycle of E3 at the position of CG². Preferably, a so-called Suzuki coupling reaction is used. Here, either CG¹ is chosen from Cl, Br or I, and CG⁴ is a boronic acid group or a boronic acid ester group, in particular a boronic acid pinacol ester group, or CG¹ is a boronic acid group or a boronic acid ester group, in particular a boronic acid pinacol ester group, and CG⁴ is chosen from Cl, Br or I. Analogously, either CG² is chosen from Cl, Br or I, and CG³ is a boronic acid group or a boronic acid ester group, in particular a boronic acid pinacol ester group, or CG² is a boronic acid group or a boronic acid ester group, in particular a boronic acid pinacol ester group, and CG³ is chosen from Cl, Br or I. The person skilled in the art is aware that in order to introduce different heterocycles via the coupling reactions of E3 with E2 and E4 with E2, either first E2 is reacted with E3 and the resulting intermediate is subsequently reacted with E4 to yield E1, or first E2 is reacted with E4 and the resulting intermediate is subsequently reacted with E3 to yield E1. In this constellation, either CG¹ and CG³ are independently from each other a boronic acid group or a boronic acid ester group and CG² and CG⁴ are independently from each other chosen from Cl, Br or I, or CG² and CG⁴ are independently from each other a boronic acid group or a boronic acid ester group and CG¹ and CG³ are independently from each other chosen from Cl, Br or I.

For the reaction of a nitrogen heterocycle in a nucleophilic aromatic substitution with an aryl halide, in particular an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, in particular an aryl bromide, an aryl iodide, an aryl triflate or an aryl tosylate.

A further aspect of the invention relates to the use of an organic molecule according to the invention as a luminescent emitter or as an absorber, and/or as host material and/or as electron transport material, and/or as hole injection material, and/or as hole blocking material in an optoelectronic device.

The optoelectronic device may be understood in the broadest sense as any device based on organic materials that is suitable for emitting light in the visible or nearest ultraviolet (UV) range, i.e., in the range of a wavelength of from 380 to 800 nm. In particular, the optoelectronic device may be able to emit light in the visible range, i.e., of from 400 to 800 nm.

In the context of such use, the optoelectronic device is more particularly selected from the group consisting of:
organic light-emitting diodes (OLEDs),
light-emitting electrochemical cells,
OLED sensors, especially in gas and vapour sensors not hermetically externally shielded,
organic diodes,
organic solar cells,
organic transistors,
organic field-effect transistors,
organic lasers and
down-conversion elements.

In a preferred embodiment in the context of such use, the optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention, but also a host material whose triplet (T1) and singlet (S1) energy levels are energetically higher than the triplet (T1) and singlet (S1) energy levels of the organic molecule.

A further aspect of the invention relates to a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

In one embodiment, the light-emitting layer comprises (or essentially consists of) a composition comprising or consisting of:
(a) at least one organic molecule according to the invention, in particular in the form of an emitter and/or a host, and
(b) one or more emitter and/or host materials, which differ from the organic molecule according to the invention, and (c) optionally, one or more dyes and/or one or more solvents.

In another embodiment, the light-emitting layer EML comprises (or essentially consists of) a composition comprising or consisting of:
(i) 1-50% by weight, in particular 5-40% by weight, preferably 10-30% by weight, of one or more organic molecules according to the invention;
(ii) 5-99% by weight, in particular 30-94.9% by weight, preferably 40-89% by weight, of at least one host compound H; and
(iii) optionally, 0-94% by weight, in particular 0.1-65% by weight, preferably 1-50% by weight, of at least one further host compound D with a structure differing from the structure of the molecules according to the invention; and
(iv) optionally, 0-94% by weight, in particular 0-65% by weight, preferably 0-50% by weight, of a solvent; and
(v) optionally, 0-30% by weight, in particular 0-20% by weight, preferably 0-5% by weight, of at least one further emitter molecule F with a structure differing from the structure of the molecules according to the invention.

In particular, energy can be transferred from the host compound H to the one or more organic molecules according to the invention, in particular transferred from the first excited triplet state T1(H) of the host compound H to the first excited triplet state T1(E) of the one or more organic molecules according to the invention and/or from the first excited singlet state S1(H) of the host compound H to the first excited singlet state S1(E) of the one or more organic molecules according to the invention.

In a further embodiment, the light-emitting layer EML comprises (or essentially consists of) a composition comprising or consisting of:
(i) 1-50% by weight, in particular 5-40% by weight, preferably 10-30% by weight, of one organic molecule according to the invention;
(ii) 5-99% by weight, in particular 30-94.9% by weight, preferably 40-89% by weight, of one host compound H; and
(iii) optionally, 0-94% by weight, in particular 0.1-65% by weight, preferably 1-50% by weight, of at least one further host compound D with a structure differing from the structure of the molecules according to the invention; and
(iv) optionally, 0-94% by weight, in particular 0-65% by weight, preferably 0-50% by weight, of a solvent; and
(v) optionally, 0-30% by weight, in particular 0-20% by weight, preferably 0-5% by weight, of at least one further emitter molecule F with a structure differing from the structure of the molecules according to the invention.

In one embodiment of the invention, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H) > E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$.

In another embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and the at least one further host compound D has a highest occupied molecular orbital HOMO(D) having an energy $E^{HOMO}(D)$ and a lowest unoccupied molecular orbital LUMO(D) having an energy $E^{LUMO}(D)$, the organic molecule according to the invention has a highest occupied molecular orbital HOMO(E) having an energy $E^{HOMO}(E)$ and a lowest unoccupied molecular orbital LUMO(E) having an energy $E^{LUMO}(E)$,
wherein
$E^{HOMO}(H) > E^{HOMO}(D)$ and the difference between the energy level of the highest occupied molecular orbital HOMO(E) of organic molecule according to the invention ($E^{HOMO}(E)$) and the energy level of the highest occupied molecular orbital HOMO(H) of the host compound H ($E^{HOMO}(H)$) is between −0.5 eV and 0.5 eV, in particular between −0.3 eV and 0.3 eV, preferably between −0.2 eV and 0.2 eV or even between −0.1 eV and 0.1 eV; and
$E^{LUMO}(H) > E^{LUMO}(D)$ and the difference between the energy level of the lowest unoccupied molecular orbital LUMO(E) of organic molecule according to the invention ($E^{LUMO}(E)$) and the lowest unoccupied molecular orbital LUMO(D) of the at least one further host compound D ($E^{LUMO}(D)$) is between −0.5 eV and 0.5 eV, in particular between −0.3 eV and 0.3 eV, preferably between −0.2 eV and 0.2 eV or even between −0.1 eV and 0.1 eV.

In a further aspect, the invention relates to an optoelectronic device comprising an organic molecule or a composition as described herein, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a particular embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention is used as emission material in a light-emitting layer EML.

In one embodiment of the optoelectronic device of the invention, the light-emitting layer EML consists of the composition according to the invention described herein.

When the optoelectronic device is an OLED, it may, for example, exhibit the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, wherein the OLED comprises each layer only optionally, different layers may be merged and the OLED may comprise more than one layer of each layer type defined above.

Furthermore, the optoelectronic device may optionally comprise one or more protective layers protecting the device from damaging exposure to harmful species in the environment including, exemplarily moisture, vapor and/or gases.

In one embodiment of the invention, the optoelectronic device is an OLED, which exhibits the following inverted layer structure:

1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A wherein the OLED with an inverted layer structure comprises each layer only optionally, different layers may be merged and the OLED may comprise more than one layer of each layer types defined above.

In one embodiment of the invention, the optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may, for example, comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

In particular, the anode layer A (essentially) consists of indium tin oxide (ITO) (e.g., (InO3)0.9(SnO2)0.1). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene:polystyrene sulfonate), PEDOT (poly-3,4-ethylendioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). In particular, hole transport compounds bear comparably high energy levels of their triplet states T1. Exemplarily the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane (F4-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particular, the EML comprises at least one light emitting molecule according to the invention. In one embodiment, the light-emitting layer comprises only the organic molecules according to the invention. Typically, the EML additionally comprises one or more host material. Exemplarily, the host material is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris (biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, in particular 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, in particular 10-30% by weight of light emitting molecule according to the invention.

Adjacent to the light-emitting layer EML an electron transport layer (ETL) may be located. Herein, any electron transporter may be used. Exemplarily, compounds poor of electrons such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may, for example, comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl) benzene).

A cathode layer C may be located adjacent to the electron transport layer (ETL). For example, the cathode layer C may comprise or may consist of a metal (e.g., Al, Au, Ag, Pt, Cu, Zn, Ni, Fe, LiF, Ca, Ba, Mg, In, W, or Pd) or a metal alloy. For practical reasons, the cathode layer may also consist of (essentially) intransparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds.

In order to modify the emission spectrum and/or the absorption spectrum of the light-emitting layer EML further, the light-emitting layer EML may further comprise one or more further emitter molecule F. Such an emitter molecule F may be any emitter molecule known in the art. In particular, such an emitter molecule F is a molecule with a structure differing from the structure of the molecules according to the invention. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the emitter molecule according to the invention to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an optoelectronic device (e.g., an OLED) may exemplarily be an essentially white optoelectronic device. For example, such a white optoelectronic device may comprise at least one (deep) blue emitter molecule and one or more emitter molecules emitting green and/or red light. Then, there may also be energy transmittance between two or more molecules as described above.

As used herein, if not defined more specifically in the particular context, the designation of the colors of emitted and/or absorbed light is as follows:
  violet: wavelength range of >380-420 nm;
  deep blue: wavelength range of >420-480 nm;
  sky blue: wavelength range of >480-500 nm;
  green: wavelength range of >500-560 nm;
  yellow: wavelength range of >560-580 nm;
  orange: wavelength range of >580-620 nm;
  red: wavelength range of >620-800 nm.

With respect to emitter molecules, such colors refer to the emission maximum. Therefore, exemplarily, a deep blue emitter has an emission maximum in the range of from >420 to 480 nm, a sky-blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may have an emission maximum of below 480 nm, preferably below 470 nm, more preferably below 465 nm or even below 460 nm. It will typically be above 420 nm, in particular above 430 nm, preferably above 440 nm or even above 450 nm.

Accordingly, a further aspect of the present invention relates to an OLED, which exhibits an external quantum efficiency at 1000 cd/m2 of more than 8%, preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/m2 of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The optoelectronic device, in particular the OLED according to the present invention can be fabricated by any means of vapor deposition and/or liquid processing. Accordingly, at least one layer is
  prepared by means of a sublimation process,
  prepared by means of an organic vapor phase deposition process,
  prepared by means of a carrier gas sublimation process, solution processed or printed.

The methods used to fabricate the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMO-LED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General Synthesis Scheme I

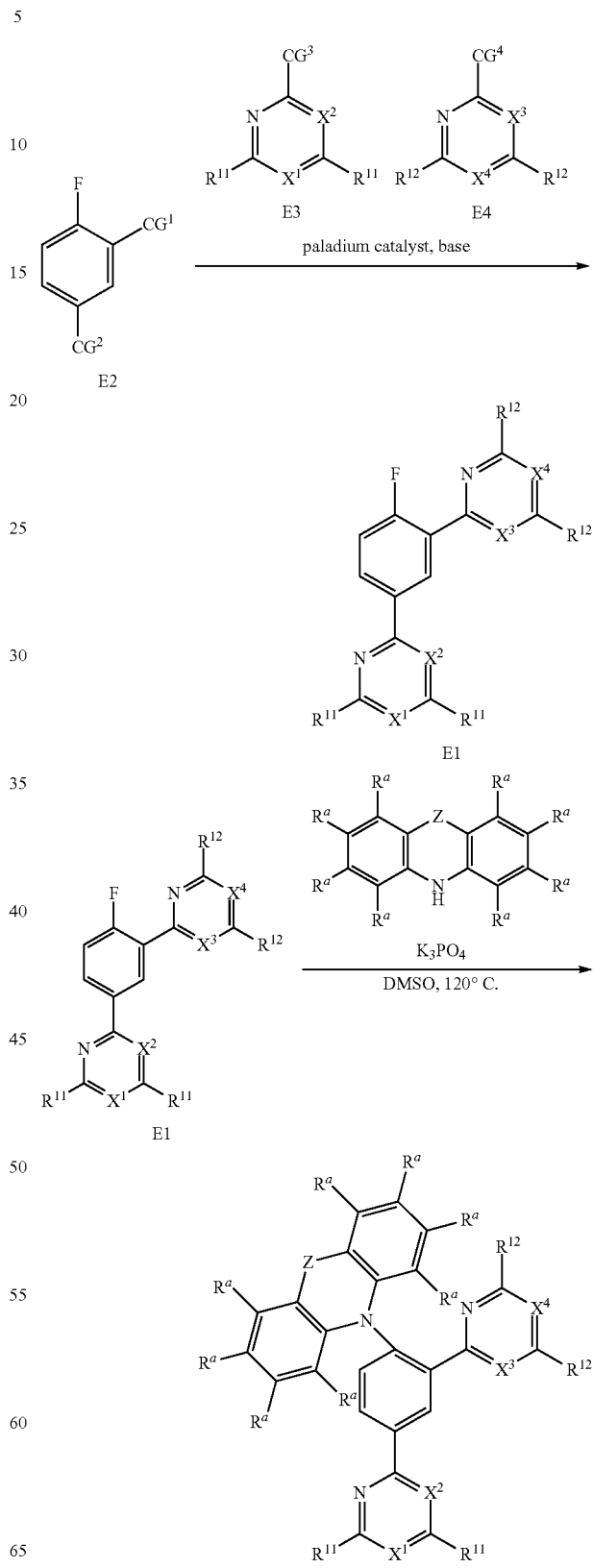

General Procedure for Synthesis AAV1:

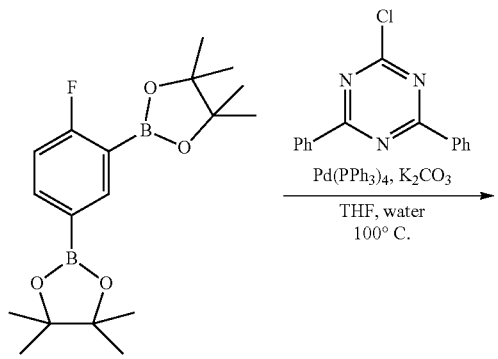

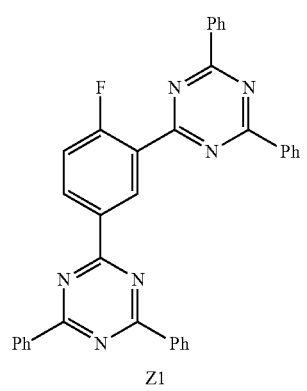

2-fluorophenyl-1,4-diboronic acid pinacol ester (1.00 equivalents), 2-chloro-4,6-diphenyl-1,3,5-triazine (2.50 equivalents), tetrakis(triphenylphosphine)palladium(0) (0.12 equivalent), and tribasic potassium phosphate (6.00 equivalents) are stirred under nitrogen atmosphere in a tetrahydrofuran (THF)/water mixture (ratio of 3:1) at 100° C. for 16 h. After cooling down to room temperature (rt), the reaction mixture is poured into water, the product is filtered and washed with ethanol (EtOH).

General Procedure for Synthesis AAV2:

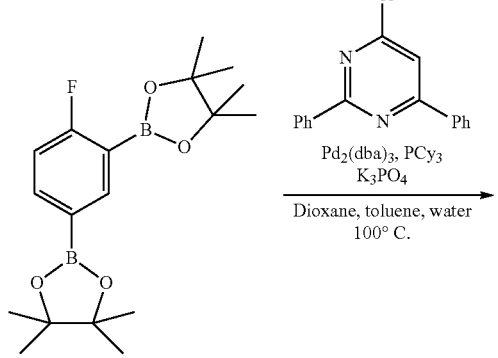

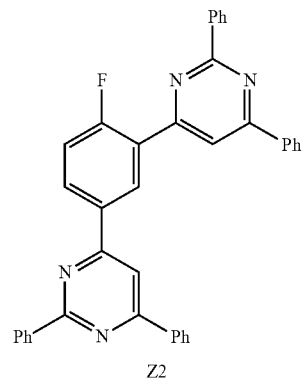

2-fluorophenyl-1,4-diboronic acid pinacol ester (1.00 equivalent), 4-chloro-2,6-diphenyl-1,3-pyrimidine (2.25 equivalents), Pd$_2$(dba)$_3$ (0.06 equivalents), Tricyclohexylphosphine (PCy$_3$, 0.14 equivalents), and tribasic potassium phosphate (6.00 equivalents) are stirred under nitrogen atmosphere in a dioxane/toluene/water mixture (ratio: 3:1:1) at 100° C. overnight. After cooling down to room temperature (rt), the reaction mixture is poured into water, the product is filtered and washed with EtOH.

General Procedure for Synthesis AAV3:

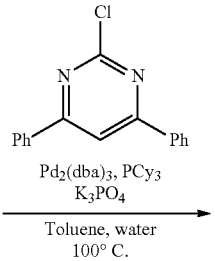

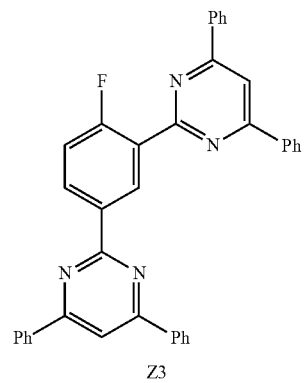

The synthesis of Z3 is carried out according to AAV2, wherein 2-fluorophenyl-1,4-diboronic acid pinacol ester reacts with 2-chloro-4,6-diphenyl-1,3-pyrimidine.

General Procedure for Synthesis AAV4:

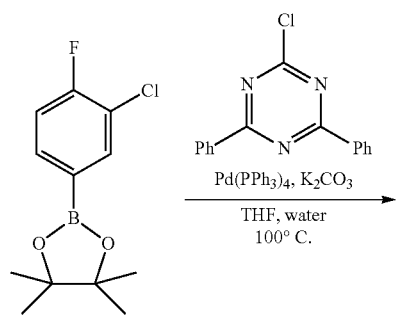

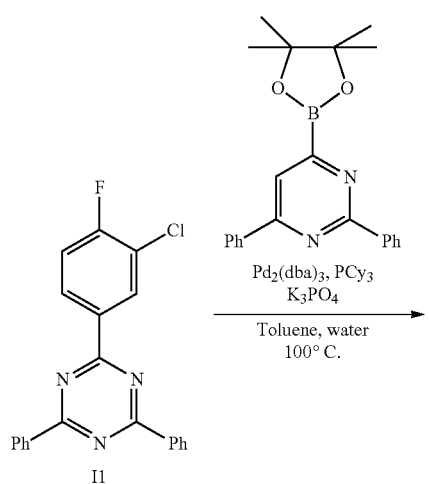

Z4

General Procedure for Synthesis AAV4-2:

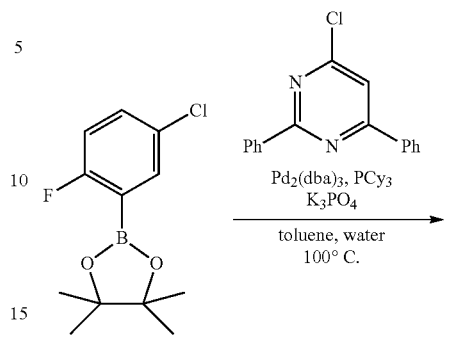

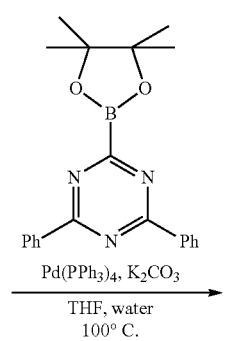

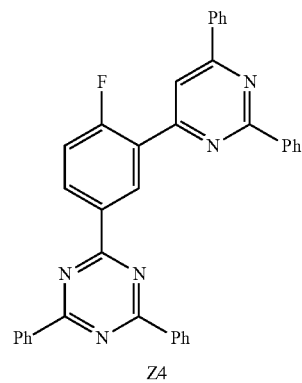

Z4

3-chloro-4-fluorophenyl-boronic acid pinacol ester (1.00 equivalent) is reacted with 2-chloro-4,6-diphenyl-1,3,5-triazine (1.25 equivalents) to yield intermediate I1 employing similar conditions as in AAV1. Subsequently the intermediate I1 (1.00 equivalent) is reacted with 2,6-diphenyl-1,3-pyrimidine-4-boronic acid pinacol ester (1.10 equivalents) employing similar conditions as in AAV2 to yield Z4.

5-chloro-2-fluorophenyl-boronic acid pinacol ester (1.00 equivalent) is reacted with 4-chloro-2,6-diphenyl-1,3-pyrimidine (1.10 equivalents) to yield intermediate I2 employing similar conditions as in AAV2. Subsequently the intermediate I2 (1.00 equivalent) is reacted with 4,6-diphenyl-1,3,5-triazine-2-boronic acid pinacol ester (1.25 equivalents) employing similar conditions as in AAV1 to yield Z4.

General Procedure for Synthesis AAV5:

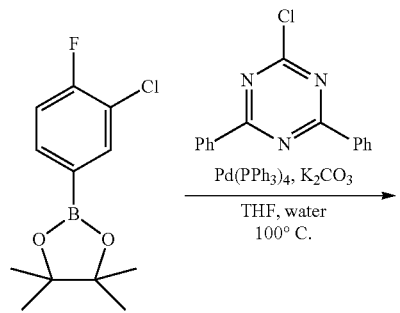

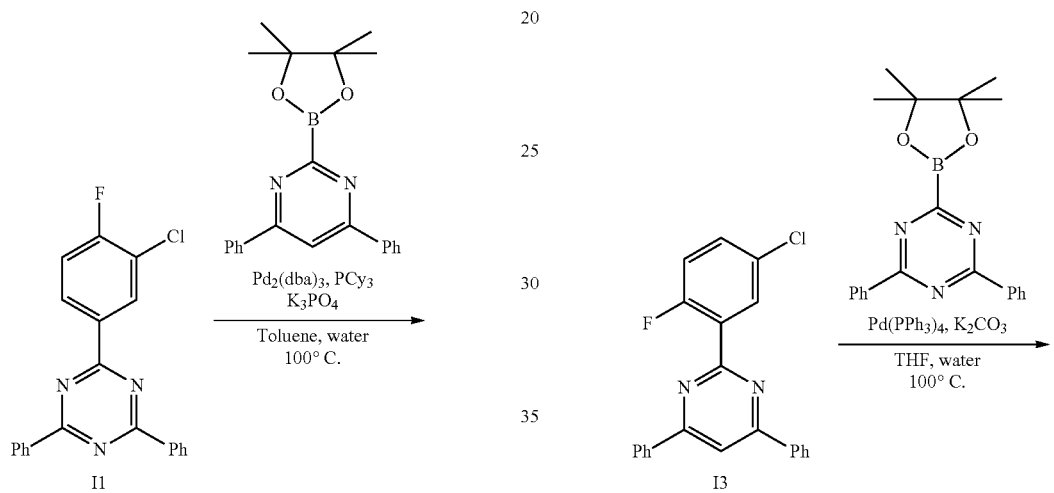

3-chloro-4-fluorophenyl-boronic acid pinacol ester (1.00 equivalent) is reacted with 2-chloro-4,6-diphenyl-1,3,5-triazine (1.25 equivalents) to yield intermediate I1 employing similar conditions as in AAV1. Subsequently the intermediate I1 (1.00 equivalent) is reacted with 4,6-diphenyl-1,3-pyrimidine-2-boronic acid pinacol ester (1.10 equivalents) employing similar conditions as in AAV3 to yield Z5.

General Procedure for Synthesis AAV5-2:

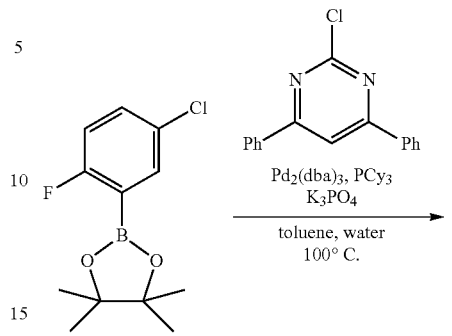

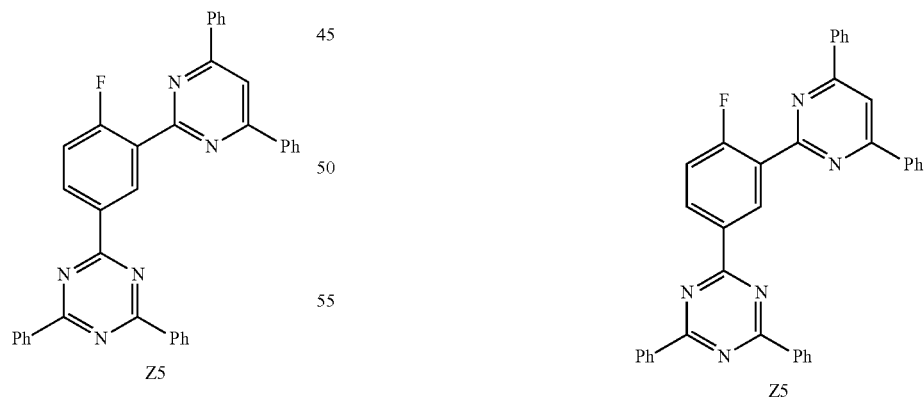

5-chloro-2-fluorophenyl-boronic acid pinacol ester (1.00 equivalent) is reacted with 2-chloro-4,6-diphenyl-1,3-pyrimidine (1.10 equivalents) to yield intermediate I3 employing similar conditions as in AAV3. Subsequently the intermediate I3 (1.00 equivalent) is reacted with 4,6-diphenyl-1,3,5-triazine-2-boronic acid pinacol ester (1.25 equivalents) employing similar conditions as in AAV1.

General Procedure for Synthesis AAV6:

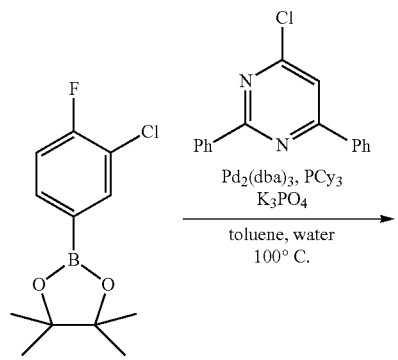

General Procedure for Synthesis AAV6-2:

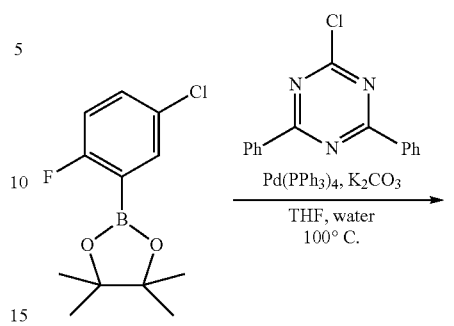

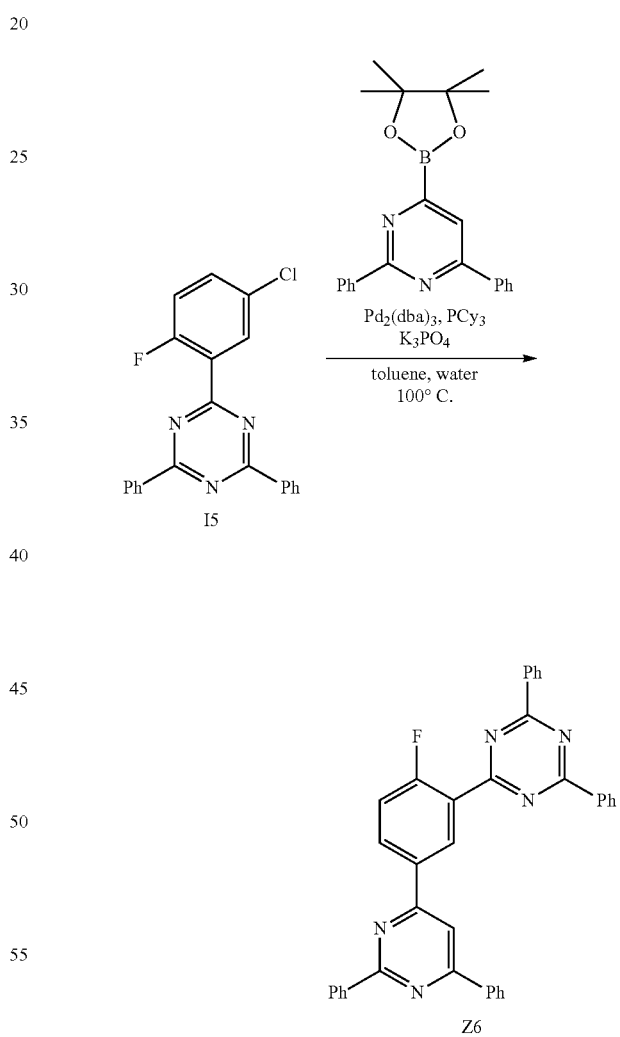

3-chloro-4-fluorophenyl-boronic acid pinacol ester (1.00 equivalent) is reacted with 4-chloro-2,6-diphenyl-1,3-pyrimidine (1.10 equivalents) to yield intermediate I4 employing similar conditions as in AAV2. Subsequently the intermediate I4 (1.00 equivalent) is reacted with 4,6-diphenyl-1,3,5-triazine-2-boronic acid pinacol ester (1.25 equivalents) employing similar conditions as in AAV1 to yield Z6.

5-chloro-2-fluorophenyl-boronic acid pinacol ester (1.00 equivalent) is reacted with 2-chloro-4,6-diphenyl-1,3,5-triazine (1.25 equivalents) to yield intermediate I5 employing similar conditions as in AAV1. Subsequently the intermediate I5 (1.00 equivalent) is reacted with 2,6-diphenyl-1,3-pyrimidine-4-boronic acid pinacol ester (1.10 equivalents) employing similar conditions as in AAV2 to yield Z6.

General Procedure for Synthesis AAV7:

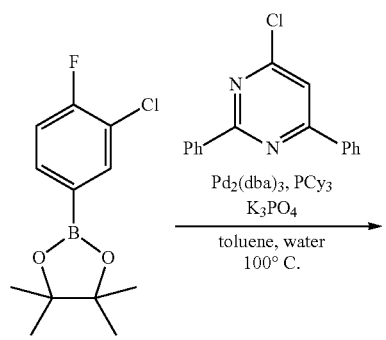

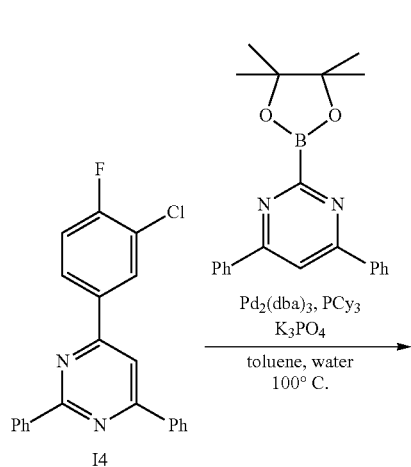

General Procedure for Synthesis AAV7-2:

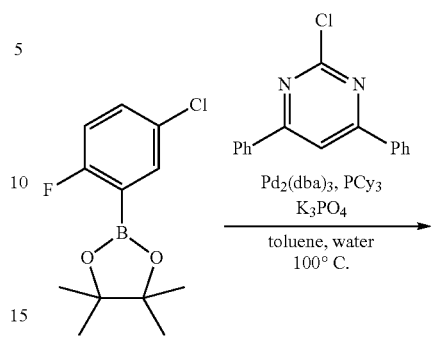

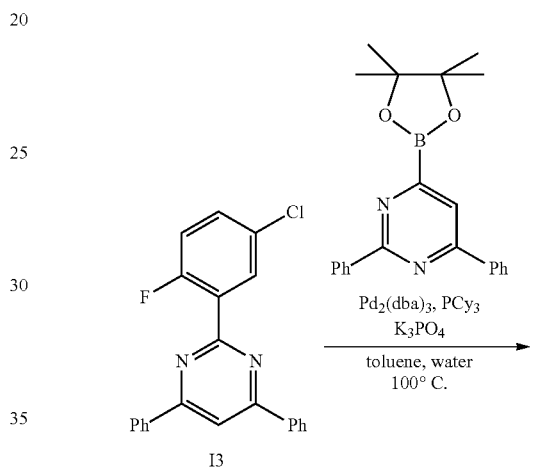

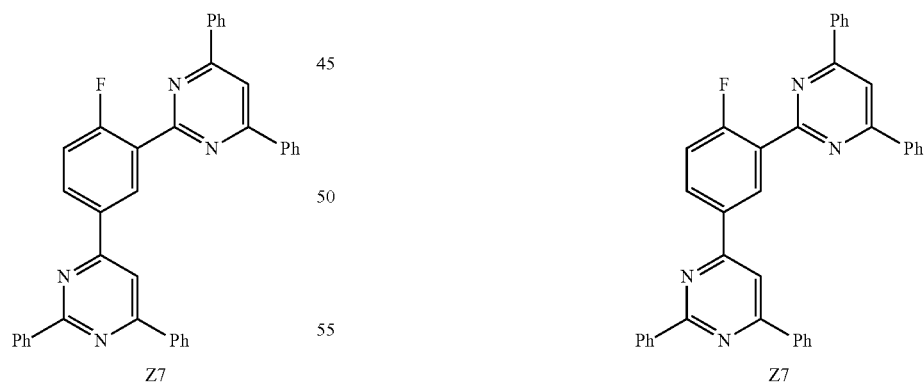

3-chloro-4-fluorophenyl-boronic acid pinacol ester (1.00 equivalent) is reacted with 4-chloro-2,6-diphenyl-1,3-pyrimidine (1.10 equivalents) to yield intermediate I4 employing similar conditions as in AAV2. Subsequently the intermediate I4 (1.00 equivalent) is reacted with 4,6-diphenyl-1,3-pyrimidine-2-boronic acid pinacol ester (1.10 equivalents) employing similar conditions as in AAV3 to yield Z7.

5-chloro-2-fluorophenyl-boronic acid pinacol ester (1.00 equivalent) is reacted with 2-chloro-4,6-diphenyl-1,3-pyrimidine (1.10 equivalents) to yield intermediate I3 employing similar conditions as in AAV3. Subsequently the intermediate I3 (1.00 equivalent) is reacted with 2,6-diphenyl-1,3,5-triazine-4-boronic acid pinacol ester (1.10 equivalents) employing similar conditions as in AAV2 to yield Z7.

General Procedure for Synthesis AAV8:

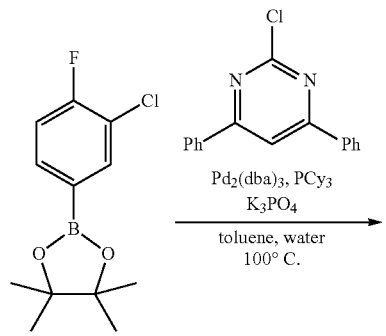

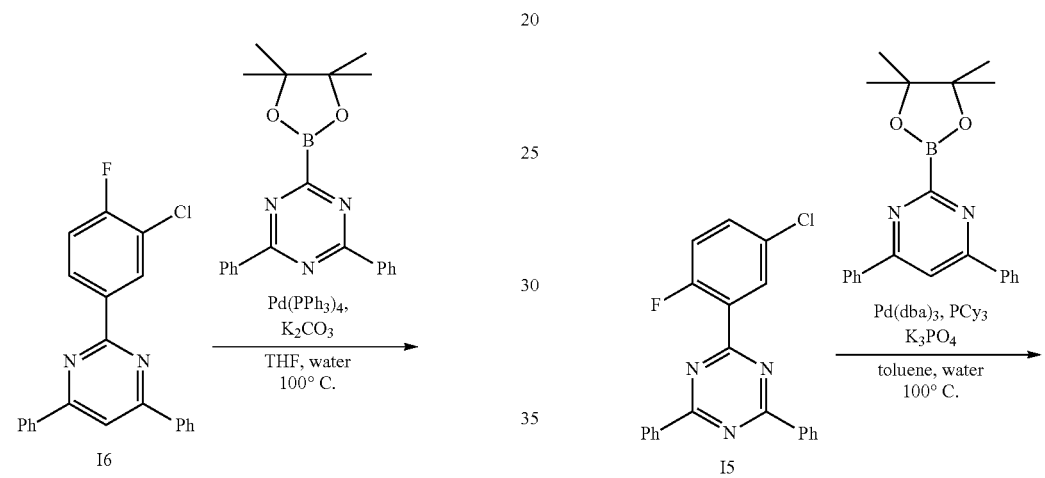

3-chloro-4-fluorophenyl-boronic acid pinacol ester (1.00 equivalent) is reacted with 2-chloro-4,6-diphenyl-1,3-pyrimidine (1.10 equivalents) to yield intermediate I6 employing similar conditions as in AAV3. Subsequently the intermediate I6 (1.00 equivalent) is reacted with 4,6-diphenyl-1,3,5-triazine-2-boronic acid pinacol ester (1.25 equivalents) employing similar conditions as in AAV1 to yield Z8.

General Procedure for Synthesis AAV8-2:

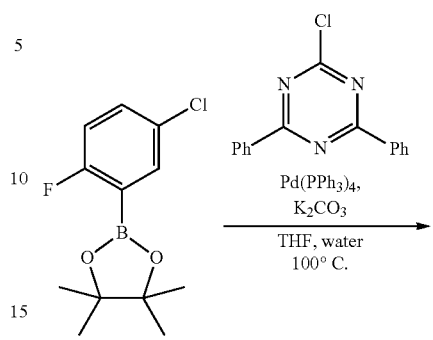

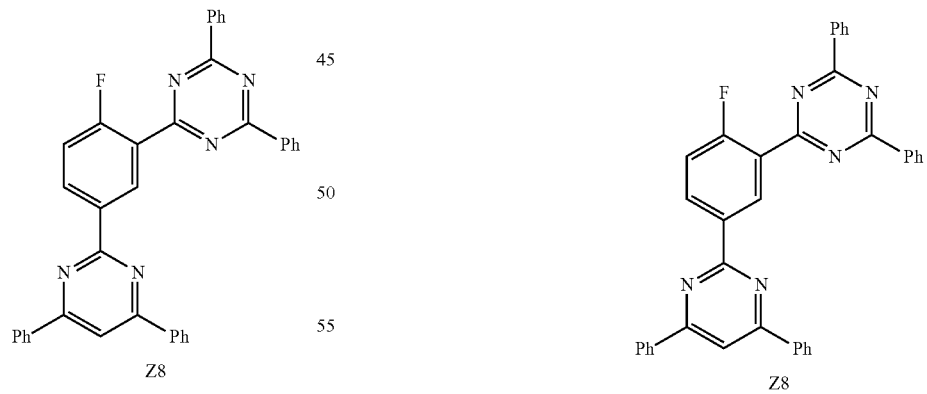

5-chloro-2-fluorophenyl-boronic acid pinacol ester (1.00 equivalent) is reacted with 2-chloro-4,6-diphenyl-1,3,5-triazine (1.25 equivalents) to yield intermediate I5 employing similar conditions as in AAV1. Subsequently the intermediate I5 (1.00 equivalent) is reacted with 4,6-diphenyl-1,3-pyrimidine-2-boronic acid pinacol ester (1.10 equivalents) employing similar conditions as in AAV3 to yield Z8.

General Procedure for Synthesis AAV9:

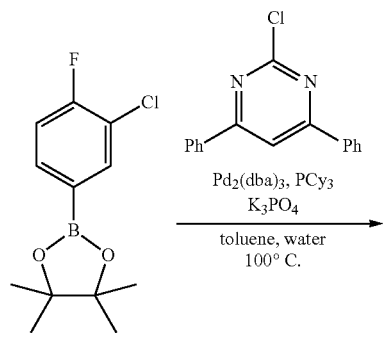

3-chloro-4-fluorophenyl-boronic acid pinacol ester (1.00 equivalent) is reacted with 2-chloro-4,6-diphenyl-1,3-pyrimidine (1.10 equivalents) to yield intermediate I6 employing similar conditions as in AAV3. Subsequently the intermediate I6 (1.00 equivalent) is reacted with 2,6-diphenyl-1,3-pyrimidine-4-boronic acid pinacol ester (1.10 equivalents) employing similar conditions as in AAV2 to yield Z9.

General Procedure for Synthesis AAV9-2:

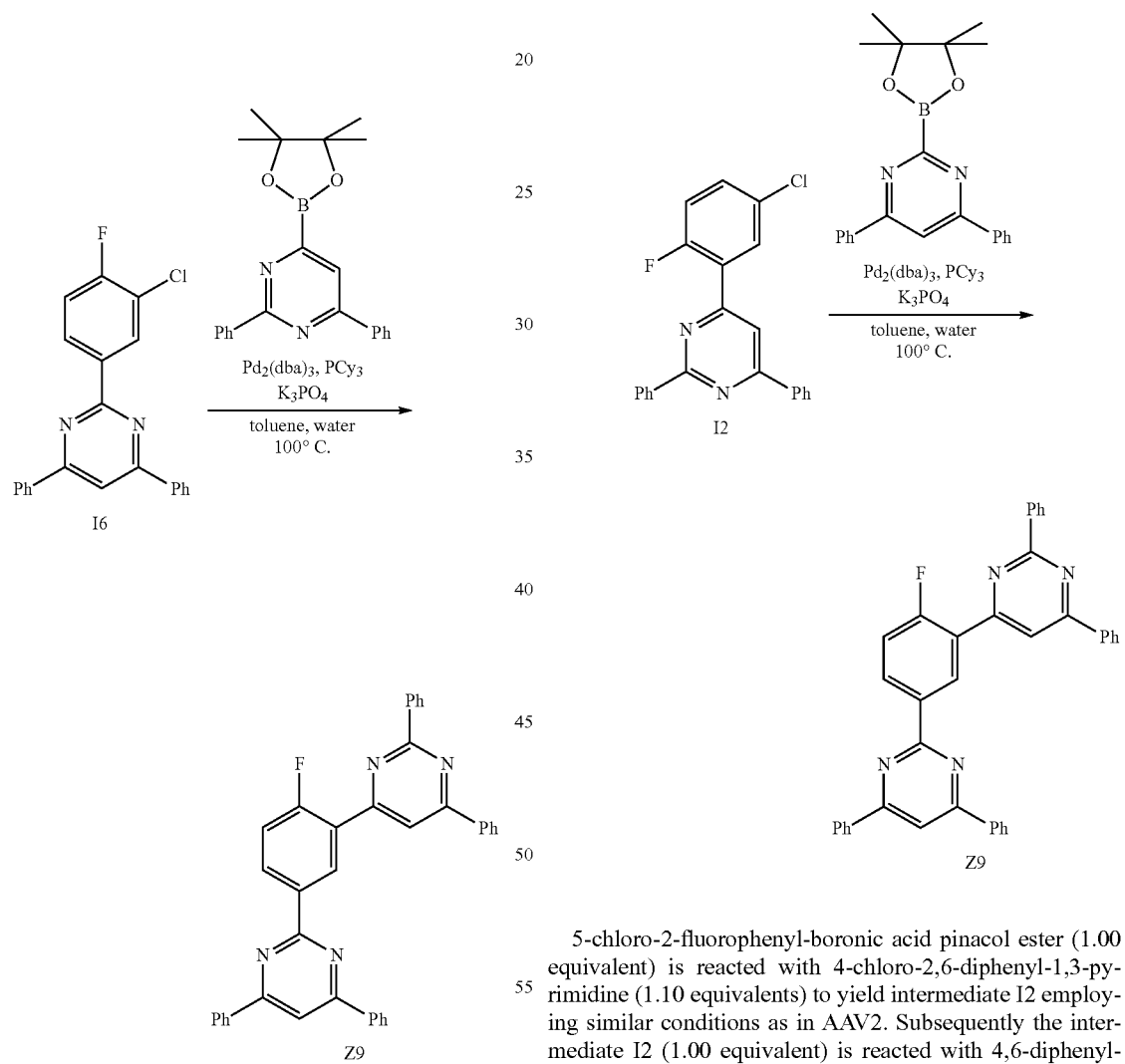

5-chloro-2-fluorophenyl-boronic acid pinacol ester (1.00 equivalent) is reacted with 4-chloro-2,6-diphenyl-1,3-pyrimidine (1.10 equivalents) to yield intermediate I2 employing similar conditions as in AAV2. Subsequently the intermediate I2 (1.00 equivalent) is reacted with 4,6-diphenyl-1,3,5-triazine-2-boronic acid pinacol ester (1.10 equivalents) employing similar conditions as in AAV3 to yield Z9.

In a further alternative, the two respective reaction steps described in AAV4 to AAV9-2 can be performed in a one-pot reaction. In that case, the solvent mixture of either one of the two reaction steps is used for both reactions and the reactant, the base and the catalyst of the second reaction step are added after the first reaction is completed.

General Procedure for Synthesis AAV10:
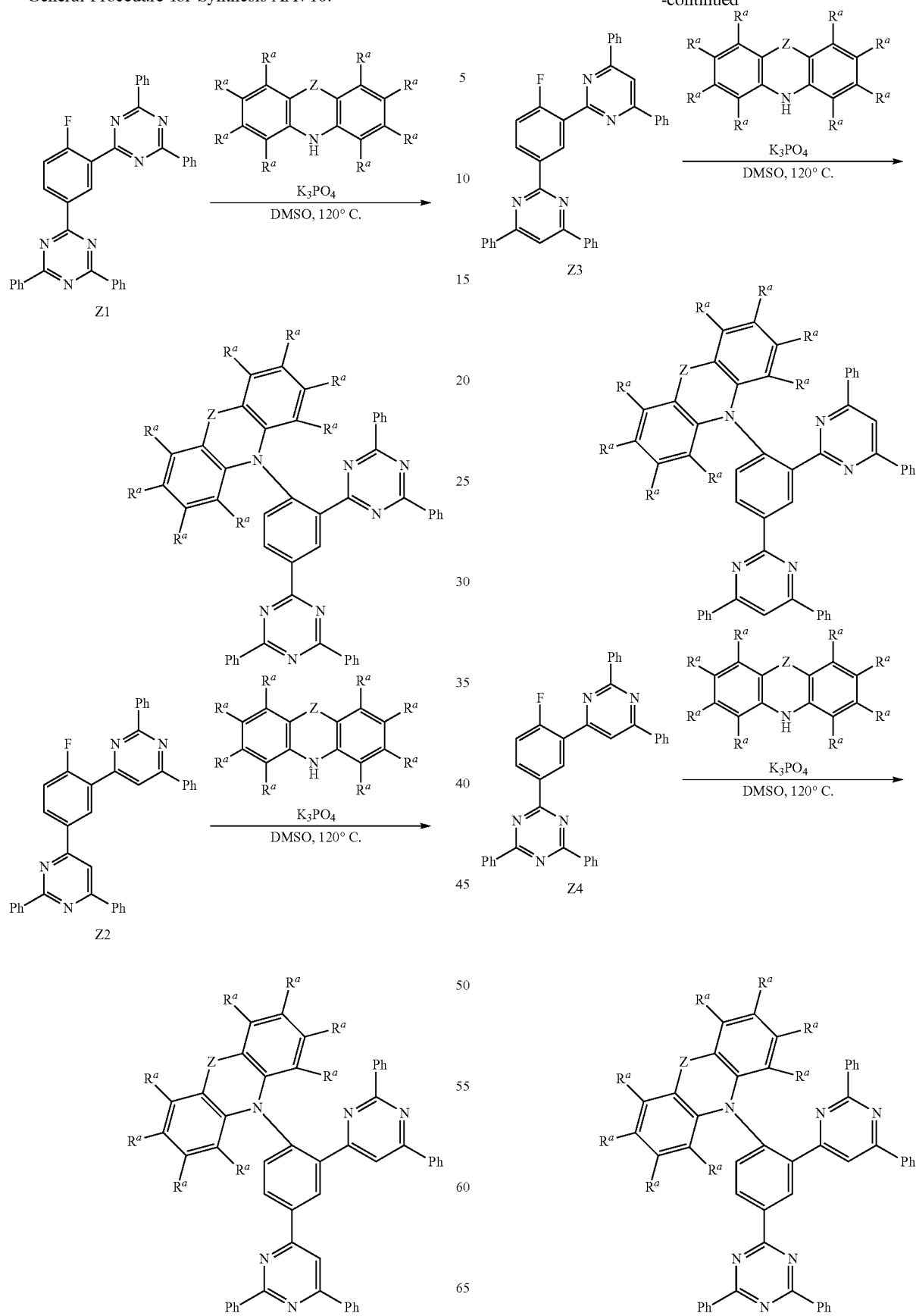

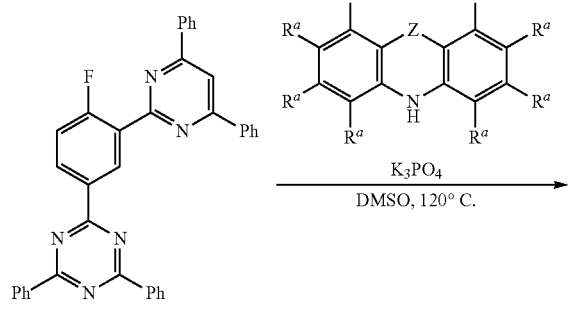
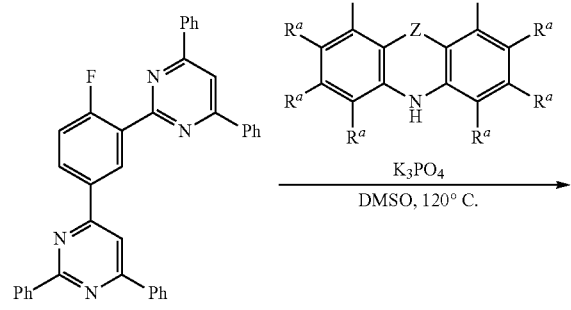
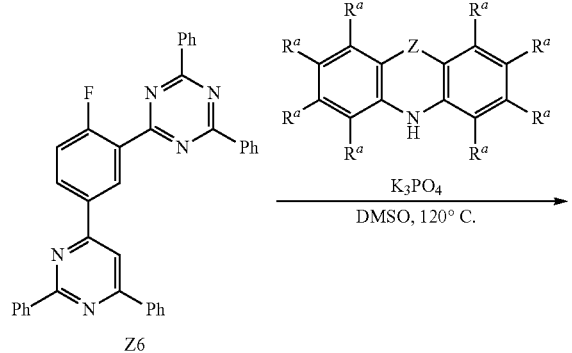
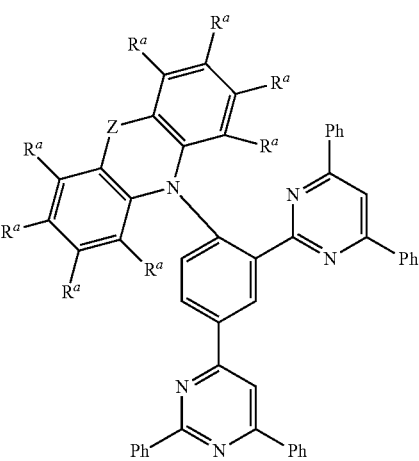
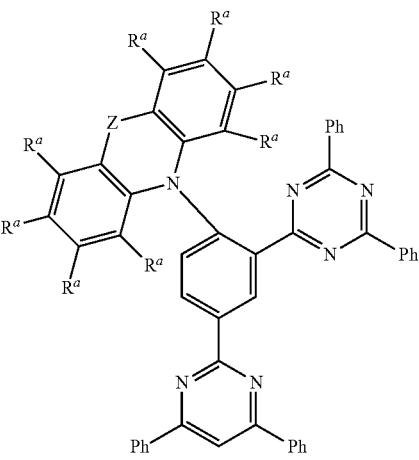

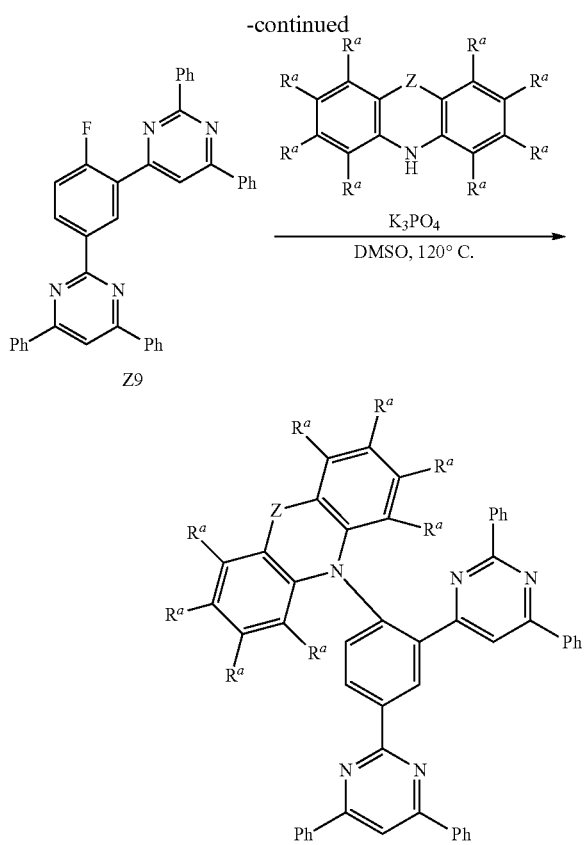

Z1, Z2, Z3, Z4, Z5, Z6, Z7, Z8 or Z9 (1 equivalent each), the corresponding donor molecule D-H (1.00 equivalents) and tribasic potassium phosphate (2.00 equivalents) are suspended under nitrogen atmosphere in DMSO and stirred at 120° C. (16 h). After chilling to rt the reaction mixture is poured into water in order to precipitate the organics. The precipitate is filtered off (fiber glass filter) and subsequently dissolved in dichloromethane. The resulting solution is added to brine and the phases were separated. After drying over MgSO$_4$, the crude product is purified by recrystallization or by flash chromatography. The product is obtained as a solid.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

For example, a halogen-substituted carbazole, particularly 3-bromocarbazole, can be used as D-H.

In a subsequent reaction, a boronic acid ester functional group or boronic acid functional group may be, for example, introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents R$^a$ may be introduced in place of the boronic acid ester group or the boronic acid group via a coupling reaction with the corresponding halogenated reactant R$^a$-Hal, preferably R$^a$—Cl and R$^a$—Br.

Alternatively, one or more substituents R$^a$ may be introduced at the position of the one or more halogen substituents, which was introduced via D-H, via the reaction with a boronic acid of the substituent R$^a$ [R$^a$—B(OH)$_2$] or a corresponding boronic acid ester.

HPLC-MS:

HPLC-MS spectroscopy is performed on a HPLC by Agilent (1100 series) with MS-detector (Thermo LTQ XL). A reverse phase column 4.6 mm×150 mm, particle size 5.0 μm from Waters (without pre-column) is used in the HPLC. The HPLC-MS measurements are performed at room temperature (rt) with the solvents acetonitrile, water and THF in the following concentrations:

solvent A: H$_2$O (90%) MeCN (10%)
solvent B: H$_2$O (10%) MeCN (90%)
solvent C: THF (100%)

From a solution with a concentration of 0.5 mg/ml an injection volume of 15 μL is taken for the measurements. The following gradient is used:

| Flow rate [ml/min] | time [min] | A [%] | B [%] | D [%] |
|---|---|---|---|---|
| 3 | 0 | 40 | 50 | 10 |
| 3 | 10 | 10 | 15 | 75 |
| 3 | 16 | 10 | 15 | 75 |
| 3 | 16.01 | 40 | 50 | 10 |
| 3 | 20 | 40 | 50 | 10 |

Ionisation of the probe is performed by APCI (atmospheric pressure chemical ionization).

Cyclic Voltammetry

Cyclic voltammograms are measured from solutions having concentration of 10$^{-3}$ mol/l of the organic molecules in dichloromethane or a suitable solvent and a suitable supporting electrolyte (e.g. 0.1 mol/l of tetrabutylammonium hexafluorophosphate). The measurements are conducted at room temperature under nitrogen atmosphere with a three-electrode assembly (Working and counter electrodes: Pt wire, reference electrode: Pt wire) and calibrated using FeCp$_2$/FeCp$_2^+$ as internal standard. The HOMO data was corrected using ferrocene as internal standard against SCE.

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence spectroscopy and TCSPC (Time-correlated single-photon counting) Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation Sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Q in % and CIE coordinates as x,y values. PLQY is determined using the following protocol:
1) Quality assurance: Anthracene in ethanol (known concentration) is used as reference
2) Excitation wavelength: the absorption maximum of the organic molecule is determined and the molecule is excited using this wavelength
3) Measurement
   Quantum yields are measured for sample of solutions or films under nitrogen atmosphere. The yield is calculated using the equation:

$$\Phi_{PL} = \frac{n_{photon}, \text{emited}}{n_{photon}, \text{absorbed}} = \frac{\int \frac{\lambda}{hc} [Int_{emitted}^{sample}(\lambda) - Int_{absorbed}^{sample}(\lambda)] d\lambda}{\int \frac{\lambda}{hc} [Int_{emitted}^{reference}(\lambda) - Int_{absorbed}^{reference}(\lambda)] d\lambda}$$

wherein $n_{photon}$ denotes the photon count and Int. the intensity.

Production and Characterization of Optoelectronic Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc. Accelerated lifetime measurements are performed (e.g. applying increased current densities). Exemplarily LT80 values at 50 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given. Figures show the data series for one OLED pixel.

Example 1

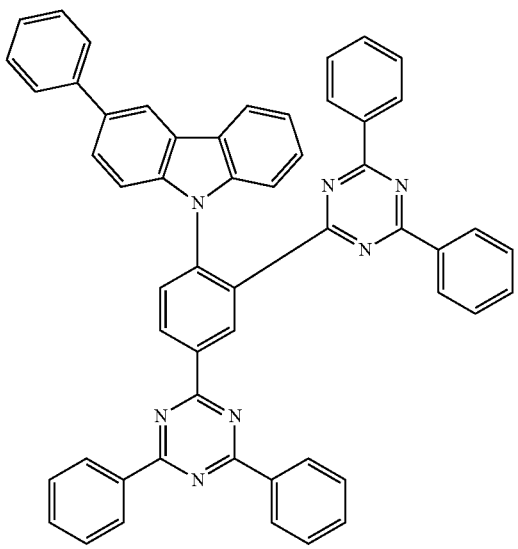 [SMILES: c1ccc(-c2ccc3c(c2)c2ccccc2n3-c2ccc(-c3nc(-c4ccccc4)nc(-c4ccccc4)n3)cc2-c2nc(-c3ccccc3)nc(-c3ccccc3)n2)cc1]

Example 1 was synthesized according to AAV1 (95% yield) and AAV10 (45% yield).

MS (HPLC-MS), m/z (13.80 min): 781

FIG. 1 depicts the emission spectrum of example 1 (10% by weight in PMMA). The emission maximum is at 484 nm. The photoluminescence quantum yield (PLQY) is 81%, the full width at half maximum is 0.39 eV, and the emission lifetime is 35 µs. The $CIE_x$ value is 0.19 and $CIE_y$ value is 0.37.

Example 2

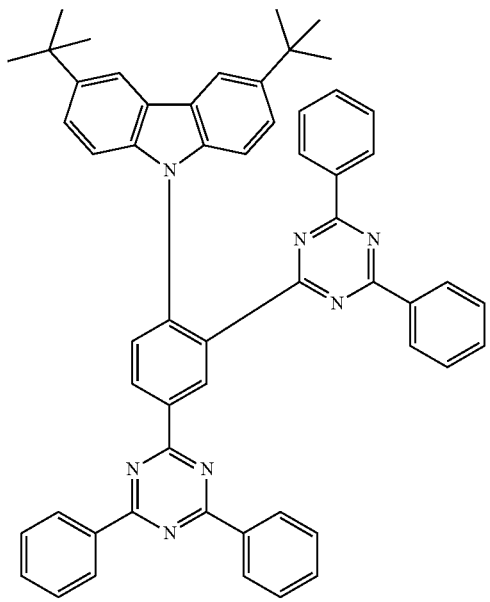 [SMILES: CC(C)(C)c1ccc2c(c1)c1cc(C(C)(C)C)ccc1n2-c1ccc(-c2nc(-c3ccccc3)nc(-c3ccccc3)n2)cc1-c1nc(-c2ccccc2)nc(-c2ccccc2)n1]

Example 2 was synthesized according to AAV1 (95% yield) and AAV10 (19% yield).

$^1$H-NMR (500 MHz, CDCl$_3$): δ=10.02 (d, 1H), 9.16 (dd, 1H), 8.88-8.90 (m, 4H), 8.14-8.16 (m, 4H), 8.02 (d, 2H), 7.91 (d, 1H), 7.61-7.68 (m, 6H), 7.49-7.52 (m, 3H), 7.34-7.38 (m, 5H), 7.18 (d, 2H), 1.56 (s, 18H) ppm.

FIG. 2 depicts the emission spectrum of example 2 (10% by weight in PMMA). The emission maximum is at 487 nm. The photoluminescence quantum yield (PLQY) is 87%, the full width at half maximum is 0.37 eV, and the emission lifetime is 26 μs. The CIE$_x$ value is 0.20 and CIE$_y$ value is 0.43.

Example 3

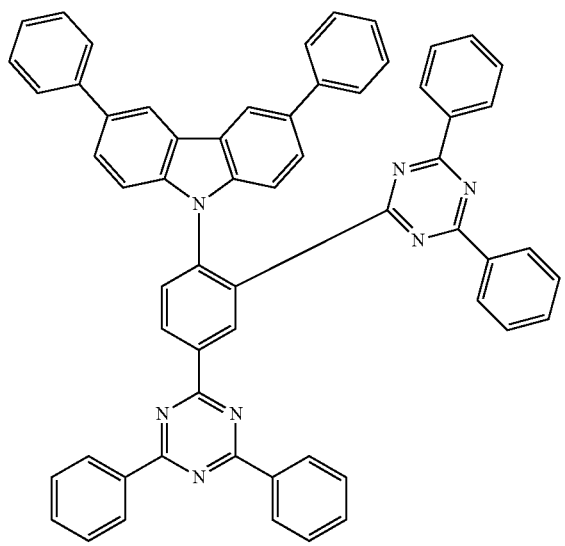 [SMILES: c1ccc(-c2ccc3c(c2)c2cc(-c4ccccc4)ccc2n3-c2ccc(-c3nc(-c4ccccc4)nc(-c4ccccc4)n3)cc2-c2nc(-c3ccccc3)nc(-c3ccccc3)n2)cc1]

Example 3 was synthesized according to AAV1 (95% yield) and AAV10 (84% yield). FIG. 3 depicts the emission spectrum of example 3 (10% by weight in PMMA). The emission maximum is at 491 nm. The photoluminescence quantum yield (PLQY) is 85%, the full width at half maximum is 0.37 eV, and the emission lifetime is 20 μs. The CIE$_x$ value is 0.20 and CIE$_y$ value is 0.42.

Example 4

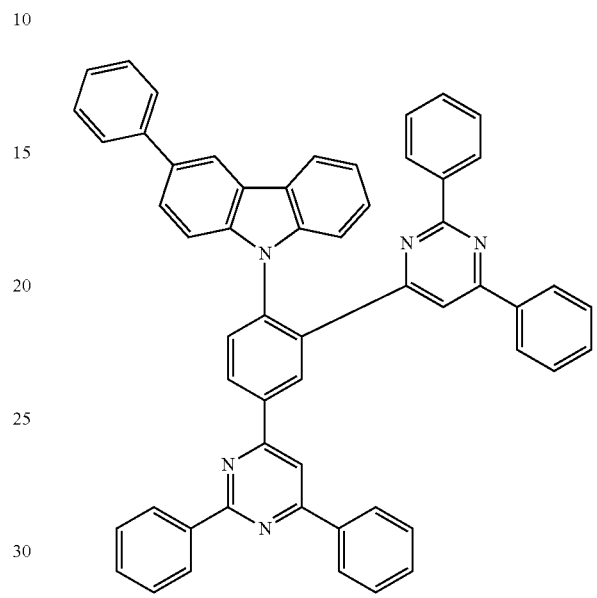

Example 4 was synthesized according to AAV2 (96% yield) and AAV10 (87% yield).

MS (HPLC-MS), m/z (12.06 min): 779

FIG. 4 depicts the emission spectrum of example 4 (10% by weight in PMMA). The emission maximum is at 447 nm. The photoluminescence quantum yield (PLQY) is 49% and the full width at half maximum is 0.43 eV. The CIE$_x$ value is 0.15 and CIE$_y$ value is 0.11.

Example 5

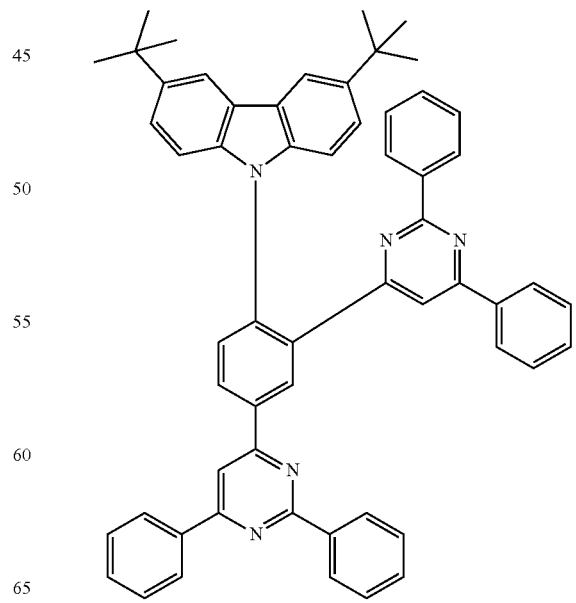

Example 5 was synthesized according to AAV2 (96% yield) and AAV10 (84% yield).

MS (HPLC-MS), m/z (14.86 min): 815

FIG. 5 depicts the emission spectrum of example 5 (10% by weight in PMMA). The emission maximum is at 453 nm. The photoluminescence quantum yield (PLQY) is 62% and the full width at half maximum is 0.42 eV. The $CIE_x$ value is 0.15 and $CIE_y$ value is 0.12.

Example 6

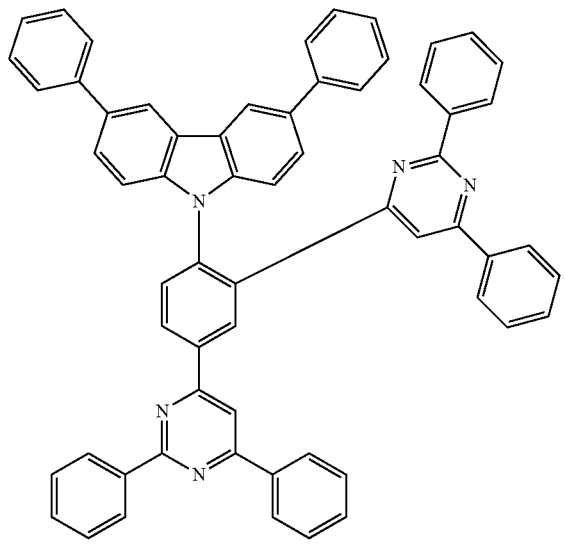 [SMILES: c1ccc(-c2ccc3c(c2)c2cc(-c4ccccc4)ccc2n3-c2ccc(-c3cc(-c4ccccc4)nc(-c4ccccc4)n3)cc2-c2cc(-c3ccccc3)nc(-c3ccccc3)n2)cc1]

Example 6 was synthesized according to AAV2 (96% yield) and AAV10 (79% yield).

MS (HPLC-MS), m/z (12.90 min): 855

FIG. 6 depicts the emission spectrum of example 6 (10% by weight in PMMA). The emission maximum is at 457 nm. The photoluminescence quantum yield (PLQY) is 54% and the full width at half maximum is 0.41 eV. The $CIE_x$ value is 0.15 and $CIE_y$ value is 0.14.

Example 7

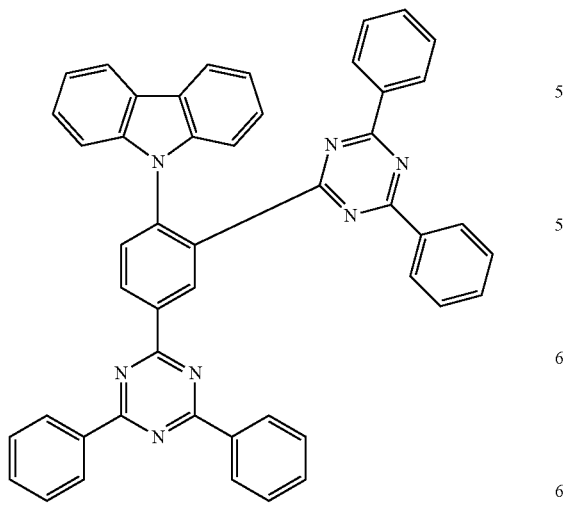

Example 7 was synthesized according to AAV1 (95% yield) and AAV10 (87% yield).

MS (HPLC-MS), m/z (12.77 min): 706

FIG. 7 depicts the emission spectrum of example 7 (10% by weight in PMMA). The emission maximum is at 458 nm. The photoluminescence quantum yield (PLQY) is 79%, the full width at half maximum is 0.40 eV, and the emission lifetime is 33 μs. The $CIE_x$ value is 0.15 and $CIE_y$ value is 0.14.

Example 8

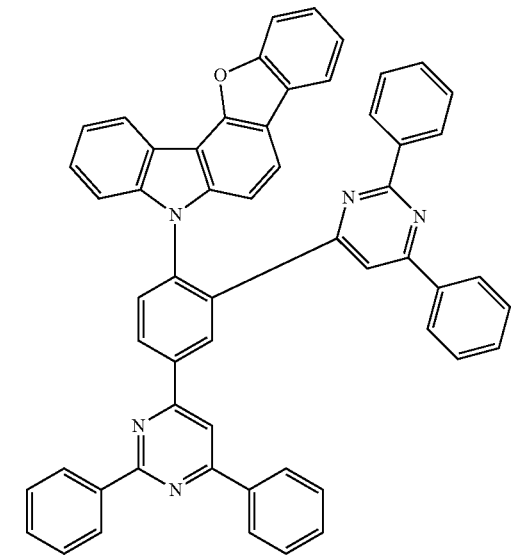 [SMILES: c1ccc(-c2cc(-c3ccc(-n4c5ccccc5c5c6oc7ccccc7c6ccc54)c(-c4cc(-c5ccccc5)nc(-c5ccccc5)n4)c3)nc(-c3ccccc3)n2)cc1]

Example 8 was synthesized according to AAV2 (96% yield) and AAV10 (99% yield).

MS (HPLC-MS), m/z (11.94 min): 793

FIG. 8 depicts the emission spectrum of example 8 (10% by weight in PMMA). The emission maximum of the emission spectrum of example 8 is at 449 nm. The photoluminescence quantum yield (PLQY) is 51% and the full width at half maximum is 0.44 eV. The $CIE_x$ value is 0.15 and $CIE_y$ value is 0.13.

Example 9

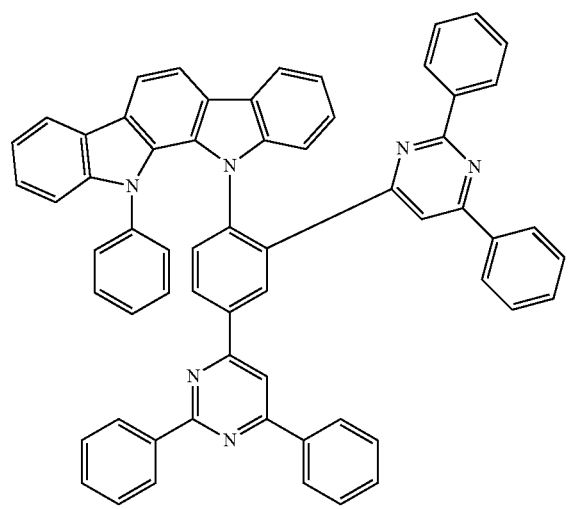 [SMILES: c1ccc(-c2cc(-c3ccc(-n4c5ccccc5c5ccc6c7ccccc7n(-c7ccccc7)c6c54)c(-c4cc(-c5ccccc5)nc(-c5ccccc5)n4)c3)nc(-c3ccccc3)n2)cc1]

Example 9 was synthesized according to AAV2 (96% yield) and AAV10 (76% yield).

MS (HPLC-MS), m/z (11.31 min): 869

FIG. 9 depicts the emission spectrum of example 9 (10% by weight in PMMA). The emission maximum of the emission spectrum of example 9 is at 471 nm. The photoluminescence quantum yield (PLQY) is 77% and the full width at half maximum is 0.46 eV. The CIEx value is 0.17 and CIEy value is 0.23.

Example 10

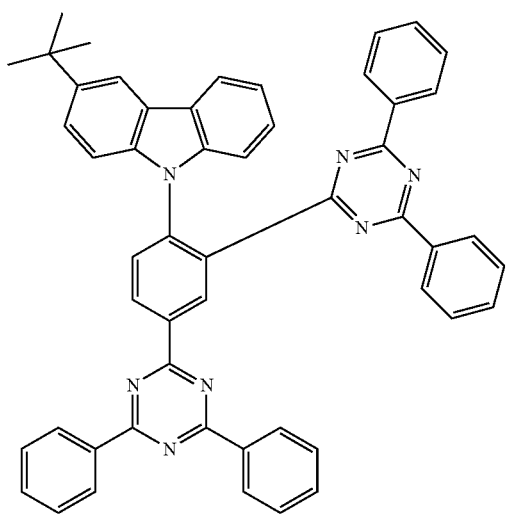 [SMILES: CC(C)(C)c1ccc2c(c1)c1ccccc1n2-c1ccc(-c2nc(-c3ccccc3)nc(-c3ccccc3)n2)cc1-c1nc(-c2ccccc2)nc(-c2ccccc2)n1]

Example 10 was synthesized according to AAV1 (95% yield) and AAV10 (85% yield). FIG. 10 depicts the emission spectrum of example 10 (10% by weight in PMMA). The emission maximum is at 482 nm. The photoluminescence quantum yield (PLQY) is 86%, the full width at half maximum is 0.38 eV, and the emission lifetime is 5 μs. The $CIE_x$ value is 0.18 and $CIE_y$ value is 0.34.

Example 11

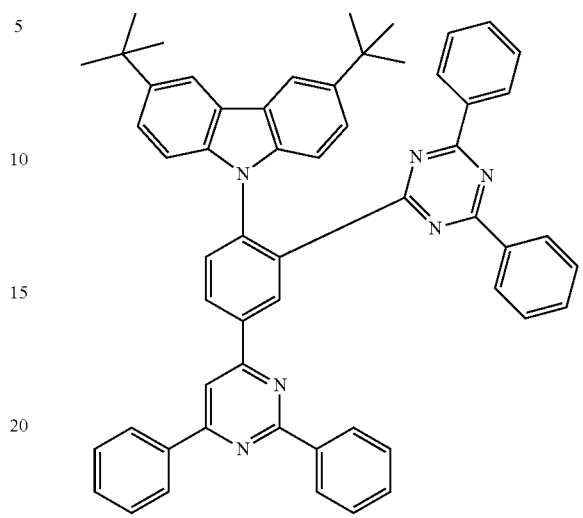

Example 11 was synthesized according to AAV6-2 (95% yield) and AAV10 (93% yield).

MS (HPLC-MS), m/z (27.63 min): 817

FIG. 11 depicts the emission spectrum of example 11 (10% by weight in PMMA). The emission maximum is at 487 nm. The photoluminescence quantum yield (PLQY) is 88%, the full width at half maximum is 0.38 eV, and the emission lifetime is 4 μs. The $CIE_x$ value is 0.19 and $CIE_y$ value is 0.39.

Example 12

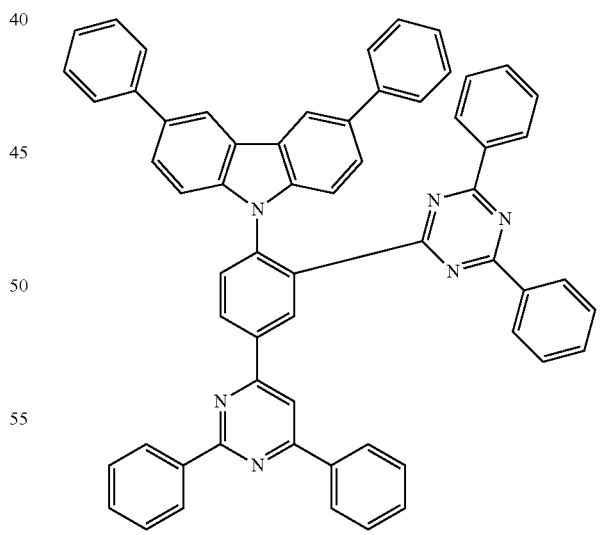

Example 12 was synthesized according to AAV6-2 (95% yield) and AAV10 (99% yield).

MS (HPLC-MS), m/z (26.11 min): 857

FIG. 12 depicts the emission spectrum of example 12 (10% by weight in PMMA). The emission maximum is at 484 nm. The photoluminescence quantum yield (PLQY) is 88%, the full width at half maximum is 0.39 eV, and the emission lifetime is 5 µs. The CIE$_x$ value is 0.18 and CIE$_y$ value is 0.36.

Example 13

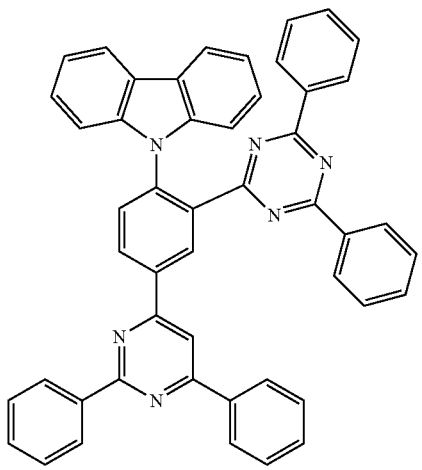 [SMILES: c1ccc(-c2cc(-c3ccc(-n4c5ccccc5c5ccccc54)c(-c4nc(-c5ccccc5)nc(-c5ccccc5)n4)c3)nc(-c3ccccc3)n2)cc1]

Example 13 was synthesized according to AAV4-2 (95% yield) and AAV10 (58% yield).

MS (HPLC-MS), m/z (24.79 min): 704

FIG. 13 depicts the emission spectrum of example 13 (10% by weight in PMMA). The emission maximum is at 465 nm. The photoluminescence quantum yield (PLQY) is 81%, the full width at half maximum is 0.39 eV, and the emission lifetime is 41 µs. The CIE$_x$ value is 0.15 and CIE$_y$ value is 0.20.

Example 14

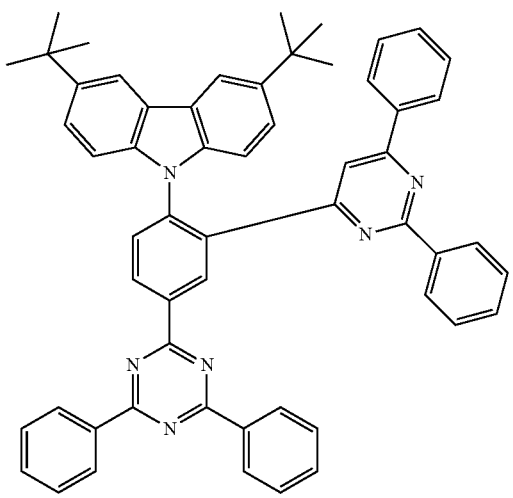 [SMILES: CC(C)(C)c1ccc2c(c1)c1cc(C(C)(C)C)ccc1n2-c1ccc(-c2nc(-c3ccccc3)nc(-c3ccccc3)n2)cc1-c1cc(-c2ccccc2)nc(-c2ccccc2)n1]

Example 14 was synthesized according to AAV4-2 (95% yield) and AAV10 (94% yield).

MS (HPLC-MS), m/z (28.65): 816

FIG. 14 depicts the emission spectrum of example 14 (10% by weight in PMMA). The emission maximum is at 465 nm. The photoluminescence quantum yield (PLQY) is 78%, the full width at half maximum is 0.41 eV, and the emission lifetime is 58 µs. The CIE$_x$ value is 0.15 and CIE$_y$ value is 0.19.

Example 15

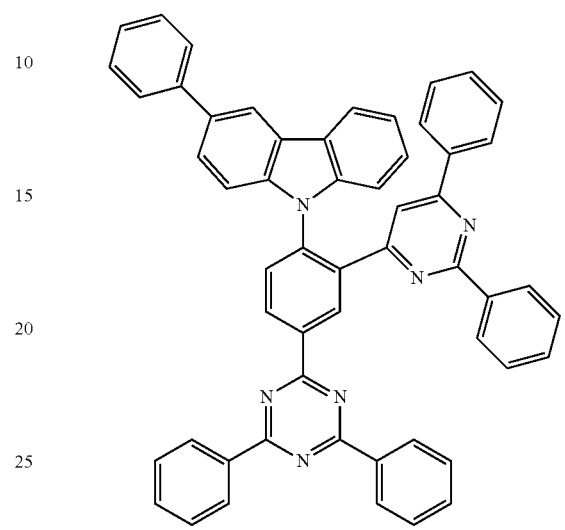

Example 15 was synthesized according to AAV4-2 (95% yield) and AAV10 (89% yield).

MS (HPLC-MS), m/z (19.17 min): 780

FIG. 15 depicts the emission spectrum of example 15 (10% by weight in PMMA). The emission maximum is at 462 nm. The photoluminescence quantum yield (PLQY) is 73%, the full width at half maximum is 0.42 eV, and the emission lifetime is 66 µs. The CIE$_x$ value is 0.15 and CIE$_y$ value is 0.17.

Example 16

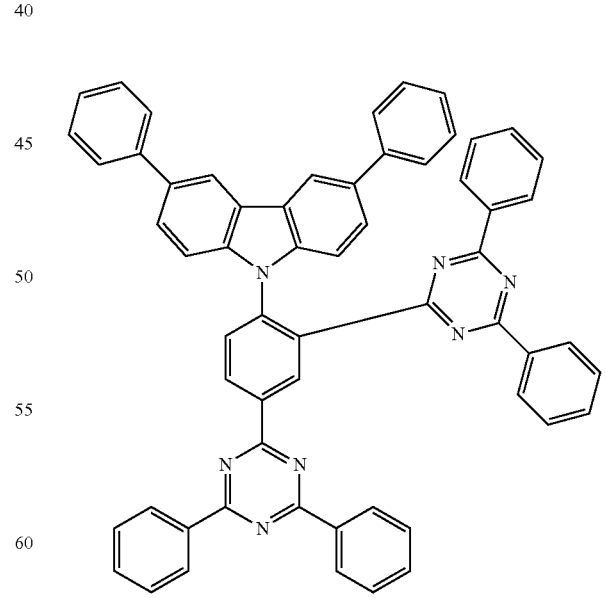

Example 16 was synthesized according to AAV5-2 and AAV10 (94% yield).

FIG. 16 depicts the emission spectrum of example 16 (10% by weight in PMMA). The emission maximum is at 466 nm. The photoluminescence quantum yield (PLQY) is 77%, the full width at half maximum is 0.40 eV, and the emission lifetime is 27 μs. The CIE$_x$ value is 0.16 and CIE$_y$ value is 0.22.

Example 17

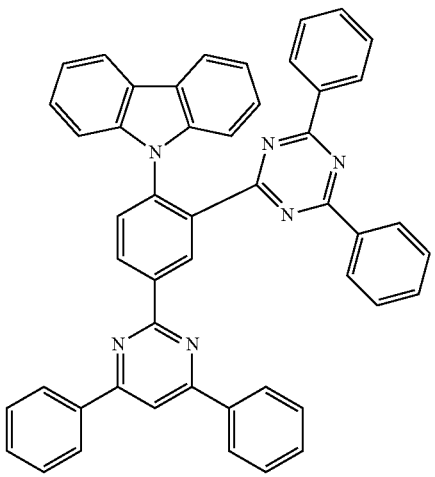 [SMILES: c1ccc(-c2cc(-c3ccccc3)nc(-c3ccc(-n4c5ccccc5c5ccccc54)c(-c4nc(-c5ccccc5)nc(-c5ccccc5)n4)c3)n2)cc1]

Example 17 was synthesized according to AAV8-2 (83% yield) and AAV10 (89% yield).

MS (HPLC-MS), m/z (16.35 min): 704

FIG. 17 depicts the emission spectrum of example 17 (10% by weight in PMMA). The emission maximum is at 450 nm. The photoluminescence quantum yield (PLQY) is 72%, the full width at half maximum is 0.41 eV, and the emission lifetime is 265 μs. The CIE$_x$ value is 0.15 and CIE$_y$ value is 0.13.

Example 18

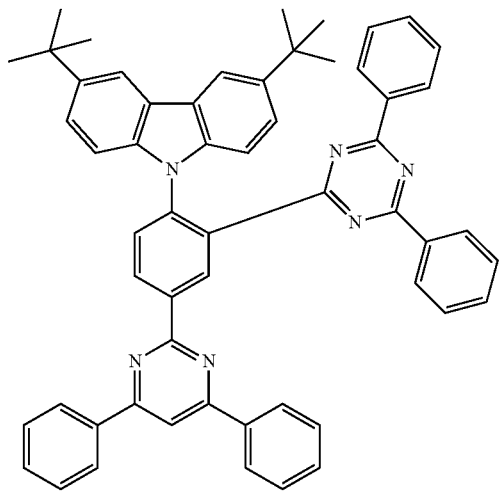 [SMILES: CC(C)(C)c1ccc2c(c1)c1cc(C(C)(C)C)ccc1n2-c1ccc(-c2nc(-c3ccccc3)cc(-c3ccccc3)n2)cc1-c1nc(-c2ccccc2)nc(-c2ccccc2)n1]

Example 18 was synthesized according to AAV8-2 (83% yield) and AAV10.

MS (HPLC-MS), m/z (27.56 min): 816

FIG. 18 depicts the emission spectrum of example 18 (10% by weight in PMMA). The emission maximum is at 481 nm. The photoluminescence quantum yield (PLQY) is 86%, the full width at half maximum is 0.38 eV, and the emission lifetime is 6 μs. The CIE$_x$ value is 0.18 and CIE$_y$ value is 0.34.

Example 19

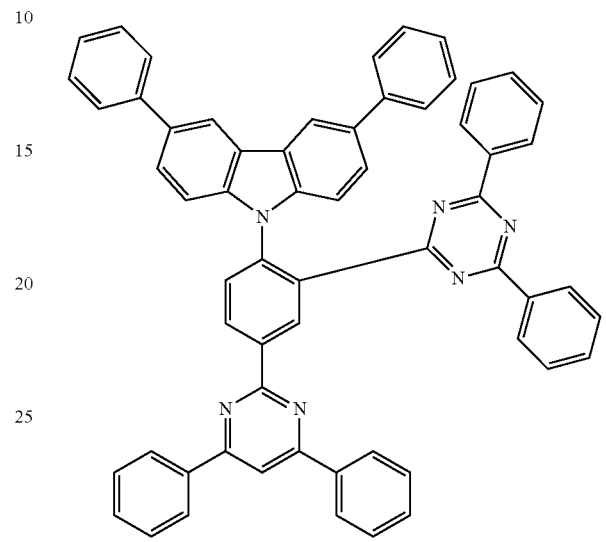

Example 19 was synthesized according to AAV8-2 (83% yield) and AAV10.

MS (HPLC-MS), m/z (26.04 min): 857

FIG. 19 depicts the emission spectrum of example 19 (10% by weight in PMMA). The emission maximum is at 482 nm. The photoluminescence quantum yield (PLQY) is 86%, the full width at half maximum is 0.38 eV, and the emission lifetime is 6 μs. The CIE$_x$ value is 0.18 and CIE$_y$ value is 0.34.

Example 20

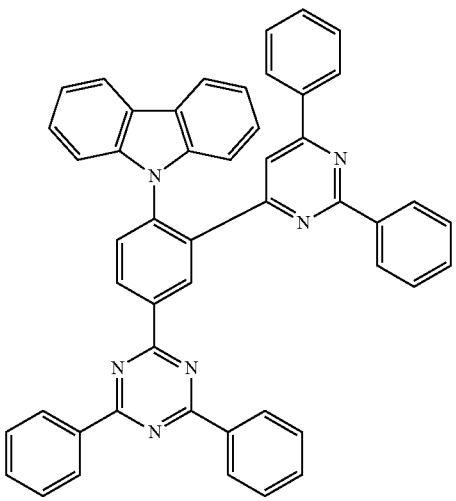 [SMILES: c1ccc(-c2cc(-c3cc(-c4nc(-c5ccccc5)nc(-c5ccccc5)n4)ccc3-n3c4ccccc4c4ccccc43)nc(-c3ccccc3)n2)cc1]

Example 20 was synthesized via the following reactions:

Z4 was synthesized similar to AAV4 via:

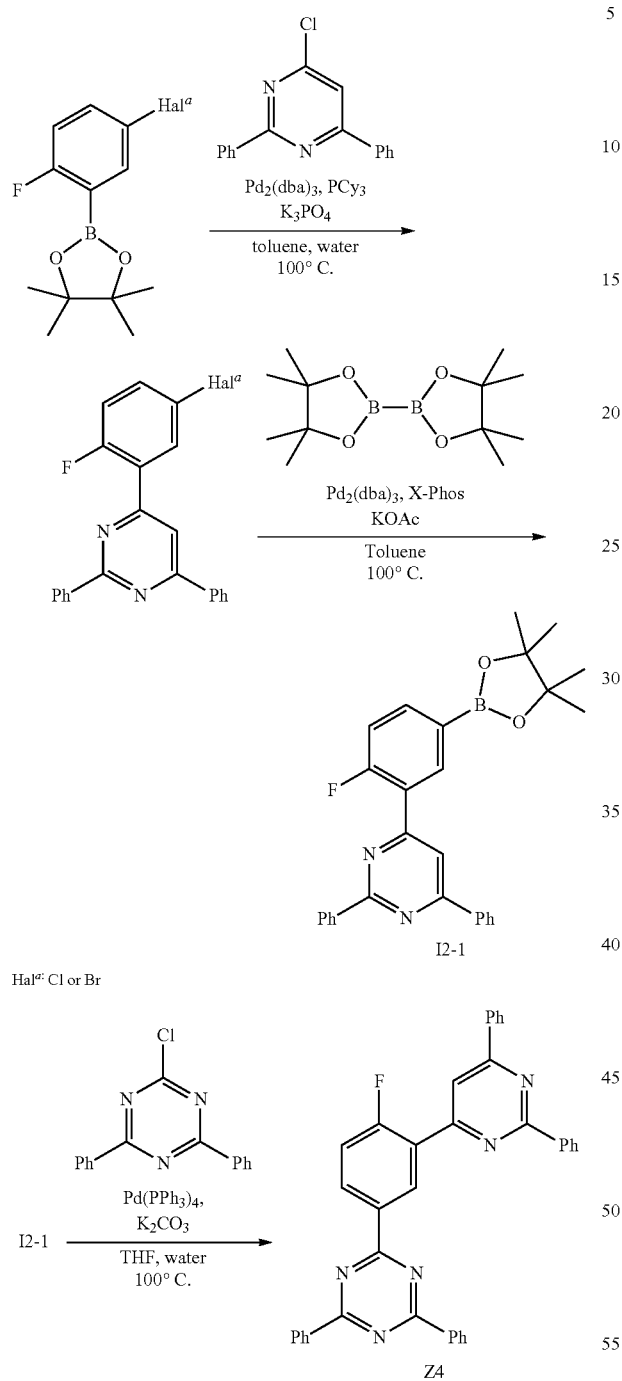

Hal$^a$: Cl or Br and example 20 was synthesized via AAV10 (90% yield).
MS (HPLC-MS), m/z (17.38 min): 704

FIG. 20 depicts the emission spectrum of example 20 (10% by weight in PMMA). The emission maximum is at 445 nm. The photoluminescence quantum yield (PLQY) is 59%, the full width at half maximum is 0.43 eV, and the emission lifetime is 139 μs. The $CIE_x$ value is 0.15 and $CIE_y$ value is 0.10.

Example 21

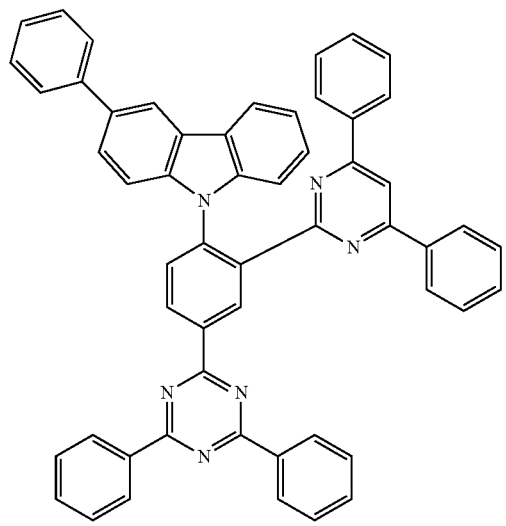 [SMILES: c1ccc(-c2ccc3c(c2)c2ccccc2n3-c2ccc(-c3nc(-c4ccccc4)nc(-c4ccccc4)n3)cc2-c2nc(-c3ccccc3)cc(-c3ccccc3)n2)cc1]

Example 21 was synthesized via the following reactions:

Z5 was synthesized similar to AAV5 via:

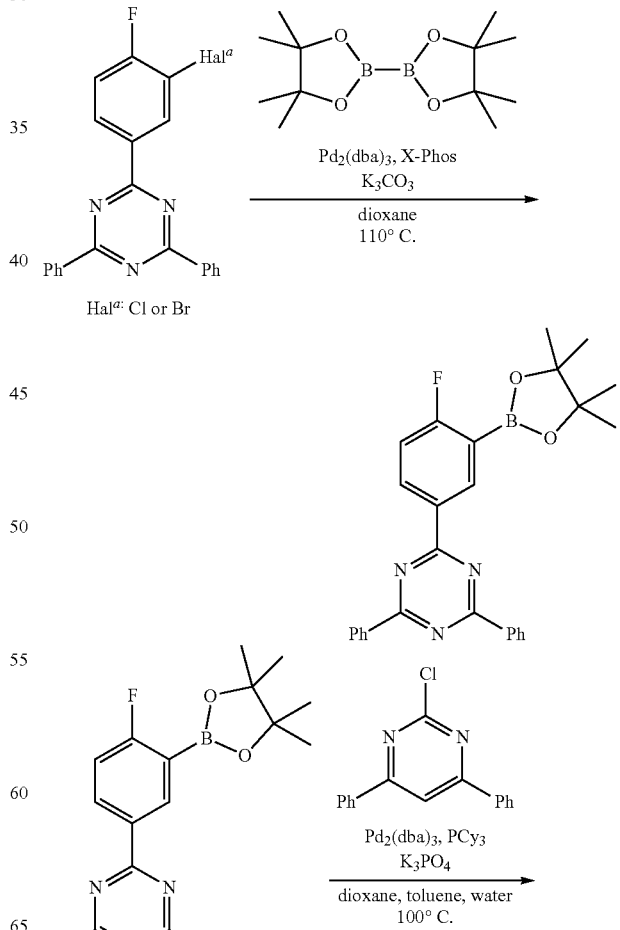

Hal$^a$: Cl or Br

-continued

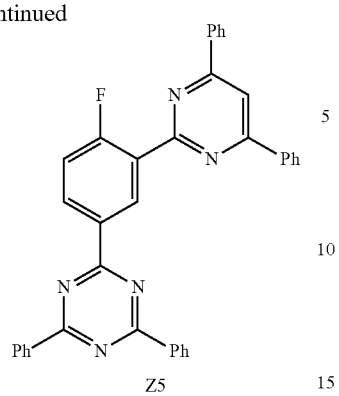

and example 21 was synthesized according to AAV10 (87% yield).

MS (HPLC-MS), m/z (25.49 min): 780.64

FIG. 21 depicts the emission spectrum of example 21 (10% by weight in PMMA). The emission maximum is at 464 nm. The photoluminescence quantum yield (PLQY) is 77%, the full width at half maximum is 0.42 eV, and the emission lifetime is 84 μs. The $CIE_x$ value is 0.15 and $CIE_y$ value is 0.16.

Example 22

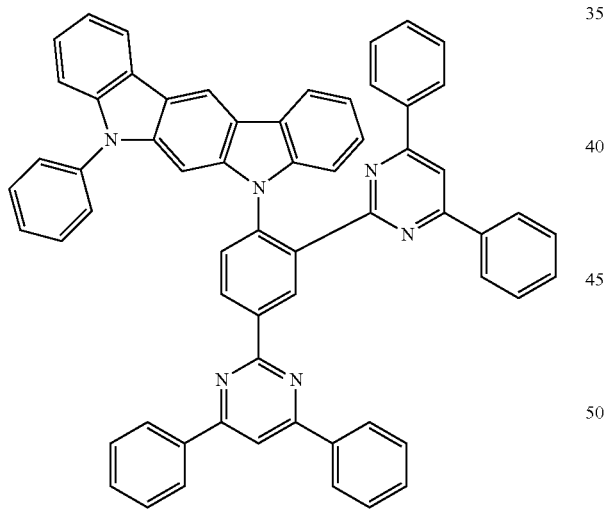

Example 22 was synthesized according to AAV3 (16% yield) and AAV10 (50% yield).

MS (HPLC-MS), m/z (16.84 min): 869

FIG. 22 depicts the emission spectrum of example 22 (10% by weight in PMMA). The emission maximum is at 459 nm. The photoluminescence quantum yield (PLQY) is 40%, the full width at half maximum is 0.39 eV, and the emission lifetime is 310 μs. The $CIE_x$ value is 0.15 and $CIE_y$ value is 0.16.

Example 23

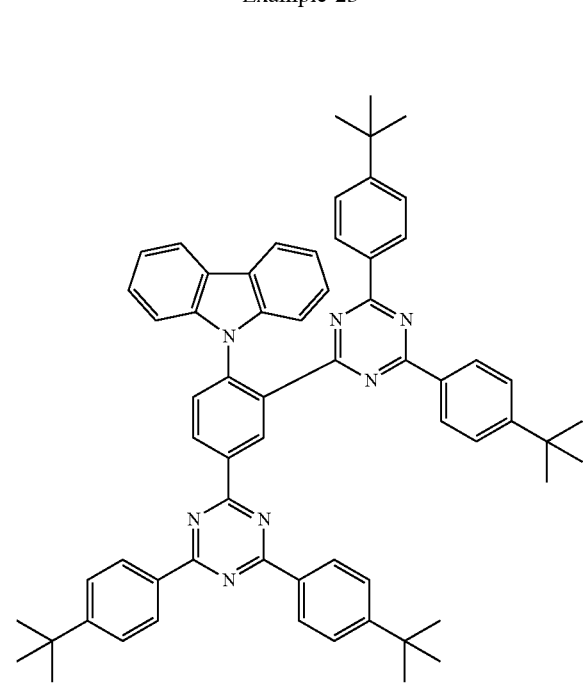

Example 23 was synthesized similar to AAV1 (63% yield), wherein

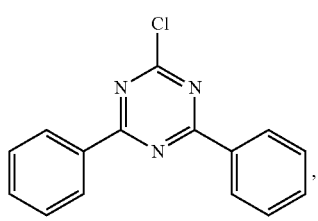 [SMILES: Clc1nc(-c2ccccc2)nc(-c2ccccc2)n1]

ptBuTrz was used as a reactant instead of yielding

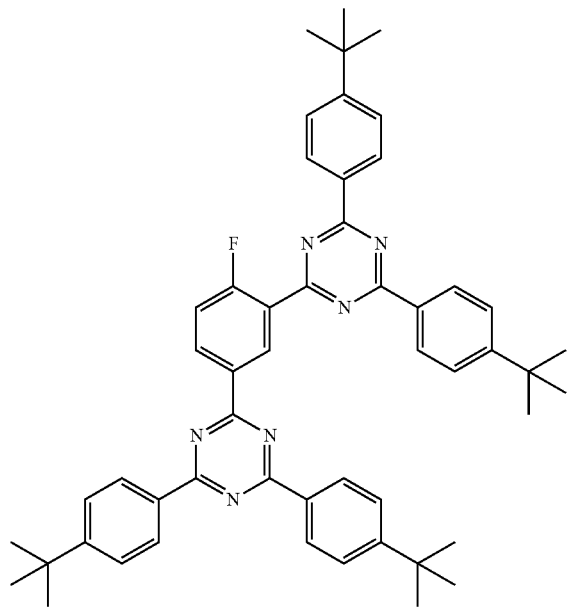 [SMILES: CC(C)(C)c1ccc(-c2nc(-c3ccc(C(C)(C)C)cc3)nc(-c3ccc(F)c(-c4nc(-c5ccc(C(C)(C)C)cc5)nc(-c5ccc(C(C)(C)C)cc5)n4)c3)n2)cc1]

which was used as reactant instead of Z1 according to AAV10 (69% yield).

ptBuTrz was synthesized via:

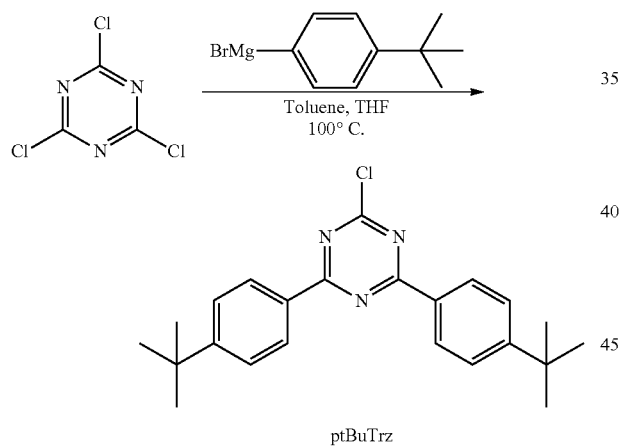

ptBuTrz

In a nitrogen atmosphere, a solution of benzene-1-magnesiumbromid-4-tert-butyl (2.50 eq.) was added dropwise to a solution of cyanuric chloride (1.00 eq.) in dry toluene. The reaction mixture was heated to 90° C. for 30 min. Reaction progress/completion of the reaction was checked using GCMS. After completion of the reaction, the reaction mixture was quenched with hydrochloric acid (1 mol/l) and afterwards neutralized with ammonium chloride solution. The reaction mixture was extracted with dichloromethane, washed with brine and dried over magnesium sulfate. Crude product was purified by recrystallization from n-hexane.

MS (HPLC-MS), m/z (34.46 min): 929

FIG. 23 depicts the emission spectrum of example 23 (10% by weight in PMMA). The emission maximum is at 457 nm. The photoluminescence quantum yield (PLQY) is 70%, the full width at half maximum is 0.39 eV, and the emission lifetime is 94 μs. The $CIE_x$ value is 0.15 and $CIE_y$ value is 0.16.

Example 24

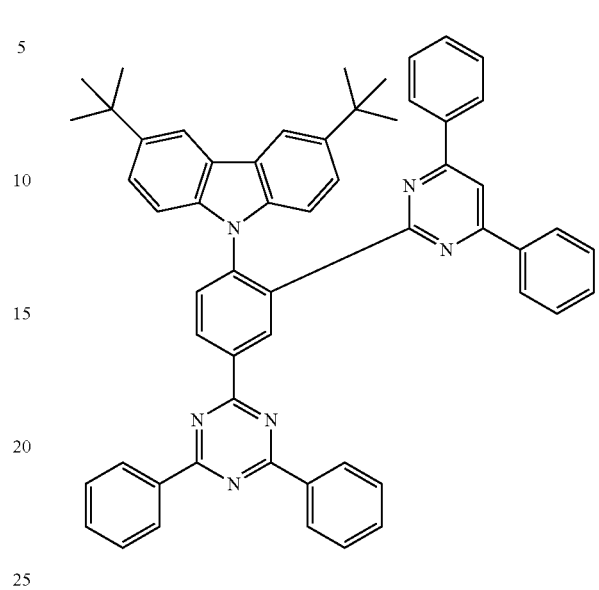

Example 24 was synthesized via the following reactions:

Z8 was synthesized similar to AAV-5 via:

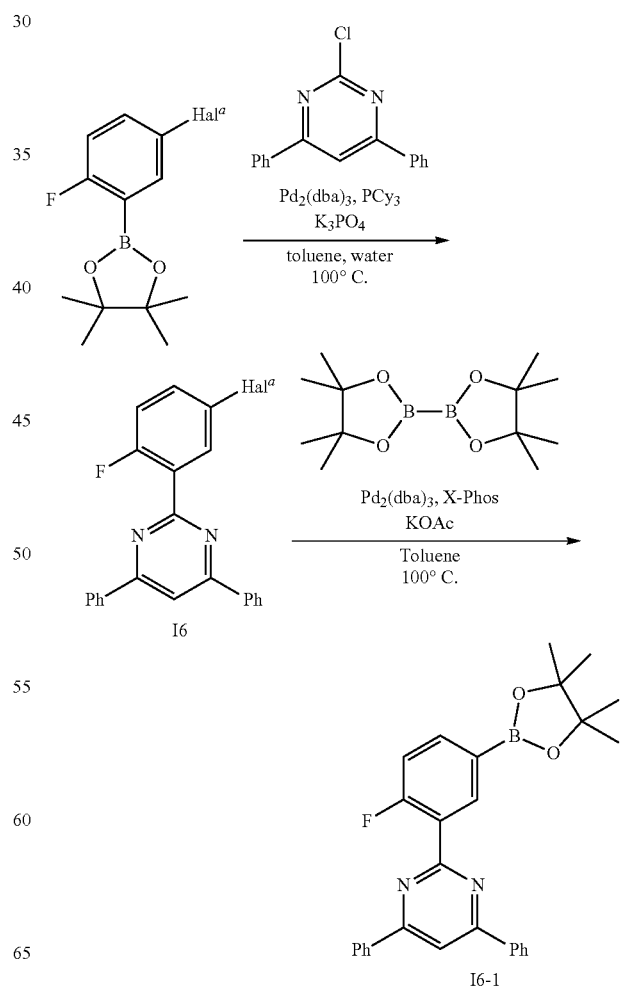

-continued

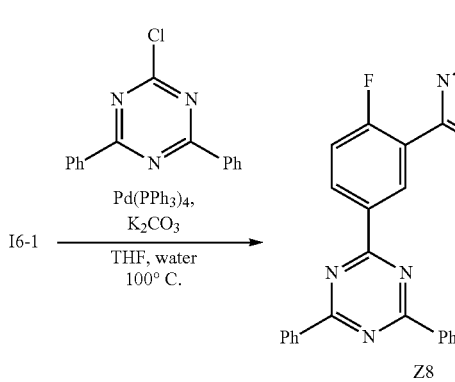

and example 24 was synthesized according to AAV10 (76% yield).

MS (HPLC-MS), m/z (21.25 min): 816.73

FIG. 24 depicts the emission spectrum of example 24 (10% by weight in PMMA). The emission maximum is at 472 nm. The photoluminescence quantum yield (PLQY) is 76%, the full width at half maximum is 0.39 eV, and the emission lifetime is 95 μs. The $CIE_x$ value is 0.16 and $CIE_y$ value is 0.24.

Example 25

Example 25 was synthesized similar to AAV8-2 via

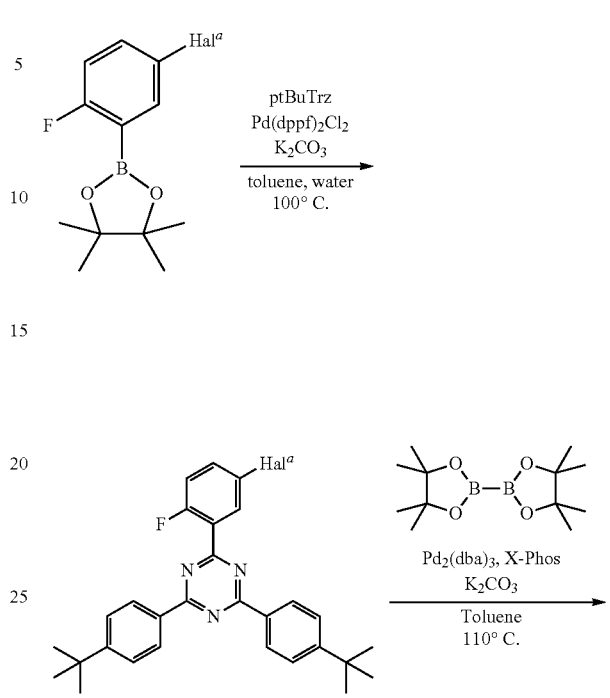

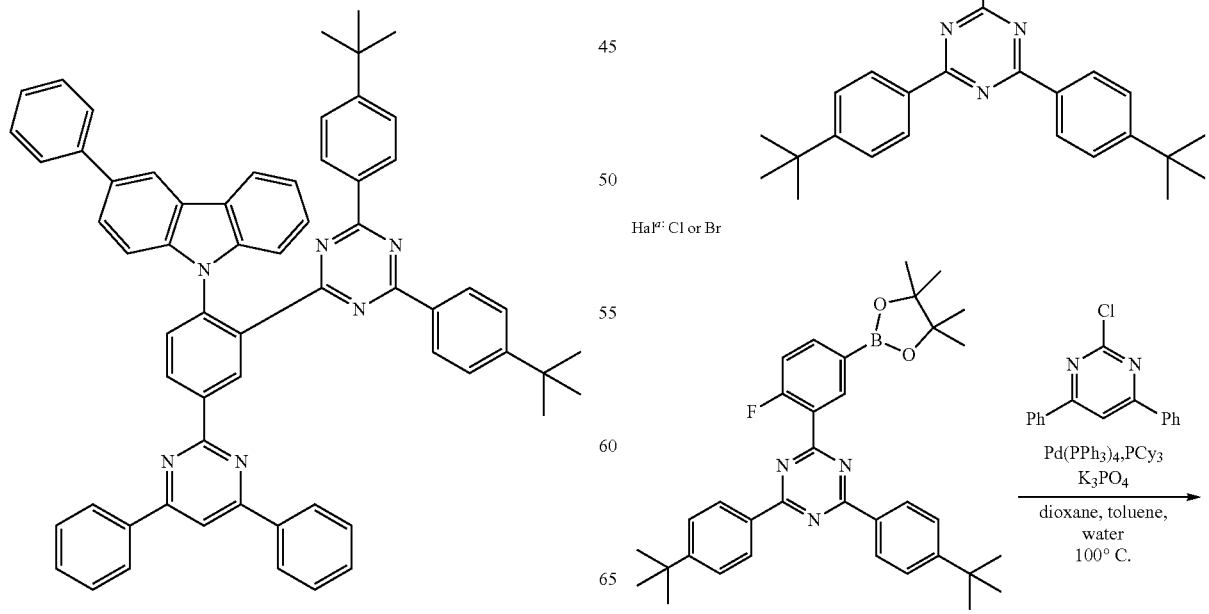

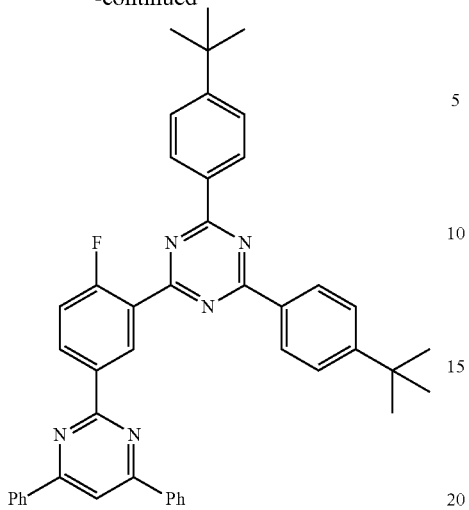

and AAV10 (37% yield).

MS (HPLC-MS), m/z (23.49 min): 892.6

FIG. 25 depicts the emission spectrum of example 25 (10% by weight in PMMA). The emission maximum is at 468 nm. The photoluminescence quantum yield (PLQY) is 69%, the full width at half maximum is 0.40 eV, and the emission lifetime is 77 μs. The $CIE_x$ value is 0.16 and $CIE_y$ value is 0.22.

Example 26

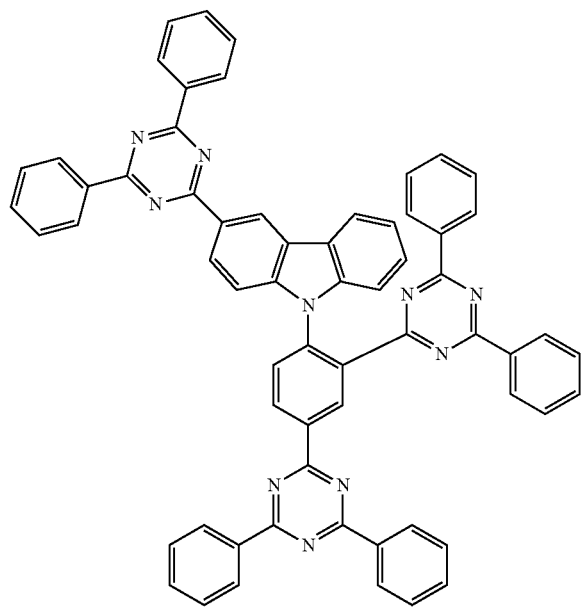 [SMILES: c1ccc(-c2nc(-c3ccccc3)nc(-c3ccc(-n4c5ccccc5c5cc(-c6nc(-c7ccccc7)nc(-c7ccccc7)n6)ccc54)c(-c4nc(-c5ccccc5)nc(-c5ccccc5)n4)c3)n2)cc1]

Example 26 was synthesized according to AAV1 and AAV0 (13% yield), wherein

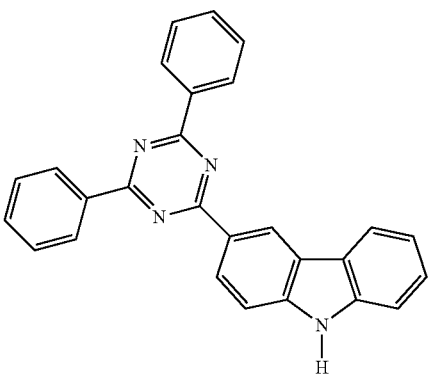 [SMILES: c1ccc(-c2nc(-c3ccccc3)nc(-c3ccc4[nH]c5ccccc5c4c3)n2)cc1]

was used as reactant D-H.

MS (HPLC-MS), m/z (28.49 min): 936.62

FIG. 26 depicts the emission spectrum of example 26 (10% by weight in PMMA). The emission maximum is at 461 nm. The photoluminescence quantum yield (PLQY) is 43%, the full width at half maximum is 0.37 eV, and the emission lifetime is 20 μs. The $CIE_x$ value is 0.16 and $CIE_y$ value is 0.18.

Example 27

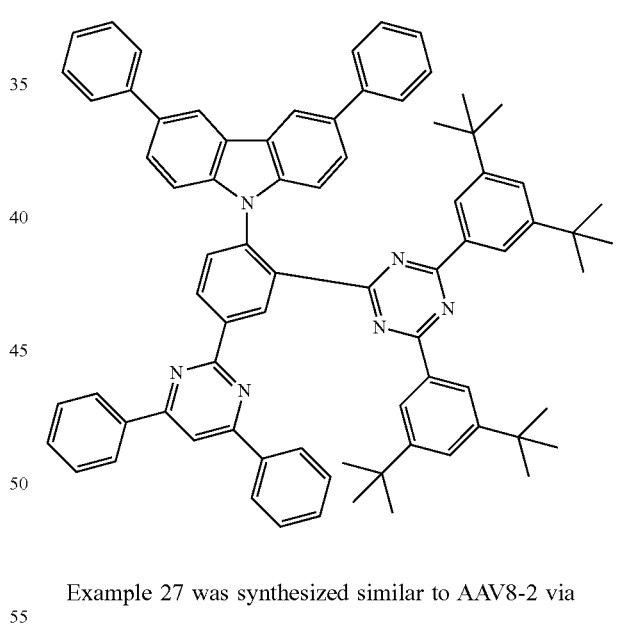

Example 27 was synthesized similar to AAV8-2 via

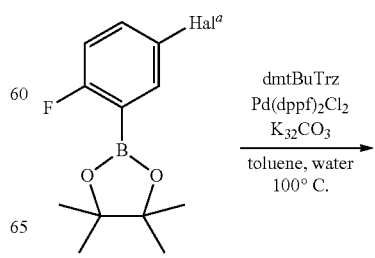

-continued

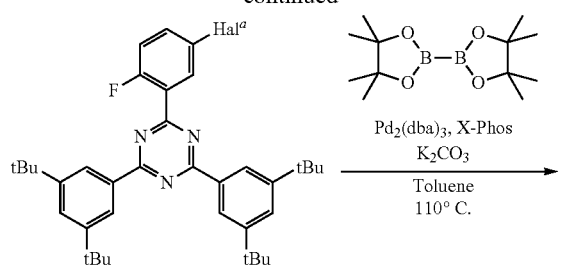

Hal$^a$: Cl or Br

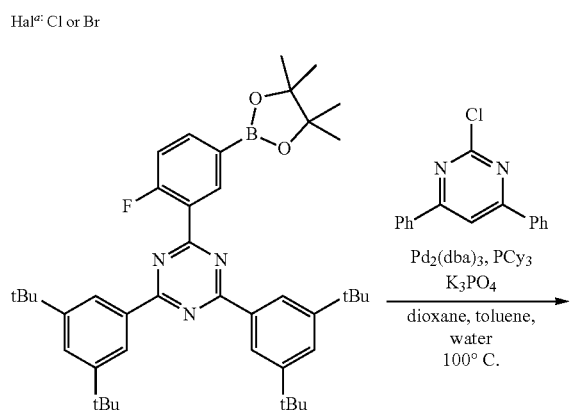

and AAV10 (95% yield);

wherein

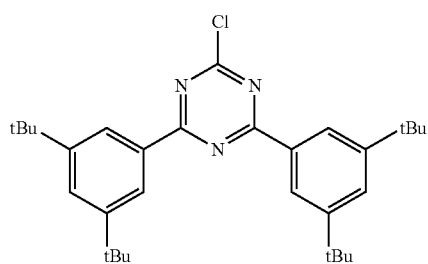

dmtBuTrz was used as a reactant instead of

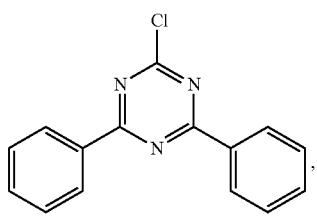 [SMILES: Clc1nc(-c2ccccc2)nc(-c2ccccc2)n1]

wherein dmtBuTrz was synthesized via:

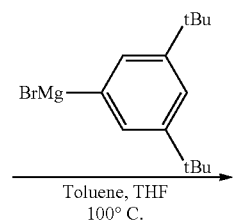

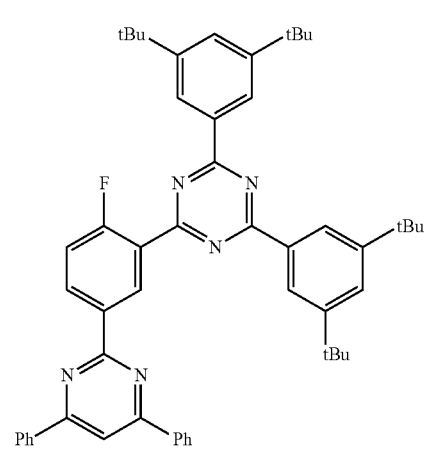

ptBuTrz

In a nitrogen atmosphere, a solution of 1-Bromo-3,5-di-tert-butylbenzene (2.50 eq.) in dry THF was added dropwise to a mixture of Mg-turnings in dry THF. After the exothermic reaction, the reaction mixture is refluxed for 3 h and then cooled to room temperature. This Grignard solution is then slowly added to cyanuric chloride (1.00 eq.) in dry toluene. The reaction mixture was heated to 90° C. for 30 min. Reaction progress/completion of the reaction was checked using GCMS. After completion of the reaction, the reaction mixture was quenched with hydrochloric acid (1 mol/l) and afterwards neutralized with ammonium chloride solution. The reaction mixture was extracted with dichloromethane, washed with brine and dried over magnesium sulfate. Crude product was purified by recrystallization from n-hexane.

MS (HPLC-MS), m/z (28.01 min): 1080.69

FIG. 27 depicts the emission spectrum of example 27 (10% by weight in PMMA). The emission maximum is at 465 nm. The photoluminescence quantum yield (PLQY) is 71%, the full width at half maximum is 0.39 eV, and the emission lifetime is 78 μs. The $CIE_x$ value is 0.15 and $CIE_y$ value is 0.20.

Example 28

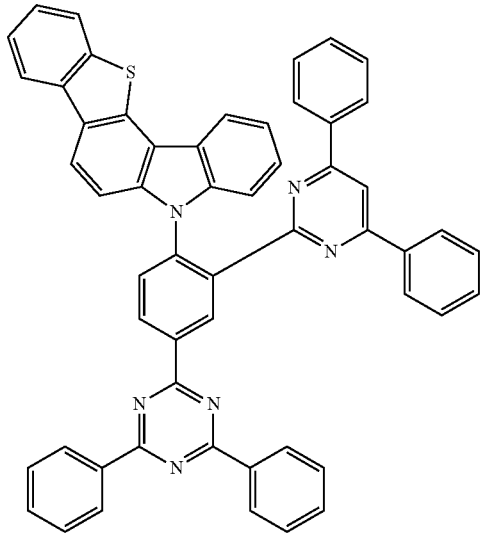 [SMILES: c1ccc(-c2cc(-c3ccccc3)nc(-c3cc(-c4nc(-c5ccccc5)nc(-c5ccccc5)n4)ccc3-n3c4ccccc4c4c5oc6ccccc6c5ccc43)n2)cc1]

Example 28 was synthesized via the following reactions:
Z5 was synthesized similar to AAV5 via:

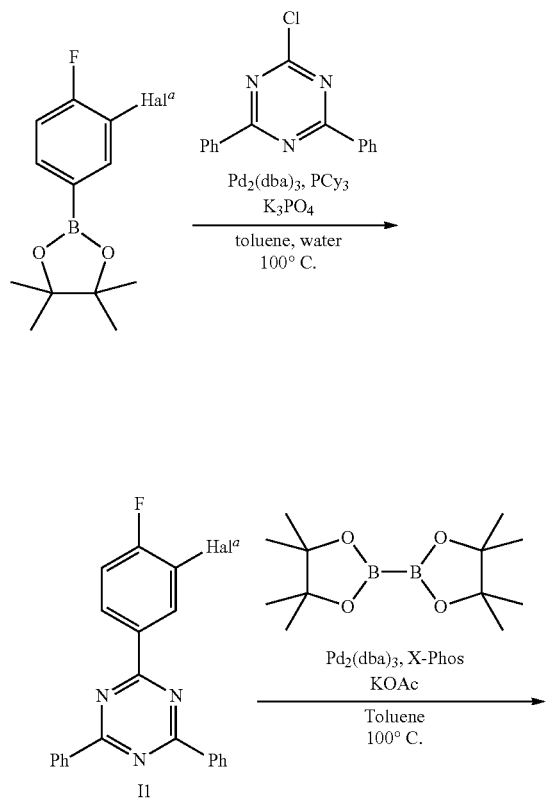

Hal$^a$: Cl or Br

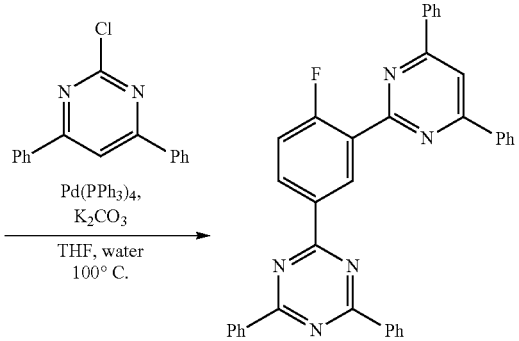

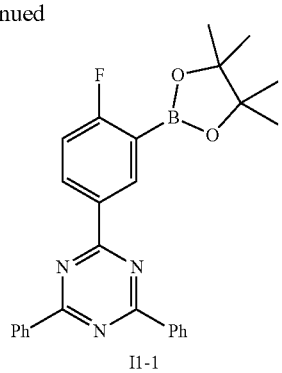

and examples 28 was synthesized accord to and AAV10 (94% yield).

MS (HPLC-MS), m/z (24.93 min): 811

FIG. 28 depicts the emission spectrum of example 28 (10% by weight in PMMA). The emission maximum is at 466 nm. The photoluminescence quantum yield (PLQY) is 69%, the full width at half maximum is 0.40 eV, and the emission lifetime is 54 μs. The $CIE_x$ value is 0.16 and $CIE_y$ value is 0.21.

Example 29

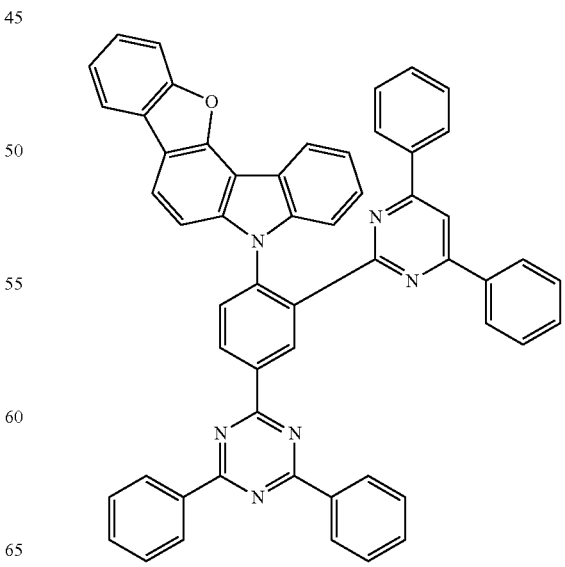

Example 29 was synthesized via the following reactions:
Z5 was synthesized similar to AAV5 via:

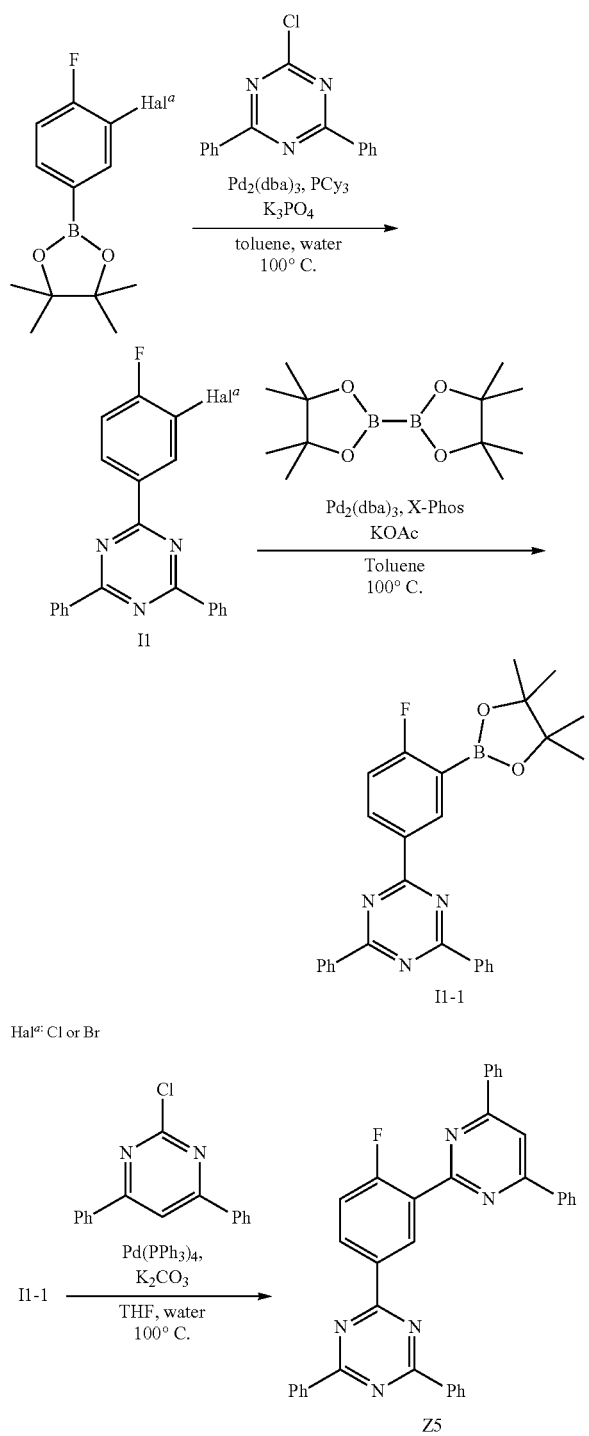

Hal$^a$: Cl or Br and example 29 was synthesized according to AAV10 (94% yield).

MS (HPLC-MS), m/z (24.67 min): 796

FIG. 29 depicts the emission spectrum of example 29 (10% by weight in PMMA). The emission maximum is at 466 nm. The photoluminescence quantum yield (PLQY) is 59%, the full width at half maximum is 0.42 eV, and the emission lifetime is 53 μs. The CIE$_x$ value is 0.16 and CIE$_y$ value is 0.21.

Example 30

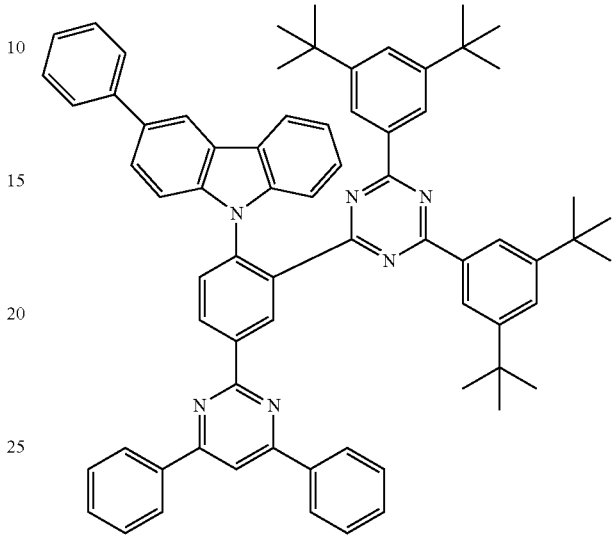

Example 30 was synthesized similar to AAV8-2 as described in the synthesis of examples 27, and AAV10 (83% yield); (cf. synthesis of example 27)

MS (HPLC-MS), m/z (26.50 min): 1004.73

FIG. 30 depicts the emission spectrum of example 30 (10% by weight in PMMA). The emission maximum is at 459 nm. The photoluminescence quantum yield (PLQY) is 65%, the full width at half maximum is 0.40 eV, and the emission lifetime is 236 μs. The CIE$_x$ value is 0.16 and CIE$_y$ value is 0.17.

Example D1

Example 3 was tested in the OLED D1, which was fabricated with the following layer structure:

| Layer | Thickness | D1 |
| --- | --- | --- |
| 9 | 100 nm | Al |
| 8 | 2 nm | Liq |
| 7 | 20 nm | NBPhen |
| 6 | 10 nm | T2T |
| 5 | 50 nm | Example 3 (10%): mCBP (90%) |
| 4 | 10 nm | mCBP |
| 3 | 10 nm | TCTA |
| 2 | 100 nm | NPB |
| 1 | 130 nm | ITO |
| Substrate | | glass |

Device D1 yielded an external quantum efficiency (EQE) at 1000 cd/m$^2$ of 15.3%. The emission maximum is at 485 nm with a FWHM of 58 nm at 5 V. The corresponding CIEx value is 0.17 and CIEy is 0.40.

Example D2

Example 16 was tested in the OLED D2, which was fabricated with the following layer structure:

| Layer | Thickness | D2 |
|---|---|---|
| 10 | 100 nm | Al |
| 9 | 2 nm | Liq |
| 8 | 20 nm | NBPhen |
| 7 | 10 nm | MAT1 |
| 6 | 30 nm | Example 16 (20%): mCBP (80%) |
| 5 | 10 nm | mCBP |
| 4 | 10 nm | TCTA |
| 3 | 40 nm | NPB |
| 2 | 5 nm | HAT-CN |
| 1 | 50 nm | ITO |
| substrate | | glass |

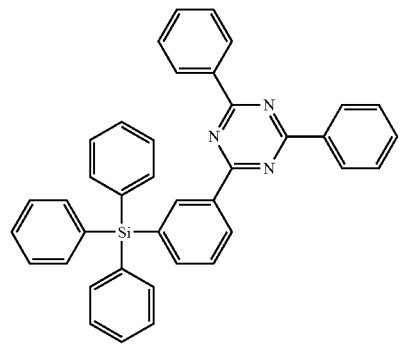 [SMILES: c1ccc(-c2nc(-c3ccccc3)nc(-c3cccc([Si](c4ccccc4)(c4ccccc4)c4ccccc4)c3)n2)cc1]

MAT1

Device D2 yielded an external quantum efficiency (EQE) at 1000 cd/m² of 16.4%. The emission maximum is at 469 nm with a FWHM of 60 nm at 6 V. The corresponding CIEx value is 0.15 and CIEy is 0.20.

Example D3

Example 7 was tested in the OLED D3, which was fabricated with the following layer structure:

| Layer | Thickness | D3 |
|---|---|---|
| 9 | 100 nm | Al |
| 8 | 2 nm | Liq |
| 7 | 30 nm | NBPhen |
| 6 | 30 nm | Example 7 (15%): MAT2 (1%): mCBP (84%) |
| 5 | 10 nm | mCBP |
| 4 | 10 nm | TCTA |
| 3 | 40 nm | NPB |
| 2 | 5 nm | HAT-CN |
| 1 | 50 nm | ITO |
| substrate | | glass |

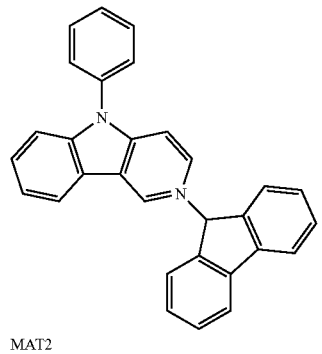

MAT2

Device D3 yielded an external quantum efficiency (EQE) at 1000 cd/m² of 11.6%. The emission maximum is at 464 nm with a FWHM of 56 nm at 5 V. The corresponding CIEx value is 0.14 and CIEy is 0.18.

Additional Examples of Organic Molecules According to the Invention

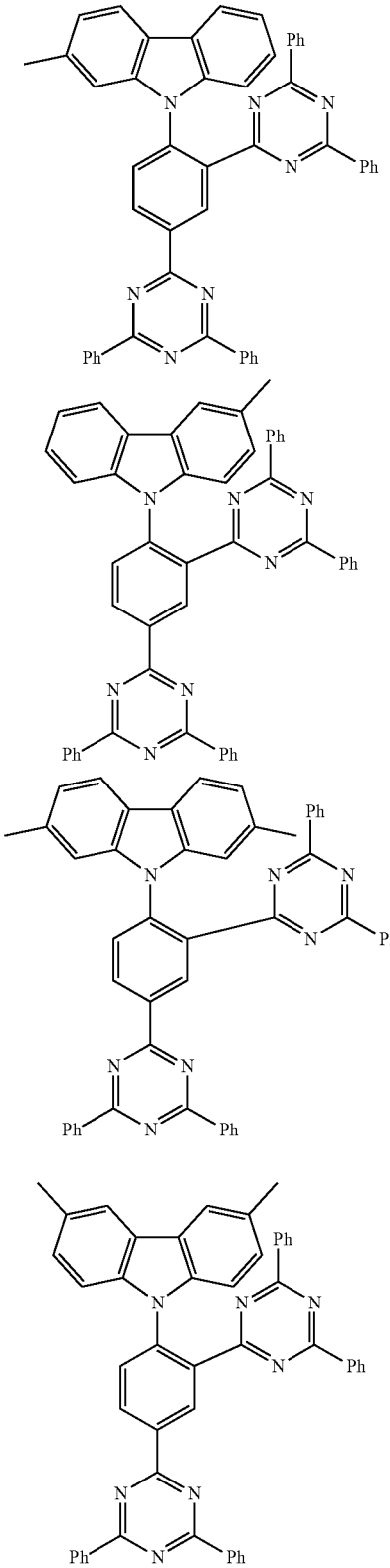

101
-continued
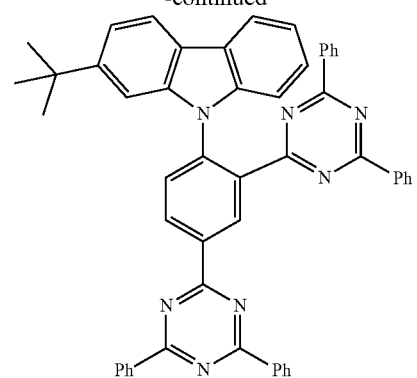
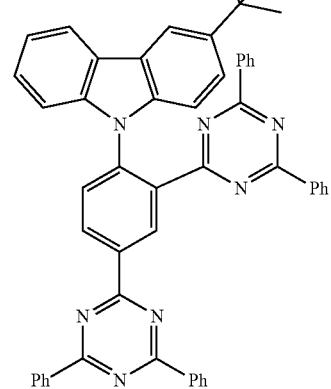
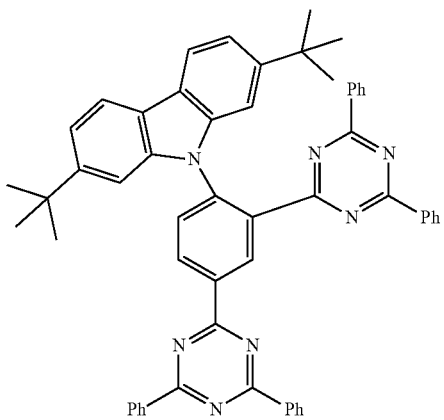
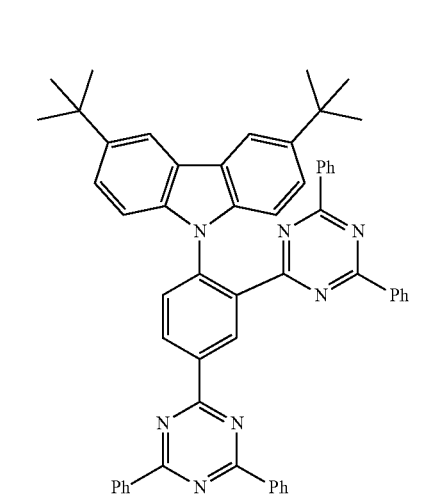
102
-continued
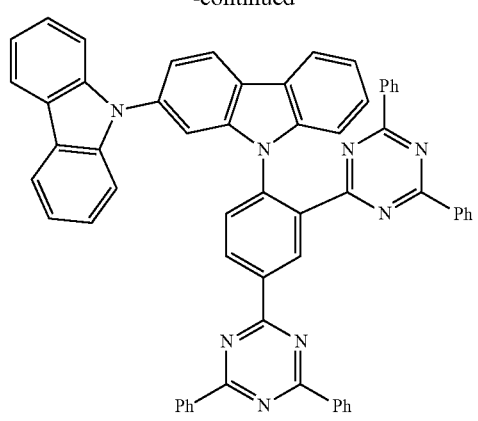
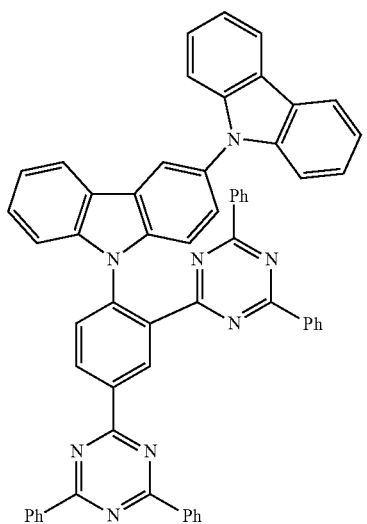
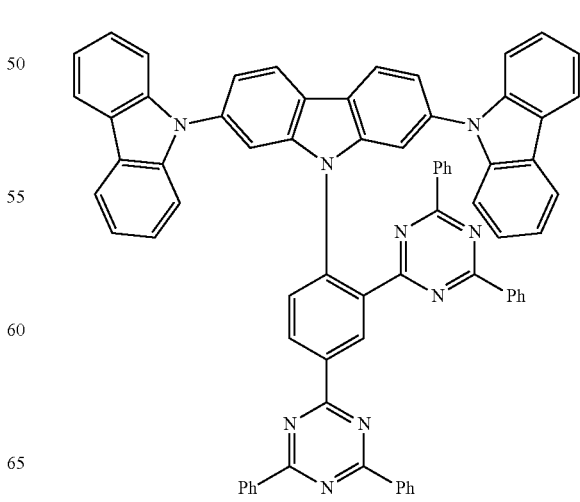

103
-continued
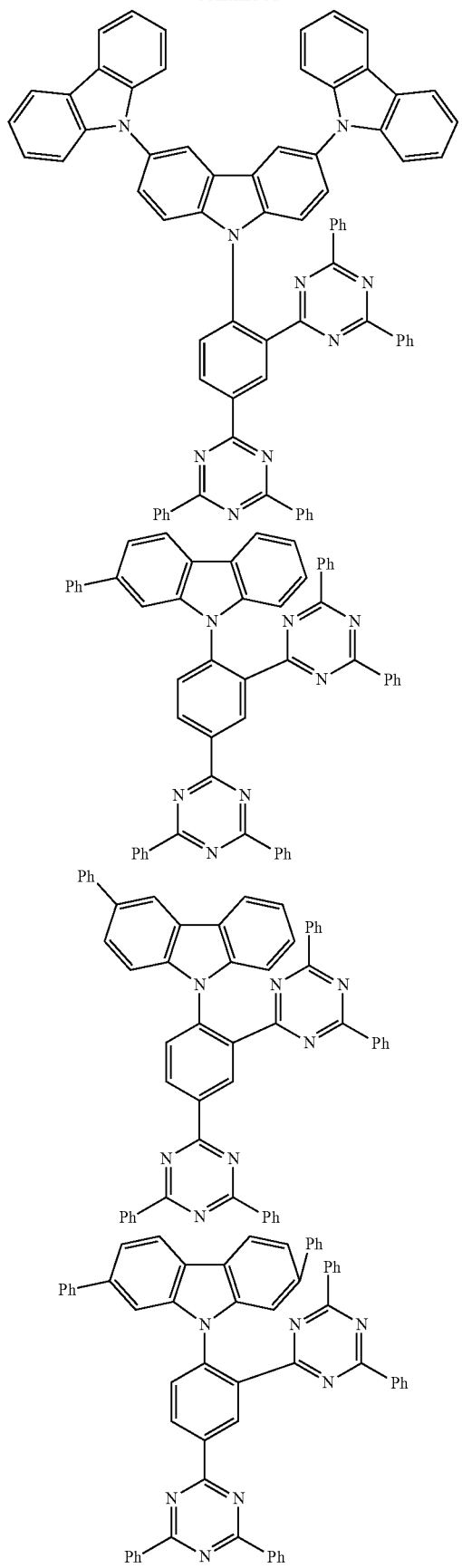
104
-continued
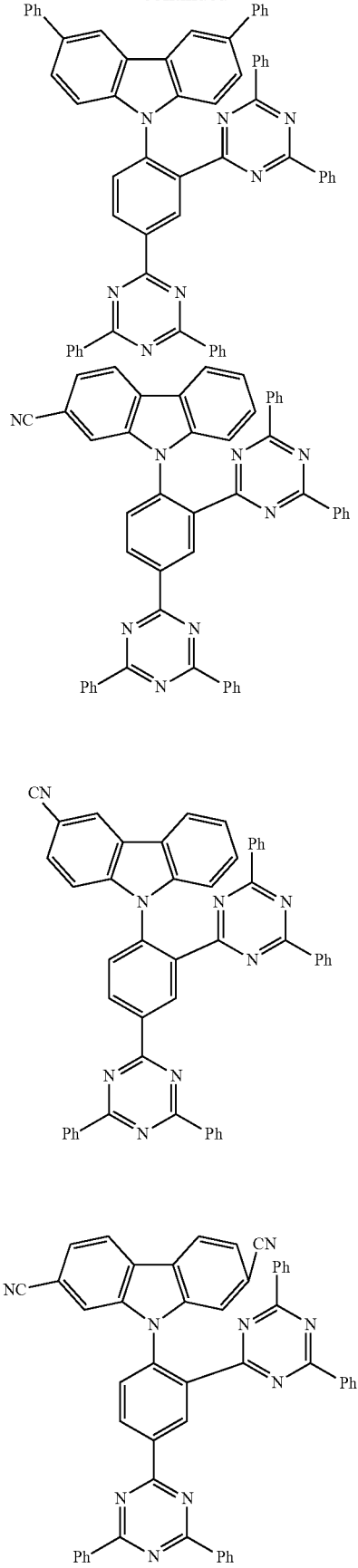

105
-continued
106
-continued
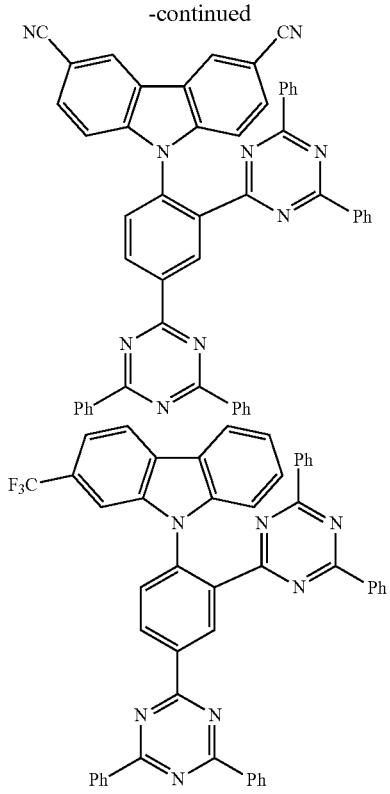
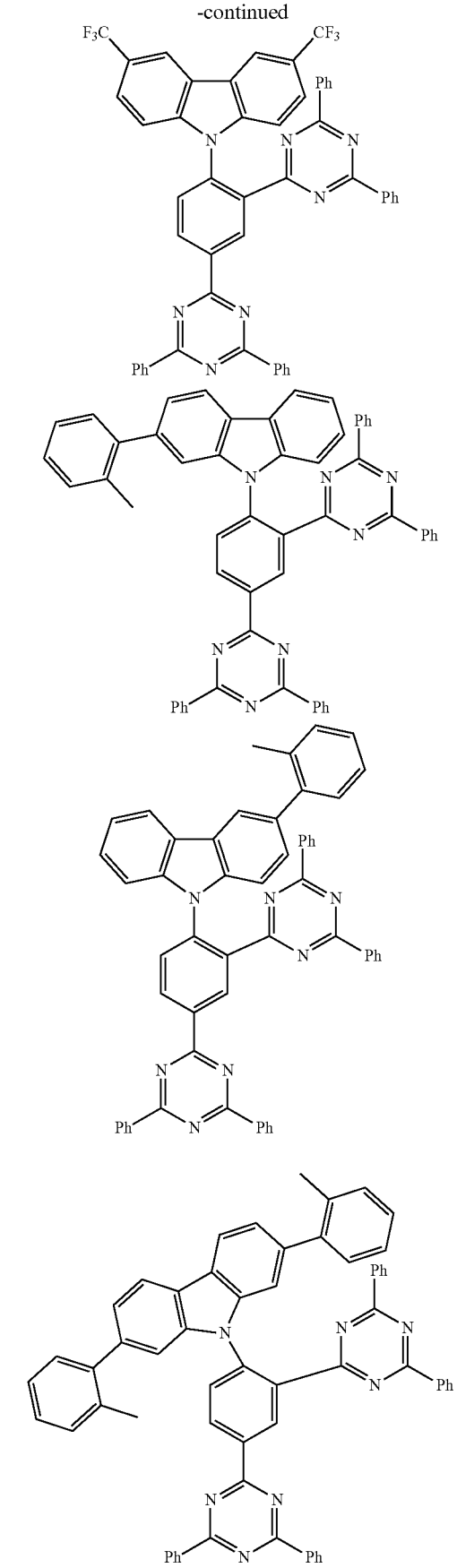

107
-continued
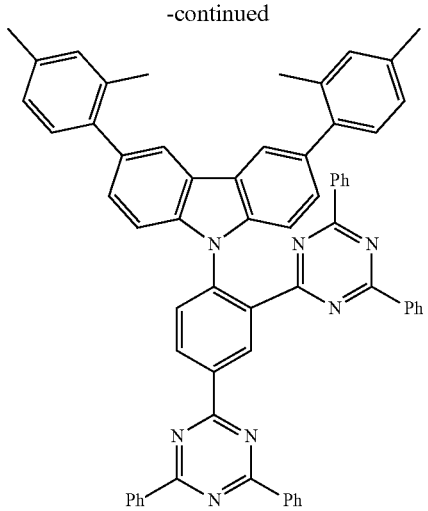
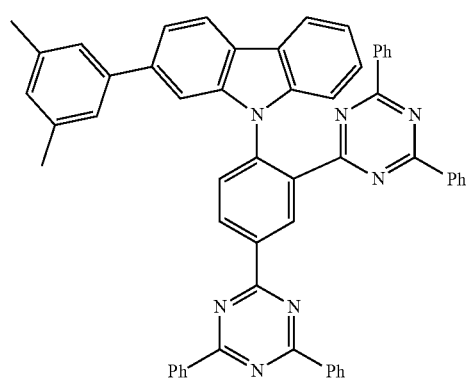
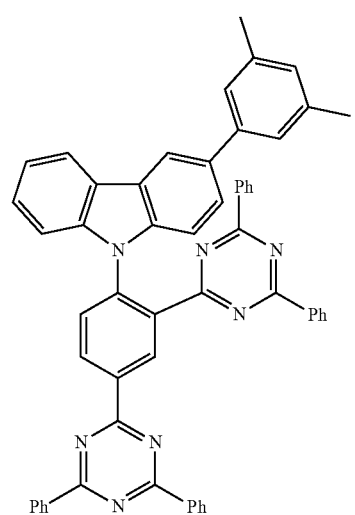
108
-continued
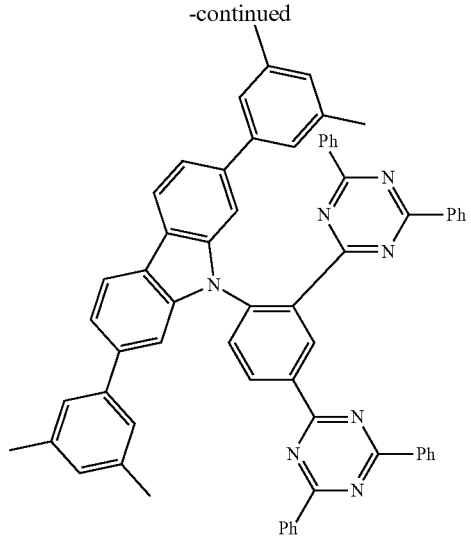
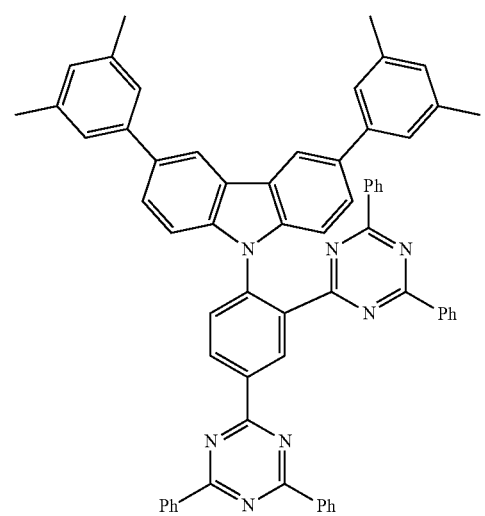
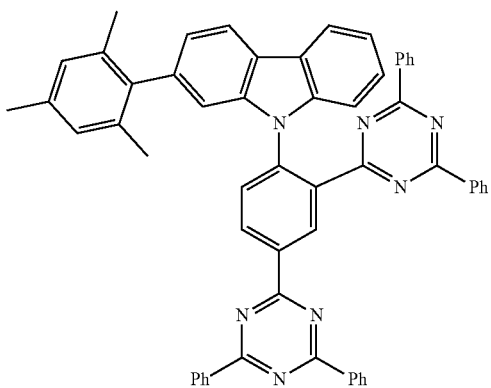

-continued
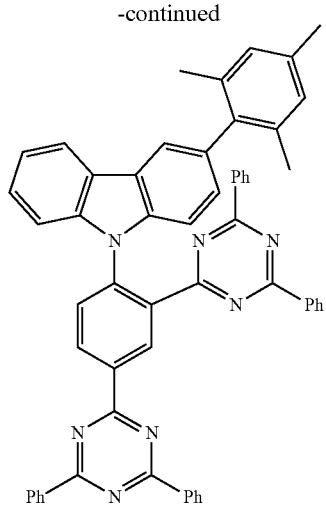
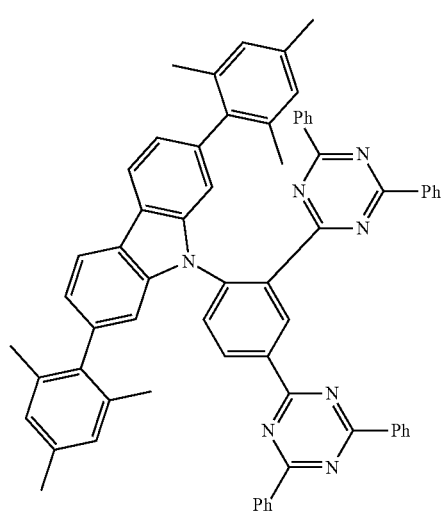
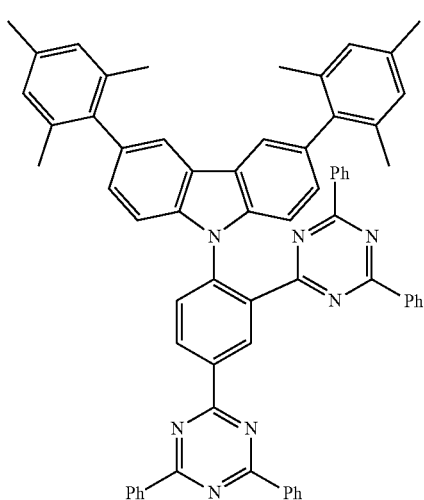
-continued
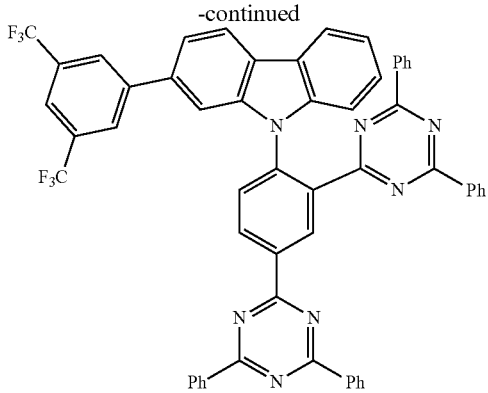
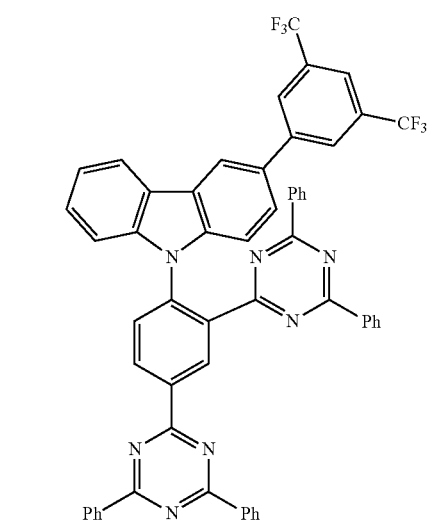
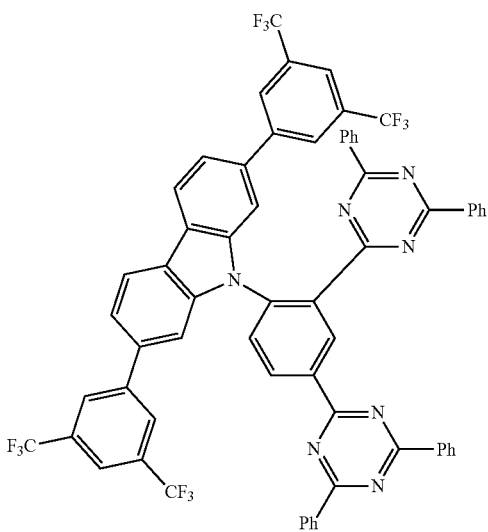

111
-continued
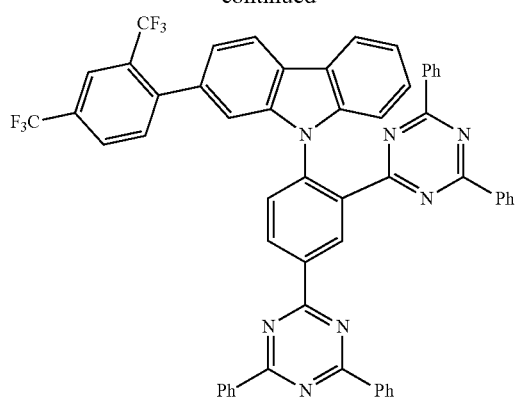
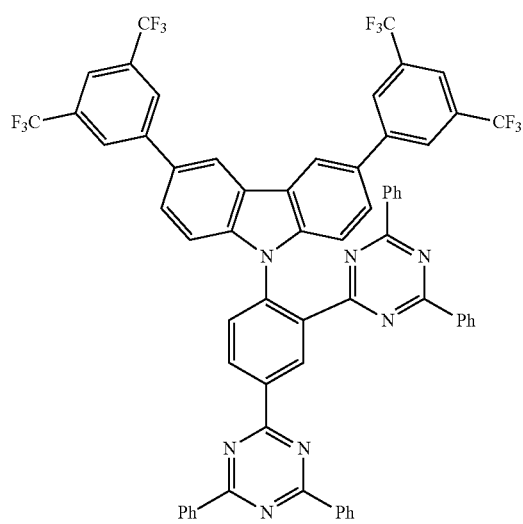
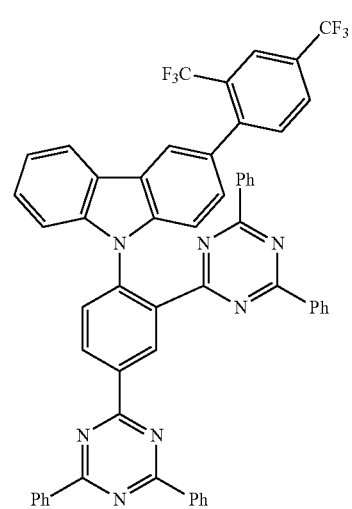
112
-continued
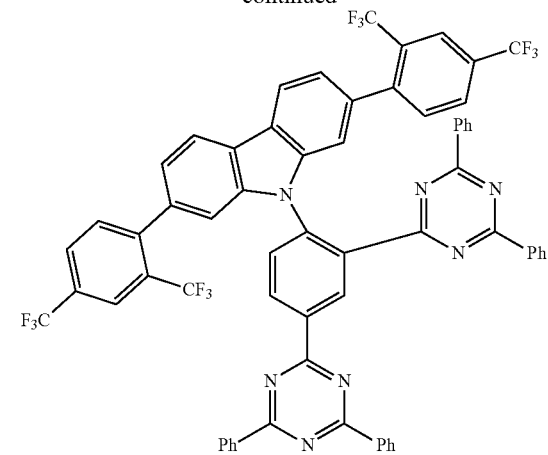
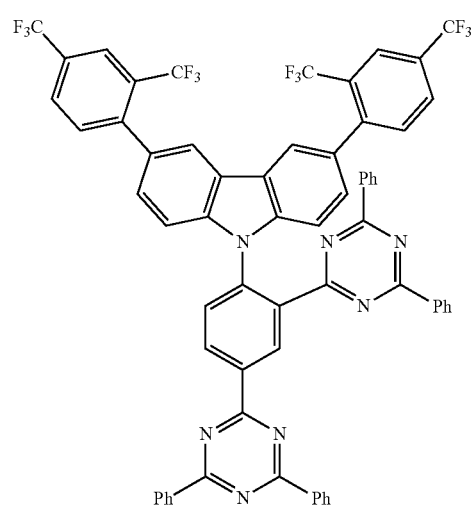
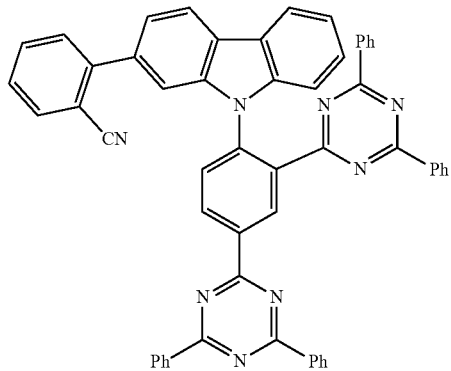

113
-continued
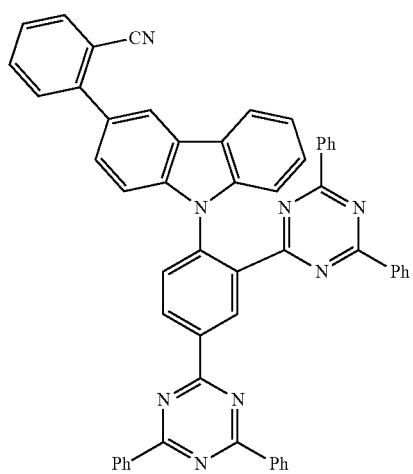
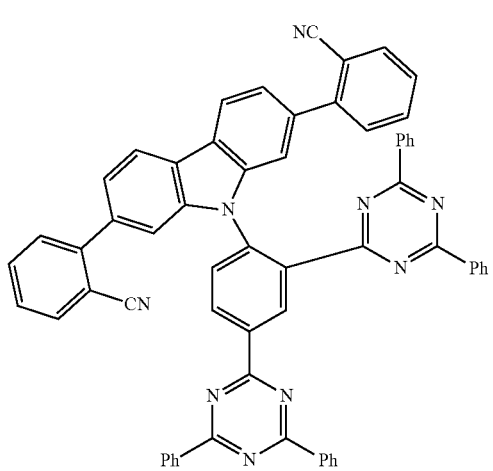
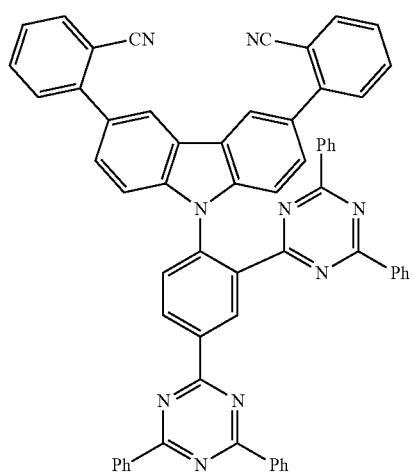
114
-continued
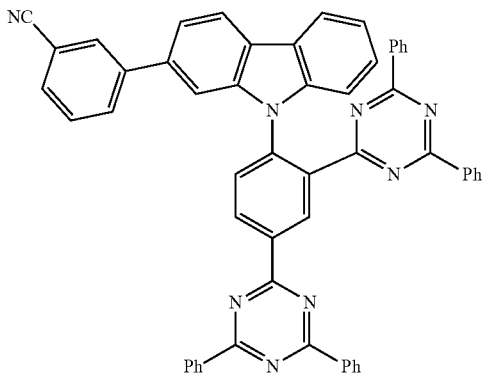
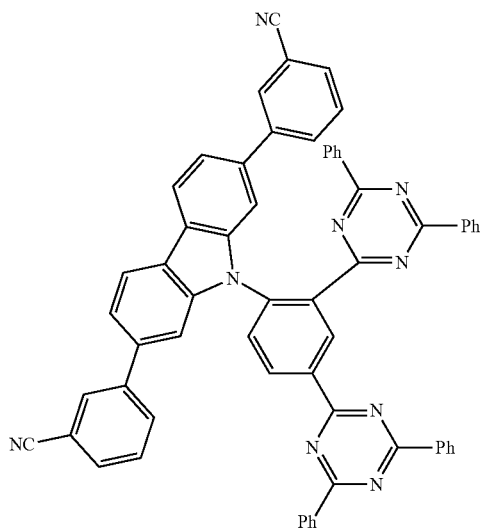

115
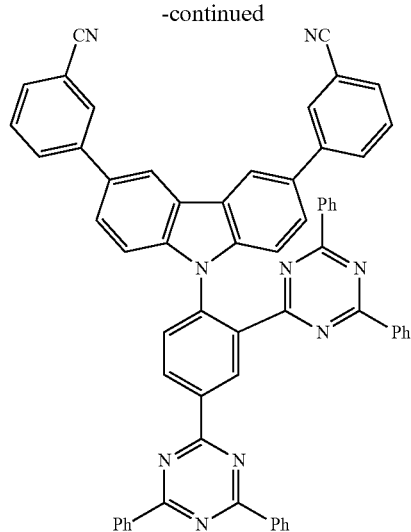
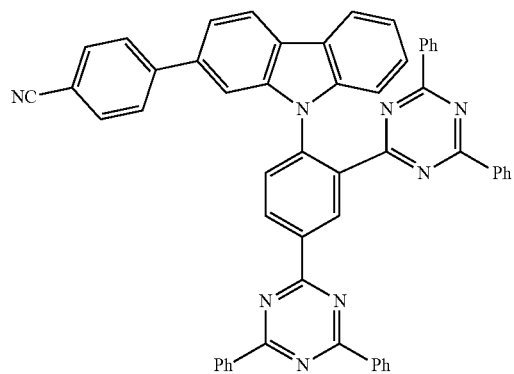
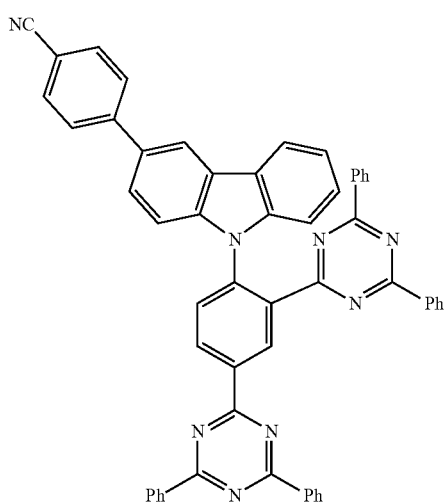
116
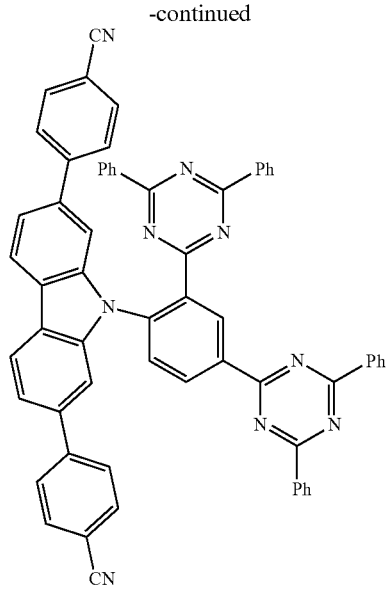
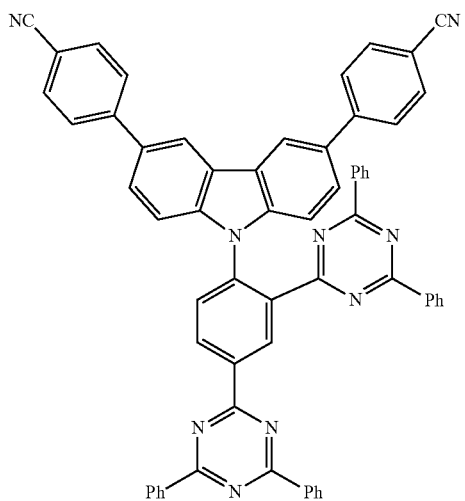 [SMILES: N#Cc1ccc(-c2ccc3c(c2)c2cc(-c4ccc(C#N)cc4)ccc2n3-c2ccc(-c3nc(-c4ccccc4)nc(-c4ccccc4)n3)cc2-c2nc(-c3ccccc3)nc(-c3ccccc3)n2)cc1]
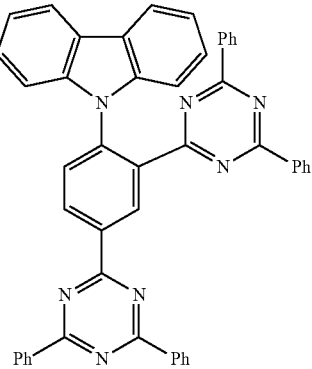

117
-continued
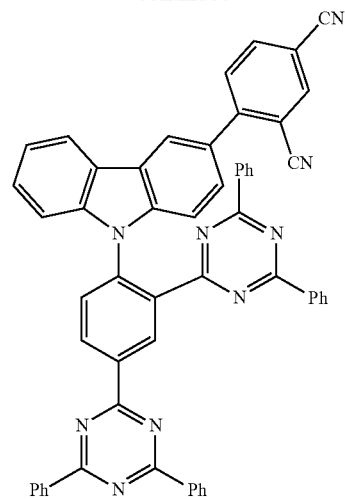
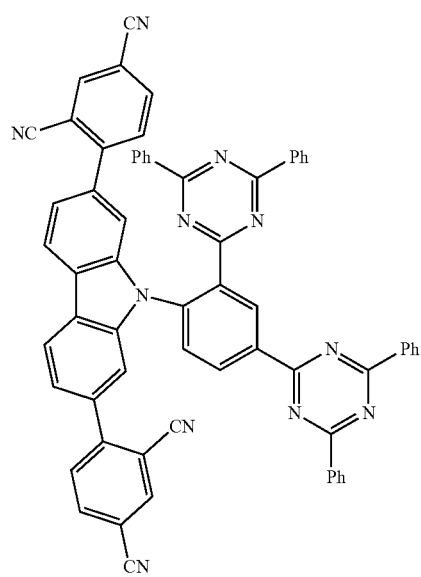
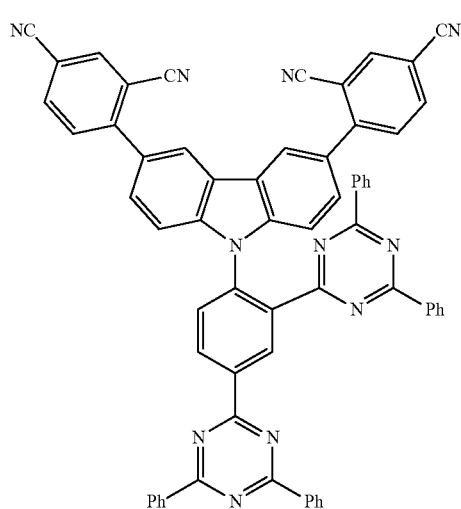 [SMILES: N#Cc1ccc(-c2ccc3c(c2)c2cc(-c4ccc(C#N)cc4C#N)ccc2n3-c2ccc(-c3nc(-c4ccccc4)nc(-c4ccccc4)n3)cc2-c2nc(-c3ccccc3)nc(-c3ccccc3)n2)c(C#N)c1]
118
-continued
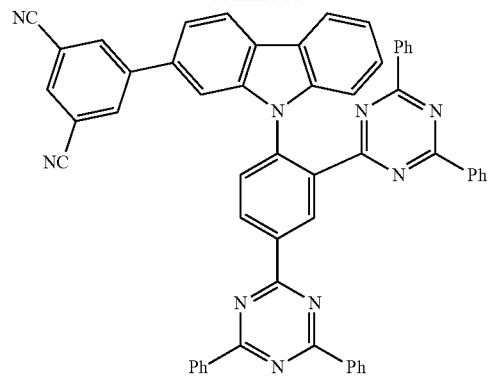
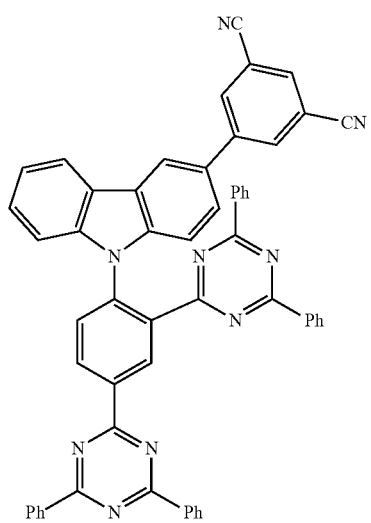
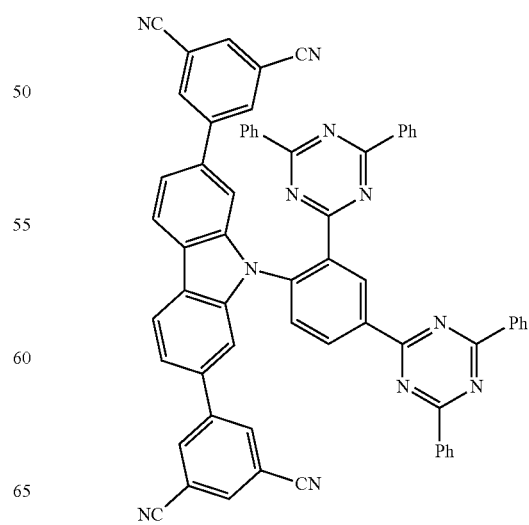

119
-continued
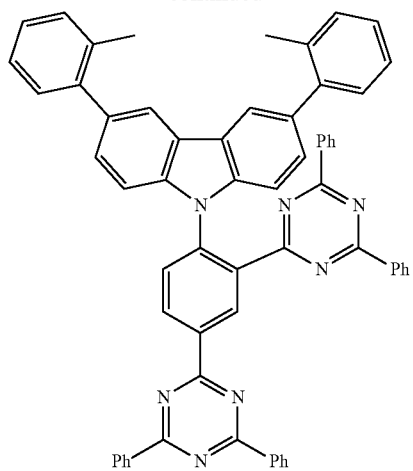 [SMILES: Cc1ccccc1-c1ccc2c(c1)c1cc(-c3ccccc3C)ccc1n2-c1ccc(-c2nc(-c3ccccc3)nc(-c3ccccc3)n2)cc1-c1nc(-c2ccccc2)nc(-c2ccccc2)n1]
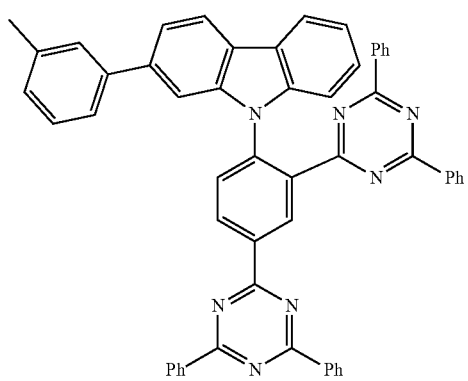
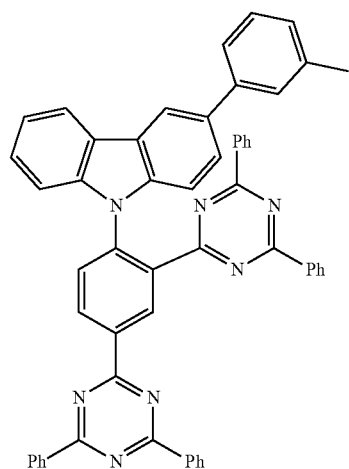
120
-continued
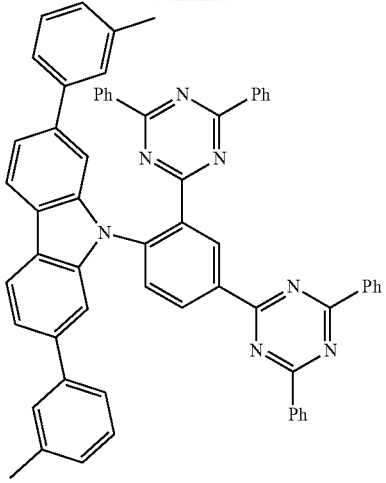
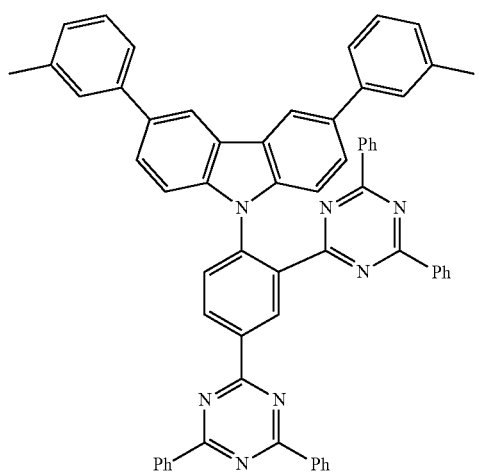
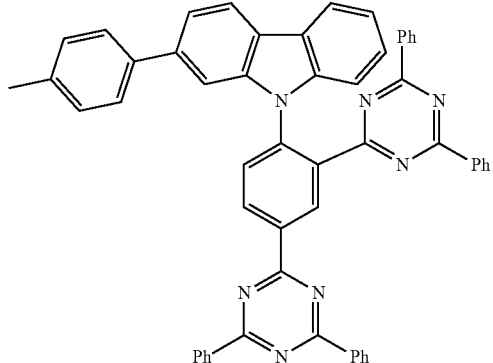

121
-continued
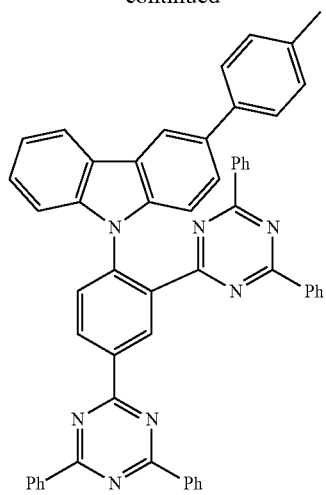
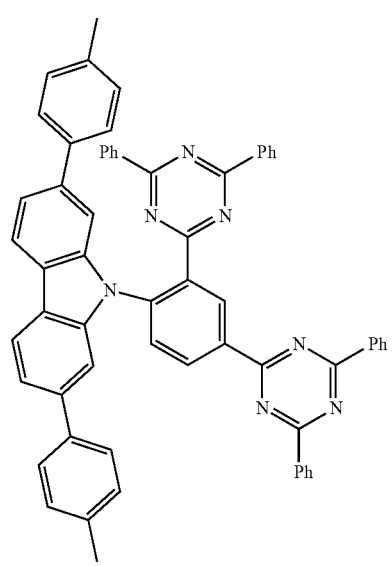
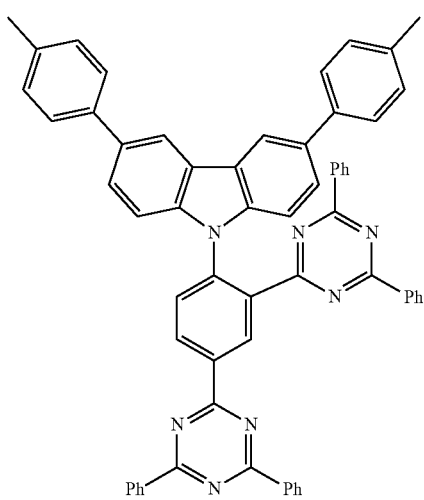
122
-continued
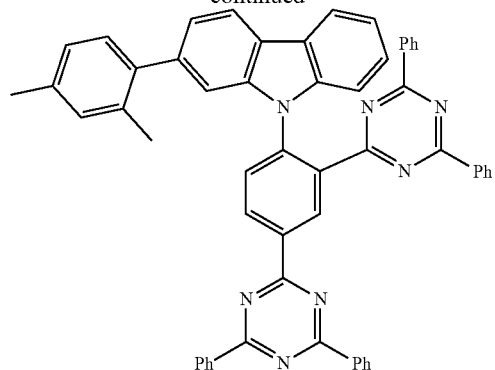
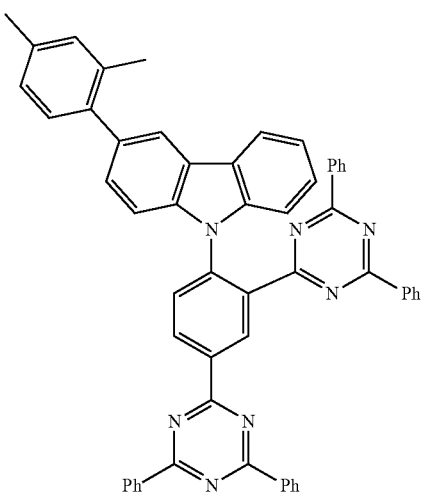
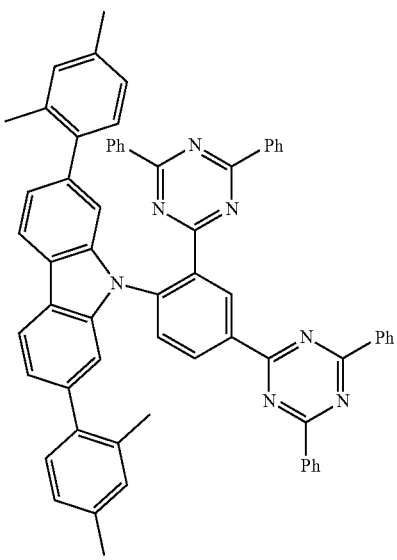

123
-continued
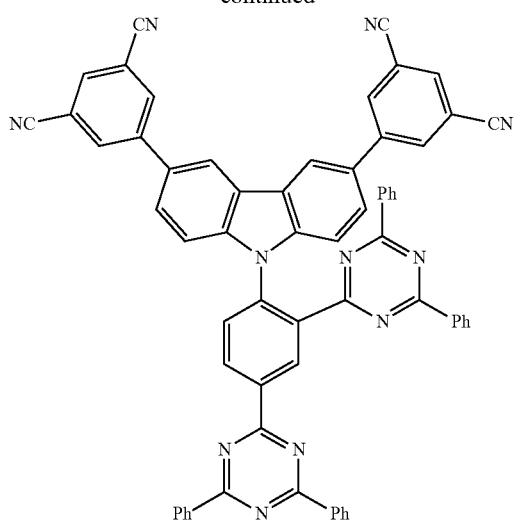
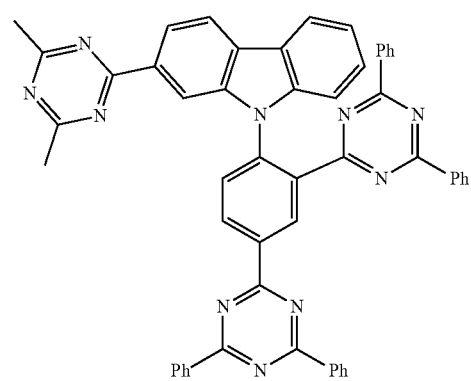
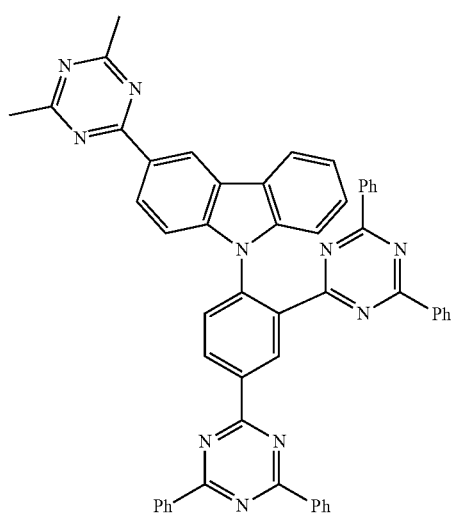
124
-continued
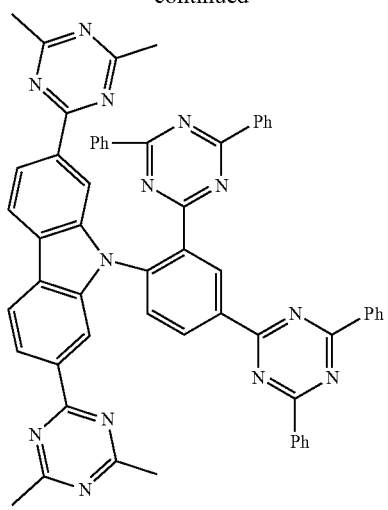
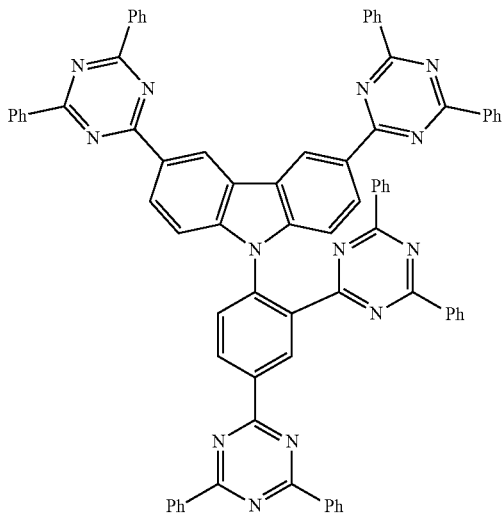 [SMILES: c1ccc(-c2nc(-c3ccccc3)nc(-c3ccc(-n4c5ccc(-c6nc(-c7ccccc7)nc(-c7ccccc7)n6)cc5c5cc(-c6nc(-c7ccccc7)nc(-c7ccccc7)n6)ccc54)c(-c4nc(-c5ccccc5)nc(-c5ccccc5)n4)c3)n2)cc1]
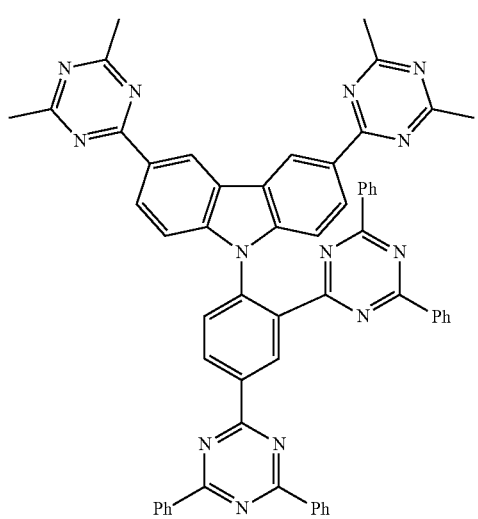

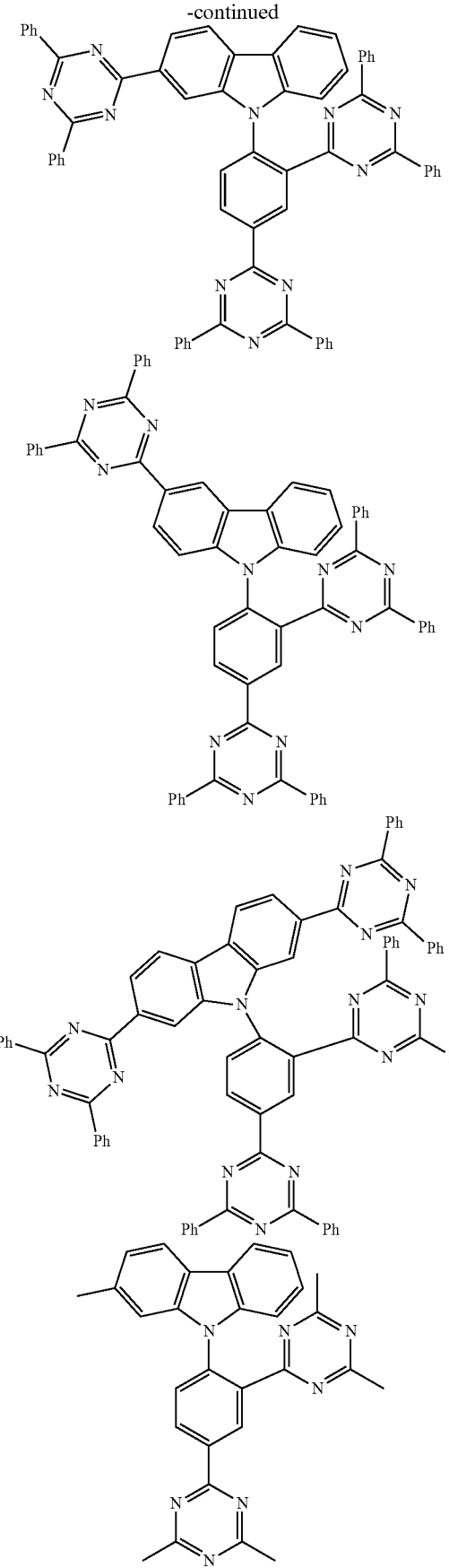
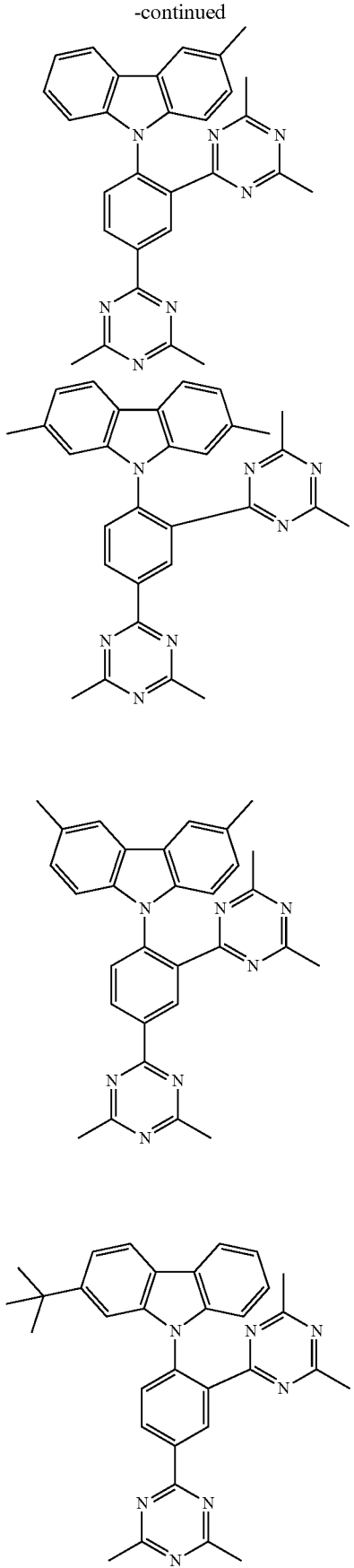

127
-continued
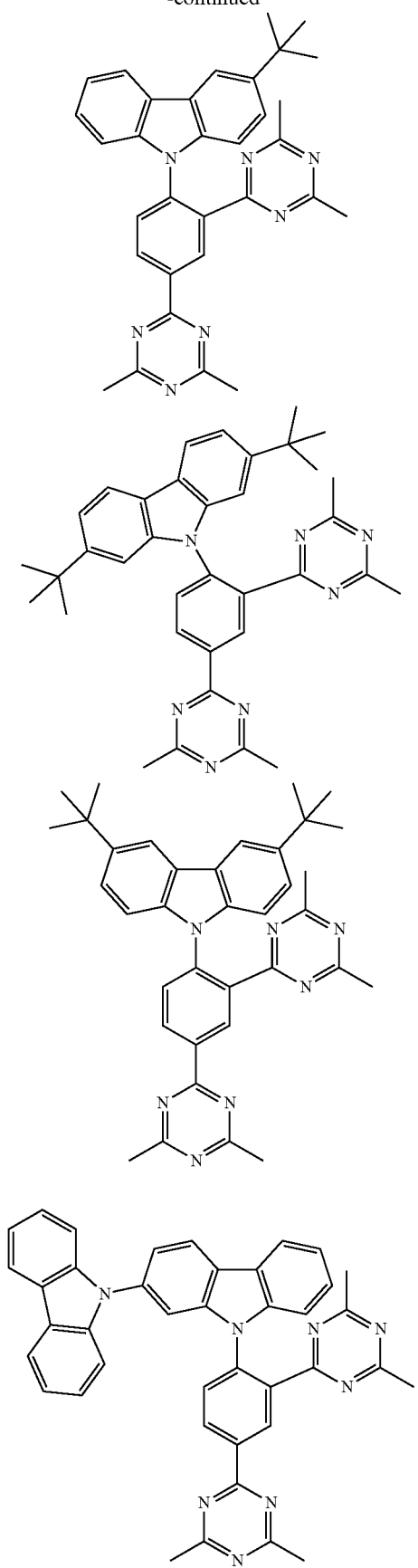
128
-continued
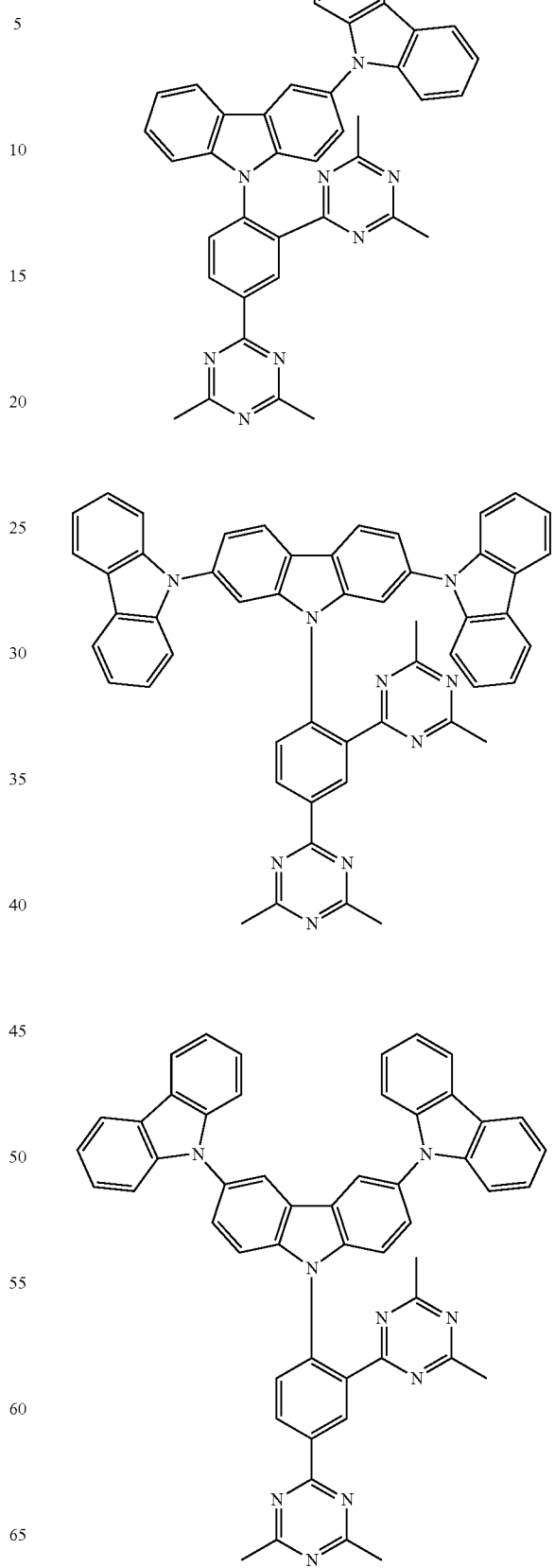

| 129 | 130 |
|---|---|
| -continued | -continued |
| 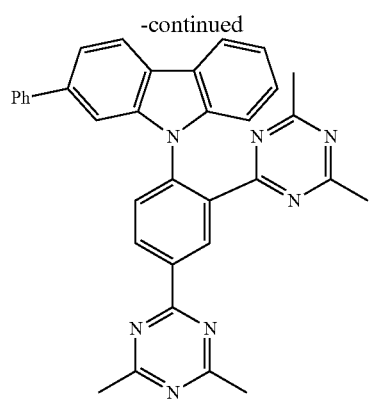 | 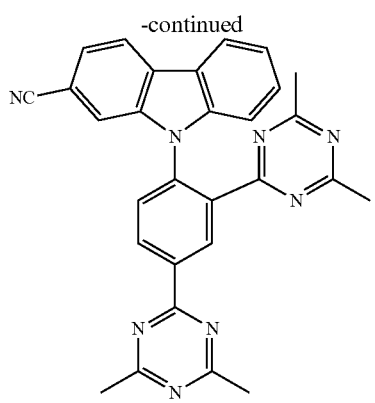 |
| 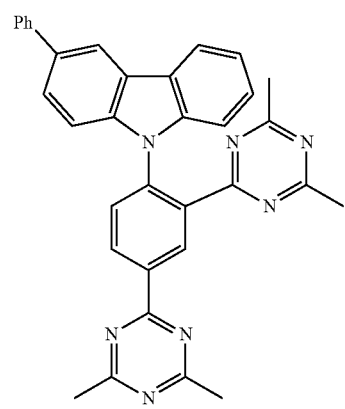 | 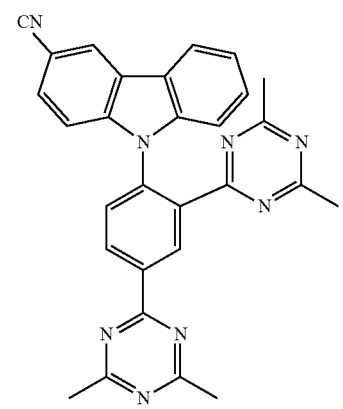 |
| 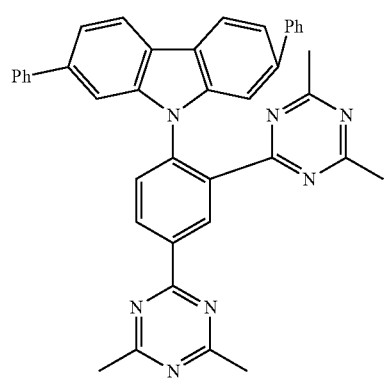 | 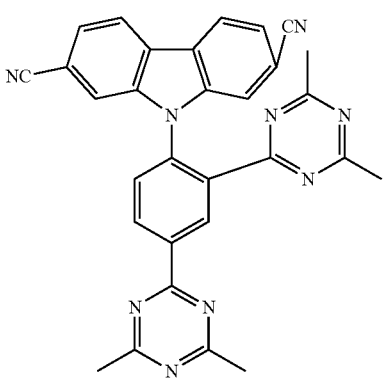 |
| 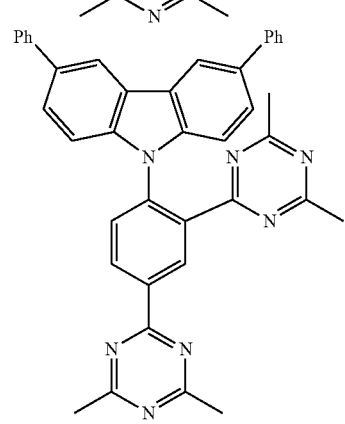 | 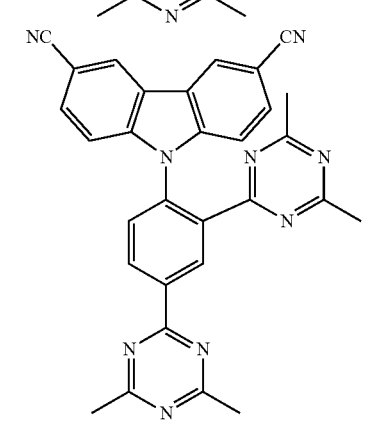 |

131
-continued
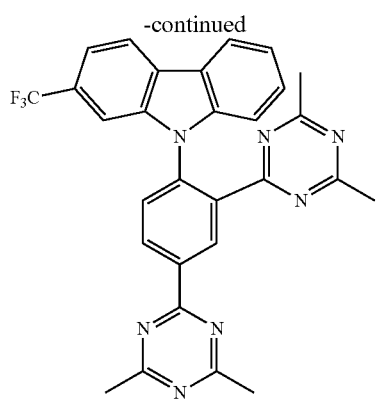
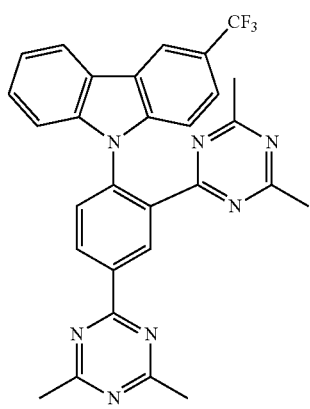
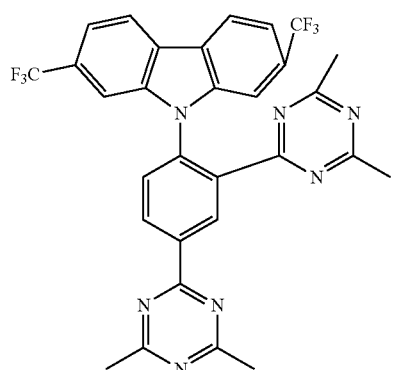
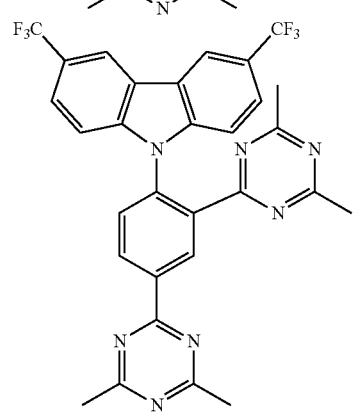
132
-continued
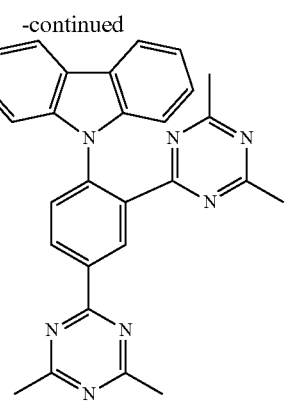
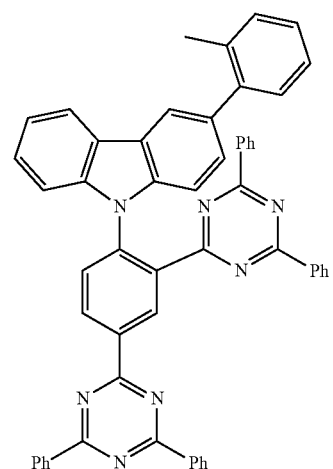
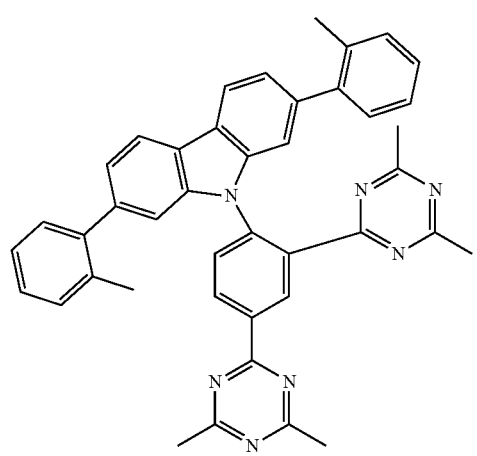

133
-continued
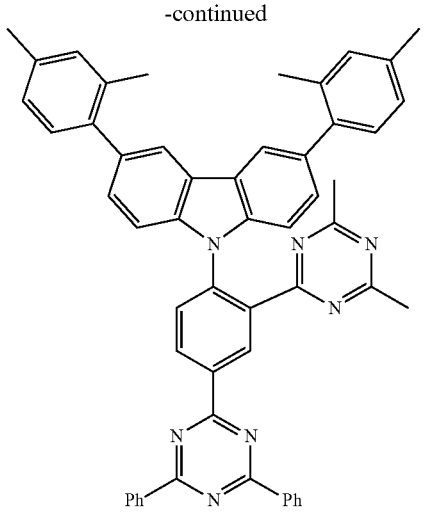
134
-continued
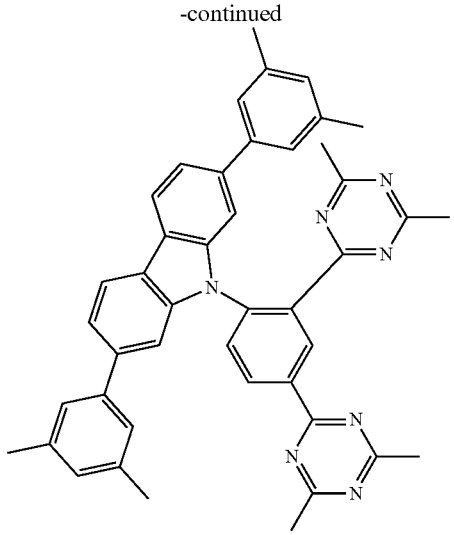
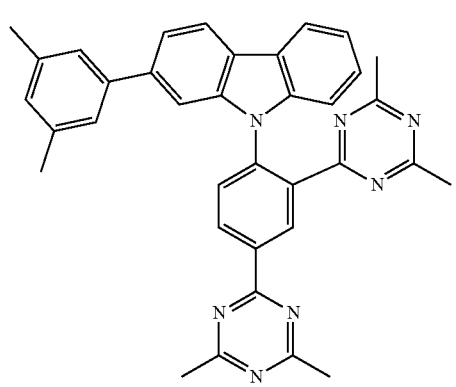
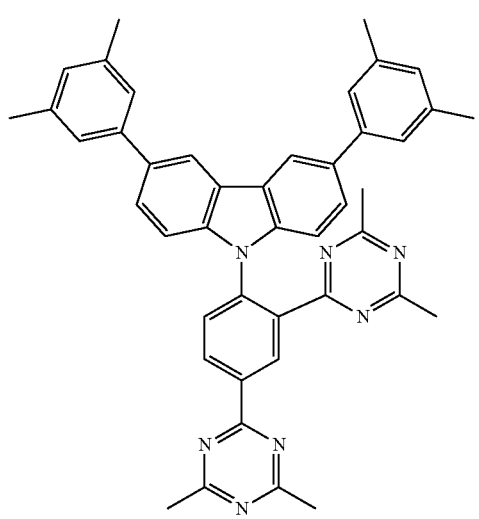
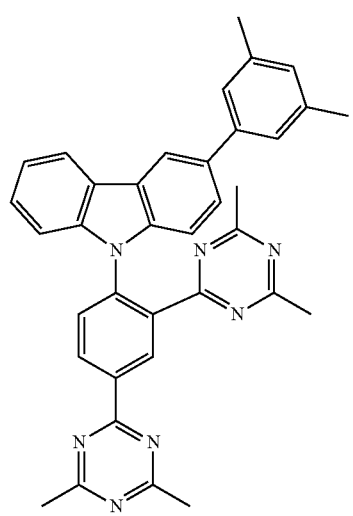

135
-continued
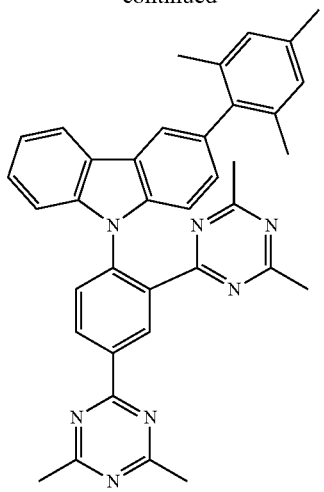
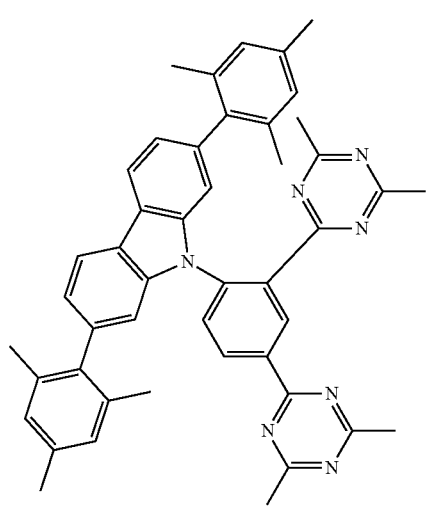
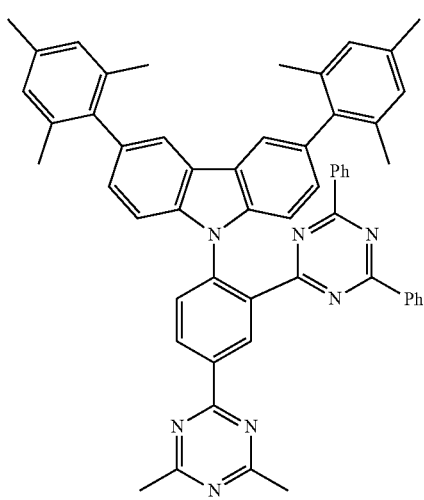
136
-continued
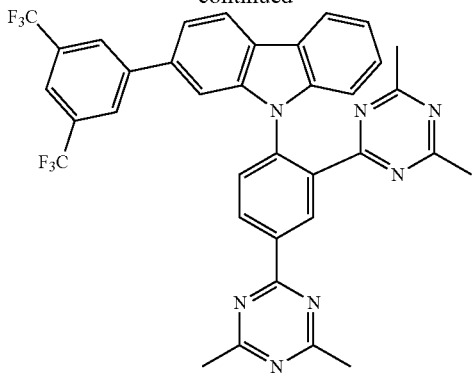
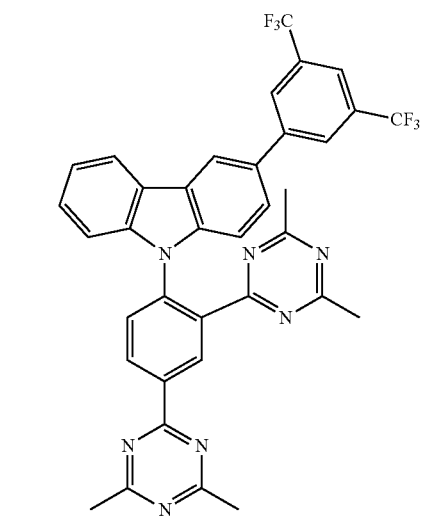
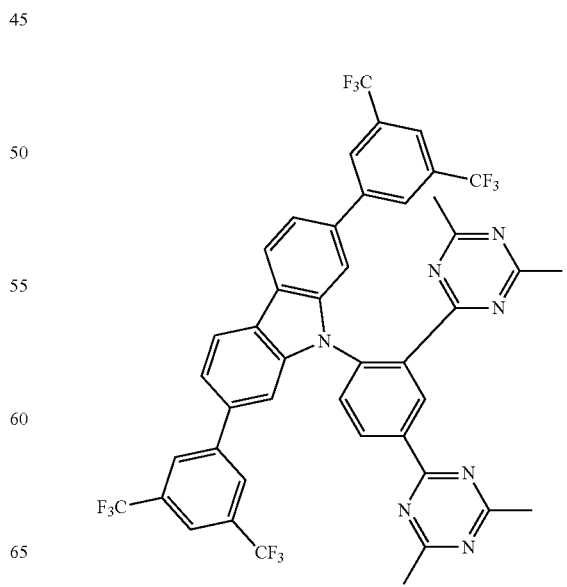

137
-continued
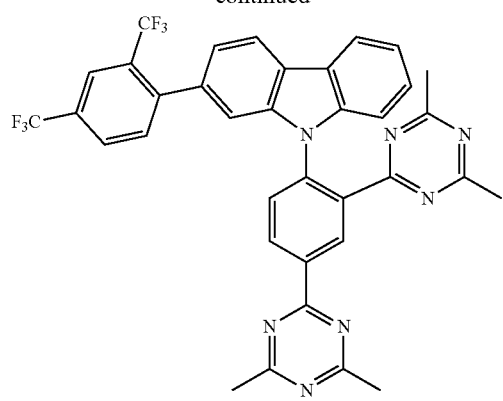
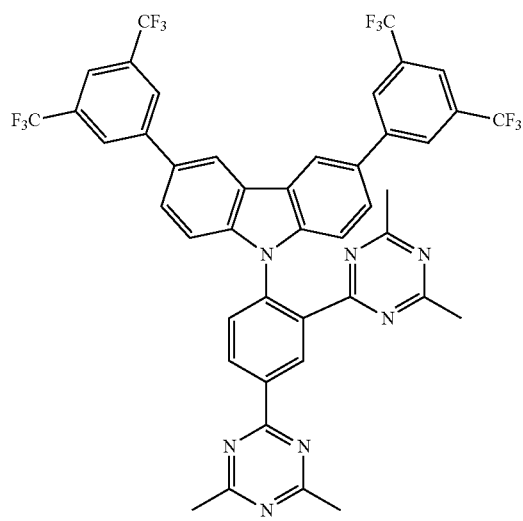
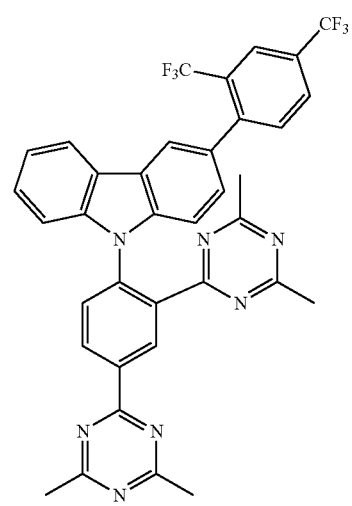
138
-continued
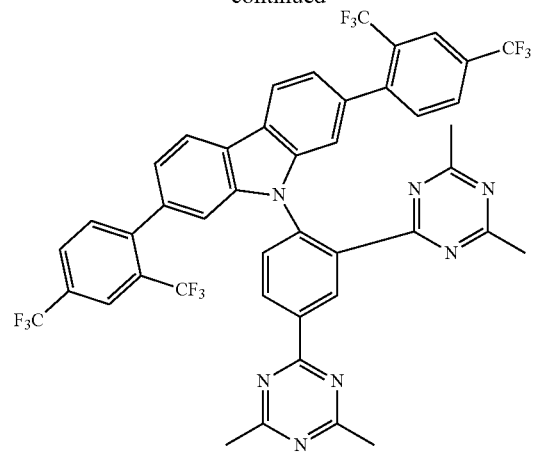
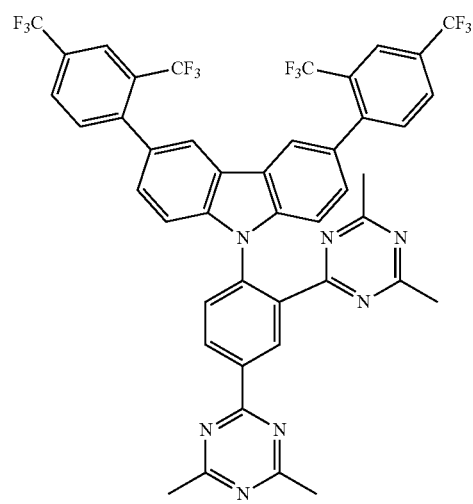
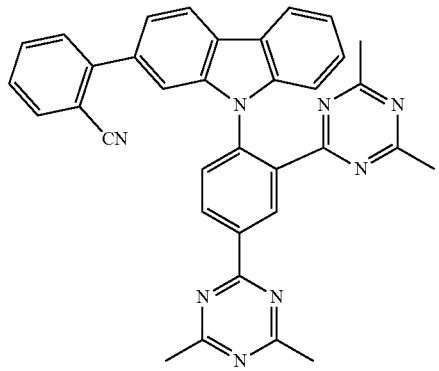

139
-continued
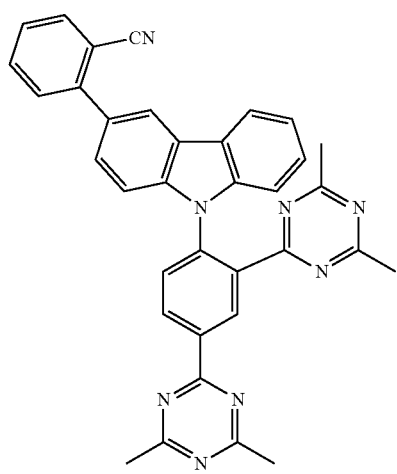
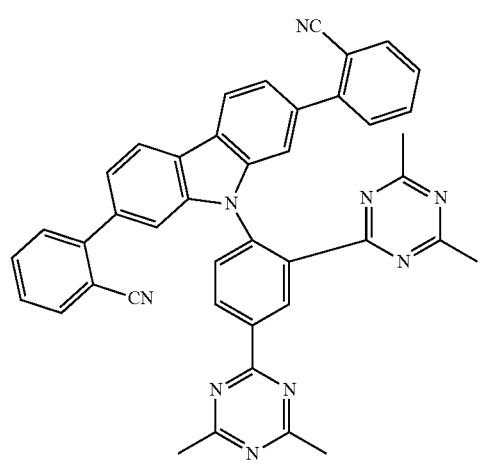
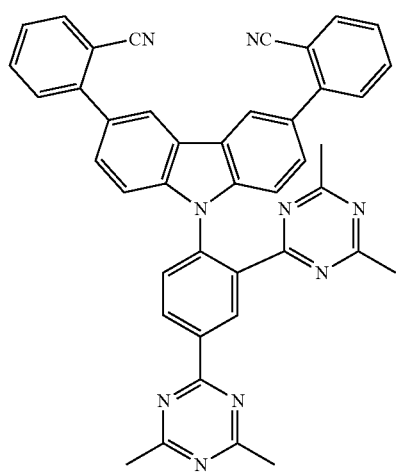
140
-continued
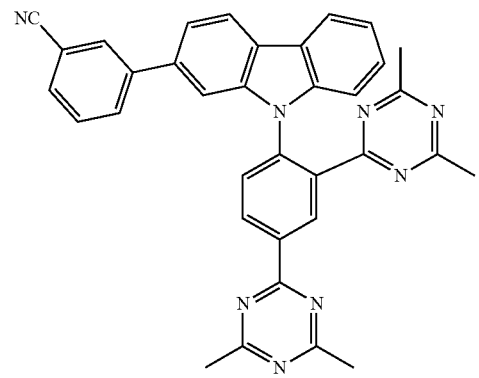
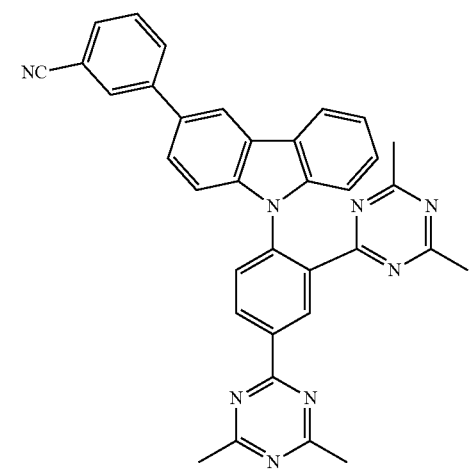
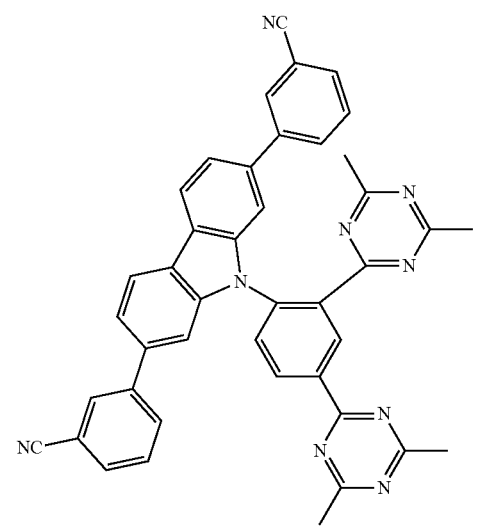

141
-continued
142
-continued
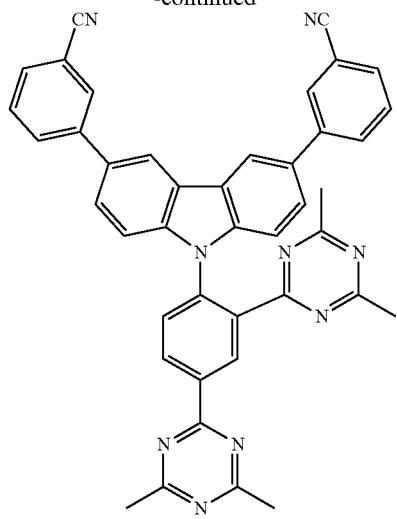
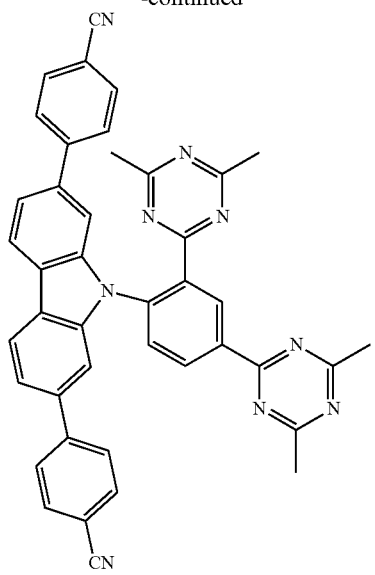
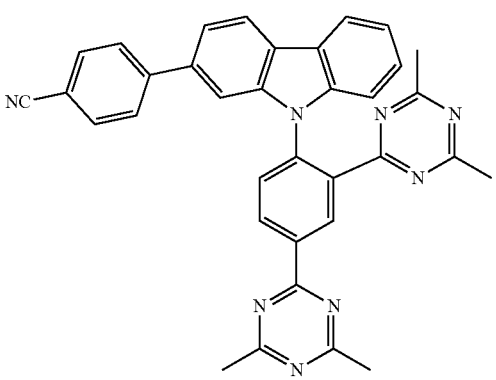
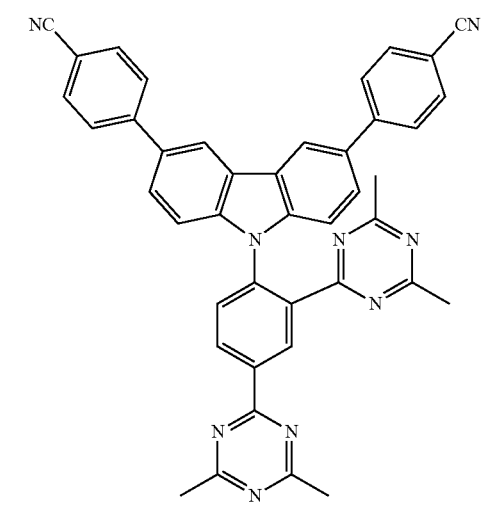 [SMILES: Cc1nc(C)nc(-c2ccc(-n3c4ccc(-c5ccc(C#N)cc5)cc4c4cc(-c5ccc(C#N)cc5)ccc43)c(-c3nc(C)nc(C)n3)c2)n1]
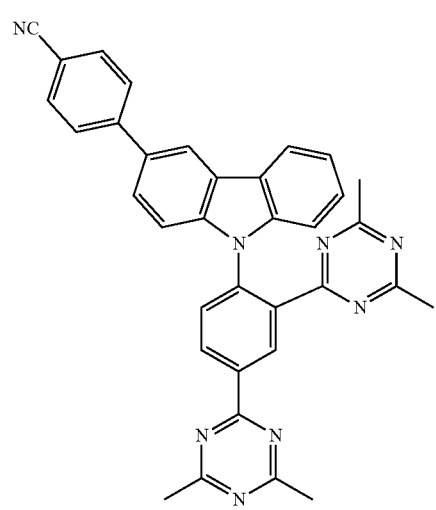
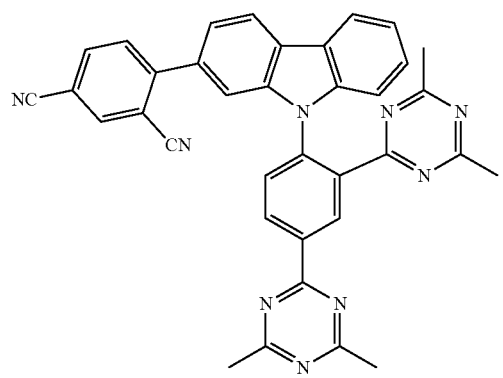

143
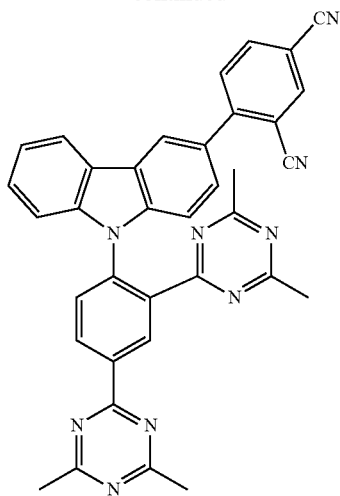
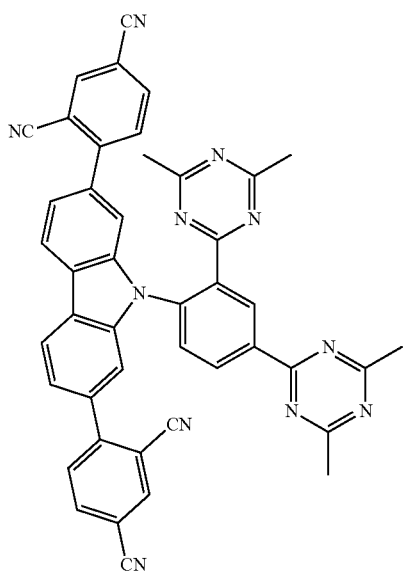
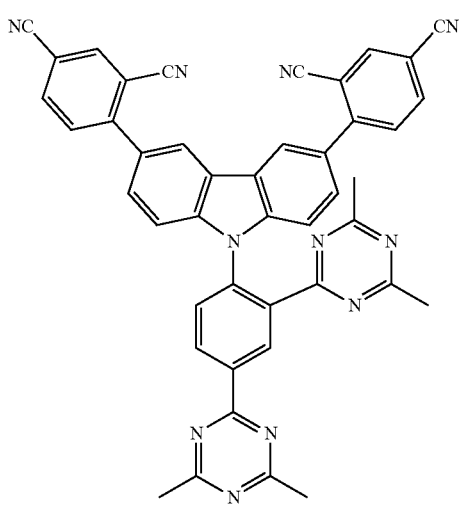 [SMILES: Cc1nc(C)nc(-c2ccc(-n3c4ccc(-c5ccc(C#N)cc5C#N)cc4c4cc(-c5ccc(C#N)cc5C#N)ccc43)c(-c3nc(C)nc(C)n3)c2)n1]
144
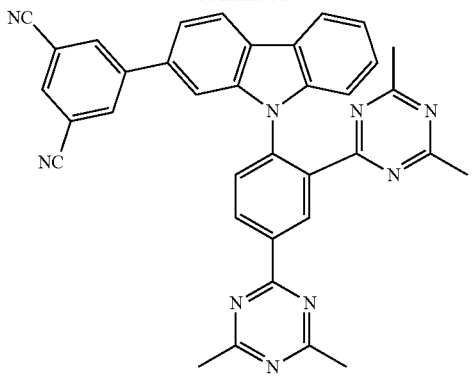
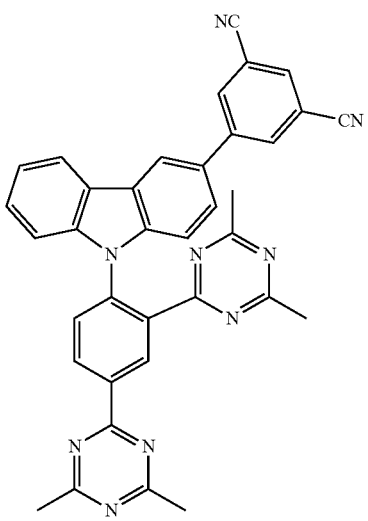
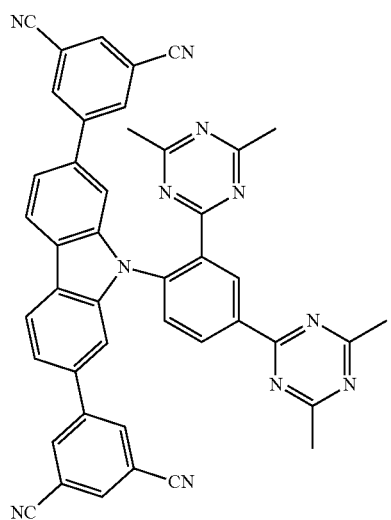

145
-continued
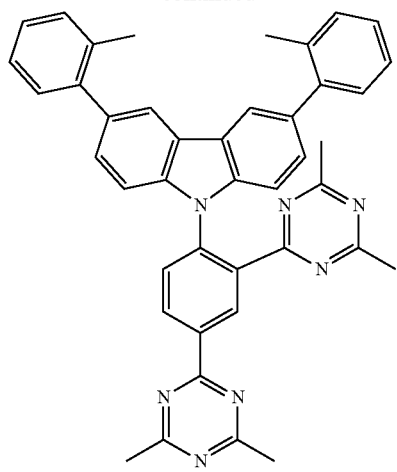 [SMILES: Cc1nc(C)nc(-c2ccc(-n3c4ccc(-c5ccccc5C)cc4c4cc(-c5ccccc5C)ccc43)c(-c3nc(C)nc(C)n3)c2)n1]
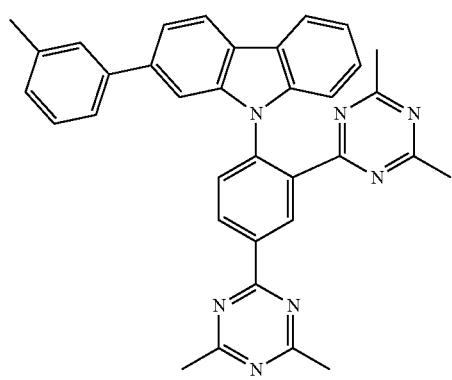
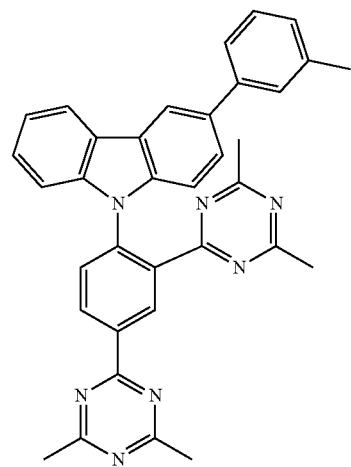
146
-continued
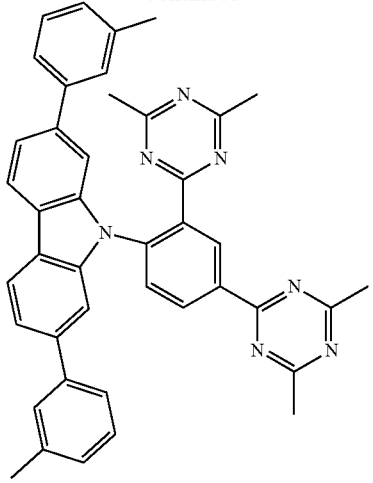
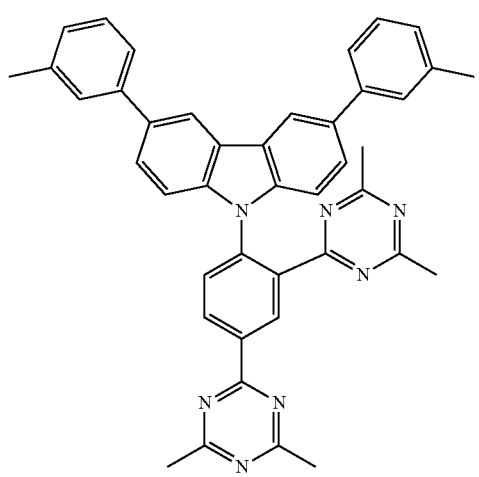
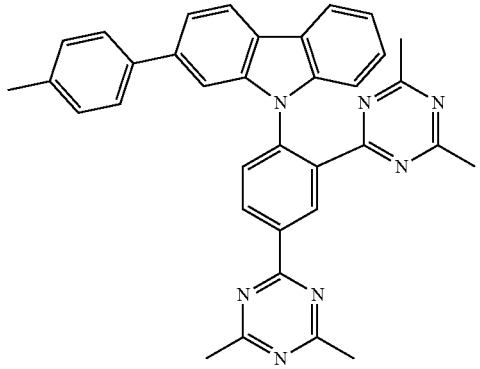

147
-continued
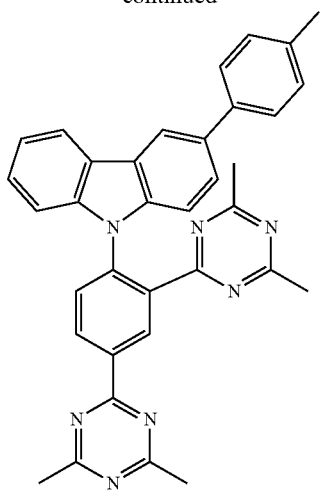
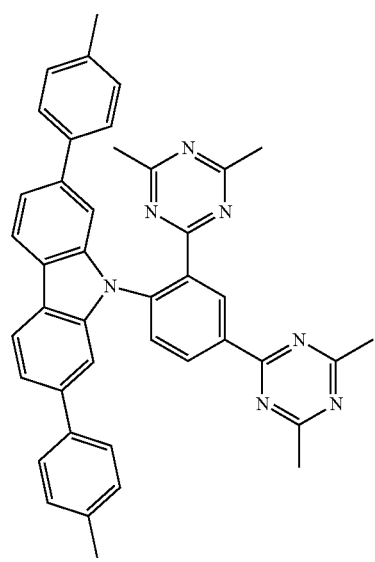
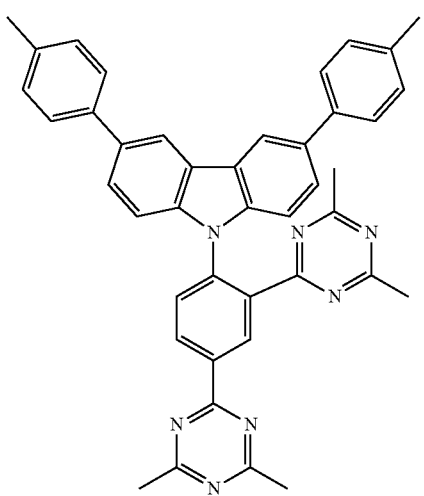
148
-continued
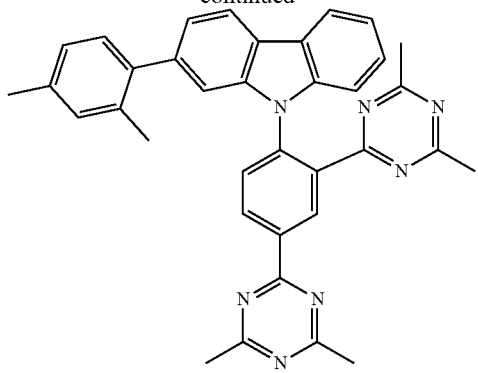
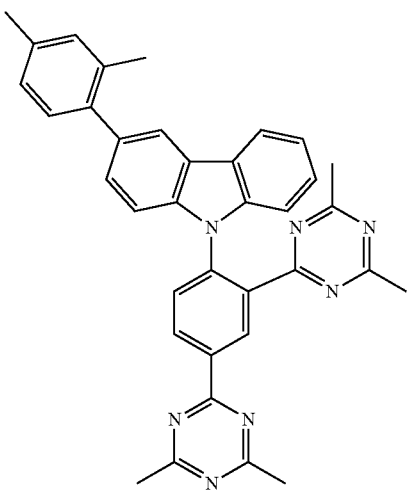
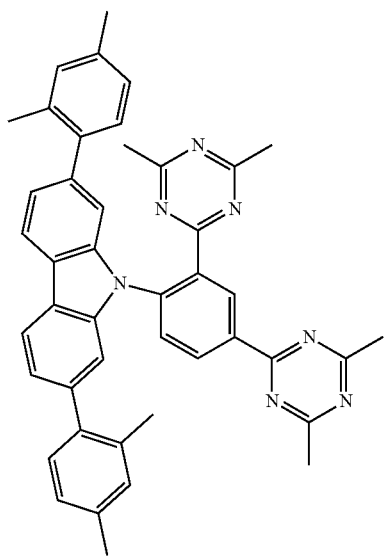

149
-continued
150
-continued
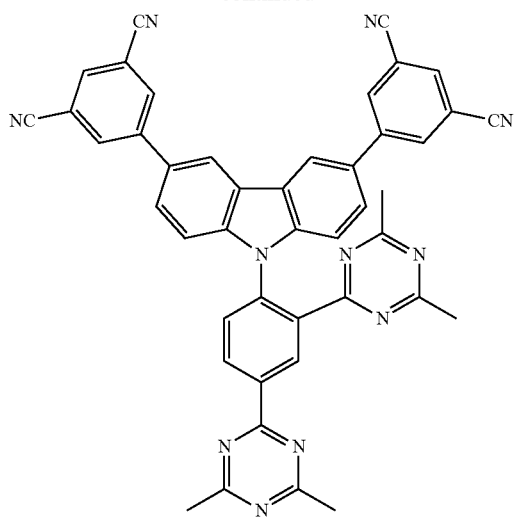 [SMILES: Cc1nc(C)nc(-c2ccc(-n3c4ccc(-c5cc(C#N)cc(C#N)c5)cc4c4cc(-c5cc(C#N)cc(C#N)c5)ccc43)c(-c3nc(C)nc(C)n3)c2)n1]
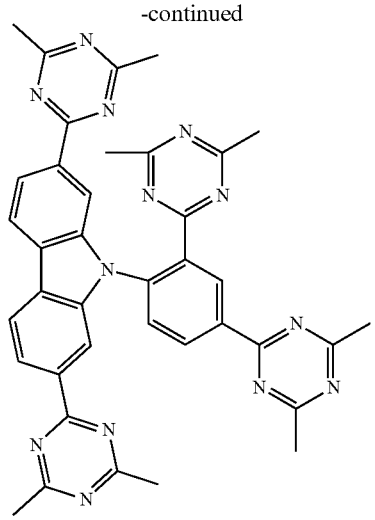
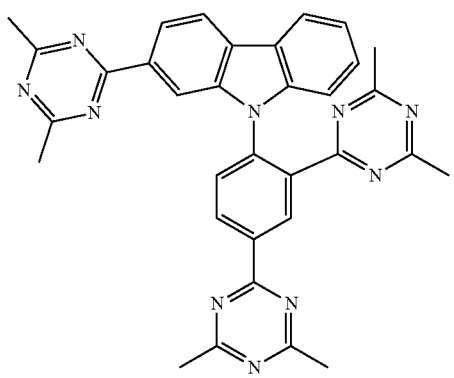
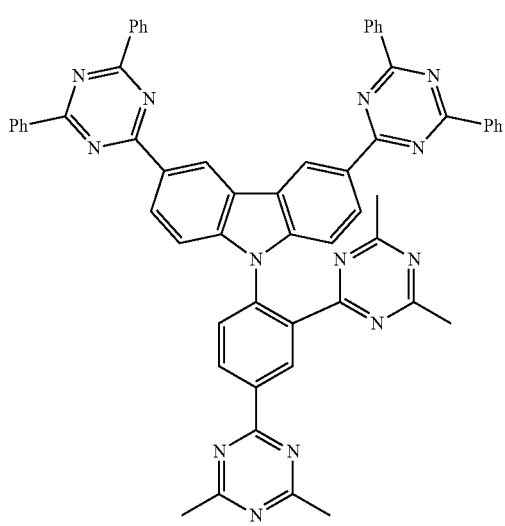 [SMILES: Cc1nc(C)nc(-c2ccc(-n3c4ccc(-c5nc(-c6ccccc6)nc(-c6ccccc6)n5)cc4c4cc(-c5nc(-c6ccccc6)nc(-c6ccccc6)n5)ccc43)c(-c3nc(C)nc(C)n3)c2)n1]
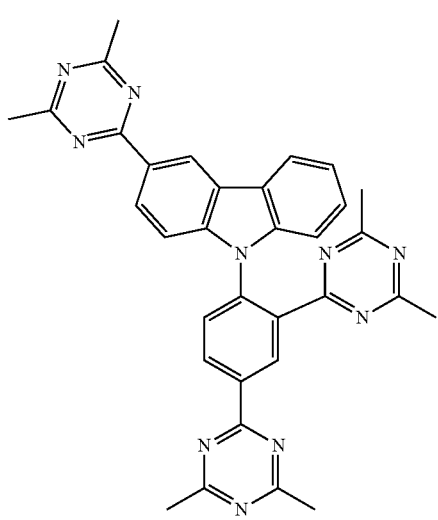
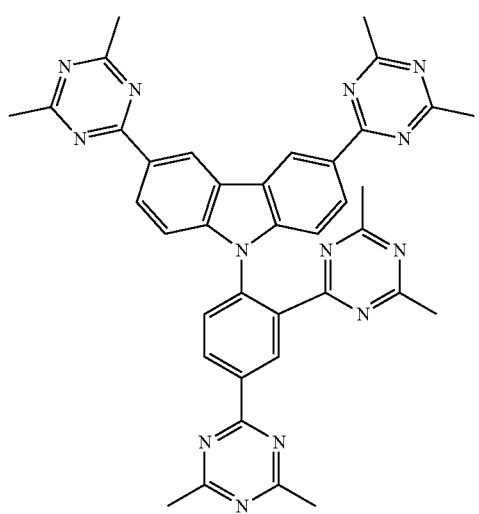

151
-continued
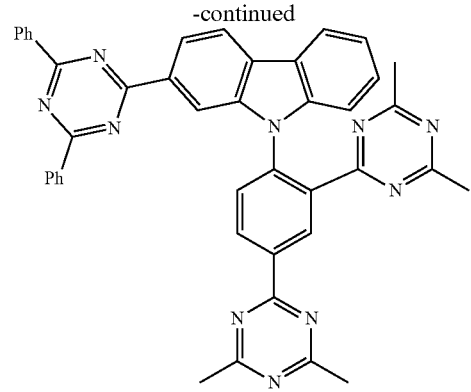
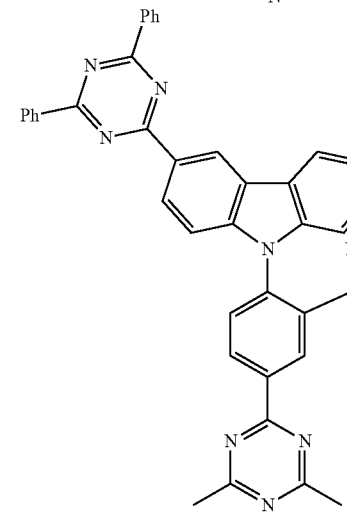
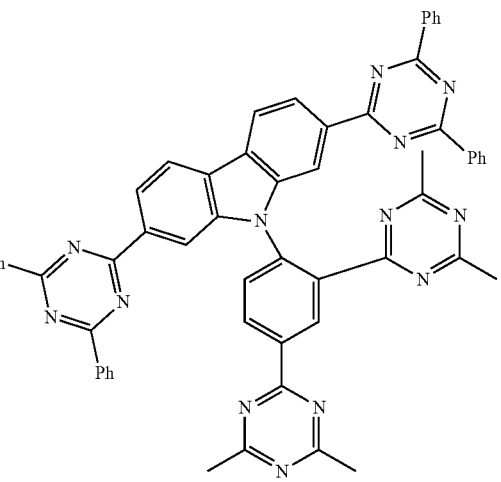
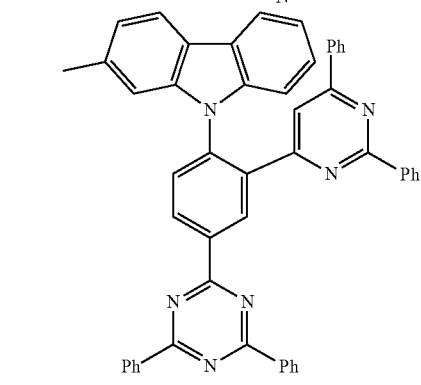
152
-continued
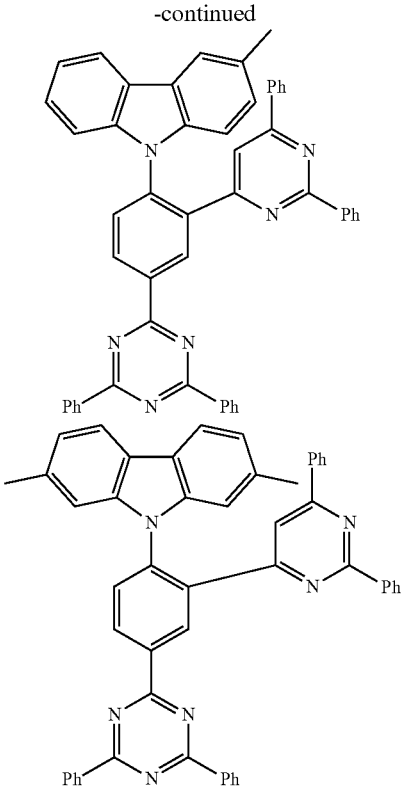
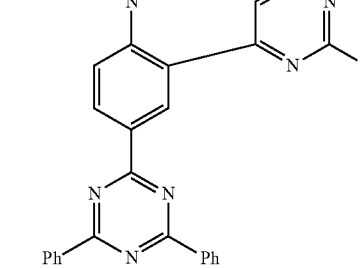
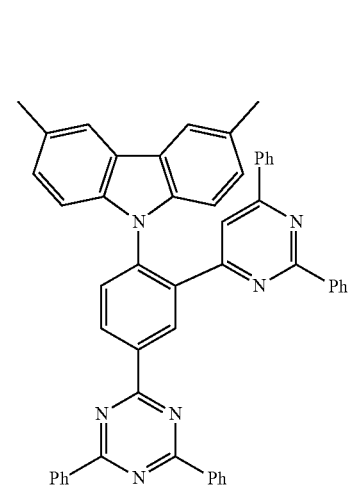
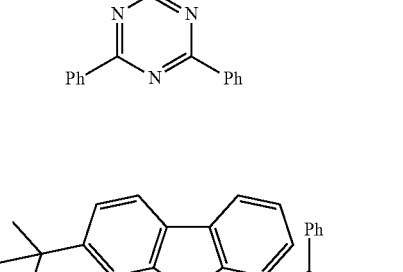
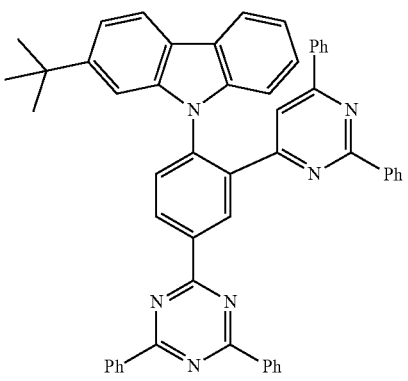

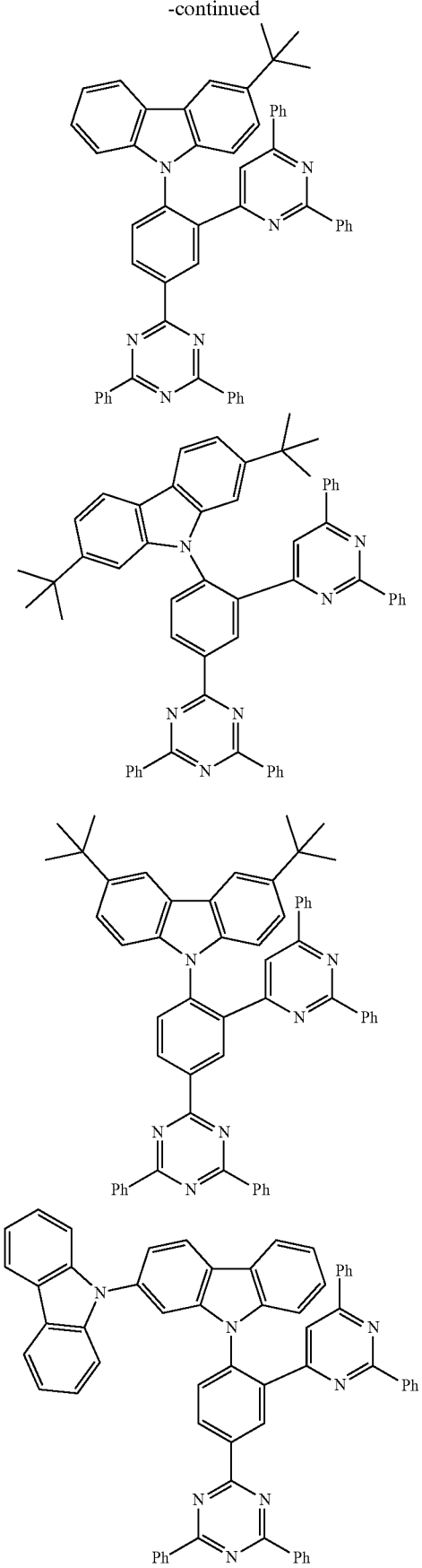

155
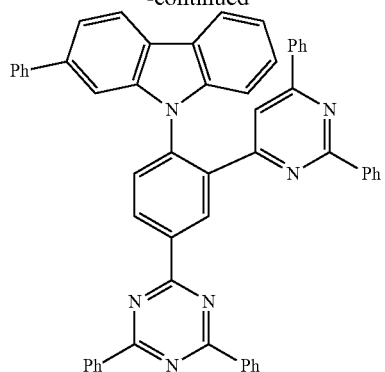
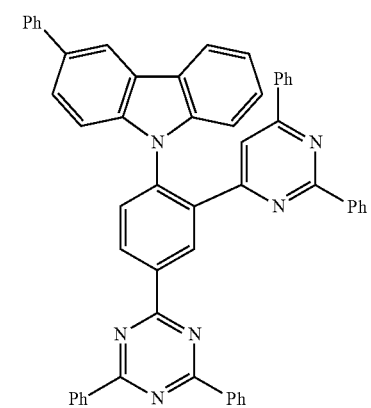
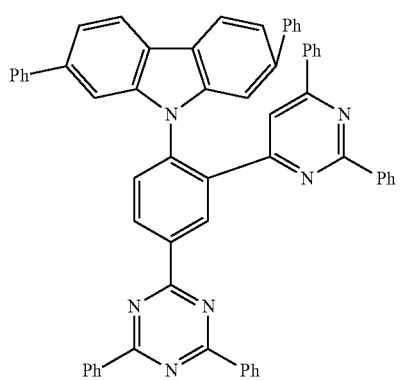
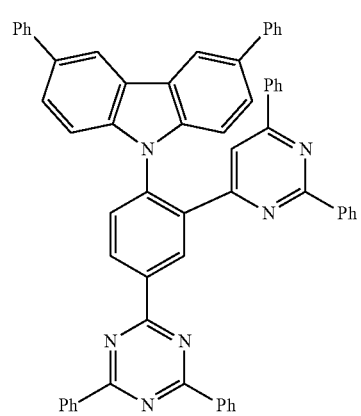
156
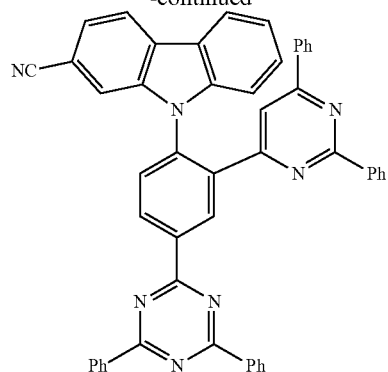
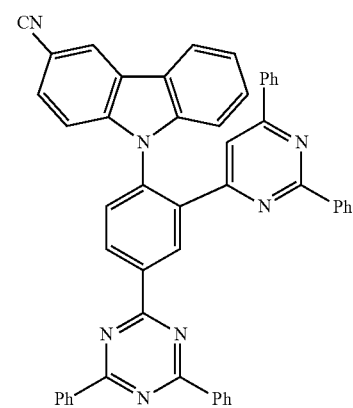
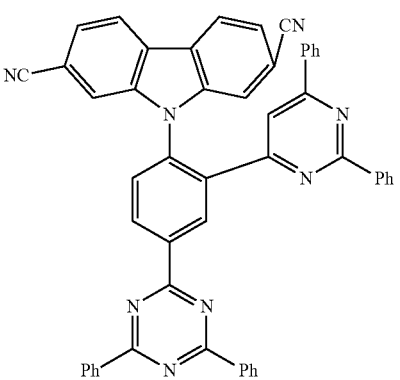
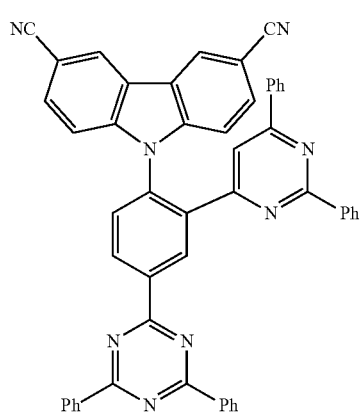

157
-continued
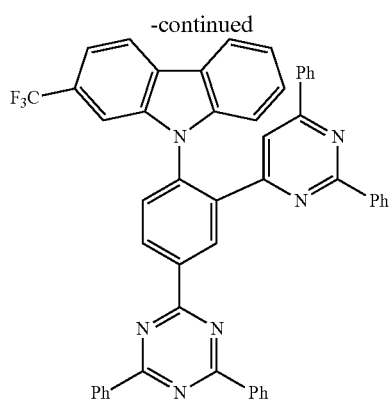
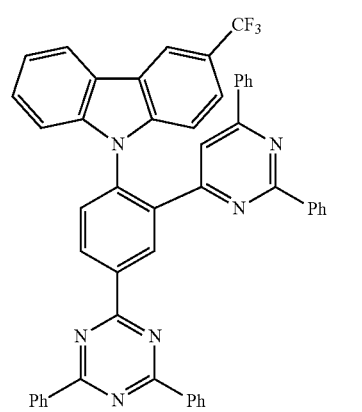
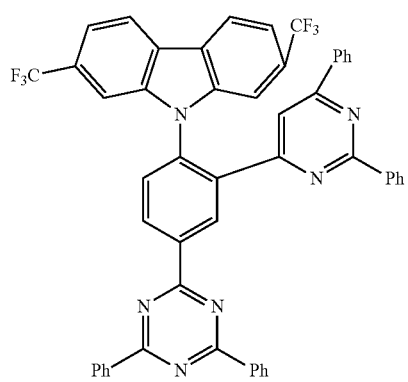
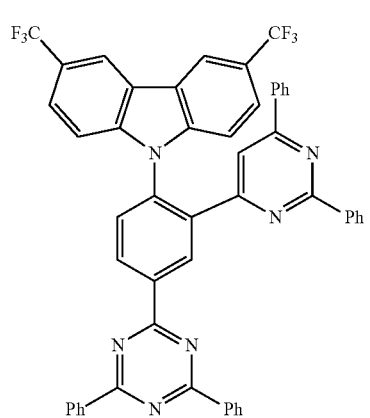
158
-continued
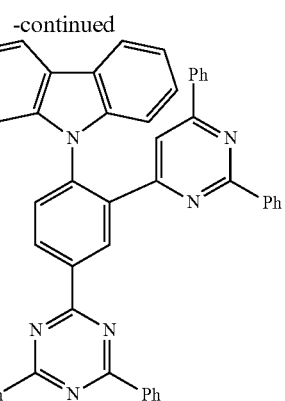
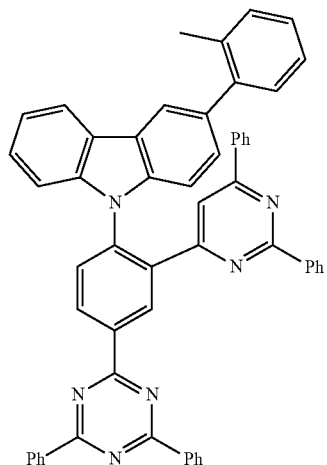
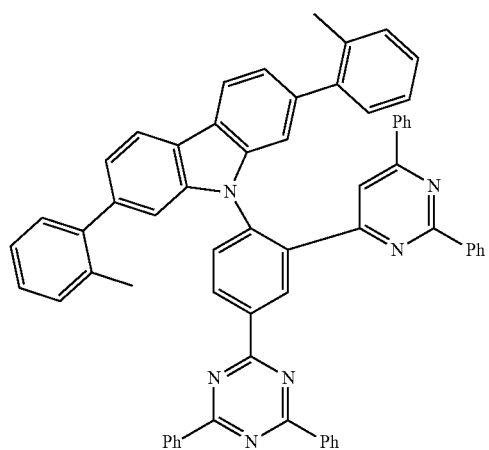

159
-continued
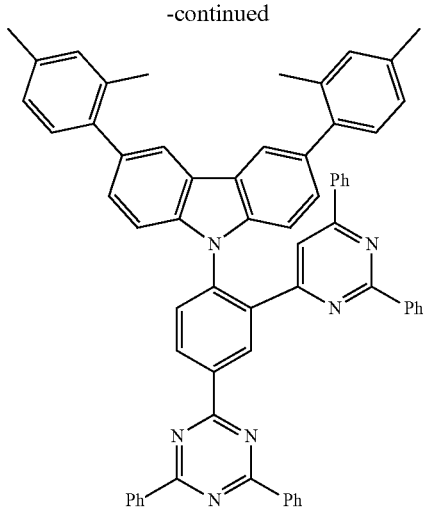
160
-continued
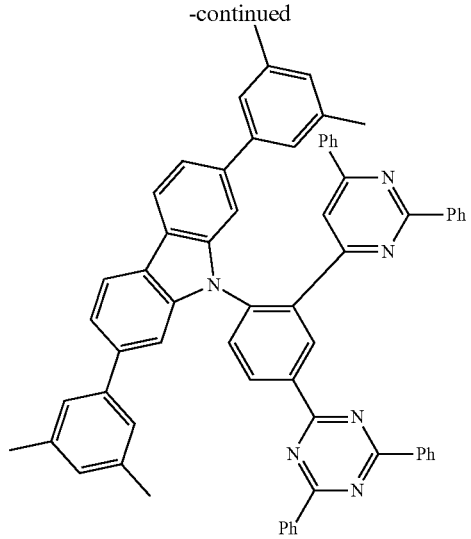
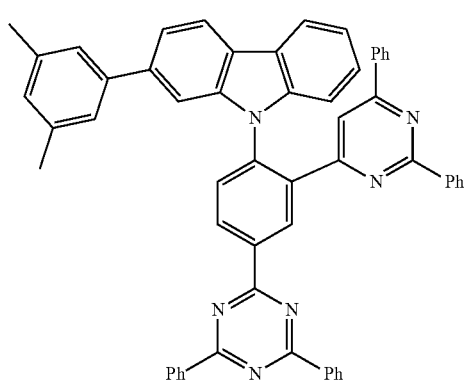
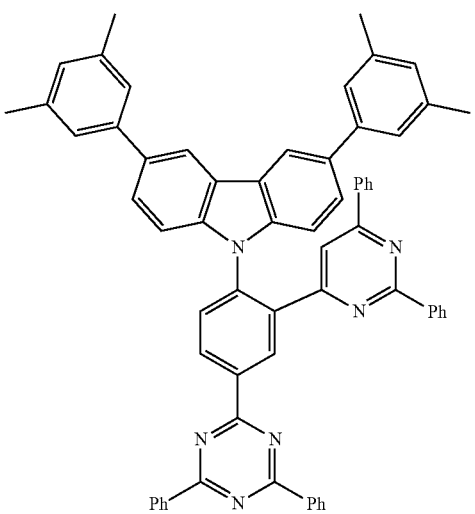
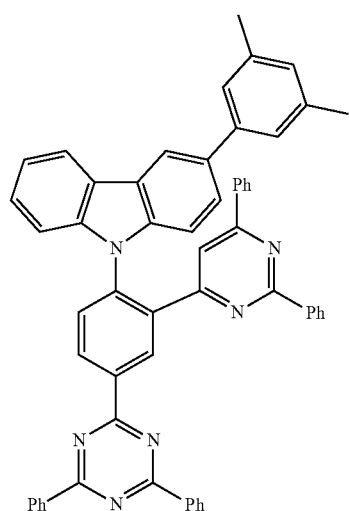
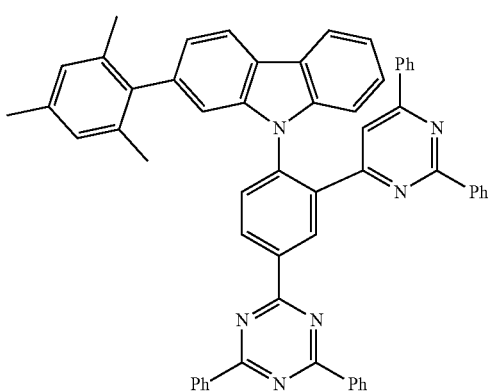

161
-continued
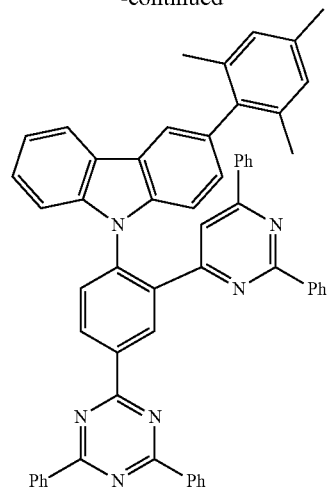
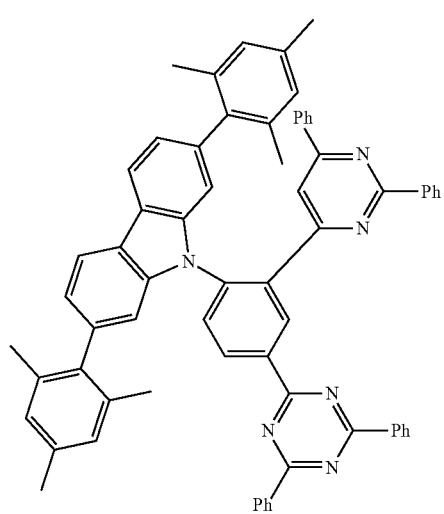
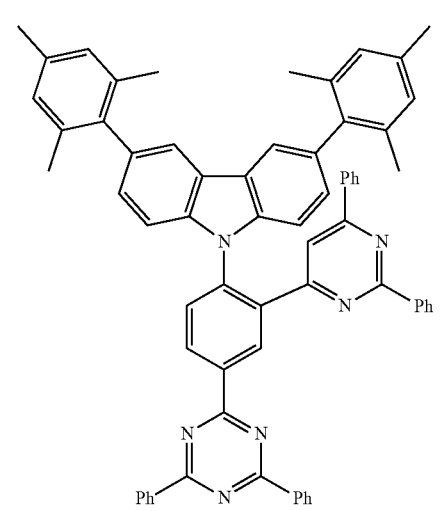
162
-continued
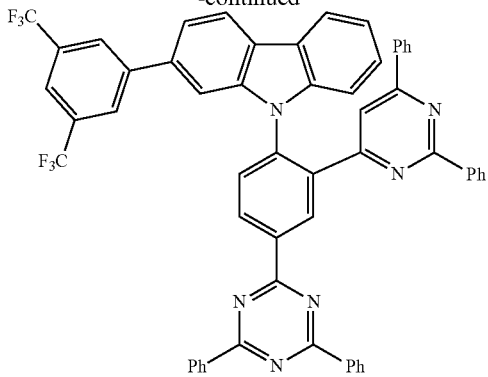
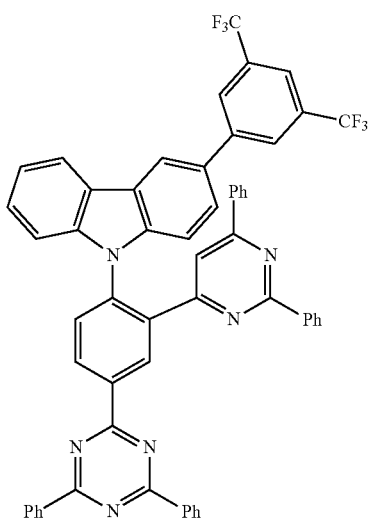
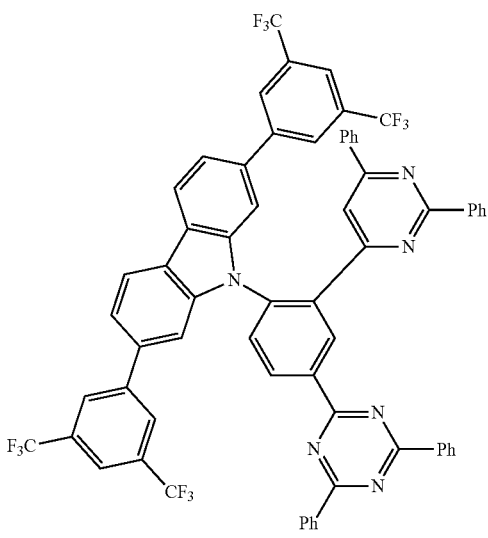

163
-continued
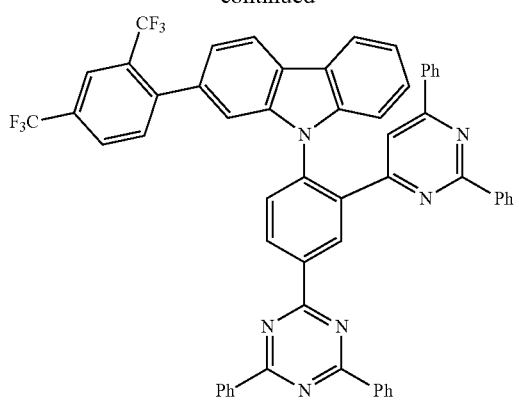
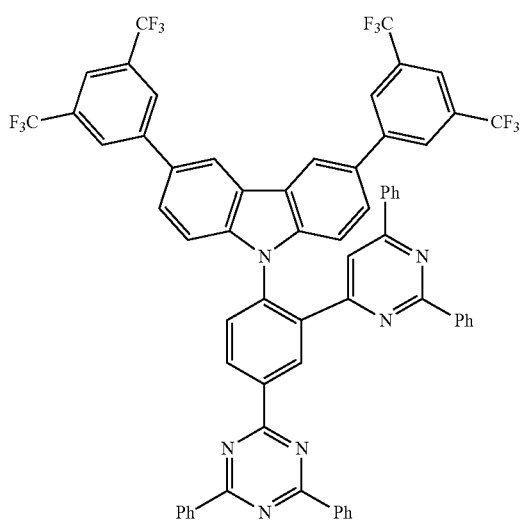
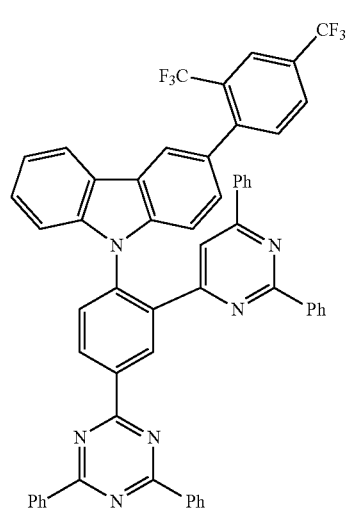
164
-continued
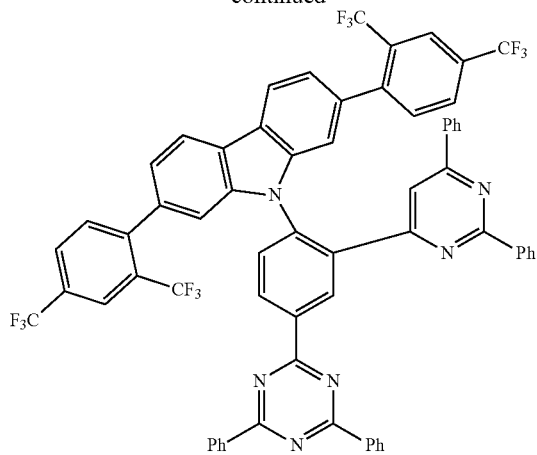
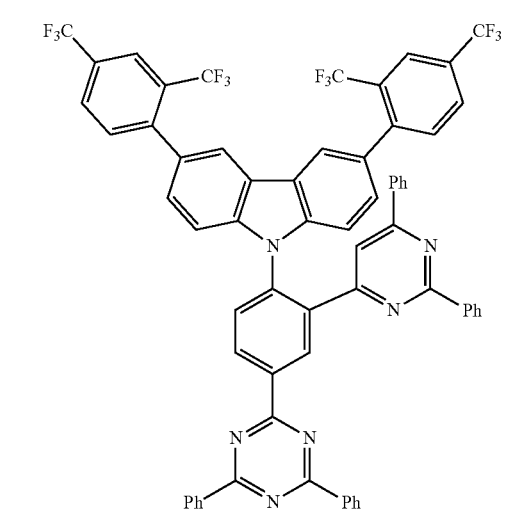
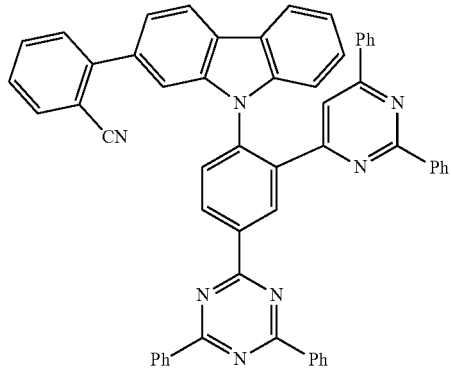

165
-continued
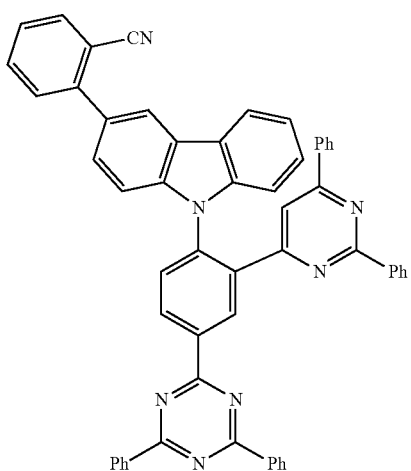
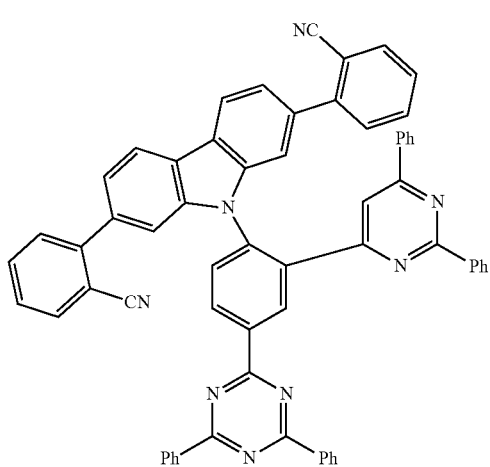
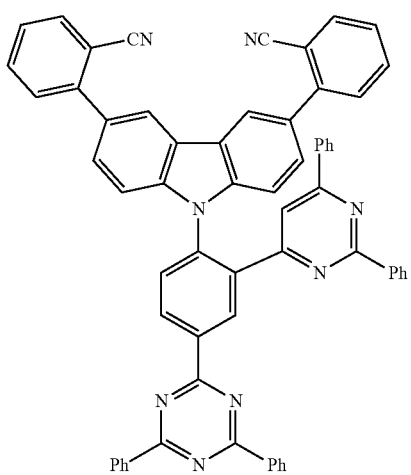
166
-continued
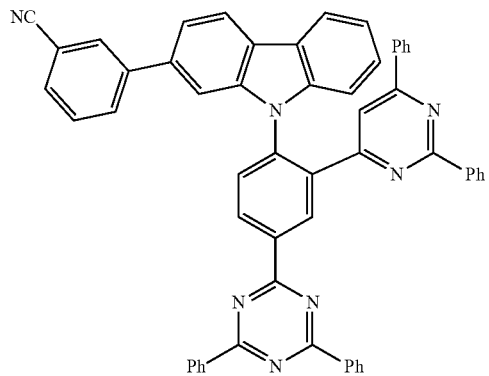
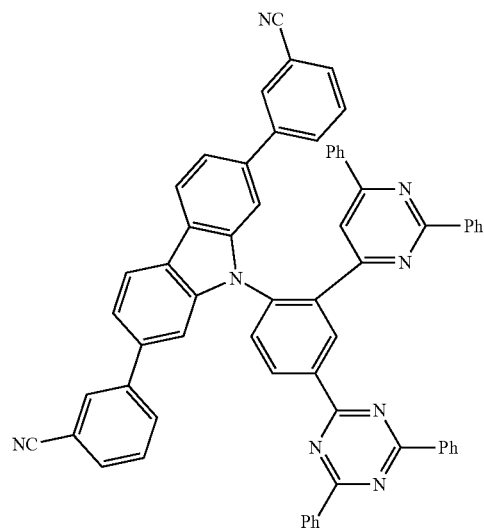

167
-continued
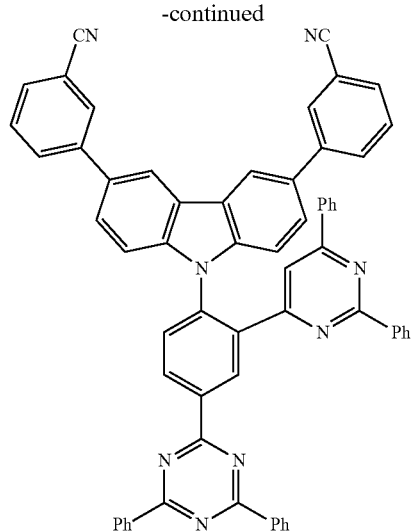
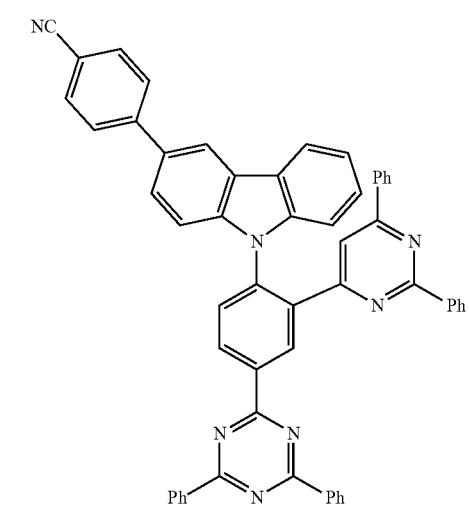
168
-continued
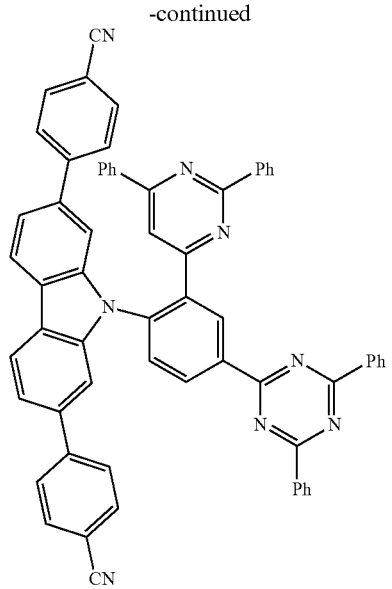
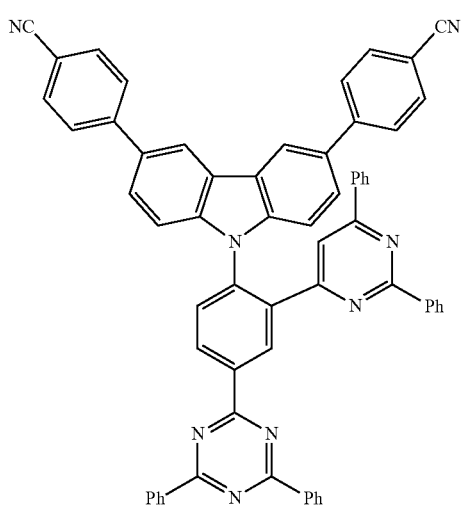 [SMILES: N#Cc1ccc(-c2ccc3c(c2)c2cc(-c4ccc(C#N)cc4)ccc2n3-c2ccc(-c3nc(-c4ccccc4)nc(-c4ccccc4)n3)cc2-c2cc(-c3ccccc3)nc(-c3ccccc3)n2)cc1]

169
-continued
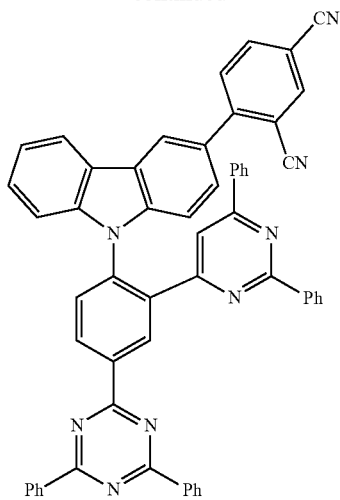
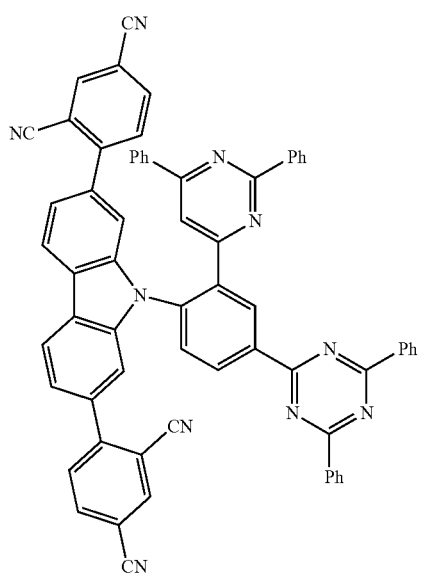
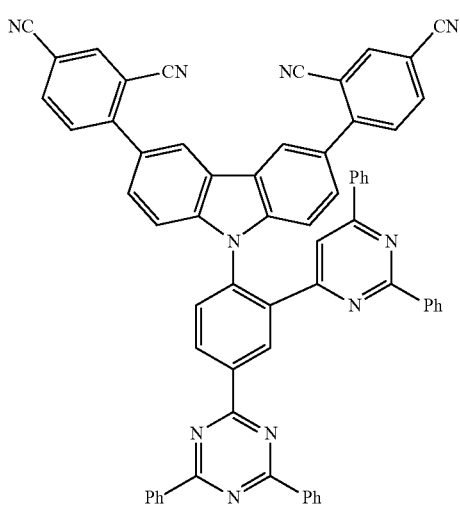 [SMILES: N#Cc1ccc(-c2ccc3c(c2)c2cc(-c4ccc(C#N)cc4C#N)ccc2n3-c2ccc(-c3nc(-c4ccccc4)nc(-c4ccccc4)n3)cc2-c2cc(-c3ccccc3)nc(-c3ccccc3)n2)c(C#N)c1]
170
-continued
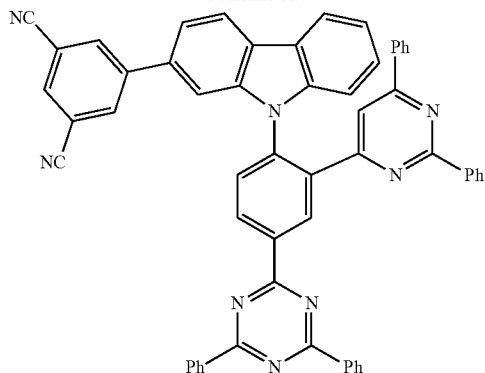
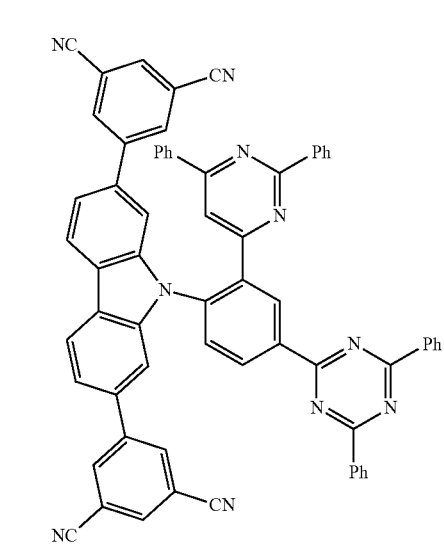

171
-continued
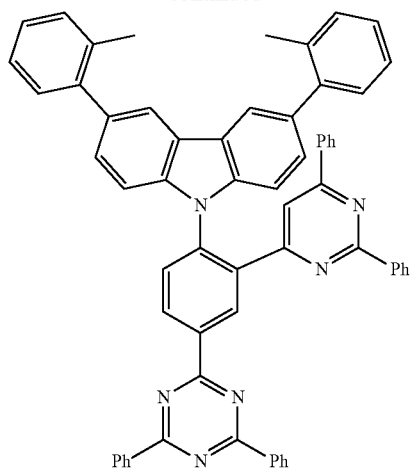
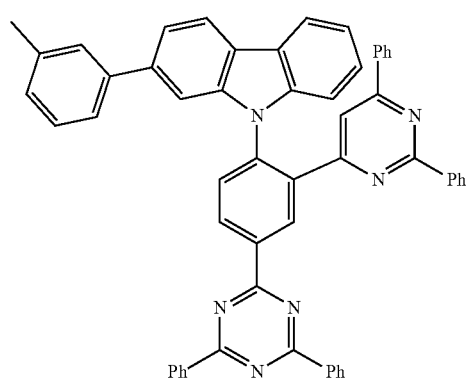
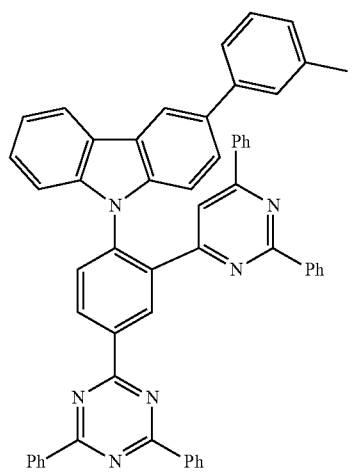
172
-continued
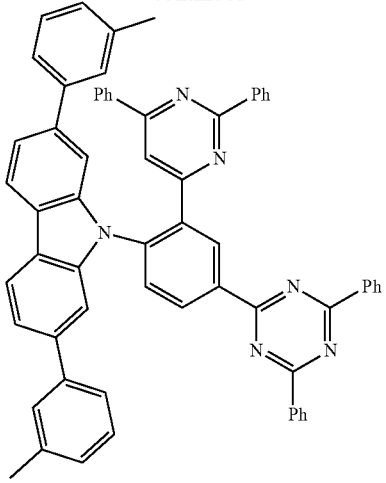
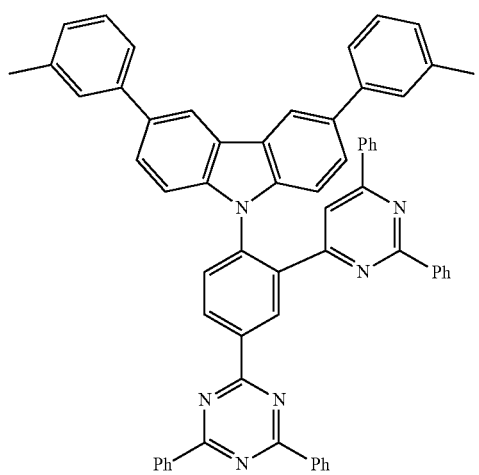
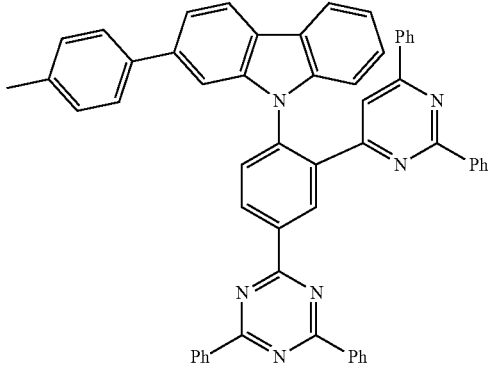

173
-continued
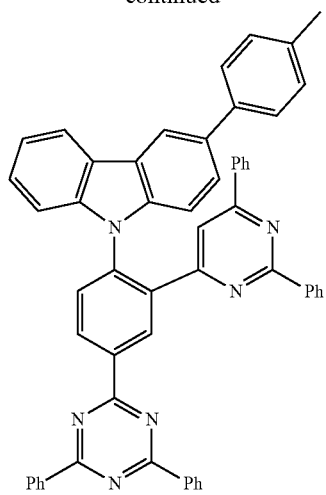
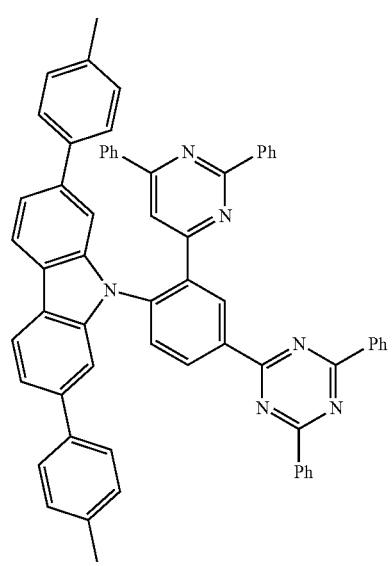
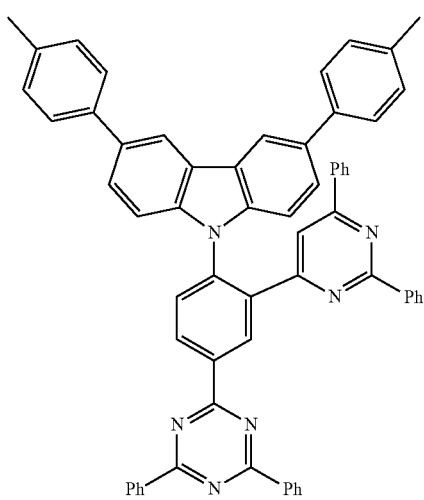
174
-continued
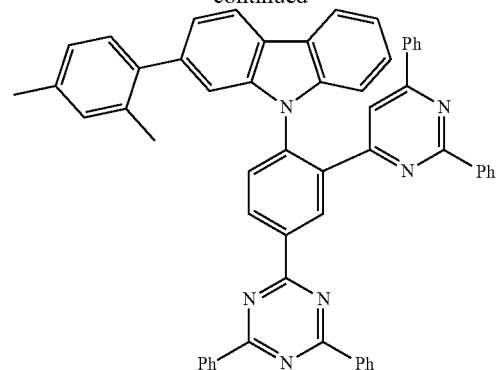
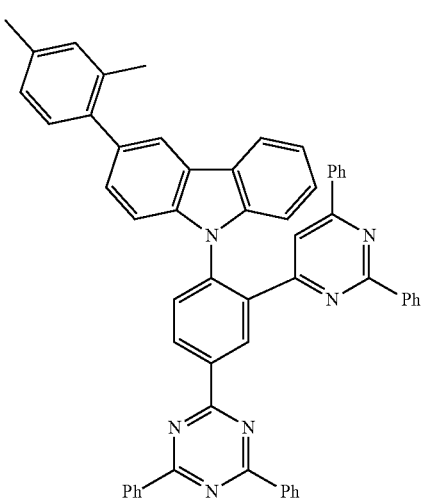
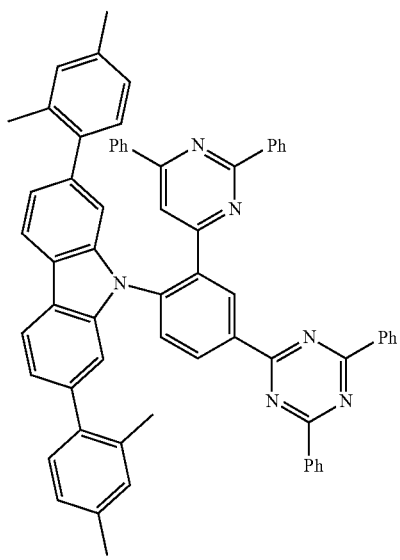

175
-continued
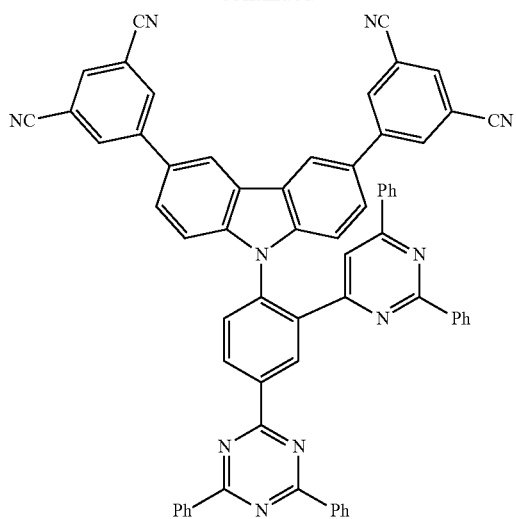 [SMILES: N#Cc1cc(C#N)cc(-c2ccc3c(c2)c2cc(-c4cc(C#N)cc(C#N)c4)ccc2n3-c2ccc(-c3nc(-c4ccccc4)nc(-c4ccccc4)n3)cc2-c2cc(-c3ccccc3)nc(-c3ccccc3)n2)c1]
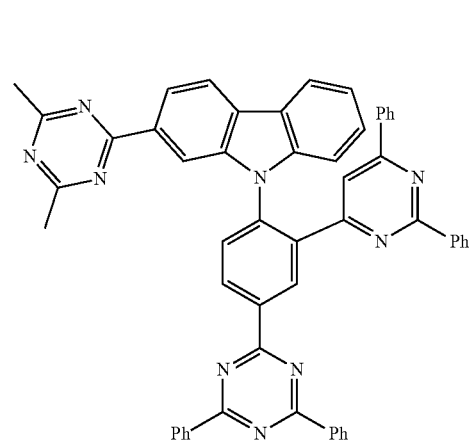
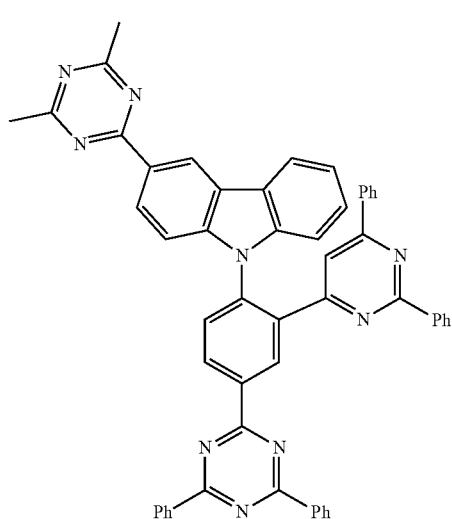
176
-continued
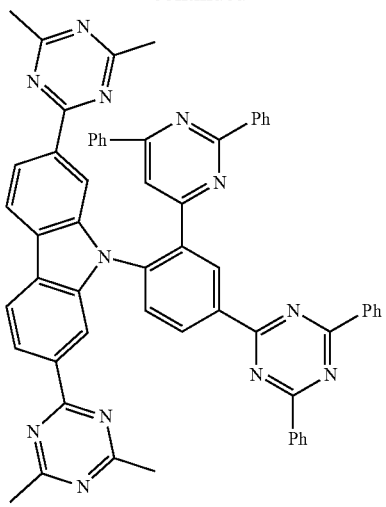
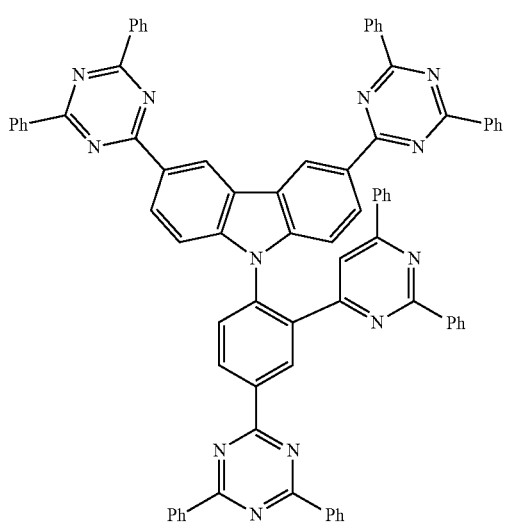 [SMILES: c1ccc(-c2cc(-c3cc(-c4nc(-c5ccccc5)nc(-c5ccccc5)n4)ccc3-n3c4ccc(-c5nc(-c6ccccc6)nc(-c6ccccc6)n5)cc4c4cc(-c5nc(-c6ccccc6)nc(-c6ccccc6)n5)ccc43)nc(-c3ccccc3)n2)cc1]
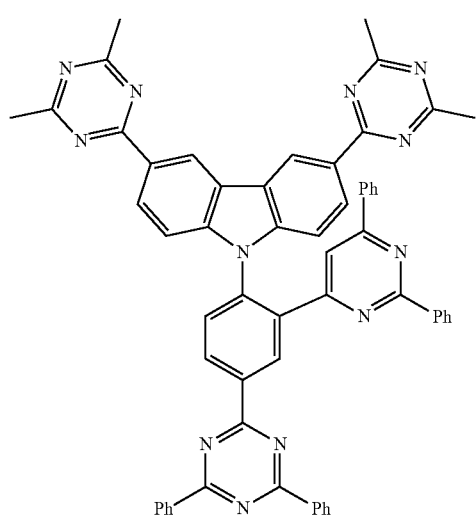

177
-continued
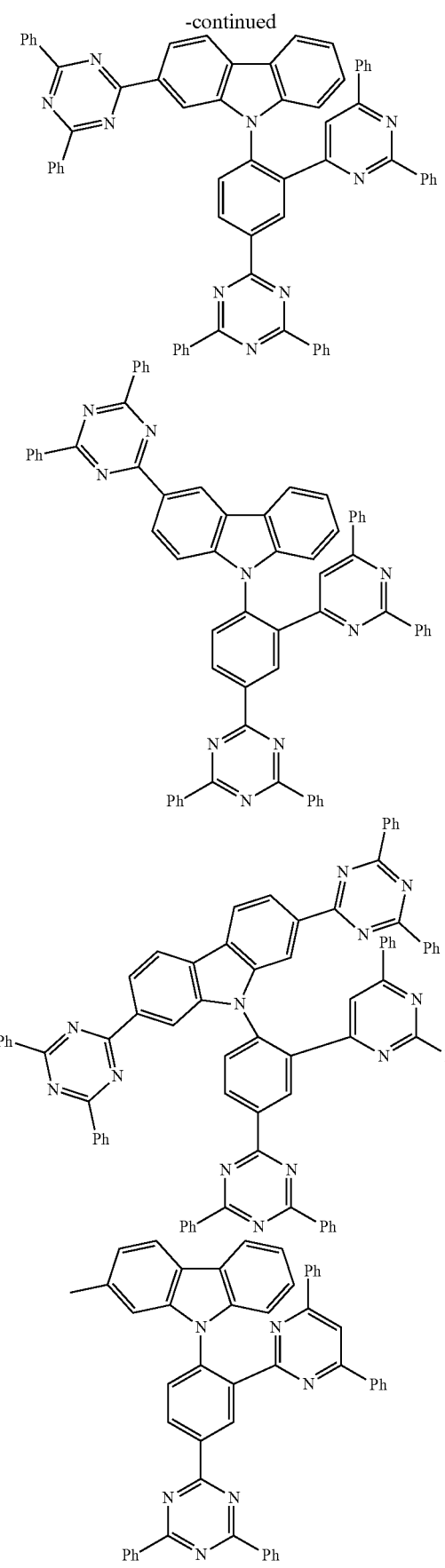
178
-continued
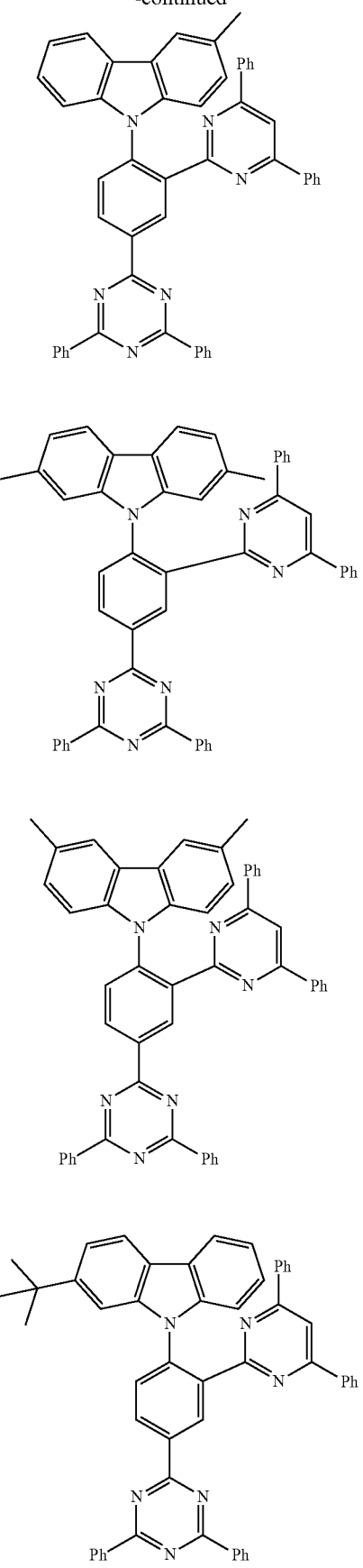

179
-continued
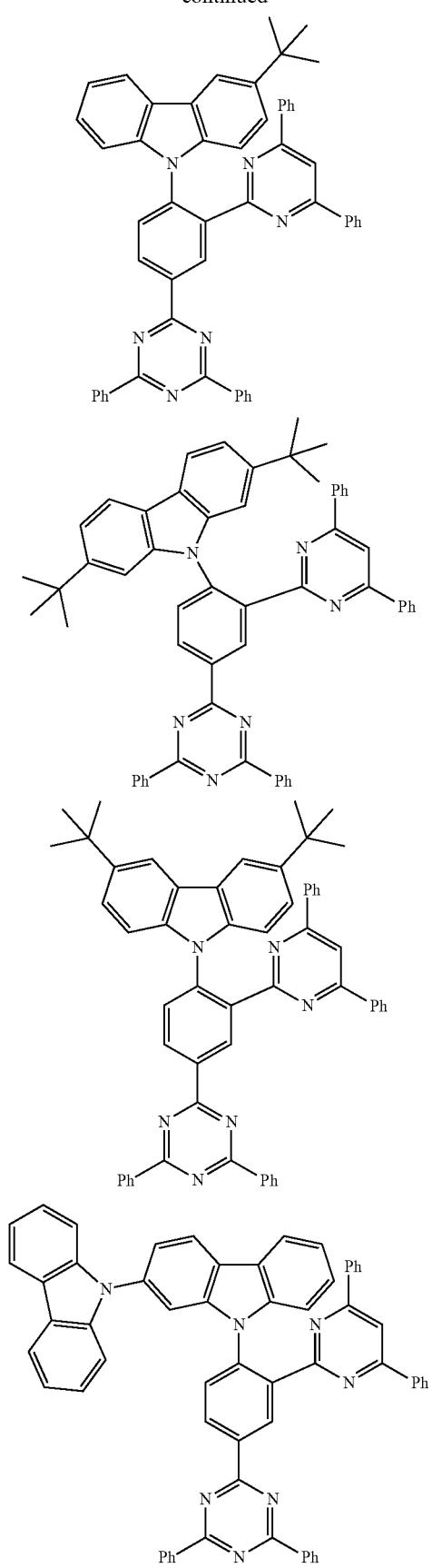
180
-continued
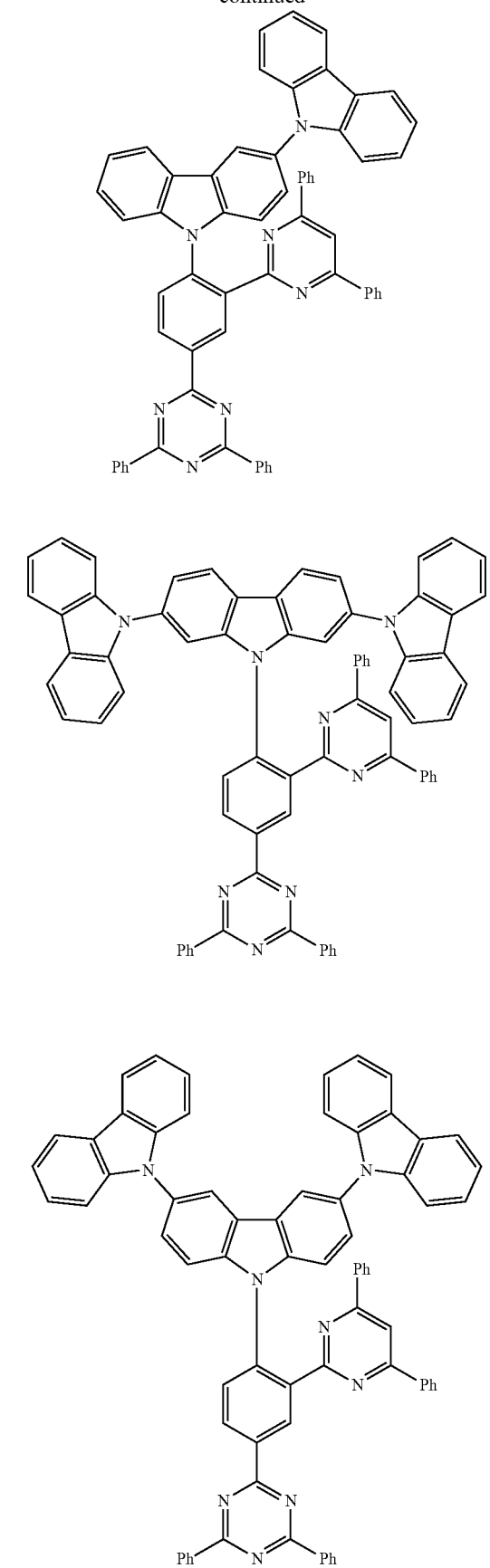

181
-continued
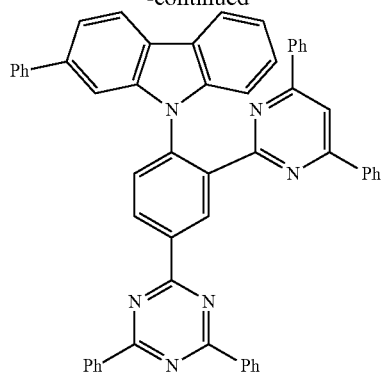
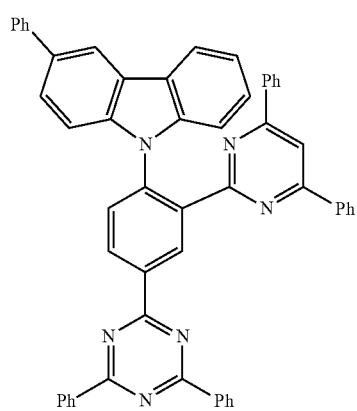
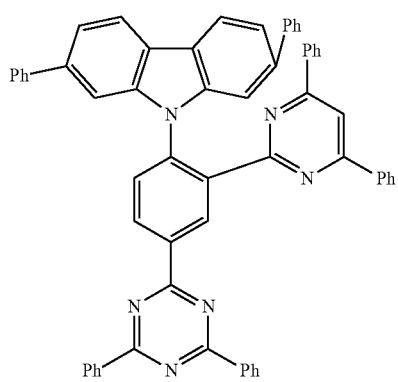
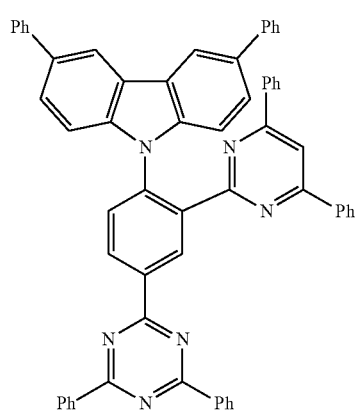
182
-continued
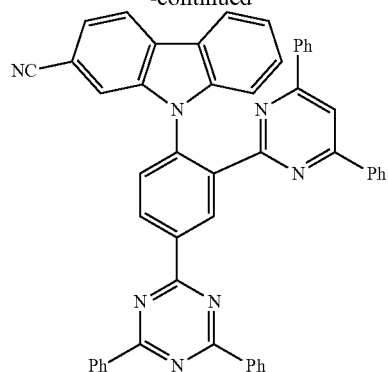
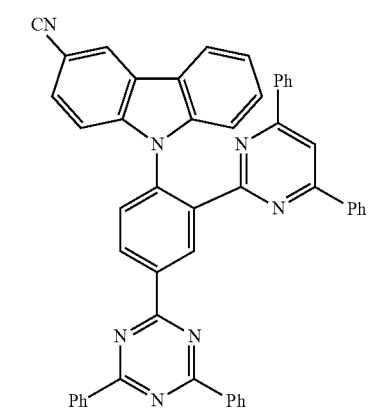
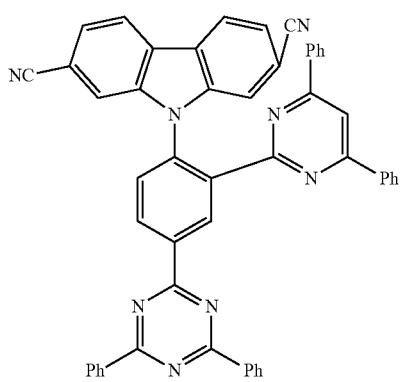
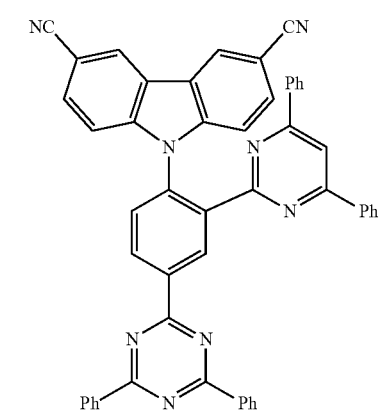

183
-continued
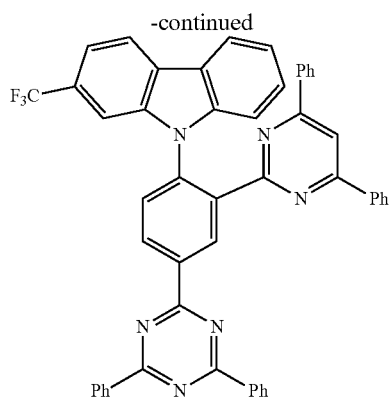
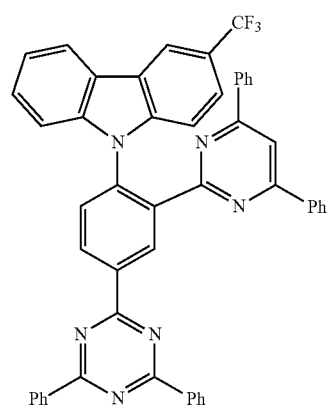
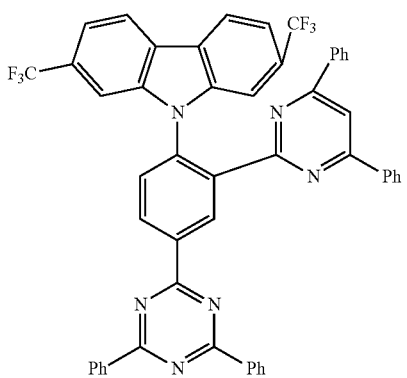
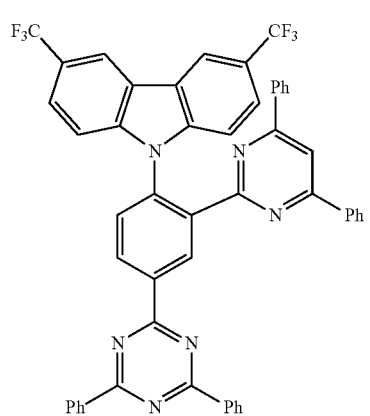
184
-continued
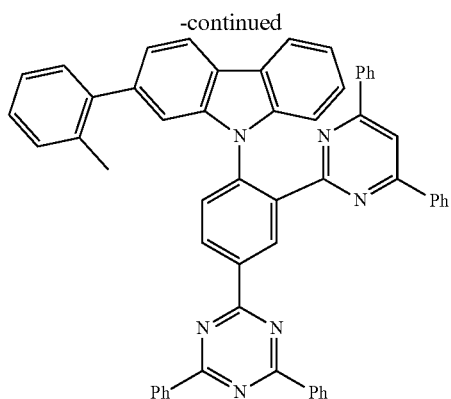
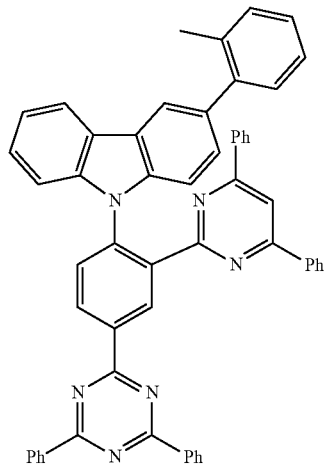
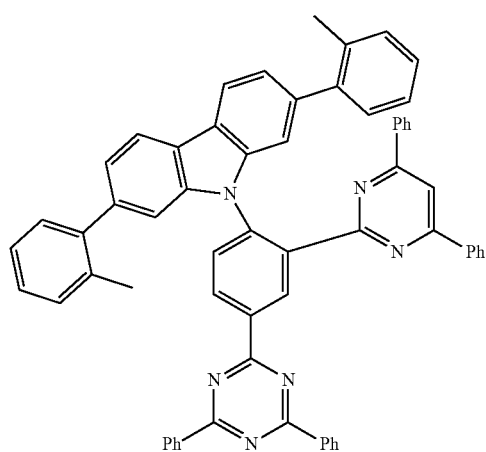

185
-continued
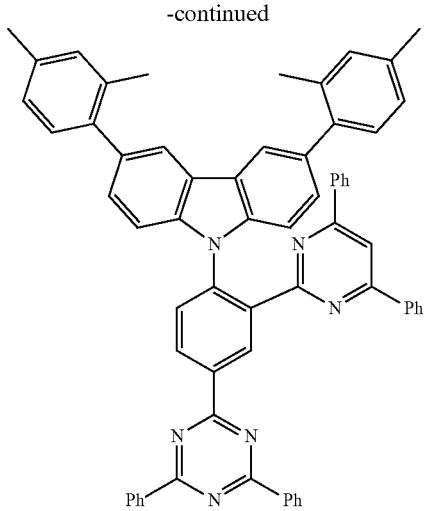
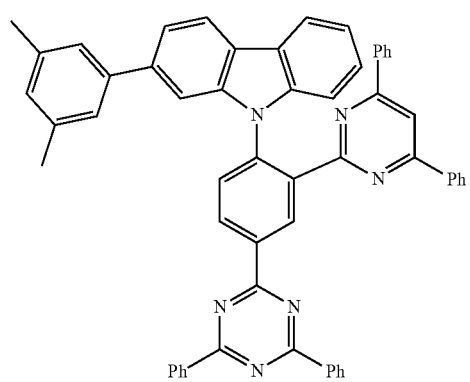
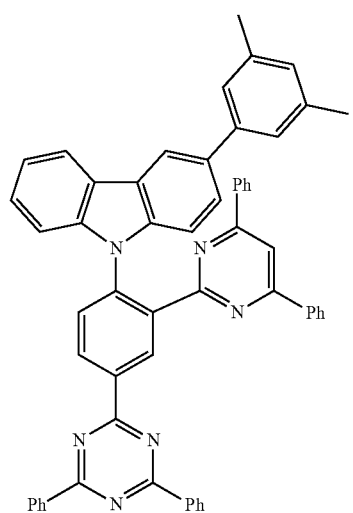
186
-continued
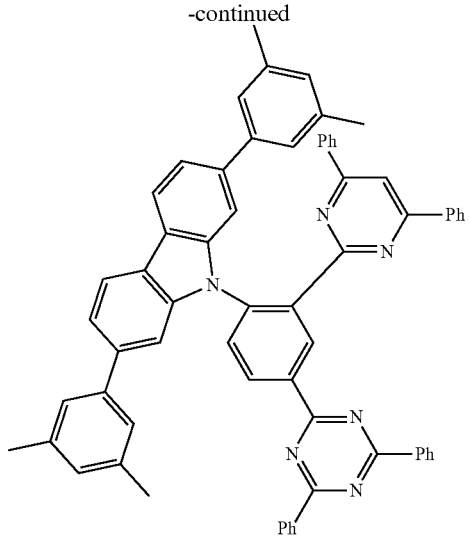
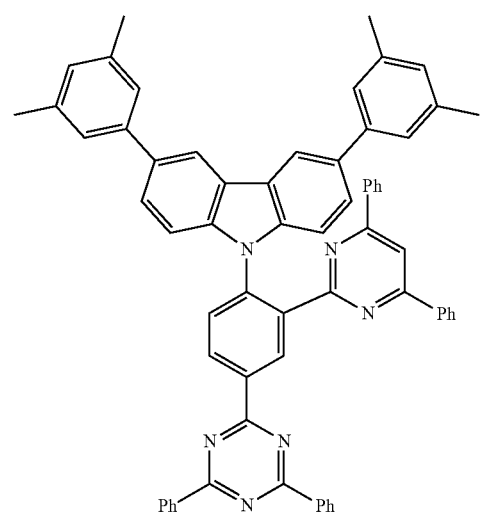
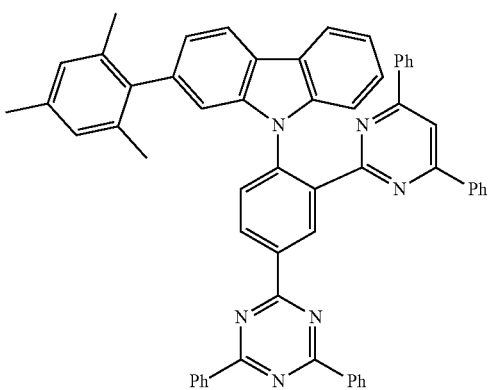

187
-continued
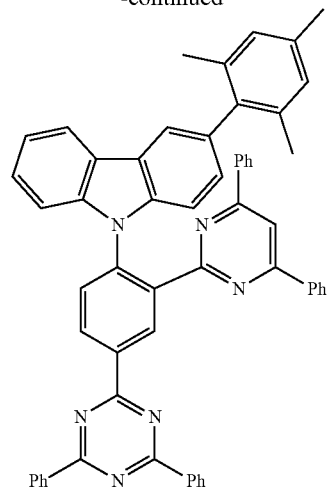
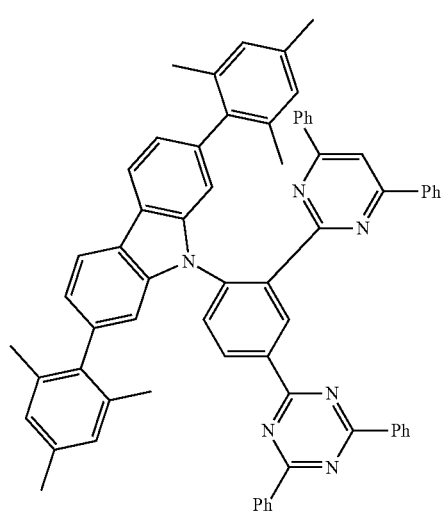
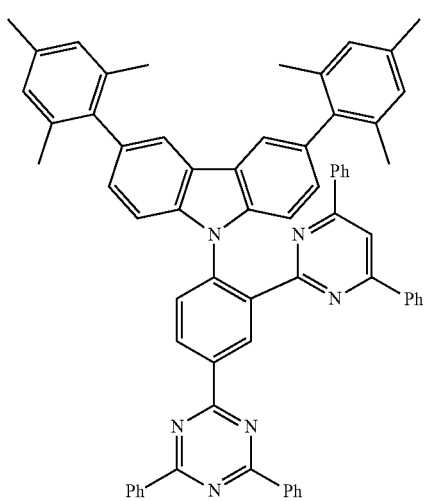
188
-continued
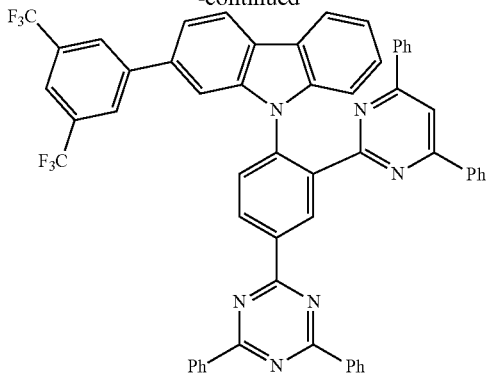
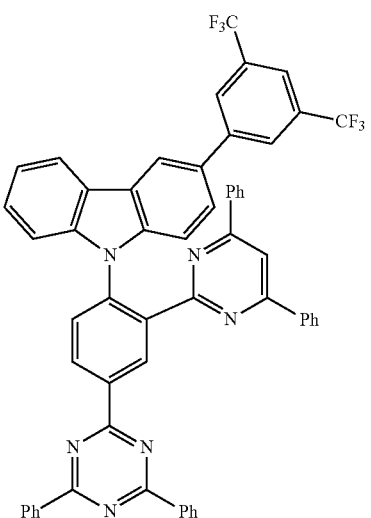
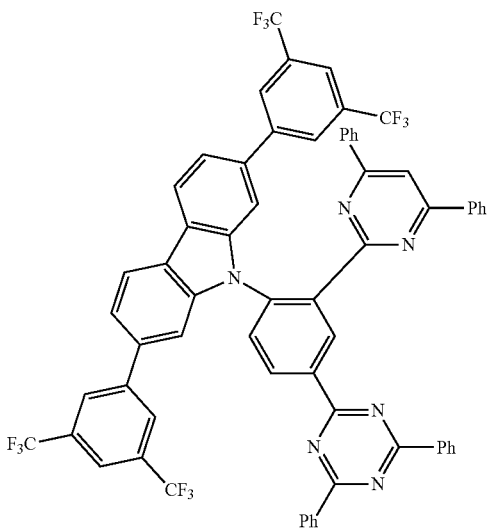

189
-continued
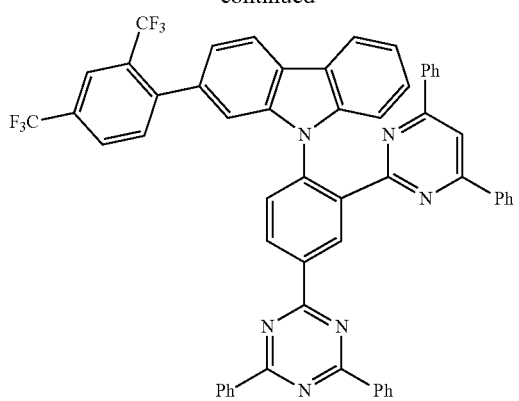
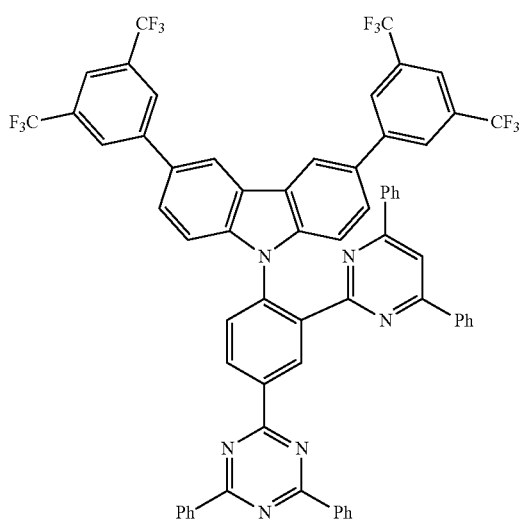
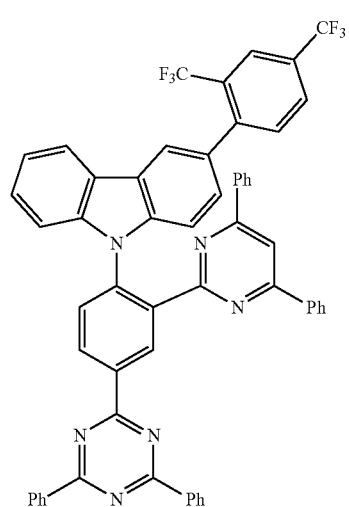
190
-continued
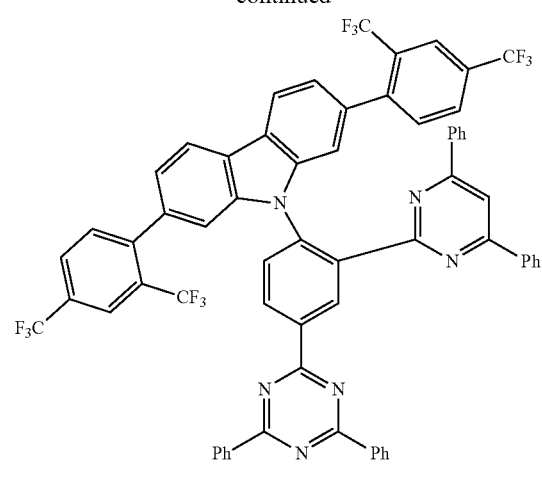
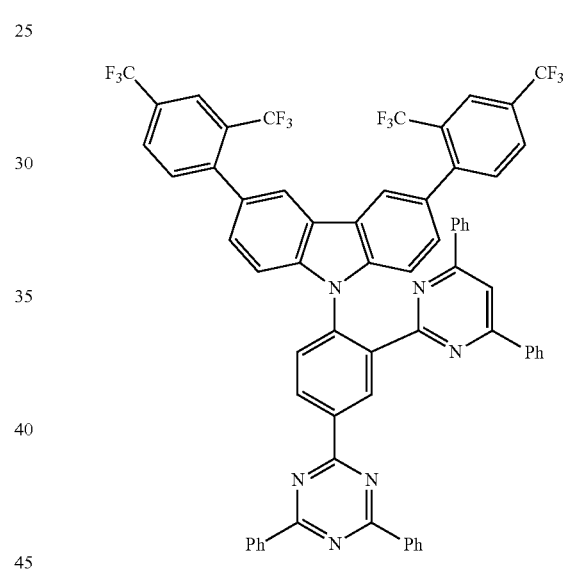
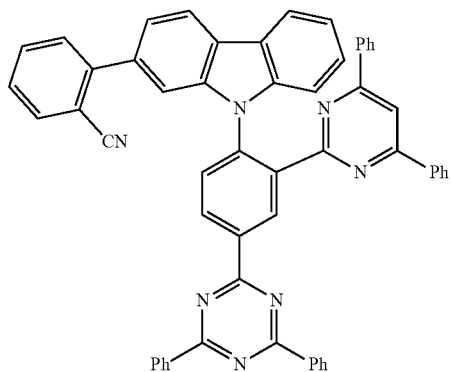

191
-continued
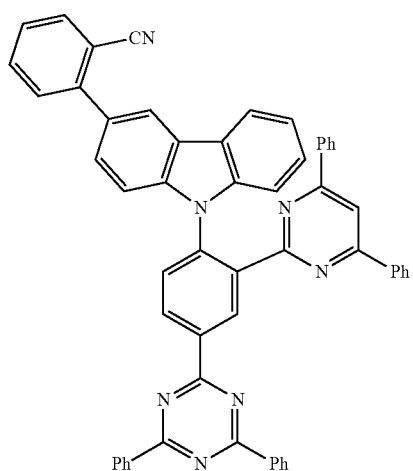
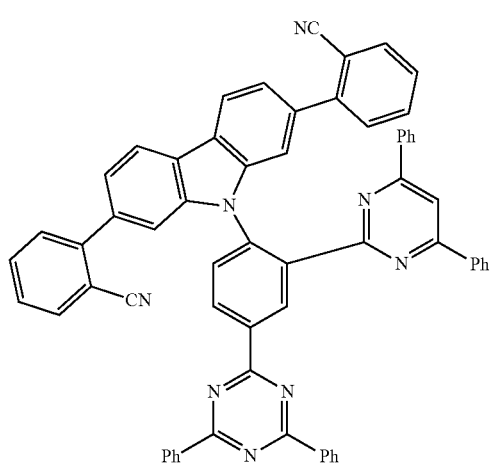
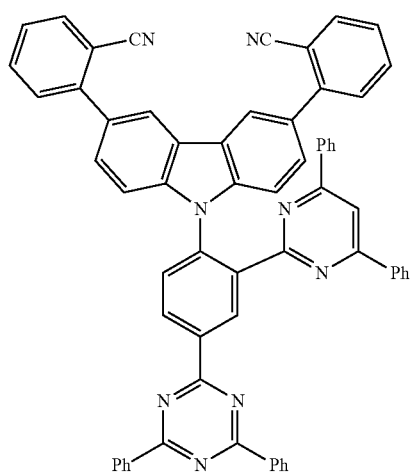
192
-continued
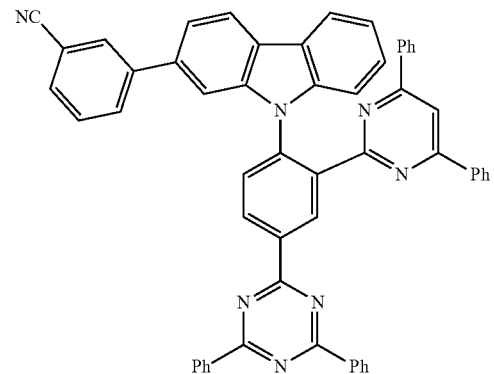
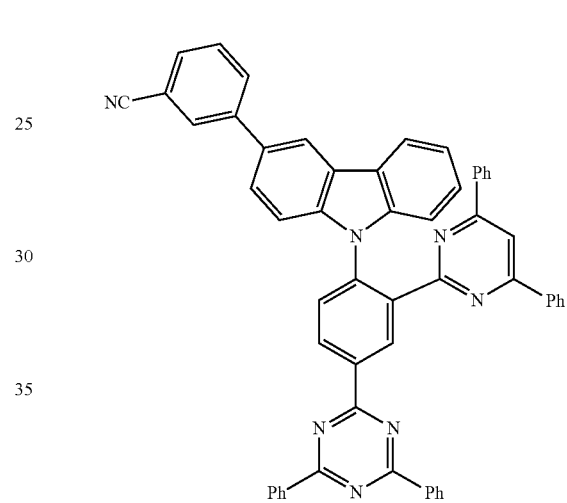
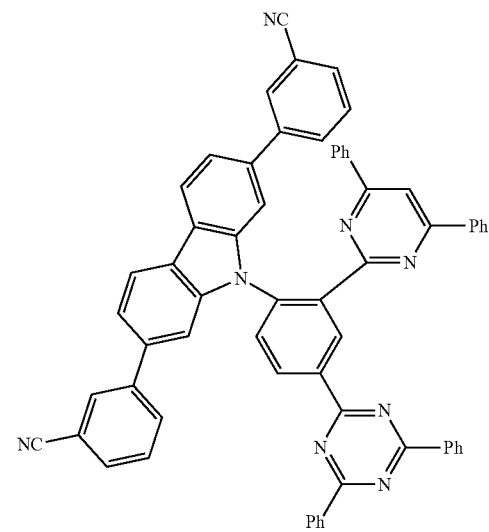

193
-continued
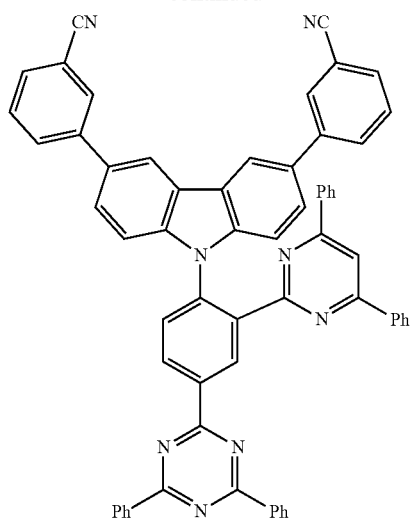 [SMILES: N#Cc1cccc(-c2ccc3c(c2)c2cc(-c4cccc(C#N)c4)ccc2n3-c2ccc(-c3nc(-c4ccccc4)nc(-c4ccccc4)n3)cc2-c2nc(-c3ccccc3)cc(-c3ccccc3)n2)c1]
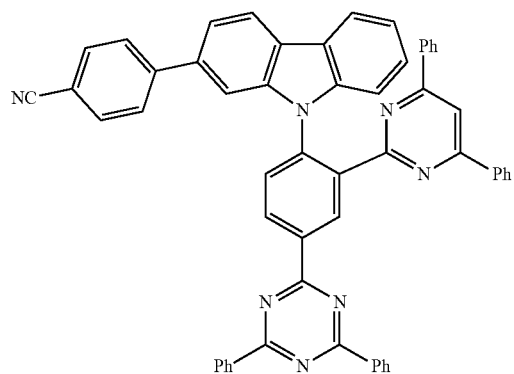
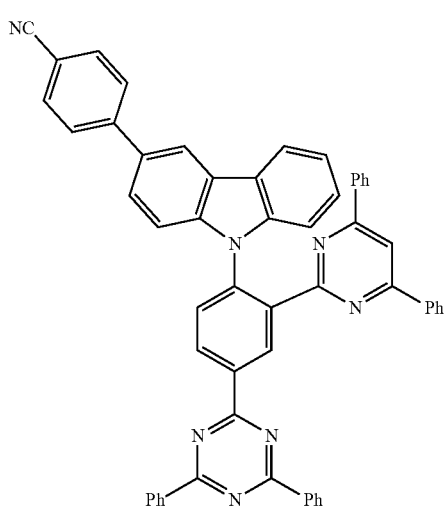
194
-continued
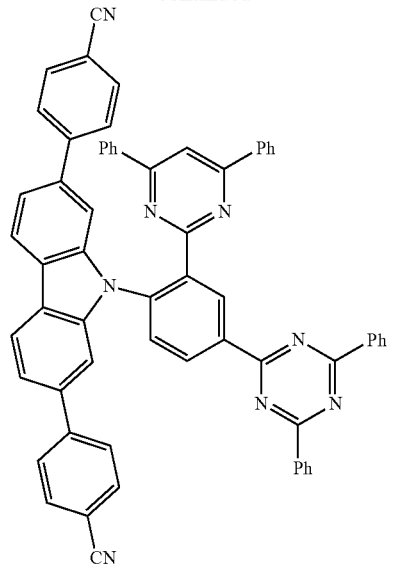
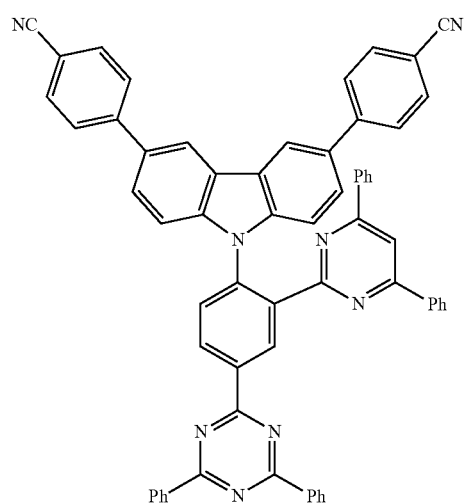 [SMILES: N#Cc1ccc(-c2ccc3c(c2)c2cc(-c4ccc(C#N)cc4)ccc2n3-c2ccc(-c3nc(-c4ccccc4)nc(-c4ccccc4)n3)cc2-c2nc(-c3ccccc3)cc(-c3ccccc3)n2)cc1]

195
-continued
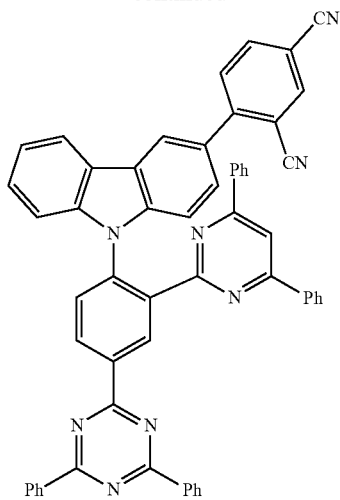
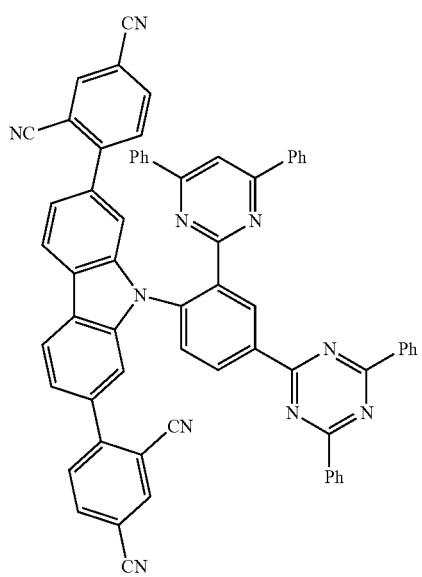
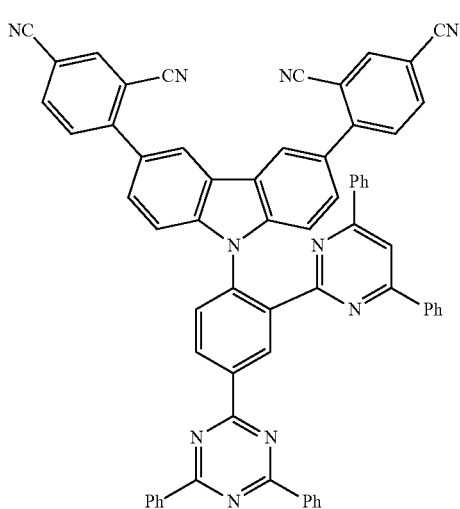 [SMILES: N#Cc1ccc(-c2ccc3c(c2)c2cc(-c4ccc(C#N)cc4C#N)ccc2n3-c2ccc(-c3nc(-c4ccccc4)nc(-c4ccccc4)n3)cc2-c2nc(-c3ccccc3)cc(-c3ccccc3)n2)c(C#N)c1]
196
-continued
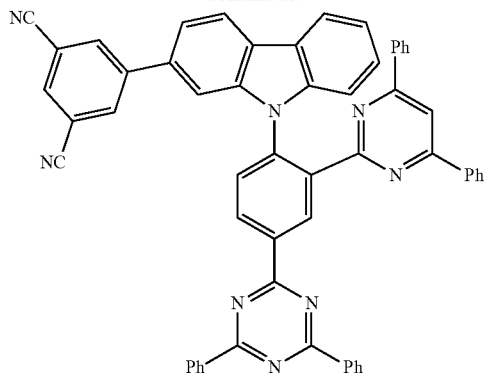
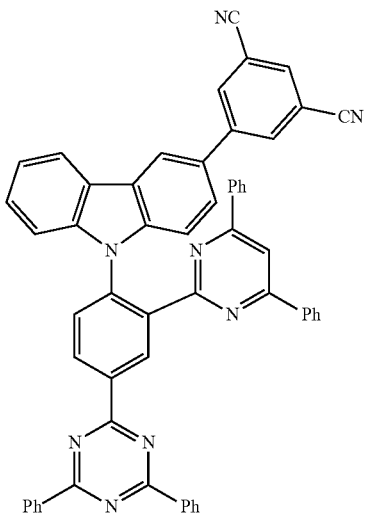
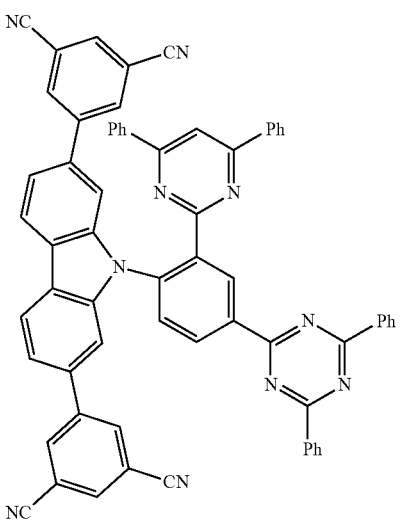

197
-continued
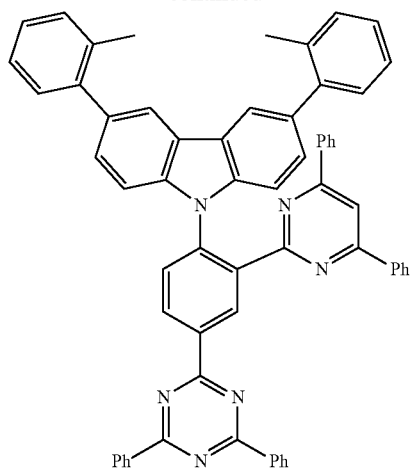 [SMILES: Cc1ccccc1-c1ccc2c(c1)c1cc(-c3ccccc3C)ccc1n2-c1ccc(-c2nc(-c3ccccc3)nc(-c3ccccc3)n2)cc1-c1nc(-c2ccccc2)cc(-c2ccccc2)n1]
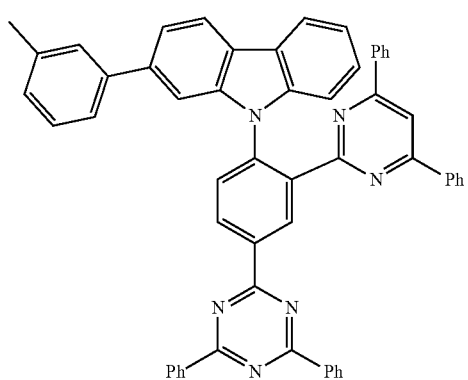
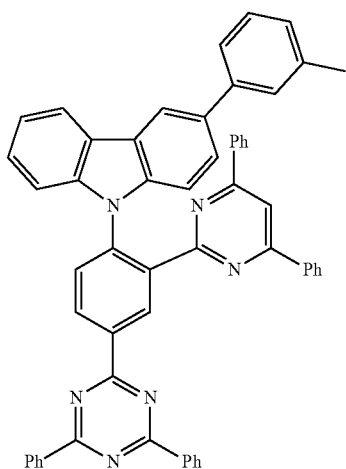
198
-continued
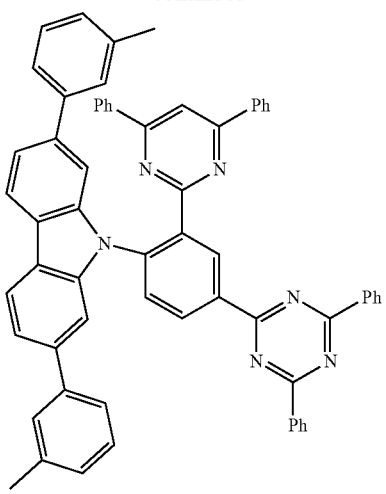
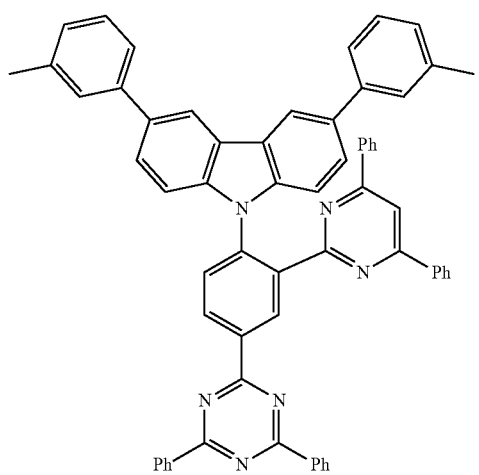
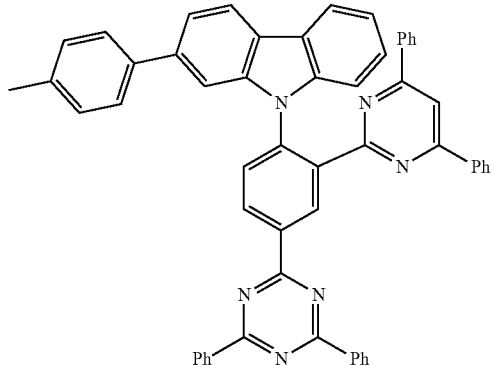

199
-continued
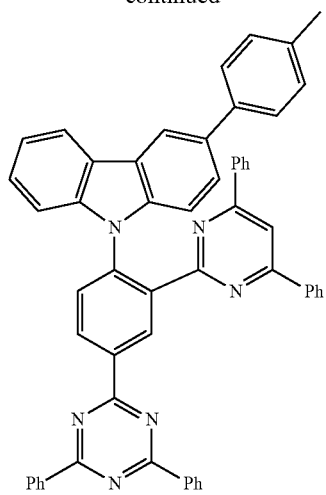
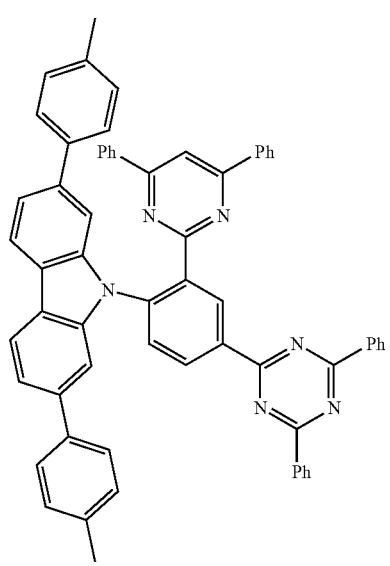
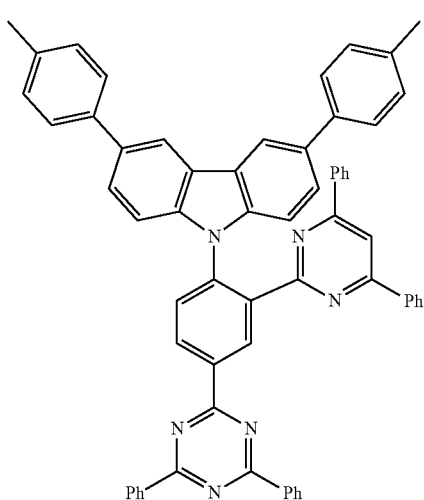
200
-continued
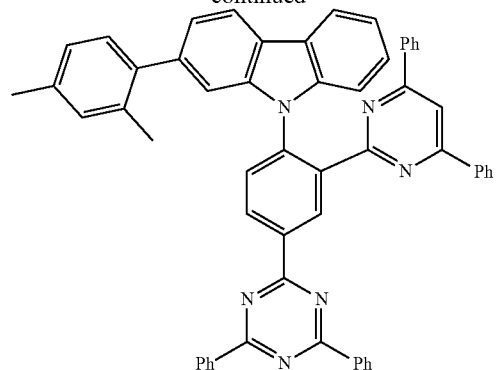
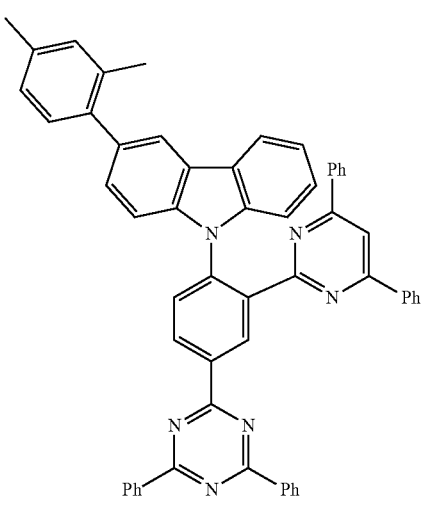
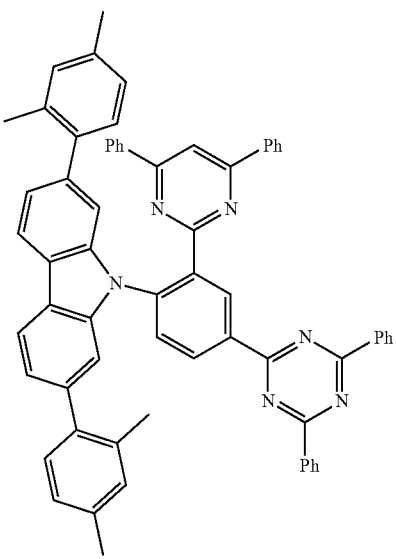

201
-continued
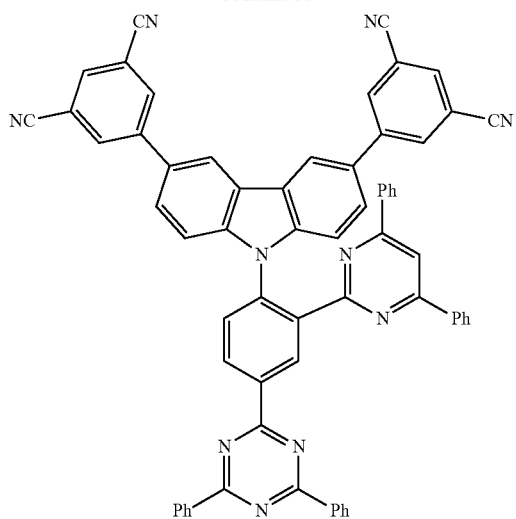 [SMILES: N#Cc1cc(C#N)cc(-c2ccc3c(c2)c2cc(-c4cc(C#N)cc(C#N)c4)ccc2n3-c2ccc(-c3nc(-c4ccccc4)nc(-c4ccccc4)n3)cc2-c2nc(-c3ccccc3)cc(-c3ccccc3)n2)c1]
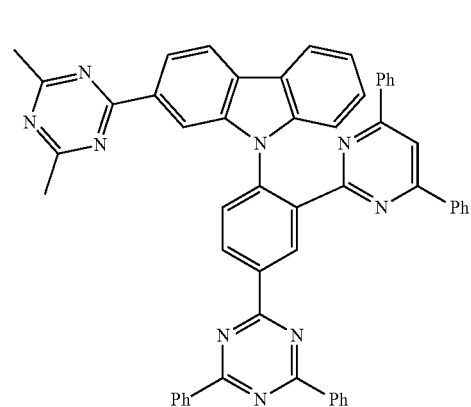
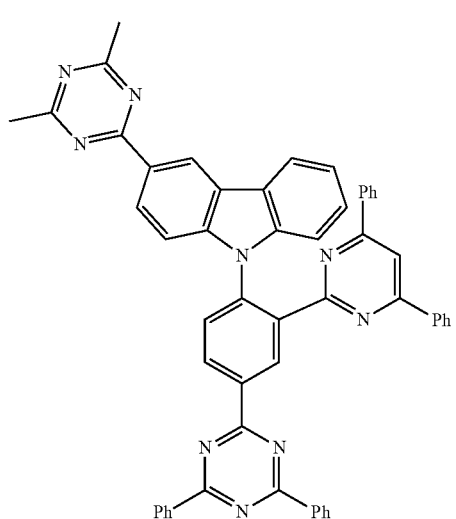
202
-continued
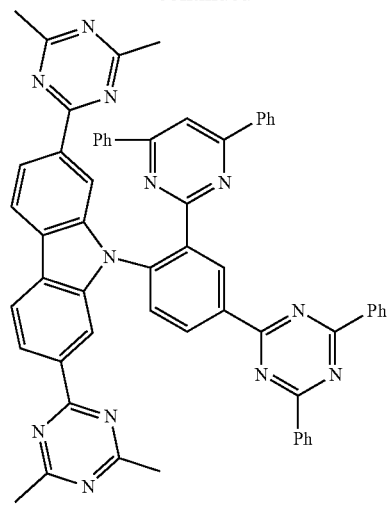
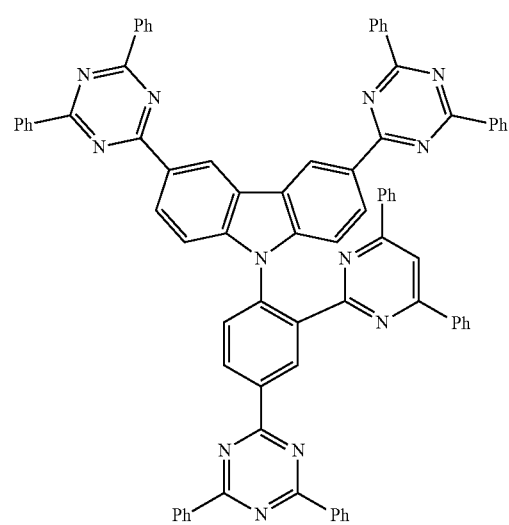 [SMILES: c1ccc(-c2cc(-c3ccccc3)nc(-c3cc(-c4nc(-c5ccccc5)nc(-c5ccccc5)n4)ccc3-n3c4ccc(-c5nc(-c6ccccc6)nc(-c6ccccc6)n5)cc4c4cc(-c5nc(-c6ccccc6)nc(-c6ccccc6)n5)ccc43)n2)cc1]
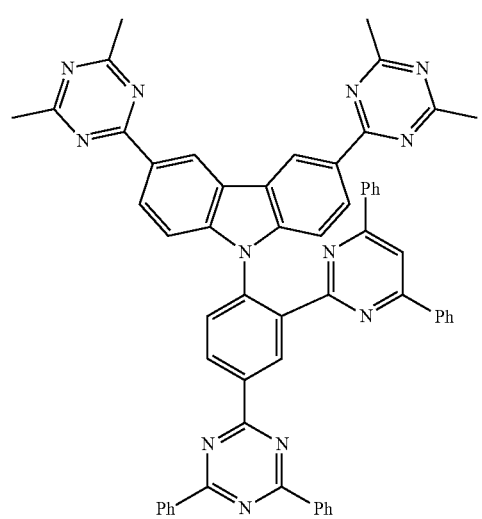

203
-continued
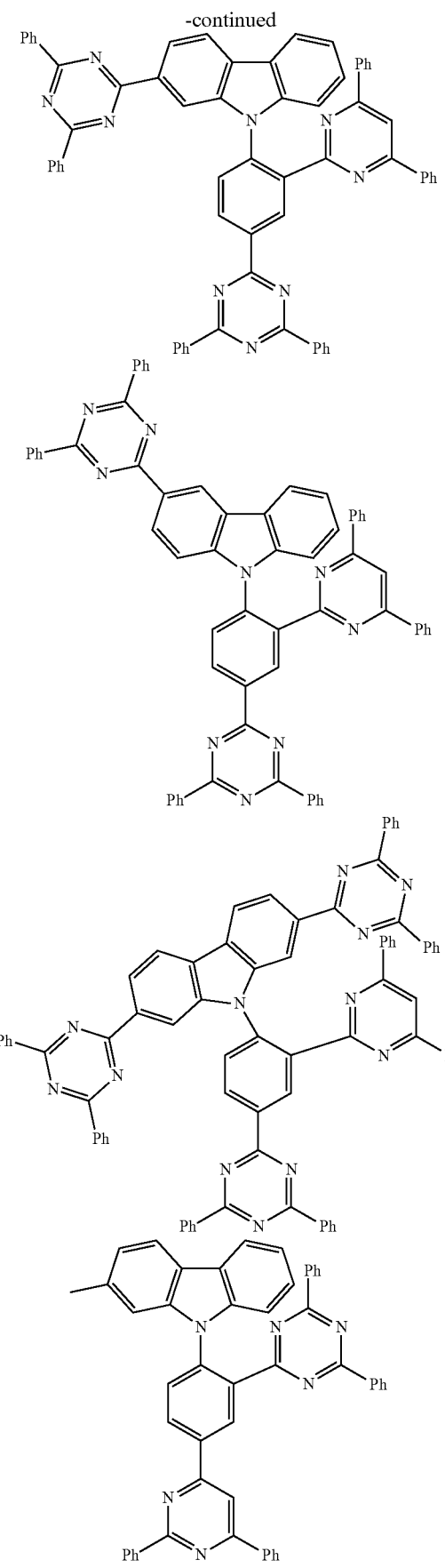
204
-continued
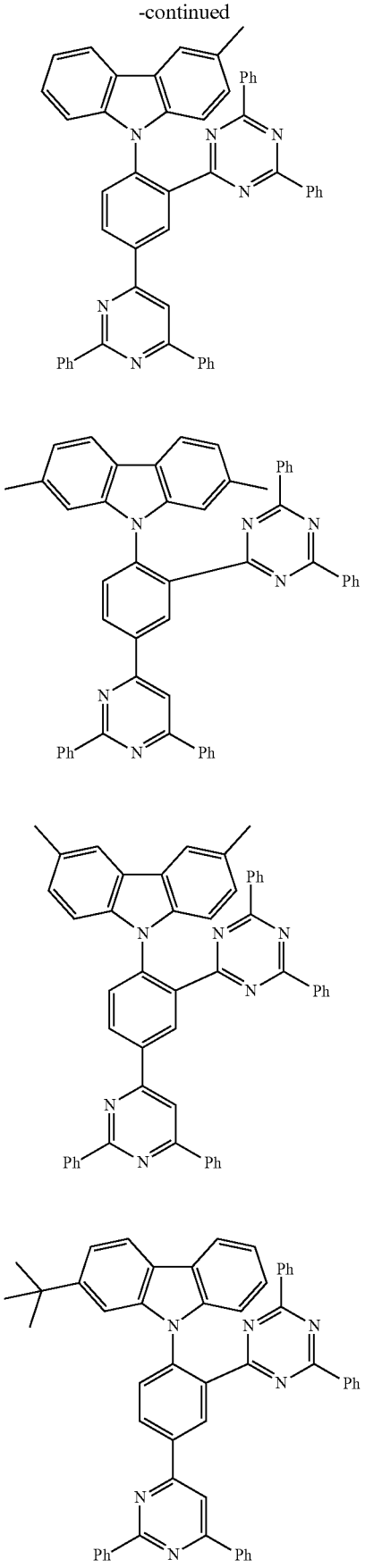

205
-continued
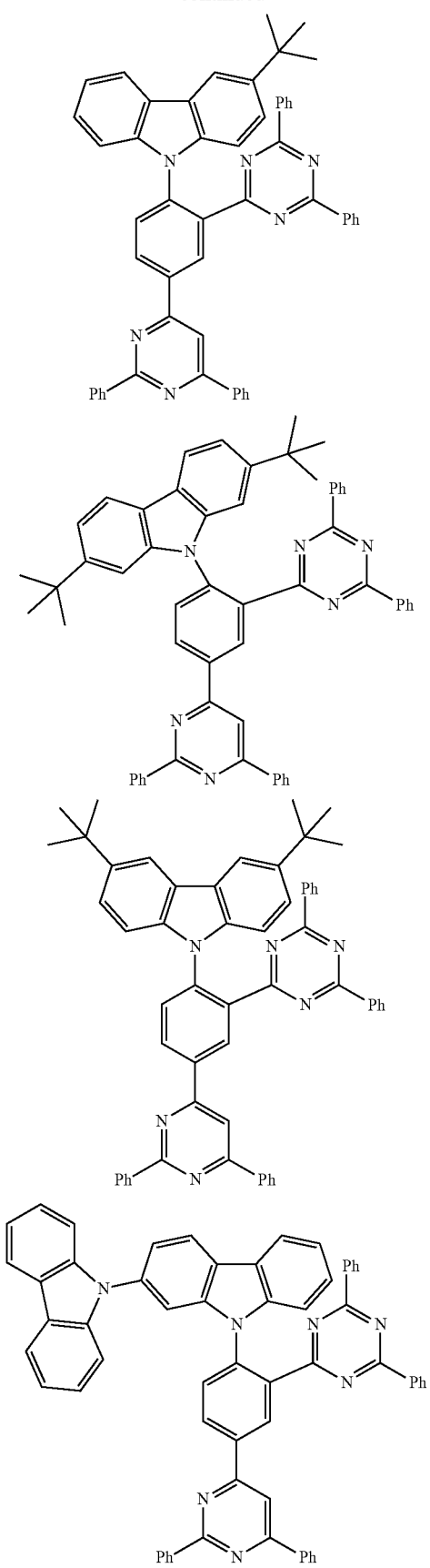
206
-continued
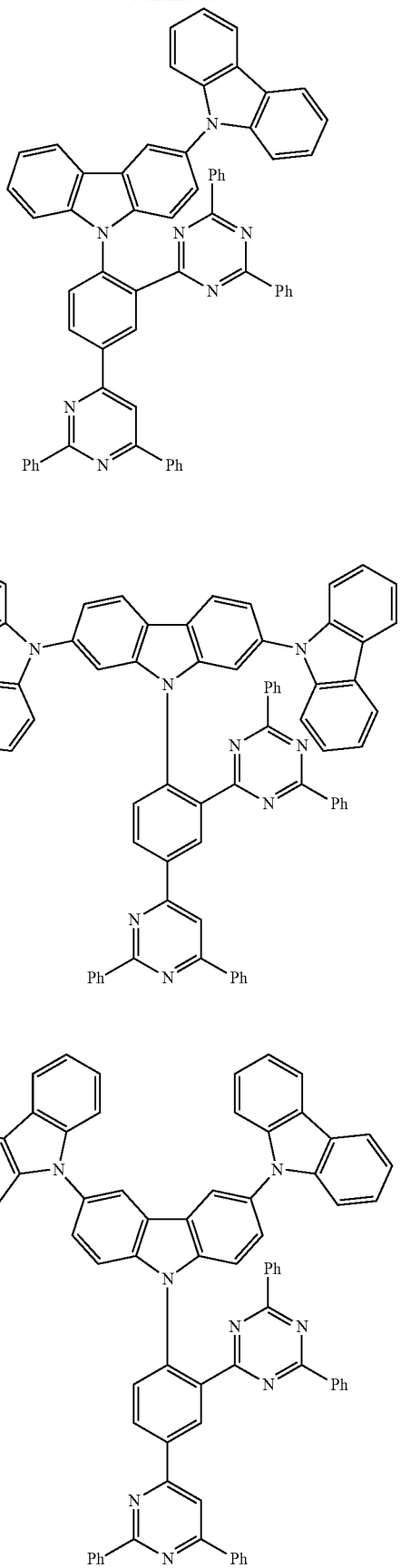

207
-continued
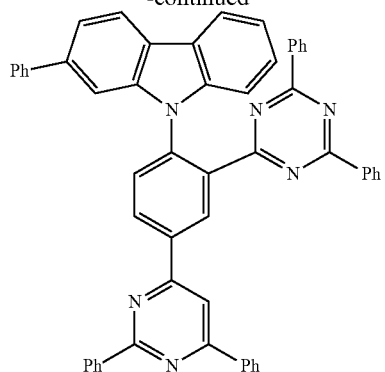
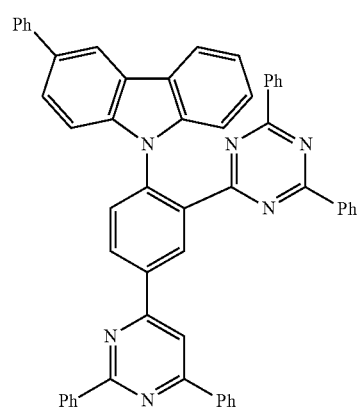
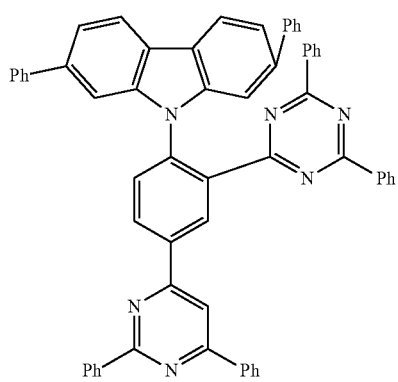
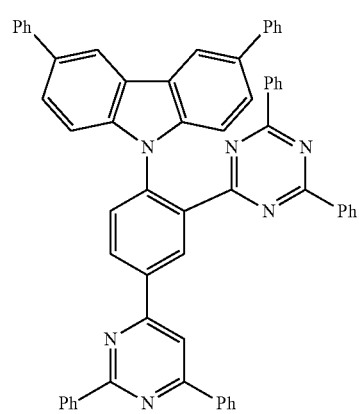
208
-continued
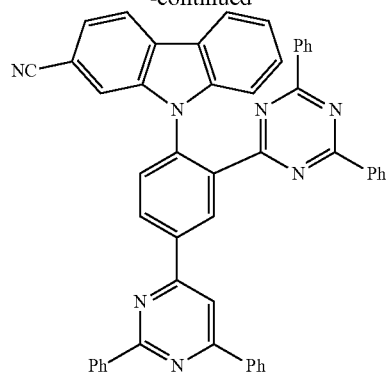
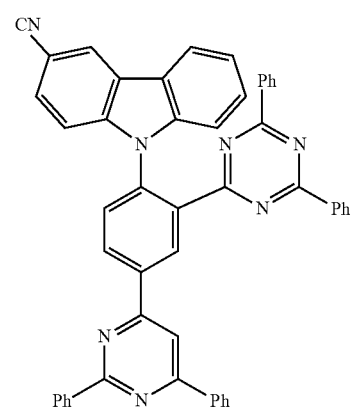
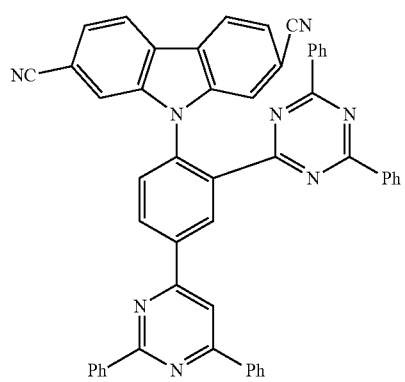
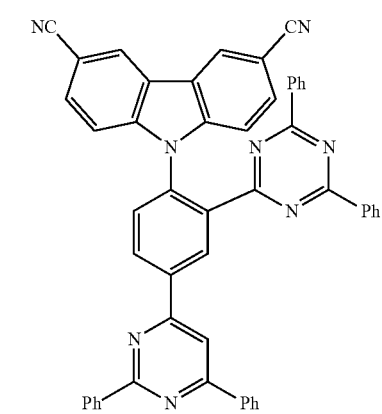

209
-continued
210
-continued
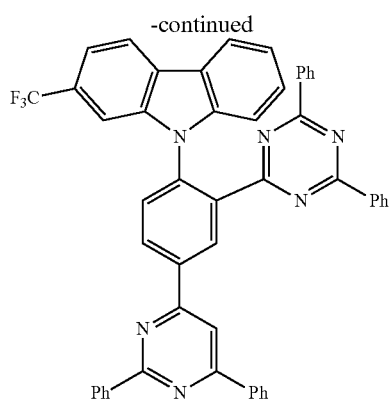
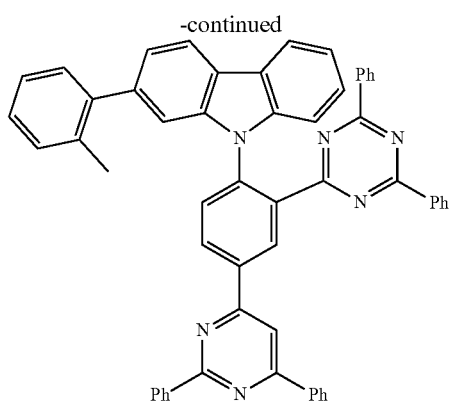
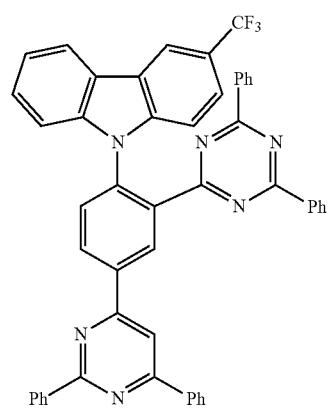
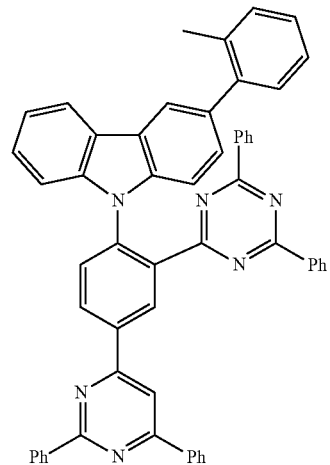
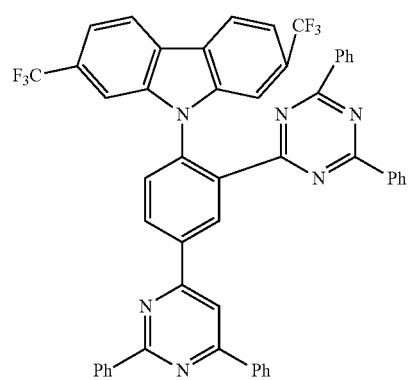
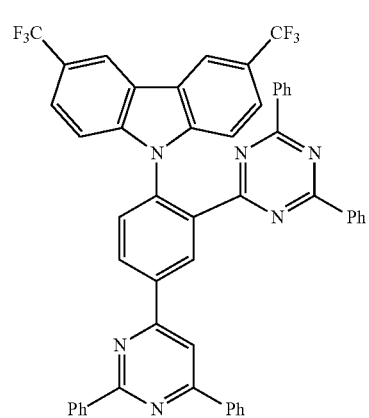
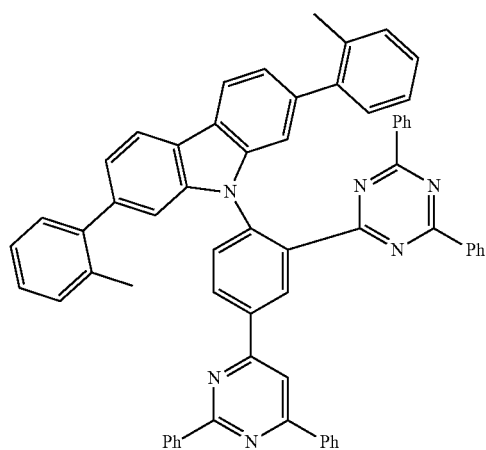

211
-continued
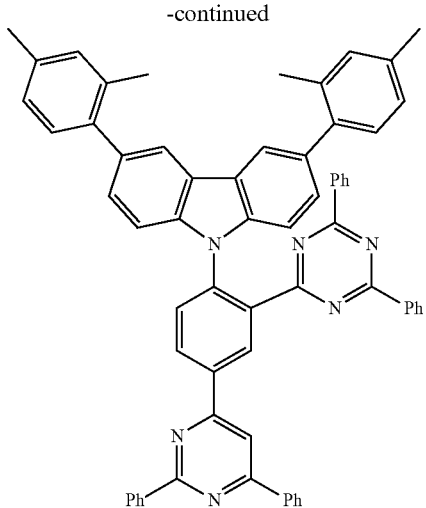
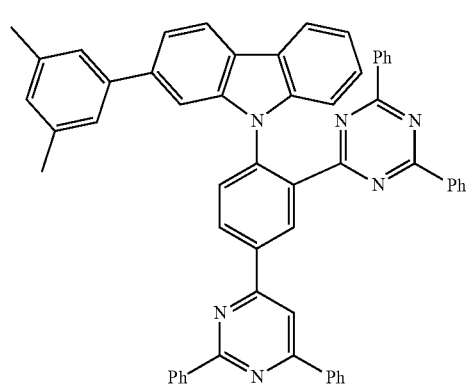
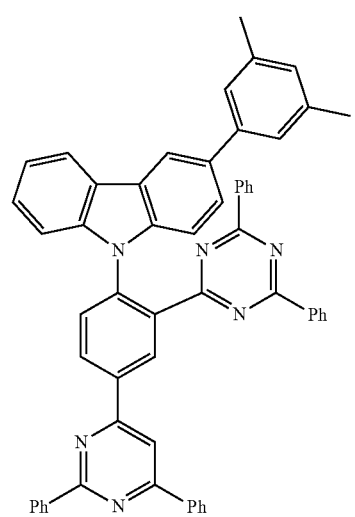
212
-continued
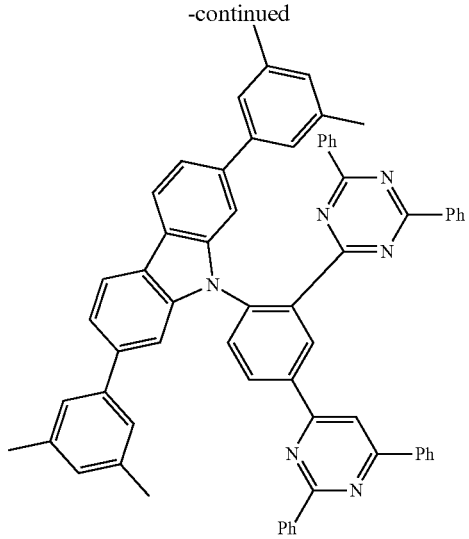
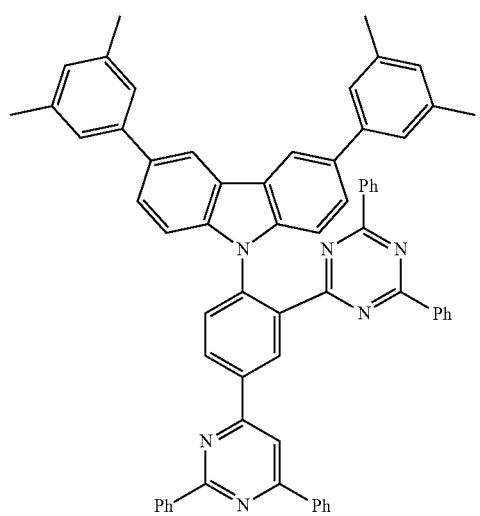
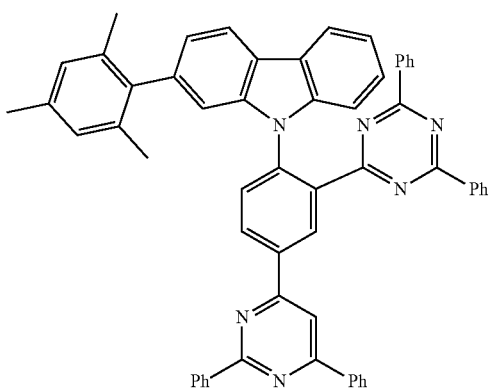

213
-continued
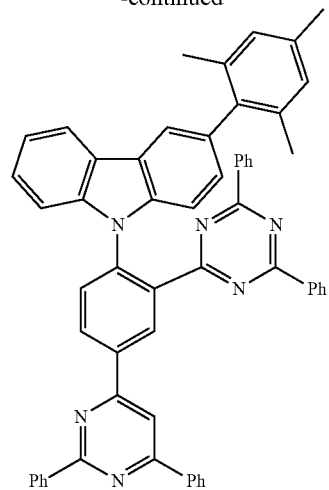
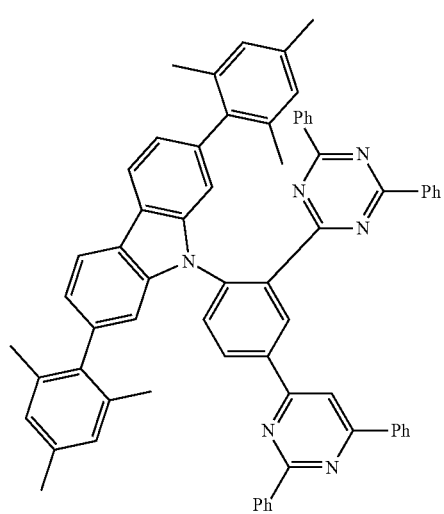
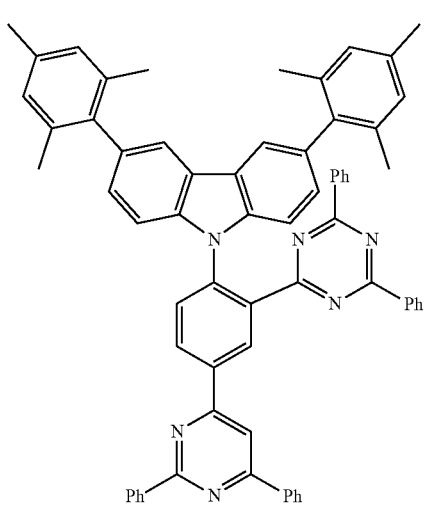
214
-continued
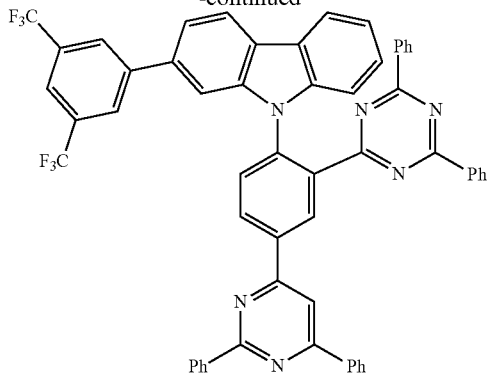
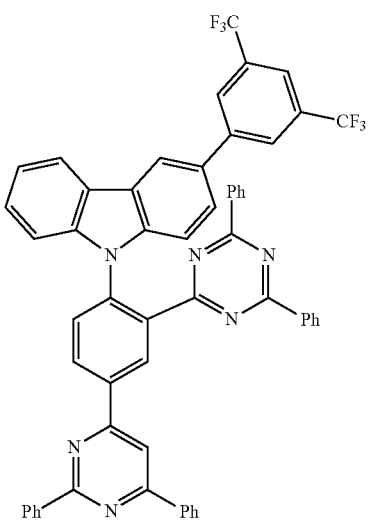
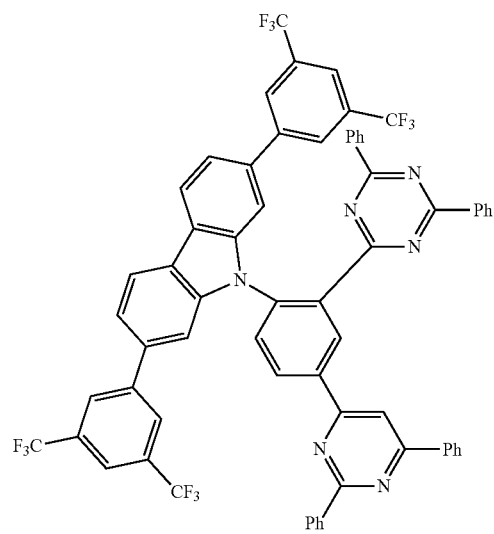

215
-continued
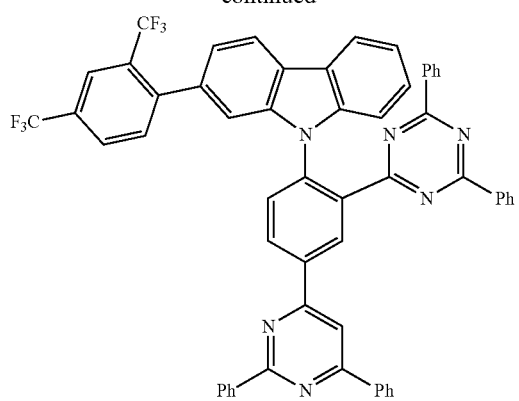
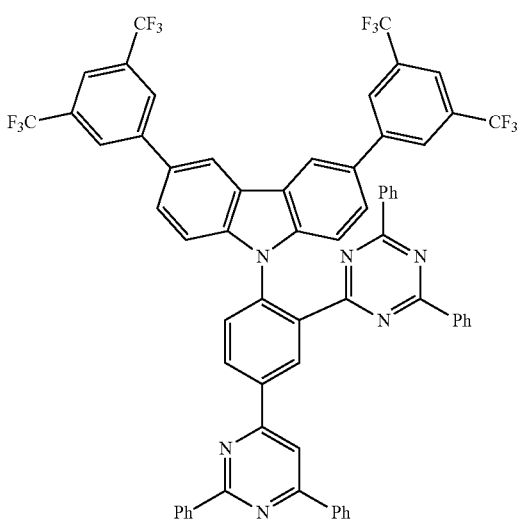
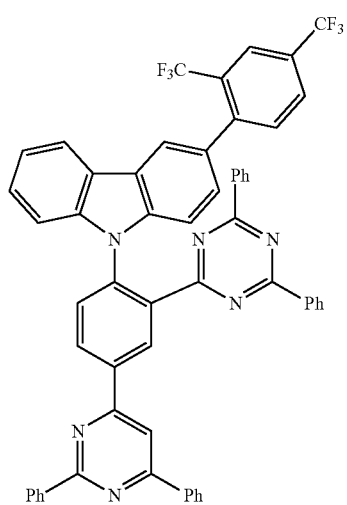
216
-continued
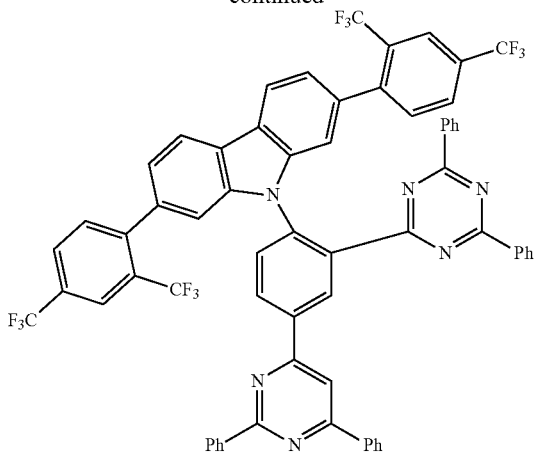
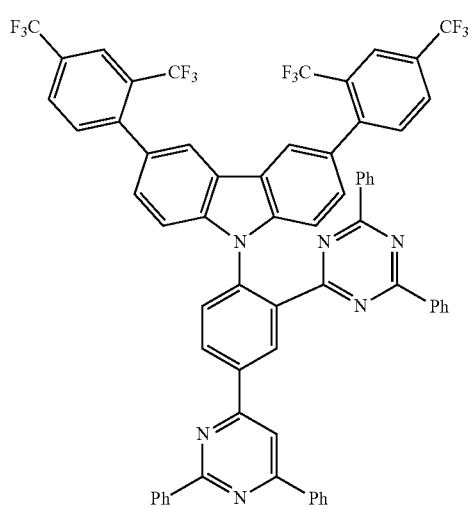
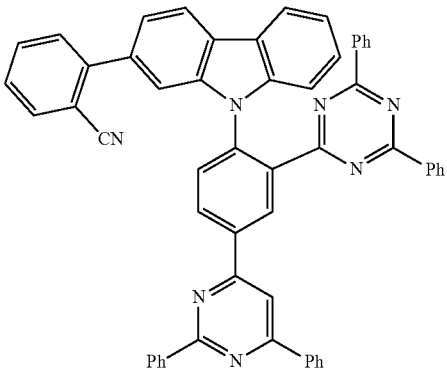

217
-continued
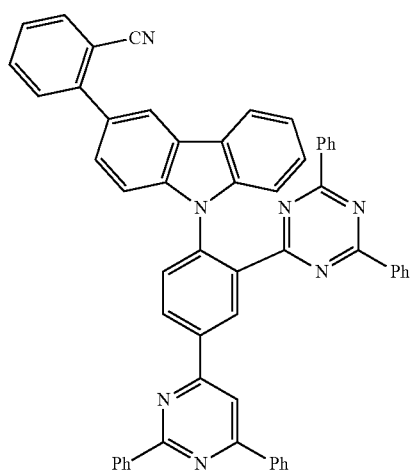
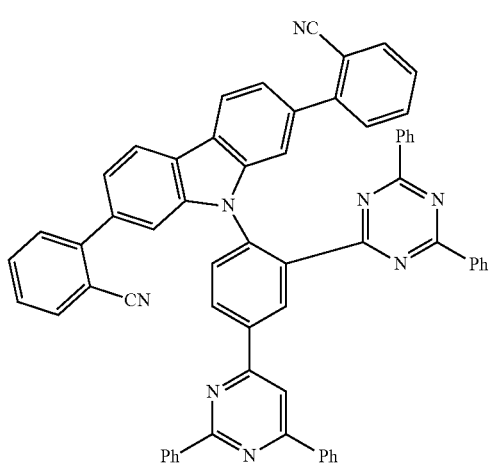
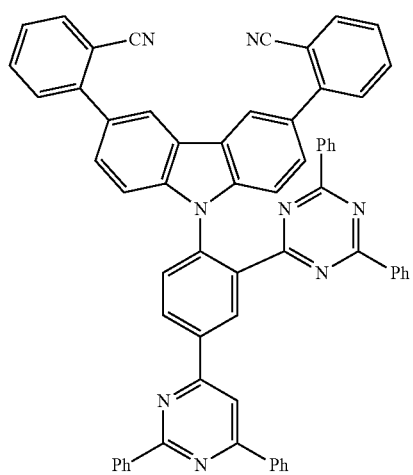
218
-continued
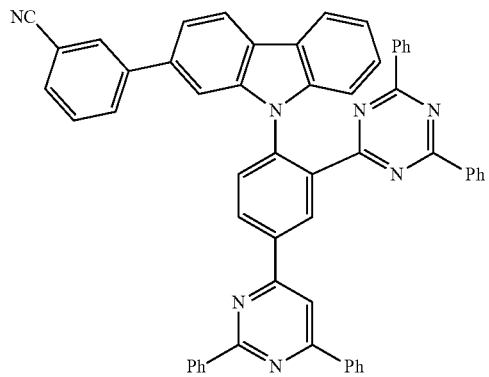
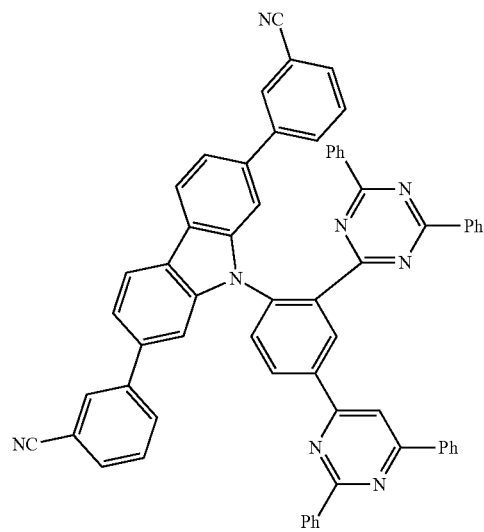

219
-continued
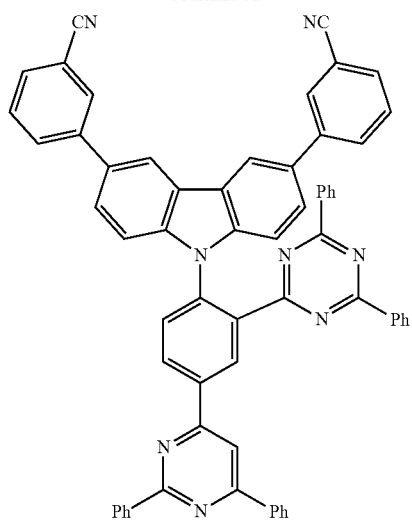 [SMILES: N#Cc1cccc(-c2ccc3c(c2)c2cc(-c4cccc(C#N)c4)ccc2n3-c2ccc(-c3cc(-c4ccccc4)nc(-c4ccccc4)n3)cc2-c2nc(-c3ccccc3)nc(-c3ccccc3)n2)c1]
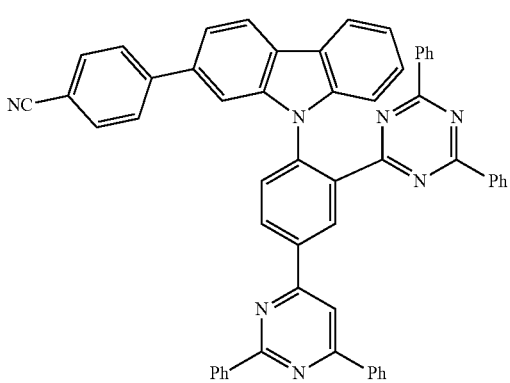
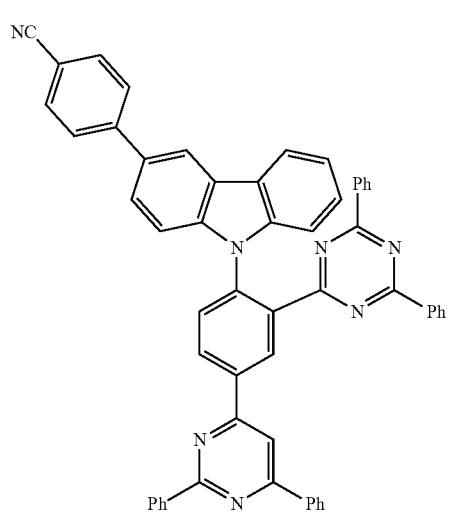
220
-continued
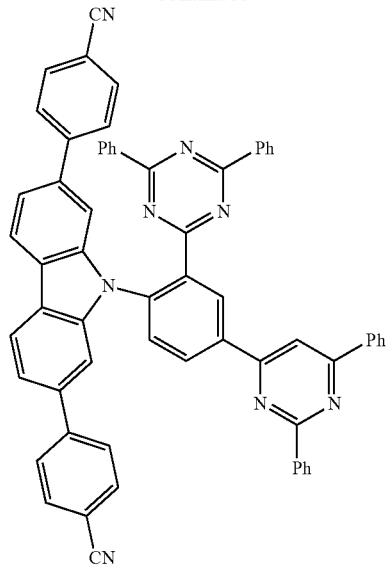
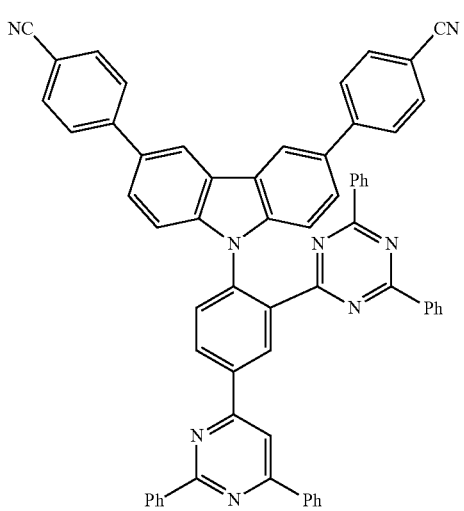 [SMILES: N#Cc1ccc(-c2ccc3c(c2)c2cc(-c4ccc(C#N)cc4)ccc2n3-c2ccc(-c3cc(-c4ccccc4)nc(-c4ccccc4)n3)cc2-c2nc(-c3ccccc3)nc(-c3ccccc3)n2)cc1]
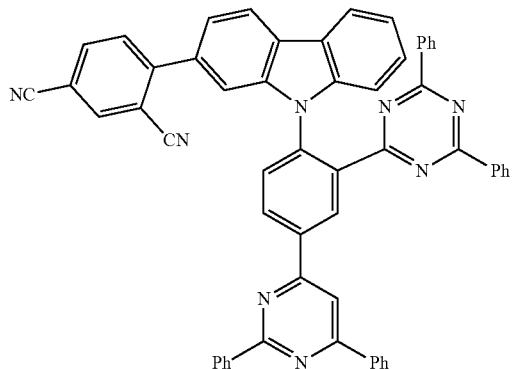

221
-continued
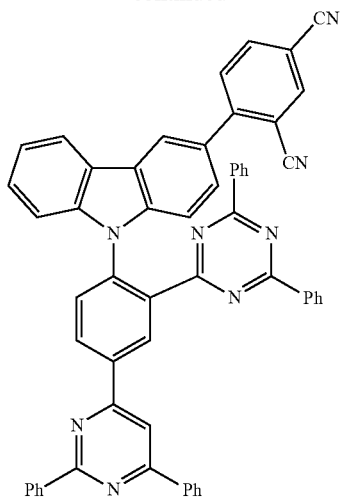
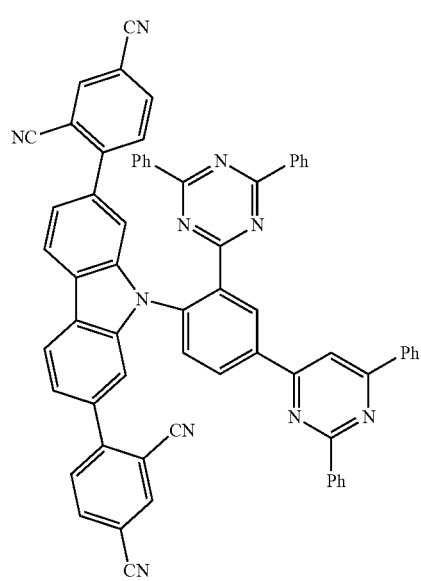
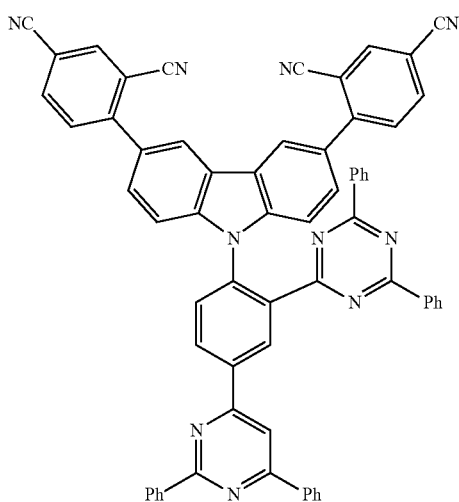 [SMILES: N#Cc1ccc(-c2ccc3c(c2)c2cc(-c4ccc(C#N)cc4C#N)ccc2n3-c2ccc(-c3cc(-c4ccccc4)nc(-c4ccccc4)n3)cc2-c2nc(-c3ccccc3)nc(-c3ccccc3)n2)c(C#N)c1]
222
-continued
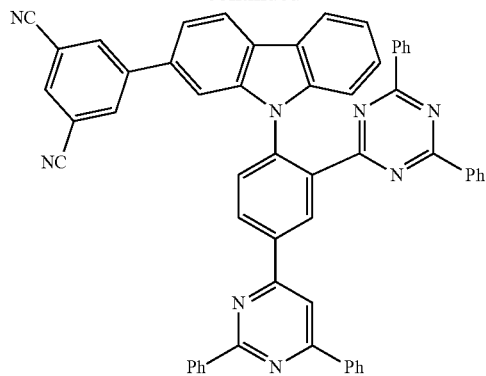
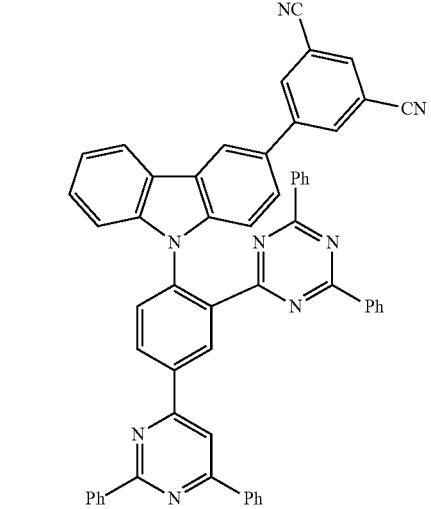
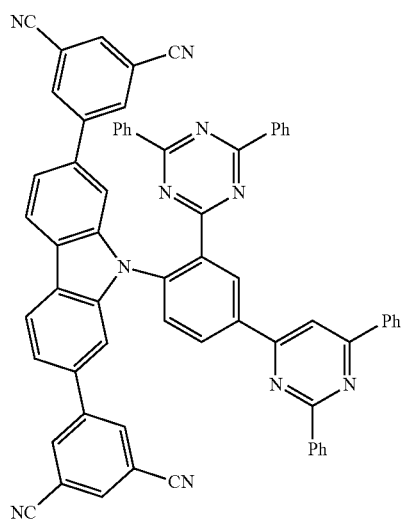

223
-continued
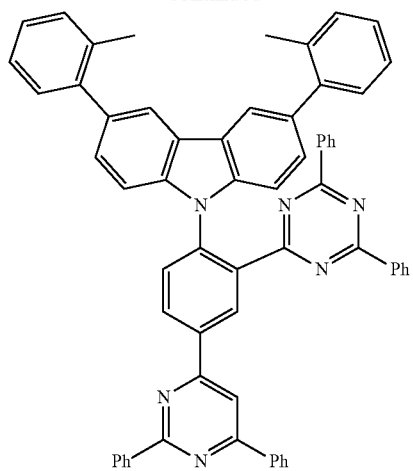 [SMILES: Cc1ccccc1-c1ccc2c(c1)c1cc(-c3ccccc3C)ccc1n2-c1ccc(-c2cc(-c3ccccc3)nc(-c3ccccc3)n2)cc1-c1nc(-c2ccccc2)nc(-c2ccccc2)n1]
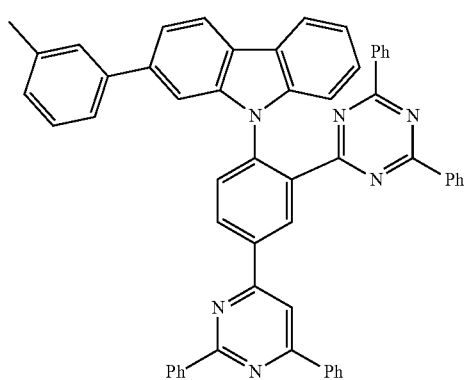
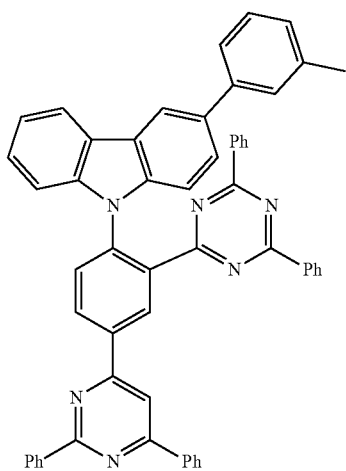
224
-continued
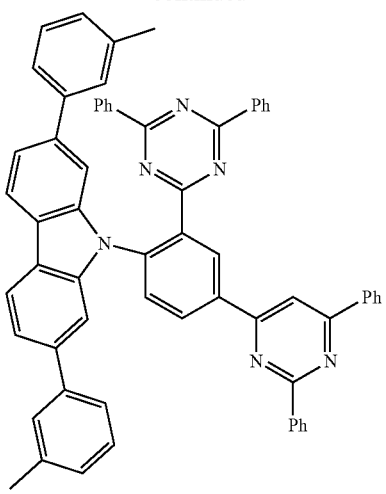
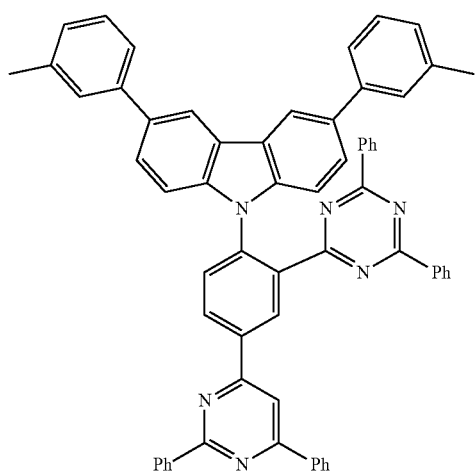
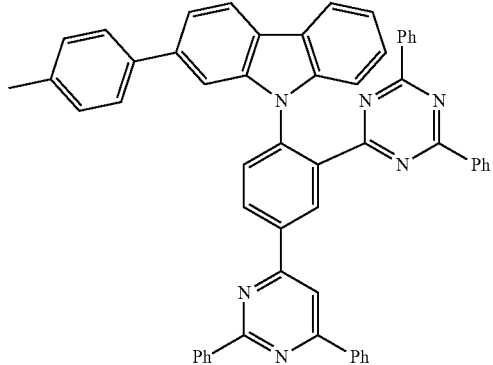

225
-continued
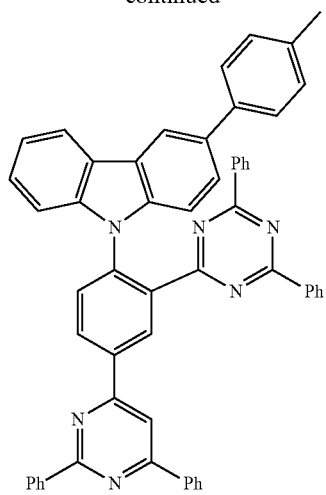
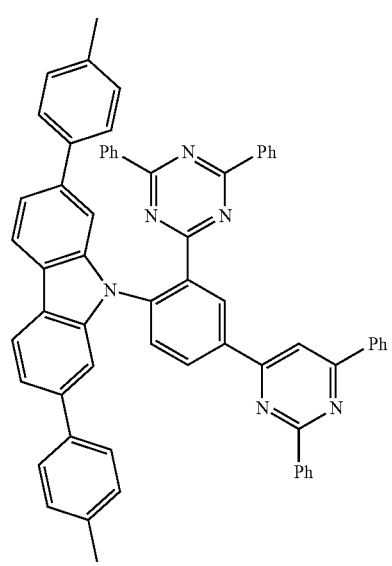
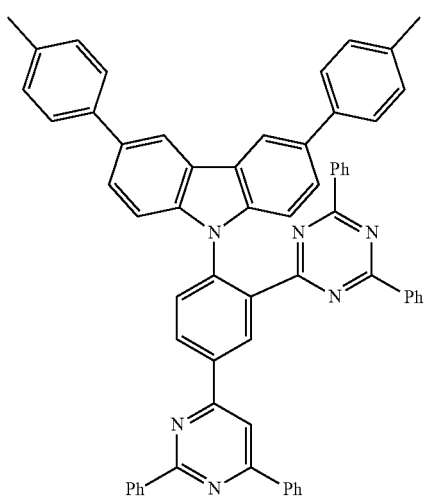
226
-continued
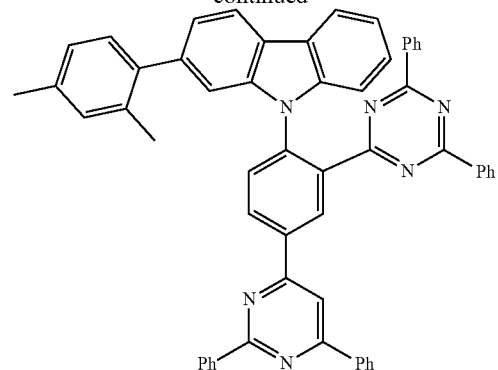
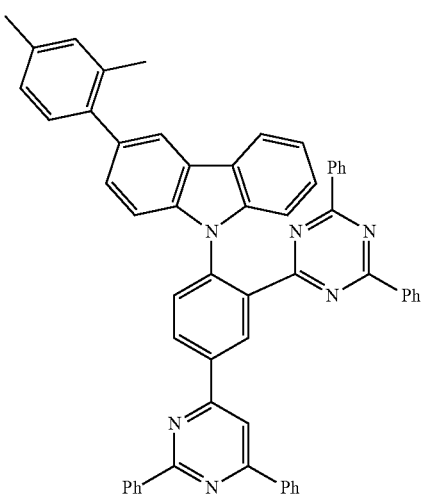
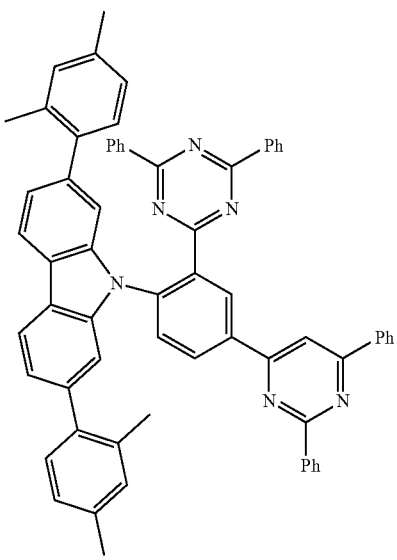

227
-continued
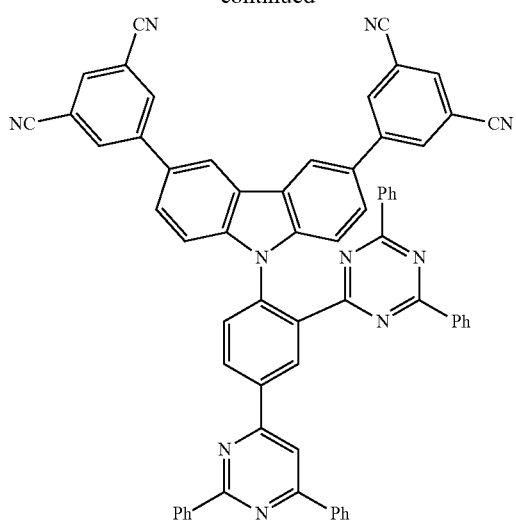
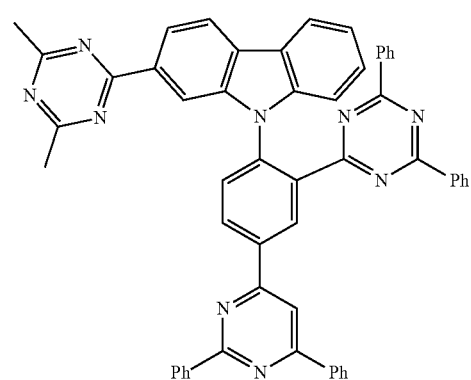
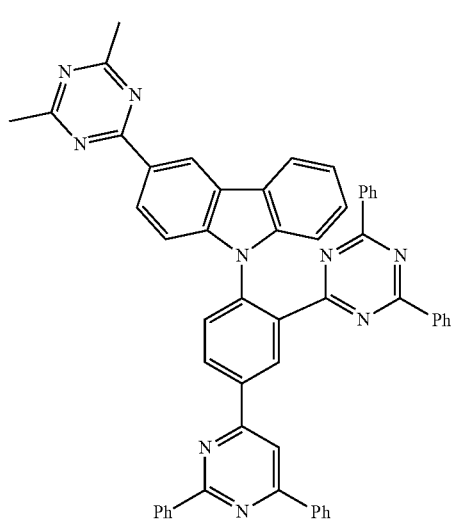
228
-continued
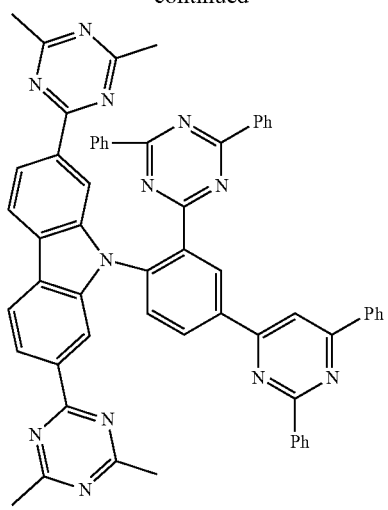
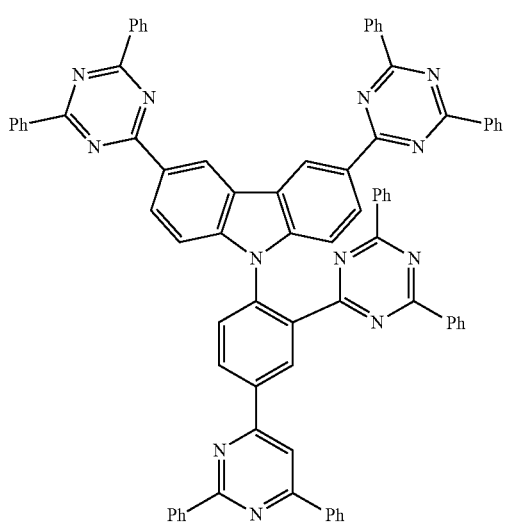 [SMILES: c1ccc(-c2cc(-c3ccc(-n4c5ccc(-c6nc(-c7ccccc7)nc(-c7ccccc7)n6)cc5c5cc(-c6nc(-c7ccccc7)nc(-c7ccccc7)n6)ccc54)c(-c4nc(-c5ccccc5)nc(-c5ccccc5)n4)c3)nc(-c3ccccc3)n2)cc1]
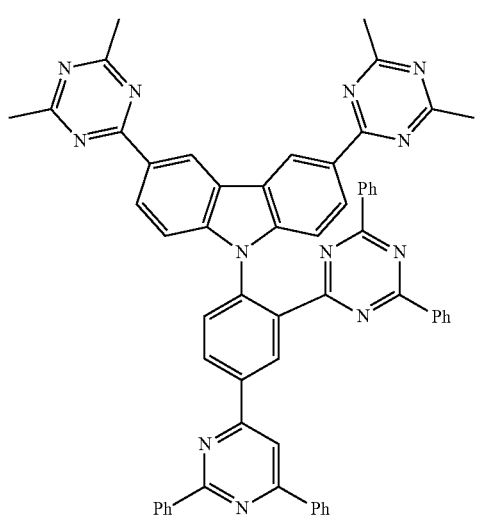

229
-continued
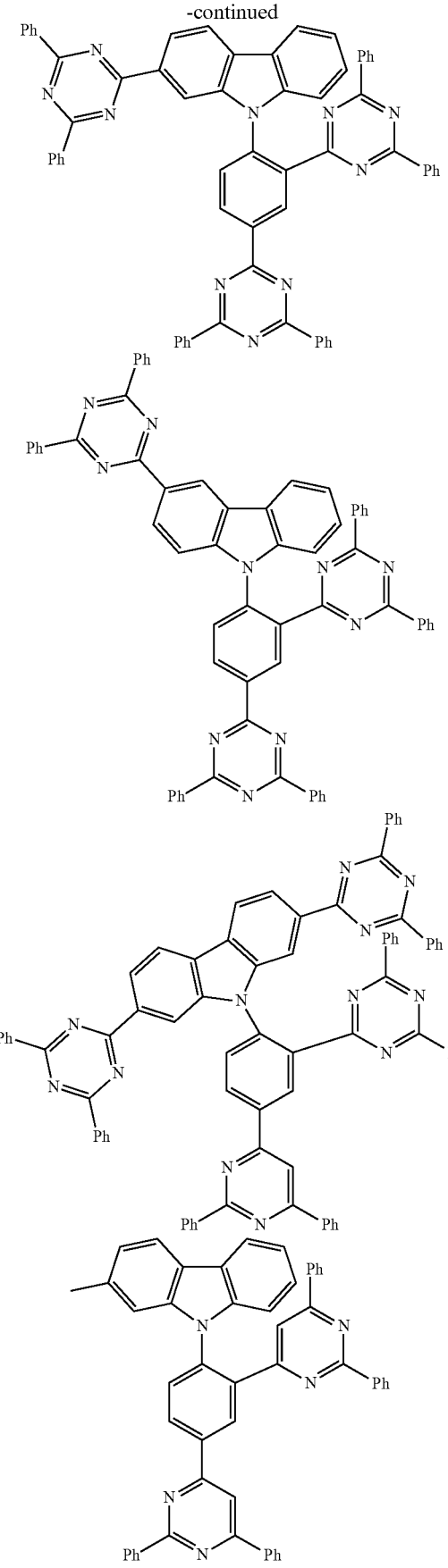
230
-continued
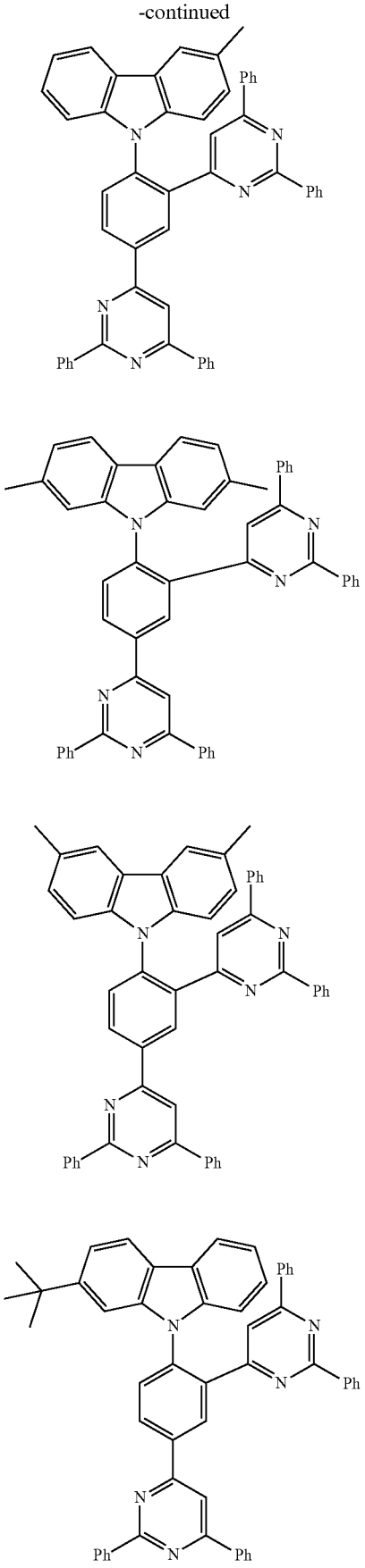

231
-continued
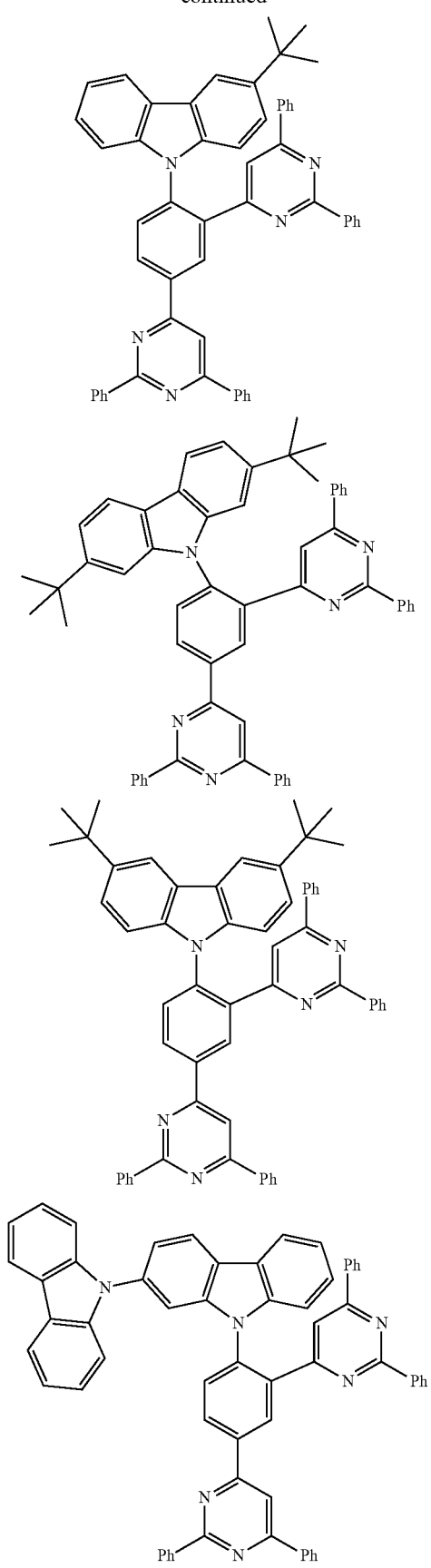
232
-continued
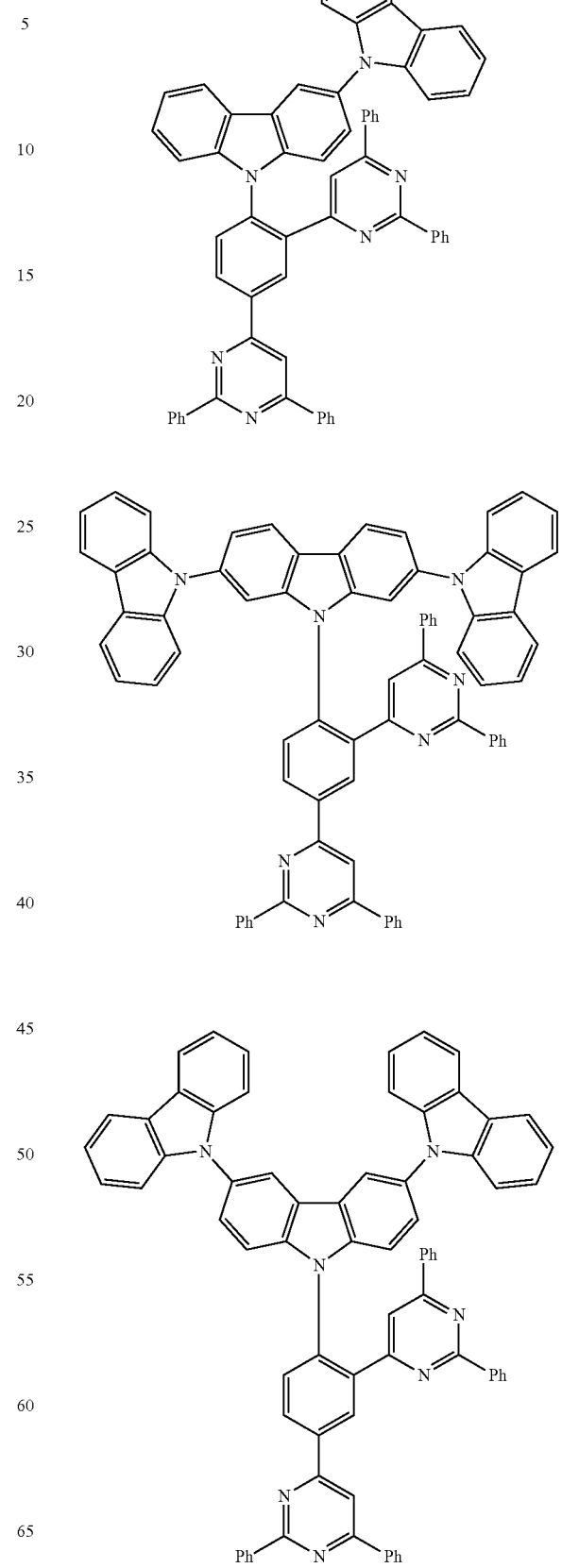

233
-continued
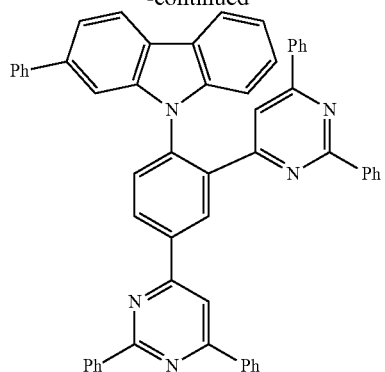
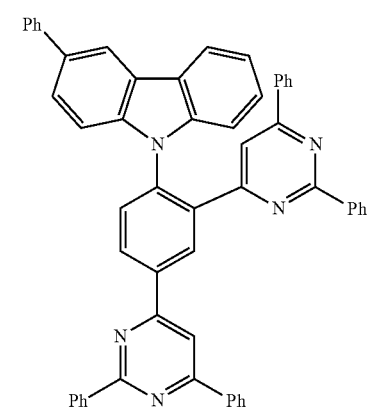
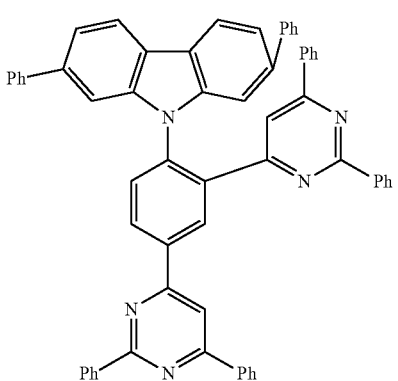
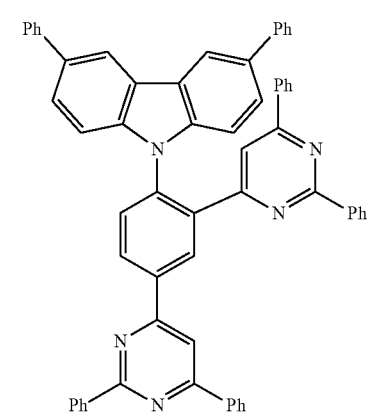
234
-continued
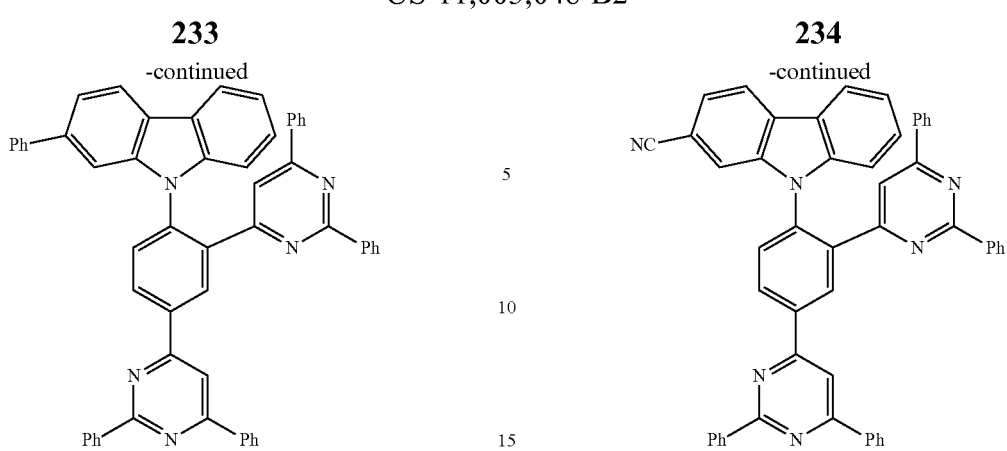
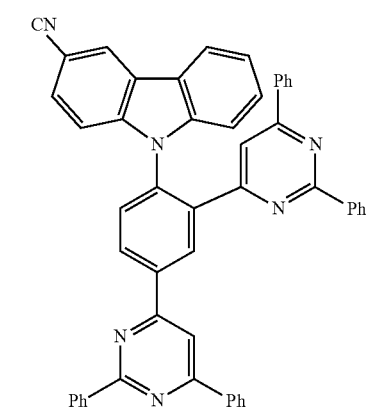
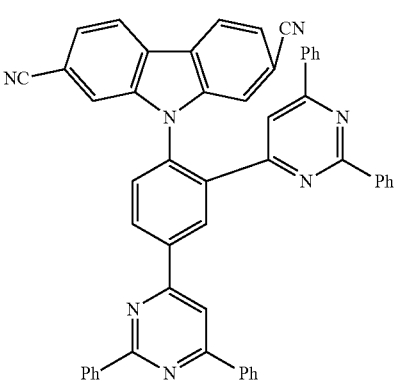
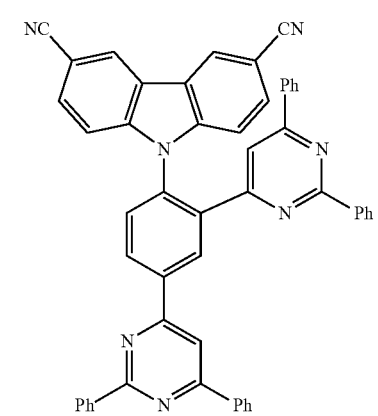

235
-continued
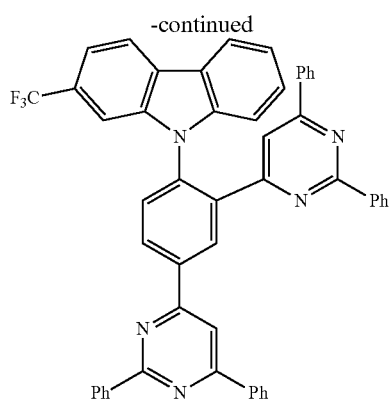
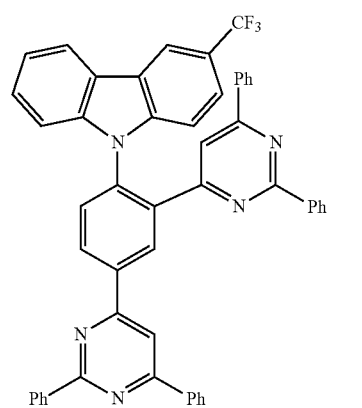
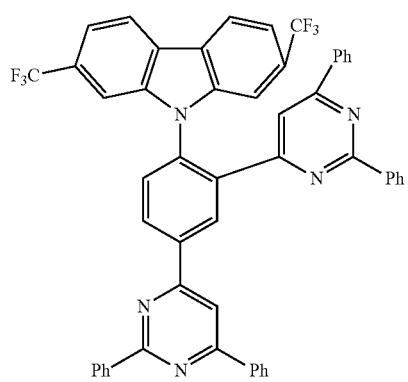
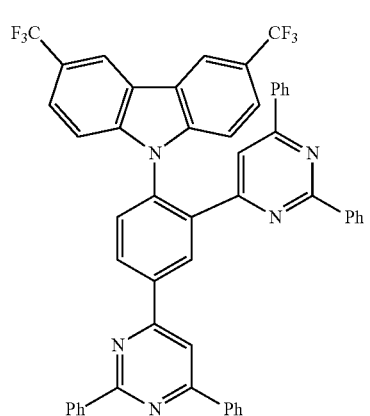
236
-continued
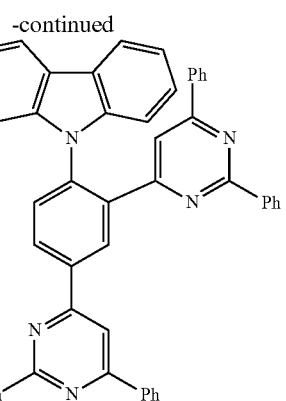
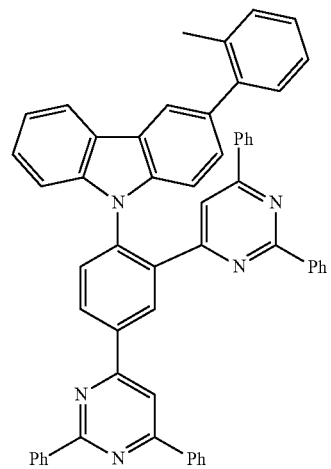

237
-continued
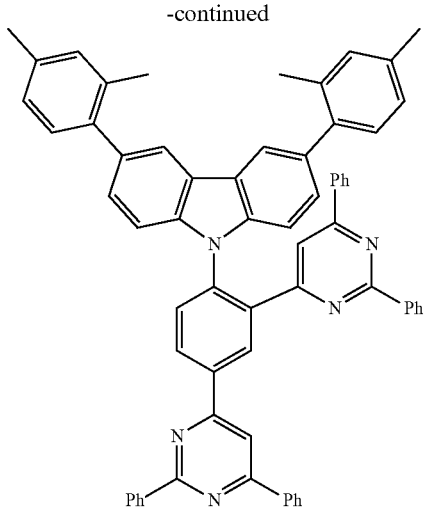
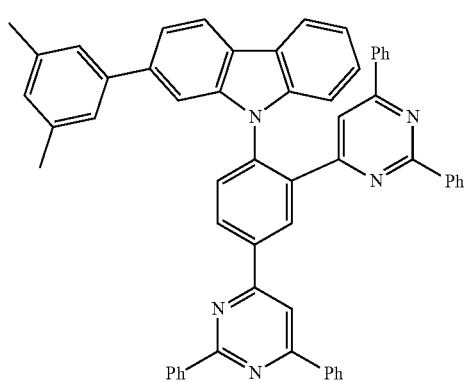
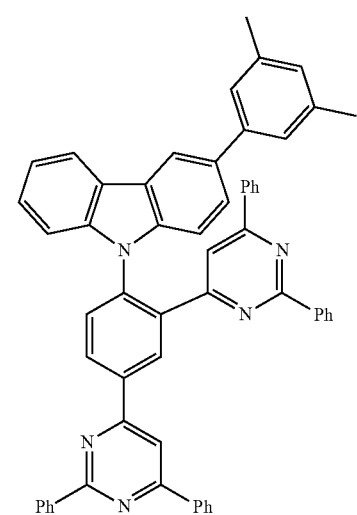
238
-continued
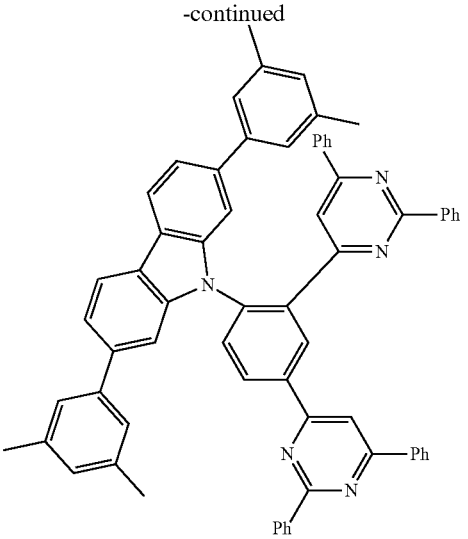
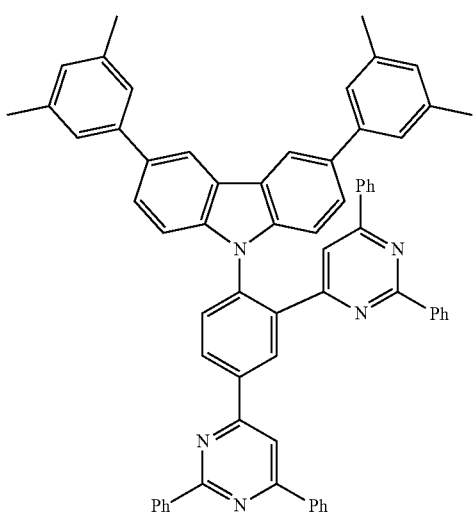
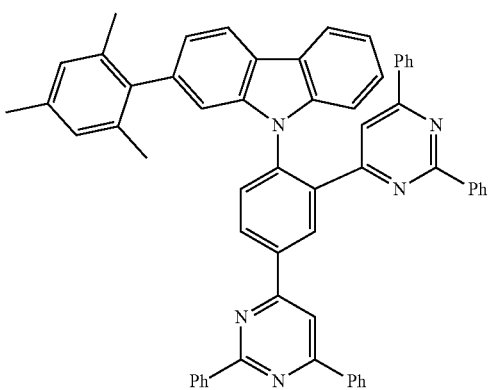

239
-continued
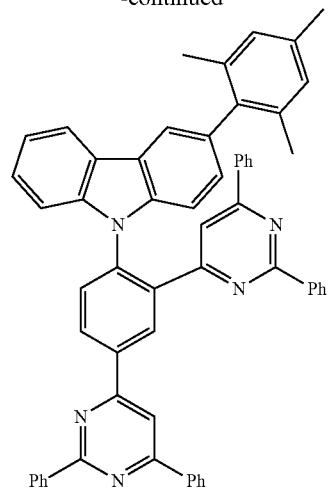
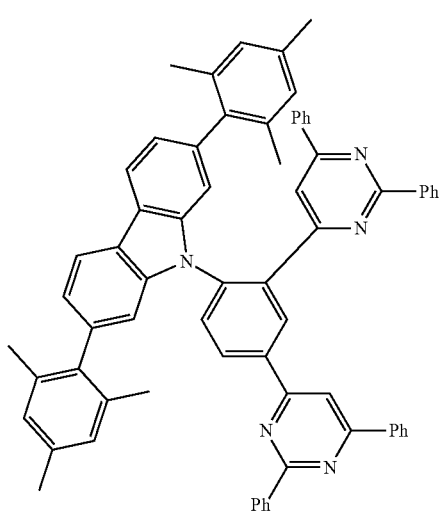
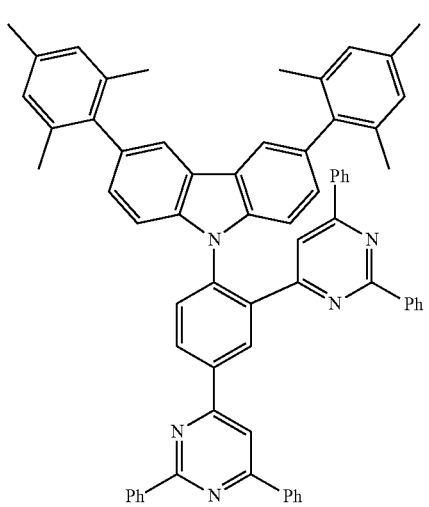
240
-continued
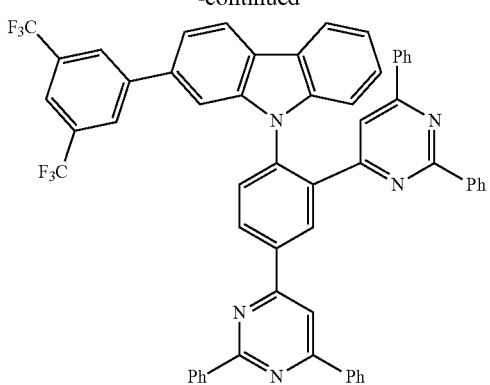
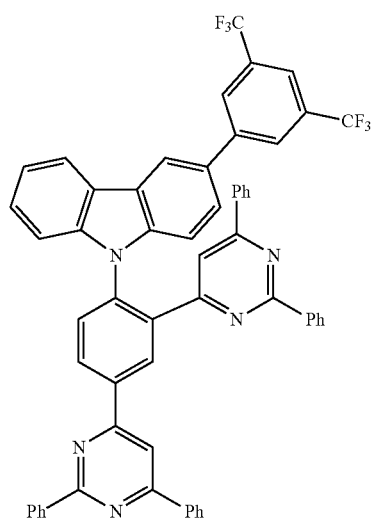
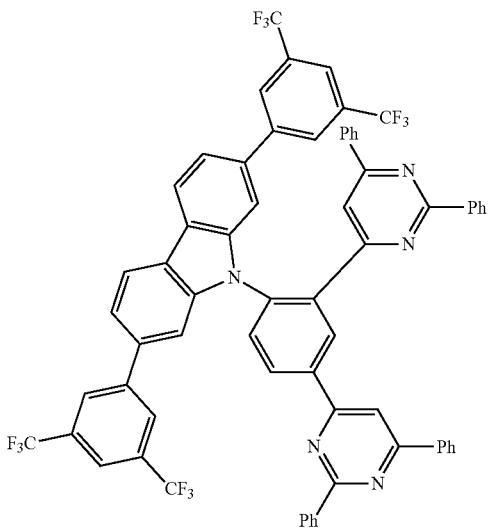

241
-continued
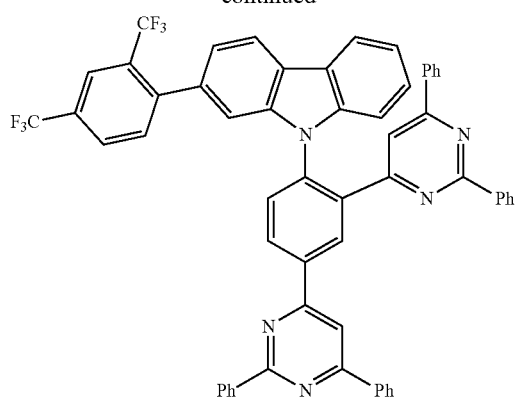
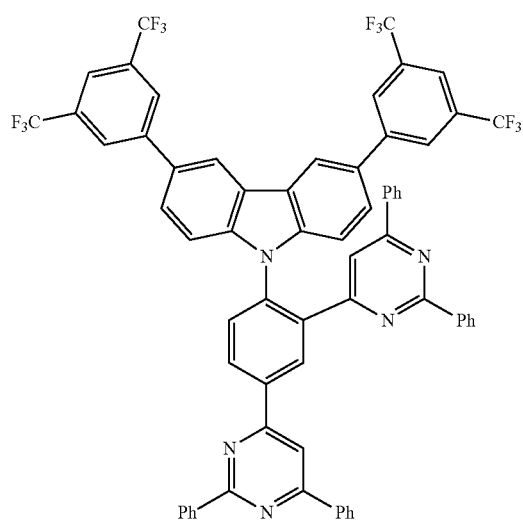
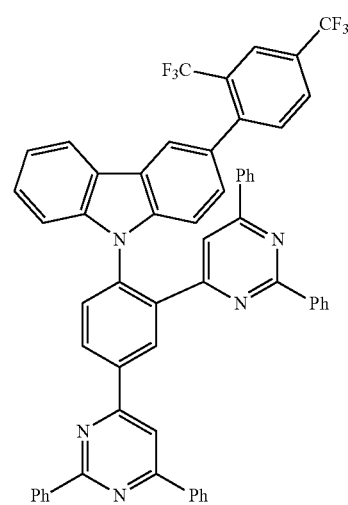
242
-continued
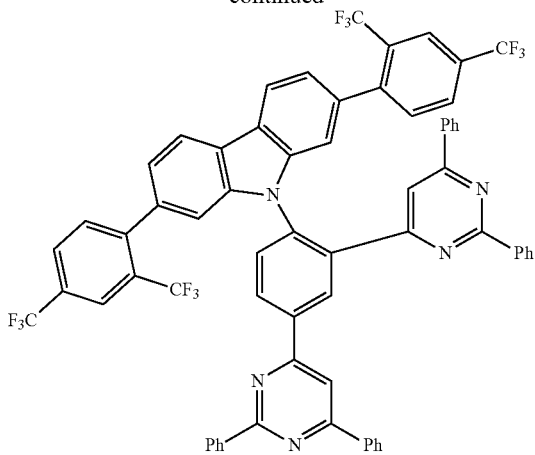
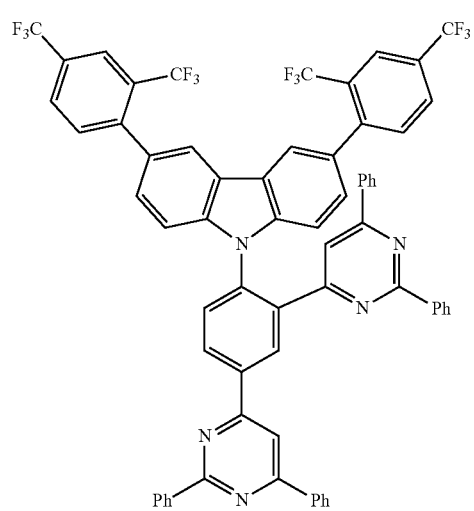
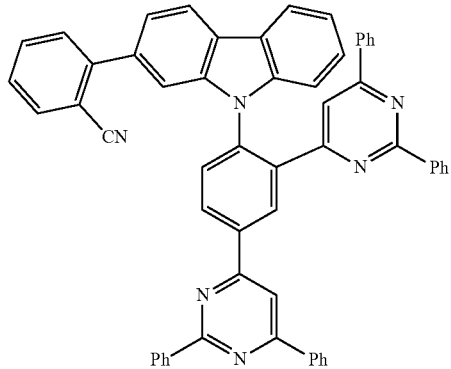

243
-continued
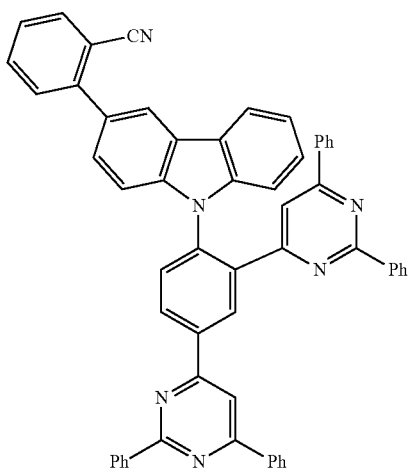
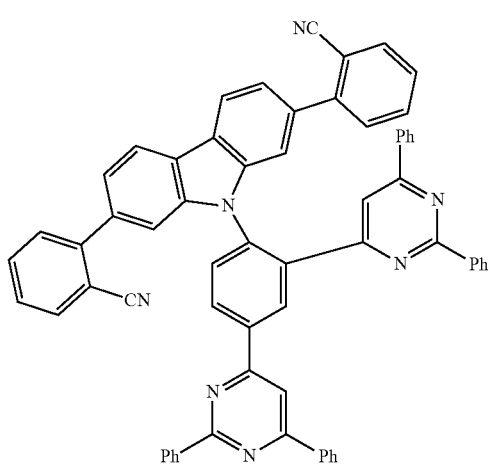
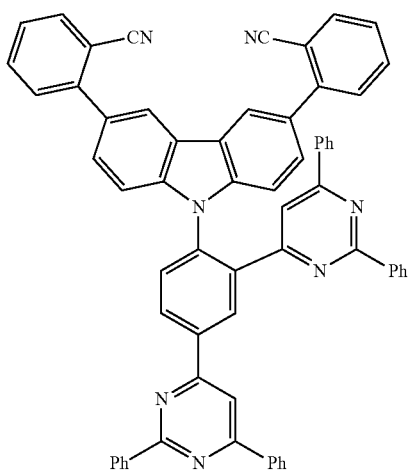
244
-continued
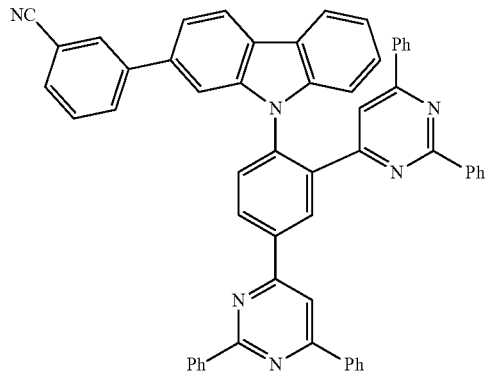
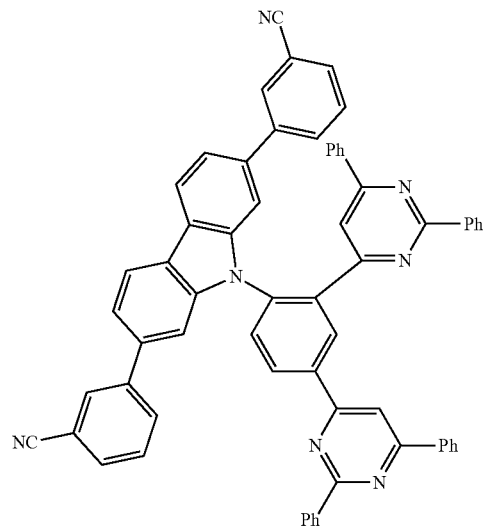

245
-continued
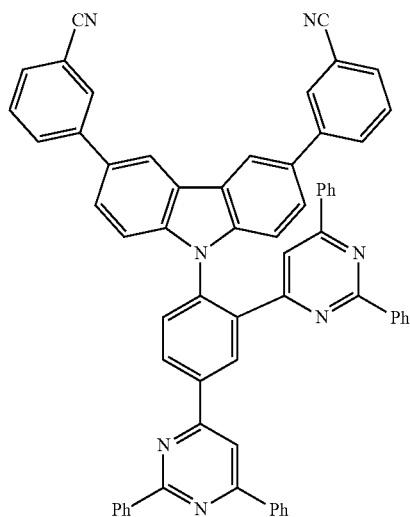
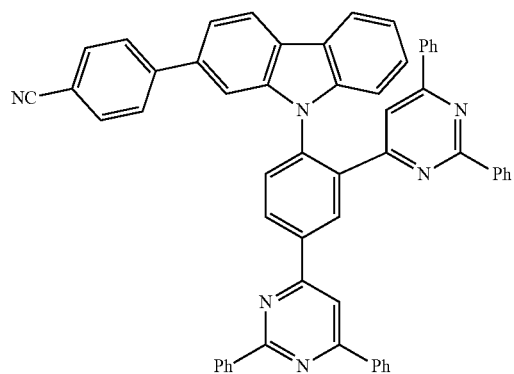
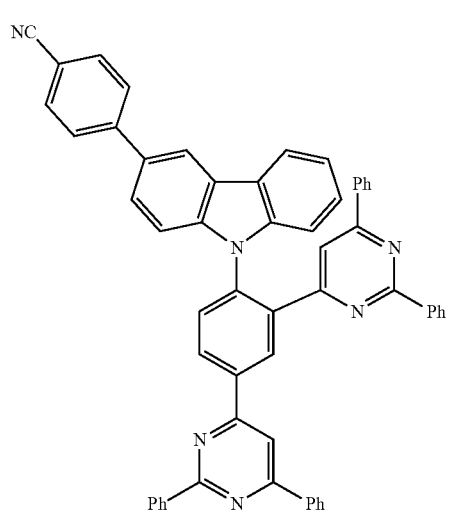
246
-continued
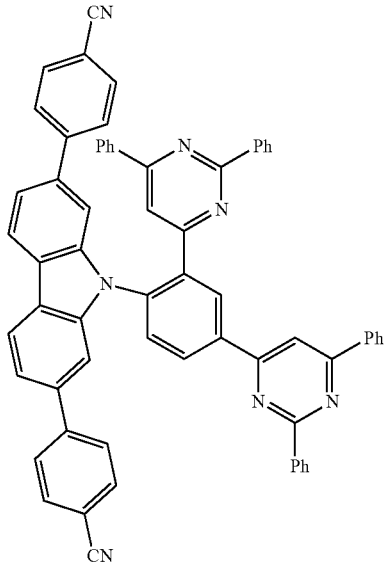
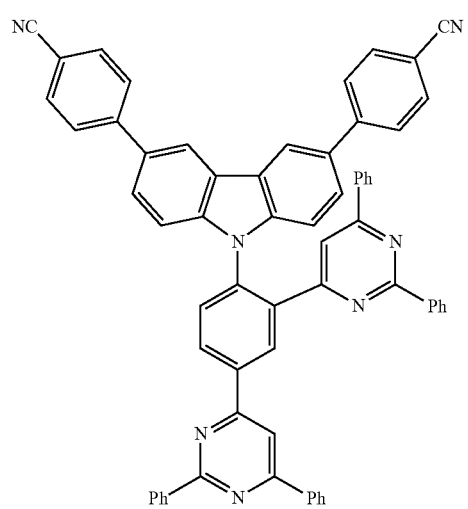 [SMILES: N#Cc1ccc(-c2ccc3c(c2)c2cc(-c4ccc(C#N)cc4)ccc2n3-c2ccc(-c3cc(-c4ccccc4)nc(-c4ccccc4)n3)cc2-c2cc(-c3ccccc3)nc(-c3ccccc3)n2)cc1]
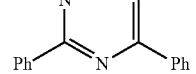

247
-continued
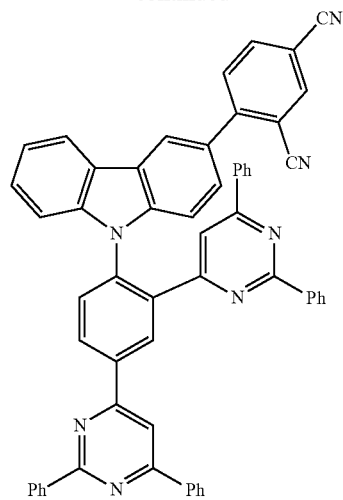
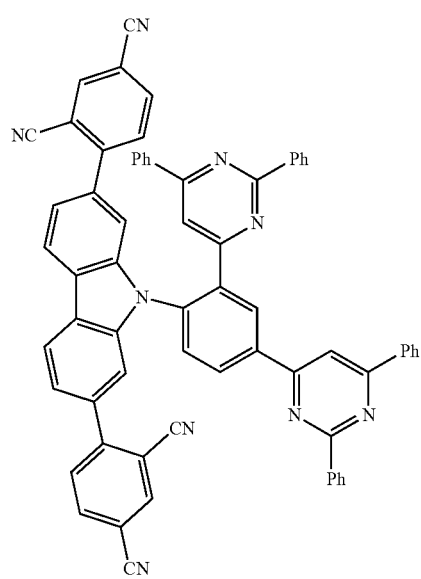
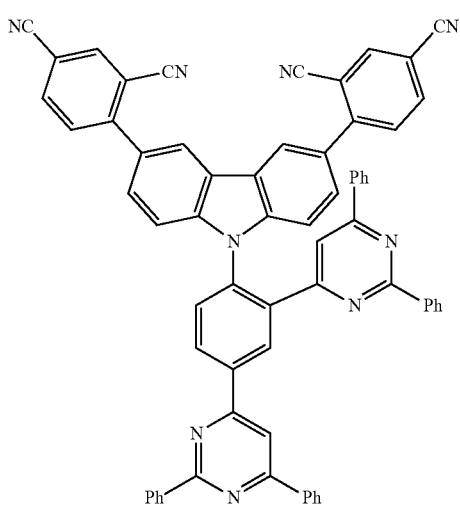 [SMILES: N#Cc1ccc(-c2ccc3c(c2)c2cc(-c4ccc(C#N)cc4C#N)ccc2n3-c2ccc(-c3cc(-c4ccccc4)nc(-c4ccccc4)n3)cc2-c2cc(-c3ccccc3)nc(-c3ccccc3)n2)c(C#N)c1]
248
-continued
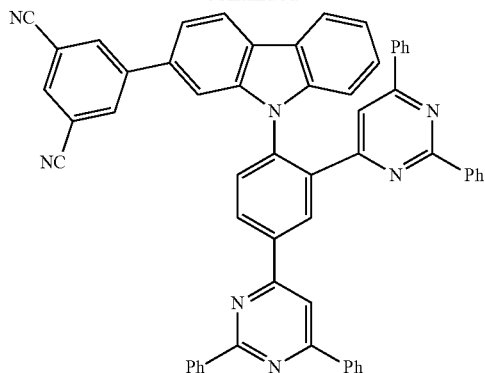
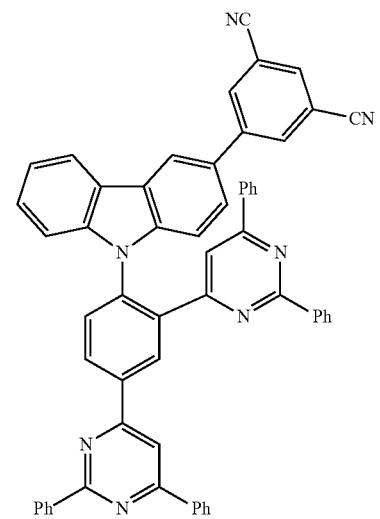
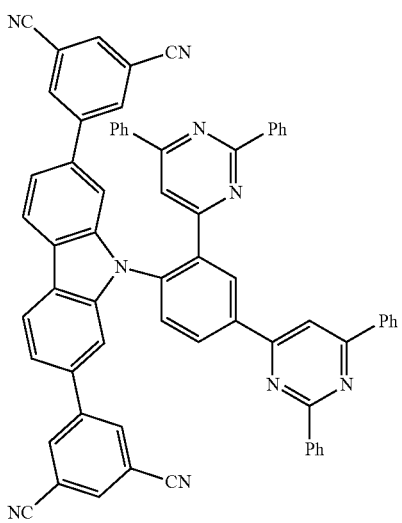

249
-continued
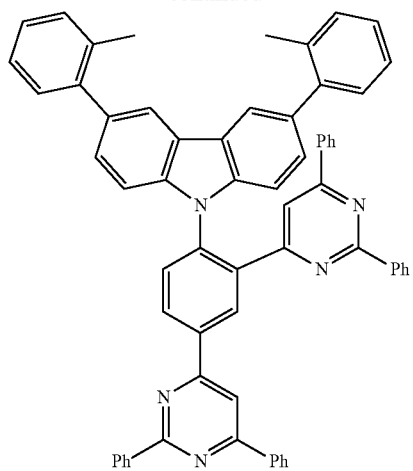
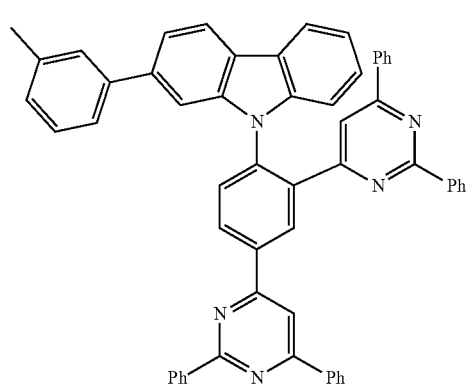
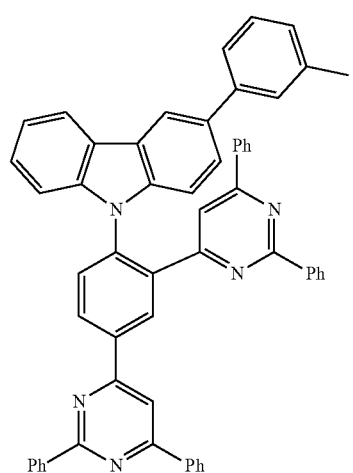
250
-continued
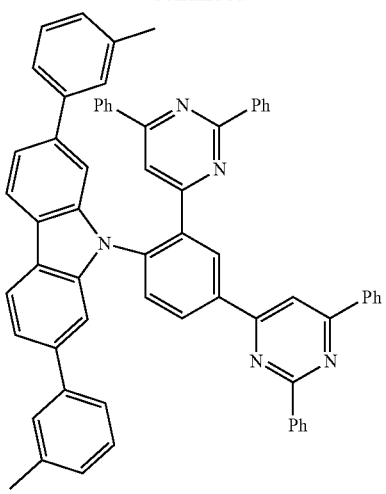
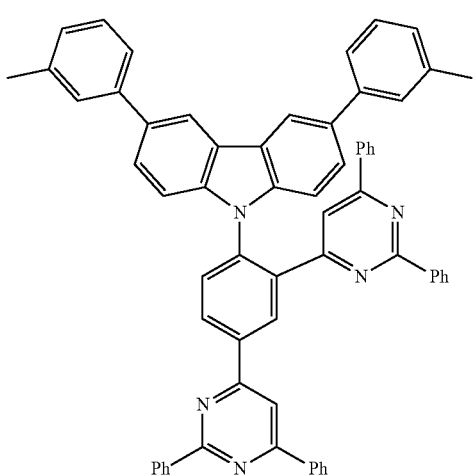
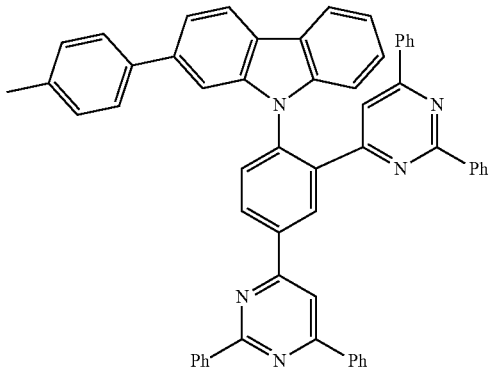

251
-continued
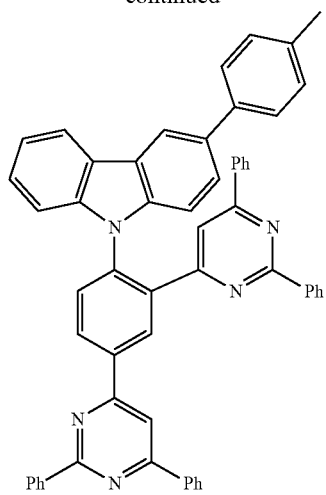
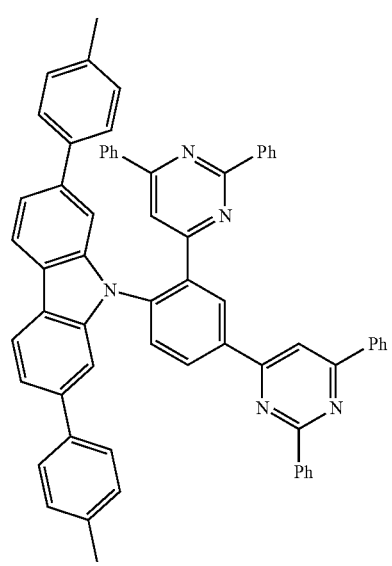
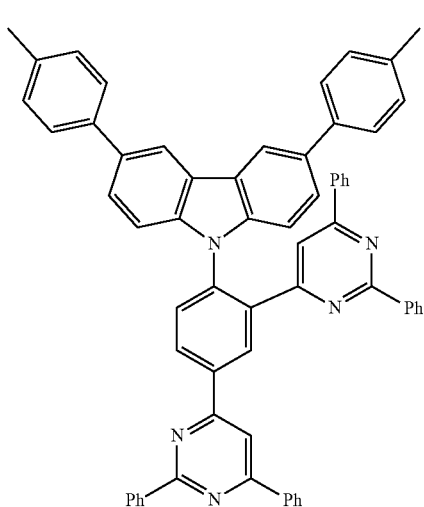
252
-continued
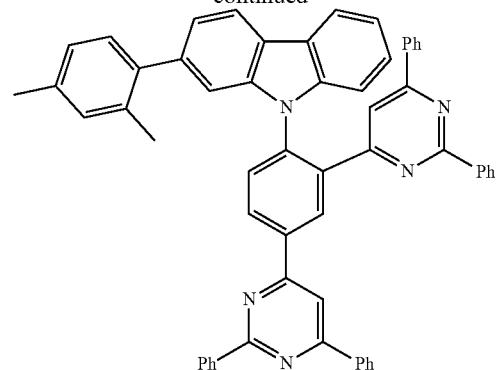
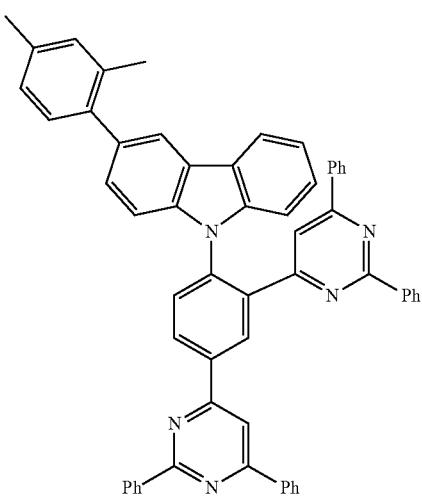
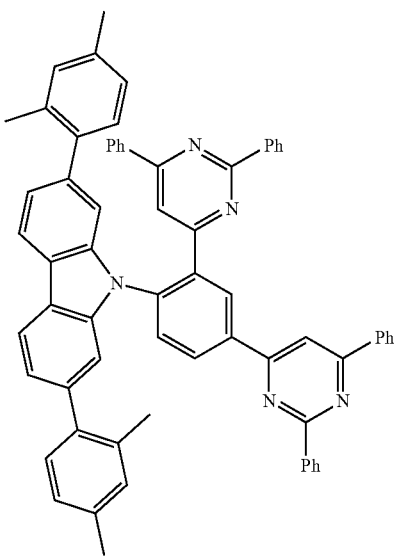

253
-continued
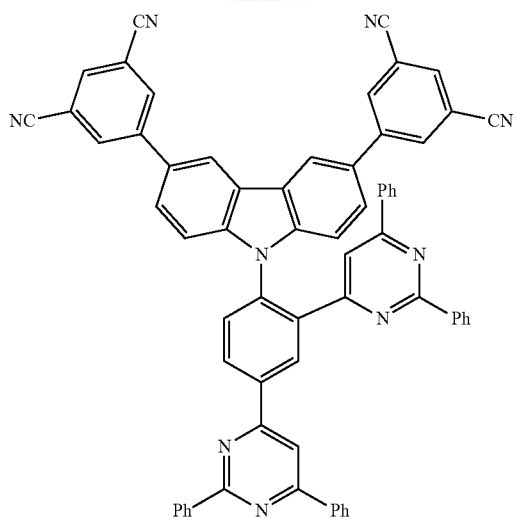 [SMILES: N#Cc1cc(C#N)cc(-c2ccc3c(c2)c2cc(-c4cc(C#N)cc(C#N)c4)ccc2n3-c2ccc(-c3cc(-c4ccccc4)nc(-c4ccccc4)n3)cc2-c2cc(-c3ccccc3)nc(-c3ccccc3)n2)c1]
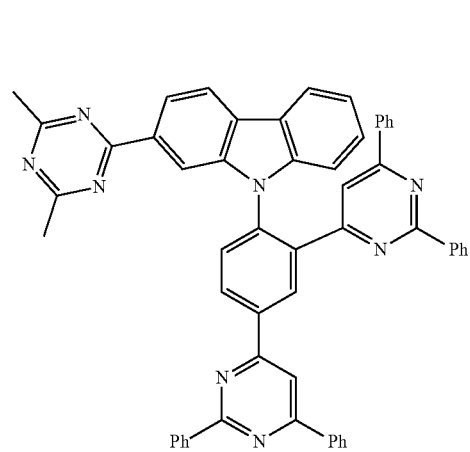
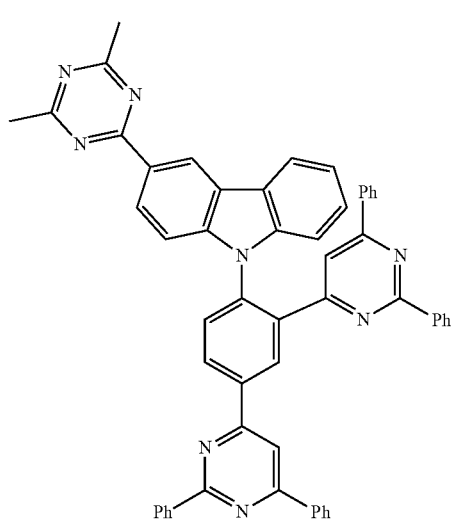
254
-continued
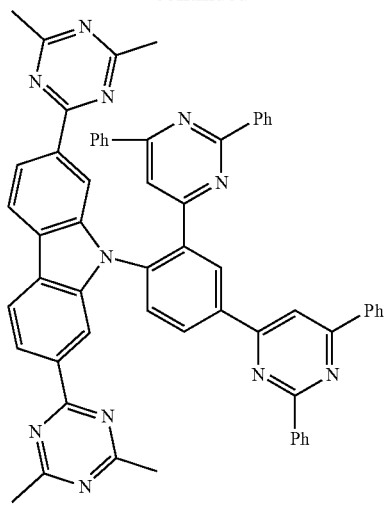
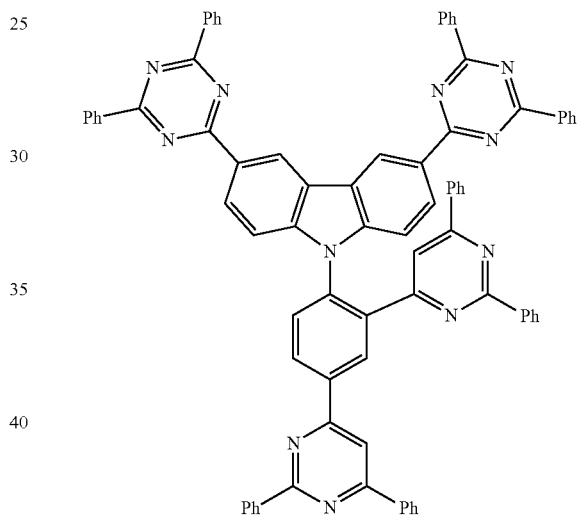
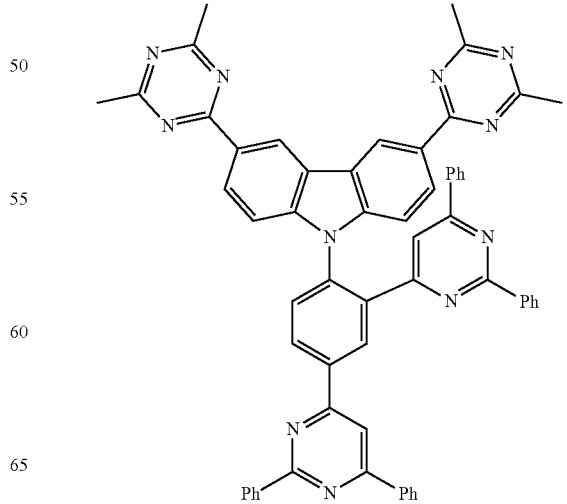

255
-continued
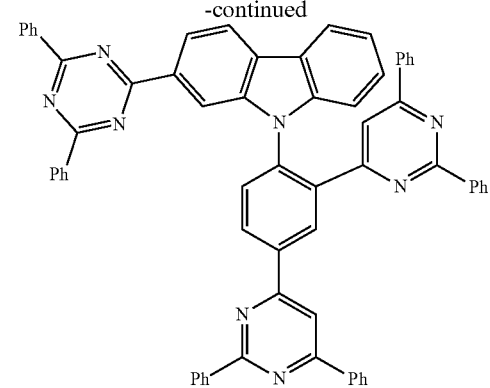
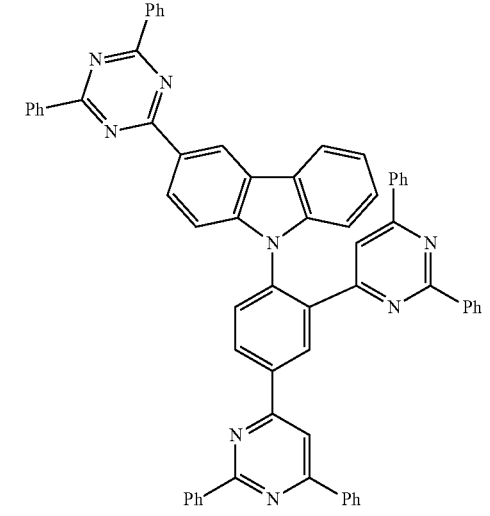
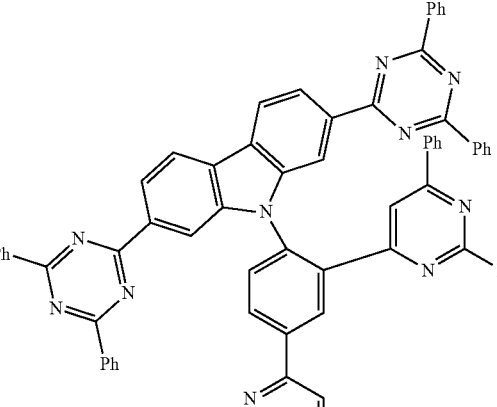
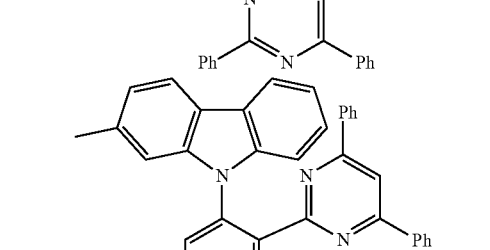
256
-continued
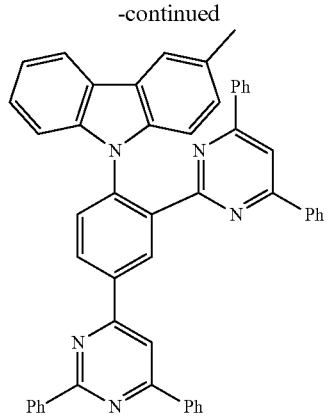
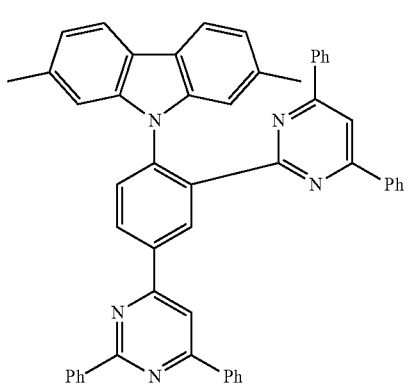
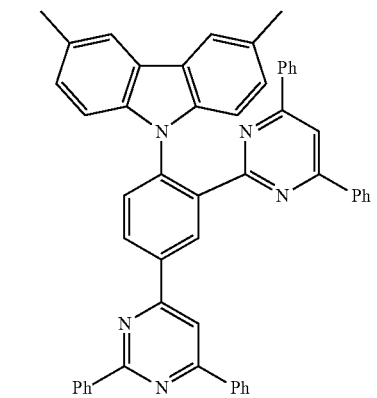
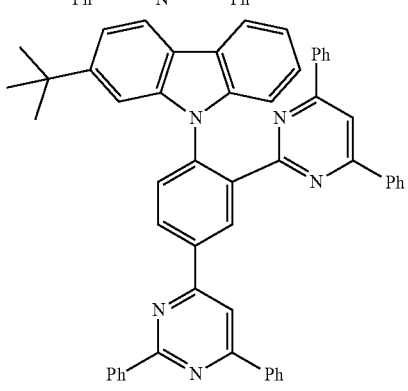

-continued
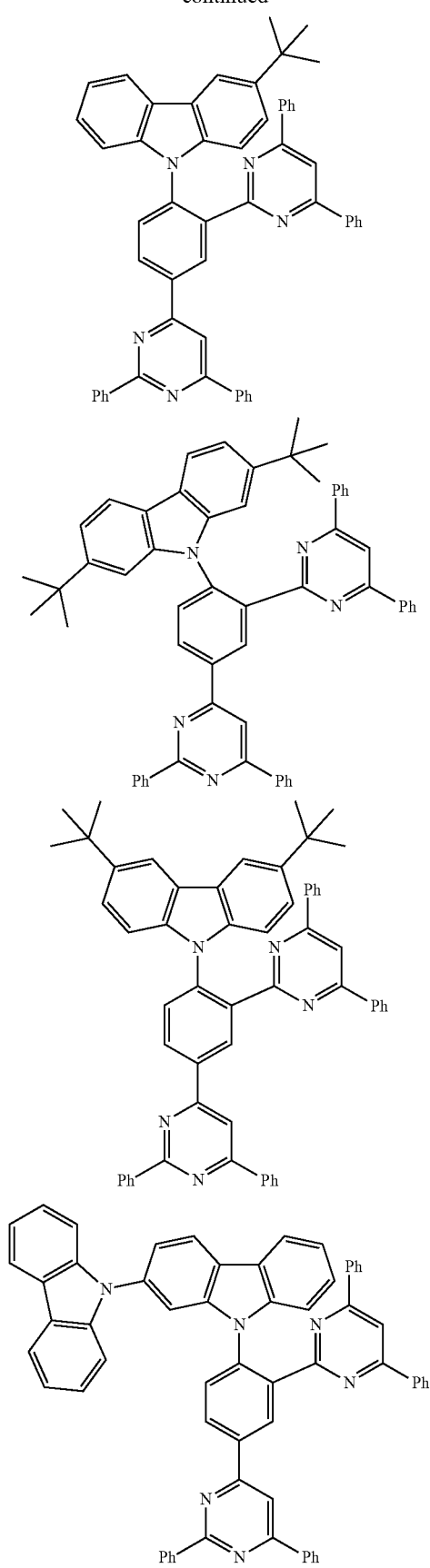
-continued
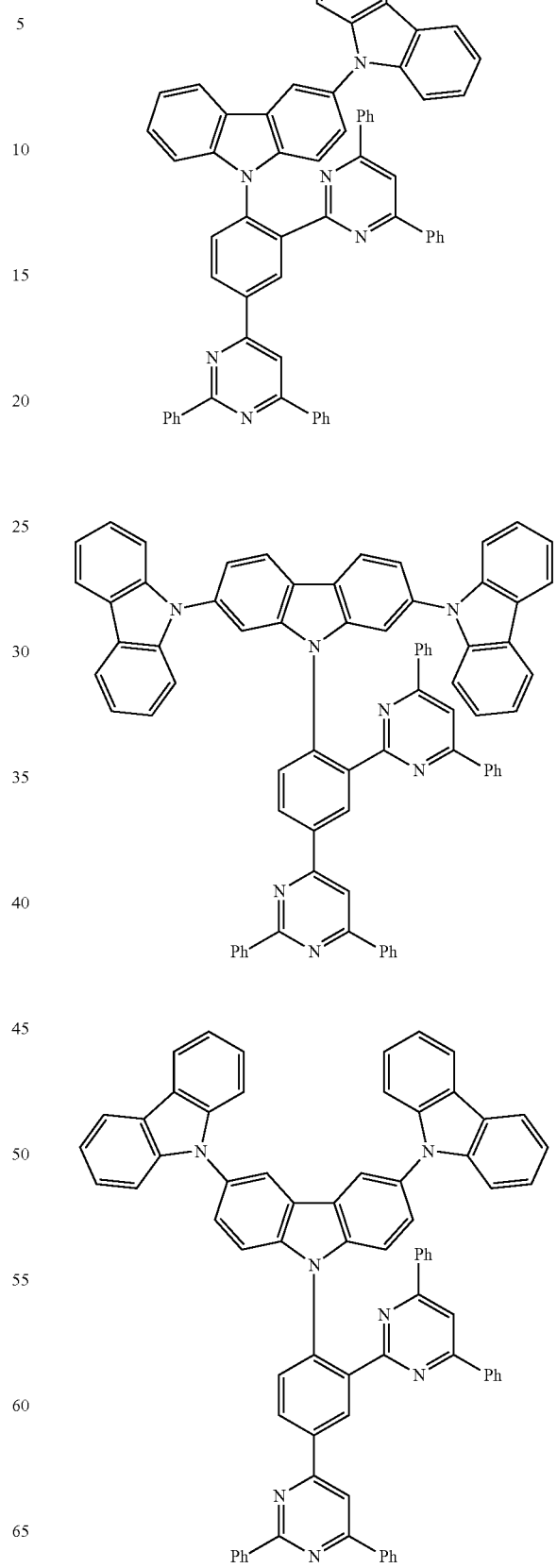

259
-continued
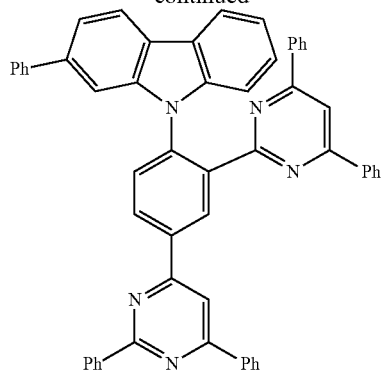
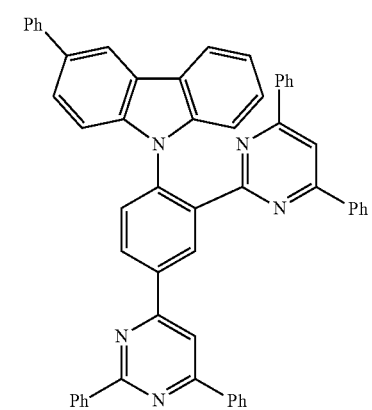
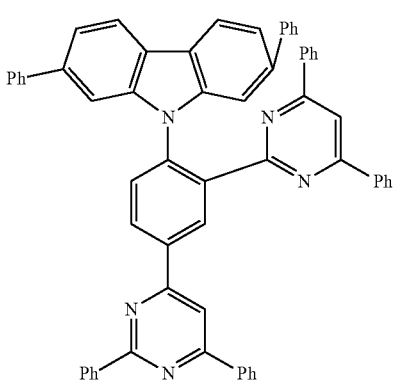
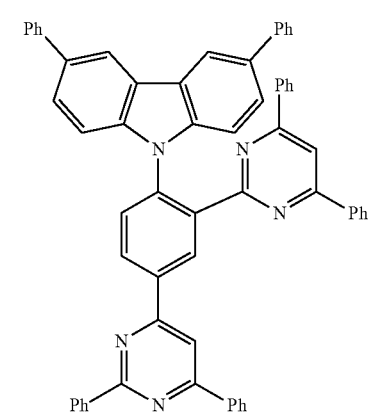
260
-continued
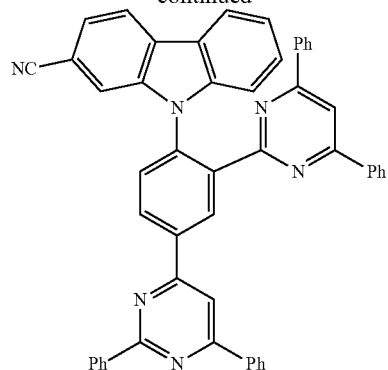
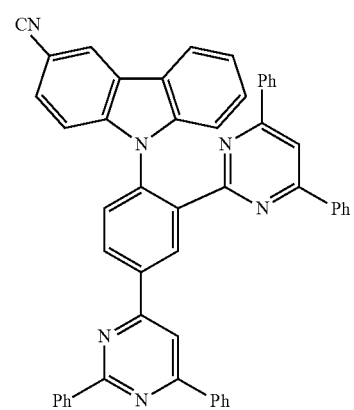
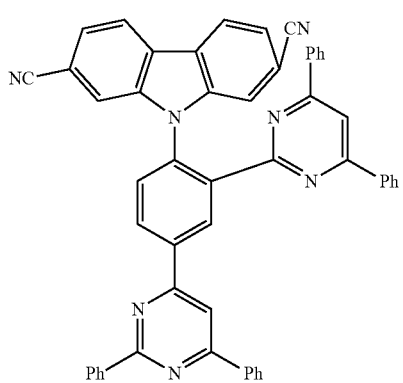
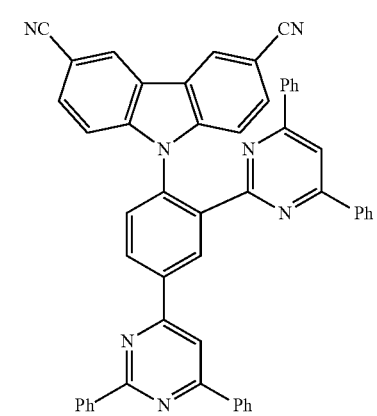

261
-continued
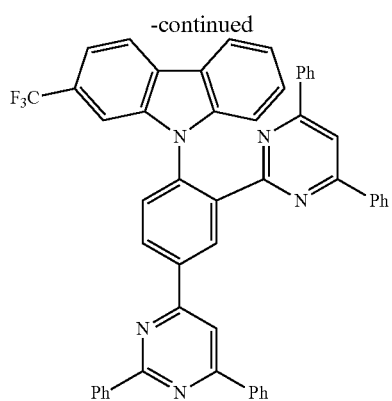
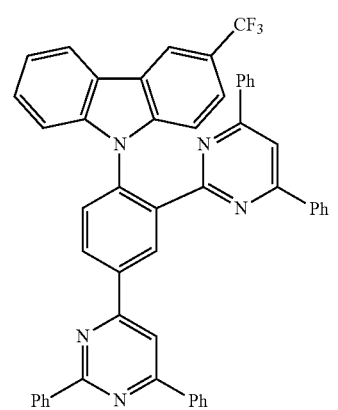
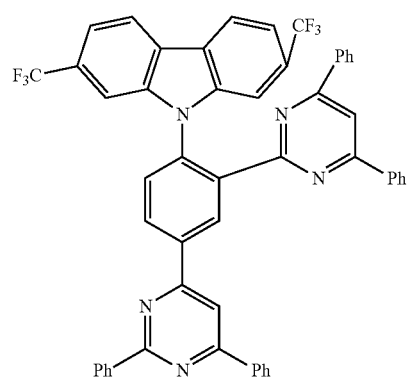
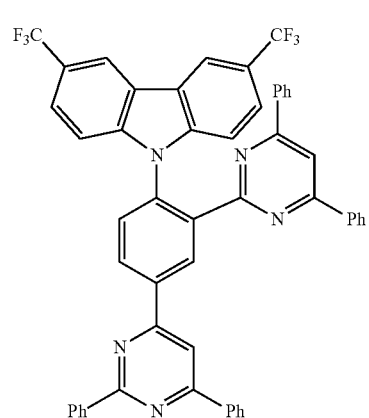
262
-continued
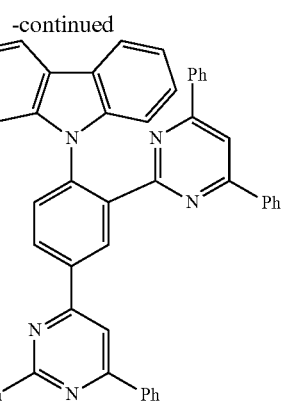
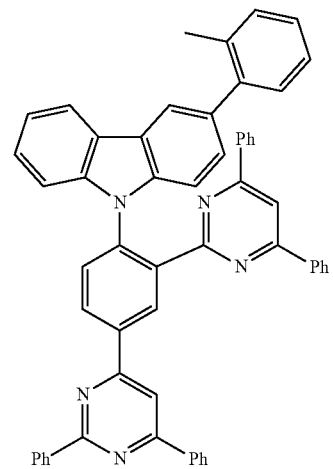
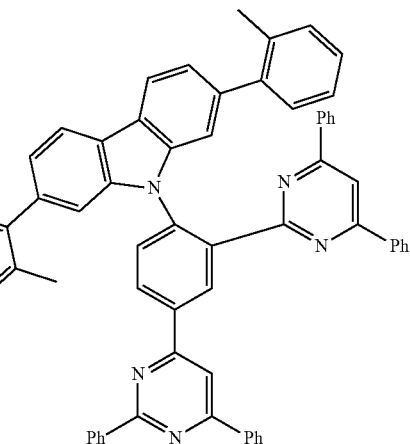

263
-continued
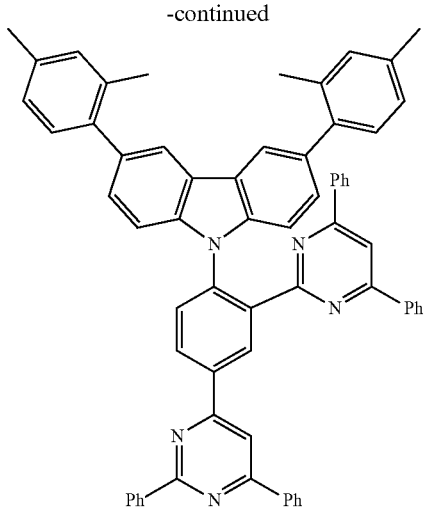
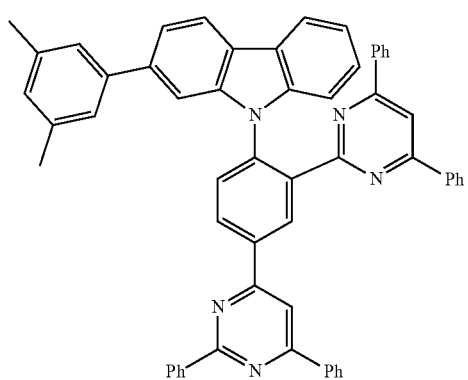
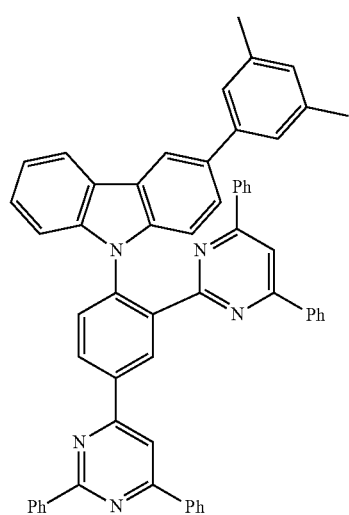
264
-continued
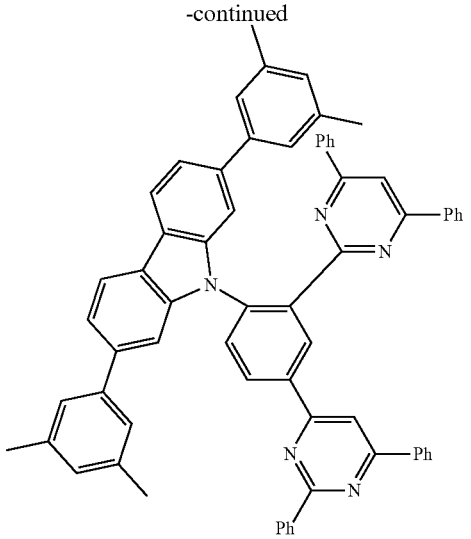
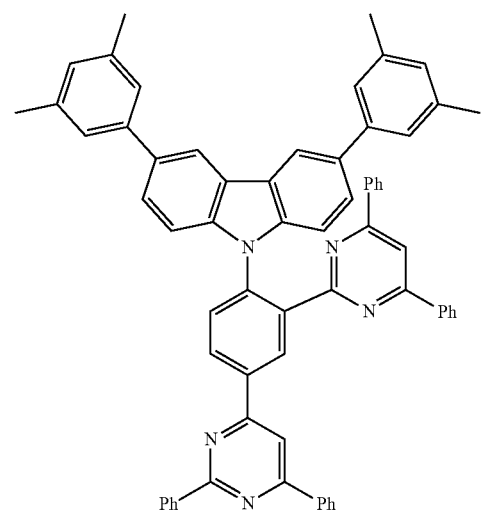
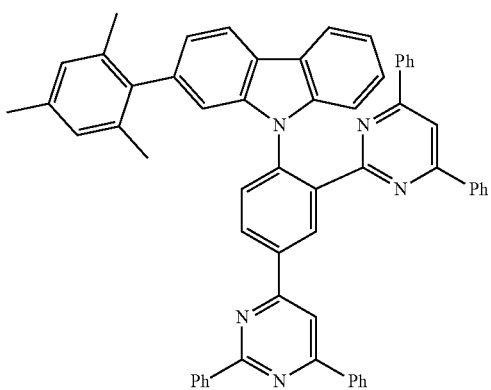

265
-continued
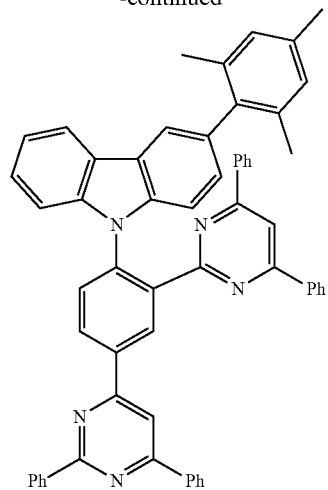
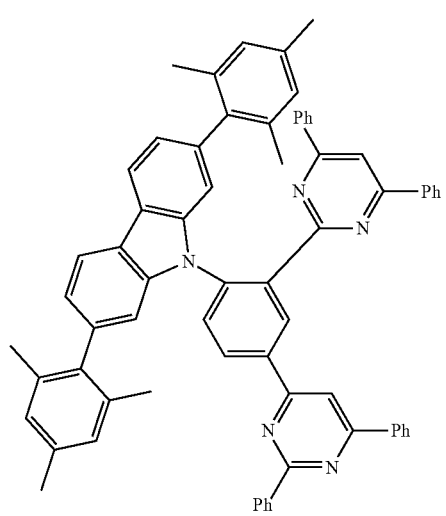
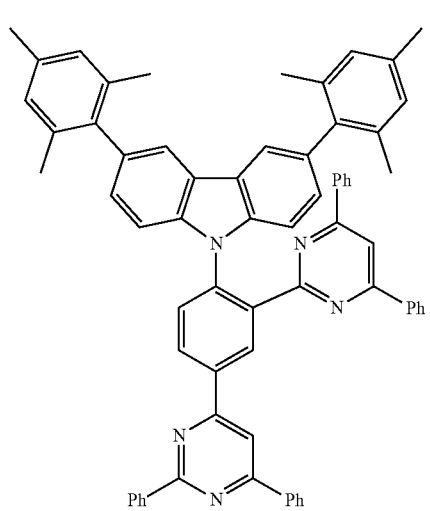
266
-continued
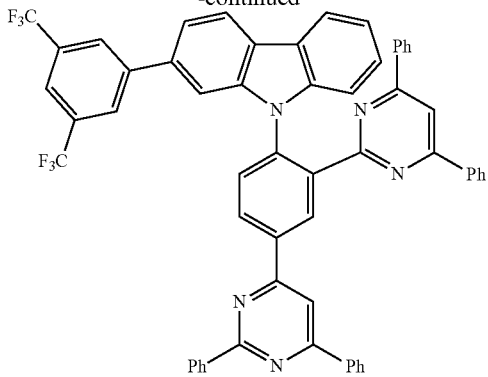
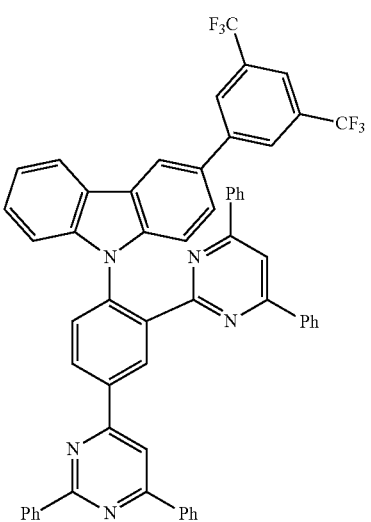
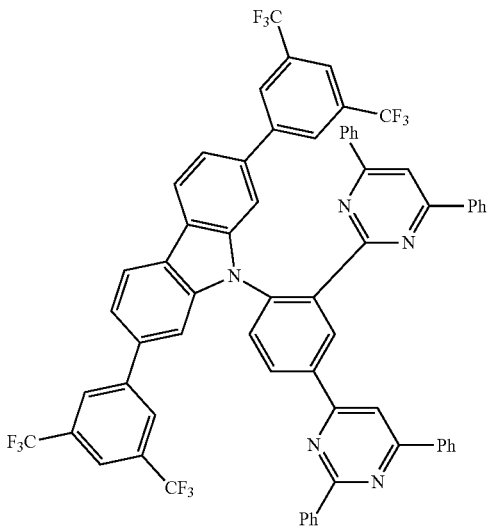

267
-continued
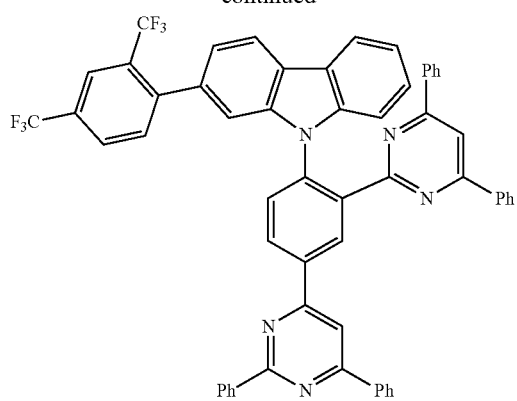
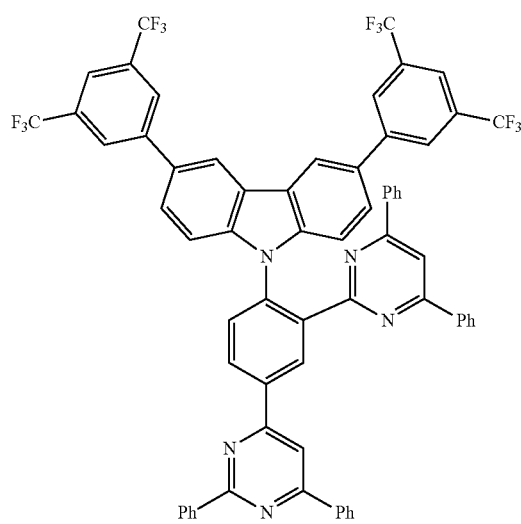
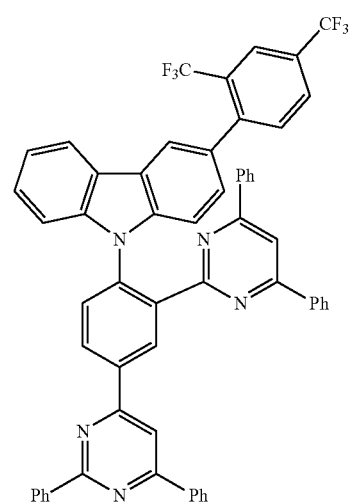
268
-continued
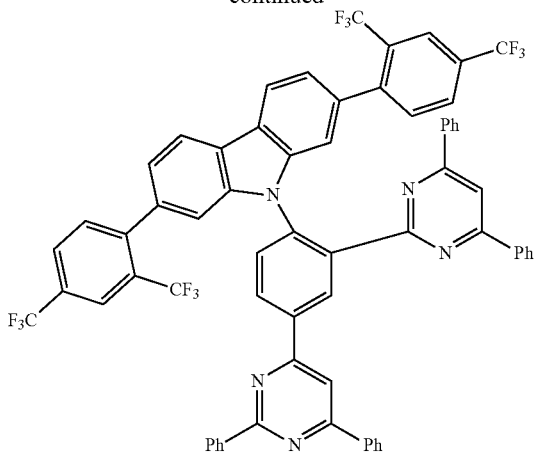
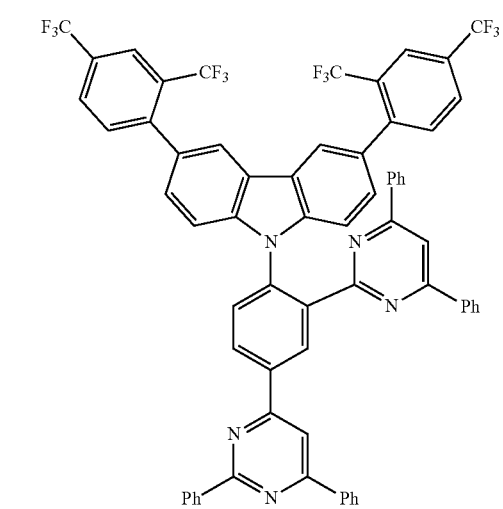
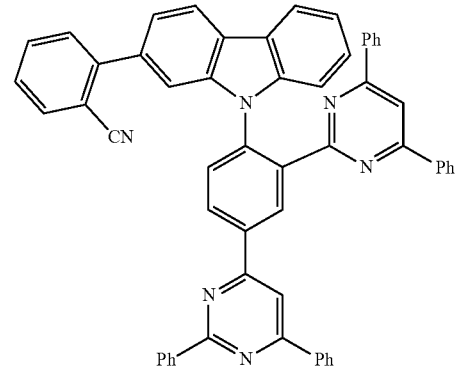

269
-continued
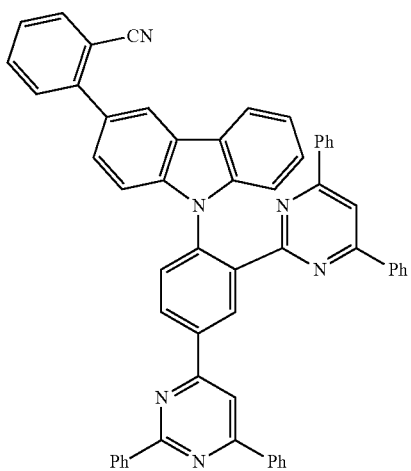
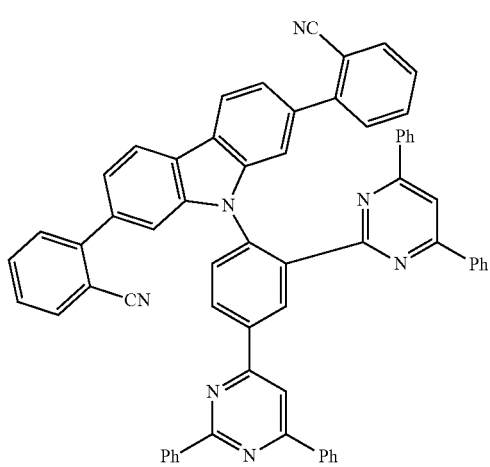
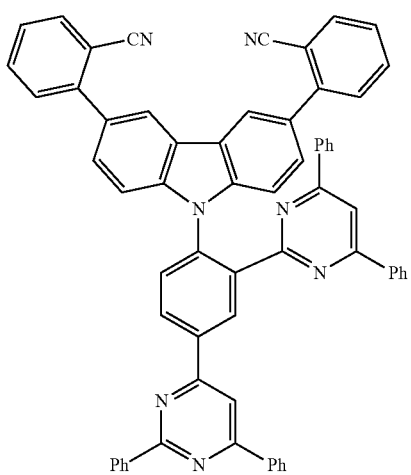
270
-continued
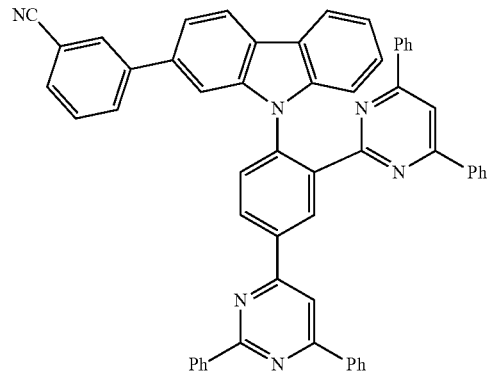
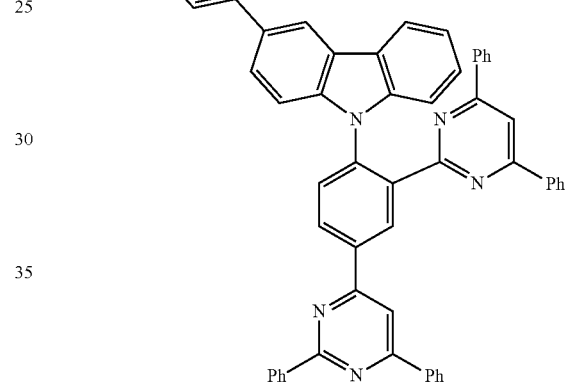
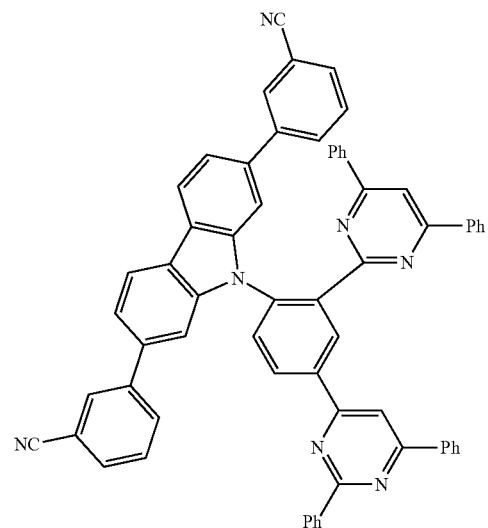

271
-continued
272
-continued
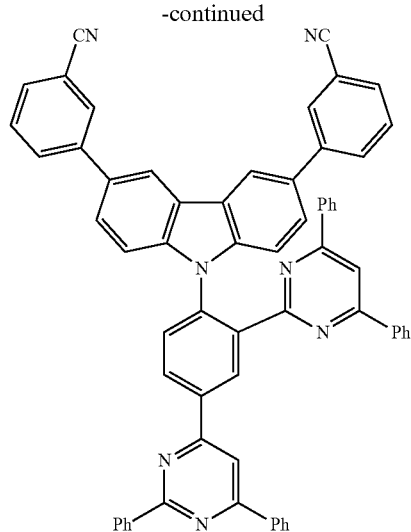
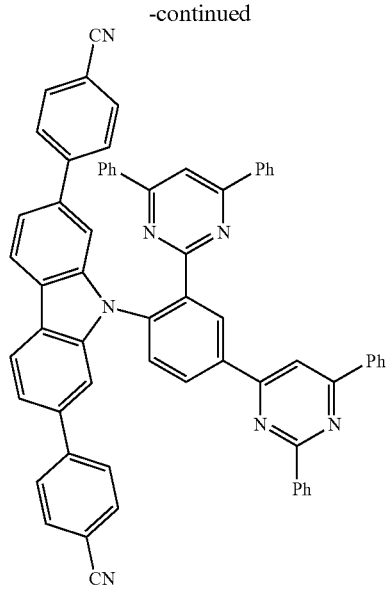
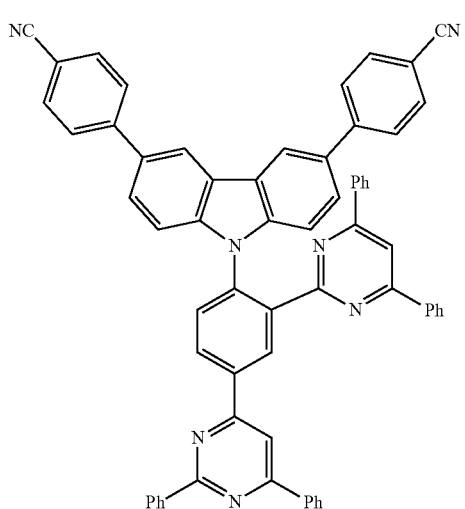 [SMILES: N#Cc1ccc(-c2ccc3c(c2)c2cc(-c4ccc(C#N)cc4)ccc2n3-c2ccc(-c3cc(-c4ccccc4)nc(-c4ccccc4)n3)cc2-c2nc(-c3ccccc3)cc(-c3ccccc3)n2)cc1]
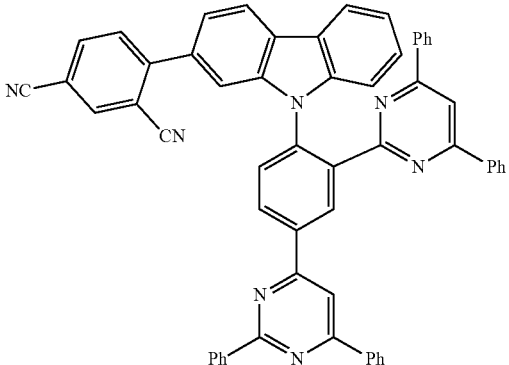

273
-continued
274
-continued
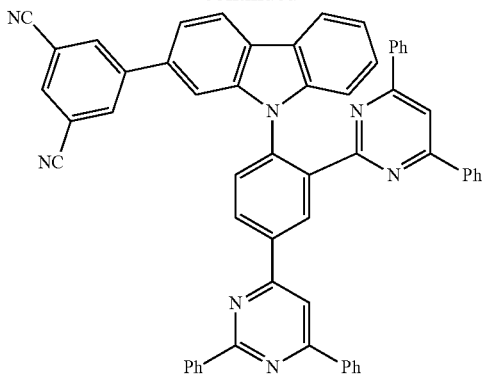
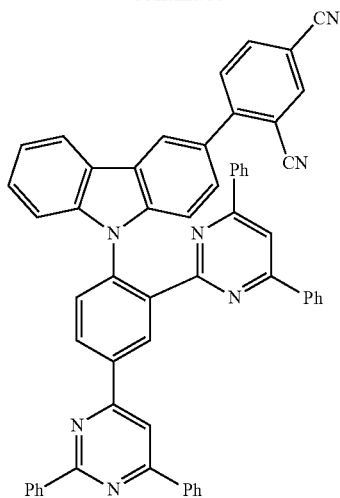
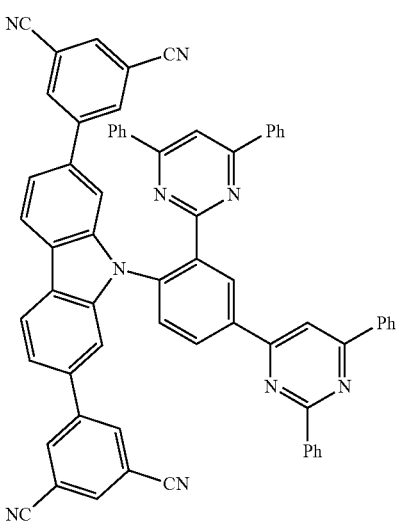

275
-continued
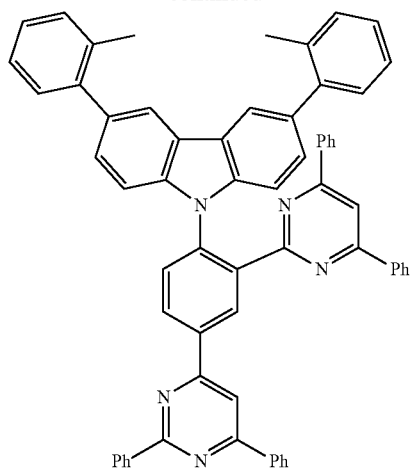 [SMILES: Cc1ccccc1-c1ccc2c(c1)c1cc(-c3ccccc3C)ccc1n2-c1ccc(-c2cc(-c3ccccc3)nc(-c3ccccc3)n2)cc1-c1nc(-c2ccccc2)cc(-c2ccccc2)n1]
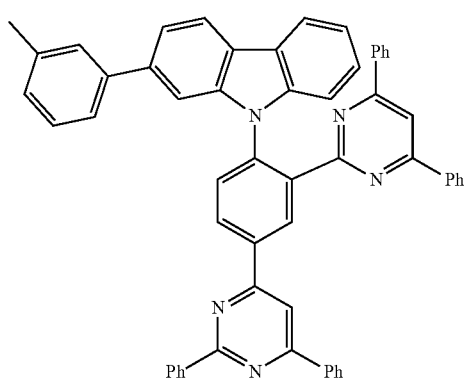
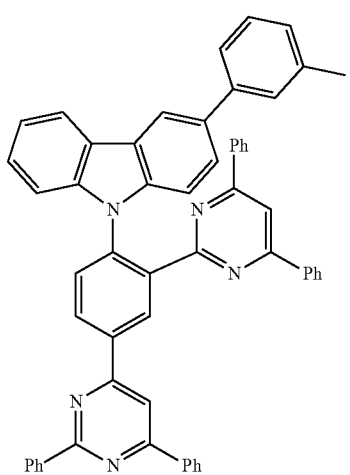
276
-continued
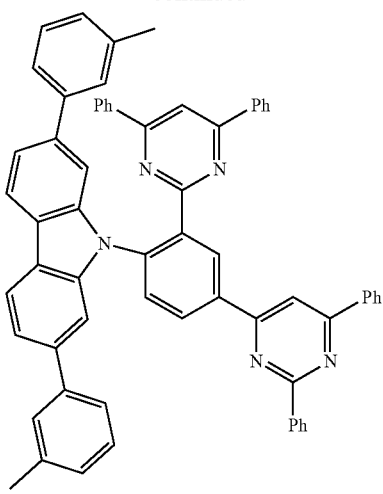
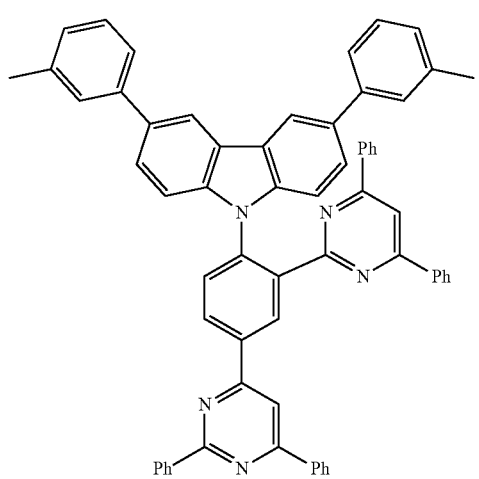
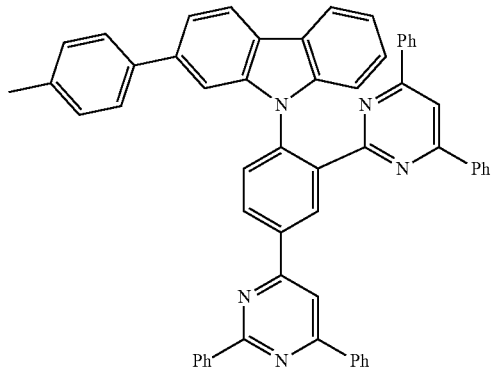

277
-continued
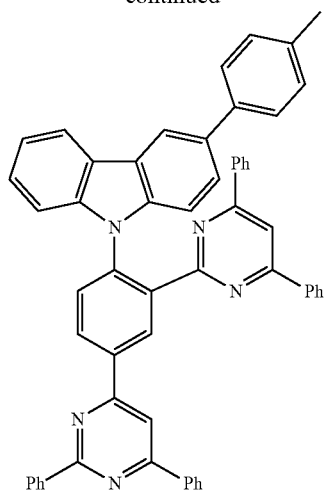
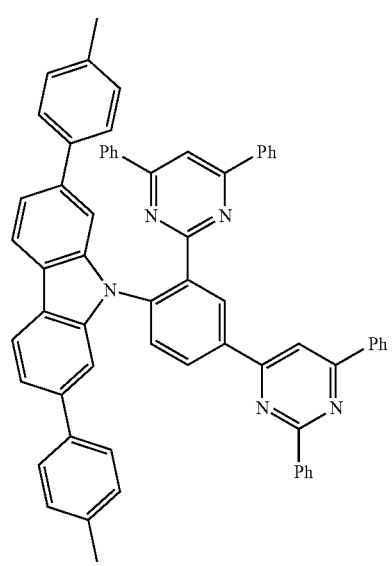
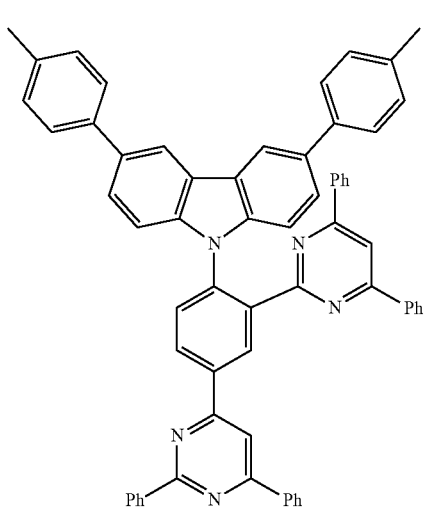
278
-continued
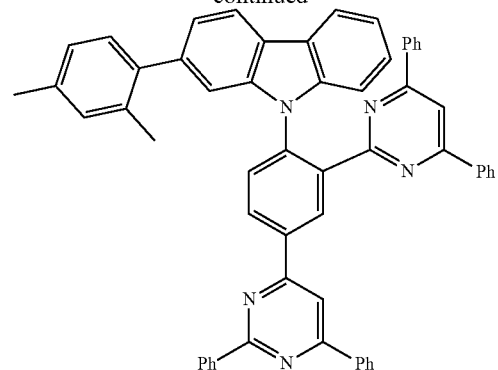
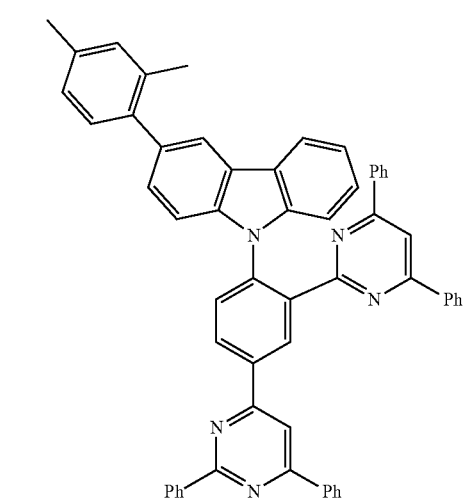
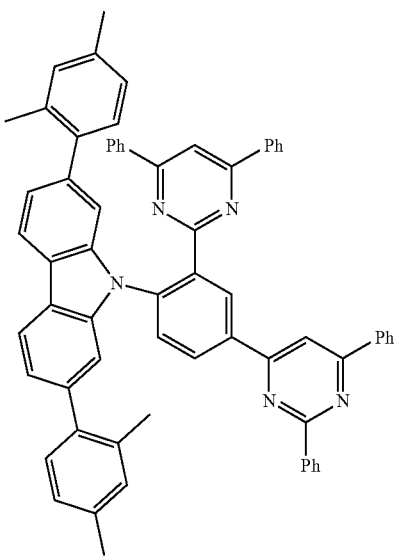

279
-continued
280
-continued
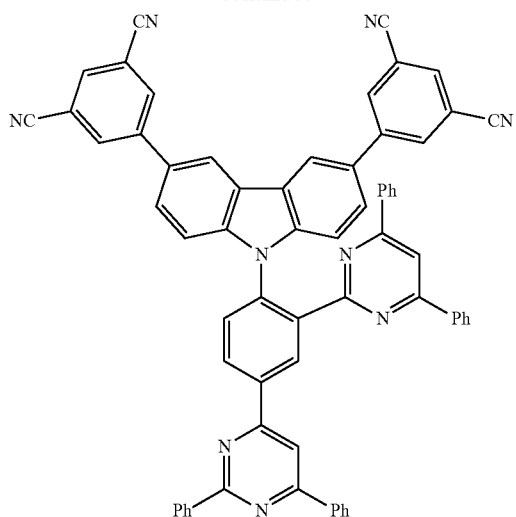 [SMILES: N#Cc1cc(C#N)cc(-c2ccc3c(c2)c2cc(-c4cc(C#N)cc(C#N)c4)ccc2n3-c2ccc(-c3cc(-c4ccccc4)nc(-c4ccccc4)n3)cc2-c2nc(-c3ccccc3)cc(-c3ccccc3)n2)c1]
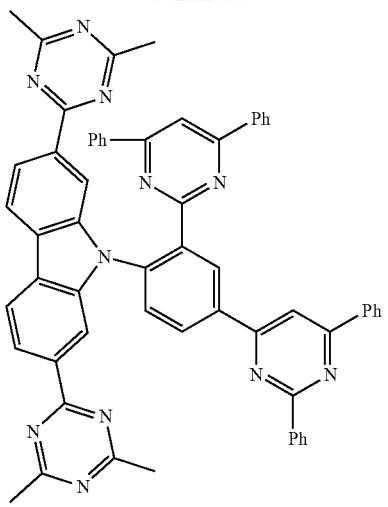
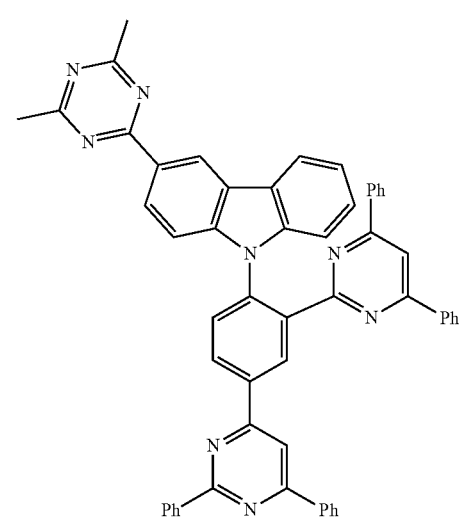

281
-continued
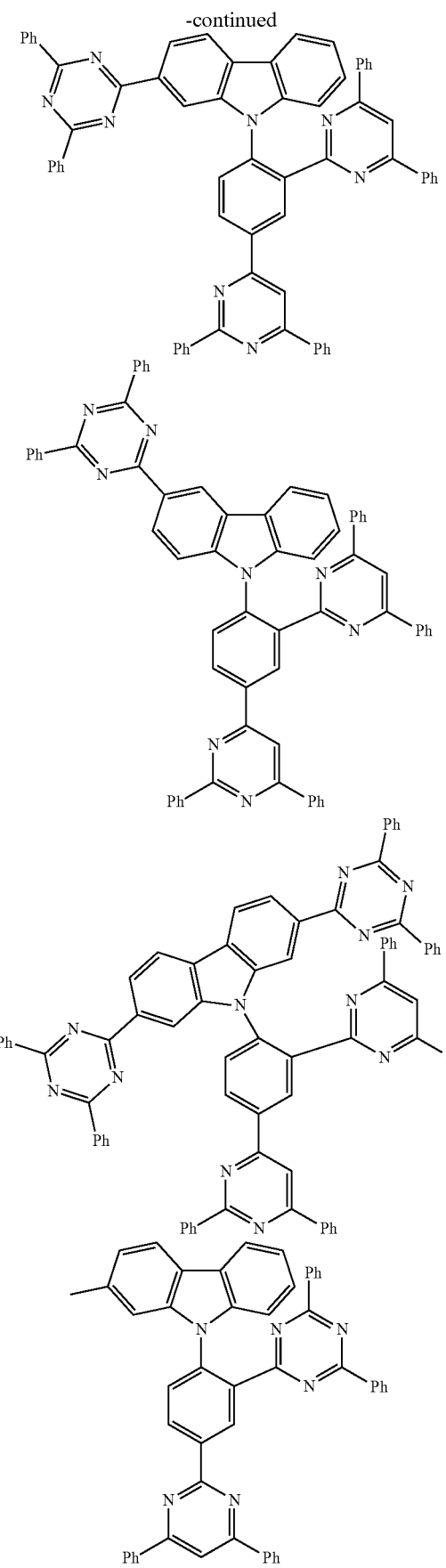
282
-continued
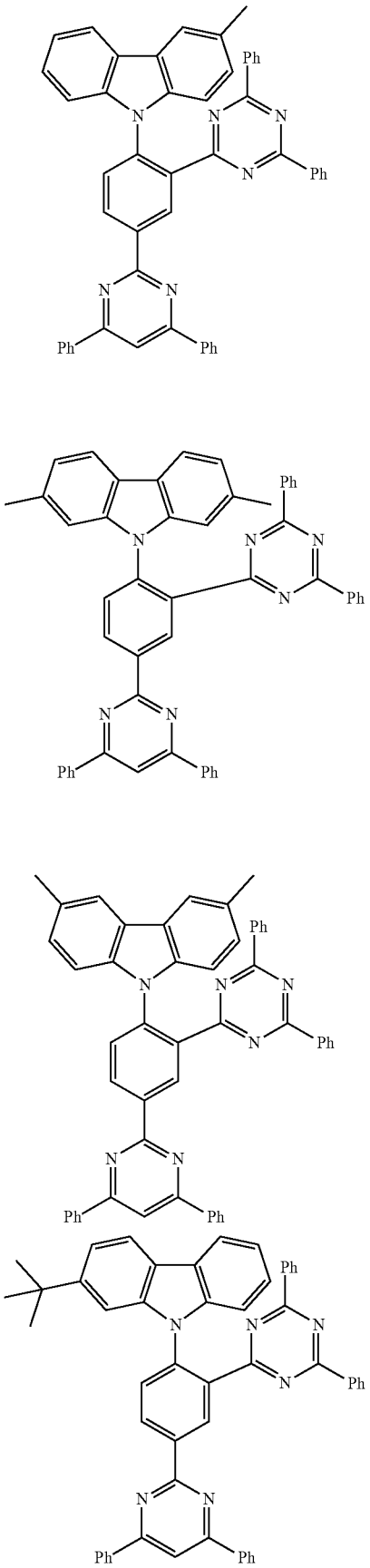

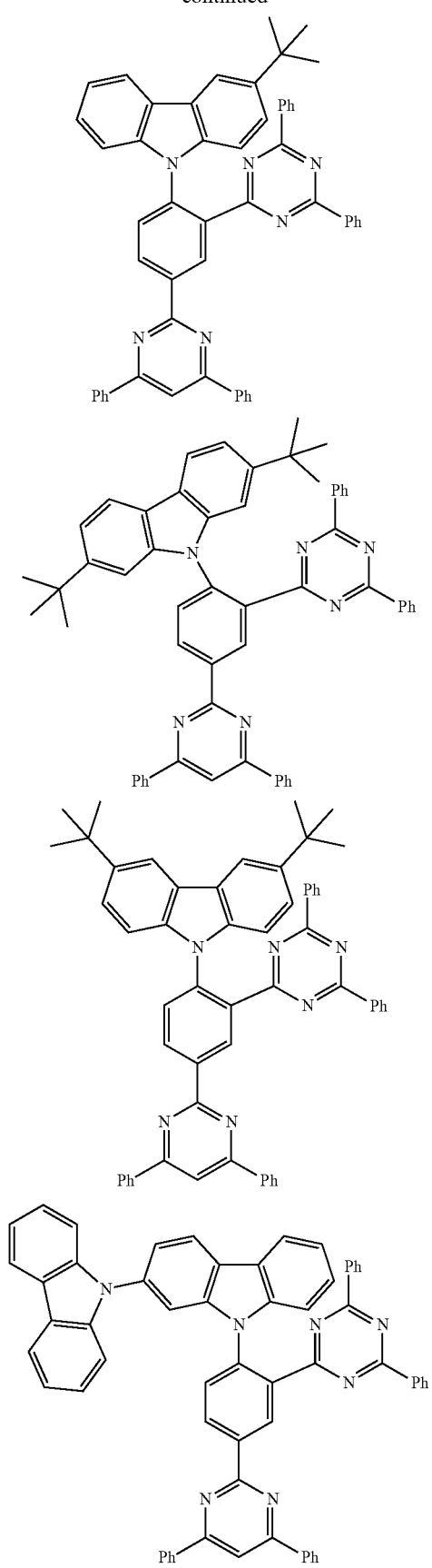
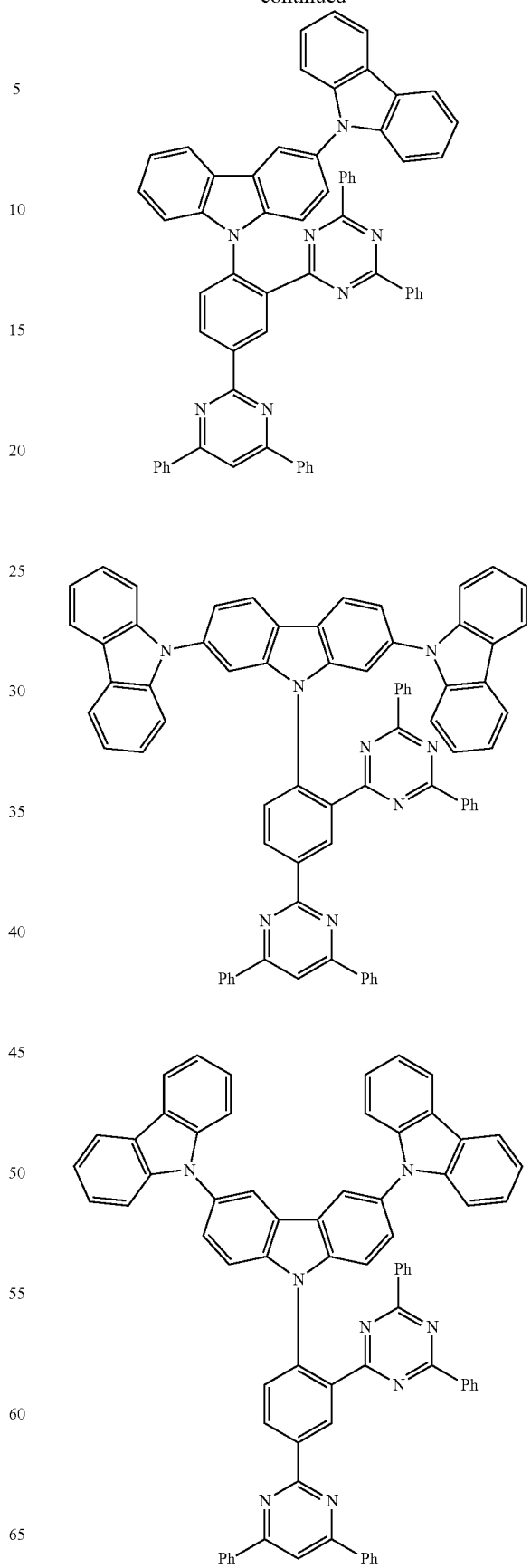

285
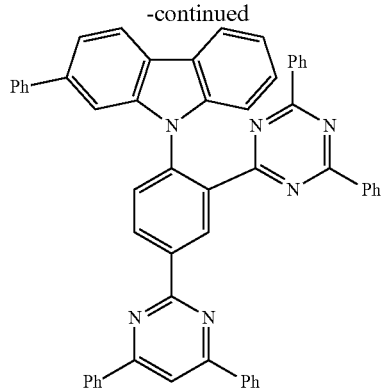
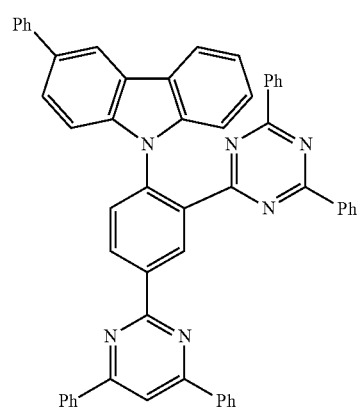
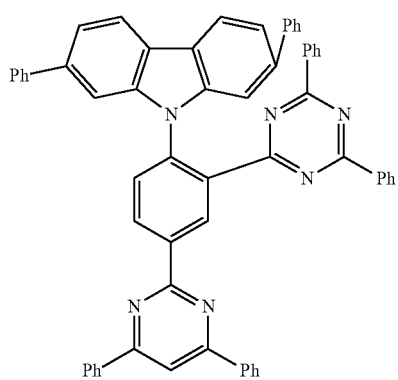
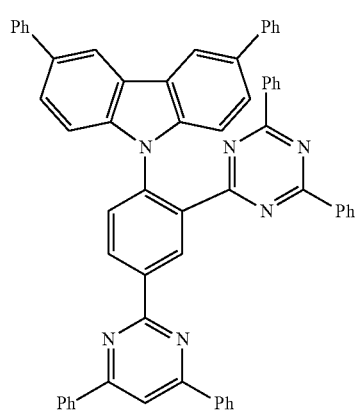
286
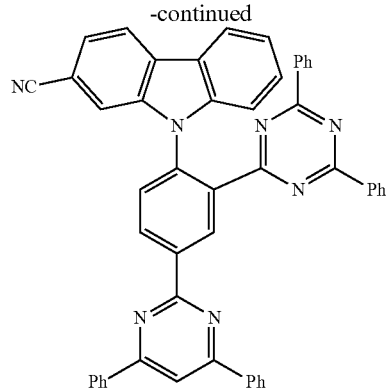
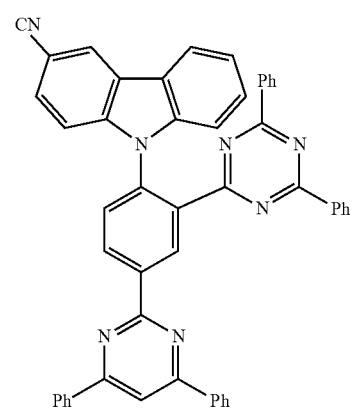
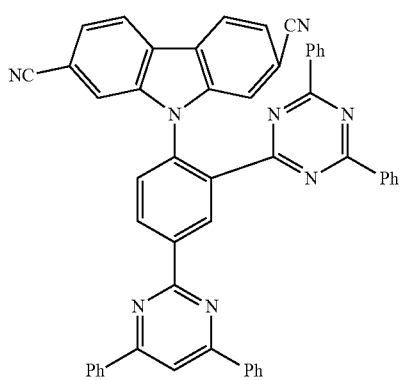
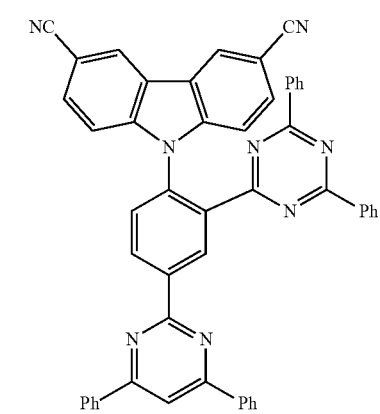

287
-continued
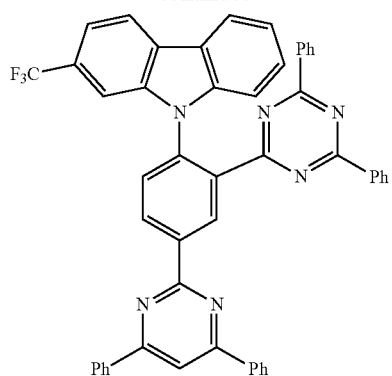
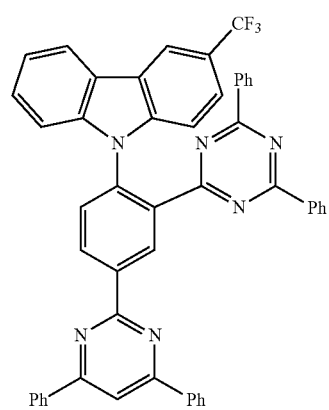
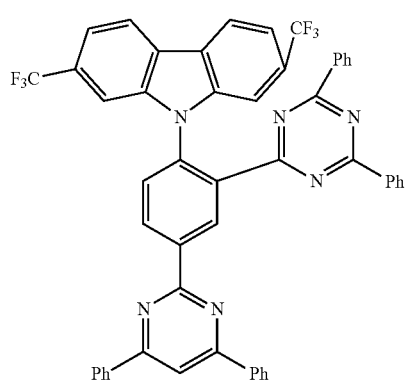
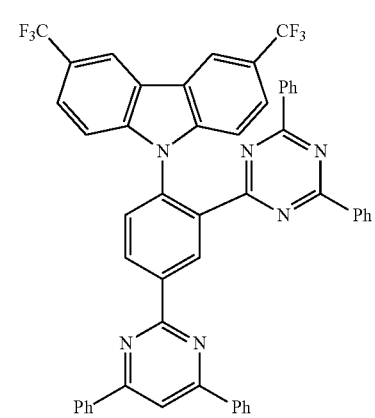
288
-continued
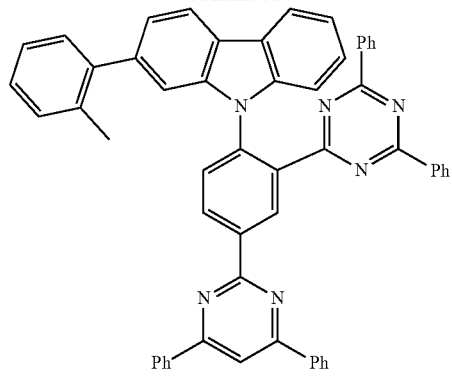
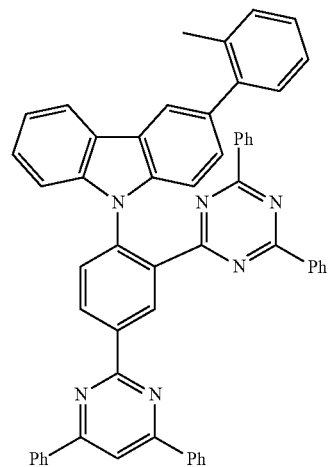
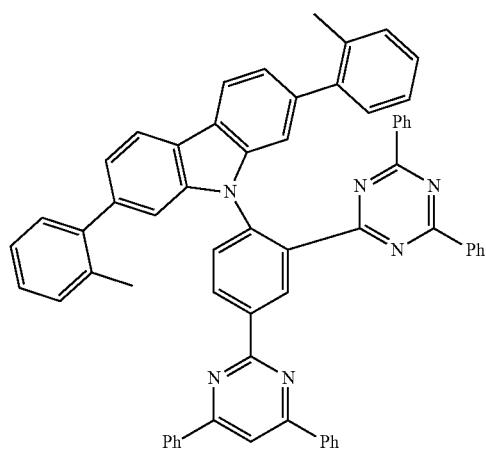

289
-continued
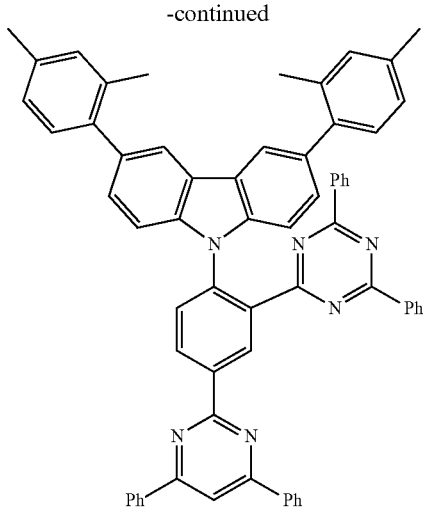
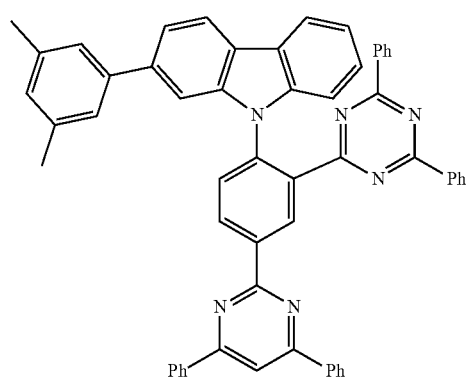
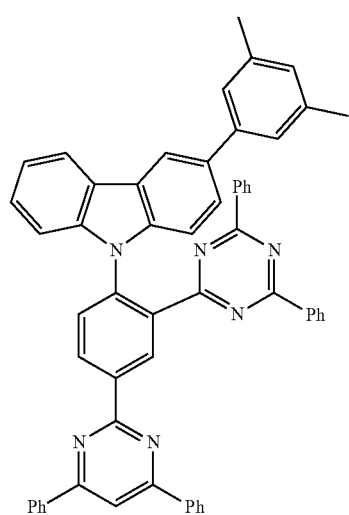
290
-continued
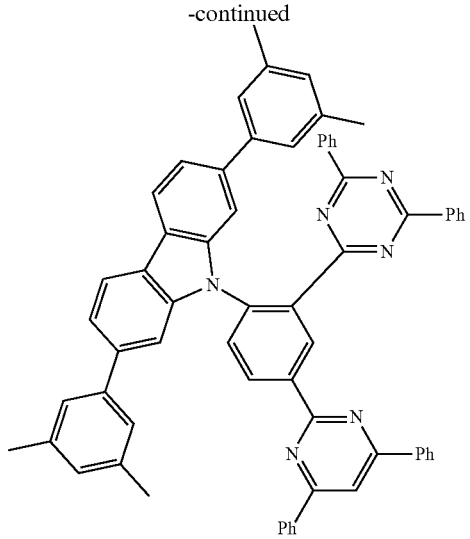
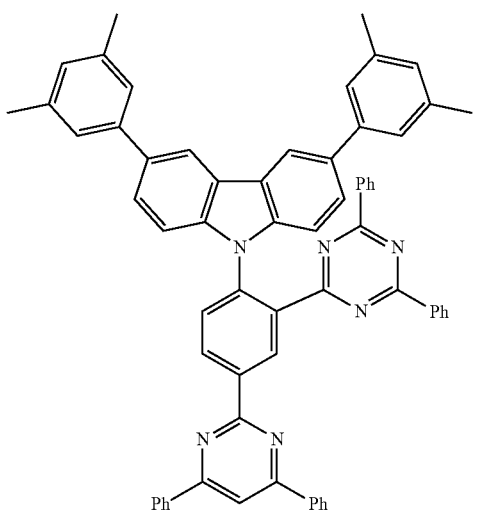
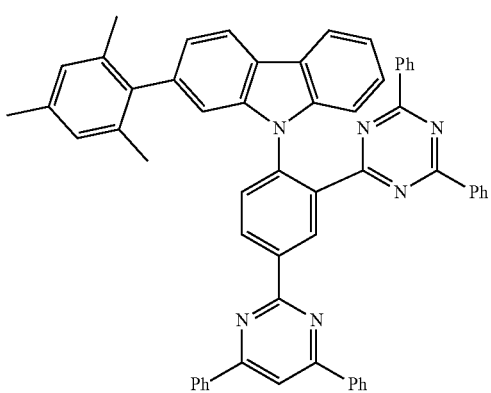

291
-continued
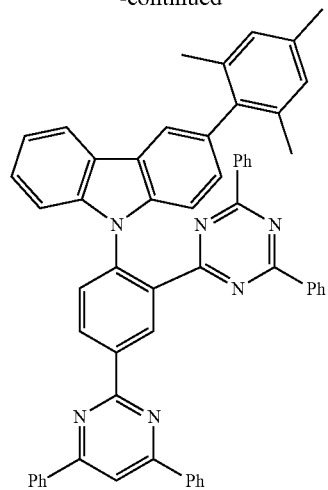
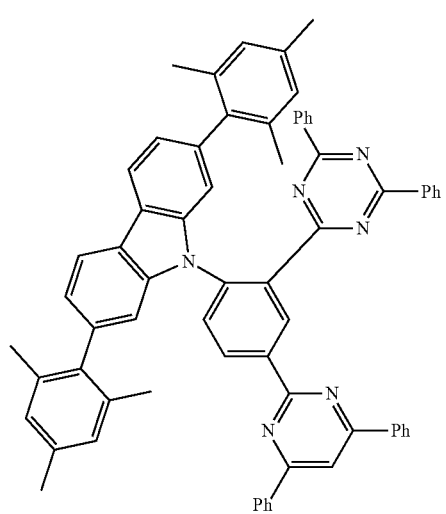
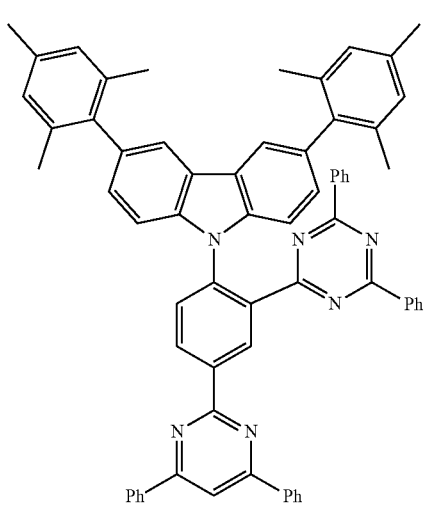
292
-continued
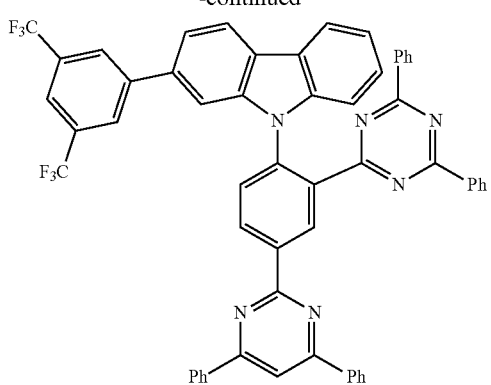
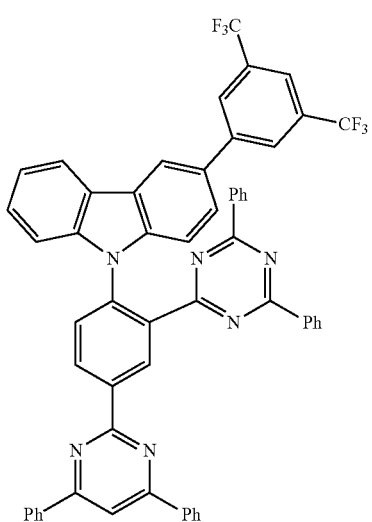
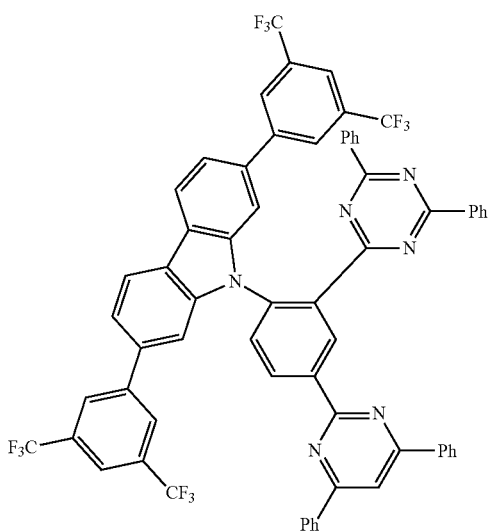

293
-continued
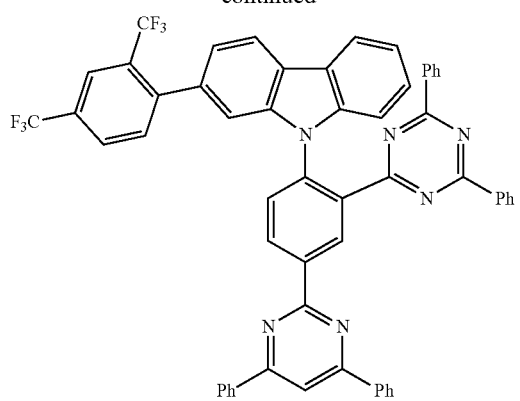
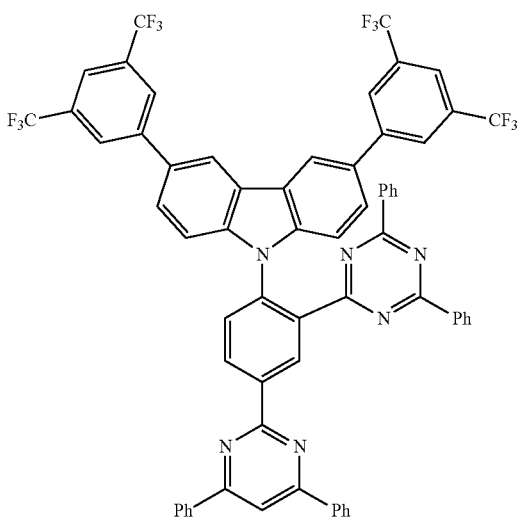
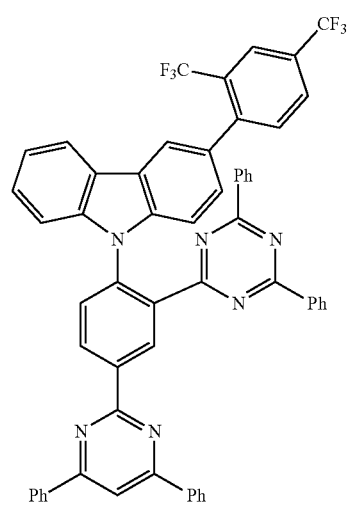
294
-continued
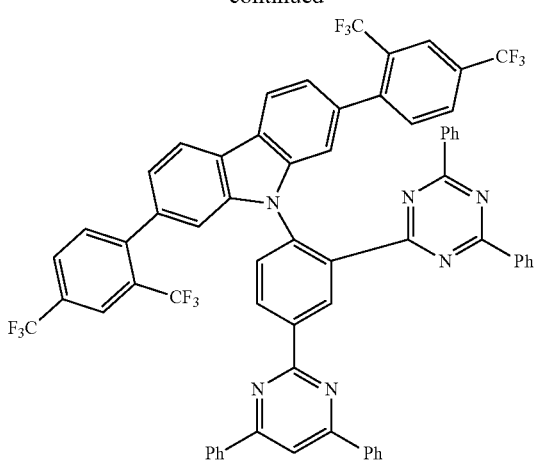
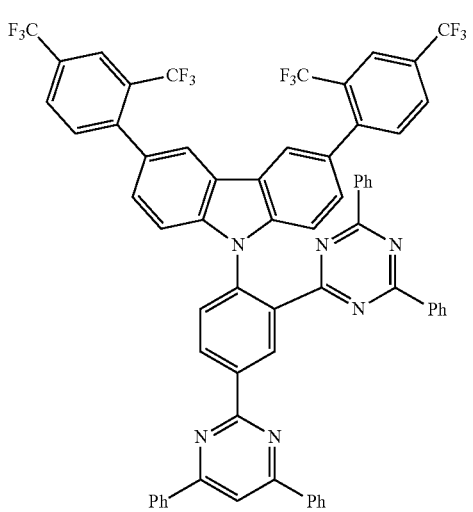
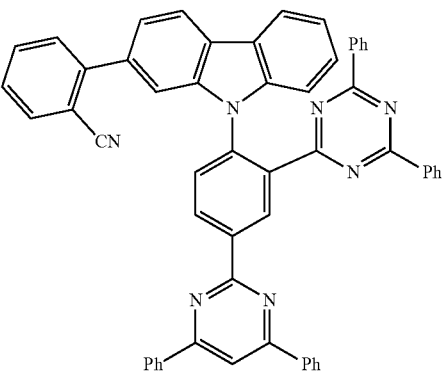

295
-continued
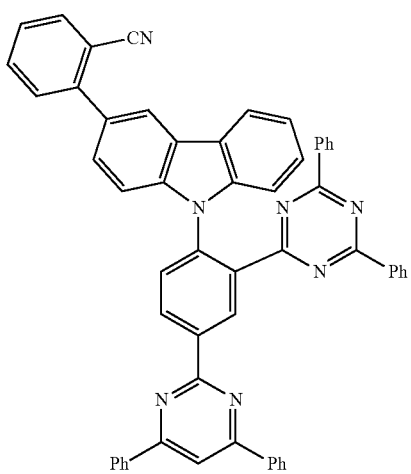
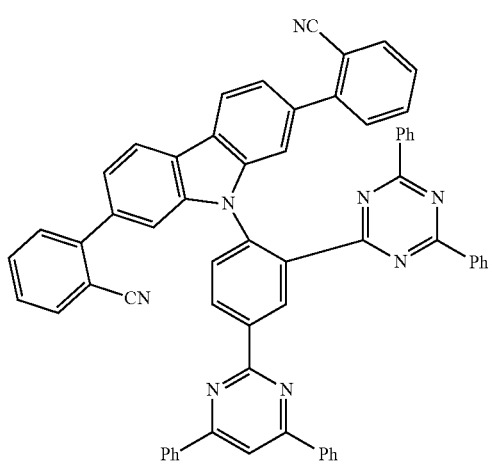
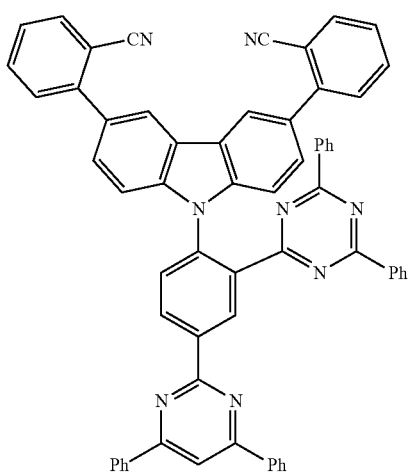
296
-continued
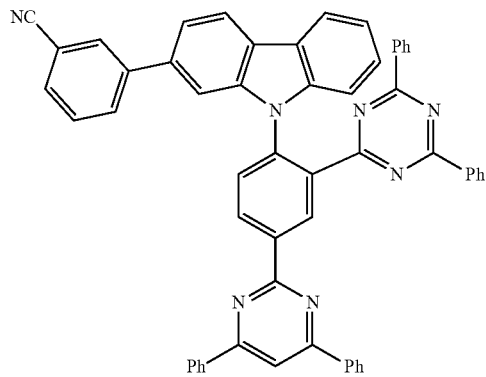
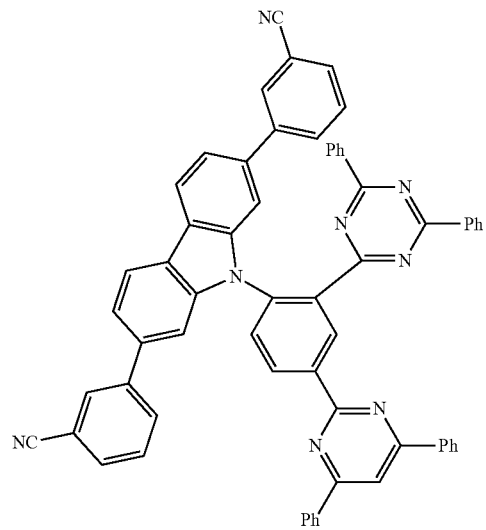

297
-continued
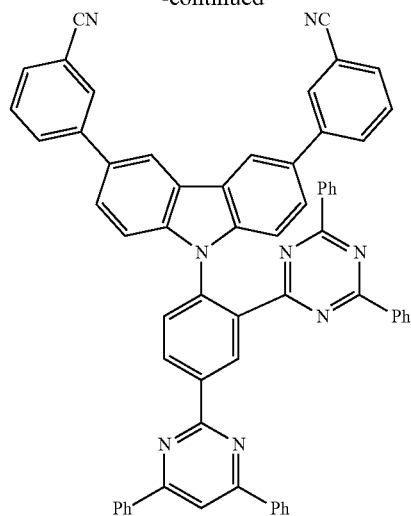
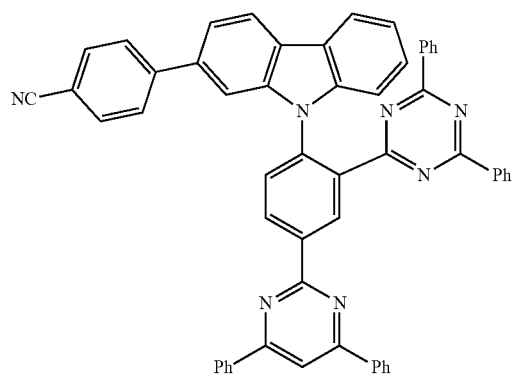
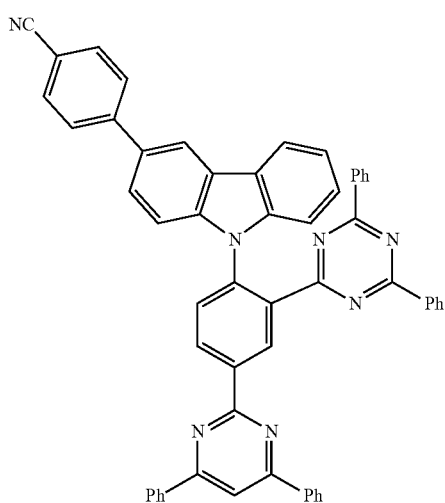
298
-continued
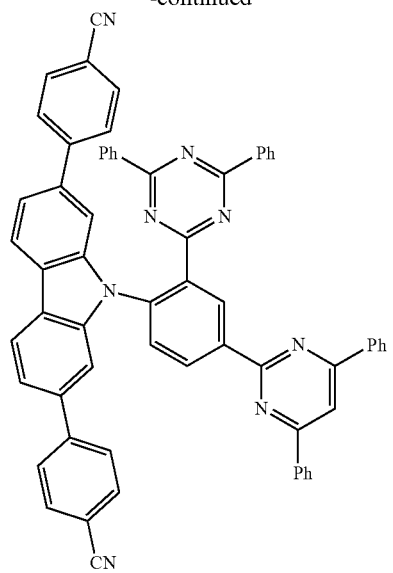
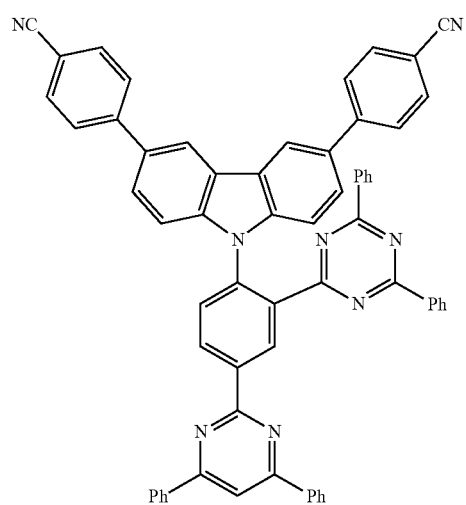 [SMILES: N#Cc1ccc(-c2ccc3c(c2)c2cc(-c4ccc(C#N)cc4)ccc2n3-c2ccc(-c3nc(-c4ccccc4)cc(-c4ccccc4)n3)cc2-c2nc(-c3ccccc3)nc(-c3ccccc3)n2)cc1]
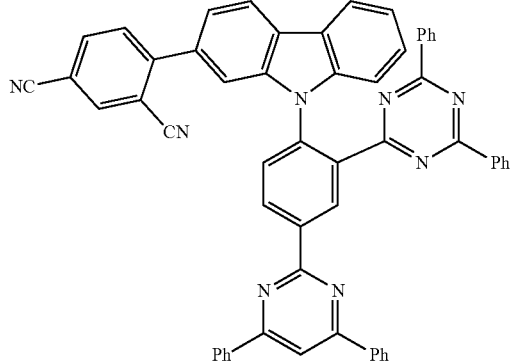

299
-continued
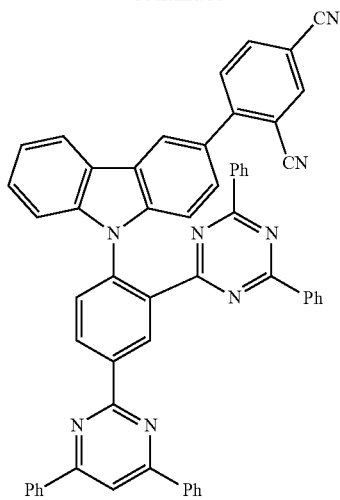
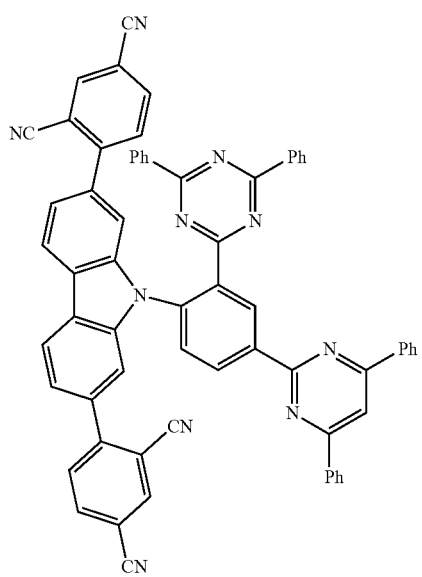
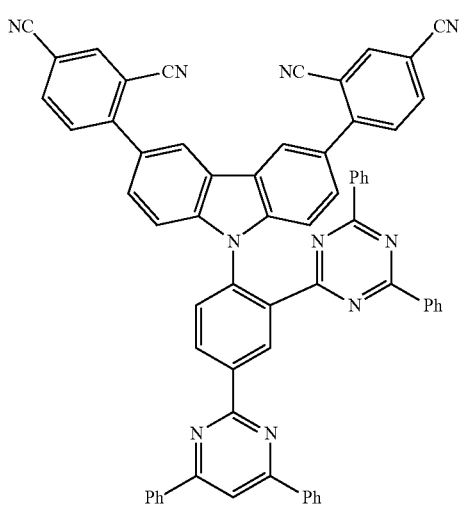 [SMILES: N#Cc1ccc(-c2ccc3c(c2)c2cc(-c4ccc(C#N)cc4C#N)ccc2n3-c2ccc(-c3nc(-c4ccccc4)cc(-c4ccccc4)n3)cc2-c2nc(-c3ccccc3)nc(-c3ccccc3)n2)c(C#N)c1]
300
-continued
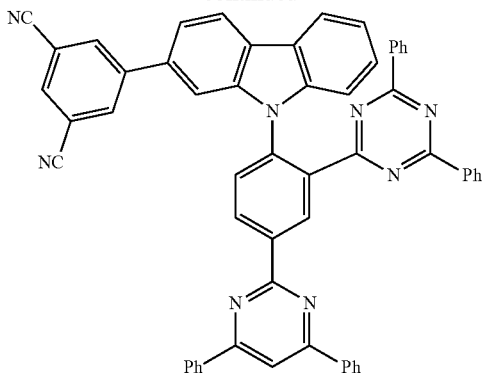
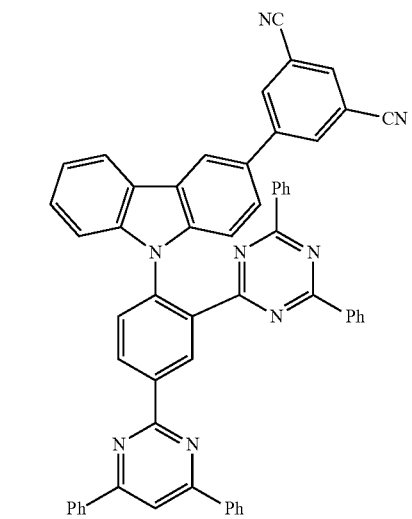
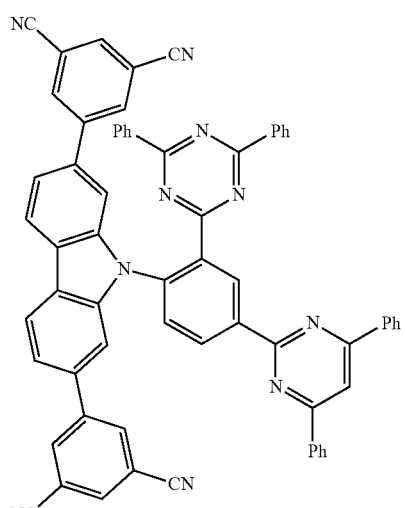

301
-continued
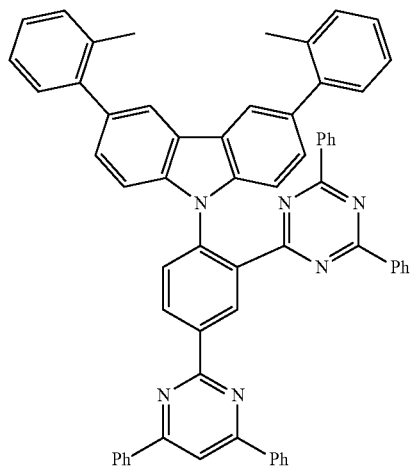 [SMILES: Cc1ccccc1-c1ccc2c(c1)c1cc(-c3ccccc3C)ccc1n2-c1ccc(-c2nc(-c3ccccc3)cc(-c3ccccc3)n2)cc1-c1nc(-c2ccccc2)nc(-c2ccccc2)n1]
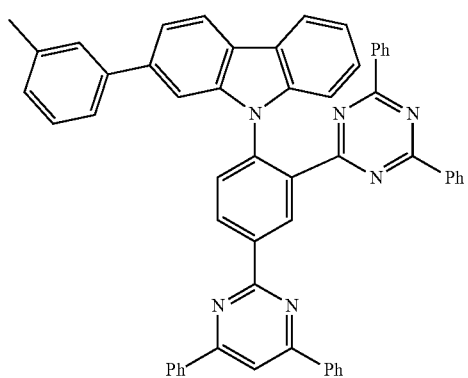
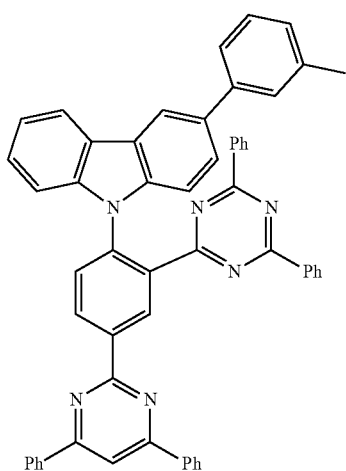
302
-continued
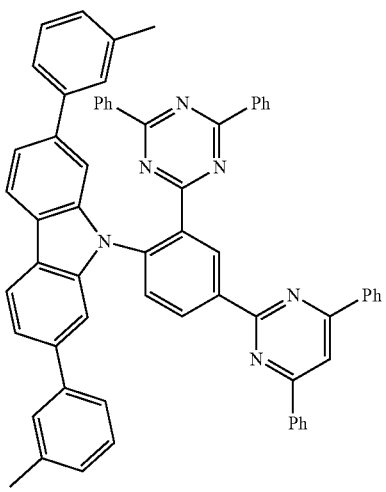
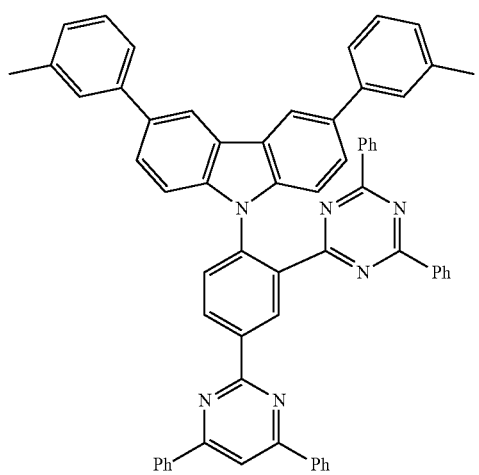
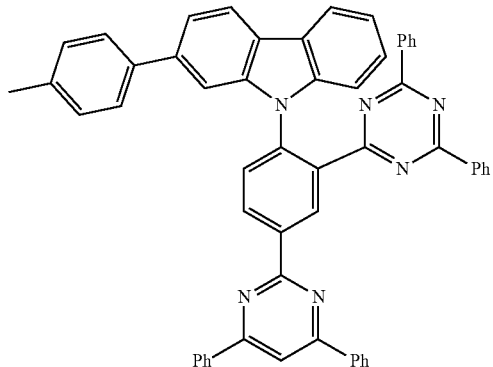

303
-continued
304
-continued
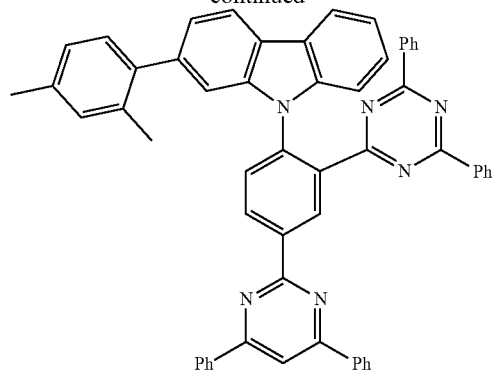
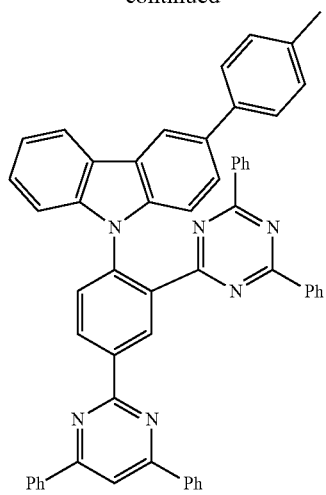
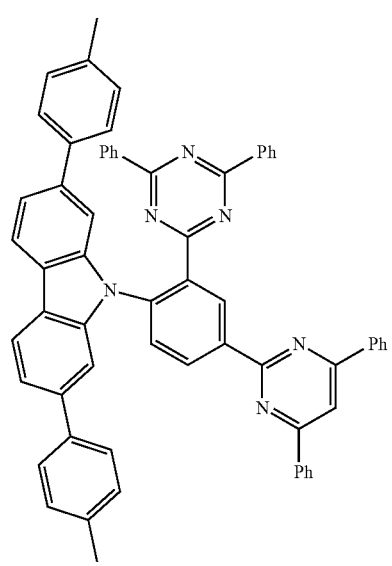
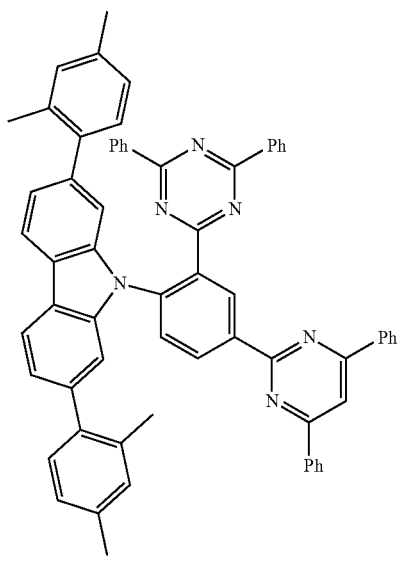
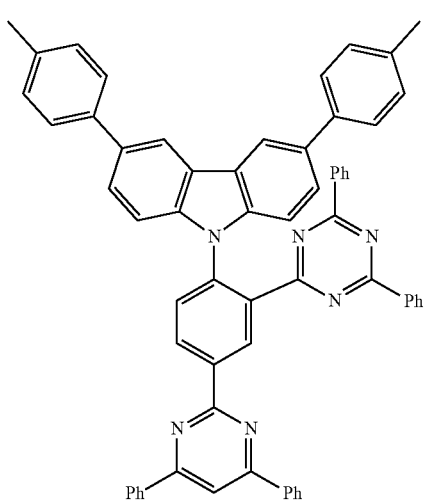

305
-continued
306
-continued
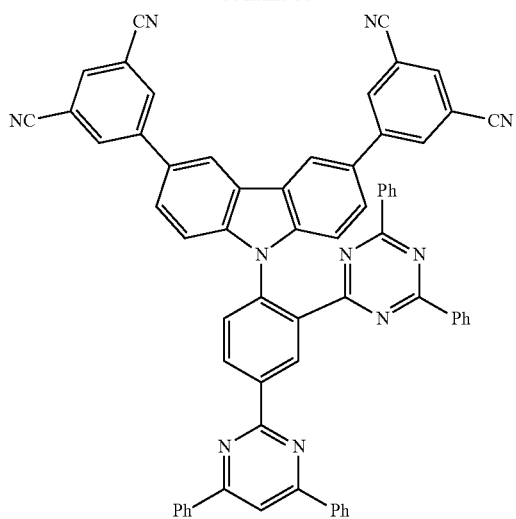 [SMILES: N#Cc1cc(C#N)cc(-c2ccc3c(c2)c2cc(-c4cc(C#N)cc(C#N)c4)ccc2n3-c2ccc(-c3nc(-c4ccccc4)cc(-c4ccccc4)n3)cc2-c2nc(-c3ccccc3)nc(-c3ccccc3)n2)c1]
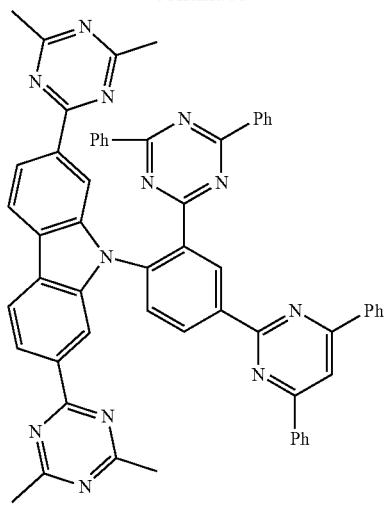
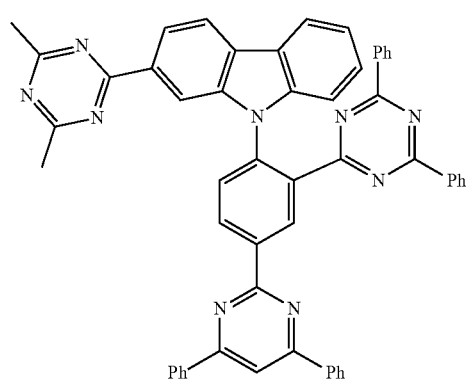
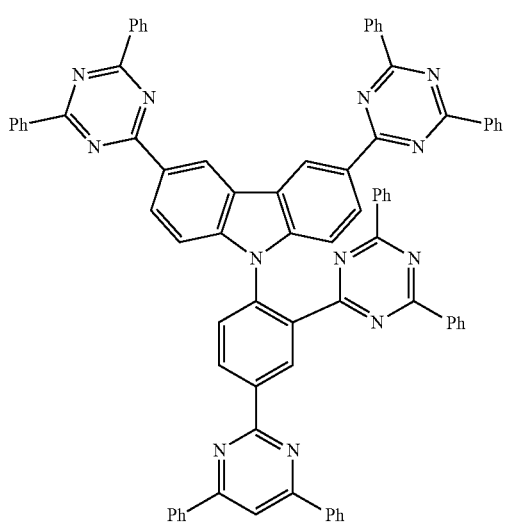 [SMILES: c1ccc(-c2cc(-c3ccccc3)nc(-c3ccc(-n4c5ccc(-c6nc(-c7ccccc7)nc(-c7ccccc7)n6)cc5c5cc(-c6nc(-c7ccccc7)nc(-c7ccccc7)n6)ccc54)c(-c4nc(-c5ccccc5)nc(-c5ccccc5)n4)c3)n2)cc1]
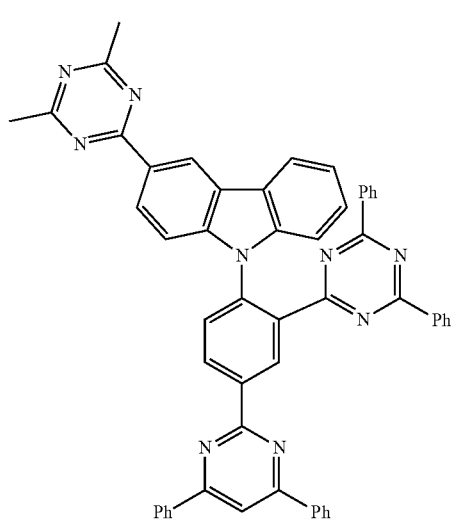
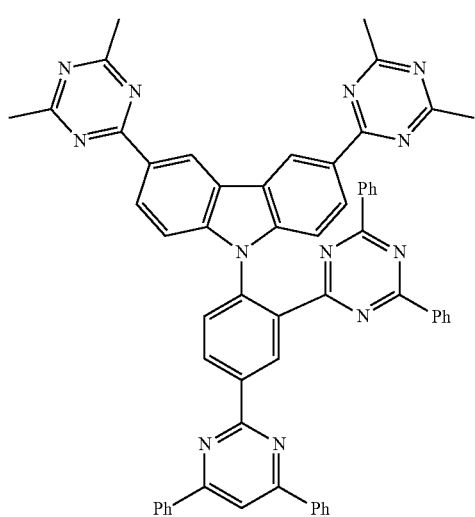

307
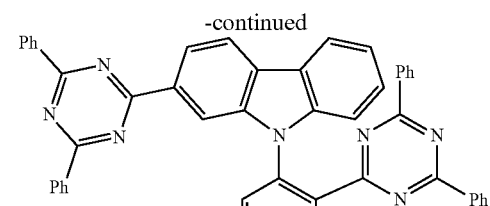
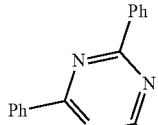
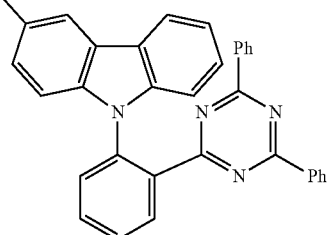
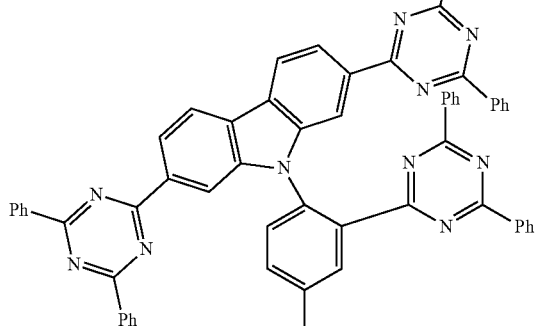
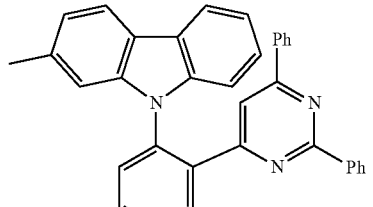
308
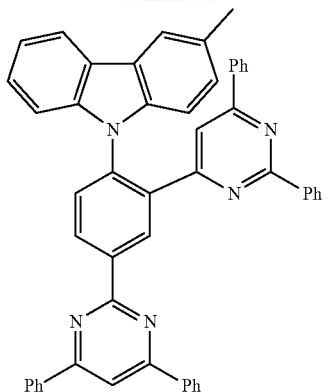
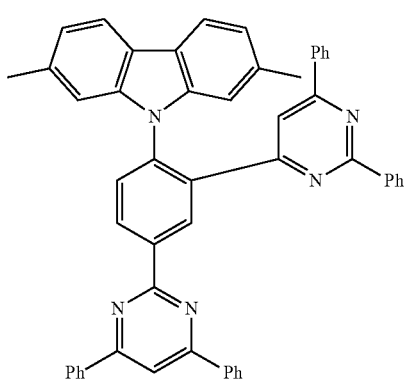
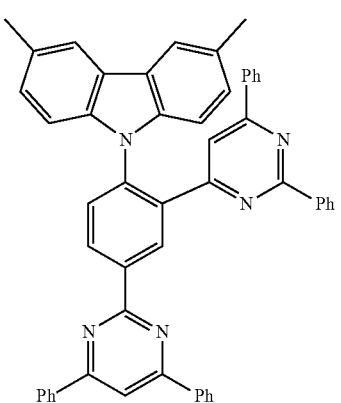
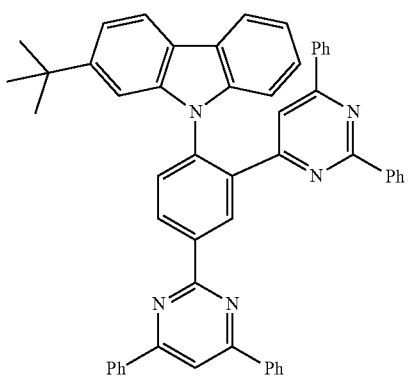

309
-continued
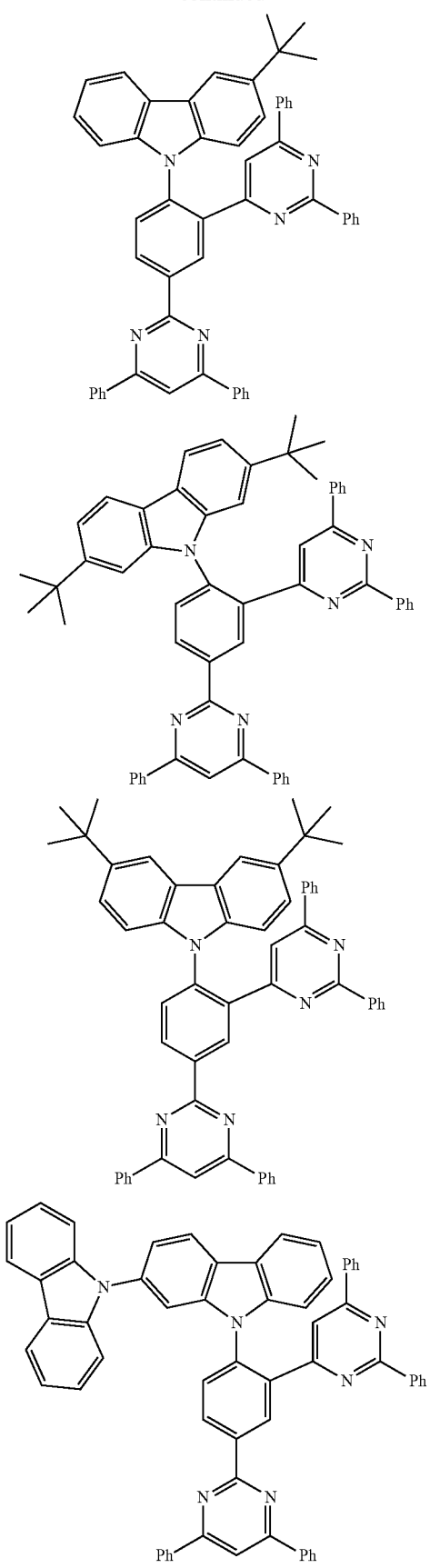
310
-continued
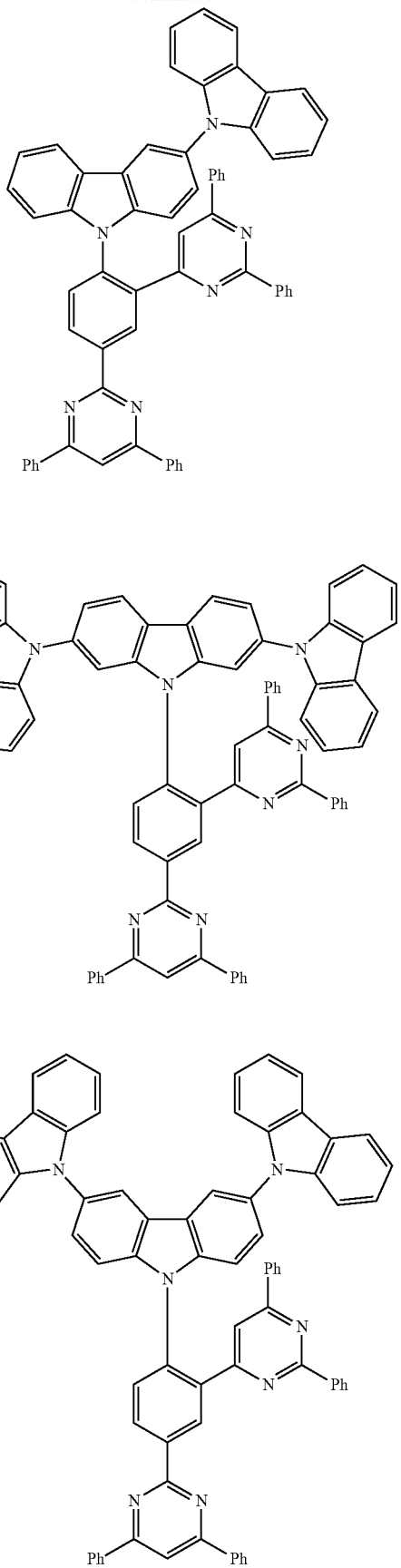

311
-continued
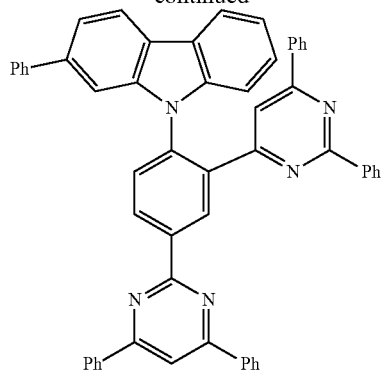
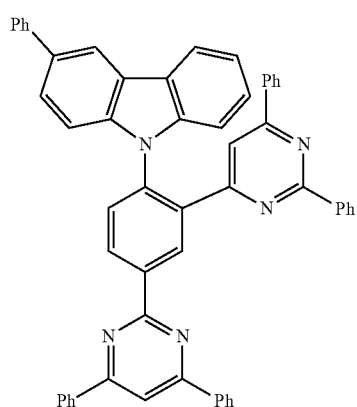
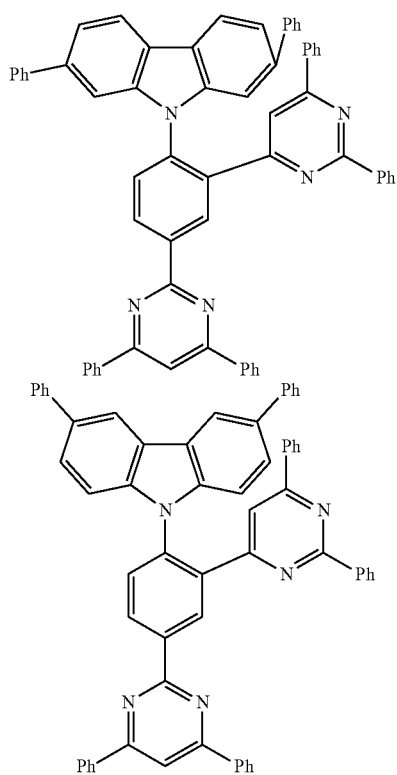
312
-continued
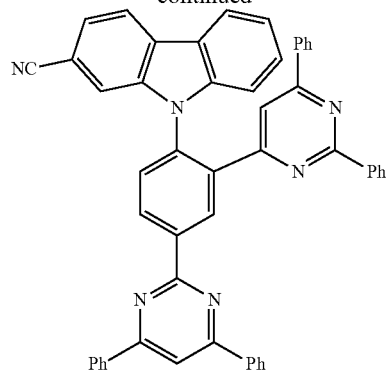
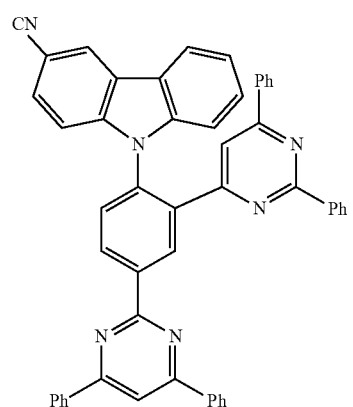
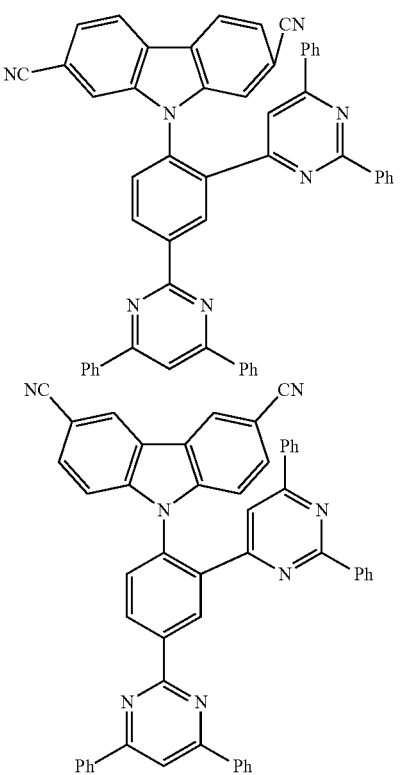

313
-continued
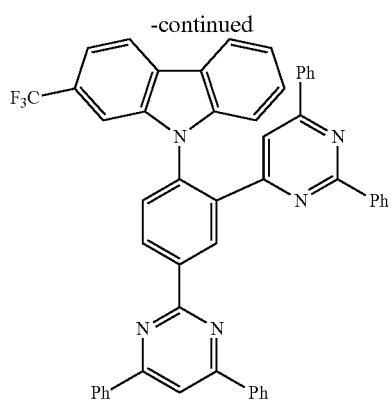
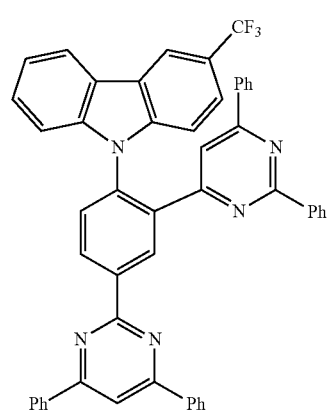
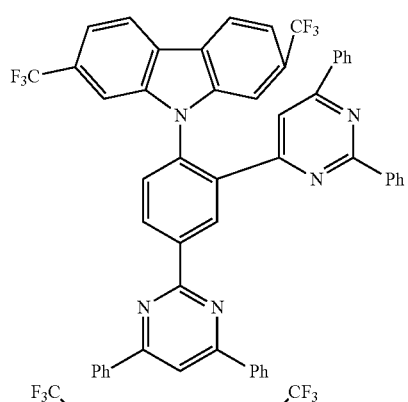
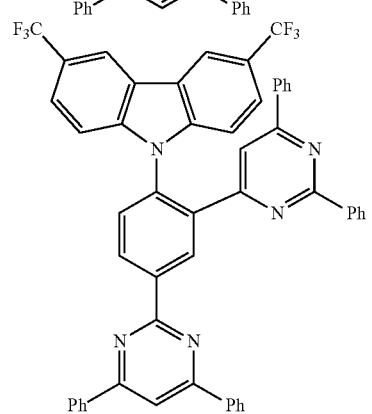
314
-continued
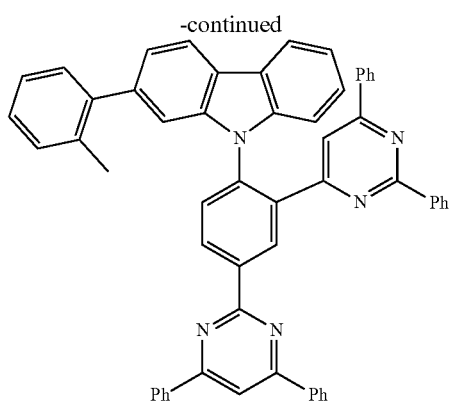
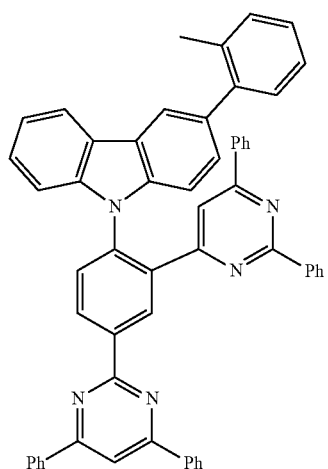
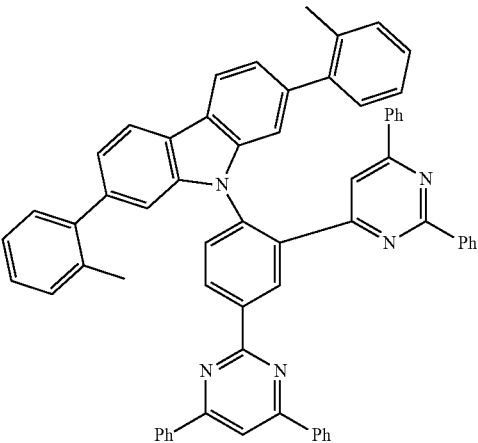

315
-continued
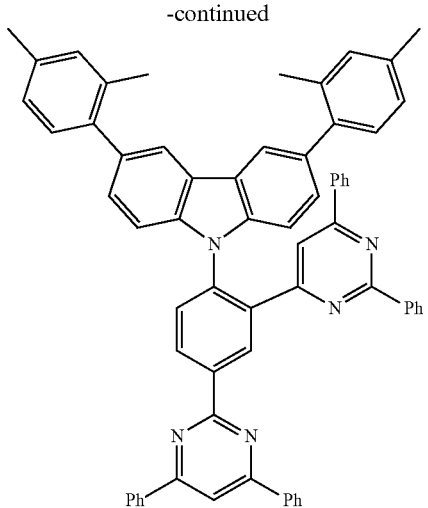
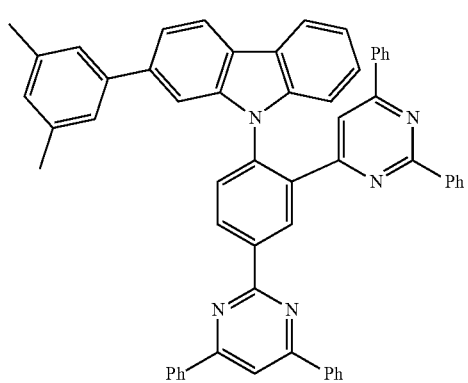
316
-continued
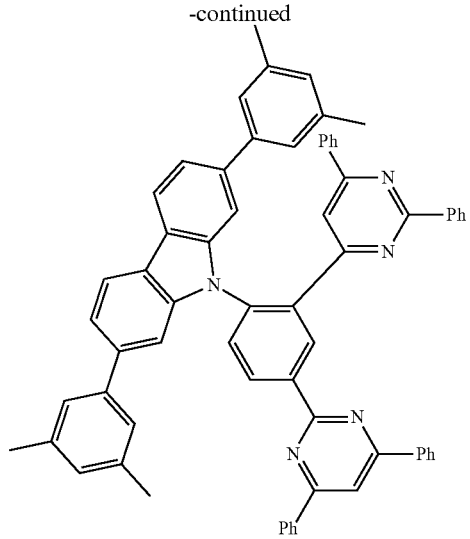
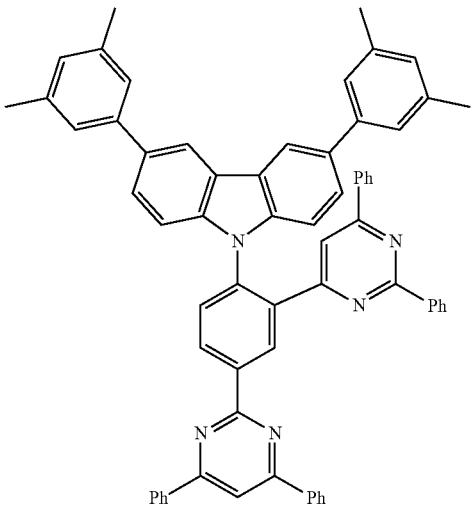
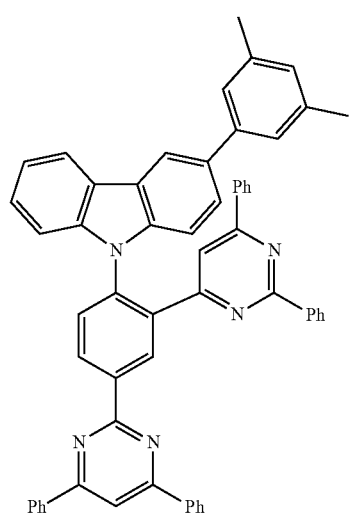
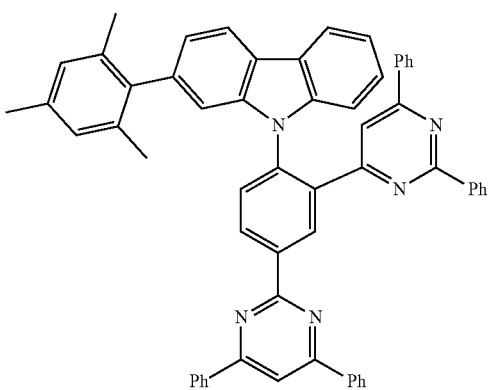

317
-continued
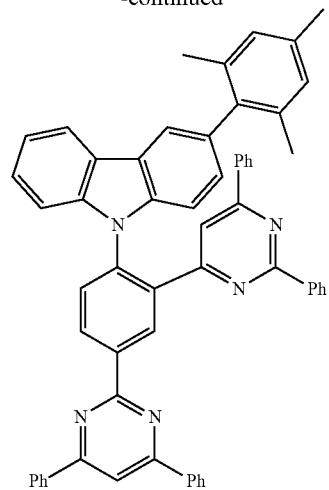
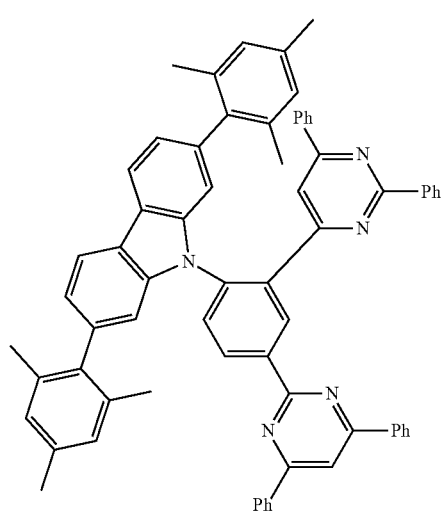
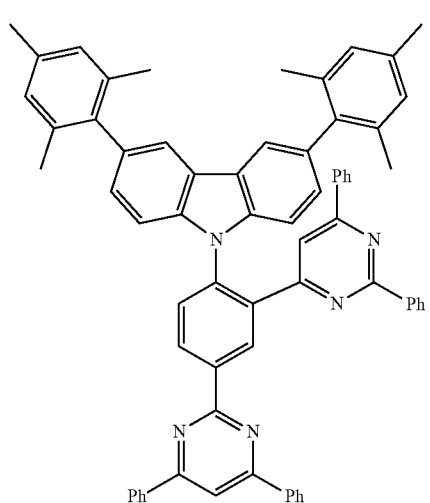
318
-continued
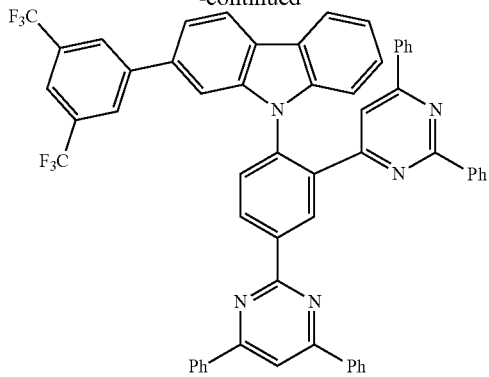
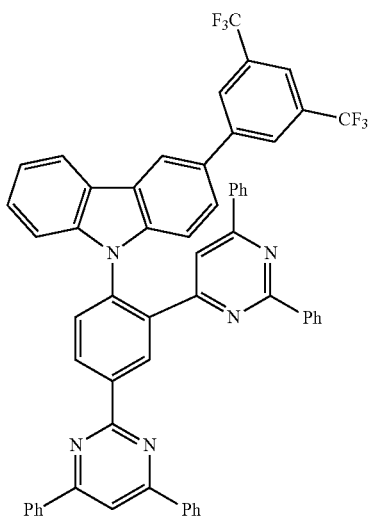
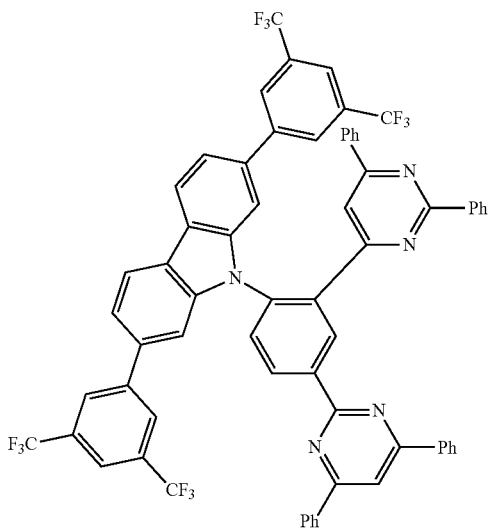

319
-continued
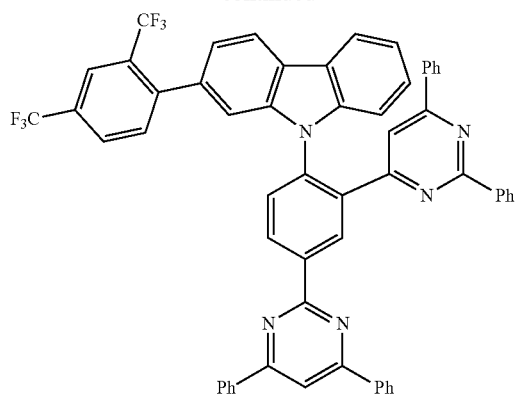
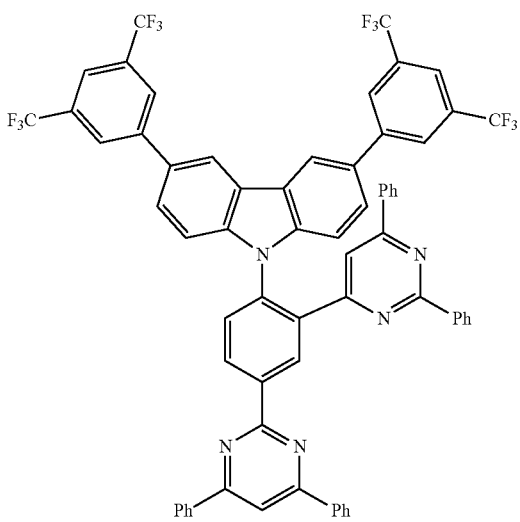
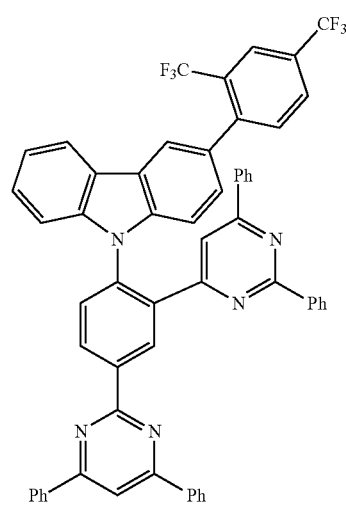
320
-continued
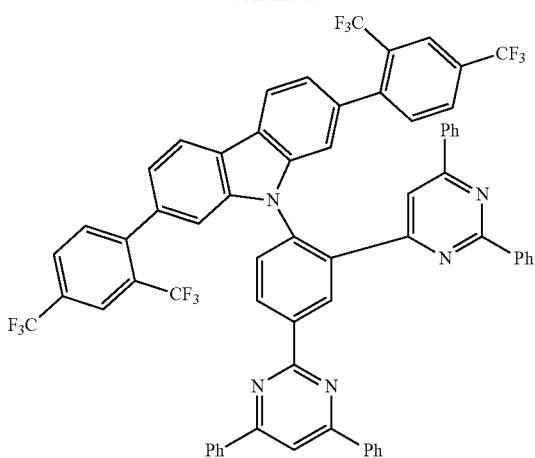
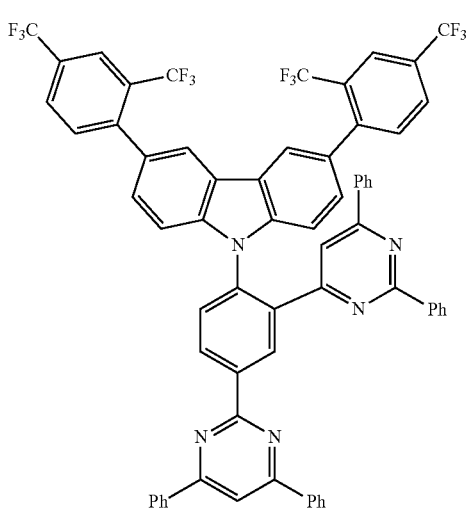
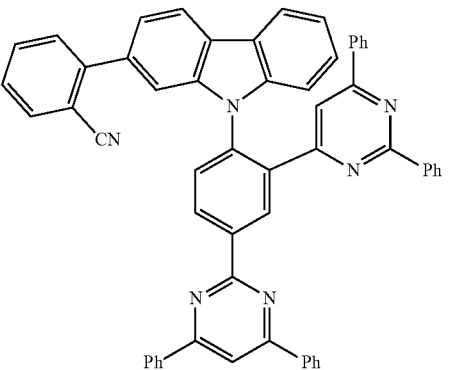

321
-continued
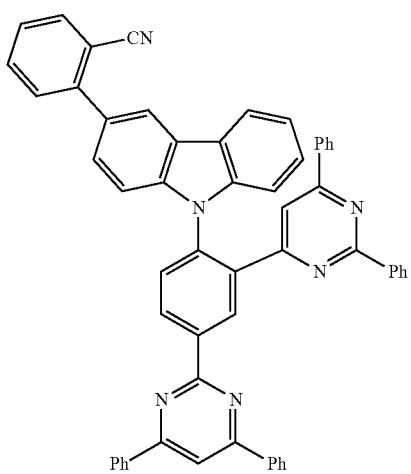
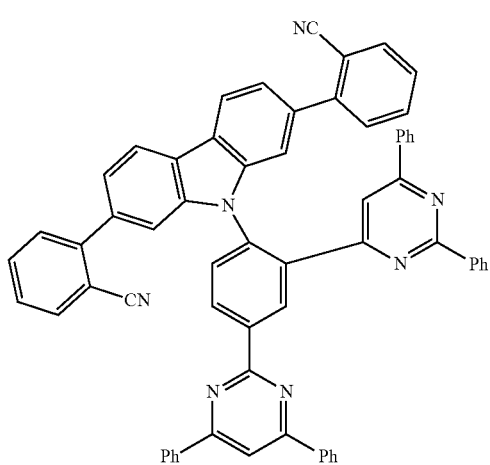
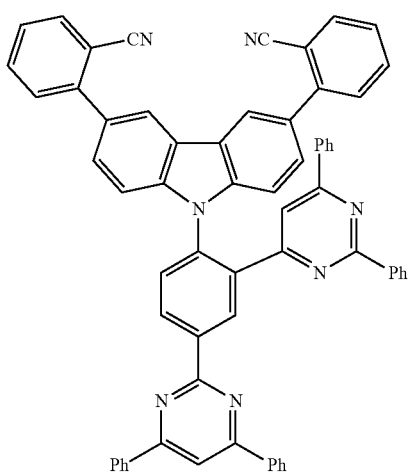
322
-continued
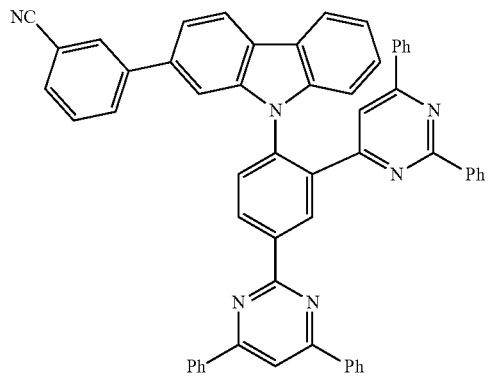
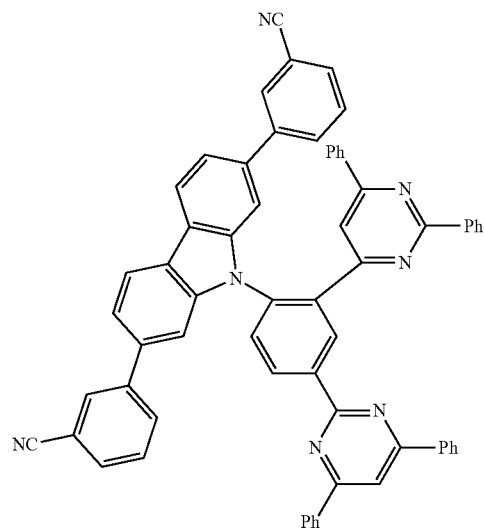

323
-continued
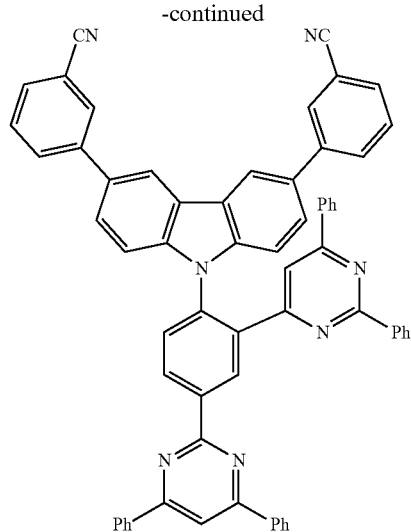
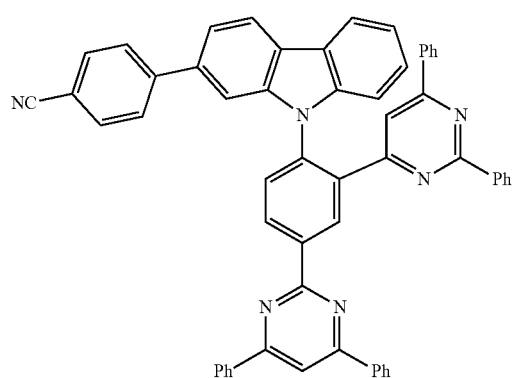
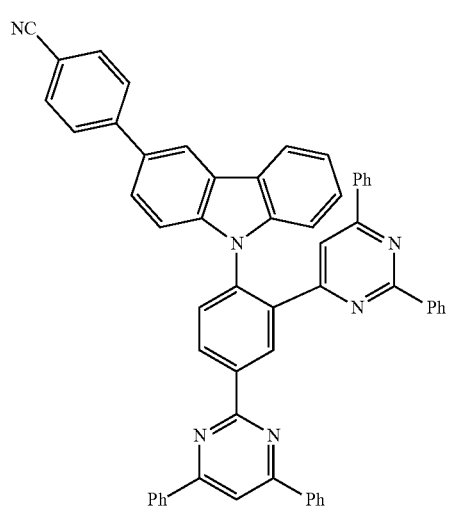
324
-continued
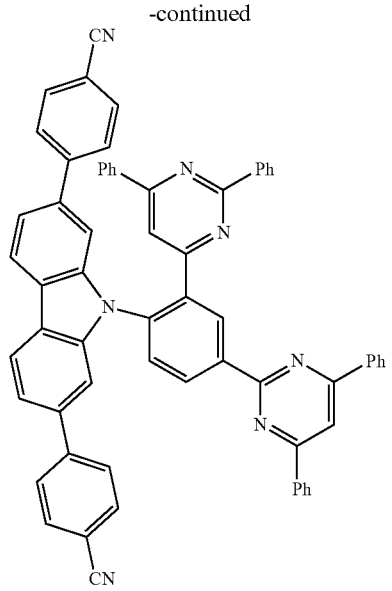
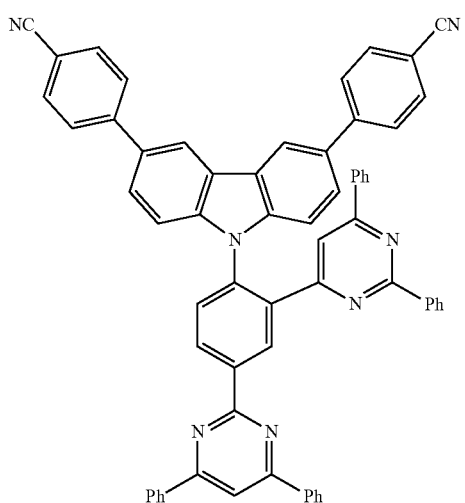 [SMILES: N#Cc1ccc(-c2ccc3c(c2)c2cc(-c4ccc(C#N)cc4)ccc2n3-c2ccc(-c3nc(-c4ccccc4)cc(-c4ccccc4)n3)cc2-c2cc(-c3ccccc3)nc(-c3ccccc3)n2)cc1]
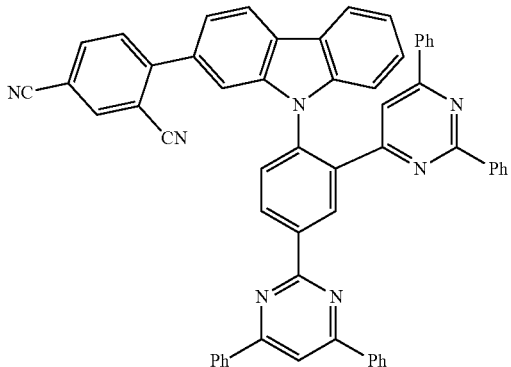

325
-continued
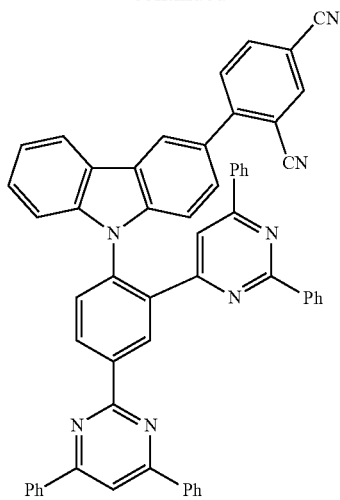
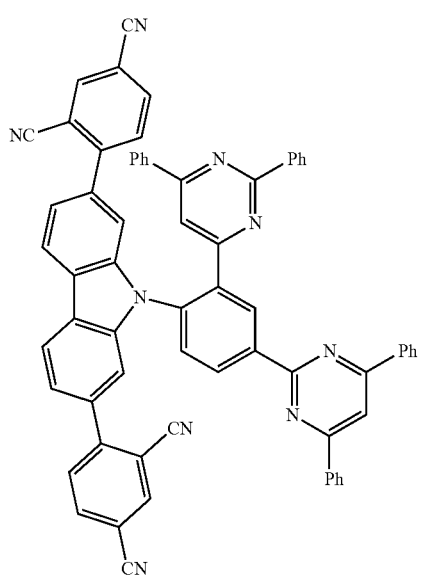
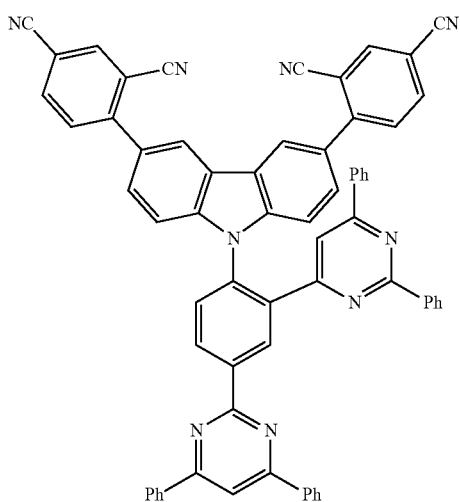 [SMILES: N#Cc1ccc(-c2ccc3c(c2)c2cc(-c4ccc(C#N)cc4C#N)ccc2n3-c2ccc(-c3nc(-c4ccccc4)cc(-c4ccccc4)n3)cc2-c2cc(-c3ccccc3)nc(-c3ccccc3)n2)c(C#N)c1]
326
-continued
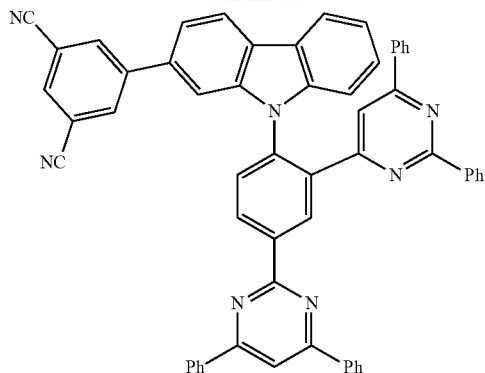
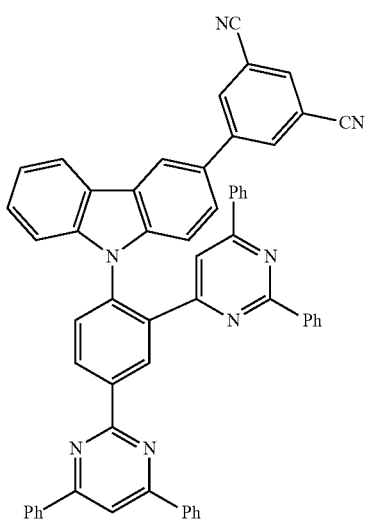
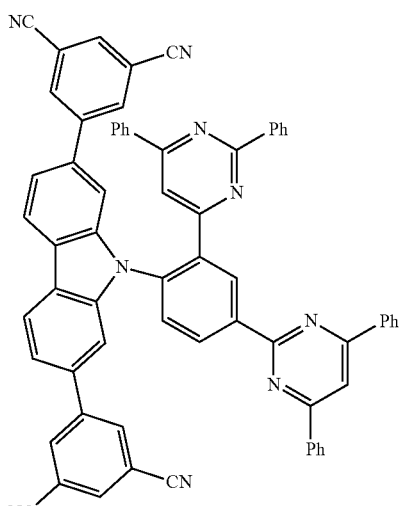

327
-continued
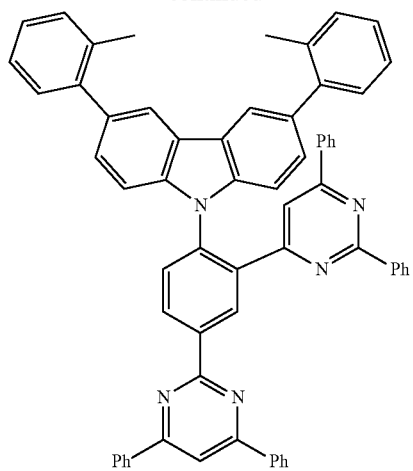
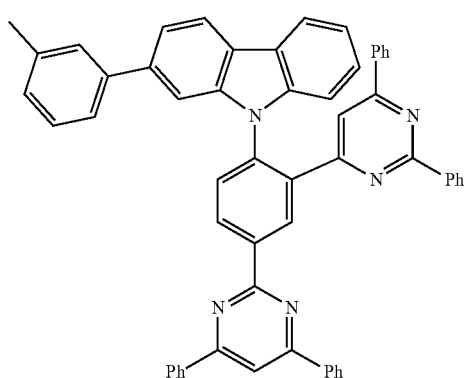
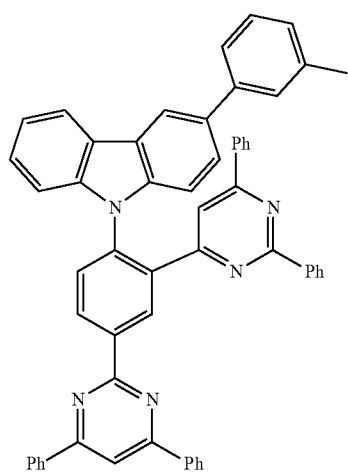
328
-continued
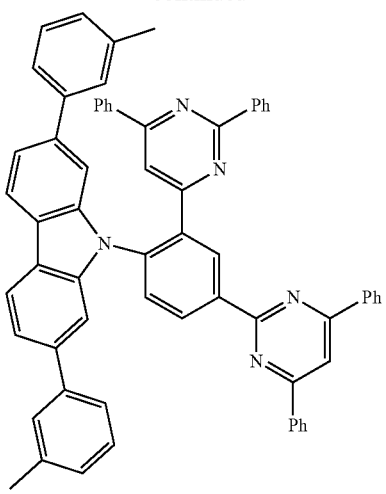
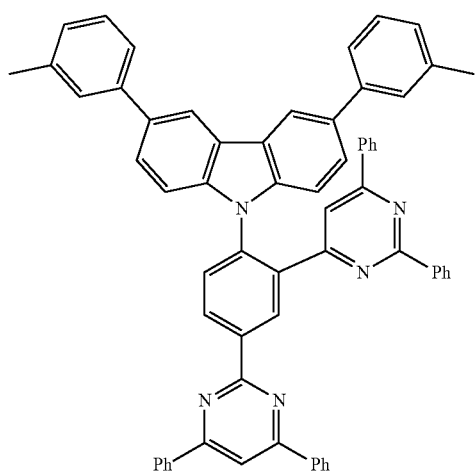
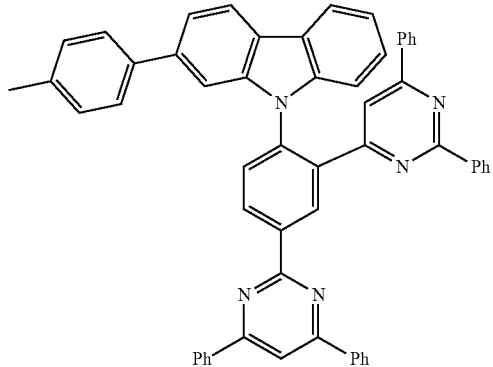

329
-continued
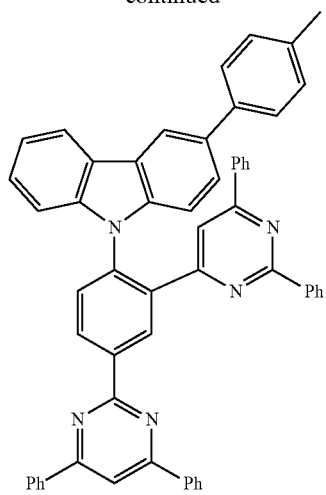
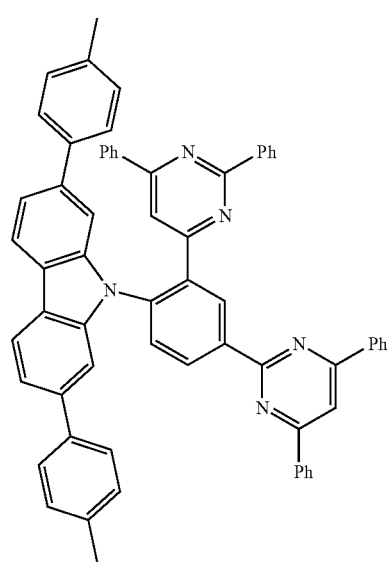
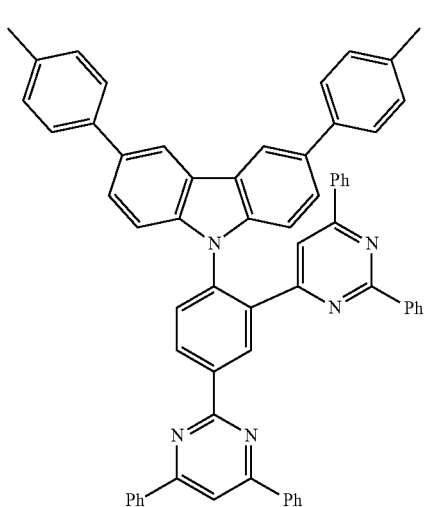
330
-continued
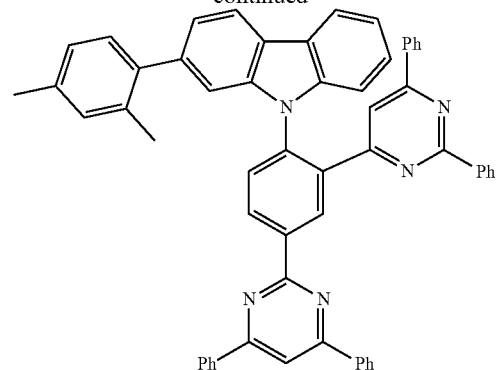
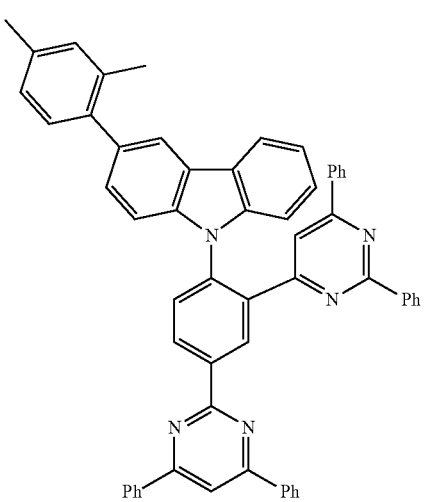
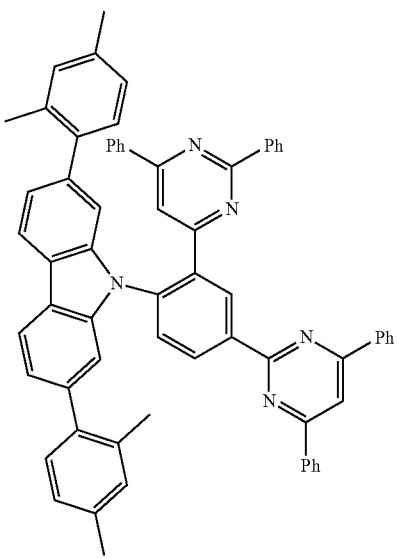

331
-continued
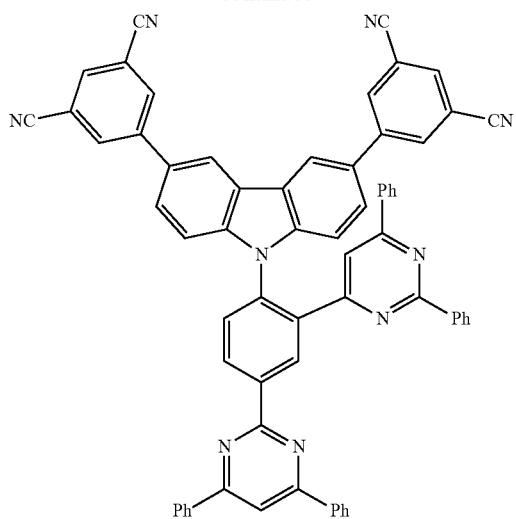 [SMILES: N#Cc1cc(C#N)cc(-c2ccc3c(c2)c2cc(-c4cc(C#N)cc(C#N)c4)ccc2n3-c2ccc(-c3nc(-c4ccccc4)cc(-c4ccccc4)n3)cc2-c2cc(-c3ccccc3)nc(-c3ccccc3)n2)c1]
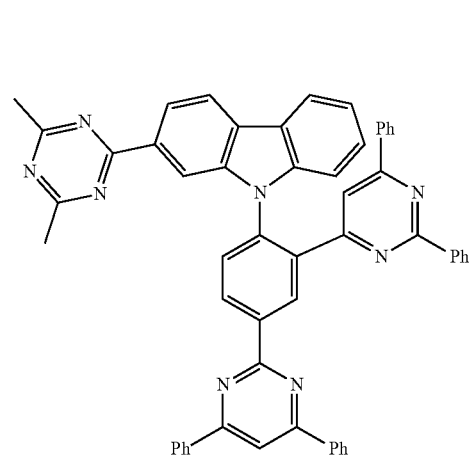
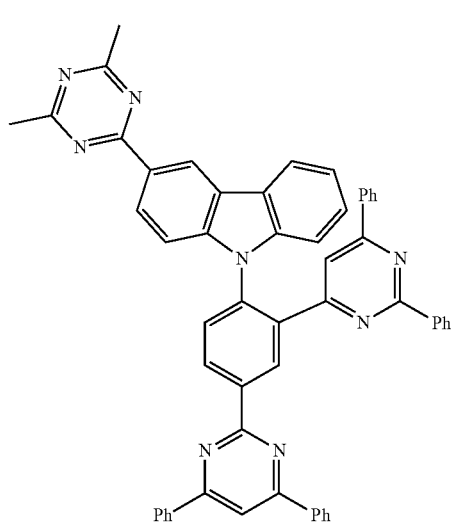
332
-continued
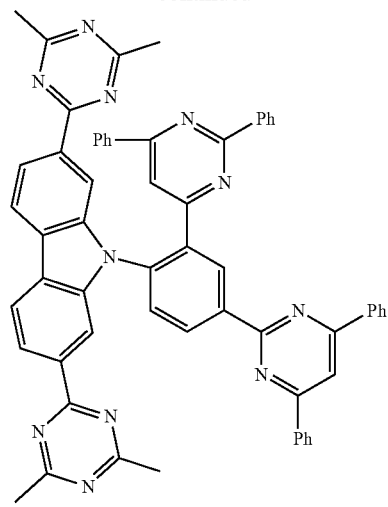
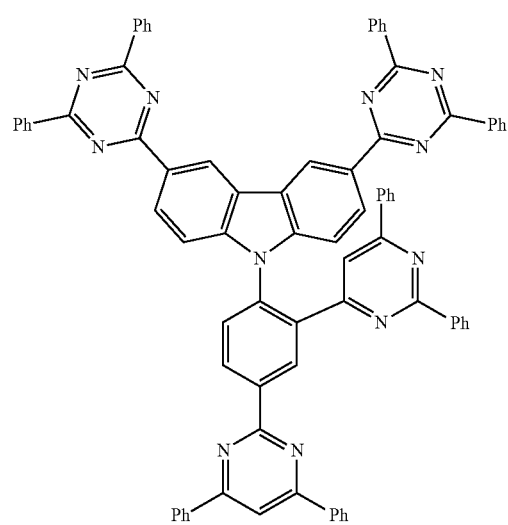 [SMILES: c1ccc(-c2cc(-c3ccccc3)nc(-c3ccc(-n4c5ccc(-c6nc(-c7ccccc7)nc(-c7ccccc7)n6)cc5c5cc(-c6nc(-c7ccccc7)nc(-c7ccccc7)n6)ccc54)c(-c4cc(-c5ccccc5)nc(-c5ccccc5)n4)c3)n2)cc1]
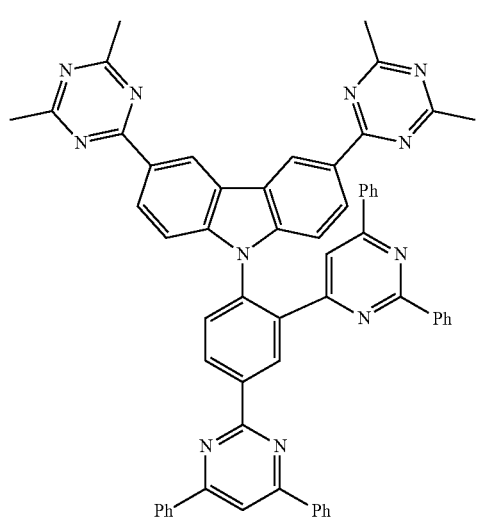

333
-continued
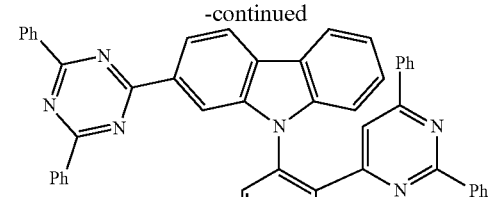
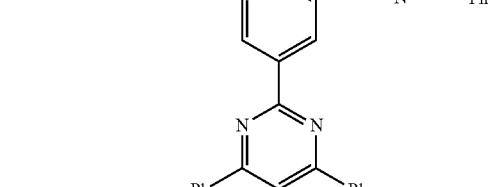
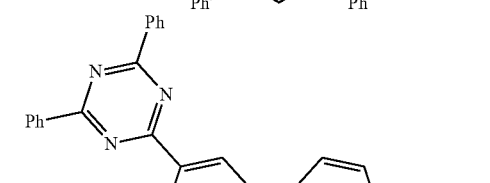
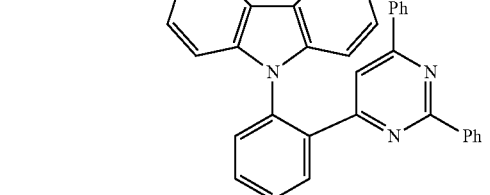
334
-continued
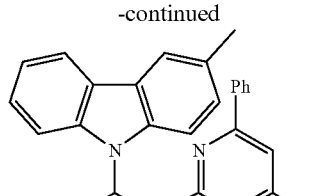
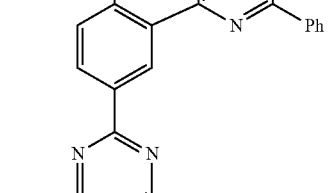
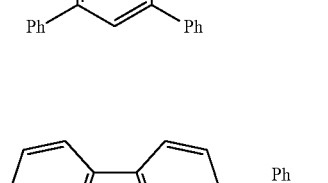
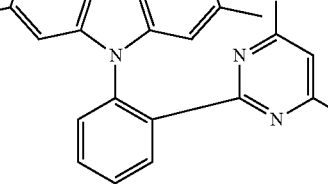

335
-continued
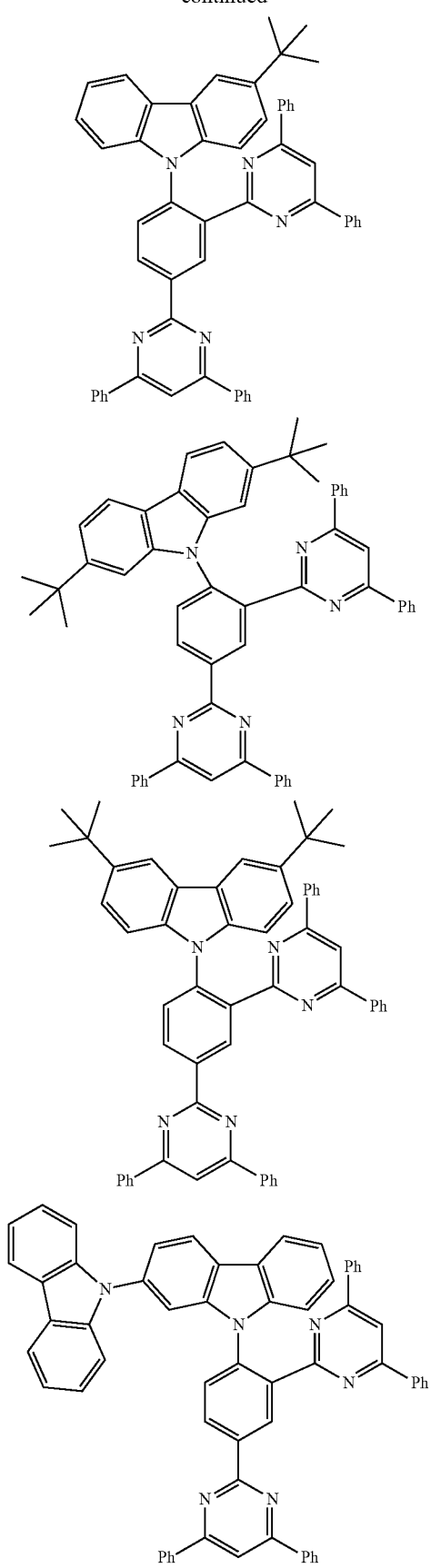
336
-continued
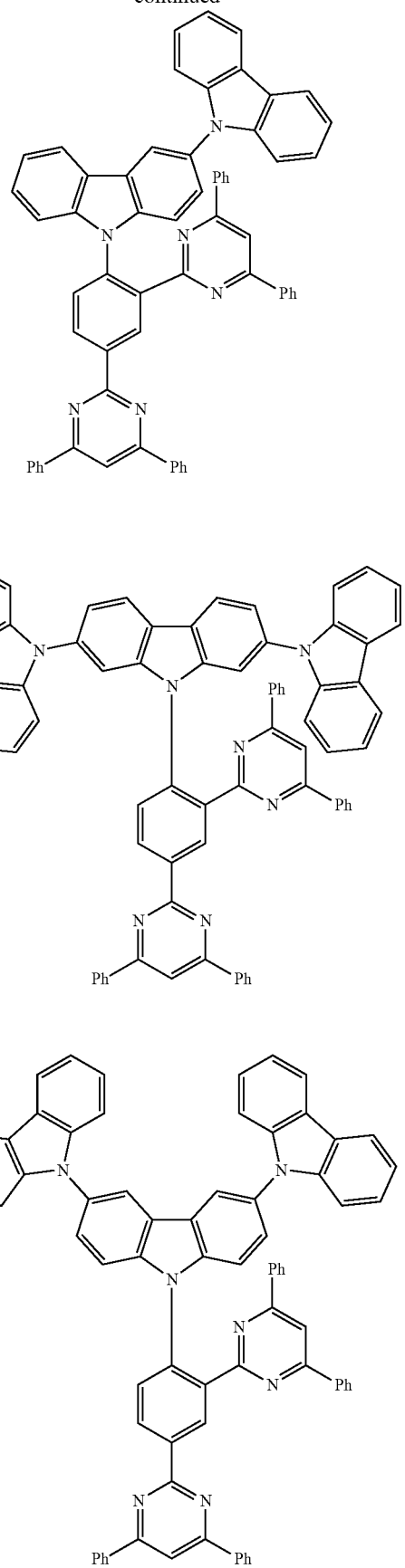

337
-continued
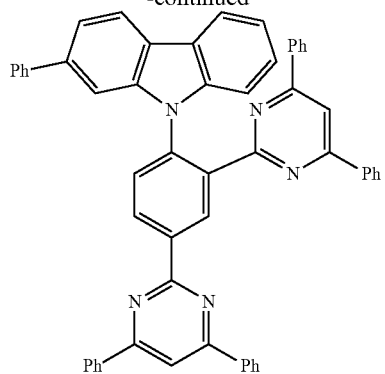
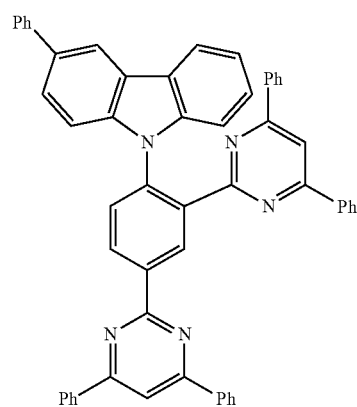
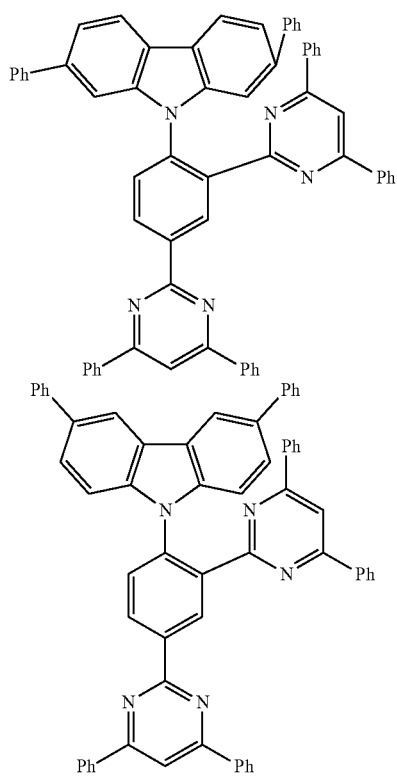
338
-continued
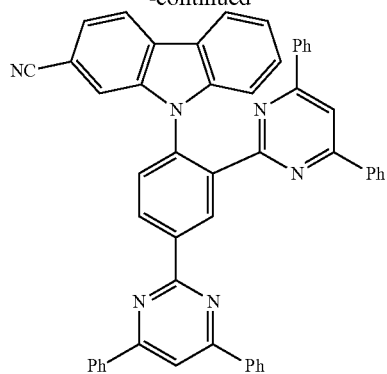
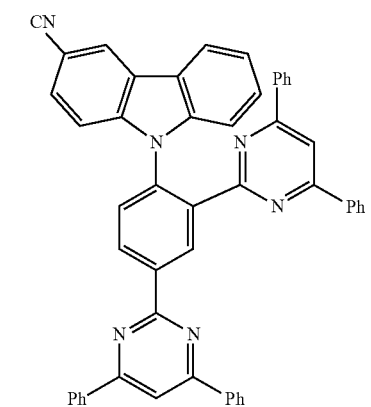
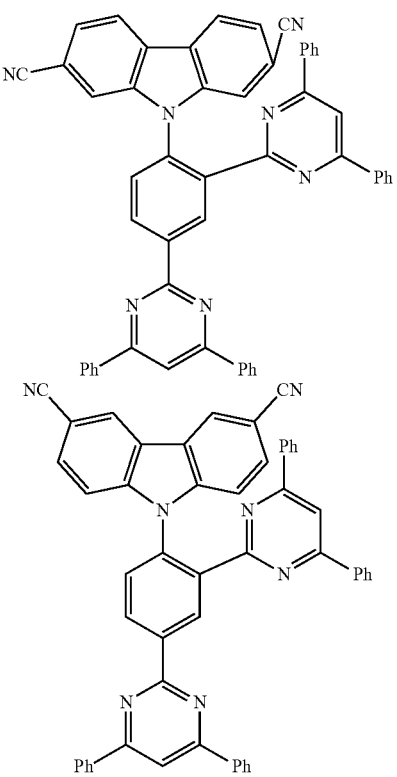

339
-continued
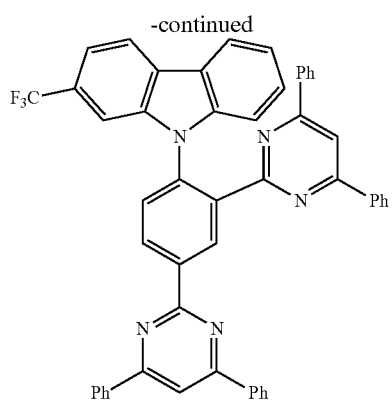
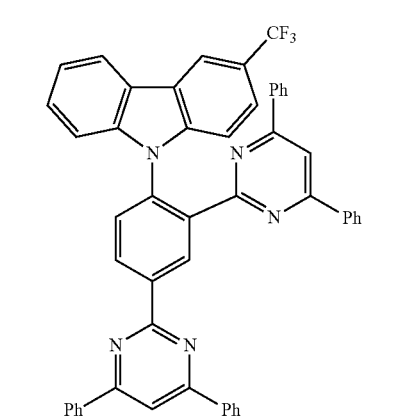
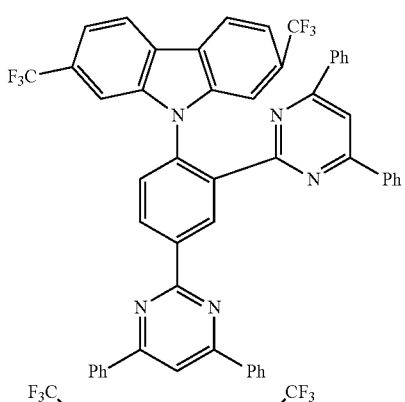
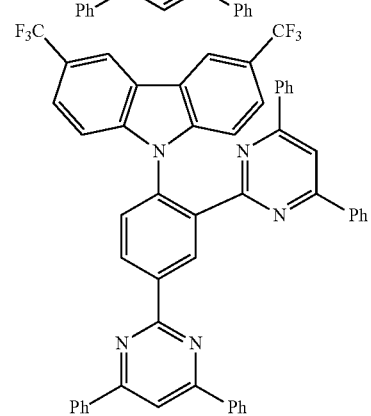
340
-continued
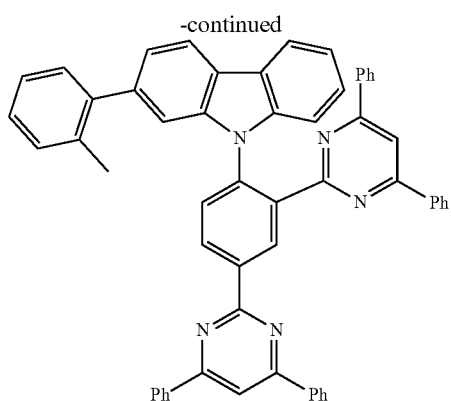
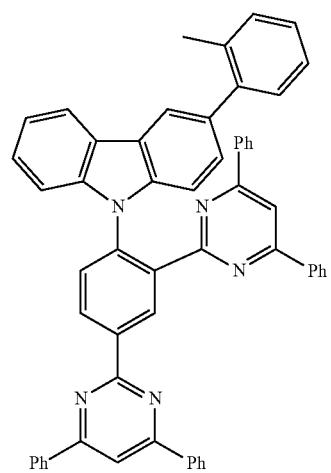
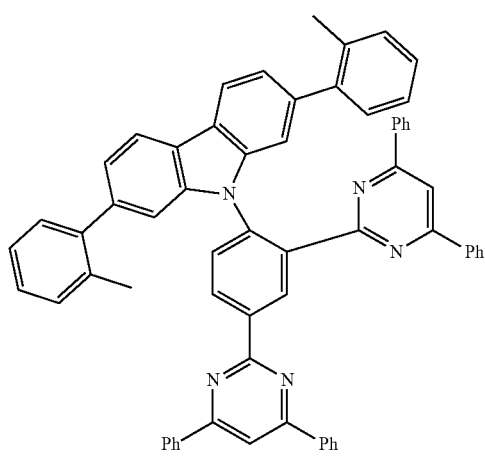

341
-continued
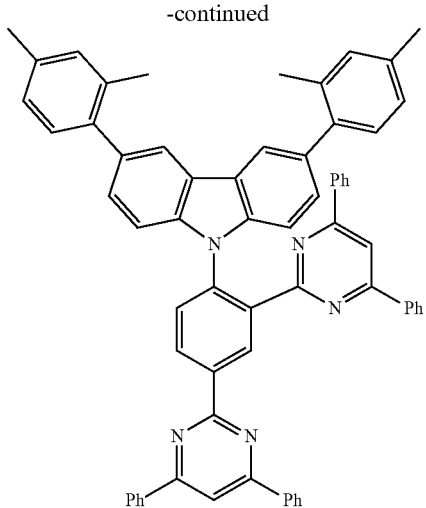
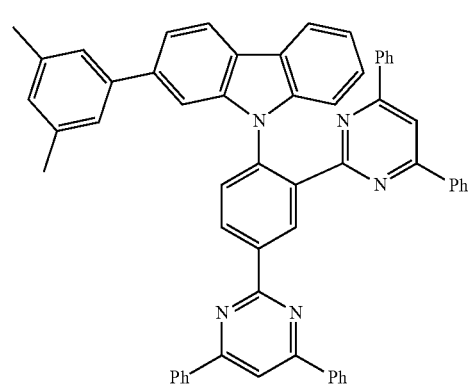
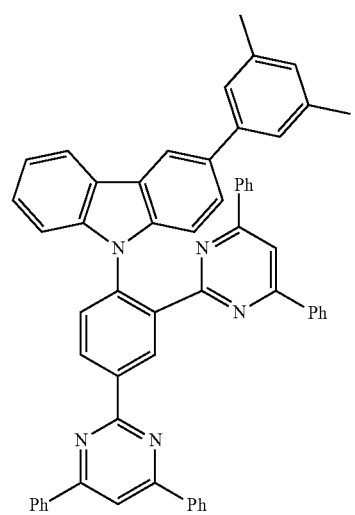
342
-continued
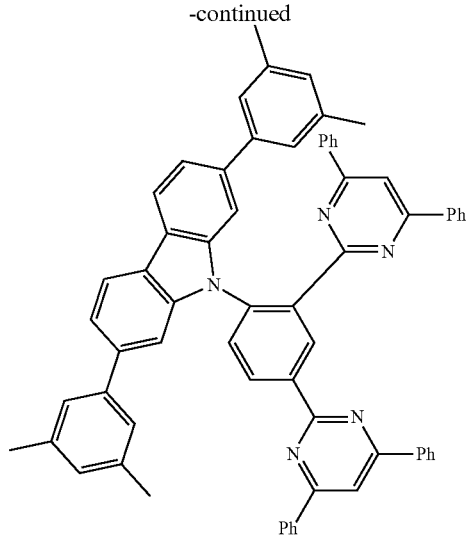
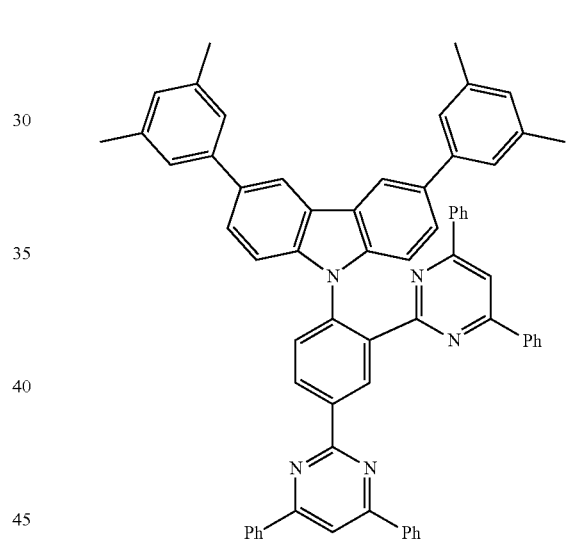
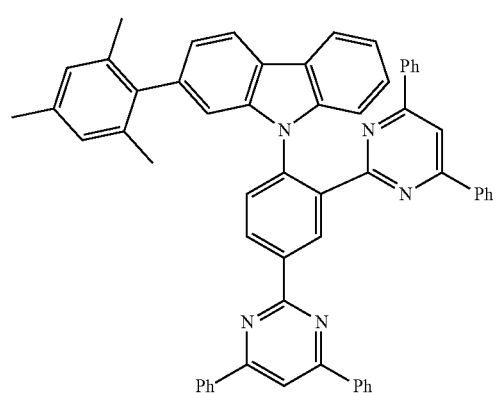

-continued
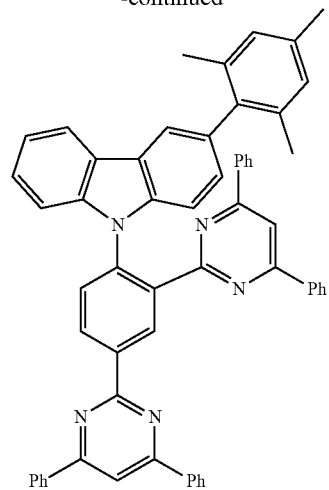
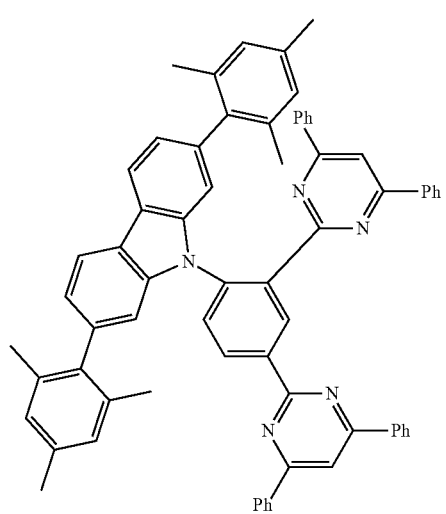
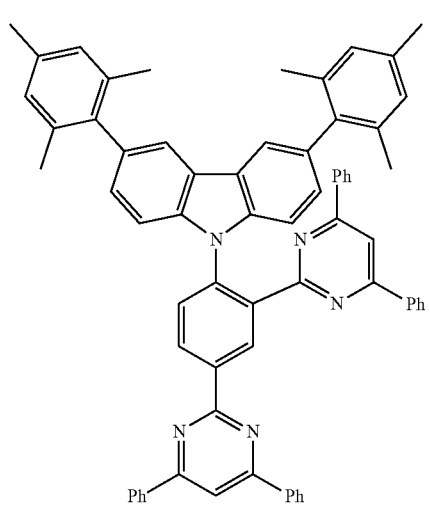
-continued
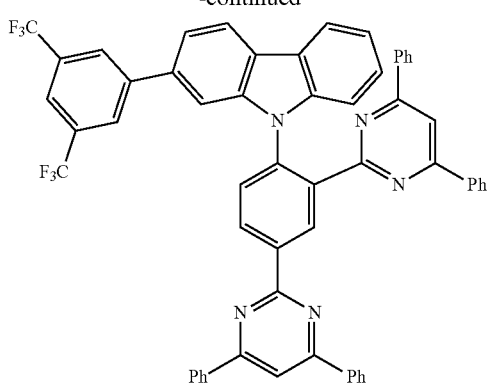
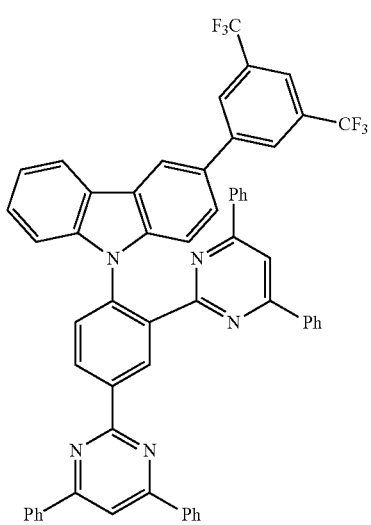
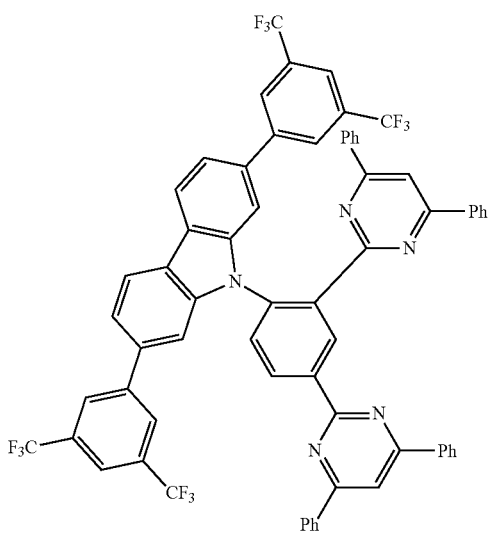

345
-continued
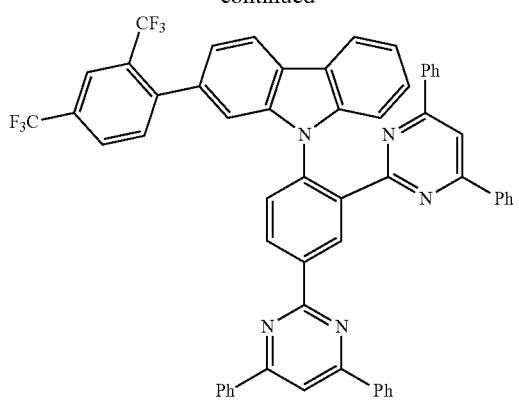
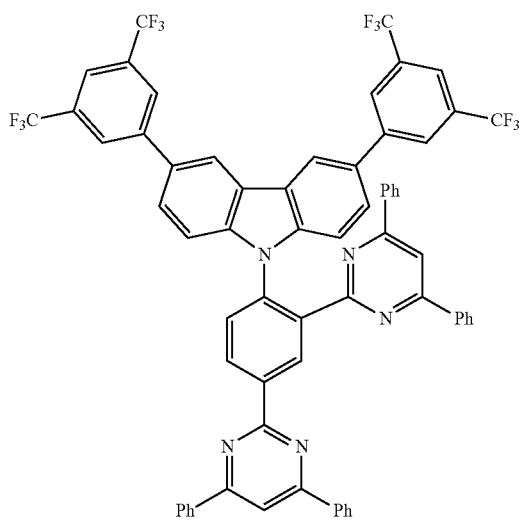
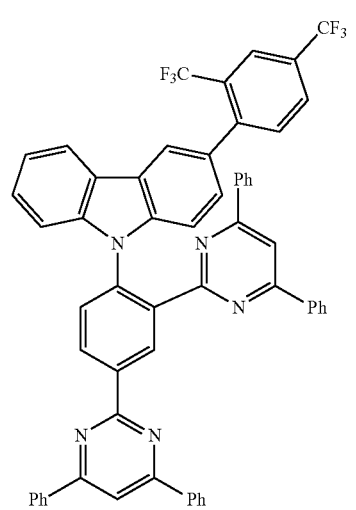
346
-continued
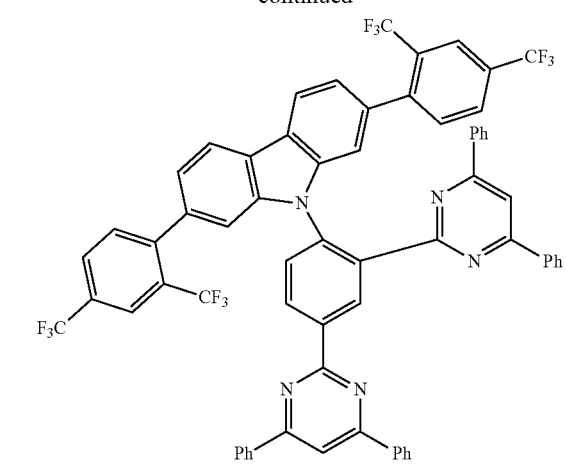
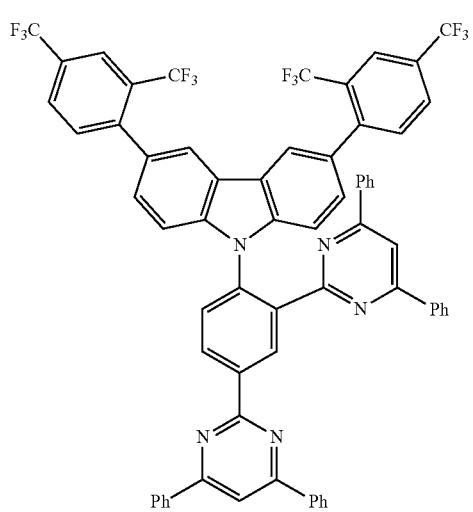
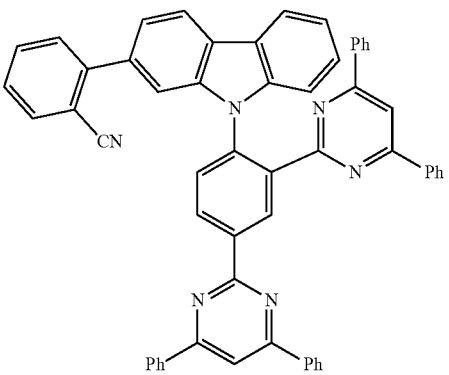

347
-continued
348
-continued
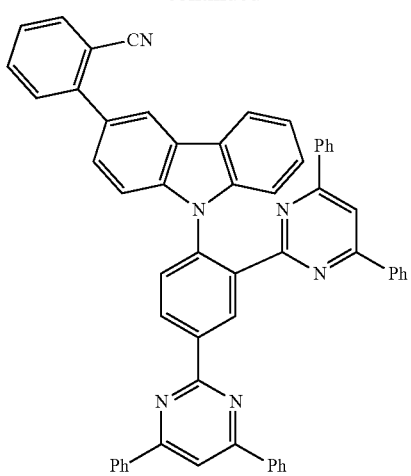
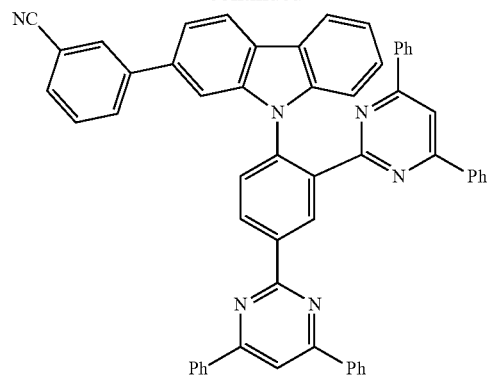
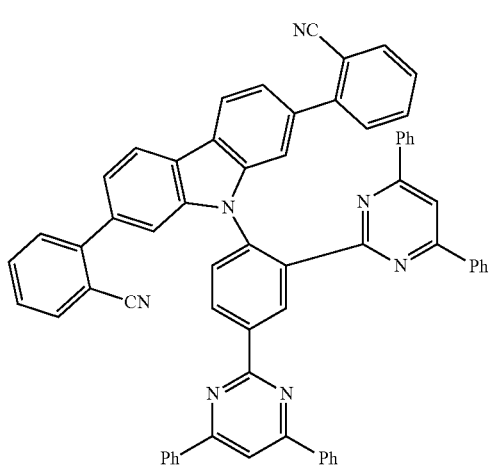
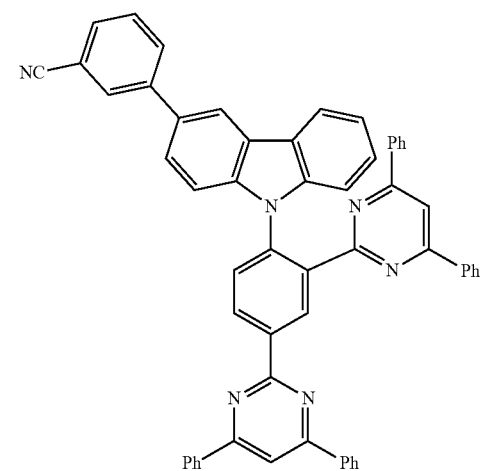
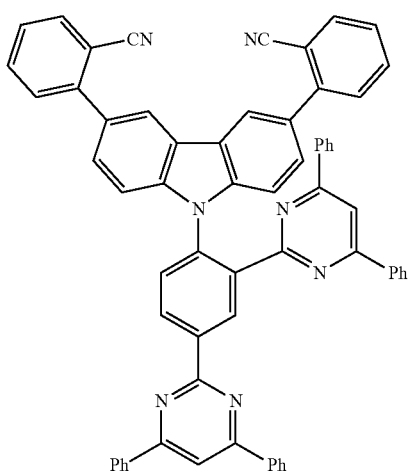
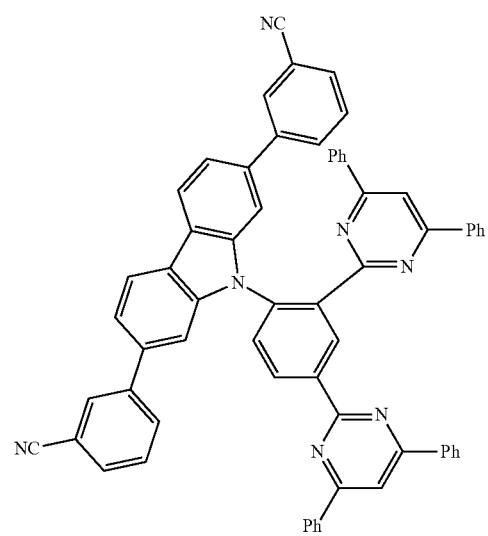

349
-continued
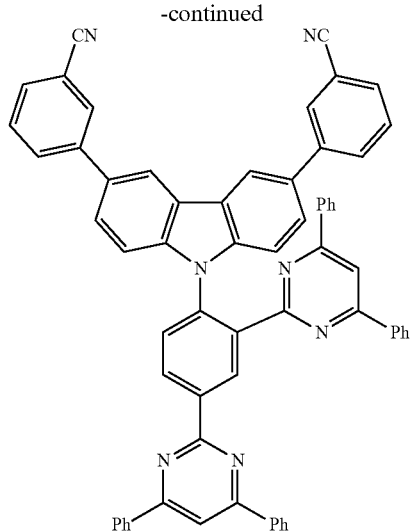
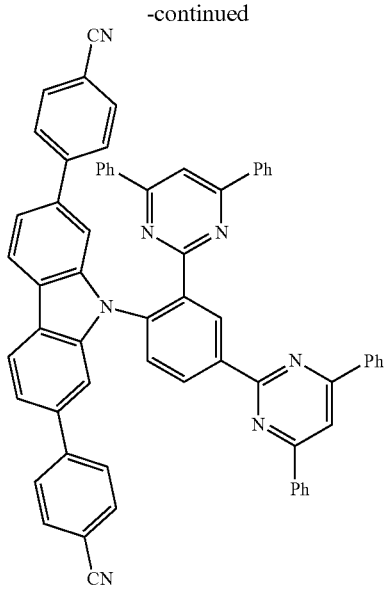
350
-continued
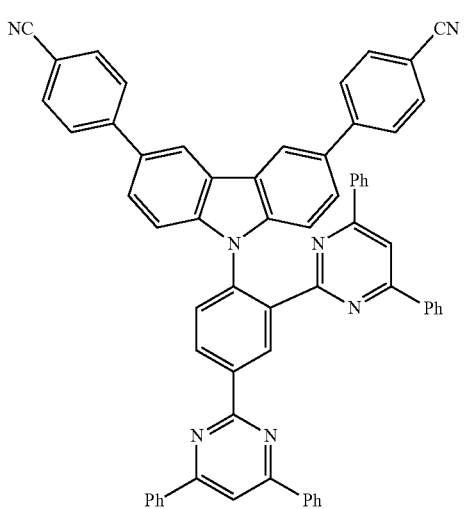 [SMILES: N#Cc1ccc(-c2ccc3c(c2)c2cc(-c4ccc(C#N)cc4)ccc2n3-c2ccc(-c3nc(-c4ccccc4)cc(-c4ccccc4)n3)cc2-c2nc(-c3ccccc3)cc(-c3ccccc3)n2)cc1]
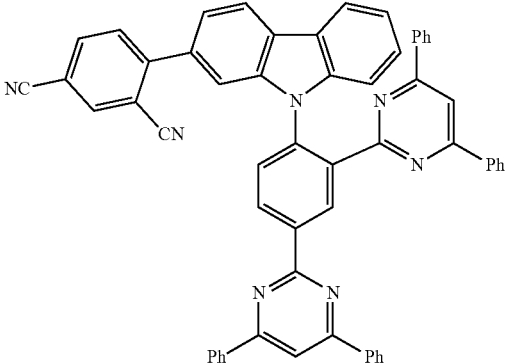

351
-continued
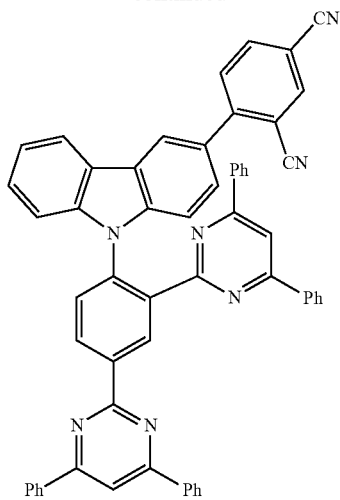
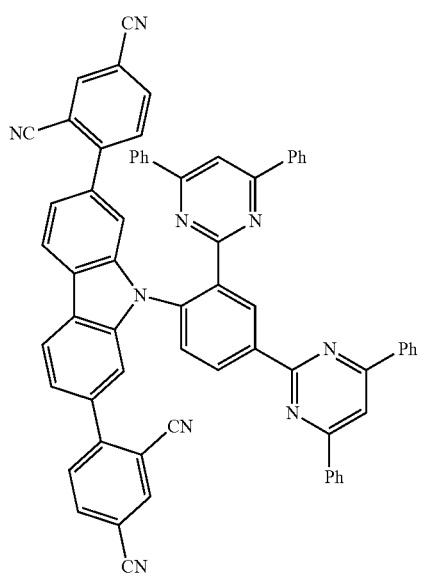
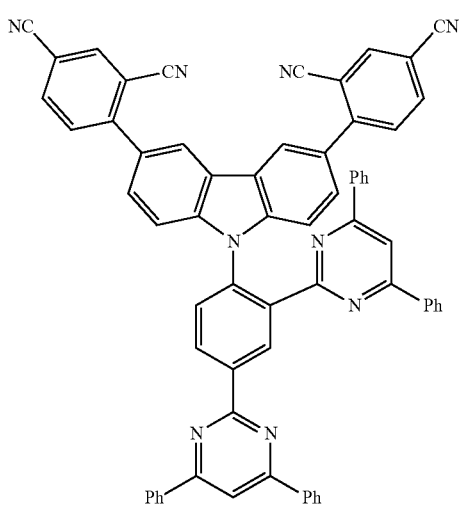 [SMILES: N#Cc1ccc(-c2ccc3c(c2)c2cc(-c4ccc(C#N)cc4C#N)ccc2n3-c2ccc(-c3nc(-c4ccccc4)cc(-c4ccccc4)n3)cc2-c2nc(-c3ccccc3)cc(-c3ccccc3)n2)c(C#N)c1]
352
-continued
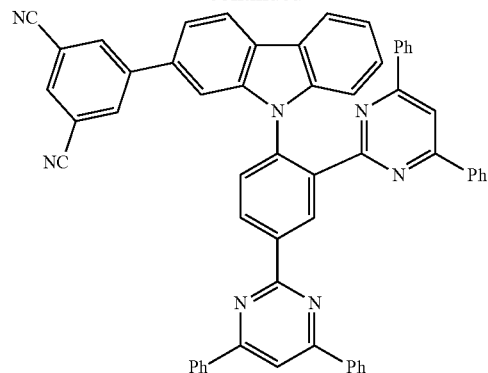
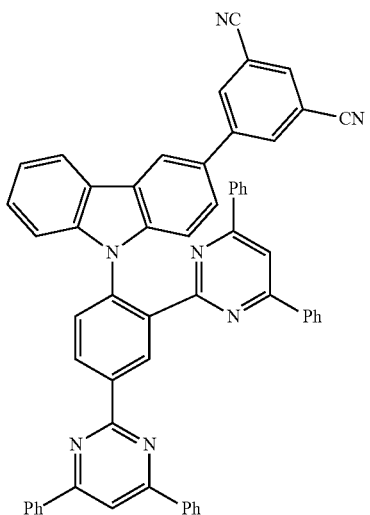
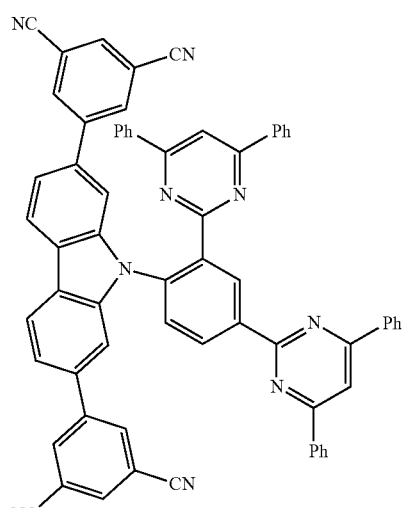

353
-continued
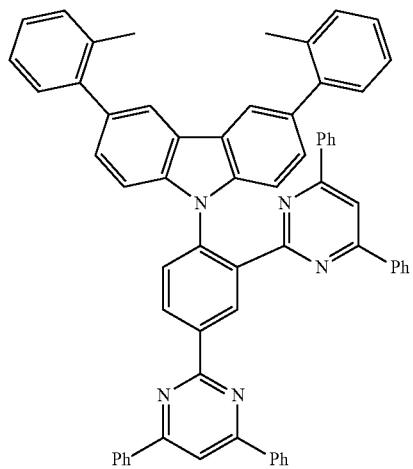 [SMILES: Cc1ccccc1-c1ccc2c(c1)c1cc(-c3ccccc3C)ccc1n2-c1ccc(-c2nc(-c3ccccc3)cc(-c3ccccc3)n2)cc1-c1nc(-c2ccccc2)cc(-c2ccccc2)n1]
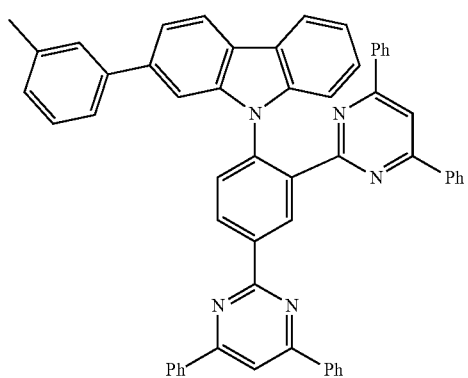
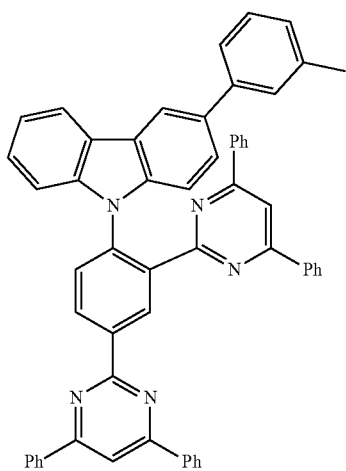
354
-continued
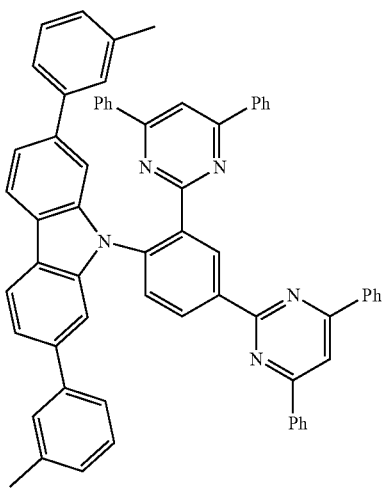
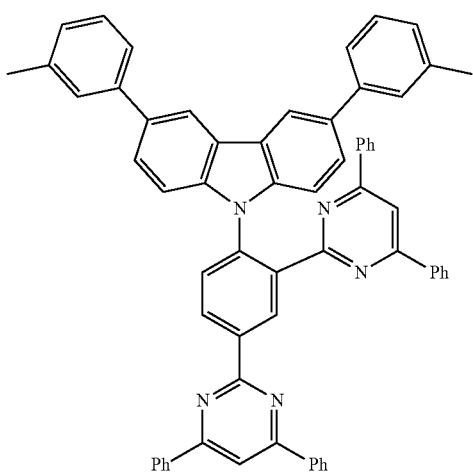
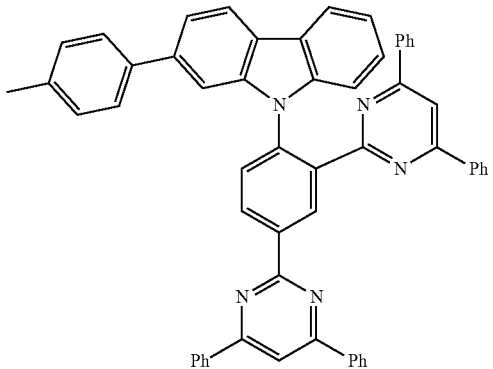

355
-continued
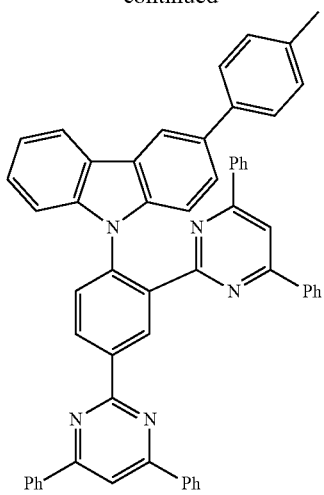
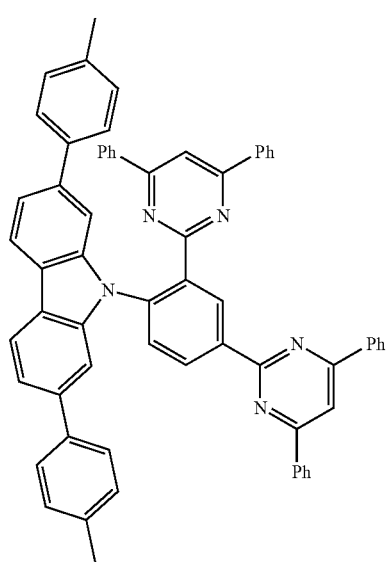
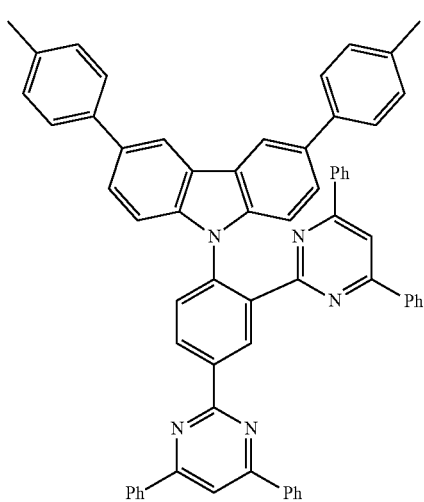
356
-continued
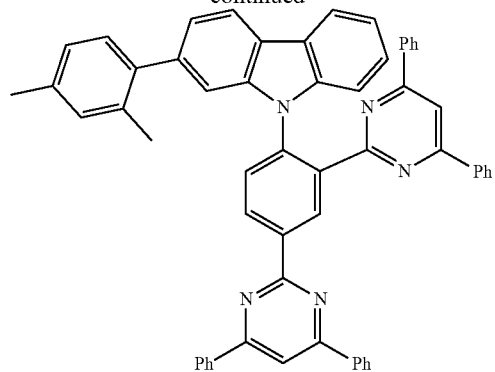
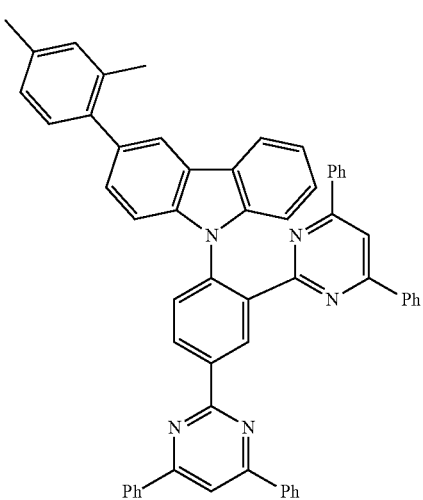
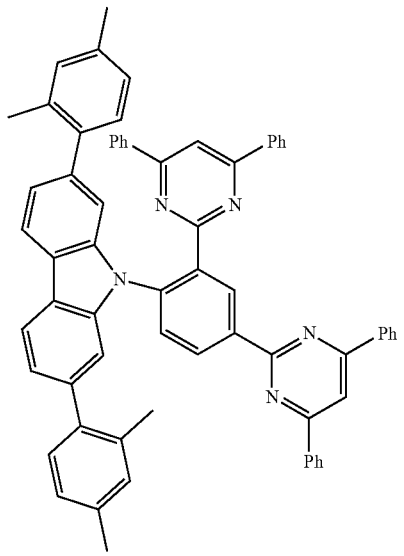

357
-continued
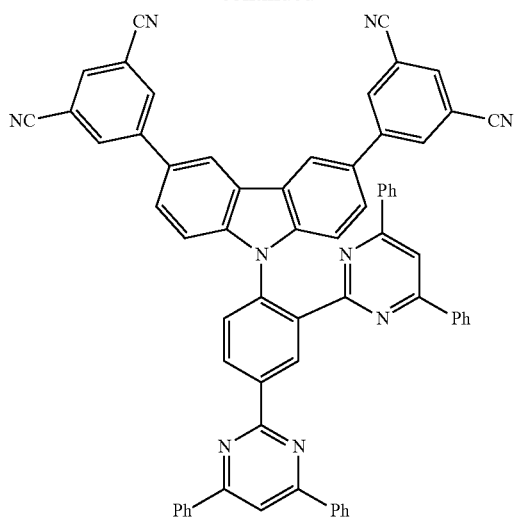 [SMILES: N#Cc1cc(C#N)cc(-c2ccc3c(c2)c2cc(-c4cc(C#N)cc(C#N)c4)ccc2n3-c2ccc(-c3nc(-c4ccccc4)cc(-c4ccccc4)n3)cc2-c2nc(-c3ccccc3)cc(-c3ccccc3)n2)c1]
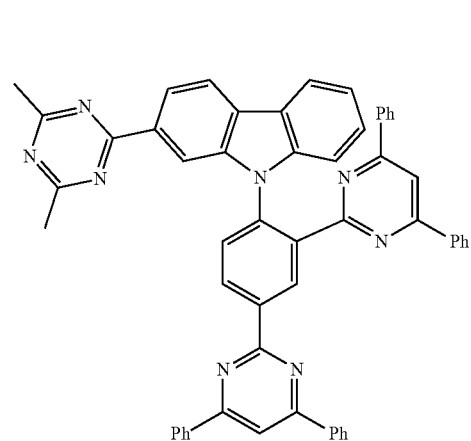
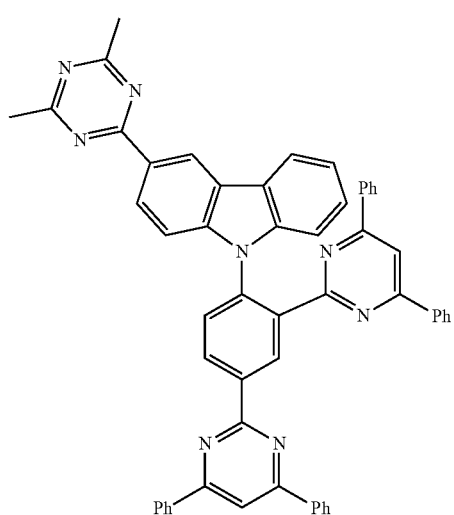
358
-continued
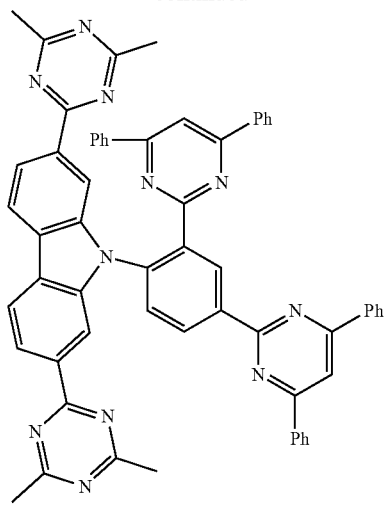
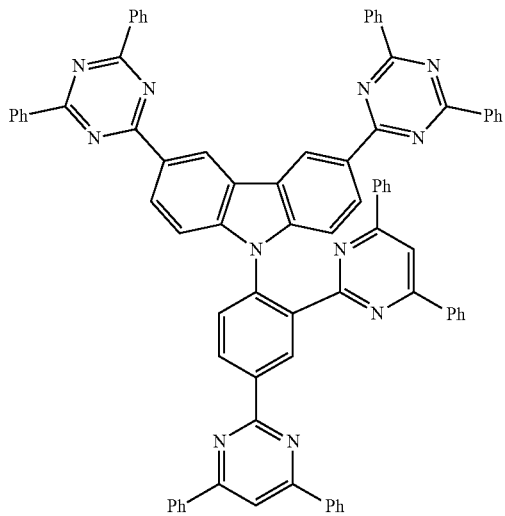 [SMILES: c1ccc(-c2cc(-c3ccccc3)nc(-c3ccc(-n4c5ccc(-c6nc(-c7ccccc7)nc(-c7ccccc7)n6)cc5c5cc(-c6nc(-c7ccccc7)nc(-c7ccccc7)n6)ccc54)c(-c4nc(-c5ccccc5)cc(-c5ccccc5)n4)c3)n2)cc1]
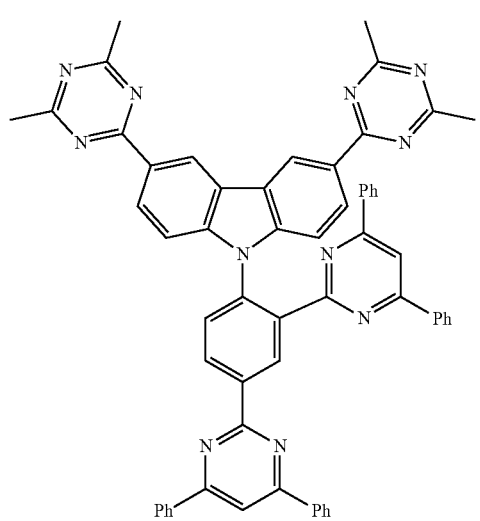

359
-continued
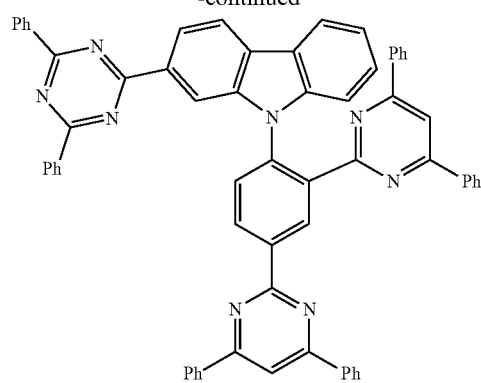
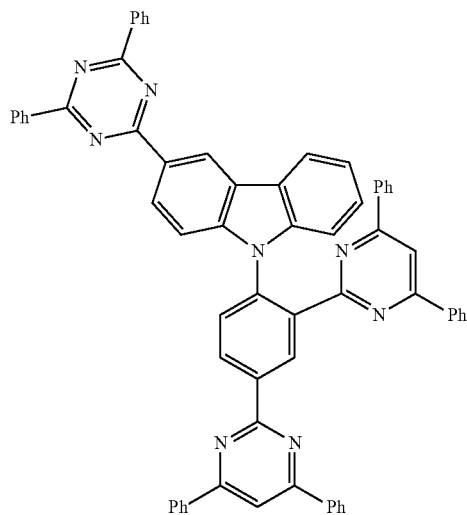
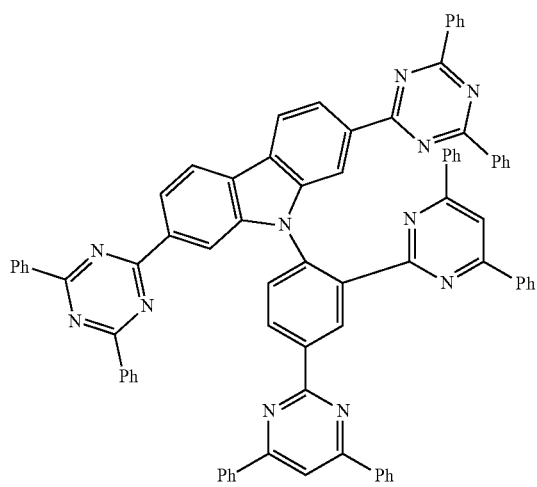 [SMILES: c1ccc(-c2cc(-c3ccccc3)nc(-c3ccc(-n4c5cc(-c6nc(-c7ccccc7)nc(-c7ccccc7)n6)ccc5c5ccc(-c6nc(-c7ccccc7)nc(-c7ccccc7)n6)cc54)c(-c4nc(-c5ccccc5)cc(-c5ccccc5)n4)c3)n2)cc1]
360
-continued
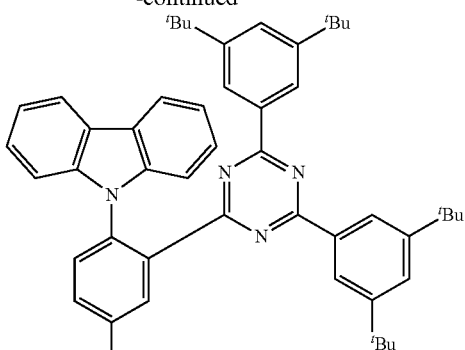
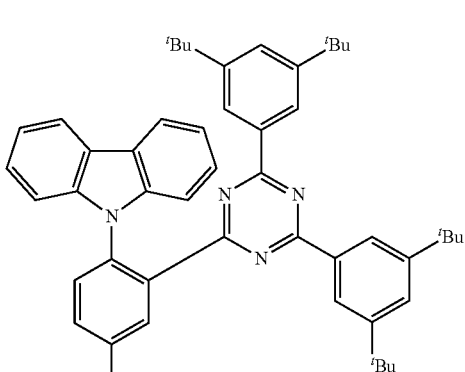
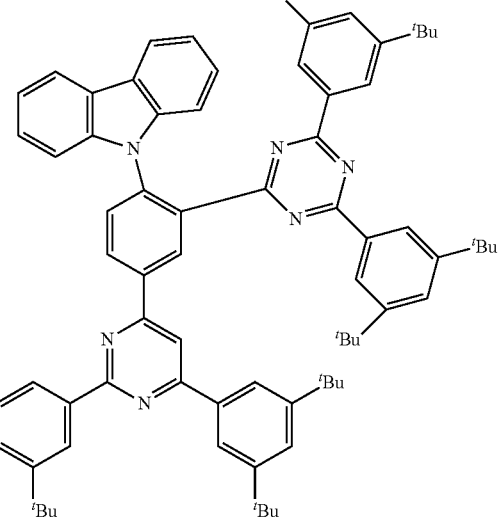

361
-continued
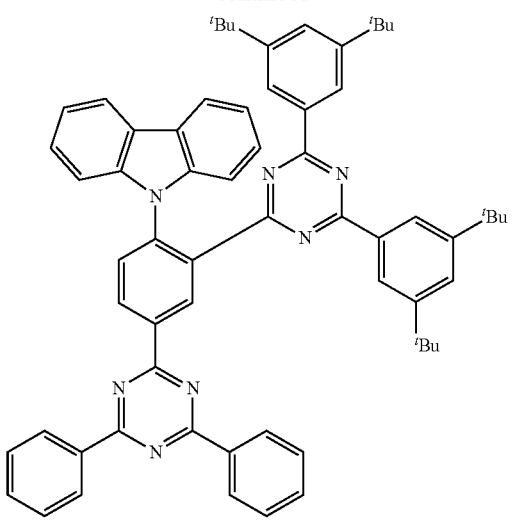
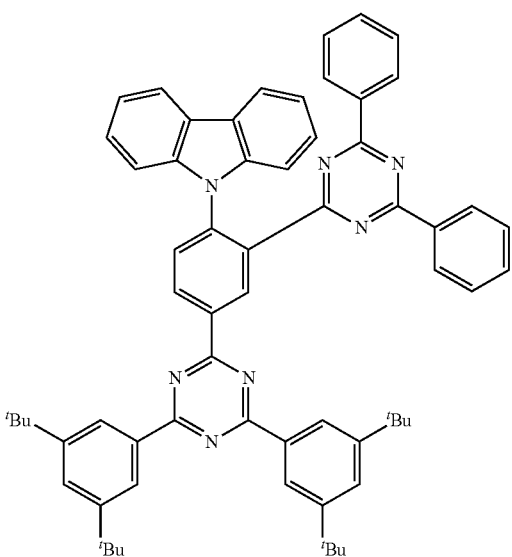
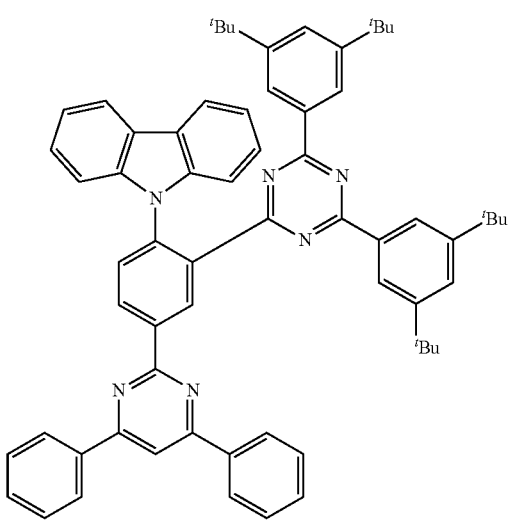
362
-continued
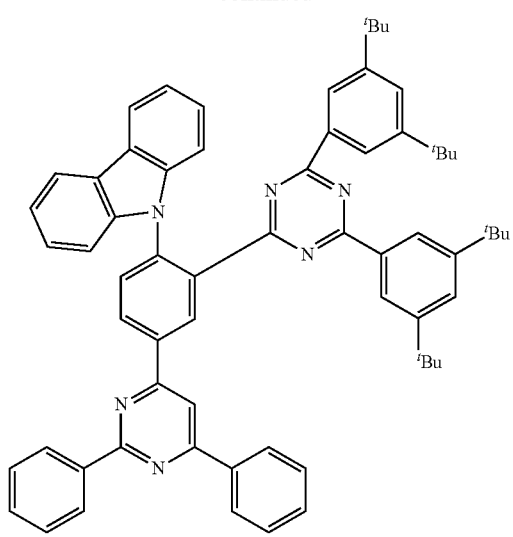
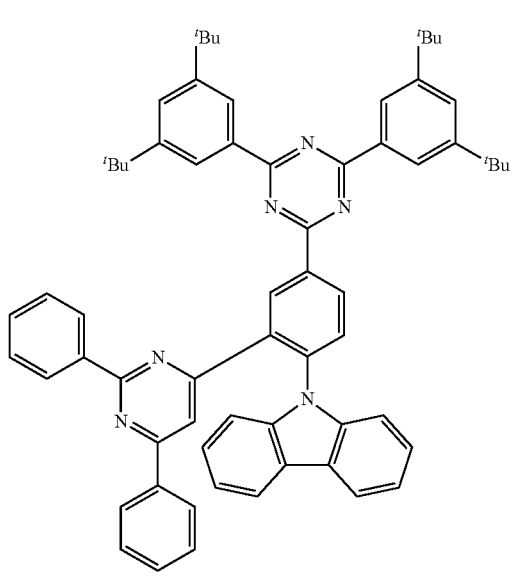
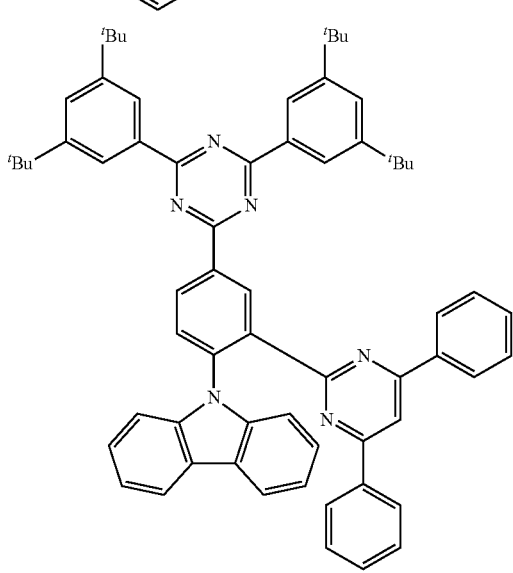

363
-continued
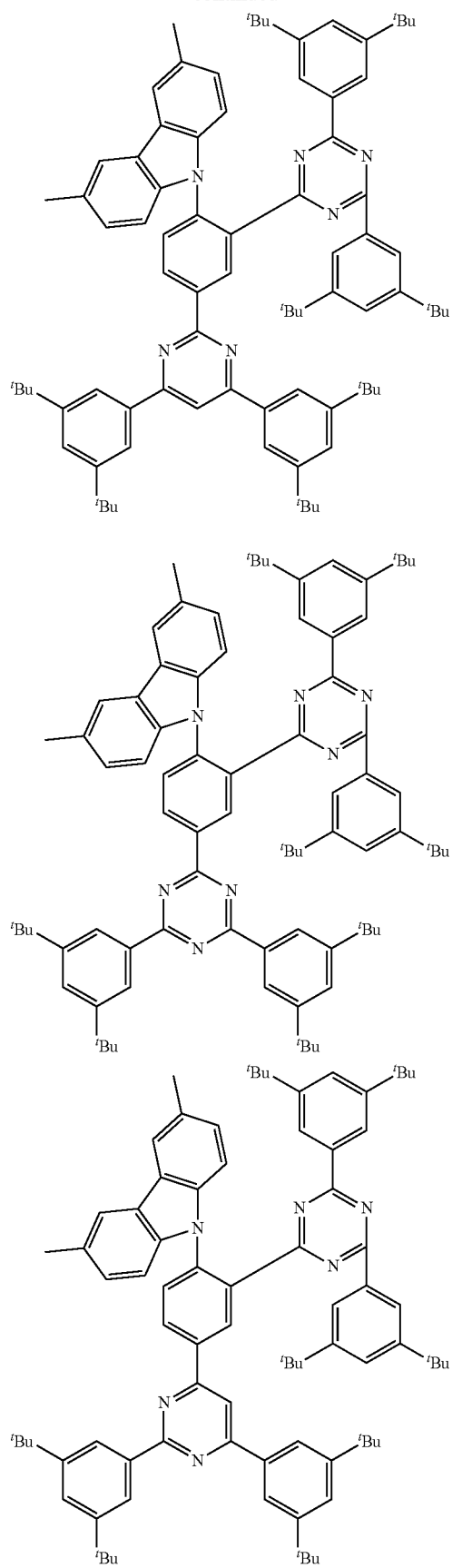
364
-continued
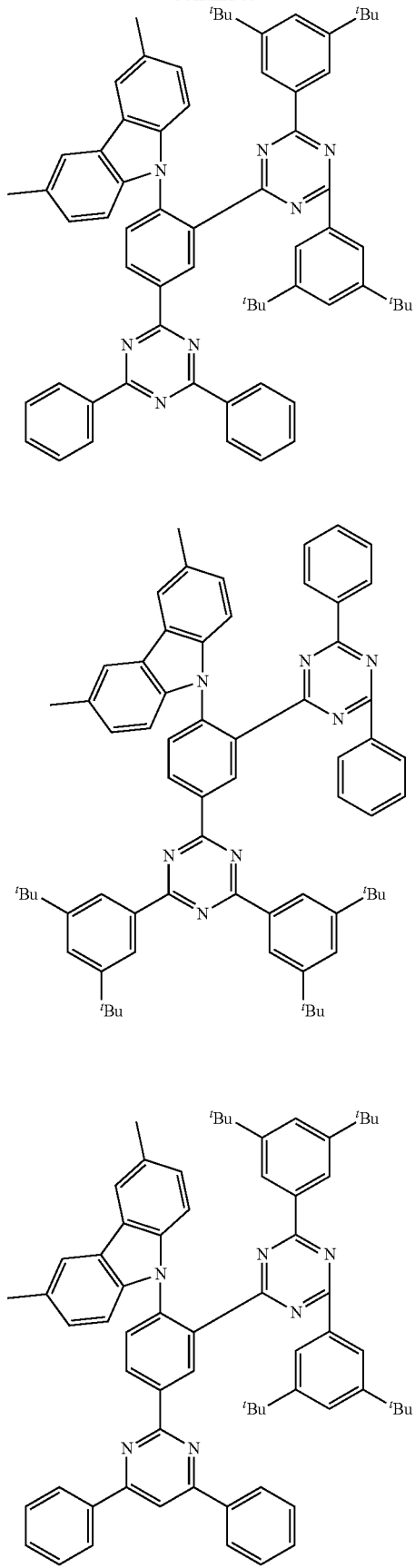

365
-continued
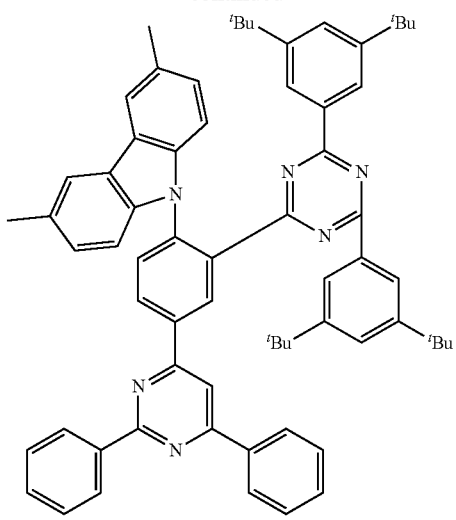
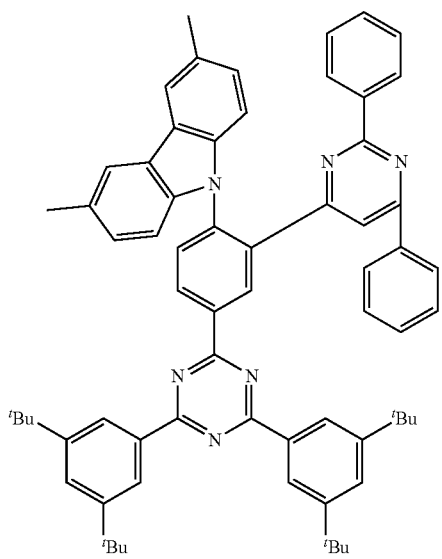
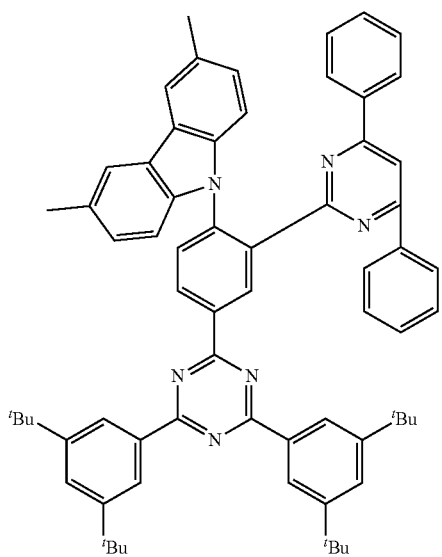
366
-continued
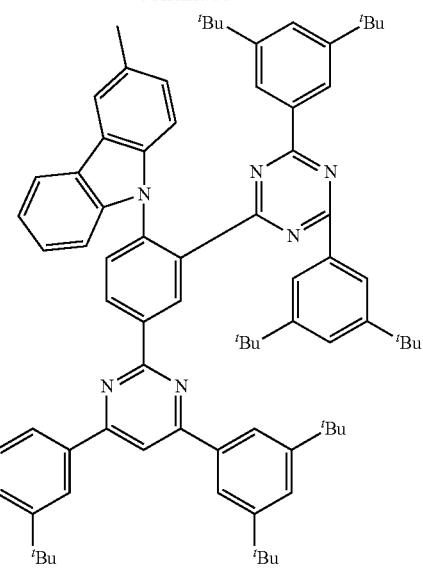
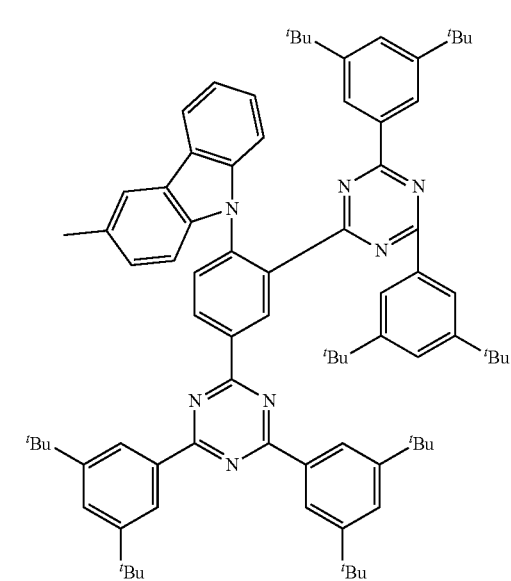
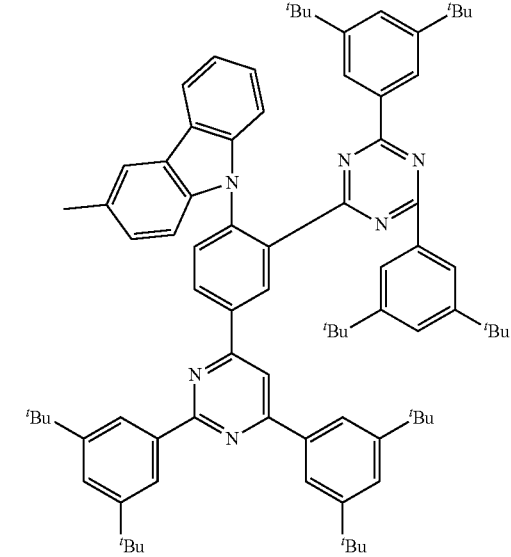

367
-continued
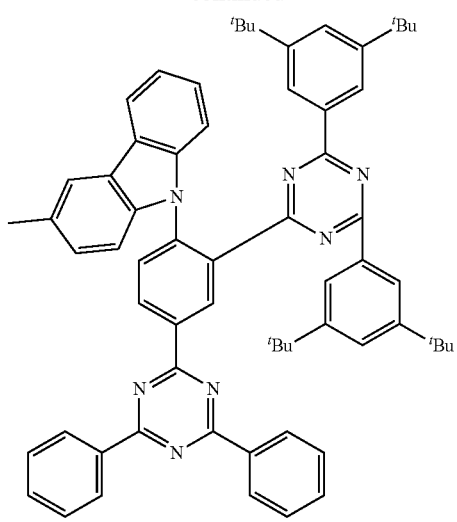
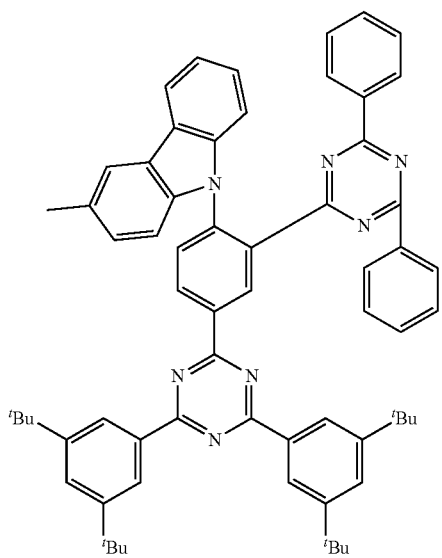
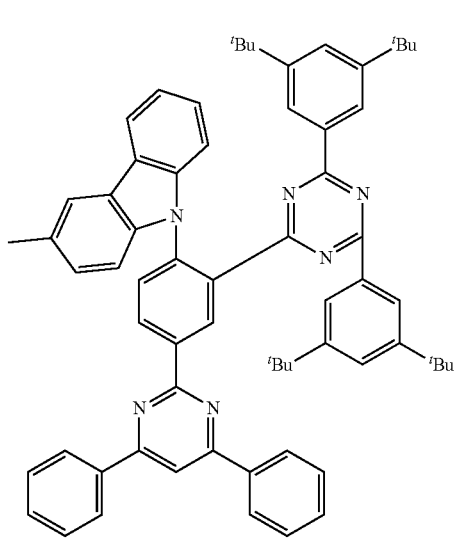
368
-continued
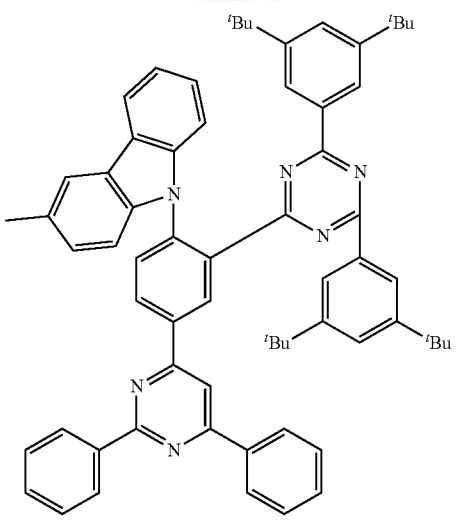
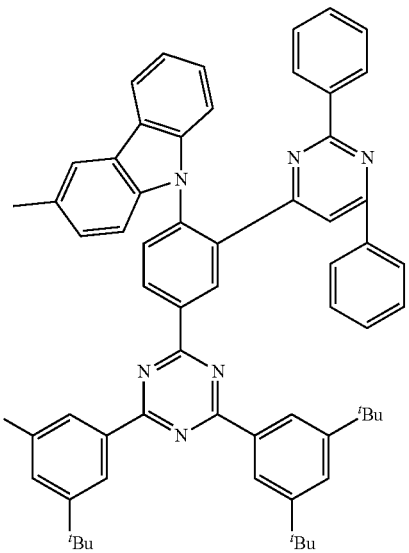
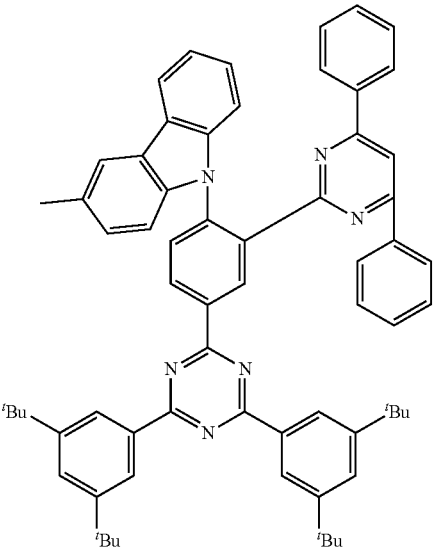

369
-continued
370
-continued
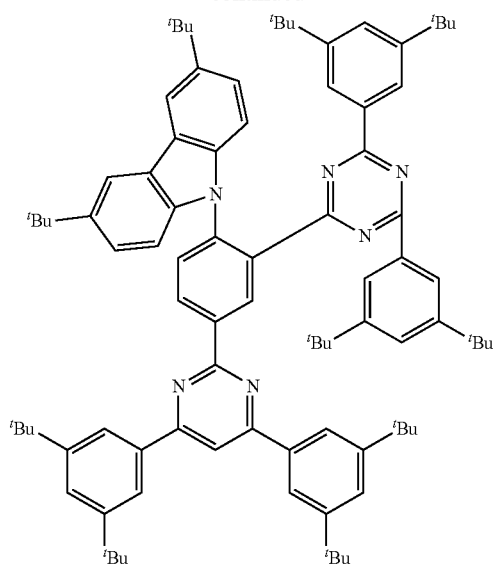
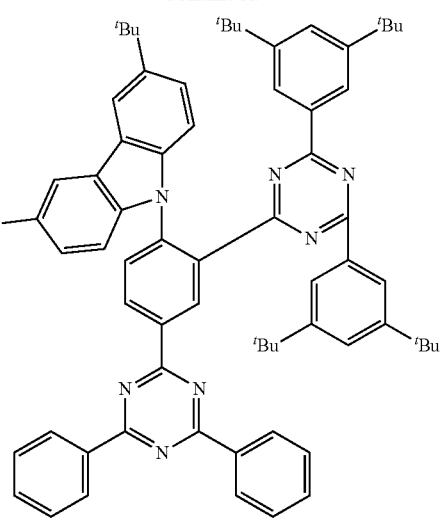
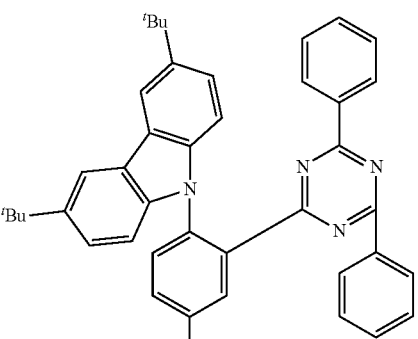
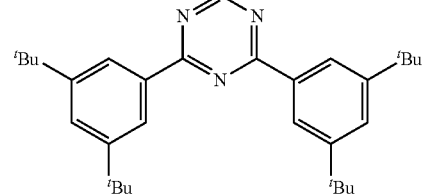
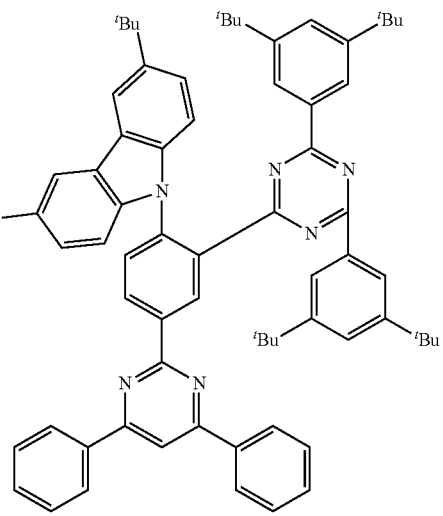

371
-continued
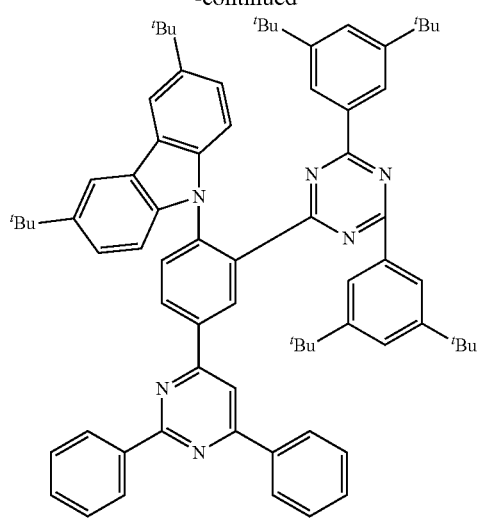
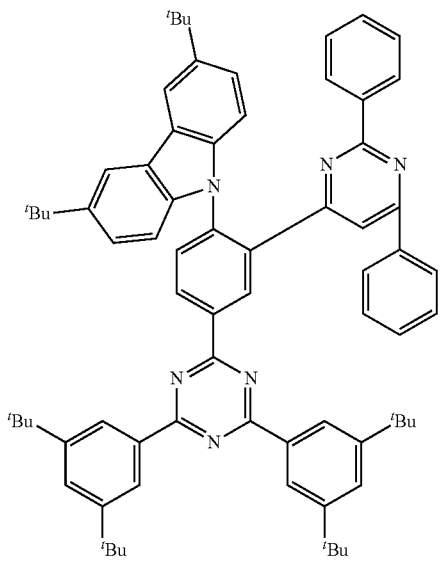
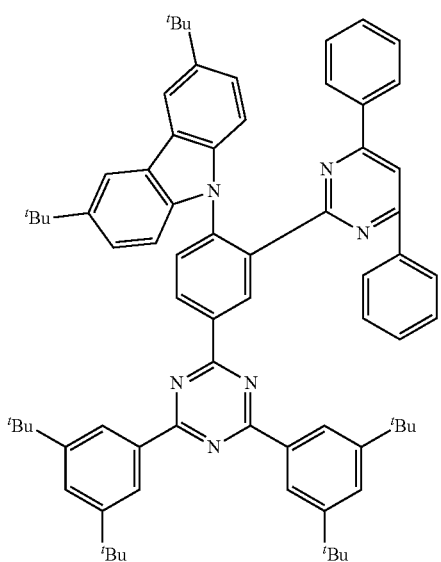
372
-continued
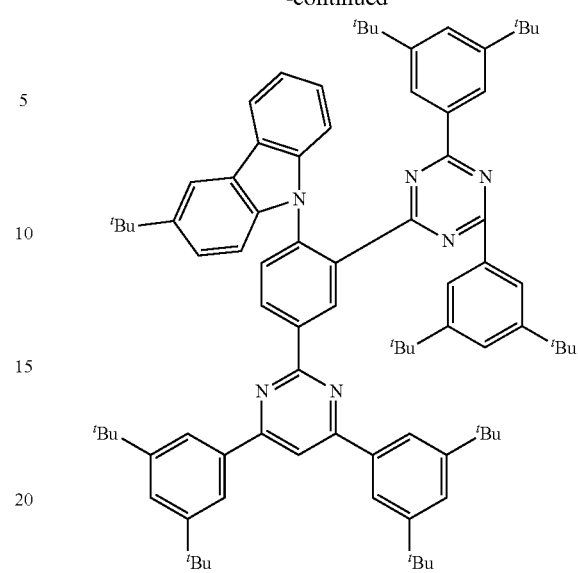
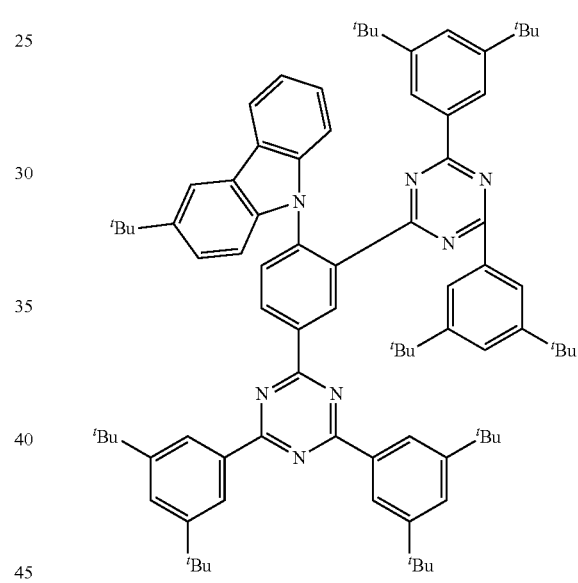
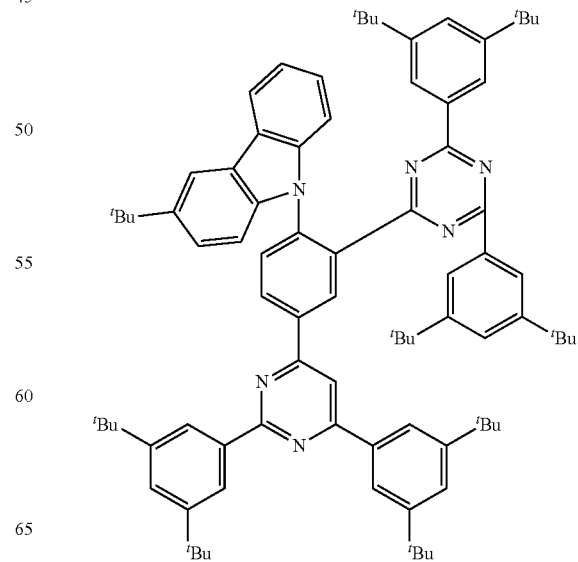

373
-continued
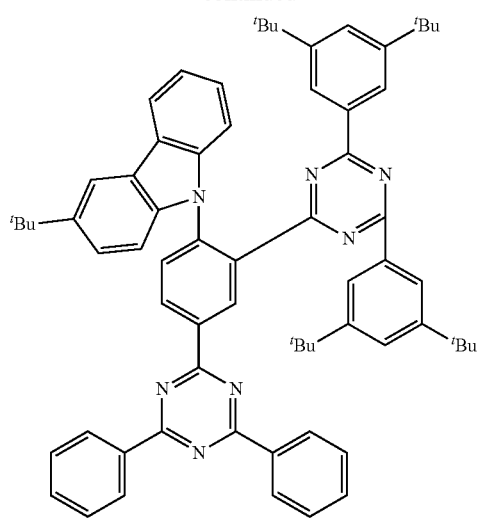
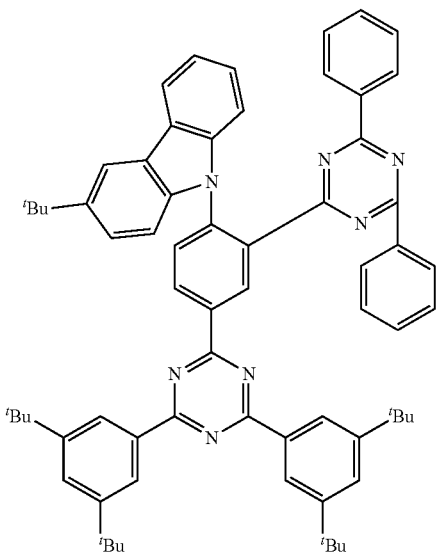
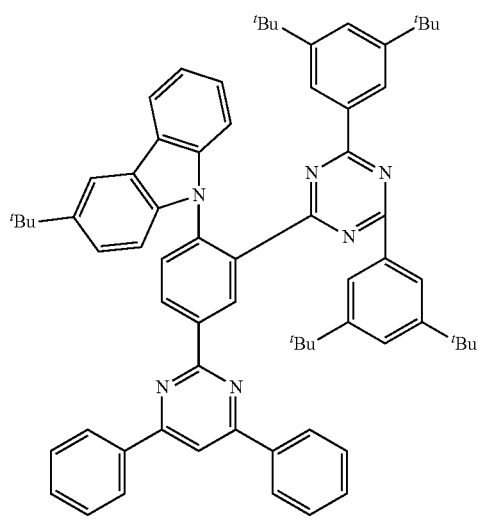
374
-continued
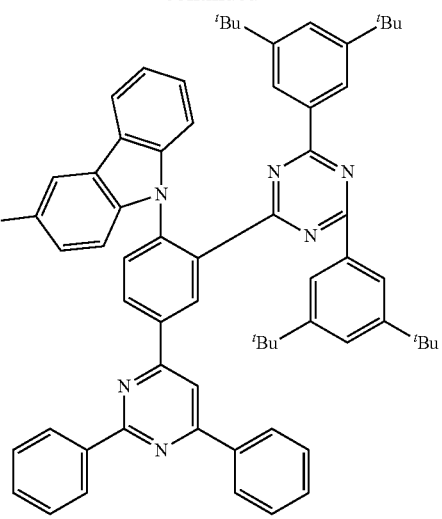
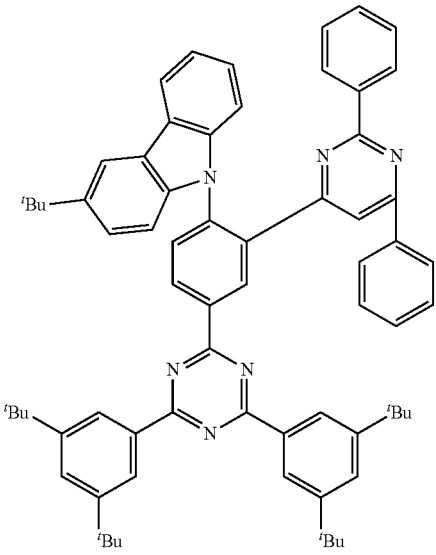
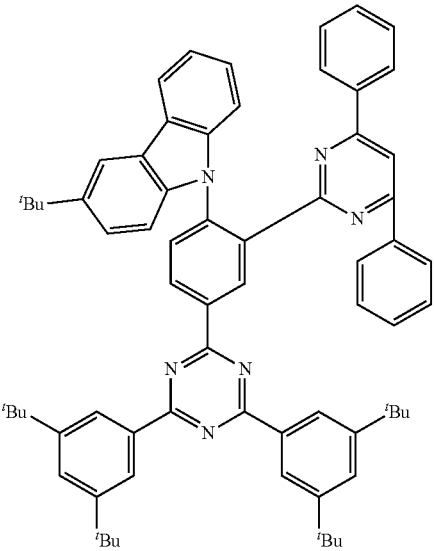

375
-continued
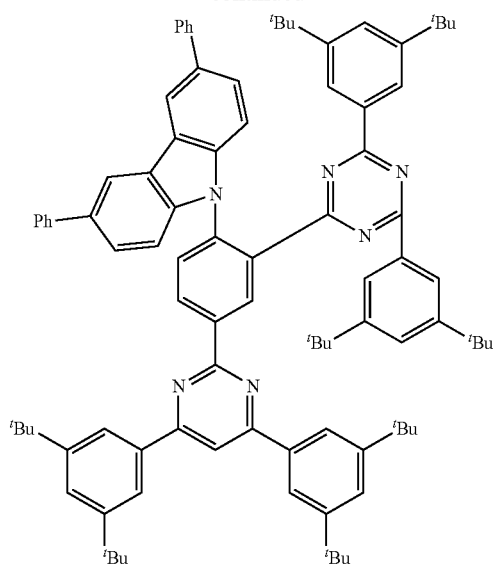
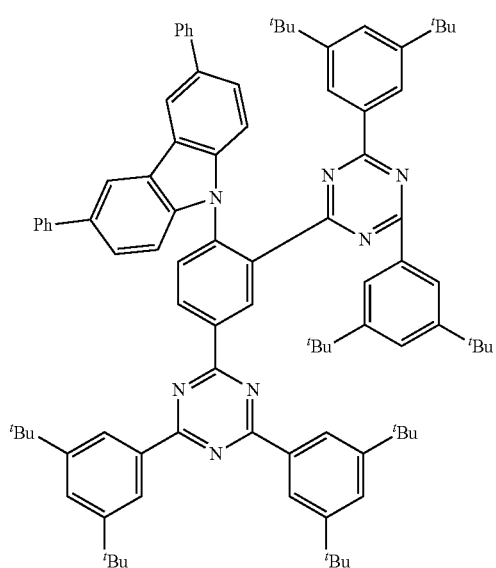
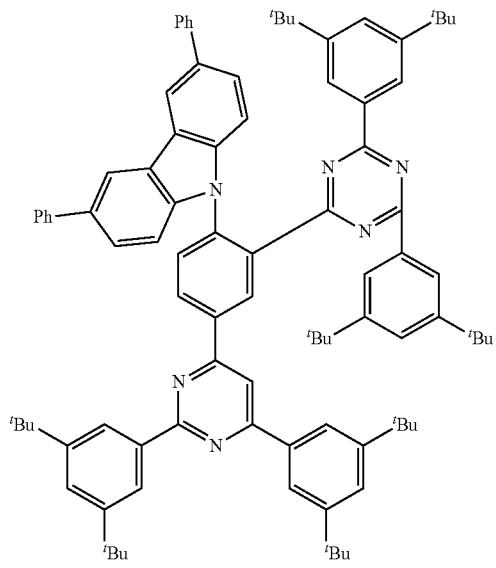
376
-continued
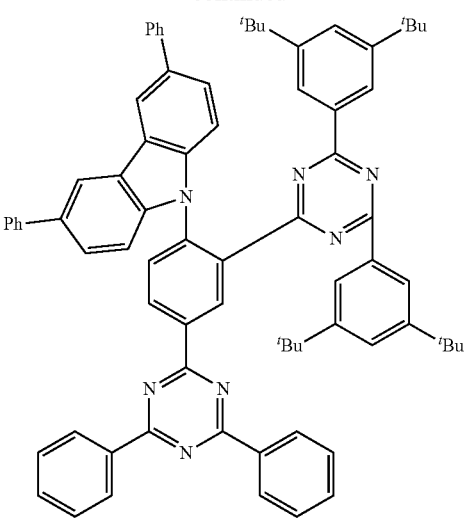
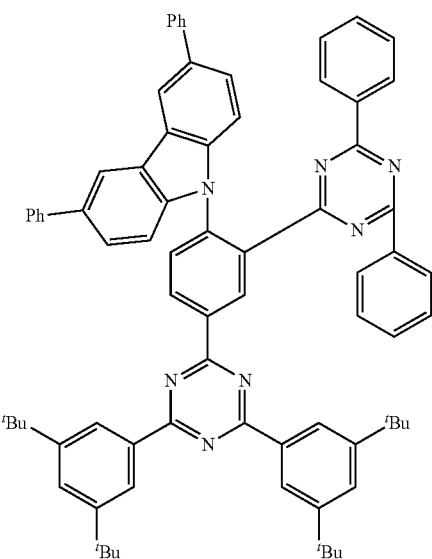
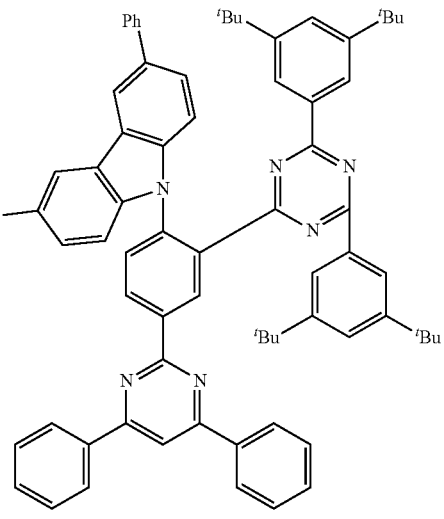

377
-continued
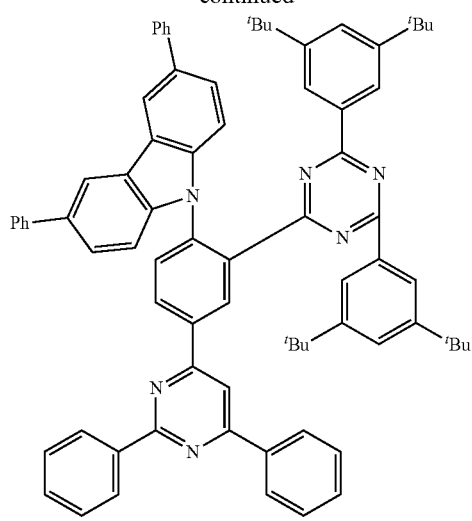
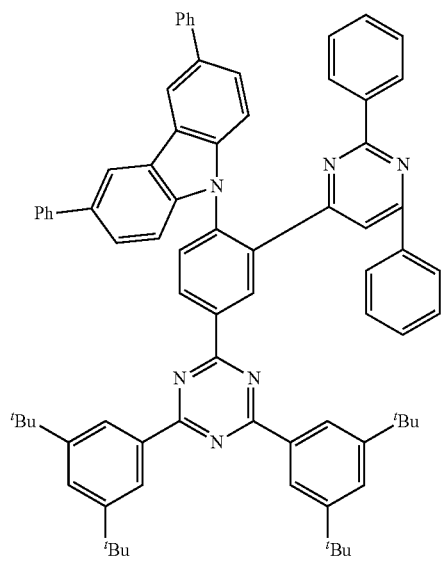
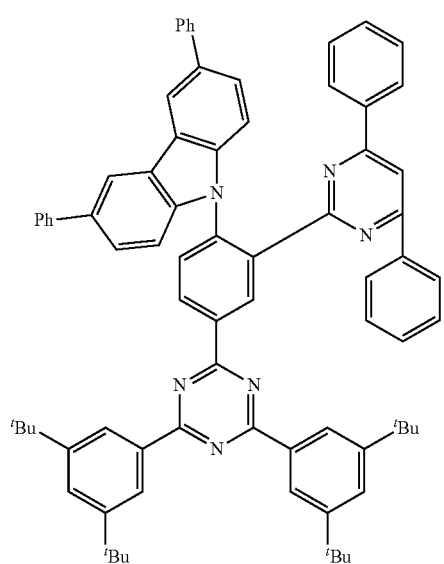
378
-continued
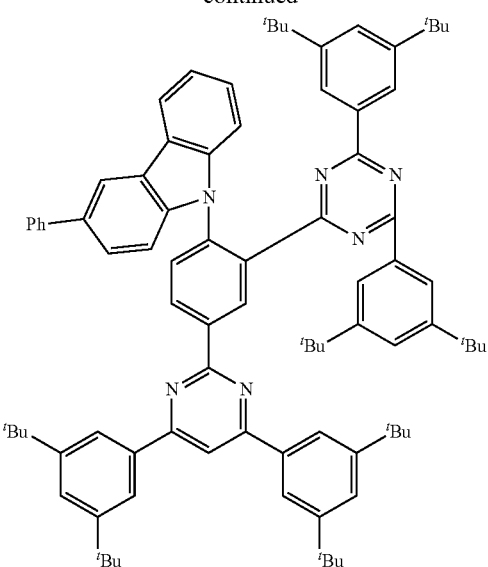
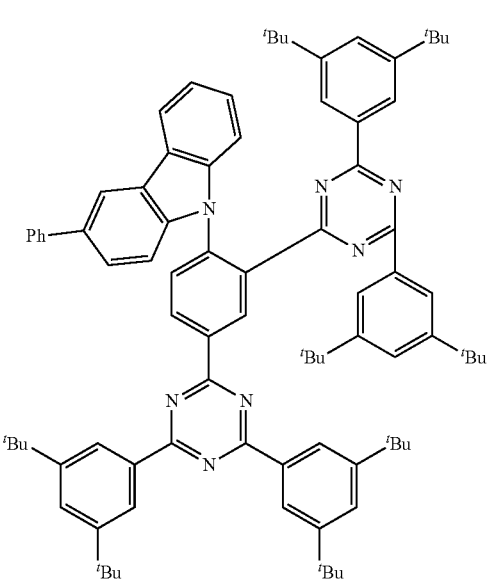
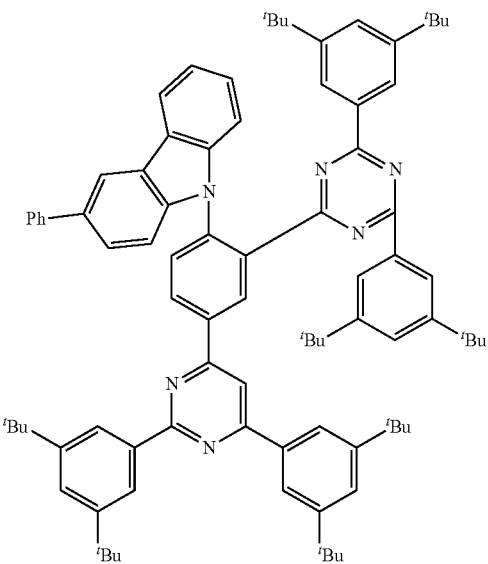

379
-continued
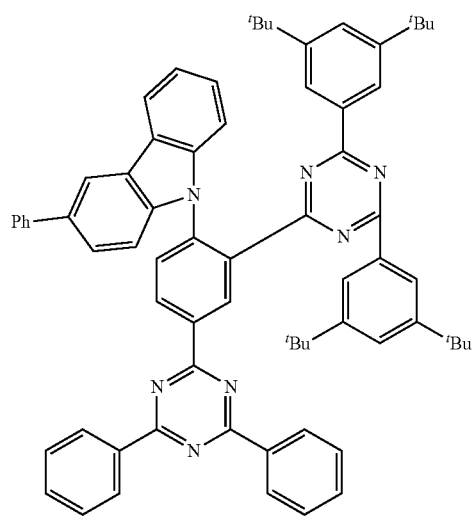
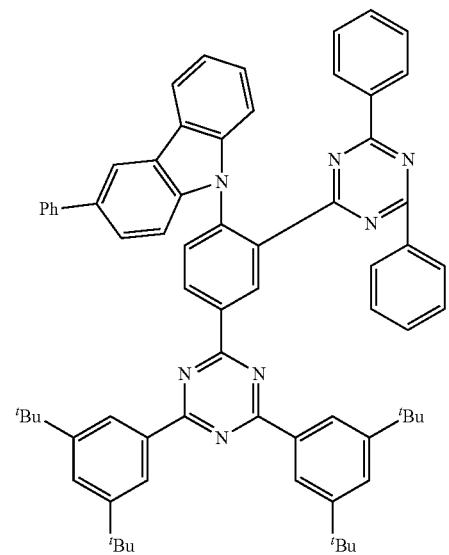
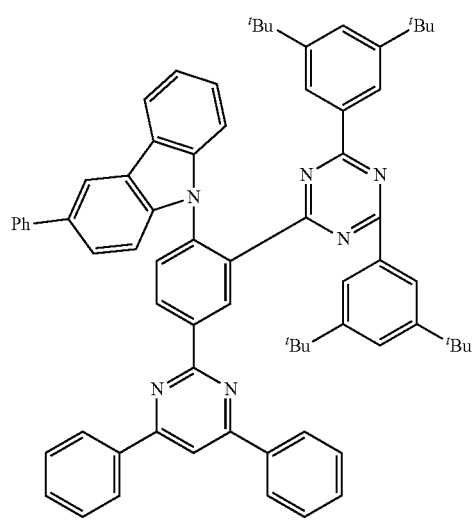
380
-continued
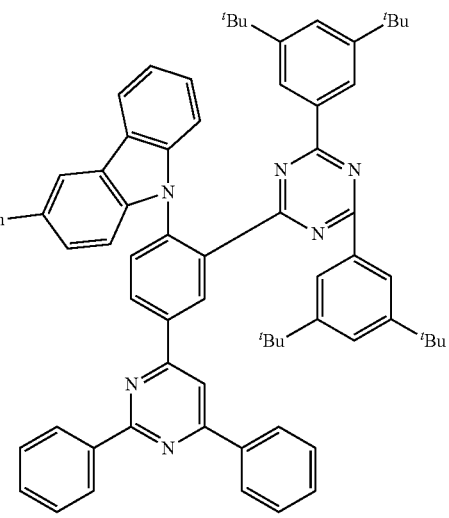
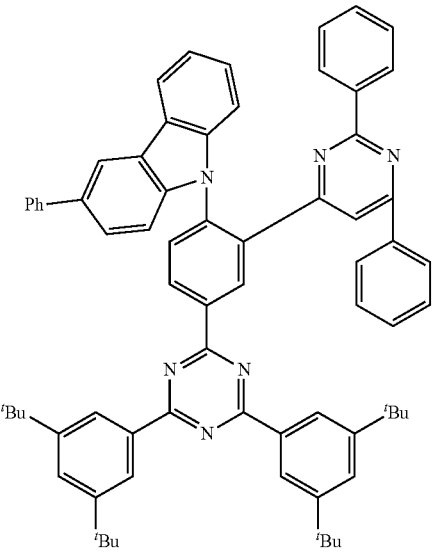
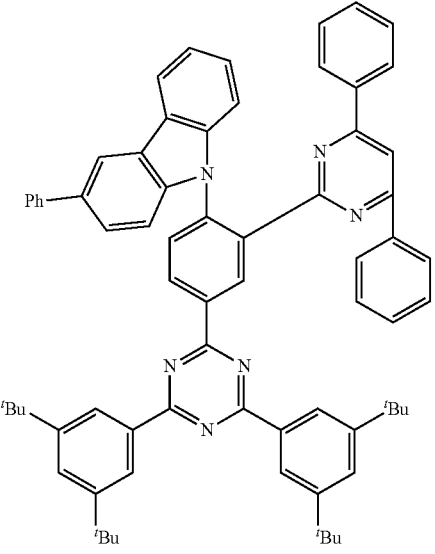

381
-continued
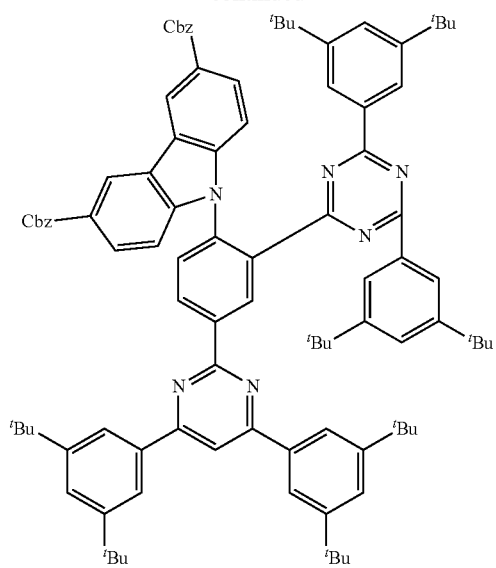
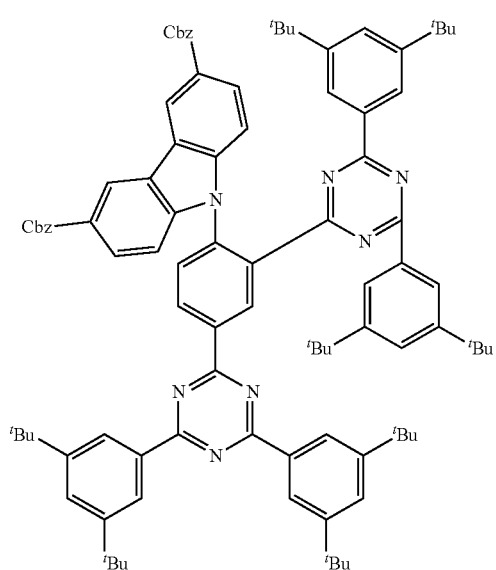
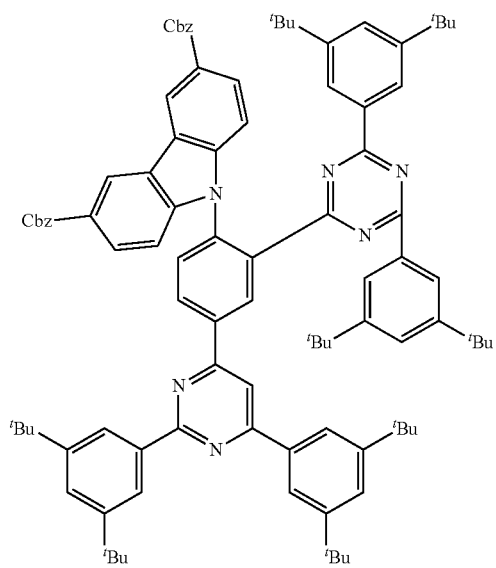
382
-continued
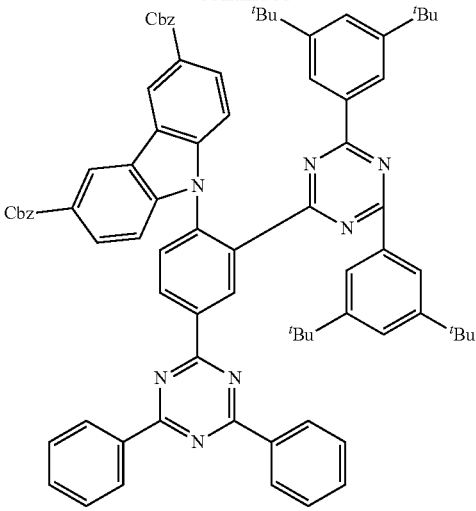
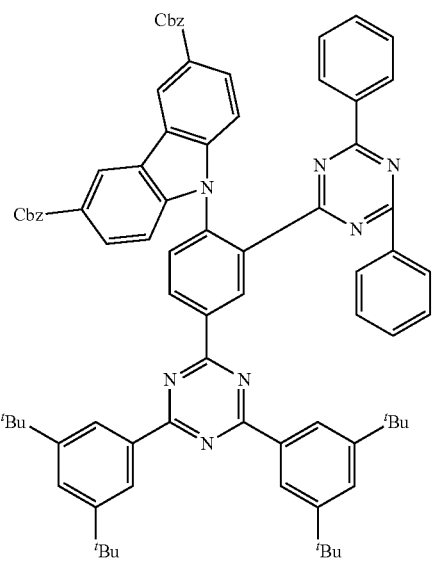
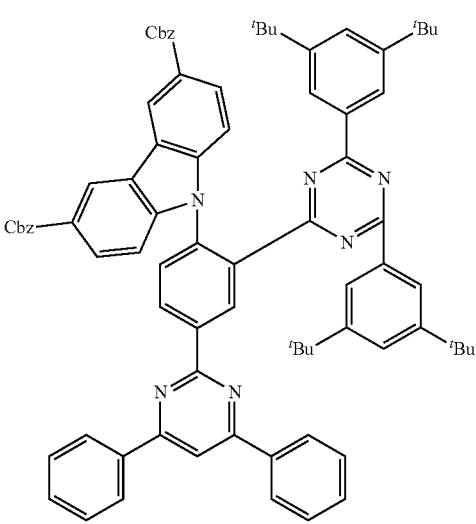

383
-continued
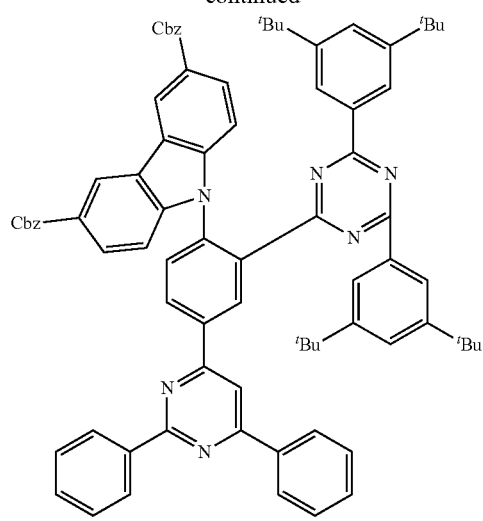
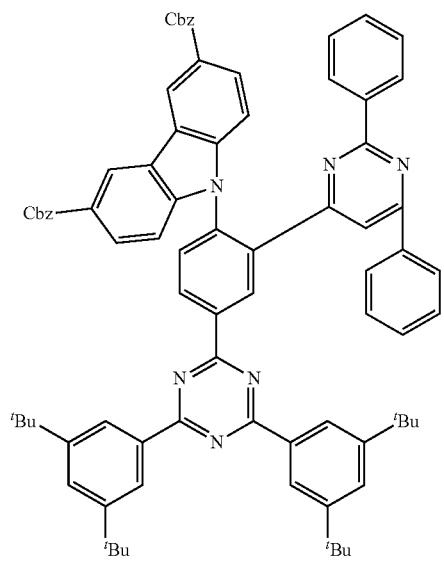
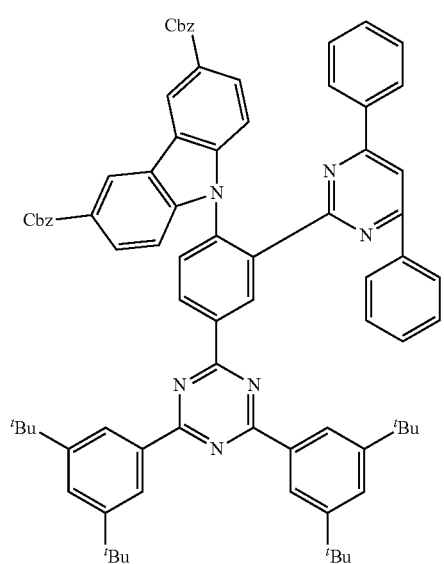
384
-continued
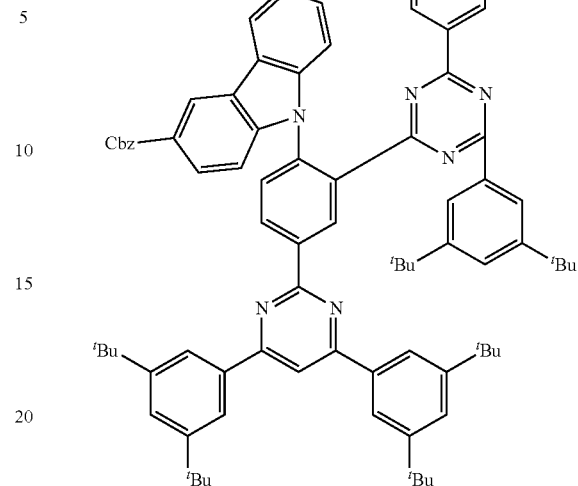
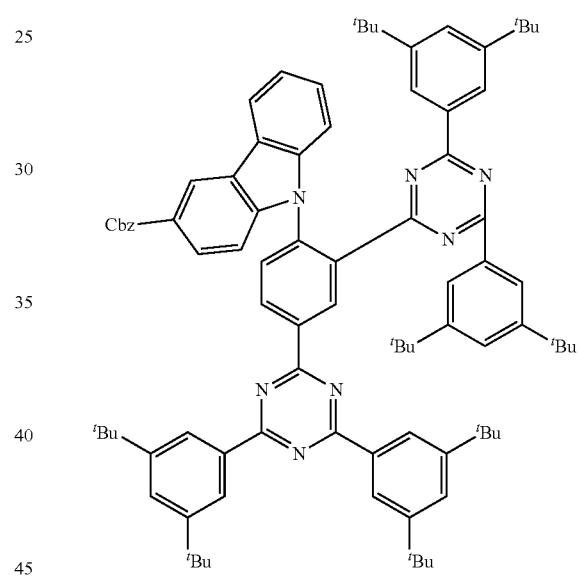
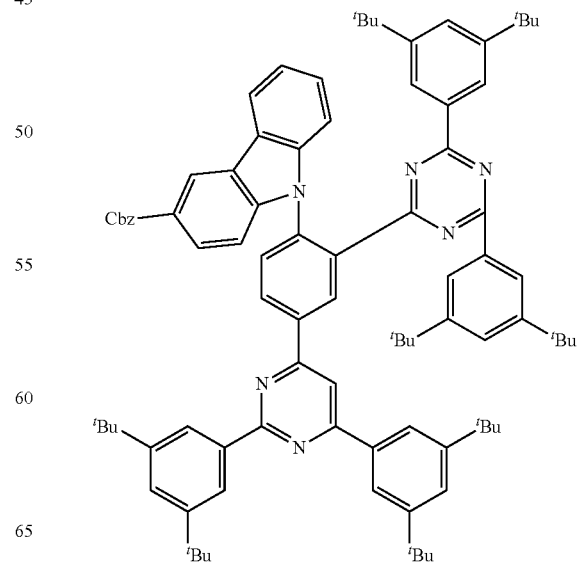

385
-continued
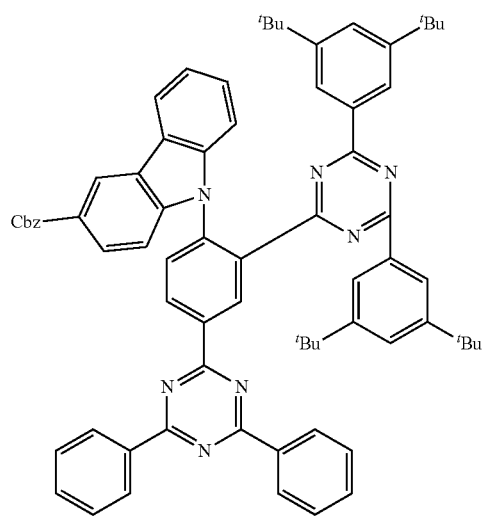
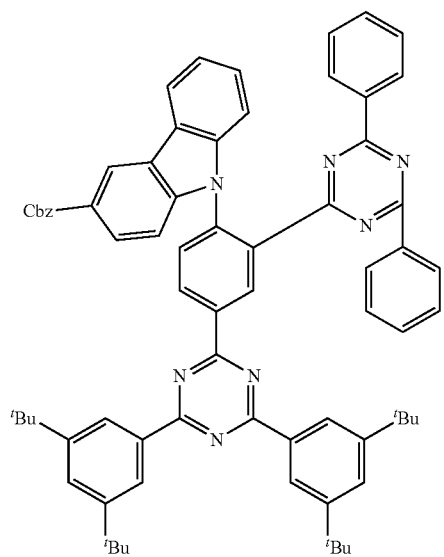
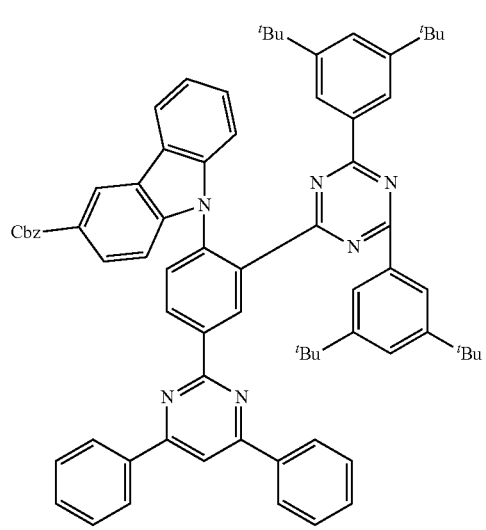
386
-continued
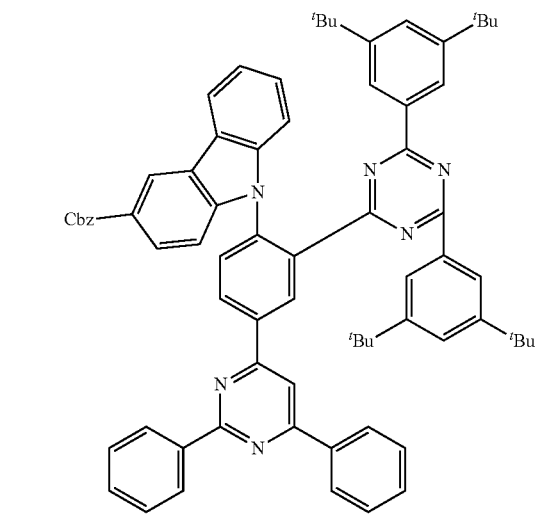
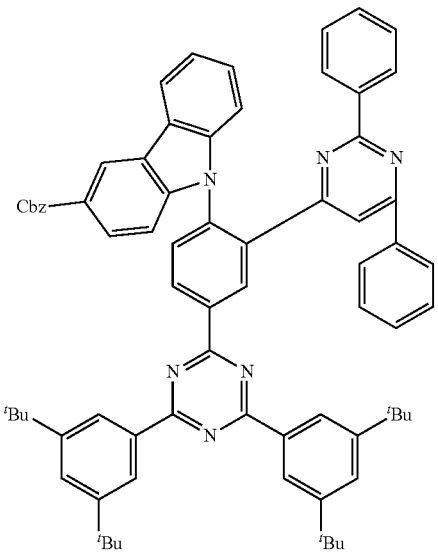
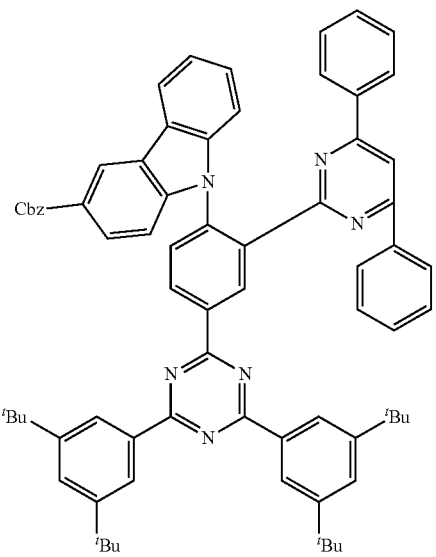

387
-continued
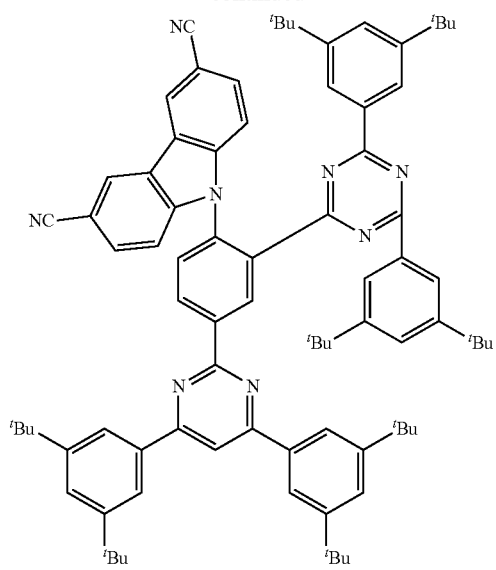
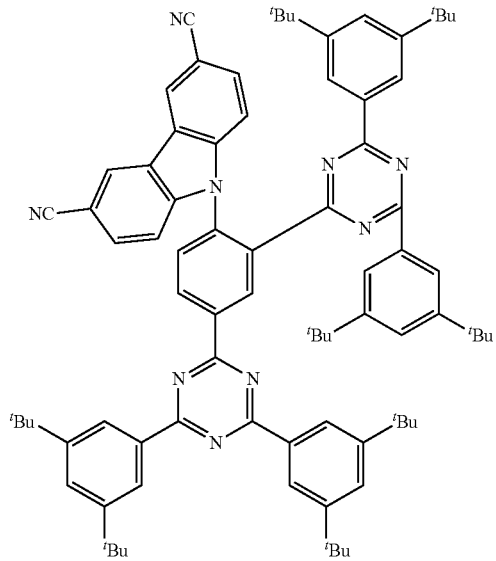
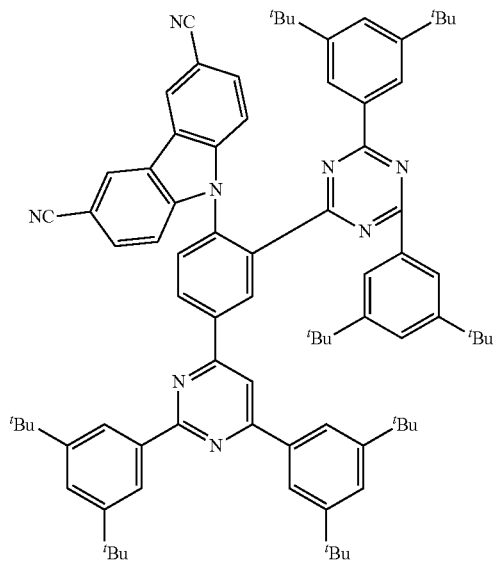
388
-continued
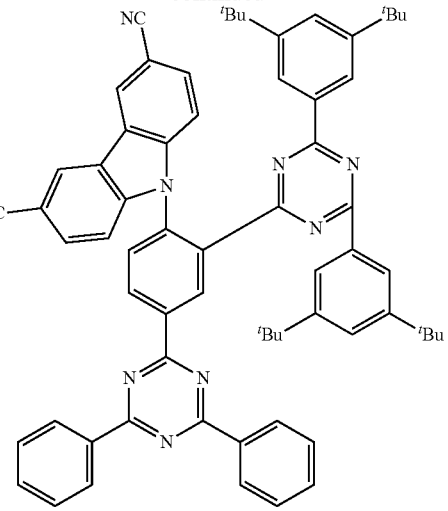
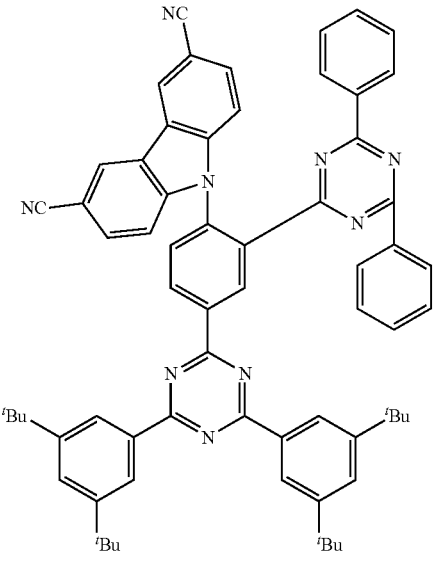
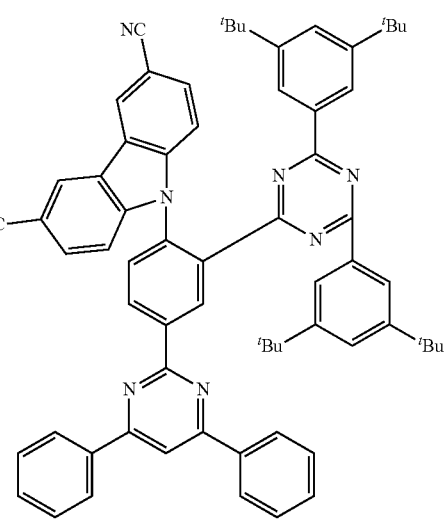

389
-continued
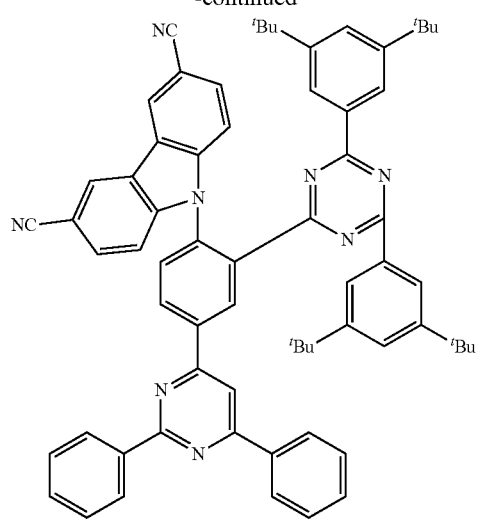
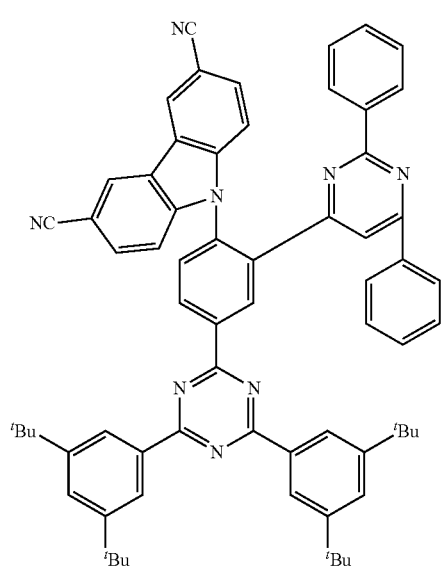
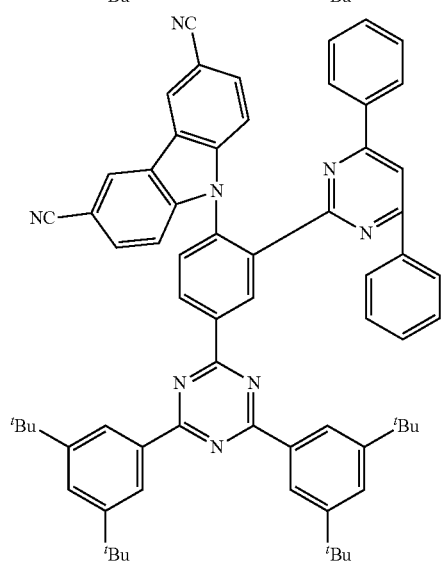
390
-continued
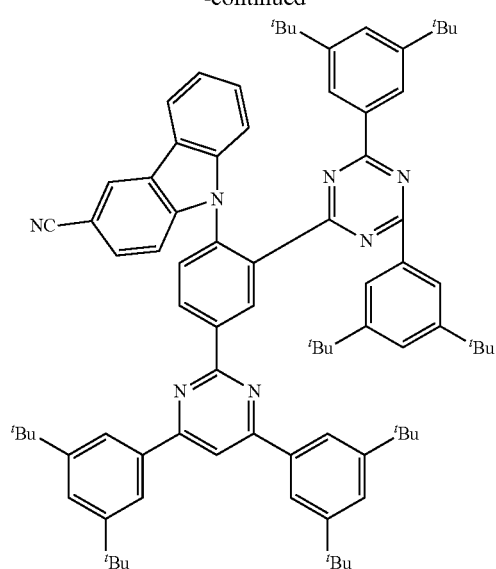
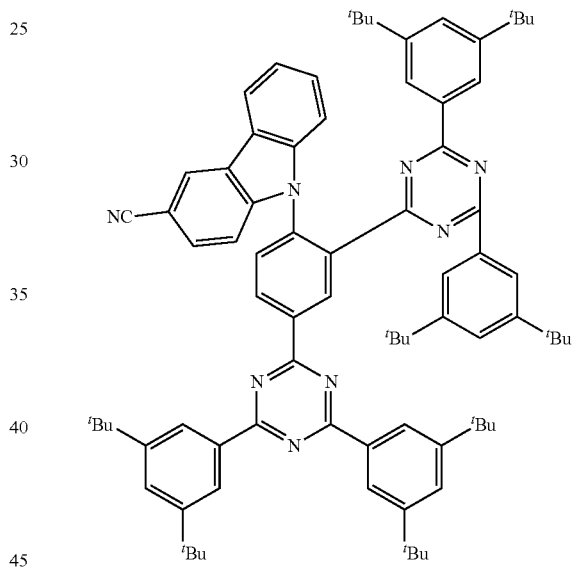
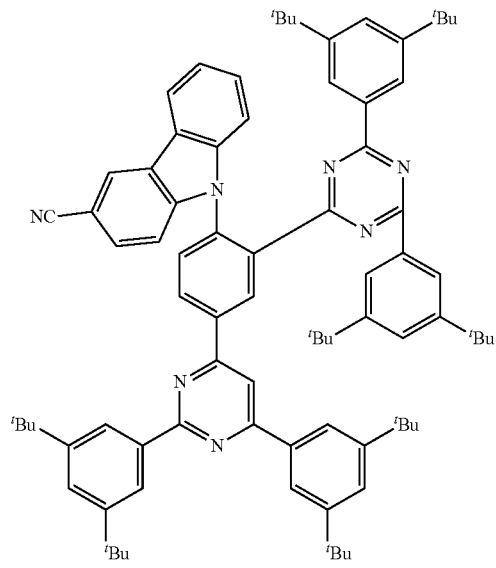

391
-continued
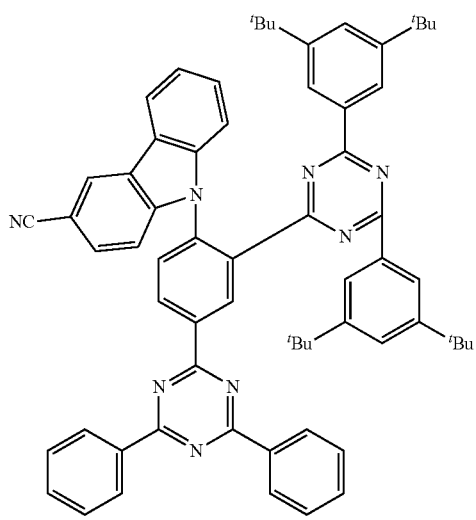
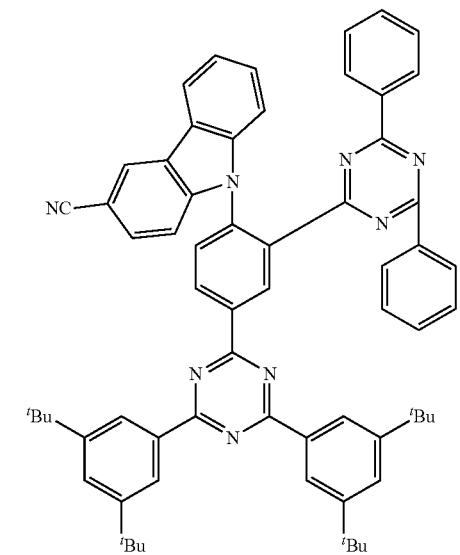
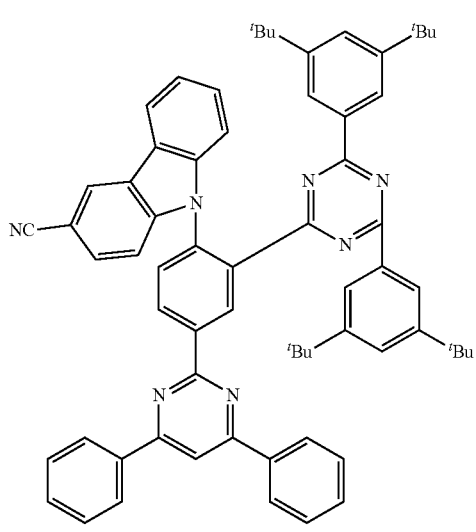
392
-continued
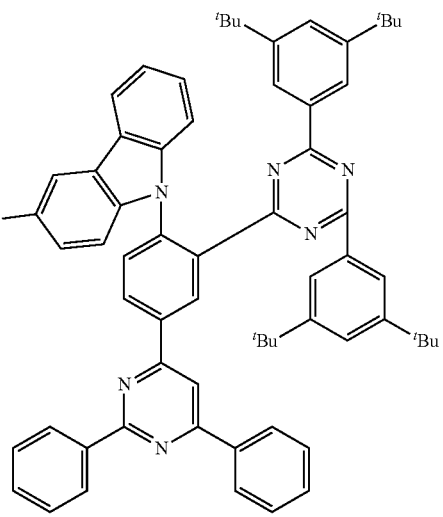
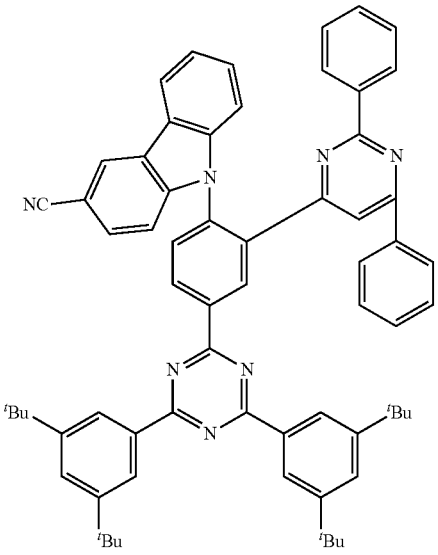
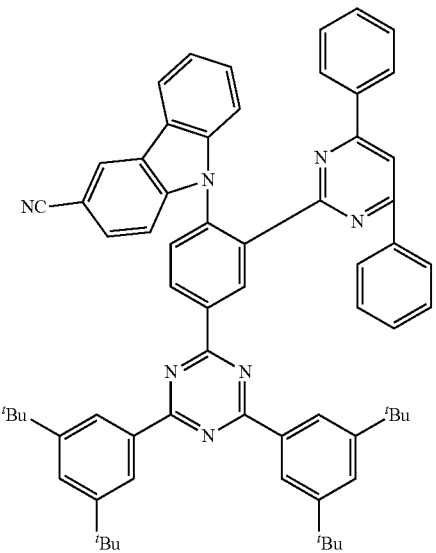

393
-continued
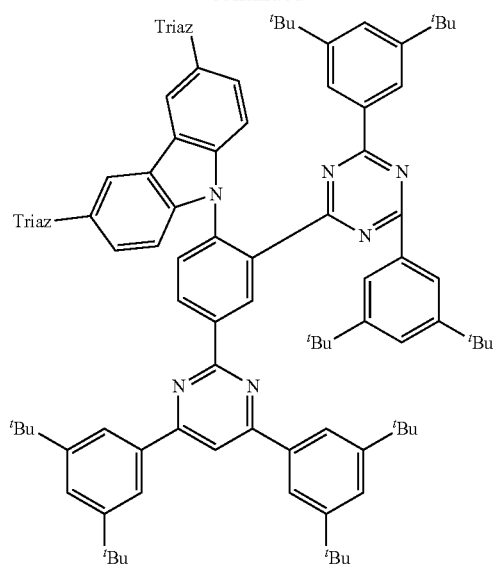
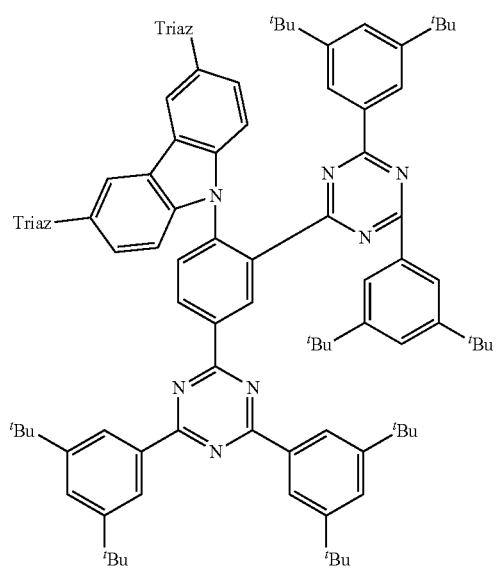
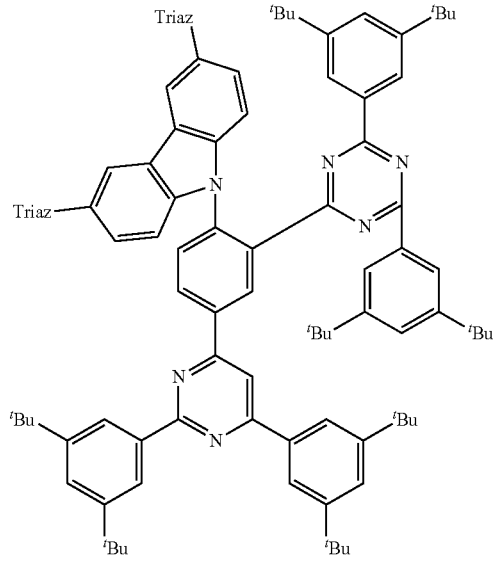
394
-continued
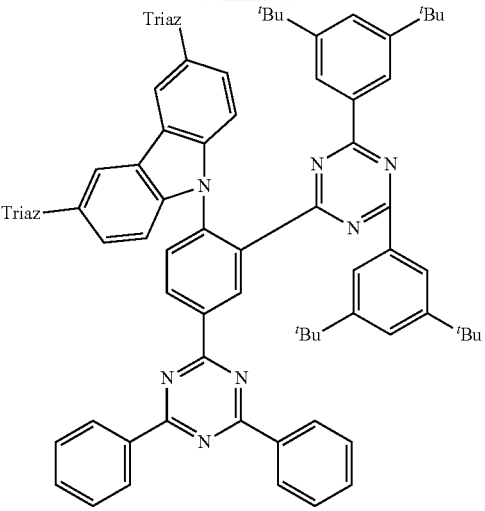
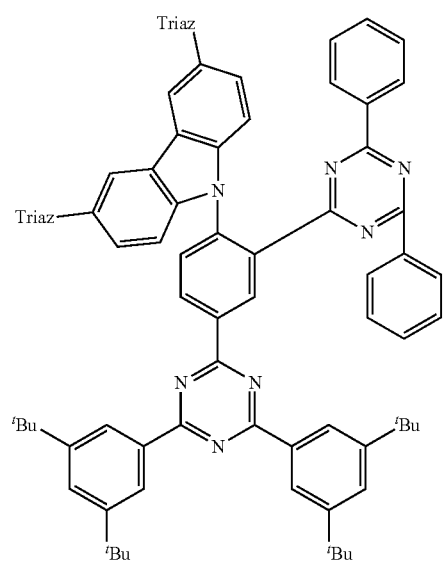
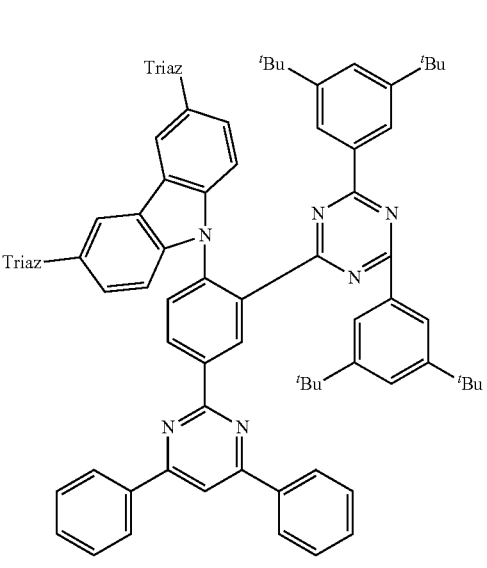

395
-continued
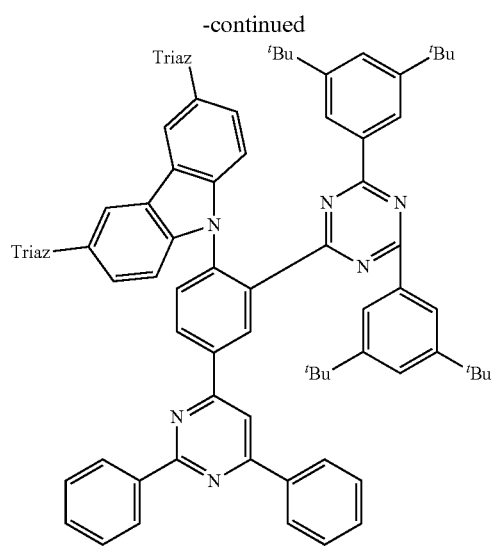
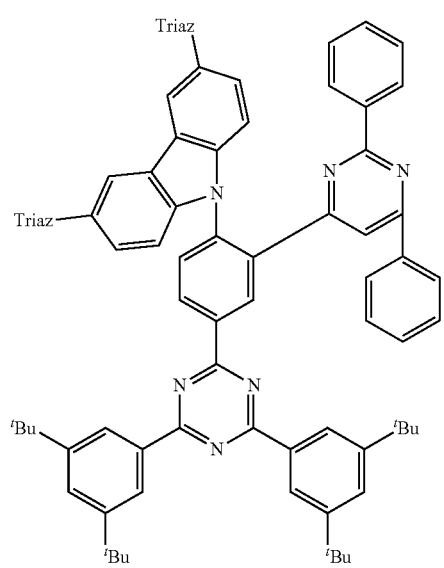
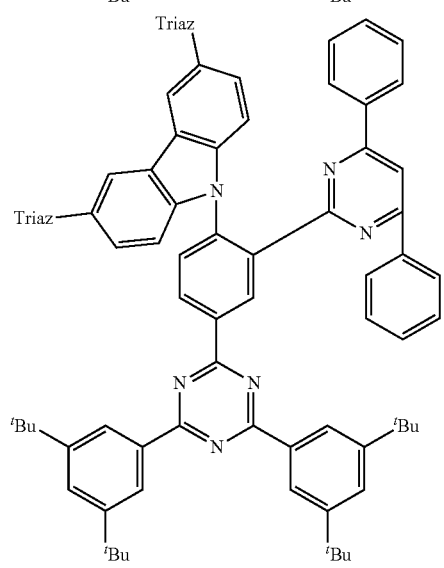
396
-continued
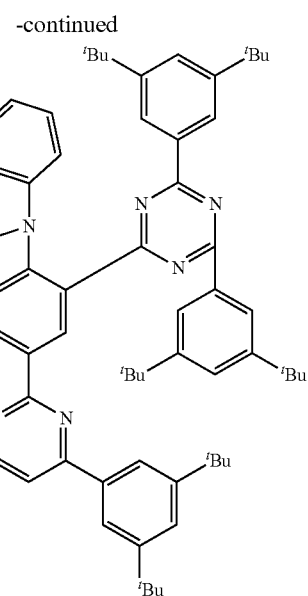
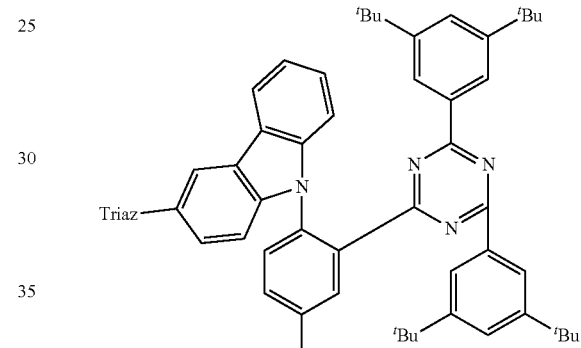
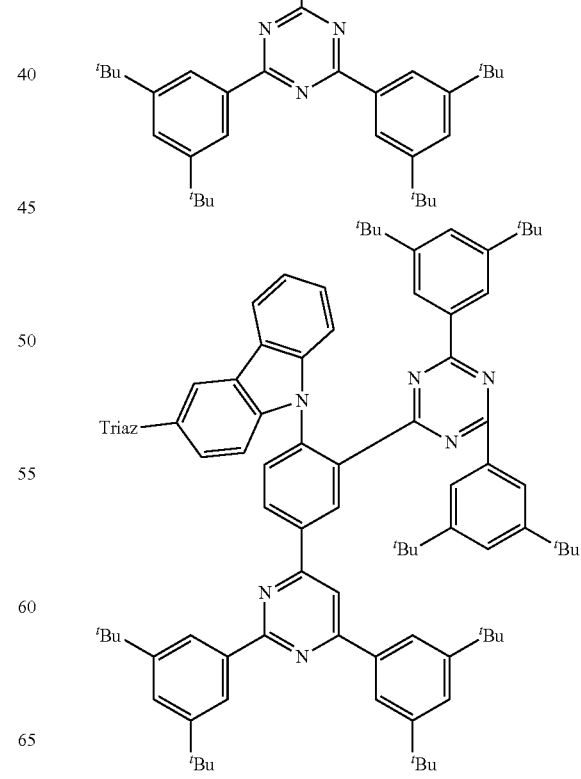

397
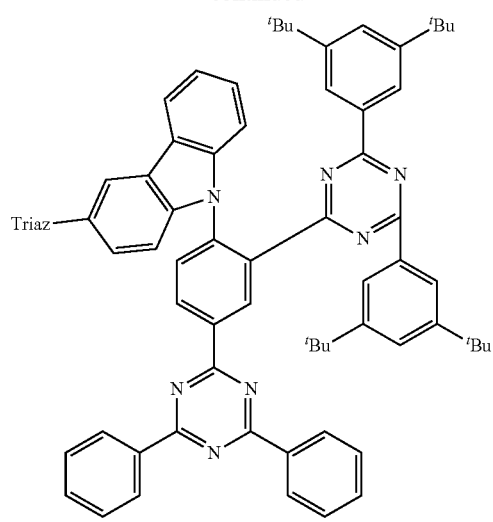
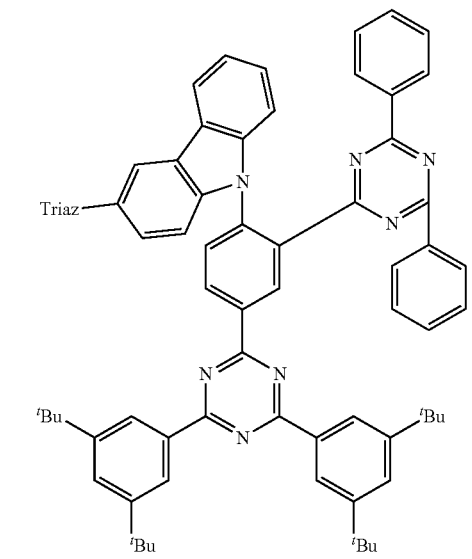
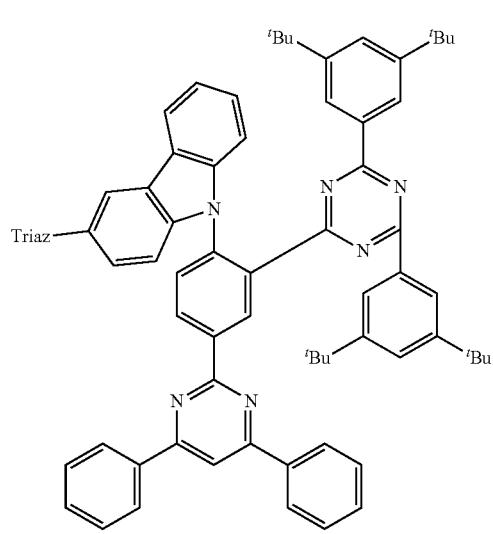
398
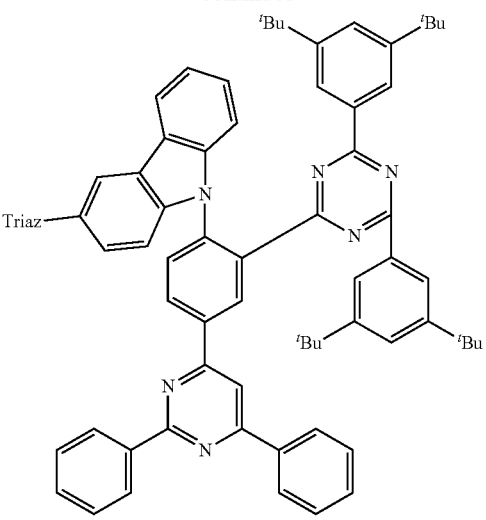
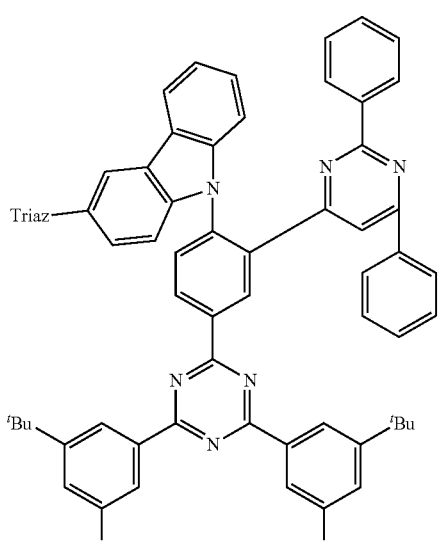
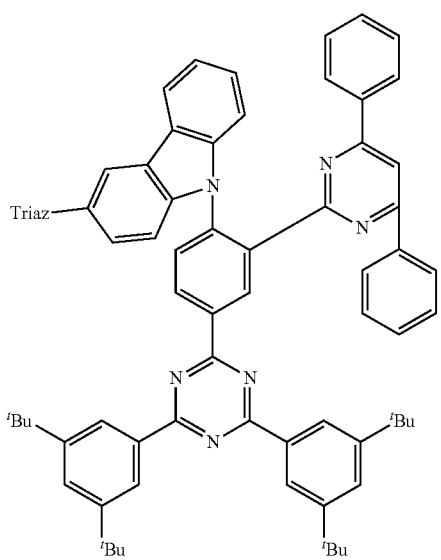

399
-continued
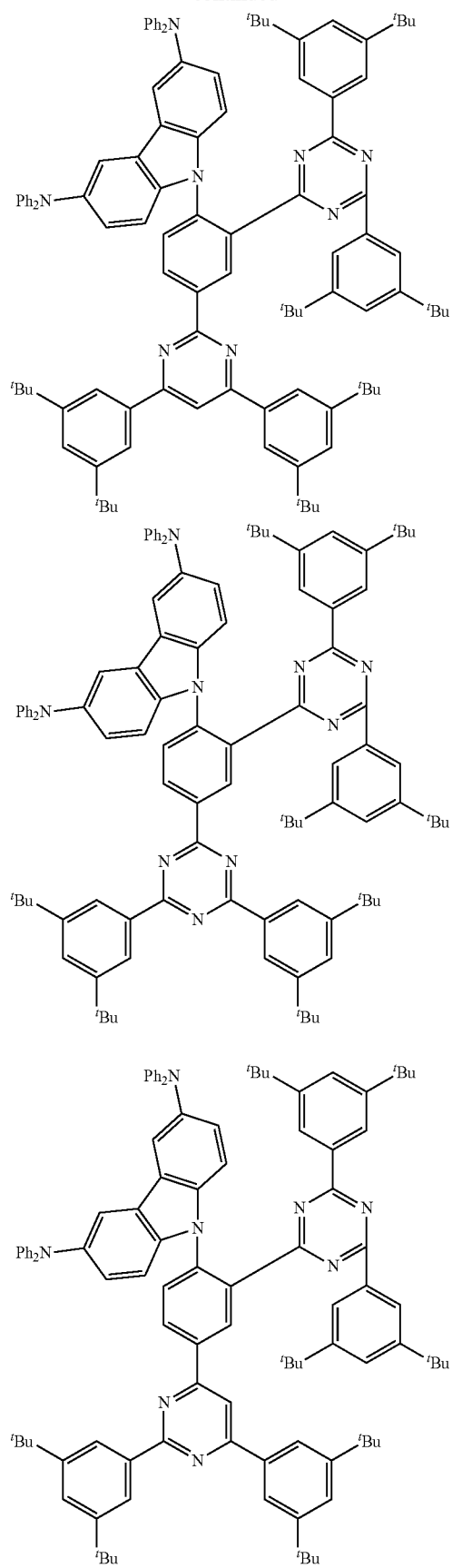
400
-continued
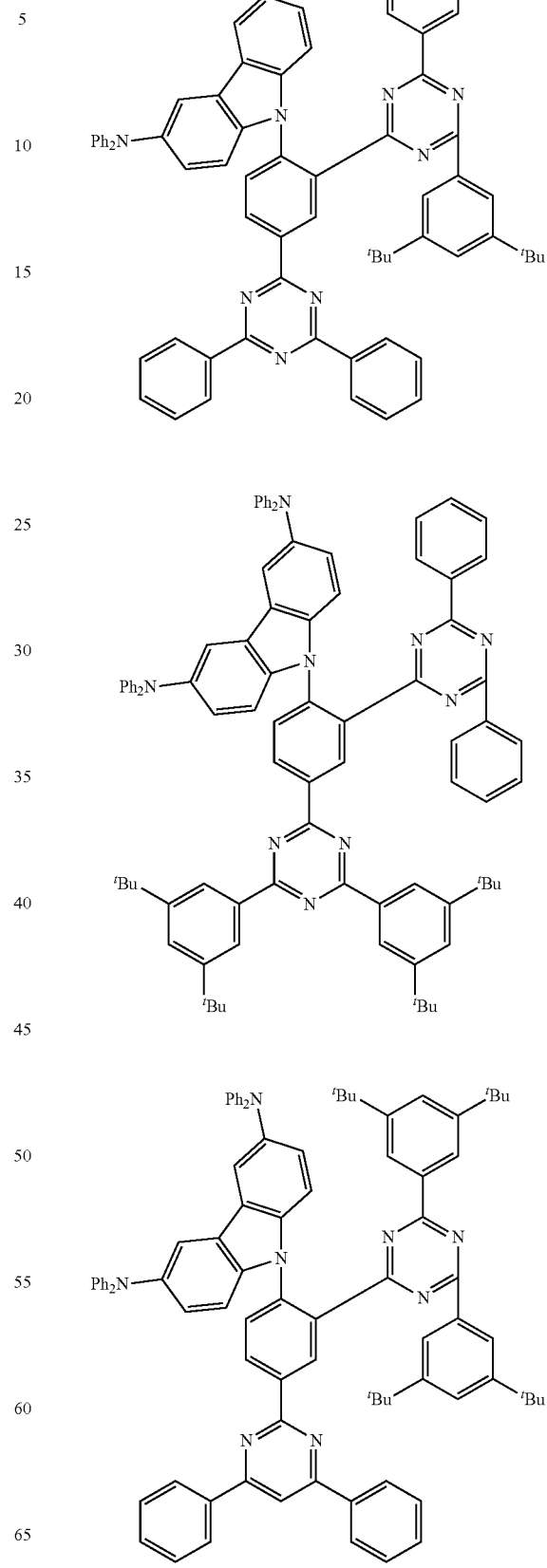

401
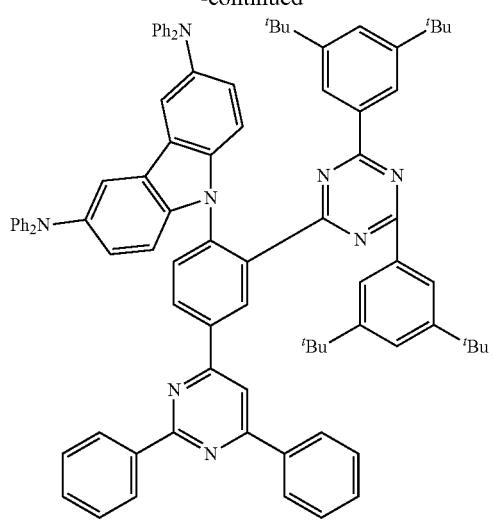
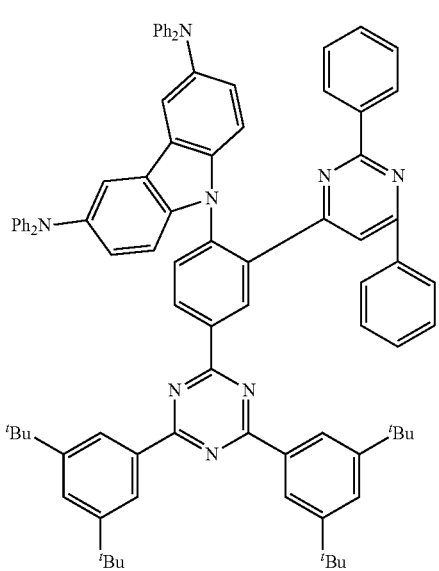
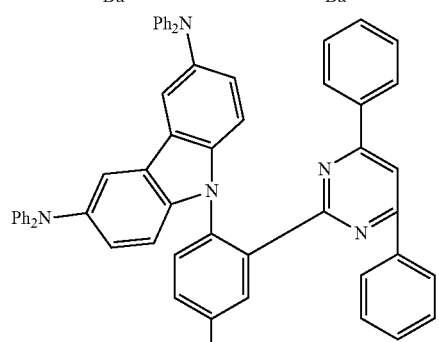
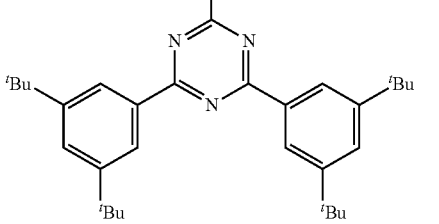
402
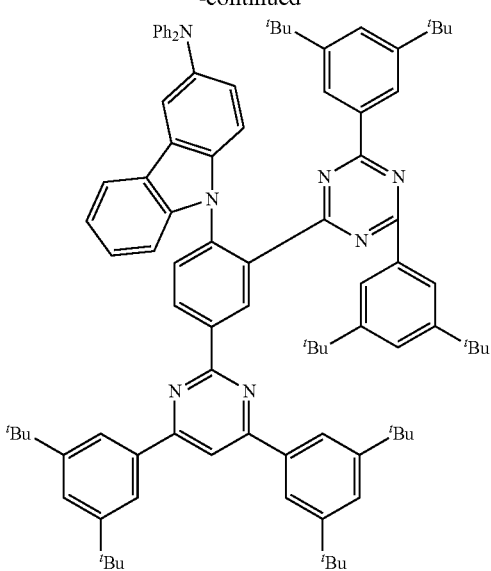
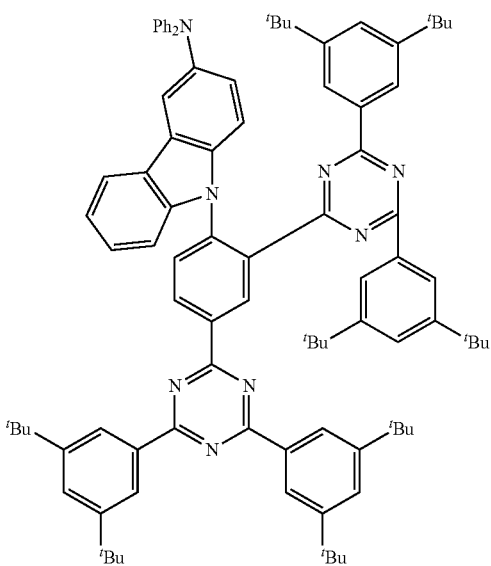
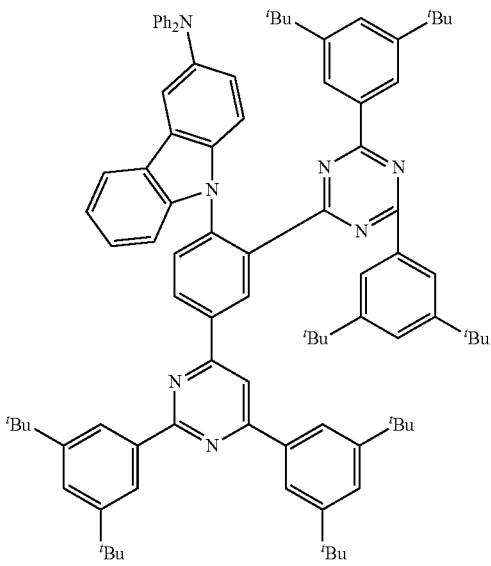

403
-continued
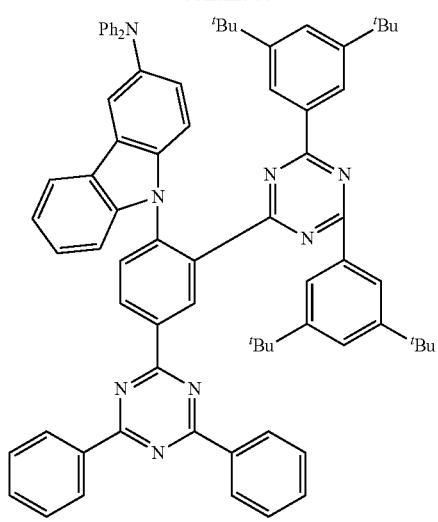
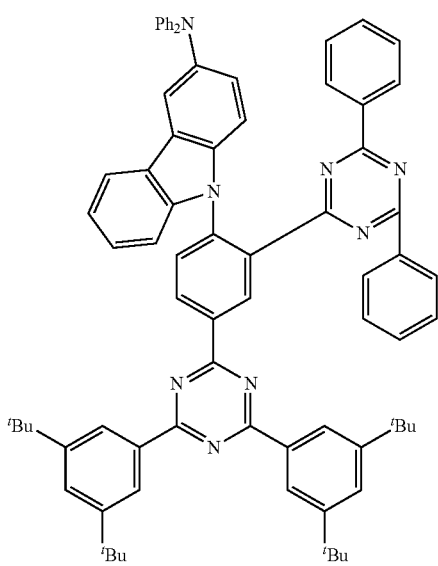
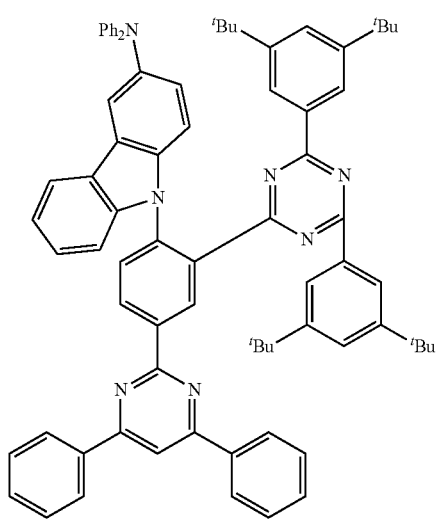
404
-continued
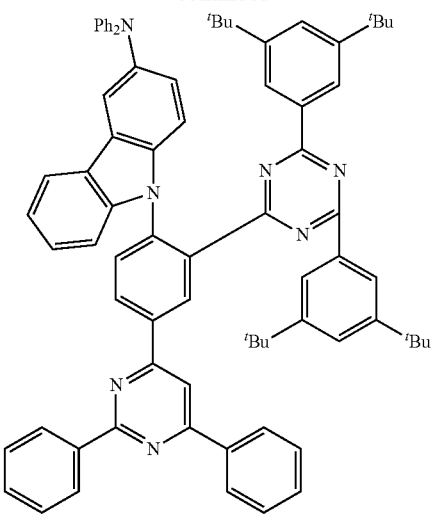
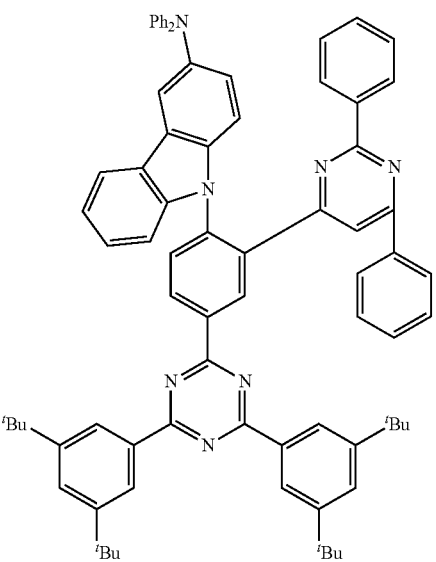
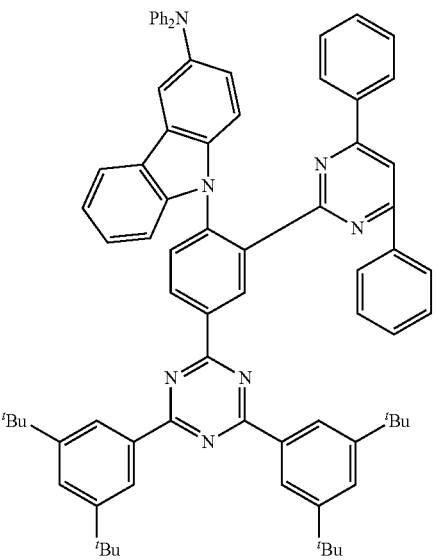

405
-continued
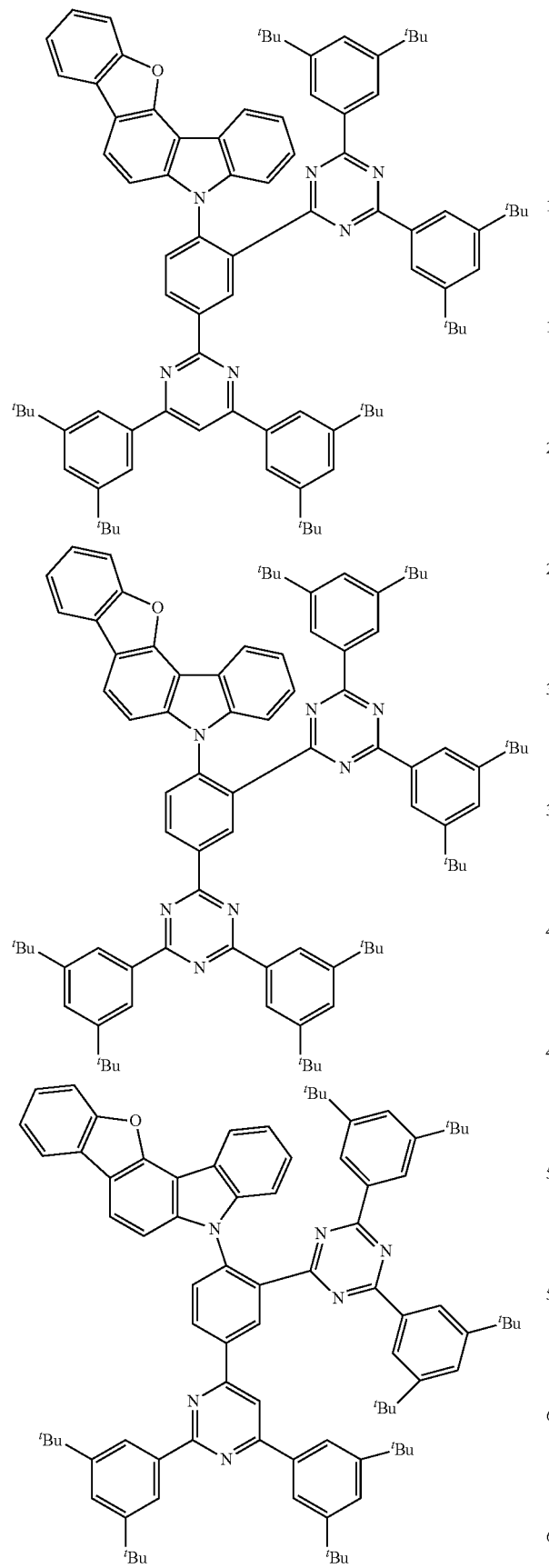
406
-continued
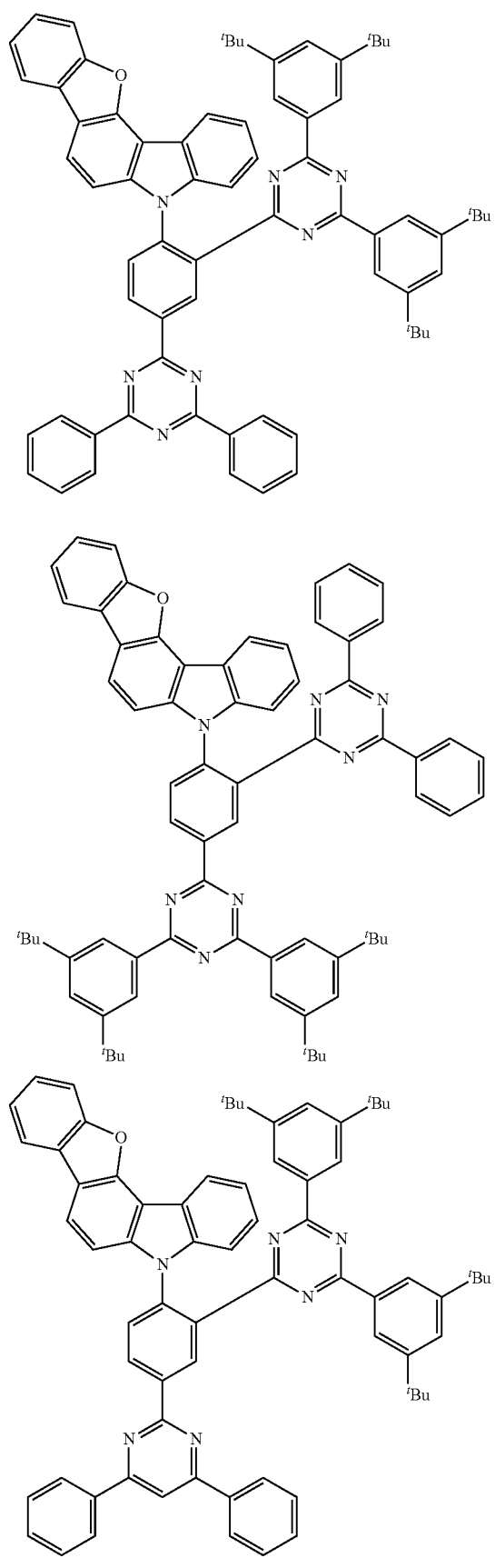

407
-continued
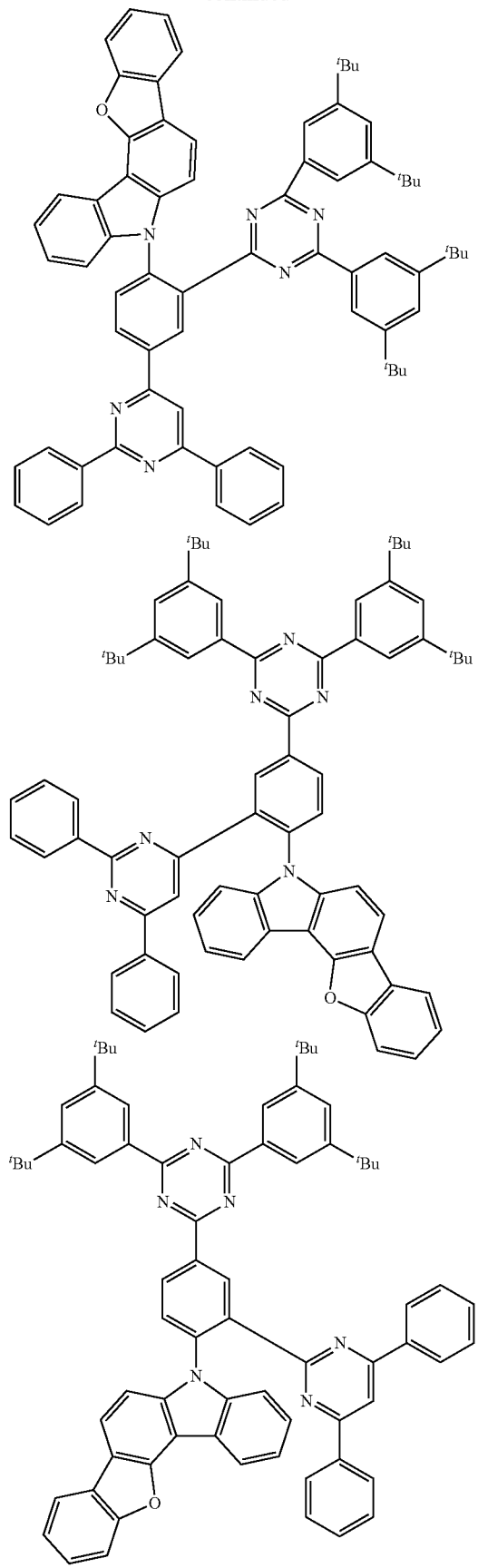
408
-continued
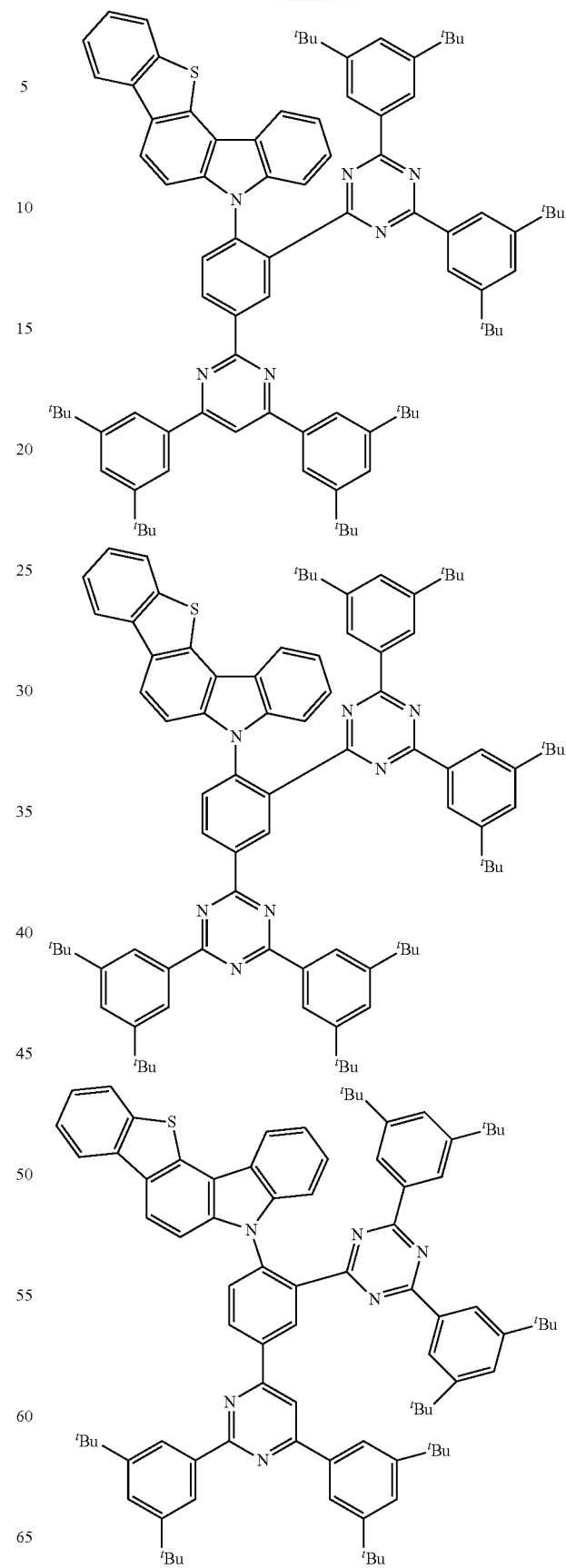

409
-continued
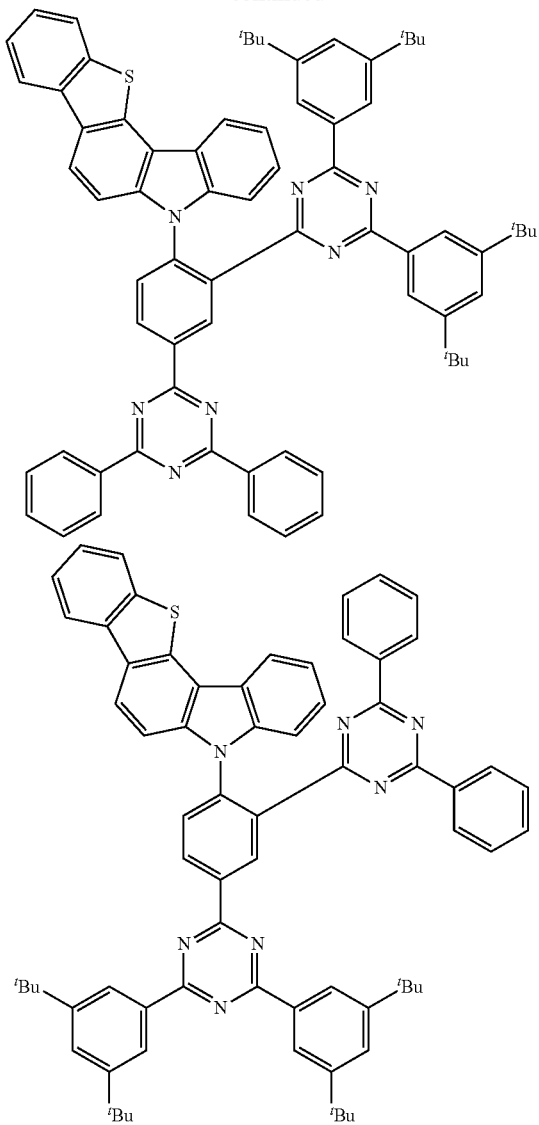
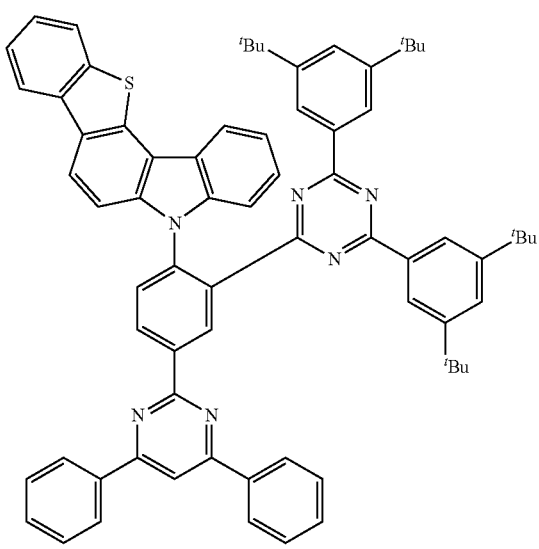
410
-continued
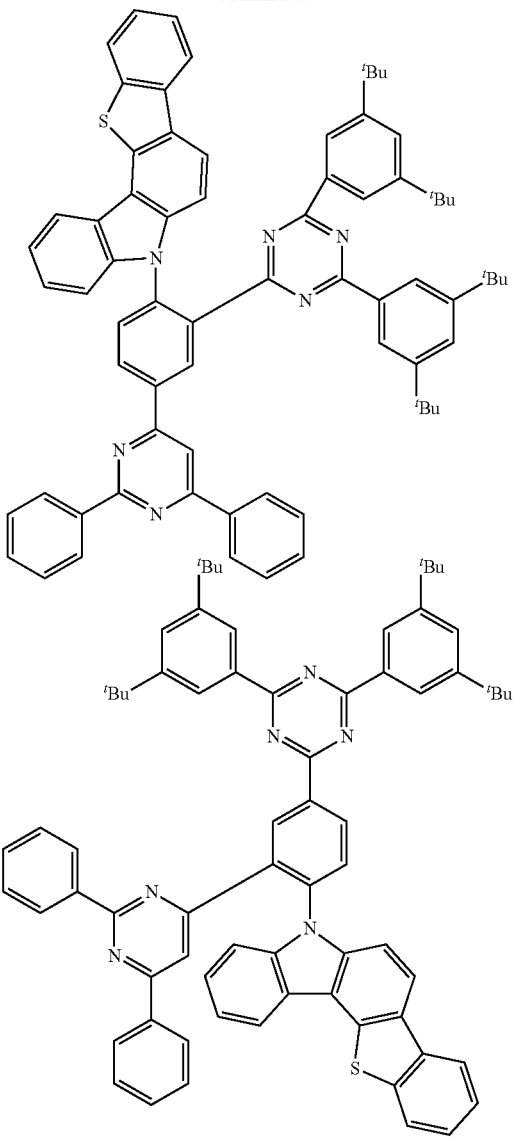
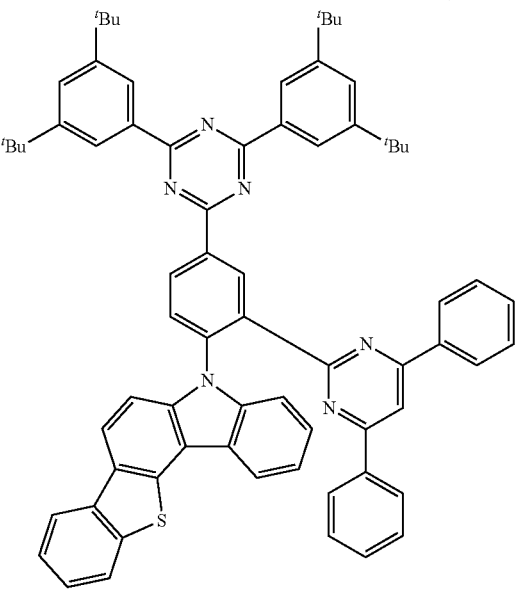

411
-continued
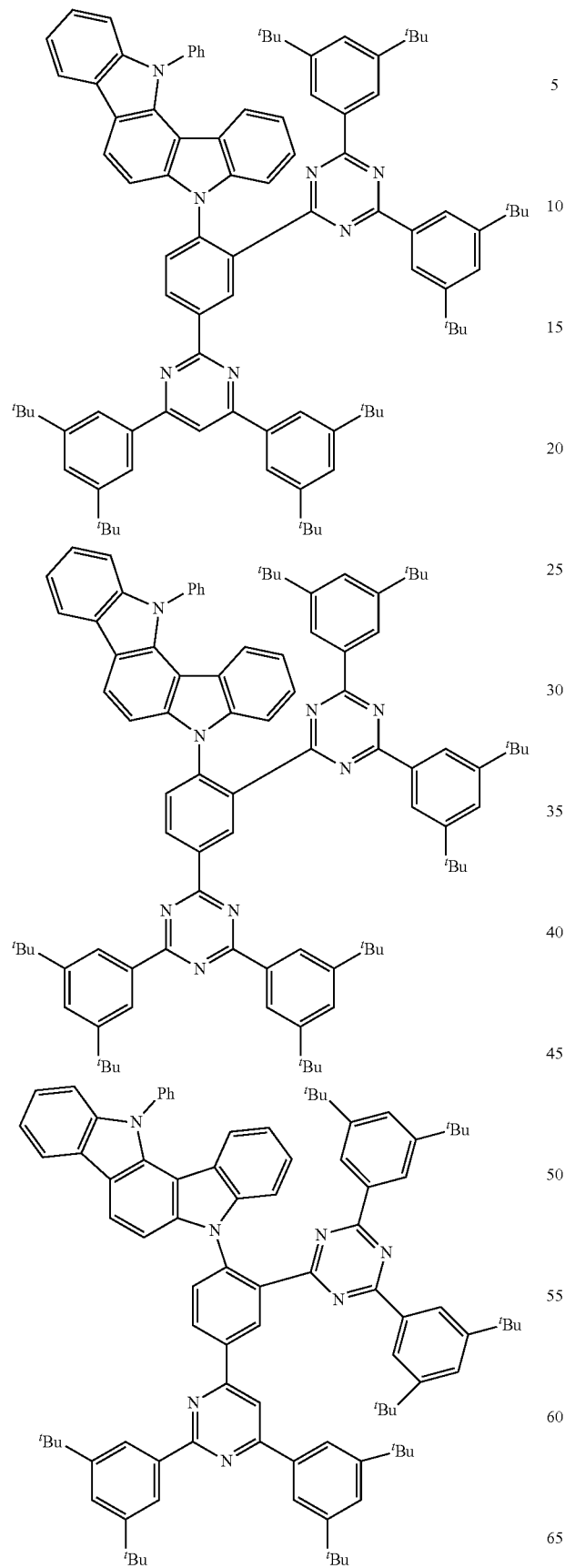
412
-continued
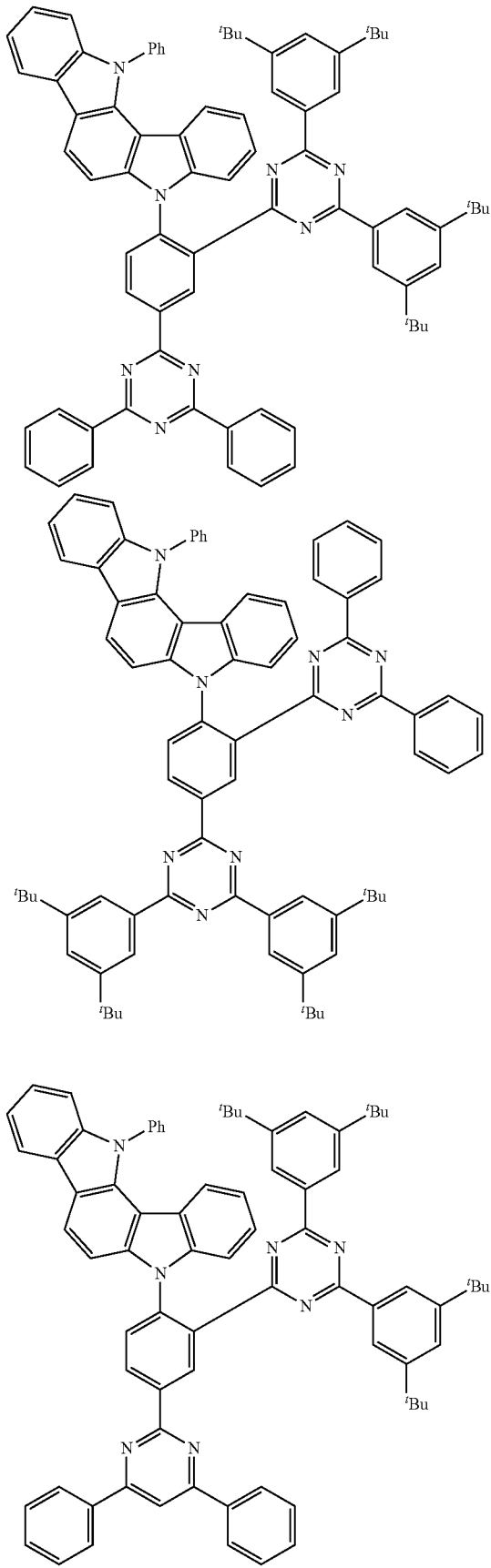

413
-continued
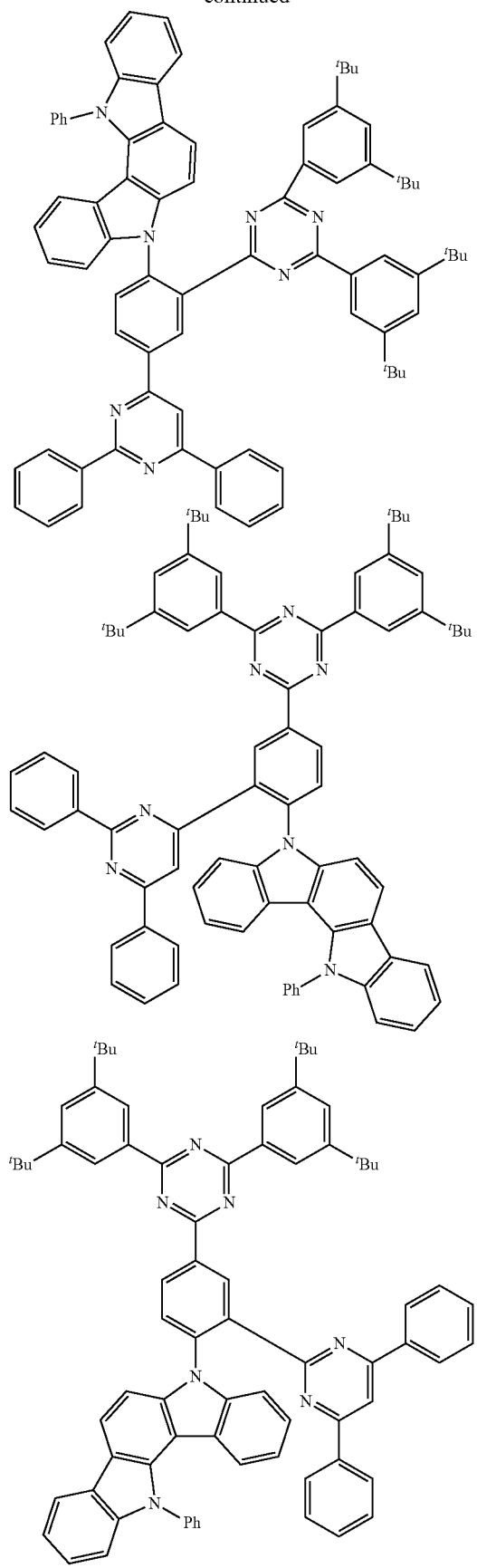
414
-continued
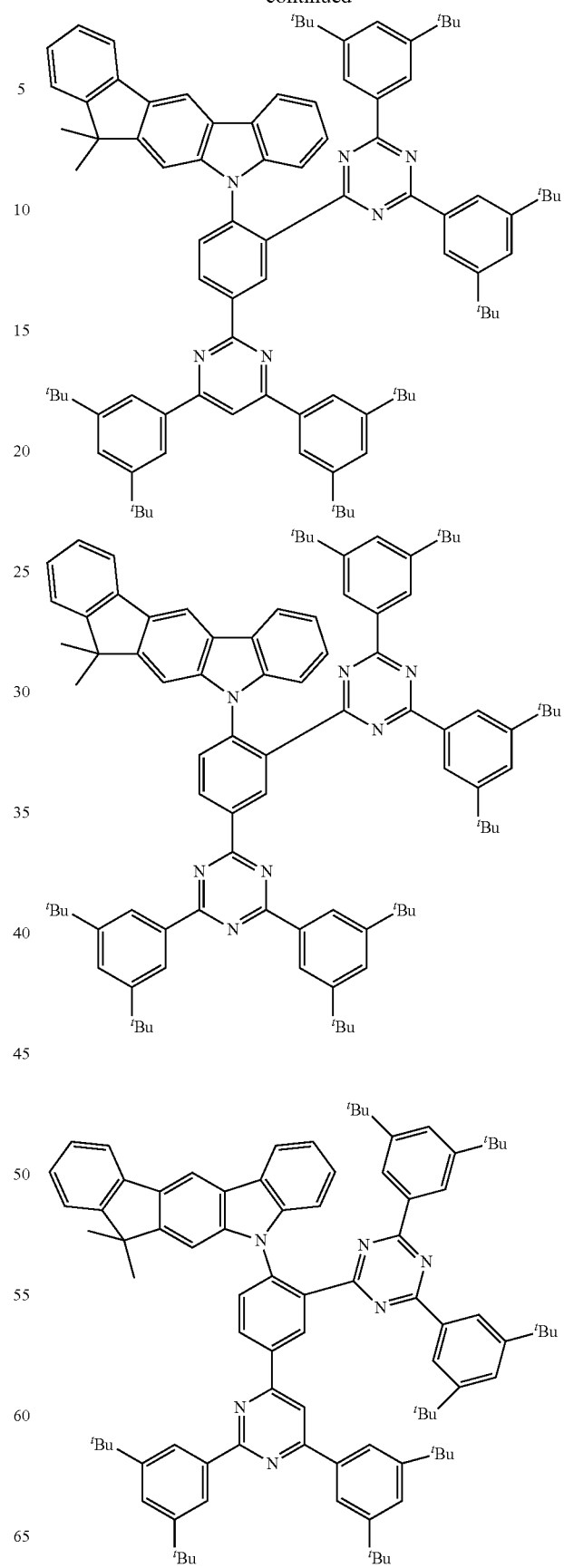

415
-continued
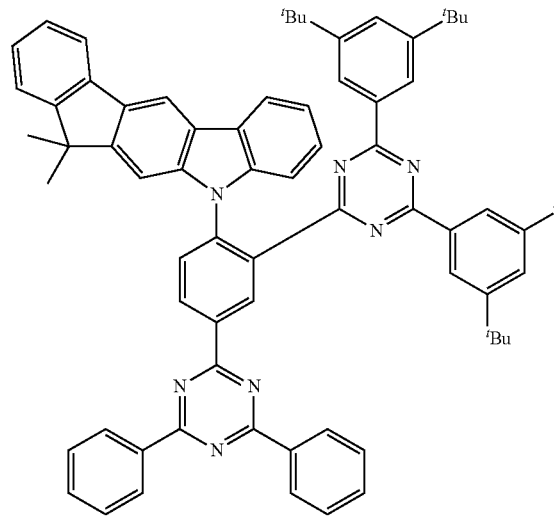
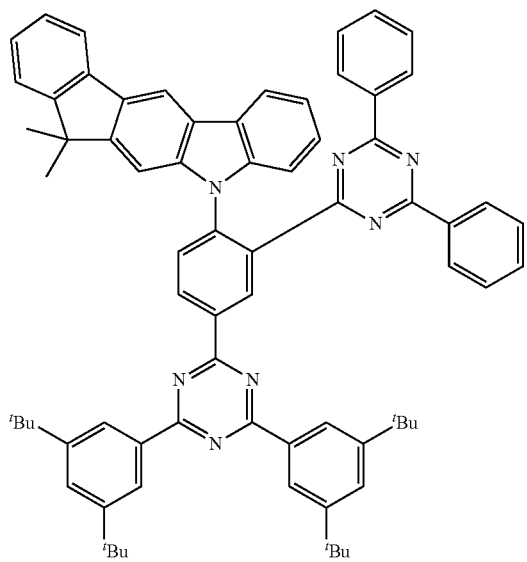
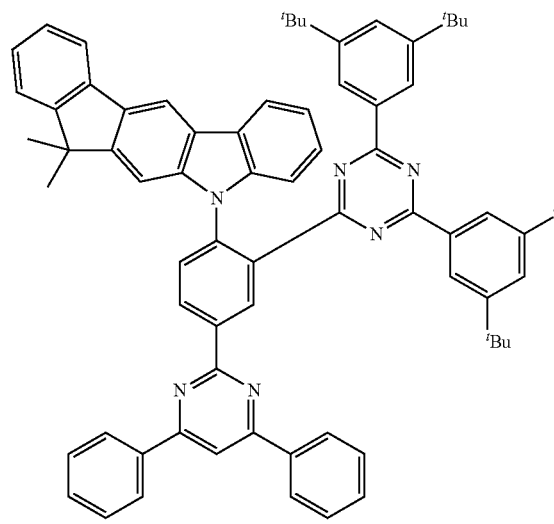
416
-continued
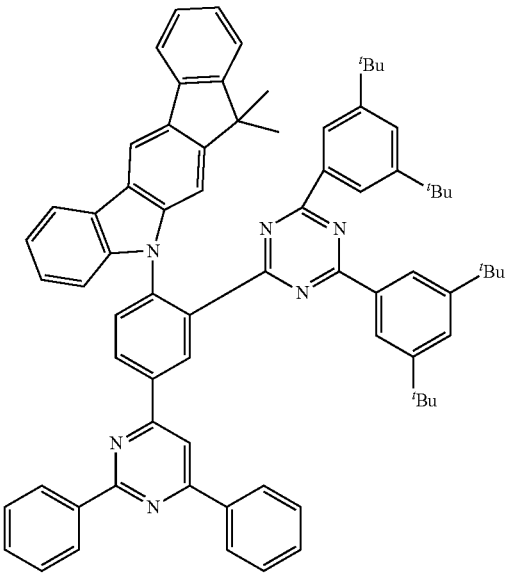
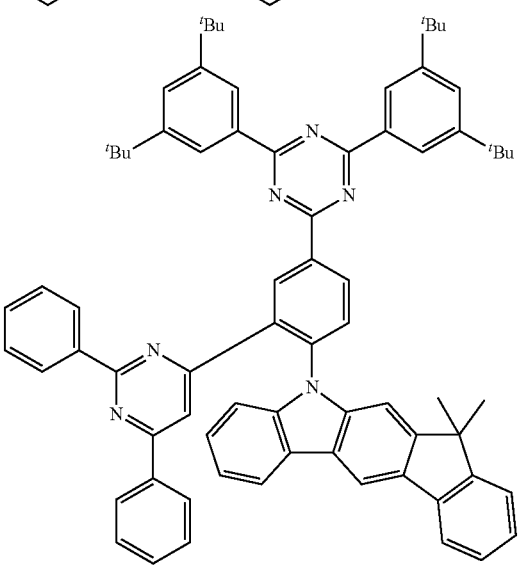
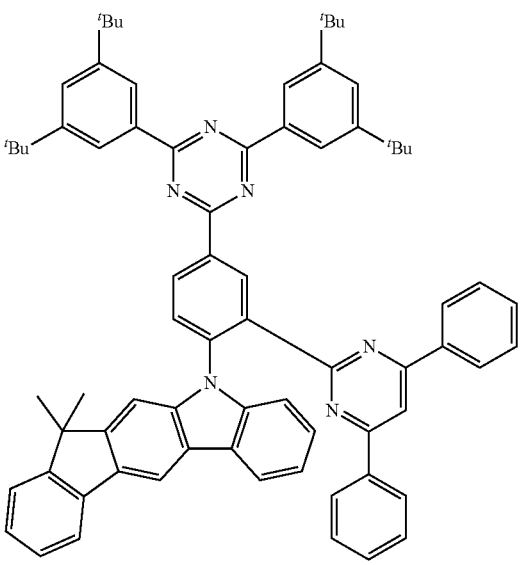

417
-continued
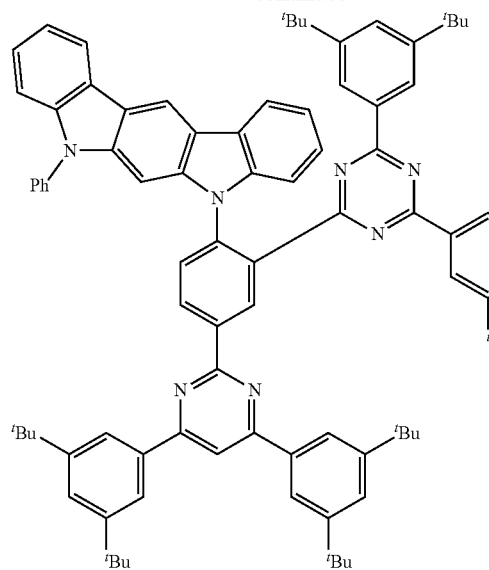
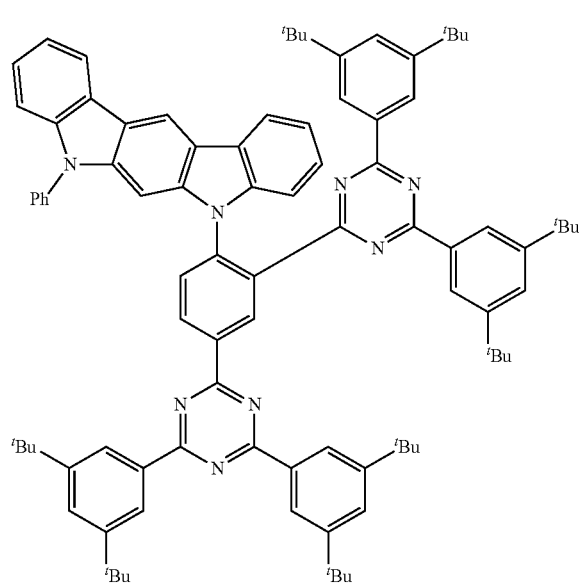
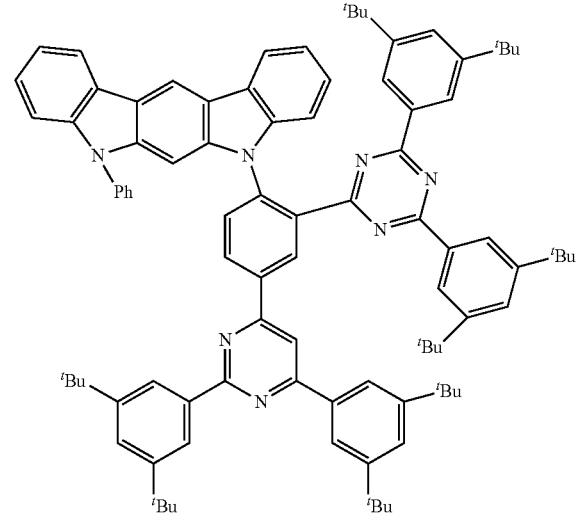
418
-continued
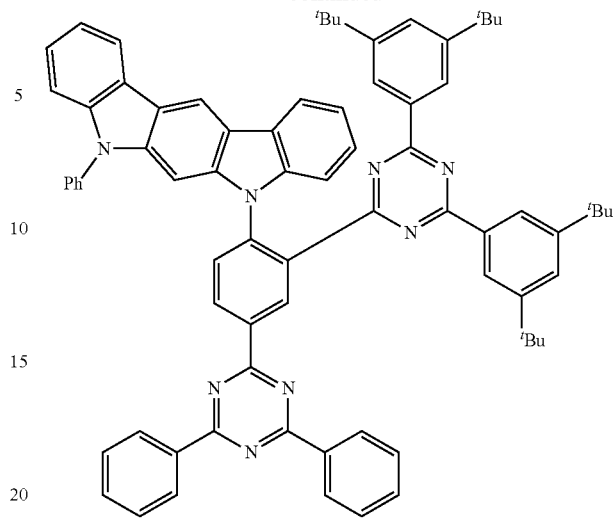
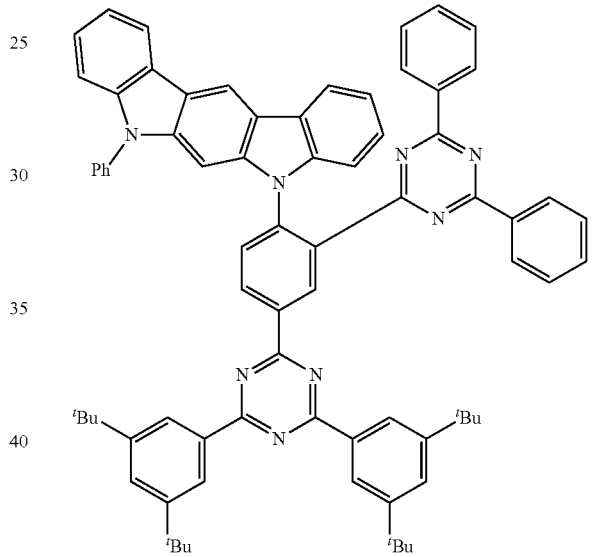
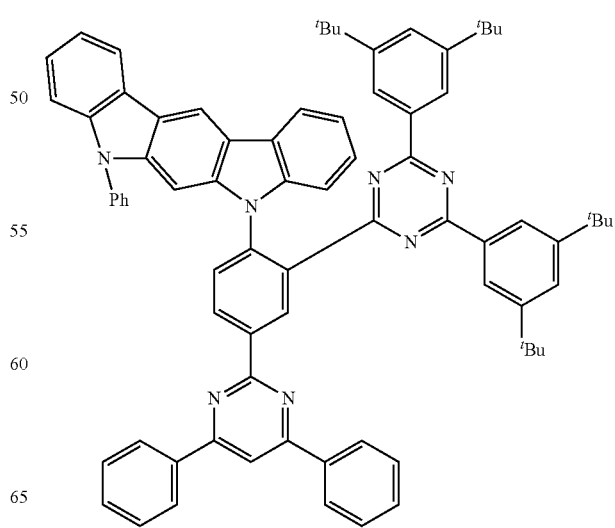

419
-continued

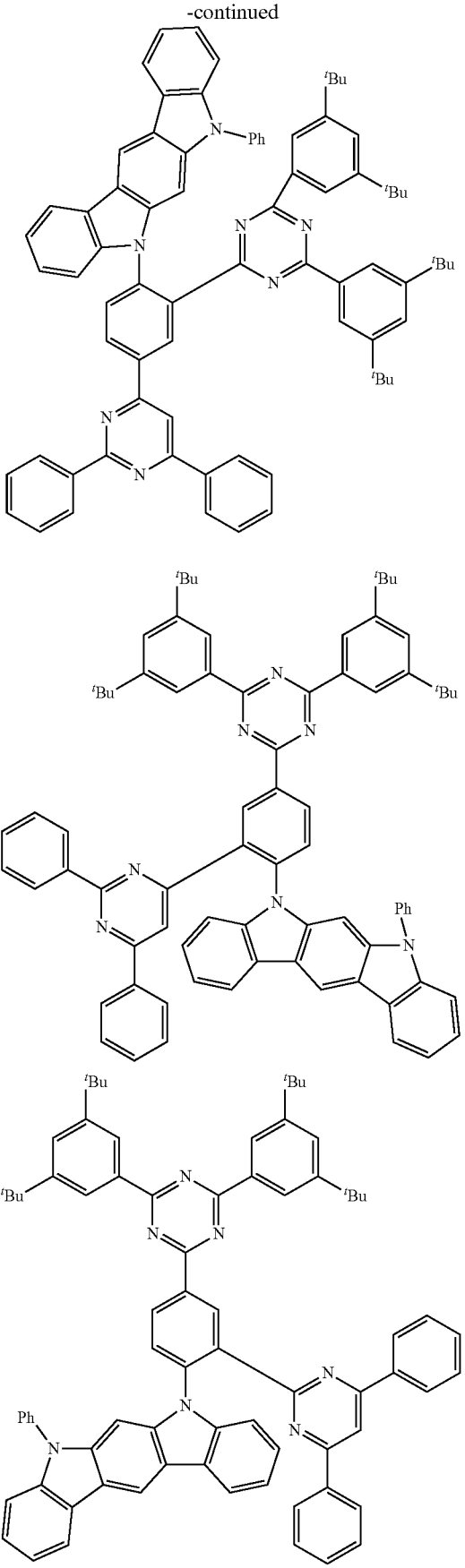

420
-continued

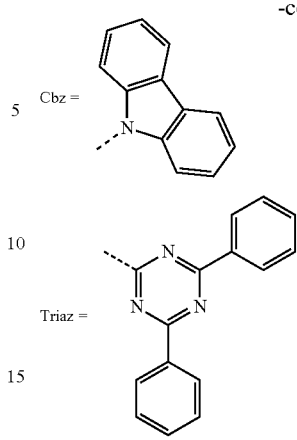

The invention claimed is:

1. An organic molecule, comprising
a first chemical moiety comprising a structure of formula I,

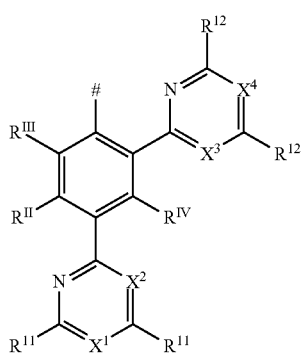

Formula I and
a second chemical moiety comprising a structure of formula II,

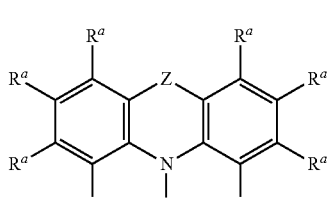

Formula II wherein the first chemical moiety is linked to the second chemical moiety via a single bond;

wherein # represents the binding site of the first chemical moiety to the second chemical moiety;

$X^1$ and $X^2$ is the same or different at each instance and is selected from the group consisting of $CR^{21}$ and N;

$X^3$ and $X^4$ is the same or different at each instance and is selected from the group consisting of $CR^{22}$ and N;

Z is the same or different at each instance and is a direct bond or is selected from the group consisting of $CR^3R^4$, $C=CR^3R^4$, $C=O$, $C=NR^3$, $NR^3$, $O$, $SiR^3R^4$, $S$, $S(O)$ and $S(O)_2$;

$R^{11}$ is the same or different at each instance and is selected from the group consisting of hydrogen, deuterium, $C_1$-$C_5$-alkyl,
where one or more hydrogen atoms in the aforementioned groups may be replaced by deuterium;

$C_2$-$C_8$-alkenyl,
where one or more hydrogen atoms in the aforementioned groups may be replaced by deuterium;

$C_2$-$C_8$-alkynyl,
where one or more hydrogen atoms in the aforementioned groups may be replaced by deuterium;

$C_6$-$C_{18}$-aryl,
which is optionally substituted with one or more substituents $R^6$; and $C_3$-$C_{17}$-heteroaryl,
which is optionally substituted with one or more substituents $R^6$;

$R^{12}$ is the same or different at each instance and is selected from the group consisting of hydrogen, deuterium, $C_1$-$C_5$-alkyl,
where one or more hydrogen in the aforementioned groups may be replaced by deuterium;

$C_2$-$C_8$-alkenyl,
where one or more hydrogen atoms in the aforementioned groups may be replaced by deuterium;

$C_2$-$C_8$-alkynyl,
where one or more hydrogen in the aforementioned groups may be replaced by deuterium;

$C_6$-$C_{18}$-aryl,
which is optionally substituted with one or more substituents $R^6$; and $C_3$-$C_{17}$-heteroaryl,
which is optionally substituted with one or more substituents $R^6$;

$R^{21}$ is the same or different at each instance and is selected from the group consisting of
hydrogen, deuterium, $C_1$-$C_5$-alkyl,
where one or more hydrogen atoms in the aforementioned groups may be replaced by deuterium;

$C_2$-$C_8$-alkenyl,
where one or more hydrogen atoms in the aforementioned groups may be replaced by deuterium;

$C_2$-$C_8$-alkynyl,
where one or more hydrogen atoms in the aforementioned groups may be replaced by deuterium;

$C_6$-$C_{18}$-aryl,
which is optionally substituted with one or more substituents $R^6$; and $C_3$-$C_{17}$-heteroaryl,
which is optionally substituted with one or more substituents $R^6$;

$R^{22}$ is the same or different at each instance and is selected from the group consisting of
hydrogen, deuterium, $C_1$-$C_5$-alkyl,
where one or more hydrogen atoms in the aforementioned groups may be replaced by deuterium;

$C_2$-$C_8$-alkenyl,
where one or more hydrogen in the aforementioned groups may be replaced by deuterium;

$C_2$-$C_8$-alkynyl,
where one or more hydrogen atoms in the aforementioned groups may be replaced by deuterium;

$C_6$-$C_{18}$-aryl,
which is optionally substituted with one or more substituents $R^6$; and $C_3$-$C_{17}$-heteroaryl,
which is optionally substituted with one or more substituents $R^6$;

$R^{II}$, $R^{III}$ and $R^{IV}$ is the same or different at each instance and is selected from the group consisting of
hydrogen, deuterium, $C_1$-$C_5$-alkyl,
where one or more hydrogen atoms in the aforementioned groups may be replaced by deuterium;

$C_2$-$C_8$-alkenyl,
where one or more hydrogen atoms in the aforementioned groups may be replaced by deuterium;

$C_2$-$C_8$-alkynyl,
where one or more hydrogen atoms in the aforementioned groups may be replaced by deuterium; and $C_6$-$C_{18}$-aryl,
which is optionally substituted with one or more substituents $R^6$;

$R^a$, $R^3$ and $R^4$ is the same or different at each instance and is selected from the group consisting of: hydrogen, deuterium, $N(R^5)_2$, $OR^5$, $Si(R^5)_3$, $B(OR^5)_2$, $OSO_2R^5$, $CF_3$, $CN$, $F$, $Br$, $I$, $C_1$-$C_{40}$-alkyl,
which is optionally substituted with one or more substituents $R^5$ and
where one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_1$-$C_{40}$-alkoxy,
which is optionally substituted with one or more substituents $R^5$ and
where one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_1$-$C_{40}$-thioalkoxy,
which is optionally substituted with one or more substituents $R^5$ and
where one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_2$-$C_{40}$-alkenyl,
which is optionally substituted with one or more substituents $R^5$ and
where one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_2$-$C_{40}$-alkynyl,
which is optionally substituted with one or more substituents $R^5$ and
where one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_6$-$C_{60}$-aryl,
which is optionally substituted with one or more substituents $R^5$; and
$C_3$-$C_{57}$-heteroaryl,
which is optionally substituted with one or more substituents $R^5$;
$R^5$ is the same or different at each instance and is selected from the group consisting of: hydrogen, deuterium, $N(R^6)_2$, $OR^6$, $Si(R^6)_3$, $B(OR^6)_2$, $OSO_2R^6$, $CF_3$, CN, F, Br, I,
$C_1$-$C_{40}$-alkyl,
which is optionally substituted with one or more substituents $R^6$ and
where one or more non-adjacent $CH_2$-groups are optionally substituted by $R^6C=CR^6$, $C\equiv C$, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$;
$C_1$-$C_{40}$-alkoxy,
which is optionally substituted with one or more substituents $R^6$ and
where one or more non-adjacent $CH_2$-groups are optionally substituted by $R^6C=CR^6$, $C\equiv C$, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$;
$C_1$-$C_{40}$-thioalkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$;
$C_2$-$C_{40}$-alkenyl,
which is optionally substituted with one or more substituents $R^6$ and
where one or more non-adjacent $CH_2$-groups are optionally substituted by $R^6C=CR^6$, $C\equiv C$, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$;
$C_2$-$C_{40}$-alkynyl,
which is optionally substituted with one or more substituents $R^6$ and
where one or more non-adjacent $CH_2$-groups are optionally substituted by $R^6C=CR^6$, $C\equiv C$, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$;
$C_6$-$C_{60}$-aryl,
which is optionally substituted with one or more substituents $R^6$; and
$C_3$-$C_{57}$-heteroaryl,
which is optionally substituted with one or more substituents $R^6$;
$R^6$ is the same or different at each instance and is selected from the group consisting of: hydrogen, deuterium, OPh, $CF_3$, CN, F,
$C_1$-$C_5$-alkyl,
where one or more hydrogen atoms may be replaced by deuterium, CN, $CF_3$, or F;
$C_1$-$C_5$-alkoxy,
where one or more hydrogen atoms may be replaced by deuterium, CN, $CF_3$, or F;
$C_1$-$C_5$-thioalkoxy,
where one or more hydrogen atoms may be replaced by deuterium, CN, $CF_3$, or F;
$C_2$-$C_5$-alkenyl,
where one or more hydrogen atoms may be replaced by deuterium, CN, $CF_3$, or F;
$C_2$-$C_5$-alkynyl,
where one or more hydrogen atoms may be replaced by deuterium, CN, $CF_3$, or F;
$C_6$-$C_{18}$-aryl,
which is optionally substituted with one or more $C_1$-$C_5$-alkyl substituents;
$C_3$-$C_{17}$-heteroaryl,
which is optionally substituted with one or more $C_1$-$C_5$-alkyl substituents;
$N(C_6$-$C_{18}$-aryl$)_2$;
$N(C_3$-$C_{17}$-heteroaryl$)_2$, and
$N(C_3$-$C_{17}$-heteroaryl)($C_6$-$C_{18}$-aryl);
wherein the substituents $R^a$, $R^3$, $R^4$ or $R^5$ independently from each other optionally form a mono- or polycyclic, aliphatic, aromatic and/or benzo-fused ring system with one or more substituents $R^a$, $R^3$, $R^4$ or $R^5$;
wherein at least one variable selected from the group consisting of $X^1$, $X^2$ is N, and at least one variable selected from the group consisting of $X^3$, $X^4$ is N.

2. The organic molecule according to claim 1, wherein $R^{11}$, $R^{12}$, $R^{21}$, $R^{22}$, $R^{II}$, $R^{III}$ and $R^{IV}$ is the same or different at each instance and is selected from the group consisting of H, methyl and phenyl.

3. The organic molecule according to claim 1, wherein $X^1$, $X^2$, $X^3$, and $X^4$ is N at each instance.

4. The organic molecule according to claim 1, wherein the second chemical moiety comprises a structure of the formula IIa:

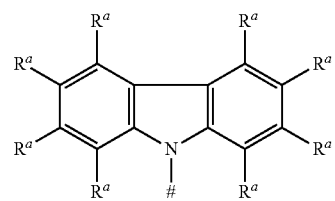

Formula IIa wherein the definitions given in claim 1 are applicable to # and $R^a$.

5. The organic molecule according to claim 1, wherein the second chemical moiety comprises a structure of Formula IIb:

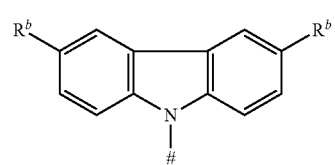

Formula IIb wherein
$R^b$ is the same or different at each instance and is selected from the group consisting of hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;

$C_1$-$C_{40}$-alkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_1$-$C_{40}$-thioalkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkenyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkynyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_6$-$C_{60}$-aryl,
which is optionally substituted with one or more substituents $R^5$; and $C_3$-$C_{57}$-heteroaryl,
which is optionally substituted with one or more substituents $R^5$;

and wherein apart from the aforementioned definitions, the definitions in claim 1 apply.

6. The organic molecule according to claim 1, wherein the second chemical moiety comprises a structure of Formula IIc:

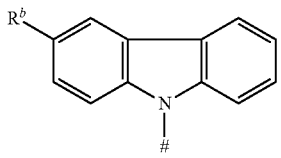

Formula IIc wherein
$R^b$ is the same or different at each instance and is selected from the group consisting of: hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_1$-$C_{40}$-alkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_1$-$C_{40}$-thioalkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkenyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkynyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_6$-$C_{60}$-aryl,
which is optionally substituted with one or more substituents $R^5$; and $C_3$-$C_{57}$-heteroaryl,
which is optionally substituted with one or more substituents $R^5$;

and wherein apart from the aforementioned definitions, the definitions in claim 1 apply.

7. The organic molecule according to claim 5, wherein $R^b$ is the same or different at each instance and is selected from the group consisting of:
Me, $^i$Pr, $^t$Bu, CN, $CF_3$,
Ph, which may be substituted in each case by one or more substituents selected from Me, $^i$Pr, $^t$Bu, CN, $CF_3$ and Ph;
pyridinyl, which may be substituted in each case by one or more substituents selected from Me, $^i$Pr, $^t$Bu, CN, $CF_3$ and Ph;
pyrimidinyl, which may be substituted in each case by one or more substituents selected from Me, $^i$Pr, $^t$Bu, CN, $CF_3$ and Ph;
carbazolyl, which may be substituted in each case by one or more substituents selected from Me, $^i$Pr, $^t$Bu, CN, $CF_3$ and Ph;
triazinyl, which may be substituted in each case by one or more substituents selected from Me, $^i$Pr, $^t$Bu, CN, $CF_3$, and Ph;
and
$N(Ph)_2$.

8. An optoelectronic device comprising at least one of a luminescent emitter, a host material, electron transport material, hole injection material and hole blocker material, wherein the luminescent emitter, the host material, the electron transport material, the hole injection material, and the hole blocker material comprise the organic molecule according to claim 1.

9. The optoelectronic device according to claim 8, wherein the optoelectronic device is selected from the group consisting of an organic light-emitting diode (OLED), a light-emitting electrochemical cell, an OLED sensor, an organic diode, an organic solar cell, an organic transistor, an organic field-effect transistor, an organic laser and a down conversion element.

10. A composition, comprising:
- at least one organic molecule according to claim 1;
- at least one of an emitter and a host material not comprising the organic molecule; and
- at least one of a dye and a solvent.

11. An optoelectronic device comprising a composition according to claim 10, wherein the optoelectronic device is selected from the group consisting of organic light-emitting diode (OLED), light-emitting electrochemical cell OLED-sensor, organic diode, organic solar cell, organic transistor, organic field-effect transistor, organic laser, and down-conversion element.

12. The optoelectronic device according to claim 11, comprising
- a substrate,
- an anode and
- a cathode, wherein the anode or the cathode has been applied to the substrate, and
- at least one light-emitting layer is arranged between the anode and the cathode, wherein at least one light-emitting layer comprises said composition.

13. A method for manufacturing an optoelectronic component, comprising performing processing of the organic molecule according to claim 1 from a solution or by using a vacuum evaporation process.

* * * * *